(12) United States Patent
Faaberg et al.

(10) Patent No.: US 8,110,390 B2
(45) Date of Patent: Feb. 7, 2012

(54) PRRS VIRUSES, INFECTIOUS CLONES, MUTANTS THEREOF, AND METHODS OF USE

(75) Inventors: Kay S. Faaberg, Ames, IA (US); Jun Han, St. Paul, MN (US); Gongping Liu, St. Paul, MN (US); Yue Wang, St. Paul, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 666 days.

(21) Appl. No.: 11/922,798

(22) PCT Filed: Jun. 23, 2006

(86) PCT No.: PCT/US2006/024355
§ 371 (c)(1),
(2), (4) Date: Sep. 12, 2008

(87) PCT Pub. No.: WO2007/002321
PCT Pub. Date: Jan. 4, 2007

(65) Prior Publication Data
US 2010/0267929 A1    Oct. 21, 2010

Related U.S. Application Data

(60) Provisional application No. 60/694,021, filed on Jun. 24, 2005.

(51) Int. Cl.
*C12N 7/00* (2006.01)
*C12N 15/40* (2006.01)
*C12N 15/85* (2006.01)
*C07K 14/08* (2006.01)

(52) U.S. Cl. ............... 435/235.1; 536/23.72; 435/320.1; 530/350

(58) Field of Classification Search .................. None
See application file for complete search history.

(56) References Cited

U.S. PATENT DOCUMENTS

| | | | |
|---|---|---|---|
| 5,223,409 A | 6/1993 | Ladner et al. | |
| 5,683,865 A | 11/1997 | Collins et al. | |
| 5,846,805 A | 12/1998 | Collins et al. | |
| 6,110,468 A | 8/2000 | Collins et al. | |
| 6,194,389 B1 | 2/2001 | Johnston et al. | |
| 6,498,008 B2 | 12/2002 | Collins et al. | |
| 6,841,364 B2 | 1/2005 | Yuan et al. | |
| 6,855,315 B2 | 2/2005 | Collins et al. | |
| 7,041,443 B2 | 5/2006 | Faaberg et al. | |
| 7,273,617 B2 | 9/2007 | Yuan et al. | |
| 7,368,117 B2 * | 5/2008 | Fetzer et al. | 424/204.1 |
| 7,691,389 B2 * | 4/2010 | Calvert et al. | 424/204.1 |

FOREIGN PATENT DOCUMENTS

| | | |
|---|---|---|
| EP | 1 018 557 A2 | 7/2000 |
| EP | 1018557 * | 7/2000 |

OTHER PUBLICATIONS

Nielsen et al, Journal of Virology 77:3702-3711, 2005.*
Genbank locus DQ176019, Jun. 1, 2006.*
Genbank locus DQ176020, Jun. 1, 2006.*
Ropp et al (Journal of Virology 78:3684-3703, 2004).*
Fang et al (Virus Research 100:229-235, 2004).*
Gao et al (Arch Virol. 149:1341-1351, 2004).*
Shen et al (Arch. Virol. 145:871-883, 2000).*
Han et al (Journal of Virology 81:9878-9890, 2007).*
Genbank AY366525, Mar. 19, 2004.*
Plotkin, Stanley A. MD et al., "New Technology for Making Vaccines", Vaccines, 1988, 568-575.
Allende et al., "North American and European porcine reproductive and respiratory syndrome viruses differ in non-structural protein coding regions," *J. Gen. Virol.*, 1999;80:307-315.
Bairoch et al., "The PROSITE database, its status in 1997," *Nucleic Acids Res.*, 1997;25(1):217-221.
Bautista et al., "Comparison of porcine alveolar macrophages and CL 2621 for the detection of porcine reproductive and respiratory syndrome (PRRS) virus and anti-PRRS antibody," *J. Vet. Diagn. Invest.*, 1993;5:163-165.
Bendtsen et al., "Improved Prediction of Signal Peptides: SignalP 3.0," *J. Mol. Biol.*, 2004;340:783-795.
Benfield et al., "Characterization of swine infertility and respiratory syndrome (SIRS) virus (isolate ATCC VR-2332)," *J. Vet. Diagn. Invest.*, 1992;4:127-133.
Cavanagh et al., "Recommendations of the Coronavirus Study Group for the Nomenclature of the Structural Proteins, mRNAs, and Genes of Coronaviruses," *Virol.*, 1990;176:306-307.
Cavanagh D., "*Nidovirales*: a new order comprising *Coronaviridae* and *Arteriviridae*," *Arch. Virol.*, 1997;142/143:629-633.
Chang et al., "Evolution of Porcine Reproductive and Respiratory Syndrome Virus during Sequential Passages in Pigs," *J. Virol.*, May 2002;76(10):4750-4763.
Chen et al., "Determination of the 5' end of the lactate dehydrogenase-elevating virus genome by two independent approaches," *J. Gen. Virol.*, 1994;75:925-930.
Choi et al., "Identification of 5' and 3' *cis*-Acting Elements of the Porcine Reproductive and Respiratory Syndrome Virus: Acquisition of Novel 5' AU-Rich Sequences Restored Replication of a 5'-Proximal 7-Nucleotide Deletion Mutant," *J. Virol.*, Jan. 2006;80(2):723-736.
Collins et al., "Isolation of swine infertility and respiratory syndrome virus (isolate ATCC VR-2332) in North America and experimental reproduction of the disease in gnotobiotic pigs," *J. Vet. Diagn. Invest.*, 1992;4:117-126.
den Boon et al., "Processing and Evolution of the N-Terminal Region of the Arterivirus Replicase ORF1a Protein: Identification of Two Papainlike Cysteine Proteases," *J. Virol.*, Jul. 1995;69(7):4500-4505.

(Continued)

*Primary Examiner* — Mary E Mosher
(74) *Attorney, Agent, or Firm* — Faegre & Benson LLP

(57) ABSTRACT

The present invention provides isolated infectious polynucleotides, such as infectious clones, having a nucleotide sequence with identity to PRRS viruses such as VR-2332, Lelystad, or others, and optionally further including a deletion in a region of ORF1 that encodes the nsp2 polypeptide.

25 Claims, 86 Drawing Sheets

OTHER PUBLICATIONS

EMBL Sequence Version Archive, Accession No. AY262352, Retrieved from the Intenret:<URL:www.ebi.ac.uk/cgi-bin/sva/sva.pl?session=%2Febi%2Fextserv%2Fold-work%2FSESSI...>; 6 pgs., (2004).

Fang et al., "Heterogeneity in Nsp2 of European-like porcine reproductive and respiratory syndrome viruses isolated in the United States," *Virus Res.*, 2004;100:229-235.

Gao et al., "Genomic characterization of two Chinese isolates of *Porcine respiratory and reproductive syndrome virus*," *Arch. Virol.*, 2004;149:1341-1351.

Gorbalenya et al., "*Nidovirales*: Evolving the largest RNA virus genome," *Virus Res.*, 2006;117:17-37. Epub Feb. 28, 2006.

Groot Bramel-Verheije et al., "Expression of a Foreign Epitope by Porcine Reproductive and Respiratory Syndrome Virus," *Virol.*, 2000;278:380-389.

Halbur et al., "Immunohistochemical Identification of Porcine Reproductive and Respiratory Syndrome Virus (PRRSV) Antigen in the Heart and Lymphoid System of Three-week-old Colostrum-deprived Pigs," *Vet. Pathol.*, 1995;32:200-204.

Halbur et al., "Comparative pathogenicity of nine US porcine reproductive and respiratory syndrome virus (PRRSV) isolates in a five-week-old cesarean-derived, colostrum-deprived pig model," *J. Vet. Diagn. Invest.*, 1996;8:11-20.

Hamajima et al., "Intranasal Administration of HIV-DNA Vaccine Formulated with a Polymer, Carboxymethylcellulose, Augments Mucosal Antibody Production and Cell-Mediated Immune Response," *Clin. Immunol. Immunopathol.*, Aug. 1998;88(2):205-210.

Han et al., "Complete genome analysis of RFLP 184 isolates of porcine reproductive and respiratory syndrome virus," *Vir. Res.*, 2006;122:175-182.

Harlow et al., *Antibodies: A Laboratory Manual*, Cold Spring Harbor Laboratory Press, Cold Spring Harbor, NY; title page, publisher's page, and table of contents only, 9 pages (1988).

Howard et al., *Veterinary Immunology and Immunopathology*, vol. 102, Issues 1-2 and 4, cover page, title page, and table of contents: 7 pgs., 2004.

Ivanov et al., "Major genetic marker of nidoviruses encodes a replicative endoribonuclease," *PNAS*, Aug. 24, 2004;101(34):12694-12699.

Johnson et al., "Replication of Flock House Virus RNAs from Primary Transcripts Made in Cells by RNA Polymerase II," *J. Virol.*, Apr. 1997;71 (4): 3323-3327.

Kapur et al., "Genetic variation in porcine reproductive and respiratory syndrome virus isolates in the midwestern United States," *J. Gen. Virol.*, 1996;77:1271-1276.

Kim et al., "Enhanced replication of porcine reproductive and respiratory syndrome (PRRS) virus in a homogeneous subpopulation of MA-104 cell line," *Arch. Virol.*, 1993;133:477-483.

Krogh et al., "Predicting Transmembrane Protein Topology with a Hidden Markov Model: Application to Complete Genomes," *J. Mol. Biol.*, 2001;305:567-580.

Lai M.M.C., "Transcription, Replication, Recombination, and Engineering of Coronavirus Genes," *Corona- and Related Viruses*, New York, NY, 1995;463-471.

Lee et al., "A DNA-launched reverse genetics system for porcine reproductive and respiratory syndrome virus reveals that homodimerization of the nucleocapsid protein is essential for virus infectivity," *Virol.*, 2005;331:47-62.

Lee et al., "Mutations within the nuclear localization signal of the porcine reproductive and respiratory syndrome virus nucleocapsid protein attenuate virus replication," *Virol.*, 2006;346:238-250.

Magar et al., "Antigenic Comparison of Canadian and US Isolates of Porcine Reproductive and Respiratory Syndrome Virus Using Monoclonal Antibodies to the Nucleocapsid Protein," *Can. J. Vet. Res.*, 1995;59:232-234.

Malet et al., "From RNA to quasispecies: a DNA polymerase with proofreading activity is highly recommended for accurate assessment of viral diversity," *J. Virol. Methods*, 2003;109:161-170.

Mardassi et al., "Identification of major differences in the nucleocapsid protein genes of a Quebec strain and European strains of porcine reproductive and respiratory syndrome virus," *J. Gen. Virol.*, 1994;75:681-685.

McGuffin et al., "The PSIPRED protein structure prediction server," *Bioinformatics Applications Note*, 2000;16(4):404-405.

Meng et al., "Phylogenetic analyses of the putative M (ORF 6) and N (ORF 7) genes of porcine reproductive and respiratory syndrome virus (PRRSV): implication for the existence of two genotypes of PRRSV in the U.S.A. and Europe," *Arch. Virol.*, 1995;140:745-755.

Meng et al., "Characterization of a high-virulence US isolate of porcine reproductive and respiratory syndrome virus in a continuous cell line, ATCC CRL11171," *J. Vet. Diagn. Invest.*, 1996;8:374-381.

Meulenberg et al., "Lelystad Virus, the Causative Agent of Porcine Epidemic Abortion and Respiratory Syndrome (PEARS), is Related to LDV and EAV," *Virology*, 1993;192:62-72.

Murtaugh et al., "Comparison of the structural protein coding sequences of the VR-2332 and Lelystad virus strains of the PRRS virus," *Arch. Virol.*, 1995;140:1451-1460.

Murtaugh et al., "Genetic Variation in the PRRS Virus," *Coronaviruses and Arteriviruses*, New York, NY, 1998;787-794.

Murtaugh et al., "Inflammatory cytokines and antigen presenting cell activation," *Vet. Immunol. Immunopathol.*, 2002;87:109-121.

National Center for Biotechnology Information, National Library of Medicine, National Institutes of Health, "BLAST 2 SEQUENCES," Bethesda, MD [retrieved on Jun. 22, 2005]. Retrieved from the Internet<URL:http://www.ncbi.nlm.nih.gov/blast/bl2seq/wblast2.cgi?0.html>; 3 pgs.

National Center for Biotechnology Information, National Library of Medicine, National Institutes of Health, GenBank Locus PRU87392, Accession No. U87392, "Porcine reproductive and respiratory syndrome," [online]. Bethesda, MD [retrieved on May 11, 2009]. Retrieved from the Internet<URL:http:www.ncbi.nlm.nih.gov/nuccore/11192298>; 9 pgs.

National Center for Biotechnology Information, National Library of Medicine, National Institutes of Health, GenBank Locus AF066183, Accession No. AF066183, "Porcine reproductive and respiratory syndrome," [online]. Bethesda, MD [retrieved on May 11, 2009]. Retrieved from the Internet:<URL:http:www.ncbi.nlm.nih.gov/nuccore/66735498>; 9 pgs.

National Center for Biotechnology Information, National Library of Medicine, National Institutes of Health, GenBank Locus AY150564, Accession No. AY150564, "Procine reproductive and respiratory syndrome," [online]. Bethesda, MD [retrieved on May 11, 2009]. Retrieved from the Internet:<URL:http:www.ncbi.nlm.nih.gov/nuccore/27549163>; 8 pgs.

National Center for Biotechnology Information, National Library of Medicine, National Institutes of Health, GenBank Locus AF223639, Accession No. AF223639, "Cloning vector pOK12, complete sequence," [online]. Bethesda, MD [retrieved on May 11, 2009]. Retrieved from the Internet:<URL:http:www.ncbi.nlm.nih.gov/nuccore/8050583>; 3 pgs.

National Center for Biotechnology Information, National Library of Medicine, National Institutes of Health, GenBank Locus LEYPOLYENV, Accession No. M96262, "Lelystad virus, complete genome," [online]. Bethesda, MD [retrieved on May 11, 2009]. Retrieved from the Internet:<URL:http:www.ncbi.nlm.nih.gov/nuccore/11125727>; 8 pgs.

Needleman et al., "A General Method Applicable to the Search for Similarities in the Amino Acid Sequence of Two Proteins," *J. Mol. Biol.*, 1970;48:443-453.

Nelsen et al., "Porcine Reproductive and Respiratory Syndrome Virus Comparison: Divergent Evolution on Two Continents," *J. Virol.*, Jan. 1999;73(1):270-280.

Nielsen et al., "Generation of an Infectious Clone of VR-2332, a Highly Virulent North American-Type Isolate of Porcine Reproductive and Respiratory Syndrome Virus," *J. Virol.*, Mar. 2003;77(6):3702-3711.

Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes," *J. Virol.*, Apr. 2001;75(7):3277-3290.

Ostrowski et al., "Identification of Neutralizing and Nonneutralizing Epitopes in the Porcine Reproductive and Respiratory Syndrome Virus GP5 Ectodomain," *J. Virol.*, May 2002;76(9):4241-4250. Erratum in *J. Virol*, Jul. 2002: 76(13):6863.

Park et al., "Pathogenesis of plaque variants of porcine reproductive and respiratory syndrome virus in pregnant sows," *Am. J Vet. Res.*, Mar. 1996;57 (3):320-323.

Pattnaik et al., "Infectious Defective Interfering Particles of VSV from Transcripts of a cDNA Clone," *Cell*, Jun. 12, 1992;69:1011-1020.

Pattnaik et al., "Comparison of liquid-phase and Mab-blocking ELISA for assessment of the reactivity of monoclonal antibodies to foot-and-mouth disease virus," *J. Immunol. Methods*, 1994;172:265-267.

Plagemann P.G., "Complexity of the Single Linear Neutralization Epitope of the Mouse Arterivirus Lactate Dehydrogenase-Elevating Virus," *Virology*, 2001;290:11-20.

Plagemann et al., "The primary neutralization epitope of porcine respiratory and reproductive syndrome virus strain VR-2332 is located in the middle of the GP5 ectodomain," *Arch. Virol.*, 2002;147:2327-2347.

Ropp et al., "Characterization of Emerging European-Like Porcine Reproductive and Respiratory Syndrome Virus Isolates in the United States," *J. Virol.*, Apr. 2004;78(7):3684-3703.

Rossow K.D., "Porcine Reproductive and Respiratory Syndrome," *Vet. Pathol.*, 1998;35:1-20.

Rost et al., "Topology prediction for helical transmembrane proteins at 86% accuracy,"*Protein Sci.*, 1996;5:1704-1718.

Rost et al.,"The PredictProtein server," *Nucleic Acids Res.*, 2004;32(Web Server issue): W321-326.

Rowland et al., "The localization of porcine reproductive and respiratory syndrome virus nucleocapsid protein to the nucleolus of infected cells and identification of a potential nucleolar localization signal sequence," *Virus Res.*, 1999;64:1-12.

Sambrook et al., *Molecular Cloning: A Laboratory Manual, Books 1-3*, Cold Spring Harbor Laboratory Press, Cold Spring Harbor, NY, 1989; title page, publisher's page and table of contents only (30) pgs.

Shen et al., "Determination of the complete nucleotide sequence of a vaccine strain of porcine reproductive and respiratory syndrome virus and identification of the Nsp2 gene with a unique insertion," *Arch. Virol.*, 2000;145:871-883.

Snijder et al., "The molecular biology of arteriviruses,"*J. Gen. Virol.*, 1998;79:961-979.

Thompson et al., "The CLUSTAL_X windows interface: flexible strategies for multiple sequence alignment aided by quality analysis tools," *Nucleic Acids Res.*, 1997;25(24):4876-4882.

Truong et al., "A highly pathogenic porcine reproductive and respiratory syndrome virus generated from an infectious cDNA clone retains the in vivo virulence and transmissibility properties of the parental virus," *Virol.*, 2004;325:308-319.

Vieira et al., "New pUC-derived cloning vectors with different selectable markers and DNA replication origins," *Gene*, 1991;100:189-194.

Wensvoort et al., "Mystery swine disease in the Netherlands: the isolation of Lelystad virus," *Vet. Q.*, Jul. 1991;13(3):121-130.

Wensvoort et al., "Lelystad virus, the cause of porcine epidemic abortion and respiratory syndrome: a review of mystery swine disease research at Lelystad," *Vet. Microbiol.*,1992;33:185-193.

Wesley et al., "Differentiation of a porcine reproductive and respiratory syndrome virus vaccine strain from North American field strains by restriction fragment length polymorphism analysis of ORF 5," *J. Vet. Diagn. Invest.*, 1998;10:140-144.

Wootton et al., "Full-length sequence of a Canadian porcine reproductive and respiratory syndrome virus (PRRSV) isolate," *Arch. Virol.*, 2000;145:2297-2323.

Wootton et al., "Homo-Oligomerization of the Porcine Reproductive and Respiratory Syndrome Virus Nucleocapsid Protein and the Role of Disulfide Linkages," *J. Virol.*, Apr. 2003;77(8):4546-4557.

Wu et al., "A 10-kDa Structural Protein of Porcine Reproductive and Respiratory Syndrome Virus Encoded by ORF2b," *Virology*, 2001;287:183-191.

Yoon et al., "Genetic and Antigenic Stability of PRRS Virus in Pigs: Field and experimental prospectives," *The Nidoviruses (Coronaviruses and Arteriviruses )*, New York, NY, 2001, 25-30.

Yuan et al., "Recombination between North American strains of porcine reproductive and respiratory syndrome virus," *Virus Res.*, 1999;61:87-98.

Yuan et al., "Heteroclite Subgenomic RNAs are Produced in Porcine Reproductive and Respiratory Syndrome Virus Infection," *Virology*, 2000;275: 158-169.

Yuan et al., "Complete genome comparison of porcine reproductive and respiratory syndrome virus parental and attenuated strains," *Virus Res.*, 2001;74:99-110.

Yuan et al., "Characterization of heteroclite subgenomic RNAs associated with PRRSV infection," *Virus Res.*, 2004;105:75-87.

Ziebuhr et al., "Virus-encoded proteinases and proteolytic processing in the *Nidovirales*," *J. Gen. Virol.*, 2000;81:853-879.

* cited by examiner

Fig. 1A-1

```
                                             ATGACGTATAGGTGTTGGCTCTATGCCTTGGCATTTGTATTGTCAGGAGCTGTGACCATT
GGCACAGCCCAAAACTTGCTGCACAGAAACACCCTTCTGTGATAGCCTCCTTCAGGGGAGCTTAGGGTTTGTCCCTAGCA
CCTTGCTTCCGGAGTTGCACTGCTTTACGGTCTCTCCACCCCTTTAACCATGTCTGGGATACTTGATCGGTGCACGTGTA
CCCCCAATGCCAGGGTGTTTATGGCGGAGGGCCAAGTCTACTGCACACGATGCCTCAGTGCACGGTCTCTCCTTCCCCTG
AACCTCCAGGTTTCTGAGCTCGGGGTGCTAGGCCTATTCTACAGGCCCGAAGAGCCACTCCGGTGGACGTTGCCACGTGC
ATTCCCCACTGTTGAGTGCTCCCCCGCCGGGGCCTGCTGGCTTTCTGCAATCTTTCCAATCGCACGAATGACCAGTGGAA
ACCTGAACTTCCAACAAAGAATGGTACGGGTCGCAGCTGAGCTTTACAGAGCCGGCCAGCTCACCCCTGCAGTCTTGAAG
GCTCTACAAGTTTATGAACGGGGTTGCCGCTGGTACCCCATTGTTGGACCTGTCCCTGGAGTGGCCGTTTTCGCCAATTC
CCTACATGTGAGTGATAAACCCTTCCCGGGAGCAACTCACGTGTTGACCAACCTGCCGCTCCCGCAGAGACCCAAGCCTG
AAGACTTTTGCCCCTTTGAGTGTGCTATGGCTACTGTCTATGACATTGGTCATGACGCCGTCATGTATGTGGCCGAAAGG
AAAGTCTCCTGGGCCCCTCGTGGCGGGGATGAAGTGAAATTTGAAGCTGTCCCCGGGGAGTTGAAGTTGATTGCGAACCG
GCTCCGCACCTCCTTCCCGCCCCACCACACAGTGGACATGTCTAAGTTCGCCTTCACAGCCCCTGGGTGTGGTGTTTCTA
TGCGGGTCGAACGCCAACACGGCTGCCTTCCCGCTGACACTGTCCCTGAAGGCAACTGCTGGTGGAGCTTGTTTGACTTG
CTTCCACTGGAAGTTCAGAACAAAGAAATTCGCCATGCTAACCAATTTGGCTACCAGACCAAGCATGGTGTCTCTGGCAA
GTACCTGCAGCGGAGGCTGCAAGTTAATGGTCTCCGAGCAGTAACTGACCTAAACGGACCTATCGTCGTACAGTACTTCT
CCGTTAAGGAGAGTTGGATCCGCCATTTGAAACTGGCGGGAGAACCCAGCTACTCTGGGTTTGAGGACCTCCTCAGAATA
AGGGTTGAGCCTAACACGTCGCCATTGGCTGACAAGGAAGAAAAAATTTTCCGGTTTGGCAGTCACAAGTGGTACGGCGC
TGGAAAGAGAGCAAGAAAAGCACGCTCTTGTGCGACTGCTACAGTCGCTGGCCGCGCTTTGTCCGTTCGTGAAACCCGGC
AGGCCAAGGAGCACGAGGTTGCCGGCGCCAACAAGGCTGAGCACCTCAAACACTACTCCCCGCCTGCCGAAGGGAATTGT
GGTTGGCACTGCATTTCCGCCATCGCCAACCGGATGGTGAATTCCAAATTTGAAACCACCCTTCCCGAAAGAGTGAGACC
TCCAGATGACTGGGCTACTGACGAGGATCTTGTGAATGCCATCCAAATCCTCAGACTCCCTGCGGCCTTAGACAGGAACG
GTGCTTGTACTAGCGCCAAGTACGTACTTAAGCTGGAAGGTGAGCATTGGACTGTCACTGTGACCCCTGGGATGTCCCCT
TCTTTGCTCCCTCTTGAATGTGTTCAGGGCTGTTGTGGGCACAAGGGCGGTCTTGGTTCCCCAGATGCAGTCGAGGTCTC
CGGATTTGACCCTGCCTGCCTTGACCGGCTGGCTGAGGTGATGCACCTGCCTAGCAGTGCTATCCCAGCCGCTCTGGCCG
AAATGTCTGGCGATTCCGATCGTTCGGCTTCTCCGGTCACCACCGTGTGGACTGTTTCGCAGTTCTTTGCCCGTCACAGC
GGAGGGAATCACCCTGACCAAGTGCGCTTAGGGAAAATTATCAGCCTTTGTCAGGTGATTGAGGACTGCTGCTGTTCCCA
GAACAAAACCAACCGGGTCACCCCGGAGGAGGTCGCAGCAAAGATTGACCTGTACCTCCGTGGTGCAACAAATCTTGAAG
AATGCTTGGCCAGGCTTGAGAAAGCGCGCCCGCCACGCGTAATCGACACCTCCTTTGATTGGGATGTTGTGCTCCCTGGG
GTTGAGGCGGCAACCCAGACGATCAAGCTGCCCCAGGTCAACCAGTGTCGTGCTCTGGTCCCTGTTGTGACTCAAAAGTC
CTTGGACAACAACTCGGTCCCCCTGACCGCCTTTTCACTGGCTAACTACTACTACCGTGCGCAAGGTGACGAAGTTCGTC
ACCGTGAAAGACTAACCGCCGTGCTCTCCAAGTTGGAAAAGGTTGTTCGAGAAGAATATGGGCTCATGCCAACCGAGCCT
GGTCCACGGCCCACACTGCCACGCGGGCTCGACGAACTCAAAGACCAGATGGAGGAGGACTTGCTGAAACTGGCTAACGC
CCAGACGACTTCGGACATGATGGCCTGGGCAGTCGAGCAGGTTGACCTAAAAACTTGGGTCAAGAACTACCCGCGGTGGA
CACCACCACCCCCTCCGCCAAAAGTTCAGCCTCGAAAAACGAAGCCTGTCAAGAGCTTGCCGGAGAGAAAGCCTGTCCCC
GCCCCGCGCAGGAAGGTTGGGTCCGATTGTGGCAGCCCGGTTTCATTAGGCGGCGATGTCCCTAACAGTTGGGAAGATTT
GGCTGTTAGTAGCCCCTTTGATCTCCCGACCCCACCTGAGCCGGCAACACCTTCAAGTGAGCTGGTGATTGTGTCCTCAC
CGCAATGCATCTTCAGGCCGGCGACACCCTTGAGTGAGCCGGCTCCAATTCCCGCACCTCGCGGAACTGTGTCTCGACCG
GTGACACCCTTGAGTGAGCCGATCCCTGTGCCCGCACCGCGGCGTAAGTTTCAGCAGGTGAAAAGATTGAGTTCGGCGGC
GGCAATCCCACCGTACCAGGACGAGCCCCTGGATTTGTCTGCTTCCTCACAGACTGAATATGAGGCCTCTCCCCCAGCAC
CGCCGCAGAGCGGGGGCGTTCTGGGAGTAGAGGGGCATGAAGCTGAGGAAACCCTGAGTGAAATCTCGGACATGTCGGGT
AACATTAAACCTGCGTCCGTGTCATCAAGCAGCTCCTTGTCCAGCGTGAGAATCACACGCCCAAAATACTCAGCTCAAGC
CATCATCGACTCGGGCGGGCCCTGCAGTGGGCATCTCCAAGAGGTAAAGGAAACATGCCTTAGTGTCATGCGCGAGGCAT
GTGATGCGACTAAGCTTGATGACCCTGCTACGCAGGAATGGCTTTCTCGCATGTGGGATCGGGTGGACATGCTGACTTGG
CGCAACACGTCTGTTTACCAGGCGATTTGCACCTTAGATGGCAGGTTAAAGTTCCTCCCAAAAATGATACTCGAGACACC
GCCGCCCTATCCGTGTGAGTTTGTGATGATGCCTCACACGCCTGCACCTTCCGTAGGTGCGGAGAGCGACCTTACCATTG
GCTCAGTTGCTACTGAAGATGTTCCACGCATCCTCGAGAAAATAGAAAATGTCGGCGAGATGGCCAACCAGGGACCCTTG
GCCTTCTCCGAGGATAAACCGGTAGATGACCAACTTGTCAACGACCCCGGATATCGTCGCGGAGGCCTGACGAGAGCAC
ATCAGCTCCGTCCGCAGGCACAGGTGGCGCCGGCTCTTTTACCGATTTGCCGCCTTCAGATGGCGCGGATGCGGACGGGG
GGGGCCGTTTCGGACGGTAAAAAGAAAAGCTGAAAGGCTCTTTGACCAACTGAGCCGTCAGGTTTTGACCTCGTCTCC
CATCTCCCTGTTTTCTTCTCACGCCTTTTCTACCCTGGCGGTGGTTATTCTCCGGGTGATTGGGTTTTGCAGCTTTTAC
TCTATTGTGCCTCTTTTTATGTTACAGTTACCCAGCCTTTGGTATTGCTCCCCTCTTGGGTGTGTTTCTGGGTCTTCTC
GGCGCGTTCGAATGGGGGTTTTTGGCTGCTGGTTGGCTTTTGCTGTTGGTCTGTTCAAGCCTGTGTCCGACCCAGTCGGC
GCTGCTTGTGAGTTTGACTCGCCAGAGTGTAGAAACATCCTTCATTCTTTTGAGCTTCTCAAACCTTGGGACCCTGTTCG
CAGCCTTGTTGTGGGCCCCGTCGGTCTCGGTCTTGCCATTCTTGGCAGGTTACTGGGCGGGCACGCTGCATCTGGCACT
TTTTGCTTAGGCTTGGCATTGTTGCAGACTGTATCTTGGCTGGAGCTTACGTGCTTTCTCAAGGTAGGTGTAAAAAGTGC
```

*Fig. 1A-2*

```
TGGGGATCTTGTATAAGAACTGCTCCCAATGAGGTCGCTTTTAACGTGTTTCCTTTCACACGTGCGACCAGGTCGTCACT
TATCGACCTGTGCGATCGGTTTTGTGCGCCAAAAGGAATGGACCCCATTTTTCTCGCCACTGGGTGGCGCGGGTGCTGGG
CCGGCCGAAGCCCCATTGAGCAACCCTCTGAAAAACCCATCGCGTTTGCCCAGTTGGATGAAAAGAAGATTACGGCTAGG
ACTGTGGTCGCCCAGCCTTATGACCCCAACCAAGCCGTAAAGTGCTTGCGGGTATTGCAGGCGGGTGGGGCGATGGTGGC
TAAGGCGGTCCCAAAAGTGGTCAAGGTTTCCGCTGTTCCATTCCGAGCCCCCTTCTTTCCCACTGGAGTGAAAGTTGACC
CTGATTGCAGGGTCGTGGTTGACCCTGACACTTTCACTGCAGCTCTCCGGTCTGGCTACTCCACCACAAACCTCGTCCTT
GGTGTGGGGACTTTGCCCAGCTGAATGGATTAAAAATCAGGCAAATTTCCAAGCCTTCAGGGGGAGGCCCACATCTCAT
GGCTGCCCTGCATGTTGCCTGCTCGATGGCTCTGCACATGCTTGCTGGGATTTATGTGACTGCGGTGGGTTCTTGCGGCA
CCGGCACCAACGACCCGTGGTGCGCTAACCCGTTTGCCGTCCCTGGCTACGGACCTGGCTCTCTCTGCACGTCCAGATTG
TGCATTTCCCAACACGGCCTTACCCTGCCCTTGACAGCACTTGTGGCGGGATTCGGTATTCAAGAAATTGCCTTGGTCGT
TTTGATTTTTGTTTCCATCGGAGGCATGGCTCATAGGTTGAGCTGTAAGGCTGACATGCTGTGTGTCTTGCTTGCAATTG
CCAGCTATGTTTGGGTACCTCTTACCTGGTTGCTTTGTGTGTTTCCTTGCTGGTTGCGCTGTTTTTCTTTGCACCCCCTC
ACCATCCTATGGTTGGTGTTTTTCTTGATTTCTGTGAATATGCCTTCAGGAATCTTGGCCATGGTGTTGTTGGTTTCTCT
TTGGCTTCTTGGTCGTTATACTAATGTTGCTGGCCTTGTCACCCCCTACGACATTCATCATTACACCAGTGGCCCCCGCG
GTGTTGCCGCCTTGGCTACCGCACCAGATGGGACCTACTTGGCCGCTGTCCGCCGCGCTGCGTTGACTGGCCGCACCATG
CTGTTTACCCCGTCCCAGCTTGGGTCTCTTCTTGAGGGTGCTTTCAGAACTCGAAAGCCCTCACTGAACACCGTCAATGT
GATCGGGTCCTCCATGGGCTCTGGCGGGGTGTTTACCATCGACGGGAAAGTCAAGTGCGTAACTGCCGCACATGTCCTTA
CGGGCAATTCAGCTCGGGTTTCCGGGGTCGGCTTCAATCAAATGCTTGACTTTGACGTAAAGGGAGATTTCGCTATAGCT
GATTGCCCGAATTGGCAAGGGGCTGCCCCCAAGACCCAATTCTGCACGGATGGATGGACTGGCCGTGCCTATTGGCTAAC
ATCCTCTGGCGTCGAACCCGGCGTCATTGGAAAAGGATTCGCCTTCTGCTTCACCGCATGTGGCGATTCCGGGTCCCAG
TGATCACCGAGGCCGGTGAGCTTGTCGGCGTTCACACGGGATCGAATAAACAAGGGGGGGGCATTGTTACGCGCCCCTCA
GGCCAGTTTTGTAATGTGGCACCCATCAAGCTAAGCGAATTAAGTGAATTCTTTGCTGGGCCTAAGGTCCCGCTCGGTGA
TGTGAAGGTCGGCAGCCACATAATTAAAGACATAAGCGAGGTGCCTTCAGATCTTTGTGCCTTGCTTGCTGCCAAACCTG
AACTGGAAGGAGGCCTCTCCACCGTCCAACTTCTTTGTGTGTTTTTTCTCCTGTGGAGAATGATGGGACATGCCTGGACG
CCCTTGGTTGCTGTGAGTTTCTTTATTTTGAATGAGGTTCTCCCAGCCGTCCTGGTCCGGAGTGTTTTCTCCTTTGGAAT
GTTTGTGCTATCCTGGCTCACGCCATGGTCTGCGCAAGTTCTGATGATCAGGCTTCTGACAGCAGCTCTTAACAGGAACA
GATGGTCACTTGCCTTTTTCAGCCTCGGTGCAGTGACCGGTTTTGTCGCAGATCTTGCGGCCACTCAGGGGCATCCGTTG
CAGGCAGTGATGAATTTGAGCACCTATGCATTCCTGCCTCGGATGATGGTTGTGACCTCACCAGTCCCAGTGATCACGTG
TGGTGTCGTGCACCTACTTGCCATCATTTTGTACTTGTTTAAGTACCGTGGCCTGCACCATATCCTTGTTGGCGATGGAG
TGTTCTCTGCGGCTTTCTTCTTGAGATACTTTGCCGAGGGAAAGTTGAGGGAAGGGGTGTCGCAATCCTGCGGAATGAAT
CATGAGTCTCTGACTGGTGCCCTCGCTATGAGACTCAATGACGAGGACTTGGATTTCCTTATGAAATGGACTGATTTTAA
GTGCTTTGTTTCTGCGTCCAACATGAGGAATGCAGCGGGTCAATTTATCGAGGCTGCCTATGCTAAAGCACTTAGAGTAG
AACTGGCCCAGTTGGTGCAGGTTGATAAAGTTCGAGGTACTTTGGCCAAACTTGAAGCTTTTGCTGATACCGTGGCACCT
CAACTCTCGCCCGGTGACATTGTTGTCGCTCTCGGCCACACGCCTGTTGGCAGTATCTTCGACCTAAAGGTTGGTAGCAC
CAAGCATACCCTCCAAGCCATTGAGACCAGAGTCCTTGCTGGGTCCAAAATGACCGTGGCGCGCGTCGTCGACCCGACCC
CCACGCCCCACCCGCACCCGTGCCCATCCCCCTCCCACCGAAAGTTCTGGAGAATGGCCCCAACGCTTGGGGGGATGAG
GACCGTTTGAATAAGAAGAAGAGGCGCAGGATGGAGCCCTCGGCCATCTATGTTATGGGCGGGAAAAAATACCAGAAATT
TTGGGACAAGAATTCCGGTGATGTGTTTTATGAGGAGGTCCATAATAACACAGATGAGTGGGAGTGTCTCAGAGTTGGCG
ACCCTGCCGACTTTGACCCTGAGAAGGGAACTCTGTGTGGACATGTCACCATTGAAAACAAGGCTTACCATGTTTACACC
TCCCCATCTGGTAAGAAGTTCTTGGTCCCCGTCAACCCAGAGAATGGAAGAGTCCAATGGGAAGCTGCAAAGCTTTCCGT
GGAGCAGGCCCTAGGTATGATGAATGTCGACGGCGAACTGACTGCCAAAGAACTGGAGAAACTGAAAAGAATAATTGACA
AACTCCAGGGCCTGACTAAGGAGCAGTGTTTAAACTGCTAGCCGCCAGCGACTTGACCCGCTGTGGTCGCGGCGGCTTGG
TTGTTACTGAAACAGCGGTAAAAATAGTCAAATTTCACAACCGGACCTTCACCCTGGGACCTGTGAATTTAAAAGTGGCC
AGTGAGGTTGAGCTAAAAGACGCGGTTGAGCACAACCAACACCCGGTTGCGAGACCGATCGATGGTGGAGTTGTGCTCCT
GCGTTCCGCGGTTCCTTCGCTTATAGACGTCTTGATCTCCGGTGCTGATGCATCTCCCAAGTTACTTGCCCATCACGGGC
CGGGAAACACTGGGATCGATGGCACGCTCTGGGATTTTGAGTCCGAAGCCACTAAAGAGGAAGTCGCACTCAGTGCGCAA
ATAATACAGGCTTGTGACATTAGGCGCGGCGACGCTCCTGAAATTGGTCTCCCTTACAAGCGTGTACCCTGTTAGGGGTAA
CCCTGAGCGGGTGAAAGGAGTTCTGCAGAATCAAGCTGTTGGAGACATACCTTACAAAACCCCCAGTGACACTGGAAGCC
CAGTGCACGCGGCTGCCTGCCTTACGCCCAACGCCACTCCGGTGACTGATGGGCGCTCCGTCTTGGCCACGACCATGCCC
CCCGGGTTTGAGTTATATGTACCGACCATACCAGCGTCTGTCCTTGATTACCTTGACTCTAGGCCTGACTGCCCTAAACA
GCTGACAGAGCACGGCTGCGAAGATGCCGCACTGAAAGACCTCTAAATATGACTTGTCCACCCAAGGCTTTGTTTTAC
CTGGAGTTCTTCGCCTTGTGCGGAAATACCTGTTTGCCCATGTAGGTAAGTGCCCACCCGTTCATCGGCCTTCTACTTAC
CCTGCTAAGAATTCTATGGCTGGAATAAATGGGAACAGGTTCCCAACCAAGGACATTCAGAGCGTCCCTGAAATCGACGT
TCTGTGCGCACAGGCTGTGCGAGAAAACTGGCAAACTGTCACCCCTTGTACTCTTAAGAAACAGTATTGCGGGAAGAAGA
AGACTAGGACCATACTCGGCACCAATAACTTCATCGCACTAGCCCACCGAGCAGTGTTGAGTGGTGTTACCCAGGGCTTC
ATGAAAAAGGCGTTTAACTCGCCCATCGCCCTCGGAAAGAACAAGTTTAAGGAGCTACAGACTCGGTCCTGGGCAGGTG
CCTTGAAGCTGATCTCGCATCCTGCGATCGATCCACGCCTGCAATTGTCCGCTGGTTTGCCGCCAACCTTCTTTATGAAC
TTGCCTGTGCTGAAGAGCATCTACCGTCGTACGTGCTGAACTGCTGCCACGACTTACTGGTCACGCAGTCCGGCGCAGTG
```

Fig. 1A-3

```
ACTAAGAGAGGTGGCCTGTCGTCTGGCGACCCGATCACCTCTGTGTCTAACACCATTTATAGTTTGGTGATCTATGCACA
GCATATGGTGCTTAGTTACTTCAAAAGTGGTCACCCCCATGGCCTTCTGTTCTTACAAGACCAGCTAAAGTTTGAGGACA
TGCTCAAGGTTCAACCCCTGATCGTCTATTCGGACGACCTCGTGCTGTATGCCGAGTCTCCCACCATGCCAAACTATCAC
TGGTGGGTTGAACATCTGAATTTGATGCTGGGGTTTCAGACGGACCCAAAGAAGACAGCAATAACAGACTCGCCATCATT
TCTAGGCTGTAGAATAATAAATGGGCGCCAGCTAGTCCCCAACCGTGACAGGATCCTCGCGGCCCTCGCCTATCACATGA
AGGCGAGTAATGTTTCTGAATACTATGCCTCAGCGGCTGCAATACTCATGGACAGCTGTGCTTGTTTGGAGTATGATCCT
GAATGGTTTGAAGAACTTGTAGTTGGAATAGCGCAGTGCGCCCGCAAGGACGGCTACAGCTTTCCCGGCACGCCGTTCTT
CATGTCCATGTGGGAAAAACTCAGGTCCAATTATGAGGGGAAGAAGTCGAGAGTGTGCGGGTACTGCGGGGCCCCGGCCC
CGTACGCTACTGCCTGTGGCCTCGACGTCTGCATTTACCACACCCACTTCCACCAGCATTGTCCAGTCACAATCTGGTGT
GGCCATCCAGCGGGTTCTGGTTCTTGTAGTGAGTGCAAATCCCCTGTAGGGAAAGGCACAAGCCCTTTAGACGAGGTGCT
GGAACAAGTCCCGTATAAGCCCCCACGGACCGTTATCATGCATGTGGAGCAGGGTCTCACCCCCCTTGATCCAGGTAGAT
ACCAAACTCGCCGCGGATTAGTCTCTGTCAGGCGTGGAATTAGGGGAAATGAAGTTGGACTACCAGACGGTGATTATGCT
AGCACCGCCTTGCTCCCTACCTGCAAAGAGATCAACATGGTCGCTGTCGCTTCCAATGTATTGCGCAGCAGGTTCATCAT
CGGCCCACCCGGTGCTGGGAAAACATACTGGCTCCTTCAACAGGTCCAGGATGGTGATGTTATTTACACACCAACTCACC
AGACCATGCTTGACATGATTAGGGCTTTGGGGACGTGCCGGTTCAACGTCCCGGCAGGCACAACGCTGCAATTCCCCGTC
CCCTCCCGCACCGGTCCGTGGGTTCGCATCCTAGCCGGCGGTTGGTGTCCTGGCAAGAATTCCTTCCTAGATGAAGCAGC
GTATTGCAATCACCTTGATGTTTTGAGGCTTCTTAGTAAAACTACCCTCACCTGTCTAGGAGACTTCAAGCAACTCCACC
CAGTGGGTTTTGATTCTCATTGCTATGTTTTGACATCATGCCTCAAACTCAACTGAAGACCATCTGGAGGTTTGGACAG
AATATCTGTGATGCCATTCAGCCAGATTACAGGGACAACATCATGTCCATGGTCAACACAACCCGTGTGACCTACGTGGA
AAAACCTGTCAGGTATGGGCAGGTCCTCACCCCCTACCACAGGGACCGAGAGGACGACGCCATCACTATTGACTCCAGTC
AAGGCGCCACATTCGATGTGGTTACATTGCATTTGCCCACTAAAGATTCACTCAACAGGCAAAGAGCCCTTGTTGCTATC
ACCAGGGCAAGACACGCTATCTTTGTGTATGACCCACACAGGCAGCTGCAGGGCTTGTTTGATCTTCCTGCAAAAGGCAC
GCCCGTCAACCTCGCAGTGCACTGCGACGGGCAGCTGATCGTGCTGGATAGAAATAACAAAGAATGCACGGTTGCTCAGG
CTCTAGGCAACGGGGATAAATTTAGGGCCACAGACAAGCGTGTTGTAGATTCTCTCCGCGCCATTTGTGCTGATCTAGAA
GGGTCGAGCTCTCCGCTCCCCAAGGTCGCACACAACTTGGGATTTTATTTCTCACCTGATTTAACACAGTTTGCTAAACT
CCCAGTAGAACTTGCACCTCACTGGCCCGTGGTGTCAACCCAGAACAATGAAAAGTGGCCGGATCGGCTGGTTGCCAGCC
TTCGCCCTATCCATAAATACAGCCGCGCGTGCATCGGTGCCGGCTATATGGTGGGCCCTTCGGTGTTTCTAGGCACTCCT
GGGGTCGTGTCATACTATCTCACAAAATTTGTTAAGGGCGGGGCTCAAGTGCTTCCGGAGACGGTTTTCAGCACCGGCCG
AATTGAGGTAGACTGCCGGGAATATCTTGATGATCGGGAGCGAGAAGTTGCTGCGTCCCTCCCACACGCTTTCATTGGCG
ACGTCAAAGGCACTACCGTTGGAGGATGTCATCATGTCACCTCCAGATACCTCCCGCGCGTCCTTCCCAAGGAATCAGTT
GCGGTAGTCGGGGTTTCAAGCCCCGGAAAAGCCGCGAAAGCATTGTGCACACTGACAGATGTGTACCTCCCAGATCTTGA
AGCCTATCTCCACCCGGAGACCCAGTCCAAGTGCTGGAAAATGATGTTGGACTTCAAAGAAGTTCGACTAATGGTCTGGA
AAGACAAAACAGCCTATTTCCAACTTGAAGGTCGCTATTTCACCTGGTATCAGCTTGCCAGCTATGCCTCGTACATCCGT
GTTCCCGTCAACTCTACGGTGTACTTGGACCCCTGCATGGGCCCCGCCCTTTGCAACAGGAGAGTCGTCGGGTCCACCCA
CTGGGGGGCTGACCTCGCGGTCACCCCTTATGATTACGGCGCTAAAATTATCCTGTCTAGCGCGTACCATGGTGAAATGC
CCCCCGGATACAAAATTCTGGCGTGCGCGGAGTTCTCGTTGGATGACCCAGTTAAGTACAAACATACCTGGGGGTTTGAA
TCGGATACAGCGTATCTGTATGAGTTCACCGGAAACGGTGAGGACTGGGAGGATTACAATGATGCGTTTCGTGCGCGCCA
GGAAGGGAAAATTTATAAGGCCACTGCCACCAGCTTGAAGTTTTATTTTCCCCCGGGCCCTGTCATTGAACCAACTTTAG
GCCTGAATTGAAATGAAATGGGGTCCATGCAAAGCCTTTTTGACAAAATTGGCCAACTTTTTGTGGATGCTTTCACGGAG
TTCTTGGTGTCCATTGTTGATATCATTATATTTTTGGCCATTTTGTTTGGCTTCACCATCGCCGGTTGGCTGGTGGTCTT
TTGCATCAGATTGGTTTGCTCCGCGATACTCCGTACGCGCCCTGCCATTCACTCTGAGCAATTACAGAAGATCTTATGAG
GCCTTTCTTTCCCAGTGCCAAGTGGACATTCCCACCTGGGGAACTAAACATCCTTTGGGGATGCTTTGGCACCATAAGGT
GTCAACCCTGATTGATGAAATGGTGTCGCGTCGAATGTACCGCATCATGGAAAAGCAGGGCAGGCTGCCTGGAAACAGG
TGGTGAGCGAGGCTACGCTGTCTCGCATTAGTAGTTTGGATGTGGTGGCTCATTTTCAGCATCTAGCCGCCATTGAAGCC
GAGACCTGTAAATATTTGGCCTCCCGGCTGCCCATGCTACACAACCTGCGCATGACAGGGTCAAATGTAACCATAGTGTA
TAATAGCACTTTGAATCAGGTGTTTGCTATTTTTCCAACCCCTGGTTCCCGGCCAAAGCTTCATGATTTTCAGCAATGGT
TAATAGCTGTACATTCCTCCATATTTTCCTCTGTTGCAGCTTCTTGTACTCTTTTTGTTGTGCTGTGGTTGCGGGTTCCA
ATACTACGTACTGTTTTTGGTTTCCGCTGGTTAGGGGCAATTTTTCTTTCGAACTCACAGTGAATTACACGGTGTGTCCA
CCTTGCCTCACCCGGCAAGCAGCCACAGAGATCTACGAACCCGGTAGGTCTCTTTGGTGCAGGATAGGGTATGACCGATG
TGGGGAGGACGATCATGACGAGCTAGGGTTTATGATACCGCCTGGCCTCTCCAGCGAAGGCCACTTGACTGGTGTTTACG
CCTGGTTGGCGTTCTTGTCCTTCAGCTACACGGCCCAGTTCATCCCGAGATATTCGGGATAGGGAATGTGAGTCGAGTT
TATGTTGACATCAAACATCAACTCATCTGCGCCGAACATGACGGGCAGAACACCACCTTGCCTCGTCATGACAACATTTC
AGCCGTGTTTCAGACCTATTACCAACATCAAGTCGACGGCGGCAATTGGTTTCACCTAGAATGGCTTCGTCCCTTCTTTT
CCTCGTGGTTGGTTTAAATGTCTCTTGGTTTCTCAGGCGTTCGCCTGCAAACCATGTTTCAGTTCGAGTCTTGCAGATA
TTAAGACCAACACCACCGCAGCGGCAAGCTTTGCTGTCCTCCAAGACATCAGTTGCCTTAGGCATCGCGACTCGGCCTCT
GAGGCGATTCGCAAAATCCCTCAGTGCCGTACGGCGATAGGGACACCCGTGTATGTTACCATCACAGCCAATGTGACAGA
TGAGAATTATTTACATTCTTCTGATCTCCTCATGCTTTCTTCTTGCCTTTTCTATGCTTCTGAGATGAGTGAAAGGGAT
TTAAGGTGGTATTTGGCAATGTGTCAGGCATCGTGGCTGTGTGTGTCAATTTTACCAGCTACGTCCAACATGTCAAGGAG
```

Fig. 1A-4

```
TTTACCCAACGCTCCCTGGTGGTCGACCATGTGCGGTTGCTCCATTTCATGACACCTGAGACCATGAGGTGGGCAACTGT
TTTAGCCTGTCTTTTTGCCATTCTGTTGGCAATTTGAATGTTTAAGTATGTTGGAGAAATGCTTGACCGCGGGCTGTTGC
TCGCGATTGCTTTCTTTGTGGTGTATCGTGCCGTTCTGTTTTGCTGTGCTCGCCAACGCCAGCAACGACAGCAGCTCCCA
TCTACAGCTGATTTACAACTTGACGCTATGTGAGCTGAATGGCACAGATTGGCTAGCTAACAAATTTGATTGGGCAGTGG
AGAGTTTTGTCATCTTTCCCGTTTTGACTCACATTGTCTCCTATGGTGCCCTCACTACCAGCCATTTCCTTGACACAGTC
GCTTTAGTCACTGTGTCTACCGCCGGGTTTGTTCACGGGCGGTATGTCCTAAGTAGCATCTACGCGGTCTGTGCCCTGGC
TGCGTTGACTTGCTTCGTCATTAGGTTTGCAAAGAATTGCATGTCCTGGCGCTACGCGTGTACCAGATATACCAACTTTC
TTCTGGACACTAAGGGCAGACTCTATCGTTGGCGGTCGCCTGTCATCATAGAGAAAAGGGGCAAAGTTGAGGTCGAAGGT
CATCTGATCGACCTCAAAAGAGTTGTGCTTGATGGCTCCGTGGCAACCCCTATAACCAGAGTTTCAGCGGAACAATGGGG
TCGTCCTTAGATGACTTCTGTCACGATAGCACGGCTCCACAAAAGGTGCTTTTGGCGTTTTCTATTACCTACACGCCAGT
GATGATATATGCCCTAAAGGTGAGTCGCGGCCGACTGCTAGGGCTTCTGCACCTTTTGATCTTCCTGAATTGTGCTTTCA
CCTTCGGGTACATGACTTTCGCGCACTTTCAGAGTACAAATAAGGTCGCGCTCACTATGGGAGCAGTAGTTGCACTCCTT
TGGGGGGTGTACTCAGCCATAGAAACCTGGAAATTCATCACCTCCAGATGCCGTTTGTGCTTGCTAGGCCGCAAGTACAT
TCTGGCCCCTGCCCACCACGTTGAAAGTGCCGCAGGCTTTCATCCGATTGCGGCAAATGATAACCACGCATTTGTCGTCC
GGCGTCCCGGCTCCACTACGGTCAACGGCACATTGGTGCCCGGGTTAAAAAGCCTCGTGTTGGGTGGCAGAAAAGCTGTT
AAACAGGGAGTGGTAAACCTTGTCAAATATGCCAAATAACAACGGCAAGCAGCAGAAGAGAAAGAAGGGGGATGGCCAGC
CAGTCAATCAGCTGTGCCAGATGCTGGGTAAGATCATCGCTCAGCAAAACCAGTCCAGAGGCAAGGGACCGGGAAAGAAA
AATAAGAAGAAAAACCCGGAGAAGCCCCATTTTCCTCTAGCGACTGAAGATGATGTCAGACATCACTTTACCCCTAGTGA
GCGGCAATTGTGTCTGTCGTCAATCCAGACCGCCTTTAATCAAGGCGCTGGGACTTGCACCCTGTCAGATTCAGGGAGGA
TAAGTTACACTGTGGAGTTTAGTTTGCCTACGCATCATACTGTGCGCCTGATCCGCGTCACAGCATCACCCTCAGCATGA
TGGGCTGGCATTCTTGAGGCATCTCAGTGTTTGAATTGGAAGAATGTGTGGTGAATGGCACTGATTGACATTGTGCCTCT
AAGTCACCTATTCAATTAGGGCGACCGTGTGGGGGTGAGATTTAATTGGCGAGAACCATGCGGCCGAAATTAAAAAAAA
```

Fig. 1B-1

```
>VR-V5.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCCAGCACCGCCGCAGAGCGGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGAATCACACGCCCAAAATACTCAGCTCAAGCCATCATCGACTCGGGCGGGC
CCTGCAGTGGGCATCTCCAAGAGGTAAAGGAAACATGCCTTAGTGTCATGCGCGAGGCATGTGATGCGACTAAGCTTGAT
GACCCTGCTACGCAGGAATGGCTTTCTCGCATGTGGGATCGGGTGGACATGCTGACTTGGCGCAACACGTCTGTTTACCA
GGCGATTTGCACCTTAGATGGCAGGTTAAAGTTCCTCCCAAAAATGATACTCGAGACACCGCCGCCCTATCCGTGTGAGT
TTGTGATGATGCCTCACACGCCTGCACCTTCCGTAGGTGCGGAGAGCGACCTTACCATTGGCTCAGTTGCTACTGAAGAT
GTTCCACGCATCCTCGAGAAAATAGAAAATGTCGGCGAGATGGCCAACCAGGGACCCTTGGCCTTCTCCGAGGATAAACC
GGTAGATGACCAACTTGTCAACGACCCCCGGATATCGTCGCGGAGGCCTGACGAGAGCACATCAGCTCCGTCCGCAGGCA
```

Fig. 1B-2

```
CAGGTGGCGCCGGCTCTTTTACCGATTTGCCGCCTTCAGATGGCGCGGATGCGGACGGGGGGGGGCCGTTTCGGACGGTA
AAAAGAAAAGCTGAAAGGCTCTTTGACCAACTGAGCCGTCAGGTTTTTGACCTCGTCTCCCATCTCCCTGTTTTCTTCTC
ACGCCTTTTCTACCCTGGCGGTGGTTATTCTCCGGGTGATTGGGGTTTTGCAGCTTTTACTCTATTGTGCCTCTTTTTAT
GTTACAGTTACCCAGCCTTTGGTATTGCTCCCCTCTTGGGTGTGTTTTCTGGGTCTTCTCGGCGCGTTCGAATGGGGGTT
TTTGGCTGCTGGTTGGCTTTTGCTGTTGGTCTGTTCAAGCCTGTGTCCGACCCAGTCGGCGCTGCTTGTGAGTTTGACTC
GCCAGAGTGTAGAAACATCCTTCATTCTTTTGAGCTTCTCAAACCTTGGGACCCTGTTCGCAGCCTTGTTGTGGGCCCCG
TCGGTCTCGGTCTTGCCATTCTTGGCAGGTTACTGGGCGGGGCACGCTGCATCTGGCACTTTTTGCTTAGGCTTGGCATT
GTTGCAGACTGTATCTTGGCTGGAGCTTACGTGCTTTCTCAAGGTAGGTGTAAAAAGTGCTGGGGATCTTGTATAAGAAC
TGCTCCCAATGAGGTCGCTTTTAACGTGTTTCCTTTCACACGTGCGACCAGGTCGTCACTTATCGACCTGTGCGATCGGT
TTTGTGCGCCAAAAGGAATGGACCCCATTTTTCTCGCCACTGGGTGGCGCGGGTGCTGGGCCGGCCGAAGCCCCATTGAG
CAACCCTCTGAAAAACCCATCGCGTTTGCCCAGTTGGATGAAAAGAAGATTACGGCTAGGACTGTGGTCGCCCAGCCTTA
TGACCCCAACCAAGCCGTAAAGTGCTTGCGGGTATTGCAGGCGGGTGGGGCGATGGTGGCTAAGGCGGTCCCAAAAGTGG
TCAAGGTTTCCGCTGTTCCATTCCGAGCCCCCTTCTTTCCCACTGGAGTGAAAGTTGACCCTGATTGCAGGGTCGTGGTT
GACCCTGACACTTTCACTGCAGCTCTCCGGTCTGGCTACTCCACCACAAACCTCGTCCTTGGTGTGGGGGACTTTGCCCA
GCTGAATGGATTAAAAATCAGGCAAATTTCCAAGCCTTCAGGGGGAGGCCCACATCTCATGGCTGCCCTGCATGTTGCCT
GCTCGATGGCTCTGCACATGCTTGCTGGGATTTATGTGACTGCGGTGGGTTCTTGCGGCACCGGCACCAACGACCCGTGG
TGCGCTAACCCGTTTGCCGTCCCTGGCTACGGACCTGGCTCTCTCTGCACGTCCAGATTGTGCATTTCCCAACACGGCCT
TACCCTGCCCTTGACAGCACTTGTGGCGGGATTCGGTATTCAAGAAATTGCCTTGGTCGTTTTGATTTTTGTTTCCATCG
GAGGCATGGCTCATAGGTTGAGCTGTAAGGCTGACATGCTGTGTGTCTTGCTTGCAATTGCCAGCTATGTTTGGGTACCT
CTTACCTGGTTGCTTTGTGTGTTTCCTTGCTGGTTGCGCTGTTTTTCTTTGCACCCCCTCACCATCCTATGGTTGGTGTT
TTTCTTGATTTCTGTGAATATGCCTTCAGGAATCTTGGCCATGGTGTTGTTGGTTTCTCTTTGGCTTCTTGGTCGTTATA
CTAATGTTGCTGGCCTTGTCACCCCCTACGACATTCATCATTACACCAGTGGCCCCCGCGGTGTTGCCGCCTTGGCTACC
GCACCAGATGGGACCTACTTGGCCGCTGTCCGCCGCGCTGCGTTGACTGGCCGCACCATGCTGTTTACCCCGTCCCAGCT
TGGGTCTCTTCTTGAGGGTGCTTTCAGAACTCGAAAGCCCTCACTGAACACCGTCAATGTGATCGGGTCCTCCATGGGCT
CTGGCGGGGTGTTTACCATCGACGGGAAAGTCAAGTGCGTAACTGCCGCACATGTCCTTACGGGCAATTCAGCTCGGGTT
TCCGGGGTCGGCTTCAATCAAATGCTTGACTTTGACGTAAAGGGAGATTTCGCTATAGCTGATTGCCCGAATTGGCAAGG
GGCTGCCCCAAGACCCAATTCTGCACGGATGGATGGACTGGCCGTGCCTATTGGCTAACATCCTCTGGCGTCGAACCCG
GCGTCATTGGAAAAGGATTCGCCTTCTGCTTCACCGCATGTGGCGATTCCGGGTCCCAGTGATCACCGAGGCCGGTGAG
CTTGTCGGCGTTCACACGGGATCGAATAAACAAGGGGGGGGCATTGTTACGCGCCCCTCAGGCCAGTTTTGTAATGTGGC
ACCCATCAAGCTAAGCGAATTAAGTGAATTCTTTGCTGGGCCTAAGGTCCCGCTCGGTGATGTGAAGGTCGGCAGCCACA
TAATTAAAGACATAAGCGAGGTGCCTTCAGATCTTTGTGCCTTGCTTGCTGCCAAACCTGAACTGGAAGGAGGCCTCTCC
ACCGTCCAACTTCTTTGTGTGTTTTTCTCCTGTGGAGAATGATGGGACATGCCTGGACGCCCTTGGTTGCTGTGAGTTT
CTTTATTTTGAATGAGGTTCTCCCAGCCGTCCTGGTCCGGAGTGTTTTCTCCTTTGGAATGTTTGTGCTATCCTGGCTCA
CGCCATGGTCTGCGCAAGTTCTGATGATCAGGCTTCTGACAGCAGCTCTTAACAGGAACAGATGGTCACTTGCCTTTTTC
AGCCTCGGTGCAGTGACCGGTTTTGTCGCAGATCTTGCGGCCACTCAGGGGCATCCGTTGCAGGCAGTGATGAATTTGAG
CACCTATGCATTCCTGCCTCGGATGATGGTTGTGACCTCACCAGTCCCAGTGATCACGTGTGGTGTCGTGCACCTACTTG
CCATCATTTTGTACTTGTTTAAGTACCGTGGCCTGCACCATATCCTTGTTGGCGATGGAGTGTTCTCTGCGGCTTTCTTC
TTGAGATACTTTGCCGAGGGAAAGTTGAGGGAAGGGGTGTCGCAATCCTGCGGAATGAATCATGAGTCTCTGACTGGTGC
CCTCGCTATGAGACTCAATGACGAGGACTTGGATTTCCTTATGAAATGGACTGATTTTAAGTGCTTTGTTTCTGCGTCCA
ACATGAGGAATGCAGCGGGTCAATTTATCGAGGCTGCCTATGCTAAAGCACTTAGAGTAGAACTGGCCCAGTTGGTGCAG
GTTGATAAAGTTCGAGGTACTTTGGCCAAACTTGAAGCTTTTGCTGATACCGTGGCACCTCAACTCTCGCCCGGTGACAT
TGTTGTCGCTCTCGGCCACACGCCTGTTGGCAGTATCTTCGACCTAAAGGTTGGTAGCACCAAGCATACCCTCCAAGCCA
TTGAGACCAGAGTCCTTGCTGGGTCCAAAATGACCGTGGCGCGCGTCGTCGACCCGACCCCCACGCCCCCACCCGCACCC
GTGCCCATCCCCCTCCCACCGAAAGTTCTGGAGAATGGCCCCAACGCTTGGGGGGATGAGGACCGTTTGAATAAGAAGAA
GAGGCGCAGGATGGAAGCCCTCGGCATCTATGTTATGGGCGGGAAAAAATACCAGAAATTTTGGGACAAGAATTCCGGTG
ATGTGTTTTATGAGGAGGTCCATAATAACACAGATGAGTGGGAGTGTCTCAGAGTTGGCGACCCTGCCGACTTTGACCCT
GAGAAGGGAACTCTGTGTGGACATGTCACCATTGGAAACAAGGCTTACCATGTTTACACCTCCCCATCTGGTAAGAAGTT
CTTGGTCCCCGTCAACCCAGAGAATGGAAGAGTCCAATGGGAAGCTGCAAAGCTTTCCGTGGAGCAGGCCCTAGGTATGA
```

Fig. 1B-3

```
TGAATGTCGACGGCGAACTGACTGCCAAAGAACTGGAGAAACTGAAAAGAATAATTGACAAACTCCAGGGCCTGACTAAG
GAGCAGTGTTTAAACTGCTAGCCGCCAGCGACTTGACCCGCTGTGGTCGCGGCGGCTTGGTTGTTACTGAAACAGCGGTA
AAAATAGTCAAATTTCACAACCGGACCTTCACCCTGGGACCTGTGAATTTAAAAGTGGCCAGTGAGGTTGAGCTAAAAGA
CGCGGTTGAGCACAACCAACACCCGGTTGCGAGACCGATCGATGGTGGAGTTGTGCTCCTGCGTTCCGCGGTTCCTTCGC
TTATAGACGTCTTGATCTCCGGTGCTGATGCATCTCCCAAGTTACTTGCCCATCACGGGCCGGGAAACACTGGGATCGAT
GGCACGCTCTGGGATTTTGAGTCCGAAGCCACTAAAGAGGAAGTCGCACTCAGTGCGCAAATAATACAGGCTTGTGACAT
TAGGCGCGGCGACGCTCCTGAAATTGGTCTCCCTTACAAGCTGTACCCTGTTAGGGGTAACCCTGAGCGGGTGAAAGGAG
TTCTGCAGAATACAAGGTTTGGAGACATACCTTACAAAACCCCAGTGACACTGGAAGCCCAGTGCACGCGGCTGCCTGC
CTTACGCCCAACGCCACTCCGGTGACTGATGGGCGCTCCGTCTTGGCCACGACCATGCCCCCCGGGTTTGAGTTATATGT
ACCGACCATACCAGCGTCTGTCCTTGATTACCTTGACTCTAGGCCTGACTGCCCTAAACAGCTGACAGAGCACGGCTGCG
AAGATGCCGCACTGAAAGACCTCTCTAAATATGACTTGTCCACCCAAGGCTTTGTTTTACCTGGAGTTCTTCGCCTTGTG
CGGAAATACCTGTTTGCCCATGTAGGTAAGTGCCCACCCGTTCATCGGCCTTCTACTTACCCTGCTAAGAATTCTATGGC
TGGAATAAATGGGAACAGGTTCCCAACCAAGGACATTCAGAGCGTCCCTGAAATCGACGTTCTGTGCGCACAGGCTGTGC
GAGAAAACTGGCAAACTGTCACCCCTTGTACTCTTAAGAAACAGTATTGCGGGAAGAAGAAGACTAGGACCATACTCGGC
ACCAATAACTTCATCGCACTAGCCCACCGAGCAGTGTTGAGTGGTGTTACCCAGGGCTTCATGAAAAAGGCGTTTAACTC
GCCCATCGCCCTCGGAAAGAACAAGTTTAAGGAGCTACAGACTCCGGTCCTGGGCAGGTGCCTTGAAGCTGATCTCGCAT
CCTGCGATCGATCCACGCCTGCAATTGTCCGCTGGTTTGCCGCCAACCTTCTTTATGAACTTGCCTGTGCTGAAGAGCAT
CTACCGTCGTACGTGCTGAACTGCTGCCACGACTTACTGGTCACGCAGTCCGGCGCAGTGACTAAGAGAGGTGGCCTGTC
GTCTGGCGACCCGATCACCTCTGTGTCTAACACCATTTATAGTTTGGTGATCTATGCACAGCATATGGTGCTTAGTTACT
TCAAAAGTGGTCACCCCCATGGCCTTCTGTTCTTACAAGACCAGCTAAAGTTTGAGGACATGCTCAAGGTTCAACCCCTG
ATCGTCTATTCGGACGACCTCGTGCTGTATGCCGAGTCTCCCACCATGCCAAACTATCACTGGTGGGTTGAACATCTGAA
TTTGATGCTGGGGTTTCAGACGGACCCAAAGAAGACAGCAATAACAGACTCGCCATCATTTCTAGGCTGTAGAATAATAA
ATGGGCGCCAGCTAGTCCCCAACCGTGACAGGATCCTCGCGGCCCTCGCCTATCACATGAAGGCGAGTAATGTTTCTGAA
TACTATGCCTCAGCGGCTGCAATACTCATGGACAGCTGTGCTTGTTTGGAGTATGATCCTGAATGGTTTGAAGAACTTGT
AGTTGGAATAGCGCAGTGCGCCCGCAAGGACGGCTACAGCTTTCCCGGCACGCCGTTCTTCATGTCCATGTGGGAAAAAC
TCAGGTCCAATTATGAGGGGAAGAAGTCGAGAGTGTGCGGGTACTGCGGGGCCCCGGCCCCGTACGCTACTGCCTGTGGC
CTCGACGTCTGCATTTACCACACCCACTTCCACCAGCATTGTCCAGTCACAATCTGGTGTGGCCATCCAGCGGGTTCTGG
TTCTTGTAGTGAGTGCAAATCCCCTGTAGGGAAAGGCACAAGCCCTTTAGACGAGGTGCTGGAACAAGTCCCGTATAAGC
CCCCACGGACCGTTATCATGCATGTGGAGCAGGGTCTCACCCCCCTTGATCCAGGTAGATACCAAACTCGCCGCGGATTA
GTCTCTGTCAGGCGTGGAATTAGGGGAAATGAAGTTGGACTACCAGACGGTGATTATGCTAGCACCGCCTTGCTCCCTAC
CTGCAAAGAGATCAACATGGTCGCTGTCGCTTCCAATGTATTGCGCAGCAGGTTCATCATCGGCCCACCCGGTGCTGGGA
AAACATACTGGCTCCTTCAACAGGTCCAGGATGGTGATGTTATTTACACACCAACTCACCAGACCATGCTTGACATGATT
AGGGCTTTGGGGACGTGCCGGTTCAACGTCCCGGCAGGCACAACGCTGCAATTCCCCGTCCCCTCCCGCACCGGTCCGTG
GGTTCGCATCCTAGCCGGCGGTTGGTGTCCTGGCAAGAATTCCTTCCTAGATGAAGCAGCGTATTGCAATCACCTTGATG
TTTTGAGGCTTCTTAGTAAAACTACCCTCACCTGTCTAGGAGACTTCAAGCAACTCCACCCAGTGGGTTTTGATTCTCAT
TGCTATGTTTTTGACATCATGCCTCAAACTCAACTGAAGACCATCTGGAGGTTTGGACAGAATATCTGTGATGCCATTCA
GCCAGATTACAGGGACAAACTCATGTCCATGGTCAACACAACCCGTGTGACCTACGTGGAAAAACCTGTCAGGTATGGGC
AGGTCCTCACCCCCTACCACAGGGACCGAGAGGACGACGCCATCACTATTGACTCCAGTCAAGGCGCCACATTCGATGTG
GTTACATTGCATTTGCCCACTAAAGATTCACTCAACAGGCAAAGAGCCCTTGTTGCTATCACCAGGGCAAGACACGCTAT
CTTTGTGTATGACCCACACAGGCAGCTGCAGGGCTTGTTTGATCTTCCTGCAAAAGGCACGCCCGTCAACCTCGCAGTGC
ACTGCGACGGGCAGCTGATCGTGCTGGATAGAAATAACAAAGAATGCACGGTTGCTCAGGCTCTAGGCAACGGGGATAAA
TTTAGGGCCACAGACAAGCGTGTTGTAGATTCTCTCCGCGCCATTTGTGCTGATCTAGAAGGGTCGAGCTCTCCGCTCCC
CAAGGTCGCACACAACTTGGGATTTTATTTCTCACCTGATTTAACACAGTTTGCTAAACTCCCAGTAGAACTTGCACCTC
ACTGGCCCGTGGTGTCAACCCAGAACAATGAAAAGTGGCCGGATCGGCTGGTTGCCAGCCTTCGCCCTATCCATAAATAC
AGCCGCGCGTGCATCGGTGCCGGCTATATGGTGGGCCCTTCGGTGTTTCTAGGCACTCCTGGGGTCGTGTCATACTATCT
CACAAAATTTGTTAAGGGCGGGGCTCAAGTGCTTCCGGAGACGGTTTTCAGCACCGGCCGAATTGAGGTAGACTGCCGGG
AATATCTTGATGATCGGGAGCGAGAAGTTGCTGCGTCCCTCCCACACGCTTTCATTGGCGACGTCAAAGGCACTACCGTT
GGAGGATGTCATCATGTCACCTCCAGATACCTCCCGCGCGTCCTTCCCAAGGAATCAGTTGCGGTAGTCGGGGTTTCAAG
```

*Fig. 1B-4*

```
CCCCGGAAAAGCCGCGAAAGCATTGTGCACACTGACAGATGTGTACCTCCCAGATCTTGAAGCCTATCTCCACCCGGAGA
CCCAGTCCAAGTGCTGGAAAATGATGTTGGACTTCAAAGAAGTTCGACTAATGGTCTGGAAAGACAAAACAGCCTATTTC
CAACTTGAAGGTCGCTATTTCACCTGGTATCAGCTTGCCAGCTATGCCTCGTACATCCGTGTTCCCGTCAACTCTACGGT
GTACTTGGACCCCTGCATGGGCCCCGCCCTTTGCAACAGGAGAGTCGTCGGGTCCACCCACTGGGGGCTGACCTCGCGG
TCACCCCTTATGATTACGGCGCTAAAATTATCCTGTCTAGCGCGTACCATGGTGAAATGCCCCCCGGATACAAAATTCTG
GCGTGCGCGGAGTTCTCGTTGGATGACCCAGTTAAGTACAAACATACCTGGGGGTTTGAATCGGATACAGCGTATCTGTA
TGAGTTCACCGGAAACGGTGAGGACTGGGAGGATTACAATGATGCGTTTCGTGCGCGCCAGGAAGGGAAAATTTATAAGG
CCACTGCCACCAGCTTGAAGTTTTATTTTCCCCCGGGCCCTGTCATTGAACCAACTTTAGGCCTGAATTGAAATGAAATG
GGGTCCATGCAAAGCCTTTTTGACAAAATTGGCCAACTTTTTGTGGATGCTTTCACGGAGTTCTTGGTGTCCATTGTTGA
TATCATTATATTTTTGGCCATTTTGTTTGGCTTCACCATCGCCGGTTGGCTGGTGGTCTTTTGCATCAGATTGGTTTGCT
CCGCGATACTCCGTACGCGCCCTGCCATTCACTCTGAGCAATTACAGAAGATCTTATGAGGCCTTTCTTTCCCAGTGCCA
AGTGGACATTCCCACCTGGGGAACTAAACATCCTTTGGGGATGCTTTGGCACCATAAGGTGTCAACCCTGATTGATGAAA
TGGTGTCGCGTCGAATGTACCGCATCATGGAAAAAGCAGGGCAGGCTGCCTGGAAACAGGTGGTGAGCGAGGCTACGCTG
TCTCGCATTAGTAGTTTGGATGTGGTGGCTCATTTTCAGCATCTAGCCGCCATTGAAGCCGAGACCTGTAAATATTTGGC
CTCCCGGCTGCCCATGCTACACAACCTGCGCATGACAGGGTCAAATGTAACCATAGTGTATAATAGCACTTTGAATCAGG
TGTTTGCTATTTTTCCAACCCCTGGTTCCCGGCCAAAGCTTCATGATTTTCAGCAATGGTTAATAGCTGTACATTCCTCC
ATATTTTCCTCTGTTGCAGCTTCTTGTACTCTTTTTGTTGTGCTGTGGTTGCGGGTTCCAATACTACGTACTGTTTTTGG
TTTCCGCTGGTTAGGGGCAATTTTTCTTTCGAACTCACAGTGAATTACACGGTGTGTCCACCTTGCCTCACCCGGCAAGC
AGCCACAGAGATCTACGAACCCGGTAGGTCTCTTTGGTGCAGGATAGGGTATGACCGATGTGGGGAGGACGATCATGACG
AGCTAGGGTTTATGATACCGCCTGGCCTCTCCAGCGAAGGCCACTTGACTGGTGTTTACGCCTGGTTGGCGTTCTTGTCC
TTCAGCTACACGGCCCAGTTCCATCCCGAGATATTCGGGATAGGGAATGTGAGTCGAGTTTATGTTGACATCAAACATCA
ACTCATCTGCGCCGAACATGACGGGCAGAACACCACCTTGCCTCGTCATGACAACATTTCAGCCGTGTTTCAGACCTATT
ACCAACATCAAGTCGACGGCGGCAATTGGTTTCACCTAGAATGGCTTCGTCCCTTCTTTTCCTCGTGGTTGGTTTTAAAT
GTCTCTTGGTTTCTCAGGCGTTCGCCTGCAAACCATGTTTCAGTTCGAGTCTTGCAGATATTAAGACCAACACCACCGCA
GCGGCAAGCTTTGCTGTCCTCCAAGACATCAGTTGCCTTAGGCATCGCGACTCGGCCTCTGAGGCGATTCGCAAAATCCC
TCAGTGCCGTACGGCGATAGGGACACCCGTGTATGTTACCATCACAGCCAATGTGACAGATGAGAATTATTTACATTCTT
CTGATCTCCTCATGCTTTCTTCTTGCCTTTTCTATGCTTCTGAGATGAGTGAAAAGGGATTTAAGGTGGTATTTGGCAAT
GTGTCAGGCATCGTGGCTGTGTGTGTCAATTTTACCAGCTACGTCCAACATGTCAAGGAGTTTACCCAACGCTCCCTGGT
GGTCGACCATGTGCGGTTGCTCCATTTCATGACACCTGAGACCATGAGGTGGGCAACTGTTTTAGCCTGTCTTTTTGCCA
TTCTGTTGGCAATTTGAATGTTTAAGTATGTTGGAGAAATGCTTGACCGCGGGCTGTTGCTCGCGATTGCTTTCTTTGTG
GTGTATCGTGCCGTTCTGTCTTGCTGTGCTCGCCAACGCCAGCAACGACAGCAGCTCCCATCTACAGCTGATTTACAACT
TGACGCTATGTGAGCTGAATGGCACAGATTGGCTAGCTAACAAATTTGATTGGGCAGTGGAGAGTTTTGTCATCTTTCCC
GTTTTGACTCACATTGTCTCCTATGGTGCCCTCACTACCAGCCATTTCCTTGACACAGTCGCTTTAGTCACTGTGTCTAC
CGCCGGGTTTGTTCACGGGCGGTATGTCCTAAGTAGCATCTACGCGGTCTGTGCCCTGGCTGCGTTGACTTGCTTCGTCA
TTAGGTTTGCAAAGAATTGCATGTCCTGGCGCTACGCGTGTACCAGATATACCAACTTTCTTCTGGACACTAAGGGCAGA
CTCTATCGTTGGCGGTCGCCTGTCATCATAGAGAAAAGGGGCAAAGTTGAGGTCGAAGGTCATCTGATCGACCTCAAAAG
AGTTGTGCTTGATGGCTCCGTGGCAACCCCTATAACCAGAGTTTCAGCGGAACAATGGGGTCGTCCTTAGATGACTTCTG
TCACGATAGCACGGCTCCACAAAAGGTGCTTTTGGCGTTTTCTATTACCTACACGCCAGTGATGATATATGCCCTAAAGG
TGAGTCGCGGCCGACTGCTAGGGCTTCTGCACCTTTTGATCTTCCTGAATTGTGCTTTCACCTTCGGGTACATGACTTTC
GCGCACTTTCAGAGTACAAATAAGGTCGCGCTCACTATGGGAGCAGTAGTTGCACTCCTTTGGGGGGTGTACTCAGCCAT
AGAAACCTGGAAATTCATCACCTCCAGATGCCGTTTGTGCTTGCTAGGCCGCAAGTACATTCTGGCCCCTGCCCACCACG
TTGAAAGTGCCGCAGGCTTTCATCCGATTGCGGCAAATGATAACCACGCATTTGTCGTCCGGCGTCCCGGCTCCACTACG
GTCAACGGCACATTGGTGCCCGGGTTAAAAAGCCTCGTGTTGGGTGGCAGAAAAGCTGTTAAACAGGGAGTGGTAAACCT
TGTCAAATATGCCAAATAACAACGGCAAGCAGCAGAAGAGAAAGAAGGGGGATGGCCAGCCAGTCAATCAGCTGTGCCAG
ATGCTGGGTAAGATCATCACTCAGCAAAACCAGTCCAGAGGCAAGGGACCGGGAAAGAAAAATAAGAAGAAAAACCCGGA
GAAGCCCCATTTTCCTCTAGCGACTGAAGATGATGTCAGACATCACTTTACCCCTAGTGAGCGGCAATTGTGTCTGTCGT
CAATCCAGACCGCCTTTAATCAAGGCGCTGGGACTTGCACCCTGTCAGATTCAGGGAGGATAAGTTACACTGTGGAGTTT
AGTTTGCCTACGCATCATACTGTGCGCCTGATCCGCGTCACAGCATCACCCTCAGCATGATGGGCTGGCATTCTTGAGGC
```

*Fig. 1B-5*

ATCTCAGTGTTTGAATTGGAAGAATGTGTGGTGAATGGCACTGATTGACATTGTGCCTCTAAGTCACCTATTCAATTAGG
GCGACCGTGTGGGGGTGAGATTTAATTGGCGAGAACCATGCGGCCGAAATTAAAAAAAAAAAAAAAAAAAAAAAAAAAAA
AAAAAAAAAAAAAAAAAA

Fig. 1C-1

```
>VR-V5G7475A.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCGCAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCCAGCACCGCCGCAGAGCGGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGAATCACACGCCCAAAATACTCAGCTCAAGCCATCATCGACTCGGGCGGGC
CCTGCAGTGGGCATCTCCAAGAGGTAAAGGAAACATGCCTTAGTGTCATGCGCGAGGCATGTGATGCGACTAAGCTTGAT
GACCCTGCTACGCAGGAATGGCTTTCTCGCATGTGGGATCGGGTGGACATGCTGACTTGGCGCAACACGTCTGTTTACCA
GGCGATTTGCACCTTAGATGGCAGGTTAAAGTTCCTCCCAAAAATGATACTCGAGACACCGCCGCCCTATCCGTGTGAGT
TTGTGATGATGCCTCACACGCCTGCACCTTCCGTAGGTGCGGAGAGCGACCTTACCATTGGCTCAGTTGCTACTGAAGAT
GTTCCACGCATCCTCGAGAAAATAGAAAATGTCGGCGAGATGGCCAACCAGGGACCCTTGGCCTTCTCCGAGGATAAACC
GGTAGATGACCAACTTGTCAACGACCCCCGGATATCGTCGCGGAGGCCTGACGAGAGCACATCAGCTCCGTCCGCAGGCA
```

*Fig. 1C-2*

```
CAGGTGGCGCCGGCTCTTTTACCGATTTGCCGCCTTCAGATGGCGCGGATGCGGACGGGGGGGGCCGTTTCGGACGGTA
AAAAGAAAAGCTGAAAGGCTCTTTGACCAACTGAGCCGTCAGGTTTTTGACCTCGTCTCCCATCTCCCTGTTTTCTTCTC
ACGCCTTTTCTACCCTGGCGGTGGTTATTCTCCGGGTGATTGGGGTTTTGCAGCTTTTACTCTATTGTGCCTCTTTTTAT
GTTACAGTTACCCAGCCTTTGGTATTGCTCCCCTCTTGGGTGTGTTTTCTGGGTCTTCTCGGCGCGTTCGAATGGGGGTT
TTTGGCTGCTGGTTGGCTTTTGCTGTTGGTCTGTTCAAGCCTGTGTCCGACCCAGTCGGCGCTGCTTGTGAGTTTGACTC
GCCAGAGTGTAGAAACATCCTTCATTCTTTTGAGCTTCTCAAACCTTGGGACCCTGTTCGCAGCCTTGTTGTGGGCCCCG
TCGGTCTCGGTCTTGCCATTCTTGGCAGGTTACTGGGCGGGGCACGCTGCATCTGGCACTTTTTGCTTAGGCTTGGCATT
GTTGCAGACTGTATCTTGGCTGGAGCTTACGTGCTTTCTCAAGGTAGGTGTAAAAAGTGCTGGGGATCTTGTATAAGAAC
TGCTCCCAATGAGGTCGCTTTTAACGTGTTTCCTTTCACACGTGCGACCAGGTCGTCACTTATCGACCTGTGCGATCGGT
TTTGTGCGCCAAAAGGAATGGACCCCATTTTTCTCGCCACTGGGTGGCGCGGGTGCTGGGCCGGCCGAAGCCCCATTGAG
CAACCCTCTGAAAAACCCATCGCGTTTGCCCAGTTGGATGAAAAGAAGATTACGGCTAGGACTGTGGTCGCCCAGCCTTA
TGACCCCAACCAAGCCGTAAAGTGCTTGCGGGTATTGCAGGCGGGTGGGGCGATGGTGGCTAAGGCGGTCCCAAAAGTGG
TCAAGGTTTCCGCTGTTCCATTCCGAGCCCCCTTCTTTCCCACTGGAGTGAAAGTTGACCCTGATTGCAGGGTCGTGGTT
GACCCTGACACTTTCACTGCAGCTCTCCGGTCTGGCTACTCCACCACAAACCTCGTCCTTGGTGTGGGGACTTTGCCCA
GCTGAATGGATTAAAAATCAGGCAAATTTCCAAGCCTTCAGGGGAGGCCCACATCTCATGGCTGCCCTGCATGTTGCCT
GCTCGATGGCTCTGCACATGCTTGCTGGGATTTATGTGACTGCGGTGGGTTCTTGCGGCACCGGCACCAACGACCCGTGG
TGCGCTAACCCGTTTGCCGTCCCTGGCTACGGACCTGGCTCTCTCTGCACGTCCAGATTGTGCATTTCCCAACACGGCCT
TACCCTGCCCTTGACAGCACTTGTGGCGGGATTCGGTATTCAAGAAATTGCCTTGGTCGTTTTGATTTTTGTTTCCATCG
GAGGCATGGCTCATAGGTTGAGCTGTAAGGCTGACATGCTGTGTGTCTTGCTTGCAATTGCCAGCTATGTTTGGGTACCT
CTTACCTGGTTGCTTTGTGTGTTTCCTTGCTGGTTGCGCTGTTTTTCTTTGCACCCCCTCACCATCCTATGGTTGGTGTT
TTTCTTGATTTCTGTGAATATGCCTTCAGGAATCTTGGCCATGGTGTTGTTGGTTTCTCTTTGGCTTCTTGGTCGTTATA
CTAATGTTGCTGGCCTTGTCACCCCCTACGACATTCATCATTACACCAGTGGCCCCGCGGTGTTGCCGCCTTGGCTACC
GCACCAGATGGGACCTACTTGGCCGCTGTCCGCCGCGCTGCGTTGACTGGCCGCACCATGCTGTTTACCCCGTCCCAGCT
TGGGTCTCTTCTTGAGGGTGCTTTCAGAACTCGAAAGCCCTCACTGAACACCGTCAATGTGATCGGGTCCTCCATGGGCT
CTGGCGGGGTGTTTACCATCGACGGGAAAGTCAAGTGCGTAACTGCCGCACATGTCCTTACGGGCAATTCAGCTCGGGTT
TCCGGGGTCGGCTTCAATCAAATGCTTGACTTTGACGTAAAGGGAGATTTCGCTATAGCTGATTGCCCGAATTGGCAAGG
GGCTGCCCCCAAGACCCAATTCTGCACGGATGGATGGACTGGCCGTGCCTATTGGCTAACATCCTCTGGCGTCGAACCCG
GCGTCATTGGAAAAGGATTCGCCTTCTGCTTCACCGCATGTGGCGATTCCGGGTCCCCAGTGATCACCGAGGCCGGTGAG
CTTGTCGGCGTTCACACGGGATCGAATAAACAAGGGGGGGGCATTGTTACGCGCCCCTCAGGCCAGTTTTGTAATGTGGC
ACCCATCAAGCTAAGCGAATTAAGTGAATTCTTTGCTGGGCCTAAGGTCCCGCTCGGTGATGTGAAGGTCGGCAGCCACA
TAATTAAAGACATAAGCGAGGTGCCTTCAGATCTTTGTGCCTTGCTTGCTGCCAAACCTGAACTGGAAGGAGGCCTCTCC
ACCGTCCAACTTCTTTGTGTGTTTTTTCTCCTGTGGAGAATGATGGGACATGCCTGGACGCCCTTGGTTGCTGTGAGTTT
CTTTATTTTGAATGAGGTTCTCCCAGCCGTCCTGGTCCGGAGTGTTTTCTCCTTTGGAATGTTTGTGCTATCCTGGCTCA
CGCCATGGTCTGCGCAAGTTCTGATGATCAGGCTTCTGACAGCAGCTCTTAACAGGAACAGATGGTCACTTGCCTTTTC
AGCCTCGGTGCAGTGACCGGTTTTGTCGCAGATCTTGCGGCCACTCAGGGGCATCCGTTGCAGGCAGTGATGAATTTGAG
CACCTATGCATTCCTGCCTCGGATGATGGTTGTGACCTCACCAGTCCCAGTGATCACGTGTGGTGTCGTGCACCTACTTG
CCATCATTTTGTACTTGTTTAAGTACCGTGGCCTGCACCATATCCTTGTTGGCGATGGAGTGTTCTCTGCGGCTTTCTTC
TTGAGATACTTTGCCGAGGGAAAGTTGAGGGAAGGGTGTCGCAATCCTGCGGAATGAATCATGAGTCTCTGACTGGTGC
CCTCGCTATGAGACTCAATGACGAGGACTTGGATTTCCTTATGAAATGGACTGATTTTAAGTGCTTTGTTTCTGCGTCCA
ACATGAGGAATGCAGCGGGTCAATTTATCGAGGCTGCCTATGCTAAAGCACTTAGAGTAGAACTGGCCCAGTTGGTGCAG
GTTGATAAAGTTCGAGGTACTTTGGCCAAACTTGAAGCTTTTGCTGATACCGTGGCACCTCAACTCTCGCCCGGTGACAT
TGTTGTCGCTCTCGGCCACACGCCTGTTGGCAGTATCTTCGACCTAAAGGTTGGTAGCACCAAGCATACCCTCCAAGCCA
TTGAGACCAGAGTCCTTGCTGGGTCCAAAATGACCGTGGCGCGCGTCGTCGACCCGACCCCCACGCCCCCACCCGCACCC
GTGCCCATCCCCCTCCCACCGAAAGTTCTGGAGAATGGCCCCAACGCTTGGGGGATGAGGACCGTTTGAATAAGAAGAA
GAGGCGCAGGATGGAAGCCCTCGGCATCTATGTTATGGGCGGAAAAAATACCAGAAATTTTGGGACAAGAATTCCGGTG
ATGTGTTTTATGAGGAGGTCCATAATAACACAGATGAGTGGGAGTGTCTCAGAGTTGGCGACCCTGCCGACTTTGACCCT
GAGAAGGGAACTCTGTGTGGACATGTCACCATTGAAAACAAGGCTTACCATGTTTACACCTCCCCATCTGGTAAGAAGTT
CTTGGTCCCCGTCAACCCAGAGAATGGAAGAGTCCAATGGGAAGCTGCAAAGCTTTCCGTGGAGCAGGCCCTAGGTATGA
```

Fig. 1C-3

```
TGAATGTCGACGGCGAACTGACTGCCAAAGAACTGGAGAAACTGAAAAGAATAATTGACAAACTCCAGGGCCTGACTAAG
GAGCAGTGTTTAAACTGCTAGCCGCCAGCGACTTGACCCGCTGTGGTCGCGGCGGCTTGGTTGTTACTGAAACAGCGGTA
AAAATAGTCAAATTTCACAACCGGACCTTCACCCTGGGACCTGTGAATTTAAAAGTGGCCAGTGAGGTTGAGCTAAAAGA
CGCGGTTGAGCACAACCAACACCCGGTTGCGAGACCGATCGATGGTGGAGTTGTGCTCCTGCGTTCCGCGGTTCCTTCGC
TTATAGACGTCTTGATCTCCGGTGCTGATGCATCTCCCAAGTTACTTGCCCATCACGGGCCGGGAAACACTGGGATCGAT
GGCACGCTCTGGGATTTTGAGTCCGAAGCCACTAAAGAGGAAGTCGCACTCAGTGCGCAAATAATACAGGCTTGTGACAT
TAGGCGCGGCGACGCTCCTGAAATTGGTCTCCCTTACAAGCTGTACCCTGTTAGGGGTAACCCTGAGCGGGTGAAAGGAG
TTCTGCAGAATACAAGGTTTGGAGACATACCTTACAAAACCCCAGTGACACTGGAAGCCCAGTGCACGCGGCTGCCTGC
CTTACGCCCAACGCCACTCCGGTGACTGATGGGCGCTCCGTCTTGGCCACGACCATGCCCCCCGGGTTTGAGTTATATGT
ACCGACCATACCAGCGTCTGTCCTTGATTACCTTGACTCTAGGCCTGACTGCCCTAAACAGCTGACAGAGCACGGCTGCG
AAGATGCCGCACTGAAAGACCTCTCTAAATATGACTTGTCCACCCAAGGCTTTGTTTTACCTGGAGTTCTTCGCCTTGTG
CGGAAATACCTGTTTGCCCATGTAGGTAAGTGCCCACCCGTTCATCGGCCTTCTACTTACCCTGCTAAGAATTCTATGGC
TGGAATAAATGGGAACAGGTTCCCAACCAAGGACATTCAGAGCGTCCCTGAAATCGACGTTCTGTGCGCACAGGCTGTGC
GAGAAAACTGGCAAACTGTCACCCCTTGTACTCTTAAGAAACAGTATTGCGGGAAGAAGAAGACTAGGACCATACTCGGC
ACCAATAACTTCATCGCACTAGCCCACCGAGCAGTGTTGAGTGGTGTTACCCAGGGCTTCATGAAAAAGGCGTTTAACTC
GCCCATCGCCCTCGGAAAGAACAAGTTTAAGGAGCTACAGACTCCGGTCCTGGGCAGGTGCCTTGAAGCTGATCTCGCAT
CCTGCGATCGATCCACGCCTGCAATTGTCCGCTGGTTTGCCGCCAACCTTCTTTATGAACTTGCCTGTGCTGAAGAGCAT
CTACCGTCGTACGTGCTGAACTGCTGCCACGACTTACTGGTCACGCAGTCCGGCGCAGTGACTAAGAGAGGTGGCCTGTC
GTCCTGGCGACCCGATCACCTCTGTGTCTAACACCATTTATAGTTTGGTGATCTATGCACAGCATATGGTGCTTAGTTACT
TCAAAAGTGGTCACCCCCATGGCCTTCTGTTCTTACAAGACCAGCTAAAGTTTGAGGACATGCTCAAGGTTCAACCCCTG
ATCGTCTATTCGGACGACCTCGTGCTGTATGCCGAGTCTCCCACCATGCCAAACTATCACTGGTGGGTTGAACATCTGAA
TTTGATGCTGGGGTTTCAGACGGACCCAAAGAAGACAGCAATAACAGACTCGCCATCATTTCTAGGCTGTAGAATAATAA
ATGGGCGCCAGCTAGTCCCCAACCGTGACAGGATCCTCGCGGCCCTCGCCTATCACATGAAGGCGAGTAATGTTTCTGAA
TACTATGCCTCAGCGGCTGCAATACTCATGGACAGCTGTGCTTGTTTGGAGTATGATCCTGAATGGTTTGAAGAACTTGT
AGTTGGAATAGCGCAGTGCGCCCGCAAGGACGGCTACAGCTTTCCCGGCACGCCGTTCTTCATGTCCATGTGGGAAAAAC
TCAGGTCCAATTATGAGGGGAAGAAGTCGAGAGTGTGCGGGTACTGCGGGGCCCCGGCCCCGTACGCTACTGCCTGTGGC
CTCGACGTCTGCATTTACCACACCCACTTCCACCAGCATTGTCCAGTCACAATCTGGTGTGGCCATCCAGCGGGTTCTGG
TTCTTGTAGTGAGTGCAAATCCCCTGTAGGGAAAGGCACAAGCCCTTTAGACGAGGTGCTGGAACAAGTCCCGTATAAGC
CCCCACGGACCGTTATCATGCATGTGGAGCAGGGTCTCACCCCCCTTGATCCAGGTAGATACCAAACTCGCCGCGGATTA
GTCTCTGTCAGGCGTGGAATTAGGGGAAATGAAGTTGGACTACCAGACGGTGATTATGCTAGCACCGCCTTGCTCCCTAC
CTGCAAAGAGATCAACATGGTCGCTGTCGCTTCCAATGTATTGCGCAGCAGGTTCATCATCGGCCCACCCGGTGCTGGGA
AAACATACTGGCTCCTTCAACAGGTCCAGGATGGTGATGTTATTTACACACCAACTCACCAGACCATGCTTGACATGATT
AGGGCTTTGGGGACGTGCCGGTTCAACGTCCCGGCAGGCACAACGCTGCAATTCCCCGTCCCCTCCCGCACCGGTCCGTG
GGTTCGCATCCTAGCCGGCGGTTGGTGTCCTGGCAAGAATTCCTTCCTAGATGAAGCAGCGTATTGCAATCACCTTGATG
TTTTGAGGCTTCTTAGTAAAACTACCCTCACCTGTCTAGGAGACTTCAAGCAACTCCACCCAGTGGGTTTTGATTCTCAT
TGCTATGTTTTTGACATCATGCCTCAAACTCAACTGAAGACCATCTGGAGGTTTGGACAGAATATCTGTGATGCCATTCA
GCCAGATTACAGGGACAAACTCATGTCCATGGTCAACACAACCCGTGTGACCTACGTGGAAAAACCTGTCAGGTATGGGC
AGGTCCTCACCCCCTACCACAGGGACCGAGAGGACGACGCCATCACTATTGACTCCAGTCAAGGCGCCACATTCGATGTG
GTTACATTGCATTTGCCCACTAAAGATTCACTCAACAGGCAAAGAGCCCTTGTTGCTATCACCAGGGCAAGACACGCTAT
CTTTGTGTATGACCCACACAGGCAGCTGCAGGGCTTGTTTGATCTTCCTGCAAAAGGCACGCCCGTCAACCTCGCAGTGC
ACTGCGACGGGCAGCTGATCGTGCTGGATAGAAATAACAAAGAATGCACGGTTGCTCAGGCTCTAGGCAACGGGGATAAA
TTTAGGGCCACAGACAAGCGTGTTGTAGATTCTCTCCGCGCCATTTGTGCTGATCTAGAAGGGTCGAGCTCTCCGCTCCC
CAAGGTCGCACACAACTTGGGATTTTATTTCTCACCTGATTTAACACAGTTTGCTAAACTCCCAGTAGAACTTGCACCTC
ACTGGCCCGTGGTGTCAACCCAGAACAATGAAAAGTGGCCGGATCGGCTGGTTGCCAGCCTTCGCCCTATCCATAAATAC
AGCCGCGCGTGCATCGGTGCCGGCTATATGGTGGGCCCTTCGGTGTTTCTAGGCACTCCTGGGGTCGTGTCATACTATCT
CACAAAATTTGTTAAGGGCGGGGCTCAAGTGCTTCCGGAGACGGTTTTCAGCACCGGCCGAATTGAGGTAGACTGCCGGG
AATATCTTGATGATCGGGAGCGAGAAGTTGCTGCGTCCCTCCCACACGCTTTCATTGGCGACGTCAAAGGCACTACCGTT
GGAGGATGTCATCATGTCACCTCCAGATACCTCCCGCGCGTCCTTCCCAAGGAATCAGTTGCGGTAGTCGGGGTTTCAAG
```

Fig. 1C-4

CCCCGGAAAAGCCGCGAAAGCATTGTGCACACTGACAGATGTGTACCTCCCAGATCTTGAAGCCTATCTCCACCCGGAGA
CCCAGTCCAAGTGCTGGAAAATGATGTTGGACTTCAAAGAAGTTCGACTAATGGTCTGGAAAGACAAAACAGCCTATTTC
CAACTTGAAGGTCGCTATTTCACCTGGTATCAGCTTGCCAGCTATGCCTCGTACATCCGTGTTCCCGTCAACTCTACGGT
GTACTTGGACCCCTGCATGGGCCCCGCCCTTTGCAACAGGAGAGTCGTCGGGTCCACCCACTGGGGGCTGACCTCGCGG
TCACCCCTTATGATTACGGCGCTAAAATTATCCTGTCTAGCGCGTACCATGGTGAAATGCCCCCCGGATACAAAATTCTG
GCGTGCGCGGAGTTCTCGTTGGATGACCCAGTTAAGTACAAACATACCTGGGGGTTTGAATCGGATACAGCGTATCTGTA
TGAGTTCACCGGAAACGGTGAGGACTGGGAGGATTACAATGATGCGTTTCGTGCGCGCCAGGAAGGGAAAATTTATAAGG
CCACTGCCACCAGCTTGAAGTTTTATTTTCCCCCGGGCCCTGTCATTGAACCAACTTTAGGCCTGAATTGAAATGAAATG
GGGTCCATGCAAAGCCTTTTTGACAAAATTGGCCAACTTTTTGTGGATGCTTTCACGGAGTTCTTGGTGTCCATTGTTGA
TATCATTATATTTTTGGCCATTTTGTTTGGCTTCACCATCGCCGGTTGGCTGGTGGTCTTTTGCATCAGATTGGTTTGCT
CCGCGATACTCCGTACGCGCCCTGCCATTCACTCTGAGCAATTACAGAAGATCTTATGAGGCCTTTCTTTCCCAGTGCCA
AGTGGACATTCCCACCTGGGGAACTAAACATCCTTTGGGGATGCTTTGGCACCATAAGGTGTCAACCCTGATTGATGAAA
TGGTGTCGCGTCGAATGTACCGCATCATGGAAAAAGCAGGGCAGGCTGCCTGGAAACAGGTGGTGAGCGAGGCTACGCTG
TCTCGCATTAGTAGTTTGGATGTGGTGGCTCATTTTCAGCATCTAGCCGCCATTGAAGCCGAGACCTGTAAATATTTGGC
CTCCCGGCTGCCCATGCTACACAACCTGCGCATGACAGGGTCAAATGTAACCATAGTGTATAATAGCACTTTGAATCAGG
TGTTTGCTATTTTTCCAACCCCTGGTTCCCGGCCAAAGCTTCATGATTTTCAGCAATGGTTAATAGCTGTACATTCCTCC
ATATTTTCCTCTGTTGCAGCTTCTTGTACTCTTTTTGTTGTGCTGTGGTTGCGGGTTCCAATACTACGTACTGTTTTTGG
TTTCCGCTGGTTAGGGGCAATTTTTCTTTCGAACTCACAGTGAATTACACGGTGTGTCCACCTTGCCTCACCCGGCAAGC
AGCCACAGAGATCTACGAACCCGGTAGGTCTCTTTGGTGCAGGATAGGGTATGACCGATGTGGGGAGGACGATCATGACG
AGCTAGGGTTTATGATACCGCCTGGCCTCTCCAGCGAAGGCCACTTGACTGGTGTTTACGCCTGGTTGGCGTTCTTGTCC
TTCAGCTACACGGCCCAGTTCCATCCCGAGATATTCGGGATAGGGAATGTGAGTCGAGTTTATGTTGACATCAAACATCA
ACTCATCTGCGCCGAACATGACGGGCAGAACACCACCTTGCCTCGTCATGACAACATTTCAGCCGTGTTTCAGACCTATT
ACCAACATCAAGTCGACGGCGGCAATTGGTTTCACCTAGAATGGCTTCGTCCCTTCTTTTCCTCGTGGTTGGTTTTAAAT
GTCTCTTGGTTTCTCAGGCGTTCGCCTGCAAACCATGTTTCAGTTCGAGTCTTGCAAATATTAAGACCAACACCACCGCA
GCGGCAAGCTTTGCTGTCCTCCAAGACATCAGTTGCCTTAGGCATCGCGACTCGGCCTCTGAGGCGATTCGCAAAATCCC
TCAGTGCCGTACGGCGATAGGGACACCCGTGTATGTTACCATCACAGCCAATGGGACAGATGAGAATTATCTACATTCTT
CTGATCTCCTCATGCTTTCTTCTTGCCTTTTCTATGCTTCTGAGATGAGTGAAAAGGGATTTAAGGTGGTATTTGGCAAT
GTGTCAGGCATCGTGGCTGTGTGTGTCAATTTTACCAGCTACGTCCAACATGTCAAGGAGTTTACCCAACGCTCCCTGGT
GGTCGACCATGTGCGGTTGCTCCATTTCATGACACCTGAGACCATGAGGTGGGCAACTGTTTTAGCCTGTCTTTTTGCCA
TTCTGTTGGCAATTTGAATGTTTAAGTATGTTGGAGAAATGCTTGACCGCGGGCTGTTGCTCGCGATTGCTTTCTTTGTG
GTGTATCGTGCCGTTCTGTCTTGCTGTGCTCGCCAACGCCAGCAACGACAGCAGCTCCCATCTACAGCTGATTTACAACT
TGACGCTATGTGAGCTGAATGGCACAGATTGGCTAGCTAACAAATTTGATTGGGCAGTGGAGAGTTTTGTCATCTTTCCC
GTTTTGACTCACATTGTCTCCTATGGTGCCCTCACTACCAGCCATTTCCTTGACACAGTCGCTTTAGTCACTGTGTCTAC
CGCCGGGTTTGTTCACGGGCGGTATGTCCTAAGTAGCATCTACGCGGTCTGTGCCCTGGCTGCGTTGACTTGCTTCGTCA
TTAGGTTTGCAAAGAATTGCATGTCCTGGCGCTACGCGTGTACCAGATATACCAACTTTCTTCTGGACACTAAGGGCAGA
CTCTATCGTTGGCGGTCGCCTGTCATCATAGAGAAAAGGGGCAAAGTTGAGGTCGAAGGTCATCTGATCGACCTCAAAAG
AGTTGTGCTTGATGGCTCCGTGGCAACCCCTATAACCAGAGTTTCAGCGGAACAATGGGTCGTCCTTAGATGACTTCTG
TCACGATAGCACGGCTCCACAAAAGGTGCTTTTGGCGTTTTCTATTACCTACACGCCAGTGATGATATATGCCCTAAAGG
TGAGTCGCGGCCGACTGCTAGGGCTTCTGCACCTTTTGATCTTCCTGAATTGTGCTTTCACCTTCGGGTACATGACTTTC
GCGCACTTTCAGAGTACAAATAAGGTCGCGCTCACTATGGGAGCAGTAGTTGCACTCCTTTGGGGGGTGTACTCAGCCAT
AGAAACCTGGAAATTCATCACCTCCAGATGCCGTTTGTGCTTGCTAGGCCGCAAGTACATTCTGGCCCCTGCCCACCACG
TTGAAAGTGCCGCAGGCTTTCATCCGATTGCGGCAAATGATAACCACGCATTTGTCGTCCGGCGTCCCGGCTCCACTACG
GTCAACGGCACATTGGTGCCCGGGTTAAAAAGCCTCGTGTTGGGTGGCAGAAAAGCTGTTAAACAGGGAGTGGTAAACCT
TGTCAAATATGCCAAATAACAACGGCAAGCAGCAGAAGAGAAAGAAGGGGGATGGCCAGCCAGTCAATCAGCTGTGCCAG
ATGCTGGGTAAGATCATCACTCAGCAAAACCAGTCCAGAGGCAAGGGACCGGGAAAGAAAAATAAGAAGAAAAACCCGGA
GAAGCCCCATTTTCCTCTAGCGACTGAAGATGATGTCAGACATCACTTTACCCCTAGTGAGCGGCAATTGTGTCTGTCGT
CAATCCAGACCGCCTTTAATCAAGGCGCTGGGACTTGCACCCTGTCAGATTCAGGGAGGATAAGTTACACTGTGGAGTTT
AGTTTGCCTACGCATCATACTGTGCGCCTGATCCGCGTCACAGCATCACCCTCAGCATGATGGGCTGGCATTCTTGAGGC

*Fig. 1C-5*

ATCTCAGTGTTTGAATTGGAAGAATGTGTGGTGAATGGCACTGATTGACATTGTGCCTCTAAGTCACCTATTCAATTAGG
GCGACCGTGTGGGGGTGAGATTTAATTGGCGAGAACCATGCGGCCGAAATTAAAAAAAAAAAAAAAAAAAAAAAAAAAAA
AAAAAAAAAAAAAAAAACCC

Fig. 1D-1

```
>VR-V6.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCCAGCACCGCCGCAGAGCGGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGAATCACACGCCCAAAATACTCAGCTCAAGCCATCATCGACTCGGGCGGGC
CCTGCAGTGGGCATCTCCAAGAGGTAAAGGAAACATGCCTTAGTGTCATGCGCGAGGCATGTGATGCGACTAAGCTTGAT
GACCCTGCTACGCAGGAATGGCTTTCTCGCATGTGGGATCGGGTGGACATGCTGACTTGGCGCAACACGTCTGTTTACCA
GGCGATTTGCACCTTAGATGGCAGGTTAAAGTTCCTCCCAAAAATGATACTCGAGACACCGCCGCCCTATCCGTGTGAGT
TTGTGATGATGCCTCACACGCCTGCACCTTCCGTAGGTGCGGGAGAGCGACCTTACCATTGGCTCAGTTGCTACTGAAGAT
GTTCCACGCATCCTCGAGAAAATAGAAAATGTCGGCGAGATGGCCAACCAGGGACCCTTGGCCTTCTCCGAGGATAAACC
GGTAGATGACCAACTTGTCAACGACCCCCGGATATCGTCGCGGAGGCCTGACGAGAGCACATCAGCTCCGTCCGCAGGCA
```

Fig. 1D-2

```
CAGGTGGCGCCGGCTCTTTTACCGATTTGCCGCCTTCAGATGGCGCGGATGCGGACGGGGGGGGGCCGTTTCGGACGGTA
AAAAGAAAAGCTGAAAGGCTCTTTGACCAACTGAGCCGTCAGGTTTTTGACCTCGTCTCCCATCTCCCTGTTTTCTTCTC
ACGCCTTTTCTACCCTGGCGGTGGTTATTCTCCGGGTGATTGGGGTTTTGCAGCTTTTACTCTATTGTGCCTCTTTTTAT
GTTACAGTTACCCAGCCTTTGGTATTGCTCCCCTCTTGGGTGTGTTTTCTGGGTCTTCTCGGCGCGTTCGAATGGGGGTT
TTTGGCTGCTGGTTGGCTTTTGCTGTTGGTCTGTTCAAGCCTGTGTCCGACCCAGTCGGCGCTGCTTGTGAGTTTGACTC
GCCAGAGTGTAGAAACATCCTTCATTCTTTTGAGCTTCTCAAACCTTGGGACCCTGTTCGCAGCCTTGTTGTGGGCCCCG
TCGGTCTCGGTCTTGCCATTCTTGGCAGGTTACTGGGCGGGGCACGCTGCATCTGGCACTTTTTGCTTAGGCTTGGCATT
GTTGCAGACTGTATCTTGGCTGGAGCTTACGTGCTTTCTCAAGGTAGGTGTAAAAAGTGCTGGGGATCTTGTATAAGAAC
TGCTCCCAATGAGGTCGCTTTTAACGTGTTTCCTTTCACACGTGCGACCAGGTCGTCACTTATCGACCTGTGCGATCGGT
TTTGTGCGCCAAAAGGAATGGACCCCATTTTTCTCGCCACTGGGTGGCGCGGGTGCTGGGCCGGCCGAAGCCCCATTGAG
CAACCCTCTGAAAAACCCATCGCGTTTGCCCAGTTGGATGAAAAGAAGATTACGGCTAGGACTGTGGTCGCCCAGCCTTA
TGACCCCAACCAAGCCGTAAAGTGCTTGCGGGTATTGCAGGCGGGTGGGCGATGGTGGCTAAGGCGGTCCCAAAAGTGG
TCAAGGTTTCCGCTGTTCCATTCCGAGCCCCCTTCTTTCCCACTGGAGTGAAAGTTGACCCTGATTGCAGGTCGTGGTT
GACCCTGACACTTTCACTGCAGCTCTCCGGTCTGGCTACTCCACCACAAACCTCGTCCTTGGTGTGGGGACTTTGCCCA
GCTGAATGGATTAAAAAATCAGGCAAATTTCCAAGCCTTCAGGGGGAGGCCCACATCTCATGGCTGCCCTGCATGTTGCCT
GCTCGATGGCTCTGCACATGCTTGCTGGGATTTATGTGACTGCGGTGGGTTCTTGCGGCACCGGCACCAACGACCCGTGG
TGCGCTAACCCGTTTGCCGTCCCTGGCTACGGACCTGGCTCTCTCTGCACGTCCAGATTGTGCATTTCCCAACACGGCCT
TACCCTGCCCTTGACAGCACTTGTGGCGGGATTCGGTATTCAAGAAATTGCCTTGGTCGTTTTGATTTTTGTTTCCATCG
GAGGCATGGCTCATAGGTTGAGCTGTAAGGCTGACATGCTGTGTGTCTTGCTTGCAATTGCCAGCTATGTTTGGGTACCT
CTTACCTGGTTGCTTTGTGTGTTTCCTTGCTGGTTGCGCTGTTTTCTTTGCACCCCCTCACCATCCTATGGTTGGTGTT
TTTCTTGATTTCTGTGAATATGCCTTCAGGAATCTTGGCCATGGTGTTGTTGGTTTCTCTTTGGCTTCTTGGTCGTTATA
CTAATGTTGCTGGCCTTGTCACCCCCTACGACATTCATCATTACACCAGTGGCCCCCGCGGTGTTGCCGCCTTGGCTACC
GCACCAGATGGGACCTACTTGGCCGCTGTCCGCCGCGCTGCGTTGACTGGCCGCACCATGCTGTTTACCCCGTCCCAGCT
TGGGTCTCTTCTTGAGGGTGCTTTCAGAACTCGAAAGCCCTCACTGAACACCGTCAATGTGATCGGGTCCTCCATGGGCT
CTGGCGGGGTGTTTACCATCGACGGGAAAGTCAAGTGCGTAACTGCCGCACATGTCCTTACGGGCAATTCAGCTCGGGTT
TCCGGGGTCGGCTTCAATCAAATGCTTGACTTTGACGTAAAGGGAGATTTCGCTATAGCTGATTGCCCGAATTGGCAAGG
GGCTGCCCCCAAGACCCAATTCTGCACGGATGGATGGACTGGCCGTGCCTATTGGCTAACATCCTCTGGCGTCGAACCCG
GCGTCATTGGAAAAGGATTCGCCTTCTGCTTCACCGCATGTGGCGATTCCGGGTCCCCAGTGATCACCGAGGCCGGTGAG
CTTGTCGGCGTTCACACGGGATCGAATAAACAAGGGGGGGGCATTGTTACGCGCCCCTCAGGCCAGTTTTGTAATGTGGC
ACCCATCAAGCTAAGCGAATTAAGTGAATTCTTTGCTGGGCCTAAGGTCCCGCTCGGTGATGTGAAGGTCGGCAGCCACA
TAATTAAAGACATAAGCGAGGTGCCTTCAGATCTTTGTGCCTTGCTTGCTGCCAAACCTGAACTGGAAGGAGGCCTCTCC
ACCGTCCAACTTCTTTGTGTGTTTTTTCTCCTGTGGAGAATGATGGGACATGCCTGGACGCCCTTGGTTGCTGTGAGTTT
CTTTATTTTGAATGAGGTTCTCCCAGCCGTCCTGGTCCGGAGTGTTTTCTCCTTTGGAATGTTTGTGCTATCCTGGCTCA
CGCCATGGTCTGCGCAAGTTCTGATGATCAGGCTTCTGACAGCAGCTCTTAACAGGAACAGATGGTCACTTGCCTTTTTC
AGCCTCGGTGCAGTGACCGGTTTTGTCGCAGATCTTGCGGCCACTCAGGGGCATCCGTTGCAGGCAGTGATGAATTTGAG
CACCTATGCATTCCTGCCTCGGATGATGGTTGTGACCTCACCAGTCCCAGTGATCACGTGTGGTGTCGTGCACCTACTTG
CCATCATTTTGTACTTGTTTAAGTACCGTGGCCTGCACCATATCCTTGTTGGCGATGGAGTGTTCTCTGCGGCTTTCTTC
TTGAGATACTTTGCCGAGGGAAAGTTGAGGGAAGGGGTGTCGCAATCCTGCGGAATGAATCATGAGTCTCTGACTGGTGC
CCTCGCTATGAGACTCAATGACGAGGACTTGGATTTCCTTATGAAATGGACTGATTTTAAGTGCTTTGTTTCTGCGTCCA
ACATGAGGAATGCAGCGGGTCAATTTATCGAGGCTGCCTATGCTAAAGCACTTAGAGTAGAACTGGCCCAGTTGGTGCAG
GTTGATAAAGTTCGAGGTACTTTGGCCAAACTTGAAGCTTTTGCTGATACCGTGGCACCTCAACTCTCGCCCGGTGACAT
TGTTGTCGCTCTCGGCCACACGCCTGTTGGCAGTATCTTCGACCTAAAGGTTGGTAGCACCAAGCATACCCTCCAAGCCA
TTGAGACCAGAGTCCTTGCTGGGTCCAAAATGACCGTGGCGCGCGTCGTCGACCCGACCCCCACGCCCCCACCCGCACCC
GTGCCCATCCCCCTCCCACCGAAAGTTCTGGAGAATGGCCCCAACGCTTGGGGGATGAGGACCGTTTGAATAAGAAGAA
GAGGCGCAGGATGGAAGCCCTCGGCATCTATGTTATGGGCGGAAAAAATACCAGAAATTTTGGGACAAGAATTCCGGTG
ATGTGTTTTATGAGGAGGTCCATAATAACACAGATGAGTGGGAGTGTCTCAGAGTTGGCGACCCTGCCGACTTTGACCCT
GAGAAGGGAACTCTGTGTGGACATGTCACCATTGGAAACAAGGCTTACCATGTTTACACCCTCCCCATCTGGTAAGAAGTT
CTTGGTCCCCGTCAACCCAGAGAATGGAAGAGTCCAATGGGAAGCTGCAAAGCTTTCCGTGGAGCAGGCCCTAGGTATGA
```

*Fig. 1D-3*

```
TGAATGTCGACGGCGAACTGACTGCCAAAGAACTGGAGAAACTGAAAAGAATAATTGACAAACTCCAGGGCCTGACTAAG
GAGCAGTGTTTAAACTGCTAGCCGCCAGCGACTTGACCCGCTGTGGTCGCGGCGGCTTGGTTGTTACTGAAACAGCGGTA
AAAATAGTCAAATTTCACAACCGGACCTTCACCCTGGGACCTGTGAATTTAAAAGTGGCCAGTGAGGTTGAGCTAAAAGA
CGCGGTTGAGCACAACCAACACCCGGTTGCGAGACCGATCGATGGTGGAGTTGTGCTCCTGCGTTCCGCGGTTCCTTCGC
TTATAGACGTCTTGATCTCCGGTGCTGATGCATCTCCCAAGTTACTTGCCCATCACGGGCCGGGAAACACTGGGATCGAT
GGCACGCTCTGGGATTTTGAGTCCAAGCCACTAAAGAGGAAGTCGCACTCAGTGCGCAAATAATACAGGCTTGTGACAT
TAGGCGCGGCGACGCTCCTGAAATTGGTCTCCCTTACAAGCTGTACCCTGTTAGGGGTAACCCTGAGCGGGTGAAAGGAG
TTCTGCAGAATACAAGGTTTGGAGACATACCTTACAAAACCCCAGTGACACTGGAAGCCCAGTGCACGCGGCTGCCTGC
CTTACGCCCAACGCCACTCCGGTGACTGATGGGCGCTCCGTCTTGGCCACGACCATGCCCCCGGGTTTGAGTTATATGT
ACCGACCATACCAGCGTCTGTCCTTGATTACCTTGACTCTAGGCCTGACTGCCCTAAACAGCTGACAGAGCACGGCTGCG
AAGATGCCGCACTGAAAGACCTCTCTAAATATGACTTGTCCACCCAAGGCTTTGTTTTACCTGGAGTTCTTCGCCTTGTG
CGGAAATACCTGTTTGCCCATGTAGGTAAGTGCCCACCCGTTCATCGGCCTTCTACTTACCCTGCTAAGAATTCTATGGC
TGGAATAAATGGGAACAGGTTCCCAACCAAGGACATTCAGAGCGTCCCTGAAATCGACGTTCTGTGCGCACAGGCTGTGC
GAGAAAACTGGCAAACTGTCACCCCTTGTACTCTTAAGAAACAGTATTGCGGGAAGAAGAAGACTAGGACCATACTCGGC
ACCAATAACTTCATCGCACTAGCCCACCGAGCAGTGTTGAGTGGTGTTACCCAGGGCTTCATGAAAAAGGCGTTTAACTC
GCCCATCGCCCTCGGAAAGAACAAGTTTAAGGAGCTACAGACTCCGGTCCTGGGCAGGTGCCTTGAAGCTGATCTCGCAT
CCTGCGATCGATCCACGCCTGCAATTGTCCGCTGGTTTGCCGCCAACCTTCTTTATGAACTTGCCTGTGCTGAAGAGCAT
CTACCGTCGTACGTGCTGAACTGCTGCCACGACTTACTGGTCACGCAGTCCGGCGCAGTGACTAAGAGAGGTGGCCTGTC
GTCTGGCGACCCGATCACCTCTGTGTCTAACACCATTTATAGTTTGGTGATCTATGCACAGCATATGGTGCTTAGTTACT
TCAAAAGTGGTCACCCCCATGGCCTTCTGTTCTTACAAGACCAGCTAAAGTTTGAGGACATGCTCAAGGTTCAACCCCTG
ATCGTCTATTCGGACGACCTCGTGCTGTATGCCGAGTCTCCCACCATGCCAAACTATCACTGGTGGGTTGAACATCTGAA
TTTGATGCTGGGGTTTCAGACGGACCCAAAGAAGACAGCAATAACAGACTCGCCATCATTTCTAGGCTGTAGAATAATAA
ATGGGCGCCAGCTAGTCCCCAACCGTGACAGGATCCTCGCGGCCCTCGCCTATCACATGAAGGCGAGTAATGTTTCTGAA
TACTATGCCTCAGCGGCTGCAATACTCATGGACAGCTGTGCTTGTTTGGAGTATGATCCTGAATGGTTTGAAGAACTTGT
AGTTGGAATAGCGCAGTGCGCCCGCAAGGACGGCTACAGCTTTCCCGGCACGCCGTTCTTCATGTCCATGTGGGAAAAAC
TCAGGTCCAATTATGAGGGGAAGAAGTCGAGAGTGTGCGGGTACTGCGGGGCCCCGGCCCCGTACGCTACTGCCTGTGGC
CTCGACGTCTGCATTTACCACACCCACTTCCACCAGCATTGTCCAGTCACAATCTGGTGTGGCCATCCAGCGGGTTCTGG
TTCTTGTAGTGAGTGCAAATCCCCTGTAGGGAAAGGCACAAGCCCTTTAGACGAGGTGCTGGAACAAGTCCCGTATAAGC
CCCCACGGACCGTTATCATGCATGTGGAGCAGGGTCTCACCCCCCTTGATCCAGGTAGATACCAAACTCGCCGCGGATTA
GTCTCTGTCAGGCGTGGAATTAGGGGAAATGAAGTTGGACTACCAGACGGTGATTATGCTAGCACCGCCTTGCTCCCTAC
CTGCAAAGAGATCAACATGGTCGCTGTCGCTTCCAATGTATTGCGCAGCAGGTTCATCATCGGCCCACCCGGTGCTGGGA
AAACATACTGGCTCCTTCAACAGGTCCAGGATGGTGATGTTATTTACACACCAACTCACCAGACCATGCTTGACATGATT
AGGGCTTTGGGGACGTGCCGGTTCAACGTCCCGGCAGGCACAACGCTGCAATTCCCCGTCCCCTCCCGCACCGGTCCGTG
GGTTCGCATCCTAGCCGGCGGTTGGTGTCCTGGCAAGAATTCCTTCCTAGATGAAGCAGCGTATTGCAATCACCTTGATG
TTTTGAGGCTTCTTAGTAAAACTACCCTCACCTGTCTAGGAGACTTCAAGCAACTCCACCCAGTGGGTTTTGATTCTCAT
TGCTATGTTTTTGACATCATGCCTCAAACTCAACTGAAGACCATCTGGAGGTTTGGACAGAATATCTGTGATGCCATTCA
GCCAGATTACAGGGACAAACTCATGTCCATGGTCAACACAACCCGTGTGACCTACGTGGAAAAACCTGTCAGGTATGGGC
AGGTCCTCACCCCCTACCACAGGGACCGAGAGGACGACGCCATCACTATTGACTCCAGTCAAGGCGCCACATTCGATGTG
GTTACATTGCATTTGCCCACTAAAGATTCACTCAACAGGCAAAGAGCCCTTGTTGCTATCACCAGGGCAAGACACGCTAT
CTTTGTGTATGACCCACACAGGCAGCTGCAGGGCTTGTTTGATCTTCCTGCAAAAGGCACGCCCGTCAACCTCGCAGTGC
ACTGCGACGGGCAGCTGATCGTGCTGGATAGAAATAACAAAGAATGCACGGTTGCTCAGGCTCTAGGCAACGGGGATAAA
TTTAGGGCCACAGACAAGCGTGTTGTAGATTCTCTCCGCGCCATTTGTGCTGATCTAGAAGGGTCGAGCTCTCCGCTCCC
CAAGGTCGCACACAACTTGGGATTTTATTTCTCACCTGATTTAACACAGTTTGCTAAACTCCCAGTAGAACTTGCACCTC
ACTGGCCCGTGGTGTCAACCCAGAACAATGAAAAGTGGCCGGATCGGCTGGTTGCCAGCCTTCGCCCTATCCATAAATAC
AGCCGCGCGTGCATCGGTGCCGGCTATATGGTGGGCCCTTCGGTGTTTCTAGGCACTCCTGGGGTCGTGTCATACTATCT
CACAAAATTTGTTAAGGGCGGGGCTCAAGTGCTTCCGGAGACGGTTTTCAGCACCGGCCGAATTGAGGTAGACTGCCGGG
AATATCTTGATGATCGGGAGCGAGAAGTTGCTGCGTCCCTCCCACACGCTTTCATTGGCGACGTCAAAGGCACTACCGTT
GGAGGATGTCATCATGTCACCTCCAGATACCTCCCGCGCGTCCTTCCCAAGGAATCAGTTGCGGTAGTCGGGGTTTCAAG
```

Fig. 1D-4

```
CCCCGGAAAAGCCGCGAAAGCATTGTGCACACTGACAGATGTGTACCTCCCAGATCTTGAAGCCTATCTCCACCCGGAGA
CCCAGTCCAAGTGCTGGAAAATGATGTTGGACTTCAAAGAAGTTCGACTAATGGTCTGGAAAGACAAAACAGCCTATTTC
CAACTTGAAGGTCGCTATTTCACCTGGTATCAGCTTGCCAGCTATGCCTCGTACATCCGTGTTCCCGTCAACTCTACGGT
GTACTTGGACCCCTGCATGGGCCCCGCCCTTTGCAACAGGAGAGTCGTCGGGTCCACCCACTGGGGGCTGACCTCGCGG
TCACCCCTTATGATTACGGCGCTAAAATTATCCTGTCTAGCGCGTACCATGGTGAAATGCCCCCCGGATACAAAATTCTG
GCGTGCGCGGAGTTCTCGTTGGATGACCCAGTTAAGTACAAACATACCTGGGGGTTTGAATCGGATACAGCGTATCTGTA
TGAGTTCACCGGAAACGGTGAGGACTGGGAGGATTACAATGATGCGTTTCGTGCGCGCCAGGAAGGGAAAATTTATAAGG
CCACTGCCACCAGCTTGAAGTTTTATTTTCCCCCGGGCCCTGTCATTGAACCAACTTTAGGCCTGAATTGAAATGAAATG
GGGTCCATGCAAAGCCTTTTTGACAAAATTGGCCAACTTTTTGTGGATGCTTTCACGGAGTTCTTGGTGTCCATTGTTGA
TATCATTATATTTTTGGCCATTTTGTTTGGCTTCACCATCGCCGGTTGGCTGGTGGTCTTTTGCATCAGATTGGTTTGCT
CCGCGATACTCCGTACGCGCCCTGCCATTCACTCTGAGCAATTACAGAAGATCTTATGAGGCCTTTCTTTCCCAGTGCCA
AGTGGACATTCCCACCTGGGGAACTAAACATCCTTTGGGGATGCTTTGGCACCATAAGGTGTCAACCCTGATTGATGAAA
TGGTGTCGCGTCGAATGTACCGCATCATGGAAAAAGCAGGGCAGGCTGCCTGGAAACAGGTGGTGAGCGAGGCTACGCTG
TCTCGCATTAGTAGTTTGGATGTGGTGGCTCATTTTCAGCATCTAGCCGCCATTGAAGCCGAGACCTGTAAATATTTGGC
CTCCCGGCTGCCCATGCTACACAACCTGCGCATGACAGGGTCAAATGTAACCATAGTGTATAATAGCACTTTGAATCAGG
TGTTTGCTATTTTTCCAACCCCTGGTTCCCGGCCAAAGCTTCATGATTTTCAGCAATGGTTAATAGCTGTACATTCCTCC
ATATTTTCCTCTGTTGCAGCTTCTTGTACTCTTTTTGTTGTGCTGTGGTTGCGGGTTCCAATACTACGTACTGTTTTTGG
TTTCCGCTGGTTAGGGGCAATTTTTCTTTCGAACTCACAGTGAATTACACGGTGTGTCCACCTTGCCTCACCCGGCAAGC
AGCCACAGAGATCTACGAACCCGGTAGGTCTCTTTGGTGCAGGATAGGGTATGACCGATGTGGGGAGGACGATCATGACG
AGCTAGGGTTTATGATACCGCCTGGCCTCTCCAGCGAAGGCCACTTGACTGGTGTTTACGCCTGGTTGGCGTTCTTGTCC
TTCAGCTACACGGCCCAGTTCCATCCCGAGATATTCGGGATAGGGAATGTGAGTCGAGTTTATGTTGACATCAAACATCA
ACTCATCTGCGCCGAACATGACGGGCAGAACACCACCTTGCCTCGTCATGACAACATTTCAGCCGTGTTTCAGACCTATT
ACCAACATCAAGTCGACGGCGGCAATTGGTTTCACCTAGAATGGCTTCGTCCCTTCTTTTCCTCGTGGTTGGTTTTAAAT
GTCTCTTGGTTTCTCAGGCGTTCGCCTGCAAACCATGTTTCAGTTCGAGTCTTGCAGATATTAAGACCAACACCACCGCA
GCGGCAAGCTTTGCTGTCCTCCAAGACATCAGTTGCCTTAGGCATCGCGACTCGGCCTCTGAGGCGATTCGCAAAATCCC
TCAGTGCCGTACGGCGATAGGGACACCCGTGTATGTTACCATCACAGCCAATGTGACAGATGAGAATTATTTACATTCTT
CTGATCTCCTCATGCTTTCTTCTTGCCTTTTCTATGCTTCTGAGATGAGTGAAAAGGGATTTAAGGTGGTATTTGGCAAT
GTGTCAGGCATCGTGGCTGTGTGTGTCAATTTTACCAGCTACGTCCAACATGTCAAGGAGTTTACCCAACGCTCCCTGGT
GGTCGACCATGTGCGGTTGCTCCATTTCATGACACCTGAGACCATGAGGTGGGCAACTGTTTTAGCCTGTCTTTTTGCCA
TTCTGTTGGCAATTTGAATGTTTAAGTATGTTGGAGAAATGCTTGACCGCGGGCTGTTGCTCGCGATTGCTTTCTTTGTG
GTGTATCGTGCCGTTCTGTTTTGCTGTGCTCGCCAACGCCAGCAACGACAGCAGCTCCCATCTACAGCTGATTTACAACT
TGACGCTATGTGAGCTGAATGGCACAGATTGGCTAGCTAACAAATTTGATTGGGCAGTGGAGAGTTTTGTCATCTTTCCC
GTTTTGACTCACATTGTCTCCTATGGTGCCCTCACTACCAGCCATTTCCTTGACACAGTCGCTTTAGTCACTGTGTCTAC
CGCCGGGTTTGTTCACGGGCGGTATGTCCTAAGTAGCATCTACGCGGTCTGTGCCCTGGCTGCGTTGACTTGCTTCGTCA
TTAGGTTTGCAAAGAATTGCATGTCCTGGCGCTACGCGTGTACCAGATATACCAACTTTCTTCTGGACACTAAGGGCAGA
CTCTATCGTTGGCGGTCGCCTGTCATCATAGAGAAAAGGGGCAAAGTTGAGGTCGAAGGTCATCTGATCGACCTCAAAAG
AGTTGTGCTTGATGGCTCCGTGGCAACCCCTATAACCAGAGTTTCAGCGGAACAATGGGGTCGTCCTTAGATGACTTCTG
TCACGATAGCACGGCTCCACAAAAGGTGCTTTTGGCGTTTTCTATTACCTACACGCCAGTGATGATATATGCCCTAAAGG
TGAGTCGCGGCCGACTGCTAGGGCTTCTGCACCTTTTGATCTTCCTGAATTGTGCTTTCACCTTCGGGTACATGACTTTC
GCGCACTTTCAGAGTACAAATAAGGTCGCGCTCACTATGGGAGCAGTAGTTGCACTCCTTTGGGGGGTGTACTCAGCCAT
AGAAACCTGGAAATTCATCACCTCCAGATGCCGTTTGTGCTTGCTAGGCCGCAAGTACATTCTGGCCCCTGCCCACCACG
TTGAAAGTGCCGCAGGCTTTCATCCGATTGCGGCAAATGATAACCACGCATTTGTCGTCCGGCGTCCCGGCTCCACTACG
GTCAACGGCACATTGGTGCCCGGGTTAAAAAGCCTCGTGTTGGGTGGCAGAAAAGCTGTTAAACAGGGAGTGGTAAACCT
TGTCAAATATGCCAAATAACAACGGCAAGCAGCAGAAGAGAAAGAAGGGGATGGCCAGCCAGTCAATCAGCTGTGCCAG
ATGCTGGGTAAGATCATCGCTCAGCAAAACCAGTCCAGAGGCAAGGGACCGGGAAAGAAAAATAAGAAGAAAAACCCGGA
GAAGCCCCATTTTCCTCTAGCGACTGAAGATGATGTCAGACATCACTTTACCCCTAGTGAGCGGCAATTGTGTCTGTCGT
CAATCCAGACCGCCTTTAATCAAGGCGCTGGGACTTGCACCCTGTCAGATTCAGGGAGGATAAGTTACACTGTGGAGTTT
AGTTTGCCTACGCATCATACTGTGCGCCTGATCCGCGTCACAGCATCACCCTCAGCATGATGGGCTGGCATTCTTGAGGC
```

*Fig. 1D-5*

ATCTCAGTGTTTGAATTGGAAGAATGTGTGGTGAATGGCACTGATTGACATTGTGCCTCTAAGTCACCTATTCAATTAGG
GCGACCGTGTGGGGGTGAGATTTAATTGGCGAGAACCATGCGGCCGAAATTAAAAAAAAAAAAAAAAAAAAAAAAAAAAA
AAAAAAAAAAAAAAAA

Fig. 1E-1

```
>MN184A_DQ176019.seq
ATGACGTATAGGTGTTGGCTCTATGCCACGACATTTGTATTGTCAGGAGCTGTGACCACTGGCACAGCCCAAAGCTTGCT
GCACAGAAACACCCTTCTGTGACGGCCTCCTTCAGGGGAGTTTAGGGGTTTATCCCTAGCACCTTGTTTCTGGAGTTGCA
CTGCTTTACGGTCTCTCCACCCCTTTAACCATGTCTGGGATTCTTGATCGGTGCACGTGCACCCCCAATGCCAGGGTGTT
TATGGCAGAGGGCCAAGTCTACTGCACACGATGTCTCAGTGCACGGTCCCTCCTTCCCCTGAATCTCCAAGTCCCTGAGC
TCGGAGTGTTGGGCTTGTTTTATAGGCCCGAAGAGCCGCTCCGGTGGACGTTGCCACGCGCATTCCCCACTGTTGAGTGC
TCCCCTGCTGGGGCTTGTTGGCTTTCTGCAATTTTTCCAATTGCACGAATGACCAGTGGAAACCTGAACTTTCAACAAAG
ATTAGTGCGGGTCGCAGCTGAGCTTTACAAAGCCGGCTGCCTCACCCCTATAGTCCTAAAGAATCTACAAGTCTATGAAC
GGGGTTGCCGATGGTACCCCATCGTTGGACCTGTCCCTGGAGTTGCCGTTTTCGCCAACTCCCTACATGTGAGTGATAGA
CCTTTCCCAGGGGTACTCACGTGCTAACCAACCTGCCGCTCCCGCAGAGACCTAAGCCTGAAGATTTTTGCCCCTTTGA
GTGTGCTATGGCTGMCGTCTATGAYATTGGTCATGACGCCGTTATGTTCGTGGCCGAAGGGAGAGTCTCCTGGGCTCCGC
GTGGTGGGGGAAAAGGAAAATTTGAAACTGTTCCCGAGGAGTTGAGGTTGATTGCAGAGCAACTTTATACCTCCTTCCCG
CCCCACCACGTGGTGGACATGTCGAAATTCACCTTTACGGCCCCTGAGTGTGGTGCTTCCATGCGAGTCGAACGCCATTA
TGGCTGCCTCCCCGCCGGCACTGTCCCTGACGGCAATTGCTGGTGGAGTTTGTTTAGCTCGCTCCCATTGGAAATCCAGT
ACAAAGAAATTCGCCACGCCACCCAATTTGGCTATCAAACTAAGCATGGCGTTGCTGGCAAGTACCTACAGCGGAGGCTG
CAAGTTAATGGTCTCCGAGCAGTGGTTGACTCGAATGGACCTATCGTCATACAGTACTTCTCTGTTAAGGAGAGCTGGAT
CCGCCACGTGAAACTGGCGGAAGAGTTTGACTACCCTGGGTTTGAGGATCTCCTCAGGATAAGAGTCGAGCCCAACACGT
TGCCATTGTCCAACAAGGACGAGAAAATCTTCCGGTTTGGTGGGTGCAAGTGGTACGGTGCTGGGAAGAGGGCAAGGAGG
GCACGTGCAAGTGCAGTCACCGCAGTCGCCGGTCACGCTCCGCCTACTCGTGAAACCCAGCAAGCCAAGAAACACGAGGC
TGCTAGTGCCAACAAGGCTGAGCTTCTTGAACGCTACTCCCCGCCTGCTGAAGGGAATTGCGGCTGGCACTGTATTTCCG
CCATCGCCAATCGGATGGTAAATTCTAAGTTTGAGACTGCCCTTCCCGAAAGAGTGAGATCCCCAGAAGACTGGGCTACT
GATGAGGATCTTGTGAATACTATCCARATCCTCAGGCTCCCYGCGGCCTTAGACAGGAACGGCGCCTGTGCAAGCGCCAA
GTACATCCTTAAGCTGGAAGGTGAGCACTGGACTGTTTCAGTGATTCCCGGAATGYCCCCTTCCTTGCTCCCCCTTGAAT
GCGTTCAGGGTTGCTGTGAGCATAAGGGTAATCTTGGTTCTCCGAACGCGGTCGGGGTTTTTGGATTCGACCCTGCCAGC
CTTGACCGACTTGCTGGGGTGATGCACCTGCCCAGCAGTGCCATCCCAGCCGCTCTGGCCGAGTTGTCTGGCGACCTTGA
TCGTCCAACTTCCCCGGCCGCCACTGTGTGGACTGTCTCGCAGTTTTATGCTCGTCATAGTGGAGGRGAGCATCCTGATC
AAAAGTGTTTAAAAAAAATTATCAGTCTCTGTGAGGTGATCGAGAGTTGTTGCTGTTCTCRGAACAAAACTAACCGGGTC
ACCCCGGAAGAGGTCACAGCAAAGATTGATCTGTACCTTTTTGGTGCAGCAAGTCTTGAAGAATGCTTGGCCAGGCTTGA
RAAAGCTCGCCCGCCAAGCGTATTARACACCTCCTTTGATTGGGATGTTGTGCTCCCTGGTGTTGGGRCGGCTGCTCAAG
CAGCAAAACTGCCCCTCACCAACCAGCGTCACGCTCTAGCCACTGTTGTGACYCAAAGGTCTTTGCCGAAATTTCAACCT
CGAAAAGCGGAGTCTGTCAAGAGCCTACCAGAGAGCAGGCCACTCCCTGCCCCGCGCAAAAAGATTAGGTCCAGGTGTGG
TAGTCCGATTTCATTGGGCGGCAATCTCCCTGACAGCCAGGAAGACTTGGCCGGTGGTTCCTTTGATTTCCCAACCCTAC
CTGAGTTGGTGGTAAGCTCGAGTGAGTCTGTGCCTGTCCCTGCACCGCGCAGGGTTGTGTCCCGATTAGTGTCGTCTCCG
ATAGTGTCGACCCCTGTGCCCGCACCACGACGTGGGCTTCGGCAGGTGGAGGGAATGAATTTGGCGGCAGTGACTCTAGC
GTGCCAGGACGAGCCCCTCGATTTGTCTGCGTCCTCGCAGACTGAATATGAGGCGTCCCCCTTGGCATTGCCGCTGAGTG
AGGATGTCCTGGCGGTGGAGAGACGAGAAGTTGAAGAAGTCCTGAGCGGAATATCGGGCATGTCAGATGACATCAGGTTG
GCGCCCGTGTCATCAAGTAGCTCCCTGTCAAGCATAGAGATCACACGTCCAAAGTACTCAGCTCAAGCCATCATTAACTC
AGGTGGGCCCTGTTGTGGGCACCTCCAGGAGGTGAAAGAGAAATACCTTAATGTGATGCGTGAGGCATGTGATGCGACCA
AGCTTGATGACCCTGCCACGCAAGAATGGCTTTCCCGTATGTGGGATAGGGTAGACATGCTAACCTGGCGCAACACGTCC
ATTTTTCAGGCGCCTTTCACCTTGGCTGACAAGTTTAAGTCCCTCCCGAAGATGATACTCGAAACACCGCCGCCCTACCC
TTGTGGGTTTGTGATGATGCCCCGCACGCCTGCACCTTCTGTAGGTGCGGAGAGCGACCTCACCGTTGGCTCAGTTGCTA
CTGAAGATGTCCCGCGCATTCTCGGGAAGGTACAAGGTGTTGGCGAAACGACCGACCAGGGACCCTTGGCACTCTTCGCA
GATGAATTGGCAGATGACCAACCTGCTAGAGAACCCCGGACACAAACCCCTCCTGCAAGCGCAGGTGGCGCCGGCTTAGT
TTTGGATTCTGGAGGGTCGCCGGAGCTCACTGACCTGCCGCTTCCARACGGTACAGACGCGGGCGGAGGGGGACCGTTAC
ACACGGTCAAGAAGAAAGCTGAGAGGTGCTTTGACCAGCTGAGCCGTCGGGTTTTGACATTGTCTCCCATCTCCCTGTC
TTCTTCTCACGCCTTTTCAAGCCTGACAGTCACTACTCTTCGGGTGACTGGAGTTTTGCAGCTTTTACTTTATTGTGCCT
CTTTCTATGTTACAGTTACCCGGCCTTTGGTGTTGCTCCCCTATTGGGTGTATTTTCTGGGTCTTCTCGGCGCGTTCGCA
TGGGGGTTTTTGGCTGCTGGTTGGCTTTCGCTGTTGGTTTGTTCAAGCCTGCACCCGACCCAGTCGGTGCTGCTTGTGAG
```

*Fig. 1E-2*

```
TTTGATTCGCCAGAGTGTAGAGACATCCTTCATTCTTTTGAGCTCCTGCAACCTTGGGATCCTGTTCGCAGCCTTGTGGT
GGGACCCGTCGGTCTCGGTCTTGCCATTATTGGCAGGTTACTGGGCGGGGCACGCTACGTCTGGCTGCTTTTGCTTAGGC
TTGGCATCGTTTCAGACTGTATCTTGGCTGGAGCTTACGTGCTTTCGCAAGGTAGGTGTAAAAAGTGTTGGGGATCTTGT
ATAAGAACTGCCCCCAGTGAGGTCGCCTTCAATGTGTTTCCCTTCACACGTGCAACCAGATCGTCACTTGTCGACCTGTG
CGACCGGTTTTGTGCGCCCAAGGGCATGGACCCCATCTTCCTCGCCACTGGATGGCGCGGATGCTGGTCCGGCCAGAGCC
CCGTTGAGCAACCCACTGAGAAACCCATTGCATTCGCCCAGTTGGATGAGAAGAAAATCACGGCAAGGACTGTGGTTGCC
CAACCTTATGACCCCAACCAAGCTGTGAAGTGCTTACGAGTCTTGCAGGCGGGTGGGGCGATGGTGGCTGAGGCGATTCC
AAAAGTGGTTAAGGTCTCTGCTGTCCCATTTCGAGCCCCCTTCTTCCCCACCGGAGTGAAAGTTGATCCTGAATGCAGGG
TCGTGGTTGACCCAGACACCTTCACAACTGCTCTCCGGTCCGGCTACTCCACCACAAACCTCATTCTTGGTGTGGGGGAT
TTTGCCCAGCTGAATGGGTTGAAAATCAGACAAATTTCCAAGCCTTCAGGAGGAGGCCCATACCTCATGGCGGCCTTACA
TGTCGCTTGCTCGATGGCCTTGCACATGCTCGTTGGGATTTATGTTACCGCGGTGGGTTCTTGTGGTTCTGGCACTAACG
ATCCGTGGTGCACTAACCCGTTTGCCGTCCCTGTCTACGGGCCTGGCTCTCTTTGCACGTCCAGGTTGTGCATCTCCCAG
CATGGCCTTACTCTGCCTTTAACAGCGCTTGTGGCGGGGTTTGGTATTCAGGAAGTTGCTTTGGTTGTTTTAATCTTTGC
TTCCATCGGGGTATGGCTCACAGGTTGAGTTGCAAGGCCGATGTGCTGTGCATTCTGCTTGCAATTGCCAGCTATGTTT
GGGTACCCTTCACCTGGTTGCTTTGTGTGTTTCCTTGCTGGTTGCGCTGGTTTTCTTTGCATCCCCTCACCATTCTATGG
TTGGTGTTTTTTTTGATTTCTGTGAACATGCCCTCAGGAATCTTGGCTTTAGTGTTGTTGATCTCTCTCTGGCTCCTTGG
TCGCTATACCAATGTCGCTGGCCTTGTCACCCCTTATGACATTCACCATTACACCAACGGCCCCCGCGGCGTTGCCGCCT
TGGCCACTGCCCCGGATGGGACCTATTTGGCTGCTGTCCGCCGCGCTGCGTTGACTGGCCGTACCATGCTGTTTACCCCG
TCTCAACTTGGGTCACTCCTTGAGGGCGCCTTTAGAACCCAAAAGCCTTCACTGAATACCGTCAATGTGGTTGGGTCCTC
CATGGGCTCCGGCGGGGTGTTCACCATTGACGGGAAAATTAAATGCGTGACCGCCGCACATATCCTCACGGGTAACTCTG
CTAGGGTCTCTGGGGTTGGCTTCAATCAAATGTTGGATTTTGATGTAAAAGGGGATTTTGCCATAGCCGATTGTCCGGGT
TGGCAAGGAGTCGCTCCCAAGTCCCAGATCTGCAAGGATGGGTGGACTGGCCGCGCTTATTGGCTAACGTCCTCTGGCGT
CGAACCCGGCGTCATTGGTAGGGGATTCGCCTTTTGTTTCACCGCGTGCGGCGATTCCGGGTCCCCAGTGATCACCGAGG
CCGGAGAGCTTGTCGGAGTCCACACGGGATCAAACAAAACAAGGAGGAGGCATTGTCACGCGCCCTTCAGGCCAGTTTTGT
AATGTGACACCCACCAAACTAAGTGAATTGAGTGAATTCTTCGCCGGACCCAGGGTCCCGCTTGGTGATGTGAAGGTTGG
CAACCACATAATCAAAGATACAGATGAGGTGCCCTCAGATCTTTGCGCCTTGCTTGCTGCCAAGCCCGAGTTGGAAGGAG
GCCTCTCCACCGTTCAACTTCTGTGCGTGTTTTTTCTCCTATGGAGAATGATGGGACATGCCTGGACGCCCTTGGTTGCT
GTTGGTTTTTTCATCTTGAATGARATCCTCCCAGCGGTCCTGGTCCGGAGTGTTTTCTCCTTTGGAATGTTYGYKCTRTC
YTGGCTCACGCCATGGTCTGCGCAAGTTCTGATGATCAGGCTTCTGACAGCAGCTCTTAACAGGAACAGATGGTCACTTG
CCTTTTTCAGCCTCGGTGCAGTGACCGGTTTTGTCGCAGATCTTGCGGCCACTCAGGGGCATCCGTTGCAGGCAGTGATG
AATTTGAGCACCTATGCATTCCTGCCTCGGATGATGGTTGTGACCTCACCAGTCCCAGTGATCACGTGTGGTGTCGTGCA
CCTACTTGCCATCATTTTGTACTTGTTTAAGTACCGTGGCCTGCACCATATCCTTGTTGGCGATGGAGTGTTCTCTGCGG
CTTTCTTCTTGAGATACTTTGCCGAGGGAAAGTTGAGGGAAGGGTGTCGCAATCCTGCGGAATGAATCATGAGTCTCTG
ACTGGTGCCCTCGCTATGAGACTCAATGACGAGGACTTGGATTTCCTTATGAAATGGACTGATTTTAAGTGCTTTGTTTC
TGCGTCCAACATGAGGAATGCGGCGGGTCAGTTTATCGAGGCCGCTTATGCGAAAGCGATCAGGGTGGAACTTGCCCAGT
TAGTGCAGGTCGACAAGGTTCGGGGTGTTTTAGCCAAACTTGAAGCTTTTGCTGACACCGTGGCGCCCCATCTTTCACCC
GGCGACATTGTTGTTGTTCTTGGTCATACGCCCGTTGGCAGCATCTTTGACTTAAAGATTGGCRATGCCAAGCACACCCT
ACAAGCCATCGAGACCAGAGTCCTTGCTGGGTCCAGGATGACCGTGGCGCGTGTCGTTGATCCGACTCCCGCGCCGCCAC
CCGTACCCGTGCCCGTTCCTCTCCCACCGAAAGTTTTAGAGAACGGCCCCAGTGCCTGGGGGGATGAAGACCGCCTGAAC
AAAAAGAAGCGGCGCAAGATGGAAGCCGTTGGCGTTTACGTCATGGGCGGGAAAAAGTACCAGAAATTTTGGGATAAGAA
TTCTGGTGATGTGTTCTATGAGGAAGTCCACGACAACACAGATGCGTGGGAATGCCTTAGAGCTGACGACCCTGCCGACT
TGGATCCTGAGAGGGGAACCTTGTGTGGACACGTCACCATAGAGAATAGGCCTTACCATGTTTACGCCTCCCCGTCTGGT
AGGAAGTTCCTGGTCCCTGCCGACCCAGAGAATGGGAAAGCCCAGTGGGAAGCTGCAAAGCTTTCCATAGAGCAGGCCCT
TGGTATGATGAACGTTGACGGCGAGCTGACCGCCAAAGAACTGGAGAAATTGAAGAGAATAATTGACAAACTCCAGGGCC
TGACTAAGGAGCAGTGTTTAAACTGTTAGCCGCCAGCGGCTTGACCCGCTGTGGTCGCGGCGGCTTGGTTATTACTGAGA
CAGCGGTAAAAATAGTCAGATTCCACAATCGGACCTTCACCCTGGGGCCTGTGAATTTGAAAGTGGCCAGCGAAGTTGAG
TTGAAAGACGCCGTCGAGCACAACCAACACCCGGTTGCAAGACCAGTTGACGGTGGCGTTGTGCTCCTGCGCTCTGCAGT
TCCTTCGCTTATAGACGTCTTGATCTCCGGTGCCGACGCATCTCCCCAGTTGCTCGCCCATCACGGTCCAGGAAACACTG
```

*Fig. 1E-3*

```
GGATTGATGGCACGCTCTGGGATTTTGAGTCCGTAGCCACTAAAGAGGAAGTCGCACTTAGTGCACAAATAATACAGGCT
TGTGGCATTAGGCGTGGCGATGCTCCTGAGATTGGCCTCCCTTACAAGCTGCACCCTGTTAGGGACAACCCTGAACGTGT
AAAAGGGGTTTTGAAAAACACAAGGTTTGGAGACATACCTTACAAGACCCCTAGCGACACTGGGAGCCCAGTACATGCGG
CCGCCTGCCTTACGCCTAATGCCACCCCGGTGACTGATGGGCGCTCCGTCTTGGCCACGACTATGCCCTCCGGGTTTGAG
TTGTATGTGCCGACCATTCCAGCGTCTGTCCTTGATTACCTTGATTCCAGGCCAGACTGCCCTAAACAGTTGACGGAGCA
CGGGTGTGAAAATGCTGCATTGAGAGACCTCTCCAAATATGACTTGTCCACCCAAGGTTTTGTTTTGCCCGGAGTCCTCC
GCCTCGTGCGGAAATACTTGTTTGCCCACGTGGGCAAGTGCCCACCTGTCCATCGGCCCTCCACCTACCCGGCCAAGAAT
TCCATGGCTGGAATAAACGGGAATAGGTTCCCGACCAAGGACATTCAGAGCATCCCTGAGATCGACGTTCTGTGTGCACA
GGCTGTACGAGAGAACTGGCAGACCGTTACCCCTTGCACCCTCAAGAAGCAGTATTGCGGGAAGAAGAAAACCAGGACCA
TACTCGGTACCAATAACTTCATTGCGCTGGCCCACCGGGCAGCACTGAGTGGTGTCACCCAGGGCTTCATGAAAAAGGCG
TTTAACTCGCCCATCGCCCTCGGGAAGAACAAATTCAAGGAGCTACAGACTCCGGTCCTGGGCAGATGTCTTGAGGCTGA
TCTTGCCTCTTGCGATCGGTCCACTCCCGCGATTGTCCGCTGGTTTGCCGCCCATCTCCTTTATGAACTTGCCTGCGCTG
AGGAGCACCTACCGTCGTATGTGCTGAATTGCTGCCATGACCTATTGGTCACGCAGTCCGGTGCGGTGACTAAGAGAGGT
GGCCTGTCATCTGGTGATCCGATCACCTCTGTATCCAACACCATTTACAGTCTGGTAATTTATGCGCAGCACATGGTGCT
CAGTTACTTCAAAAGTGGTCACCCACATGGTCTCCTGTATCTCCAGGACCAGCTAAAGTTTGAGGACATGCTTAAGGTTC
AGCCCCTGATYGTCTACTCGGATGATCTTGTGCTGTATGCCGAGTCCCCCACCATGCCAAACTACCACTGGTGGGTTGAG
CATCTGAACTTGATGCTAGGGTTTCAGACGGACCCAAAGAAGACAACCATTACTGACTCGCCATCTTTTCTGGGCTGTAG
GATAATGAATGGGCGTCAGCTAGTCCCAAACCGTGACAGGATTCTCGCAGCTCTTGCCTACCACATGAAGGCGAATAATG
TTTCTGAGTACTACGCCTCCGCTGCTGCAATACTCATGGACAGTTGTGCTTGTCTGGAGTACGACCCTGAATGGTTTGAA
GAACTTGTGGTTGGAATGGCGCTATGCGCCCGCAAGGACGGCTATAGCTTCCCCGGCCCGCCGTTCTTCTTATCCATGTG
GGAGAAACTTAAGTCCAATTATGAGGGGAAGAAGTCAAGGGTATGTGGGTACTGCGGAGCTTCGGCCCCGTATGCCACTG
CCTGTGGTCTTGACGTCTGTGTTTACCACACTCACTTTCACCAGCATTGTCCAGTCATAATCTGGTGTGGCCACCCTGCA
GGTTCCAGGTCCTGTGATGAGTGCAAATCCCCCATAGGGAAAGGCACAAGCCCTCTGGATGAGGTTTTGAGACAAGTCCC
GTATAAGCCTCCACGGACCGTCCTCATGCATGTGGAGCAGGGCCTCACCCCCCTTGACCCAGGCAGATATCAGACCCGCC
GTGGGTTGGTTGCCGTTAGGCGCGGGATCAGGGGAAATGAAGTTGACCTACCAGATGGTGATTATGCTAGCACCGCCTTA
CTCCCAACCTGTAAAGAGATCAACATGGTTGCTGTTGCTTCTAATGTGTTGCGCAGCAGATTTATCATCGGTCCACCCGG
TGCTGGGAAAACATACTGGCTCCTTCAACAGGTCCAGGATGGTGATGTCATATACACACCGACCCATCAGACCATGCTTG
ACATGATCAAAGCTTTRGGGACGTGCCGGTTTAACGTCCCGGCAGGCACAACGCTGCAATTCCCCGTCCCCTCCCGCACC
GGTCCGTGGGTTCGCATCCTGGCCGGCGGGTGGTGTCCTGGCAAAAACTCCTTCCTGGACGAAGCTGCGTATTGTAATCA
TCTTGATGTCTTGAGGCTTCTTAGCAAAACCACTCTCACCTGTTTGGGGACTTCAAACAACTCCACCCAGTGGGTTTTG
ATTCTCATTGCTATGTCTTTGACATTATGCCTCAGACTCAATTGAAGACCATCTGGAGATTTGGACAGAACATCTGTGAT
GCCATCCAACCAGACTACAGAGACAAGCTTATGTCCATGGTCAACACAACTCGTGTAACTTATGTGGAAAAACCTGTCAA
ATATGGGCAAGTCCTCACCCCCTTACCATAGGGACCGAGAGGATAGCGCCATTACCATTGACTCCAGTCAAGGCGCCACAT
TTGATGTGGTTACACTGCATTTGCCCACGAAAGATTCACTCAACAAACAAAGGGCCCTTGTTGCTATTACCAGGGCAAGA
CATGCCATCTTTGTGTATGACCCATATAGGCAACTGCAGAGCCTATTTGATCTTCCTGCAAAAAGCACGCCCGTCAACTT
GGCCGTGCACCACGATGGGCAACTGATTGTGCTAGATAGAAATAACAAAGAATGCACGGTTGCCCAAGCTCTGGGTAATG
GTGACAAATTTAGGGCCACAGACAAGCGCGTTGTGGATTCTCTCCGCGCCATTTGTGCTGACCTAGAAGGGTCGAGCTCT
CCACTCCCCAAGGTTGCACATAATTTGGGGTTTTATTTCTCACCTGATTTGATACAGTTTGCCAAGCTTCCAATAGAACT
TGCGCCACACTGGCCAGTAGTGACGACCCAAGACAATAAAAACTGGCCAGATCGGCTGGTTGCCAGCCTACGCCCTATTC
ACAAACATAGCCGTGCGTGTATCGGTGCCGGCTATATGGTGGGCCCCTCGGTGTTTTAGGCACCCCTGGGGTTGTGTCA
TACTATCTTACAAAATTTGTTAAGGGCGAGGCTCAAGTGCTTCCGGAAACGGTCTTCAGTACCGGCCGAATTGAGGTGGA
TTGCCGGGAATATCTTGACGACCGGGAGCGGGAAGTTGCAGCGTCCCTCCCACACGCCTTTATCGGCGACGTCAAAGGCA
CTACCGTCGGAGGGTGTCATCACATCACCTCCAAATACCTTCCGCGCTTCCTCCCCAAGGAATCAGTTGCGGTAGTCGGG
GTTTCAAGCCCCGGAAAAGCAGCGAAAGCAGTGTGTACATTGACAGATGTGTACCTCCCAGACCTTGAAGCTTACCTCCA
TCCTAAGACCCTGTCCAAGTGCTGGAAAATGATGTTGGACTTCAAAGAAGTTCGGCTGATGGTCTGGAAGGACAAGACGG
CCTATTTCCAACTCGAAGGTCGCCATTTCACCTGGTATCAACTTGCTAGCTATGCCTCGTACATCCGTGTTCCTTTAAAC
TCCACGGTGTACCTGGACCCCTGCATGGGCCCCGCCCTTTGCAACAGAAAAGTTGTTGGGTCCACTCATTGGGGAGCTGA
CCTCGCAGTCACCCCTTATGATTATGGGGCAAGAATTATTTTGTCTAGTGCGTACCATGGTGAGATGCCTCCTGGGTACA
```

Fig. 1E-4

```
AGATTCTGGCGTGCGCGGAGTTCTCGCTGGACGACCCAGTCAGATACAAGCACACTTGGGGGTTTGAGTCGGATACAGCG
TACTTGTACGAGTTCACTGGAAACGGTGAGGACTGGGAGGATTATAACGACGCGTTTCGTGCGCGACAGAAAGGAAAGAT
TTACAAGGCCACTGCCACCAGCCTGAAGTTCCATTTTCCTCCGGGTCATACCGTTGAACCAACTTTGGGCCTAGACTGAA
ATGAAATGGGGGCTGTGCAGAGCCTATTTGATAAAATTGGCCAACTGTTTGTGGACGCTTTCACGGAGTTCTTGGTGTCC
ATTGTTGATATCATCATATTTTTGGCCATTTTGTTCGGCTTCACAATCGCCGGTTGGCTGGTGGTCTTTTGCATCAGATT
GGTTTGCTCCGCGATACTCCGTTCGCGCTCTGCCGTTCACCCTGAGCAATTACAGAAGATCCTATGAGGCATTTCTCTCC
CAGTGCCGGACGGAYATTCCCACCTGGGGAACTAAACATCCCTTGGGGATGCTCTGGCACCACAAGGTGTCGACCCTAAT
TGATGAAATGGTGTCGCGTCGAATGTACCGCATCATGGAACAAGCAGGGCAGGCTGCCTGGAAACAGGTGGTGACCGAGG
CAACGTTGTCTCGTATTAGTAGCTTGGATGTGGTGGCTCATTTCCAGCACCTTGCCGCCATAGAAGCCGAGACTTGTAAA
TACTTGGCCTCCCGGCTGCCAATGCTGCACAACCTGCGCATGACAGGGTCAAATGTAACCATAGTGTATAATAGCTCTCT
AGAACAGGTGTTTGCTGTTTTCCCGACCCTCAGTTCCCGGCCAAAGCTTCATGATTTTCGGCAATGGCTAATAGCTGTGC
ATTCCTCCATATTCTCTTCTGTTGCGGCTTCCTGTACCCTTTTCGTCGTGCTGTGGTTGCGGCTTCCAATAATACGTACT
GTTTTTGGTTTCCACTGGTTAGGGGCAATTTTTCCTTCGAGCTCACAGTGAACTACACGGTGTGTCCTCCCTGCCTCACC
CGGCAGGCGGCCGCAGAGATCTACGAACCTAGTGGGTCTCTTTGGTGCAGGATAGGGCACGATCGATGCTCGGAGGACGA
TCACGACGAGCTAGGATTTCTGGTGCCGCCTGGCCTCTCCAGCGAAGGCCACTTGACCAGTGTTTACGCCTGGTTGGCGT
TCTTGTCCTTCAGTTACACGGCCCAGTTTCACCCCGAGATATTCGGGATAGGGAATGTGAGTAAAGTTTATGTTGACATC
AAGCATCAATTTATTTGCGCTGTTCATGACGGGCAAAACACCACCTTGCCTCGCCATGACAACGTCTCAGCCGTGTTCCA
GACTTATTACCAGCATCAGGTCGACGGCGGCAATTGGTTTCACCTGGAATGGCTGCGCCCCTTCTTCTCCTCCTGGTTGG
TTTTGAACGTCTCTTGGTTTCTCAGGCGTTCGCCTGTAAGCCGTGTTTCAGTTCGAGTCTCTCAGACATTAAGACCAACA
CCACCGCAGCTGCAGGCTTTGCTGTCCTCCAAGACATCAGTTGTCTTAGGCATGGCCACTCGTCCTCTGAGGCGACTCGC
AAAAGCCGTCAATGTCGCACGGCGATAGGAACGCCCGTATACATTACTGTCACAGCCAATGTAACAGATGAGAATTATTT
GCATTCCTCTGACCTTCTCATGCTTTCCTCTTGCCTTTTCTACGCTTCCGAGATGAGTGAAAAGGGATTTGAAGTGATAT
TTGGCAATGTGTCAGGCATAGTGGCTGTGTGTCAACTTTACCAGCTATGTCCAACATGTCAAGGAGTTCACCCAGCGC
TCCTTGGTGGTTGACCATGTGCGGTTACTTCATTTTATGACACCTGAGACTATGAGGTGGGCGACCGTTTTAGCCTGTCT
TTTTGCCATTCTGTTGGCCATTTGAATGTTCAGATATGTTGGGGAAATGCTTGACCGCGGGCTATTGCTCGCAATTGCTT
TTTTTTGTGGTGTATCGTGCCGTTCTGTCTTGCTGCGCTCGTCAACGCCGACAGCAACAGCAGCTCCCATTTACAGTTGAT
TTATAAMTTAACGATATGTGAGCTGAATGGCACAGACTGGCTGAACAATCATTTTAGTTGGGCAGTGGAGACTTTCGTTA
TCTTTCCTGTGTTGACTCATATTGTTTCCTACGGCGCCCTCACTACCAGCCACCTCCTTGACACGGTCGGCCTGATCACT
GTGTCCACCGCCGGATACTGCCATAAGCGGTATGTCTTGAGTAGCATCTATGCTGTCTGCGCCCTGGCTGCGCTGATTTG
CTTCGTCATCAGGTTGACGAAAAATTGTATGTCCTGGCGCTACTCATGTACCAGATATACCAACTTTCTTCTGGACACCA
AGGGCAGACTCTATCGCTGGCGGTCACCCGTCATCATAGAGAAAGGGGTAAAATTGAGGTTGGAGGTGACCTGATCGAC
CTCAAGAGAGTTGTGCTTGATGGTTCCGCGGCAACCCCTGTAACCAAAGTTTCAGCGGAACAATGGGGTCGTCCTTAGAC
GACTTCTGCAATGACAGCACGGCTCCACAAAAGGTGATCTTGGCATTTTCTATCACCTACACACCAGTGATGATATATGC
CCTAAAGGTGAGTCGTGGCCGGCTGCTAGGGCTTTTACACCTTTTGATTTTTYTAAACTGTGCTTTTACCTTCGGGTATA
TGACATTTGTGCACTTTCAGAGCACAAACAGAGTTGCACTCACTATGGGAGCAGTAGTCGCGCTCCTTTGGGGGGTGTAC
TCAGCTATAGAAACCTGGAAATTCATCACTTCCAGATGCCGTTTGTGCTTGCTAGGCCGCAAGTACATTCTGGCCCCTGC
CCACCACGTTGAGAGTGCCGCAGGCTTTCATCCGATTGCGGCAAGTGATAACCACGCATTTGTCGTCCGGCGTCCCGGTT
CCACTACGGTTAACGGCACATTGGTGCCCGGGTTGAAAAGCCTCGTGTTGGGTGGCAGAAGAGCTGTCAAACGGGGAGTG
GTAAACCTCGTTAAATATGCCAAATAACAACGGCAGGCAGCAGAAGAAAAAGAAAGGGGACGGCCAGCCAGTCAATCAGC
TGTGCCAAATGTTGGGCAGGATCATCGCCCAGCAAAACCAGTCCAGAGGTAAGGGACCGGGGAAGAAAAGTAAGAAGAAA
AGCCCGGAGAAGCCCCATTTTCCTCTCGCGACTGAAGATGACGTTAGACATCACTTCACCCCTAGTGAGCGGCAATTGTG
TCTGTCGTCAATCCAGACTGCCTTTAACCAAGGCGCTGGAACTTGTACCCTGTCGGATTCAGGGAGAATAAGTTACGCTG
TGGAGTTTAGTTTGCCTACGCATCATACTGTGCGCCTAATTCGCGTCACAGCATCACCCTCAGCATGATGAGCTGGCATT
CTTGAGACATCCCAGTGTTTGAATTGGAAGGATGTGTGGTGAATGGCACTGATTGATATTGTGCCTYTAAGTCACCTATT
CAATTAGGGCGACCGTATGGGGGTAATATTTAATTGGCGTGAACCATGCGGCCGAAATT
```

Fig. 1F-1

```
>MN184B_DQ176020.seq
ATGACGTATAGGTGTTGGCTCTATGCCACGACATTTGTATTGTCAGGAGCTGTGACCACTGGCACAGCCCAAAGCTTGCT
GCACAGAAACACCCTTCTGTGACGGCCTCCTTCAGGGGAGTTTAGGGGTTTGTCCCTAGCACCTTGTTTCTGGAGTTGCA
CTGCTTTACGGTCTCTCCACCCCTTTAACCATGTCTGGGATTCTTGATCGGTGCACGTGCACCCCCAATGCCAGGGTGTT
TATGGCAGAGGGCCAAGTCTACTGCACACGATGTCTCAGTGCACGGTCCCTCCTTCCCCTGAATCTCCAAGTCTCTGAGC
TCGGAGTGTTGGGCTTGTTTTATAGGCCTGAAGAGCCGCTCCGGTGGACGTTGCCACGCGCATTCCCCACTGTTGAGTGC
TCCCCTGCTGGGGCTTGTTGGCTTTCTGCAATTTTTCCAATTGCACGAATGACCAGTGGAAACCTGAACTTTCAACAAAG
ATTAGTGCGGGTCGCAGCTGAGCTTTACAAAGCCGGCTGCCTCACCCCTACAGTCCTAAAGAGTCTACAAGTCTATGAAC
GGGGTTGCCGCTGGTACCCCATCGTTGGACCTGTCCCTGGAGTTGCCGTTTTCGCCAACTCCCTACATGTGAGTGATAGA
CCTTTCCCAGGTGCTACTCACGTGCTAACCAACCTGCCGCTCCCGCAGAGACCTAAGCCTGAAGATTTTTGCCCCTTTGA
GTGTGCTATGGCTGCCGTCTATGACATTGGTCATGACGCCGTTATGTTCGTGGCCGAAGGGAGAGTCTCTTGGGCTCCGC
GTGGTGGGGAAAAAGGAAAATTTGAAACTGTTCCCGAGGAGTTGGGGTTGATTGCAGAGCAACTTTATACCTCCTTCCCG
CCCCACCACTTGGTGGACATGTCGAAATTCACCTTTACGGCCCCTGAGTGTGGTGCTTCCATGCGAGTCGAACGCCAGTA
TGGCTGCCTCCCCGCTGGCACTGTCCCTGACGGCAATTGCTGGTGGAGCTTGTTTAGCTCGCTCCCATTGGAAGTCCAGT
ATAAAGAAATTCGCTACGCCACCCAATTTGGCTATCAAACTAAGCATGGCGTTGCTGGCAAGTACCTACAGCGGAGGCTG
CAAATTAATGGTCTCCGAGCAGTGGTTGACTCGAATGGACCCATCGTCATACAGTACTTCTCTGTTAAGGAGAGCTGGAT
CCGCCACGTGAAACTGGCGGAAGAGTTTGACTACCCTGGGTTTGAGGATCTCCTCAGGATAAGAGTCGAGCCCAACACGT
TGCCATTGTCCAACAAGGACGAGAAAATCTTCCGGTTTGGTGGGTGCAAGTGGTACGGTGCTGGGAAGAGGGCAAGGAGG
GCACGTGCAAGTGCAGTCACCGCAGTCGCCGGTCACGCTCCGCCTACTCGTGAAACCCAGCAAGCCAAGAAACACGAAGC
TGCTAGTGCCAACAAGGCTGAGCTTCTTGAACGCTACTCCCCGCCTGCTGAAGGGAATTGCGGCTGGCACTGTATCTCCG
CCATCGCCAACCGGATGGTRAATTCYAARTTTGAAACYRCCCTTCCCGAAAGAGTGAGACCTCCAGATGACTGGGCTACT
GACGAGGATCTTGTGAATGCCATCCAAATCCTCAGACTCCCTGCGGCCTTAGACAGGAACGGTGCTTGTACTAGCGCCAA
GTACGTACTTAAGCTGGAAGGTGAGCATTGGACTGTCACTGTGACCCCTGGGATGTCCCCTTCTTTGCTCCCTCTTGAAT
GTGTTCAGGGCTGTTGTGGGCACAAGGGCGGTCTTGGTTCCCAGATGCAGTCGAGGTCTCCGGATTTGACCCTGCCTGC
CTTGACCGGCTGGCTGAGGTGATGCACCTGCCTAGCAGTGCTATCCCAGCCGCTCTGGCCGAAATGTCTGGCGATTCCGA
TCGTTCGGCTTCTCCGGTCACCACCGTGTGGACTGTTTCGCAGTTCTTTGCCCGTCACAGCGGAGGGAATCACCCTGACC
AAGTGCGCTTAGGGAAAATTATCAGCCTTTGTCAGGTGATTGAGGACTGCTGCTGTTCCCAGAACAAAACCAACCGGGTC
ACCCCGGAGGAGGTCGCAGCAAAGATTGAYCAGTACCTTTTTGGTGCAGCAAGTCTTGAAGAATGCTTGGCCAGGCTTGA
RAAAGCTCGCCCGCCAAGCGTATTARACACCTCCTTTGATTGGGATGTTGTGCTCCCTGGTGTCGGGCGGCTGCTCAAG
CAGCAAAACTGCCCCTCACCAACCAGCGTCACGCTCTAGCCACTGTTGTGACTCAAAGGTCTTTGCCGAAATTTCAACCT
CGAAAAGCGGAGTCTGTCAAGAGCCTACCAGAGAGCAGGCCCCTCCCTGCCCCGCGCAAAAAGATTGGGTCCAGGTGTGG
TAGTCCGATTTCATTGGGCGGCAATCTCCCTGACAGCCGGGAAGACTTGGCCGGTGGTTCCTTTGATTTCCCAACCCTAC
CTGAGTTGGTGGCAAGCTCGAGCGAGCCTGTGCCTGTCCCTGCACCGCGCAGGGTTGTGTCCCGATTAGTGTCGTCTCCG
ATAGTGTCGACCCCTGTGCCCGCACCACGACGTGGGCTTCGGCAGGTGGAGGGAATGAATTTGGCGGCGGTGACTCTAGC
GTGCCAGGACGAGCCCCTCGATTTGTCTGCGTCCTCGCAGACTGAATATGAGGCGTCCCCCTTGGCATTGCCGCTGAGTG
AGGATGTCCTGGCGGTGGAGAGACGAGAAGTTGAAGAAGTCCTGAGCGGAATATGGGCATGCCAGATGACATCAGGTTG
GCGCCCGTGTCATCAAGTAGCTCCCTGTCAAGCATAGAGATCACACGTCCAAAGTACTCAGCTCAAGCCATCATTAACTC
AGGTGGGCCCTGTTGTGGGCACCTCCAGGAGGTAAAAGAGAAATACCTTAATGTGATGCGTGAGGCATGTGATGCGACCA
AGCTTGATGACCCTGCCACGCAAGAATGGCTTTCCCGCATGTGGGATAGGGTAGACATGCTAACCTGGCGCAACACGTCC
ATTTTTCAGGCGCCTTTCACCTTGGCTGACAAGTTTAAGACCCTCCCGAAGATGATACTCGAAACACCGCCGCCCTACCC
TTGTGGGTTTGTGATGATGCCCCGCACGCCTGCACCTTCTGTAGGTGCGGAGAGCGACCTCACCGTTGGCTCAGTTGCTA
CTGAGGATGTCCCGCGCATTCTCGGGAATGTACAAGGTGTTGGCGAAACGACCGACCAGGGACCCTTGGCACCCTTCGCA
GACGAATTGGCAGATGACCAACTTGCTAGAGAACCCCGGACACAAACCCCTCCTGCAAGCACAGGTGGCGCCGGCTTGGT
TTCGGATTCTGGAAGGTCGCCGGAGCTCACTGACCTGCCGCTTTCAAACGGTACAGACGCGGGCGGAGGGGGGCCGTTAC
ACACGGTCAAGAAGAAAGCTGAGAGGTGCTTTGACCAGCTGAGCCGTCGGGTTTTTGACATTGTCTCCCATCTCCCTGTT
TTCTTCTCACGCCTTTTCAAGCCTGACAGTCACTACTCTTCGGGTGACTGGAGTTTTGCAGCTTTTACTTTATTGTGCCT
CTTTCTATGTTACAGTTACCCAGCCTTTGGTGTTGCTCCCCTATTGGGTGTATTTTCTGGGTCTTCTCGGCGCGTTCGCA
TGGGGGTTTTTGGCTGCTGGTTGGCTTTCGCTGTTGGTTTGTTCAAGCCTGCACCCGACCCAGTCGGTGCTGCTTGTGAG
```

Fig. 1F-2

```
TTTGATTCGCCAGAGTGTAGAGACATCCTTCATTCTTTTGAGCTTCTGCAACCTTGGGACCCTGTTCGCAGCCTTGTGGT
GGGGCCCGTCGGTCTCGGTCTTGCCATTATTGGCAGGTTACTGGGCGGGGCACGCTACGTCTGGCTGCTTTTGCTTAGGC
TTGGCATCGTTTCAGACTGTATCTTGGCTGGAGCTTATGTGCTTTCGCAAGGTAGGTGTAAAAAGTGTTGGGGATCTTGT
ATAAGAACTGCTCCCAGTGAGGTCGCCTTCAATGTGTTTCCCTTCACACGTGCAACCAGATCGTCACTTGTCGACCTGTG
CGACCGGTTTTGTGCGCCCAAGGGCATGGACCCCATCTTCCTCGCCACTGGATGGCGCGGATGTTGGTCCGGCCAGAGCC
CCATTGAGCAACCCACTGAGAAACCCATTGCGTTCGCCCAGTTGGATGAAAAGAAAATCACGGCAAGGACTGTGGTTGCC
CAACCTTATGACCCCAACCAAGCTGTGAAGTGCTTACGAGTCTTGCAGGCGGGTGGGGCGATGGTGGCTGAGGCGGTTCC
AAAAGTGGTTAAGGTCTCTGCTGTCCCATTTCGAGCCCCCTTCTTCCCCGCCGGAGTGAAAGTTGATCCTGAATGCAGGG
TCGTGGTTGACCCAGACACCTTCACAACTGCTCTCCGGTCCGGCTACTCCACCACAAACCTCATTCTTGGTATGGGGGAT
TTTGCCCAACTGAATGGGTTGAAAATCAGACAAATTTCCAAGCCTTCAGGAGGTGGTCCATACCTCATGGCGGCCTTACA
TGTCGCTTGCTCGATGGCCTTGCACATGCTCGTTGGGATTTATGTTACCGCGGTGGGTTCTTGTGGTTCTGGCACTAACG
ATCCGTGGTGCACTAACCCGTTTGCCGTCCCTGTCTACGGGCCTGGCTCTCTTTGCACGTCCAGGTTGTGCATCTCCCAG
CATGGCCTTACTCTGCCTTTAACAGCGCTTGTGGCGGGGTTTGGCATTCAGGAAGTTGCTTTGGTTGTTTAATCTTTAC
TTCCATCGGGGGTATGGCTCACAGGTTGAGCTGCAAGGCCGATGTGCTGTGTATTCTGCTTGCAATTGCCAGCTATGTTT
GGGTACCCTTCACCTGGTTGCTTTGTGTGTTTCCTTGCTGGTTGCGCTGGTTTTCTTTGCATCCCCTCACCATTCTATGG
TTGGTGTTTTTCTTGATTTCTGTGAACATGCCCTCAGGAATCTTGGCTTTAGTGTTGTTGATCTCTCTCTGGCTCCTTGG
TCGCTATACCAATGTCGCTGGCCTTGTCACCCCTTATGACATTCACCATTACACCAACGGCCCCCGCGGCGTTGCCGCCT
TGGCCACTGCCCCGGATGGGACCTATTTGGCTGCTGTCCGCCGCGCTGCGTTGACTGGCCGCACCATGCTGTTTACCCCG
TCTCAACTTGGGTCACTCCTTGAGGGCGCCTTTAGAACCCAAAAGCCTTCACTGAATACCGTCAATGTGGTTGGGTCCTC
CATGGGCTCCGGCGGGGTGTTCACCATTGACGGGAAAATTAAGTGCGTGACCGCCGCACATATCCTCACGGGTAACTCTG
CTAGGGTCTCTGGGGTTGGCTTCAATCARATGTTGGATTTTGATGTAAAAGGGGATTTTGCCATAGCCGATTGTCCGGGT
TGGCAGGGAGTCGCTCCCAAGTCCCAGTTCTGCAAGGATGGGTGGACTGGCCGCGCTTATTGGCTAACGTCCTCTGGCGT
CGAACCCGGCGTCATTGGTAGGGGATTCGCCTTTTGTTTCACCGCGTGCGGCGATTCCGGGTCCCCAGTGATCACCGAGG
CCGGAGAGCTTGTCGGAGTCCACACGGGATCAAACAAACAAGGAGGAGGCATTGTCACGCGCCCTTCAGGCCAGTTTTGT
AATGTGRCACCCAYCAARYTAAGYGAATTRAGTGAATTCTTYGCYGGRCCTARGGTCCCGCTYGGTGAYGTGAAGGTCGG
CAGCCACATAATTAAAGACATAAGCGAGGTGCCTTCAGATCTTTGTGCCTTGCTTGCTGCCAAACCTGAACTGGAAGGAG
GCCTCTCCACCGTCCAACTTCTTTGTGTGTTTTTTCTCCTGTGGAGAATGATGGGACATGCCTGGACGCCCTTGGTTGCT
GTGAGTTTCTTTATTTTGAATGAGGTTCTCCCAGCCGTCCTGGTCCGGAGTGTTTTCTCCTTTGGAATGTTTGTGCTATC
CTGGCTCACGCCATGGTCTGCGCAAGTTCTGATGATCAGGCTTCTGACAGCAGCTCTTAACAGGAACAGATGGTCACTTG
CCTTTTTCAGCCTCGGTGCAGTGACCGGTTTTGTCGCAGATCTTGCGGCCACTCAGGGGCATCCGTTGCAGGCAGTGATG
AATTTGAGCACCTATGCATTCCTGCCTCGGATGATGGTTGTGACCTCACCAGTCCCAGTGATCACGTGTGGTGTCGTGCA
CCTACTTGCCATCATTTTGTACTTGTTTAAGTACCGTGGCCTGCACCATATCCTTGTTGGCGATGGAGTGTTCTCTGCGG
CTTTCTTCTTGAGATACTTTGCCGAGGGAAAGTTGAGGGAAGGGGTGTCGCAATCCTGCGGAATGAATCATGAGTCTCTG
ACTGGTGCCCTCGCTATGAGACTCAATGACGAGGACTTGGATTTCCTTATGAAATGGACTGATTTTAAGTGCTTTGTTTC
TGCGTCCAACATGAGGAATGCAGCGGGTCARTTTATCGAGGCYGCCTATGCGAAAGCGATCAGGGTGGAACTTGCCCAGT
TAGTGCAGGTCGACAAGGTTCGGGGTGTTTTAGCCAAACTTGAAGCTTTTGCTGACACCGTGGCGCCCCATCTTTCACCC
GGCGACATTGTTGTTGTTCTTGGTCATACGCCCGTTGGCAGCATCTTTGACTTAAAGATTGGCAATGCCAAGCACACCCT
ACAAGCCATCGAGACCAGAGTCCTTGCTGGGTCCAGGATGACCGTGGCGCGTGTCGTTGATCCGACTCCCGCGCCGCCAC
CCGTACCCGTGCCCGTTCCTCTCCCACCGAAAGTTTTAGAGAACGGCCCCAGTGCCTGGGGGATGAAGACCGCCTGAAC
AAAAAGAAGCGGCGCAAGATGGAAGCCGTTGGCATTTACGTTATGGGCGGGAAAAAGTACCAGAAATTTTGGGATAAGAA
TTCTGGTGATGTGTTCTATGAGGAAGTCCACGACAACACAGATGCGTGGGAATGCCTTAGAGCTGACGACCCCGCCGACT
TGGATCCTGAGAGGGGAACCTTGTGTGGACACGTCACCATAGAGAATAGGCCTTACCATGTTTATGCCTCCCCGTCTGGT
AGGAAGTTCCTGGTCCCTGCCGACCCAGAGAATGGGAAAGCCCAGTGGGAAGCTGCAAAGCTTTTCCATGGAGCAGGCCCT
TGGTATGATGAACGTTGACGGCGAGCTGACCGCCAAAGAACTGGAGAAATTGAAGAGAATAATTGACAAACTCCAGGGCC
TGACTAAGGAGCAGTGTTTAAACTGTTAGCCGCCAGCGGCTTGACCCGCTGTGGTCGCGGCGGCTTGGTTATTACTGAGA
CAGCGGTAAAAATAGTCAGATTCCACAATCGGACCTTCACCCTGGGGCCTGTGAATTTGAAAGTGGCCAGCGAAGTTGAG
TTGAAAGACGCCGTCGAGCACAACCAACACCCGGTTGCAAGACCAGTTGACGGTGGCGTTGTGCTCCTGCGCTCTGCAGT
TCCTTCGCTTATAGACGTCTTGATCTCCGGTGCCGACGCATCTCCCCAGTTGCTCGCCCATCACGGGCCAGGAAACACTG
```

Fig. 1F-3

```
GGATTGATGGCACGCTCTGGGATTTTGAGTCCGTAGCCACTAAAGAGGAAGTCGCACTTAGTGCACAAATAATACAGGCT
TGTGGCATTAGGCGTGGCGATGCTCCTGAGATTGGCCTCCCTTACAAGCTGCACCCTGTTAGGGGCAACCCTGAACGTGT
GAAAGGGGTTTTGAAAAACACAAGGTTTGGAGACATACCTTACAGGACCCCTAGCGACACTGGGAGCCCAGTACATGCGG
CCGCCTGCCTTACGCCTAACGCCACCCCGGTGACTGATGGGCGCTCCGTCTTGGCCACGACTATGCCCTCCGGGTTTGAG
TTGTATGTGCCGACCATTCCAGCATCTGTCCTTGATTACCTTGATTCCAGGCCAGACTGCCCTAAACAGTTGACGGAGCA
CGGGTGTGAAGATGCTGCATTGAGAGACCTCTCCAAATATGACTTGTCCRCCCAAGGTTTTGTTTTGCCCGGAGTCCTCC
GCCTCGTGCGGAAATACTTGTTTGCCCACGTGGGCAAGTGCCCACCTGTCCATCGGCCCTCCACCTACCCGGCCAAGAAT
TCCATGGCTGGAATAAACGGGAATAGGTTCCCAACCAAGGACATTCAGAGCATCCCTGAGATCGACGTTCTGTGTGCACA
GGCTGTACGAGAGAACTGGCAGACCGTTACCCCTTGCACCCTCAAGAAGCAGTATTGCGGGAAGAAGAAAACCAGGACCA
TACTCGGTACCAATAACTTCATTGCGCTGGCCCACCGGGCAGCACTGAGTGGTGTCACCCAGGGCTTCATGAAAAAGGCG
TTTAACTCGCCCATCGCCCTCGGGAAGAACAAATTCAAGGAGCTACAGACTCCGGTCCTGGGCAGATGCCTTGAGGCTGA
TCTTGCCTCTTGCGATCGATCCACTCCCGCGATTGTCCGCTGGTTTGCCGCCCATCTCCTTTATGAACTTGCCTGCGCTG
AGGAACACCTACCGTCGTATGTGCTGAATTGCTGCCATGACCTATTGGTCACGCAGTCCGGTGCGGTGACTAAGAGAGGT
GGCCTGTCATCTGGTGATCCGATCACCTCGGTATCCAACACCATTTACAGTCTGGTGATTTATGCGCAGCACATGGTGCT
CAGTTATTTCAAAAGTGGTCACCCACATGGTCTCCTGTTTCTCCAGGACCAGCTAAAGTTTGAGGACATGCTTAAGGTTC
AGCCCCTGATTGTCTACTCGGATGATCTTGTGCTGTATGCCGAGTCTCCCACCATGCCAAACTATCACTGGTGGGTTGAG
CATCTGAACTTGATGCTAGGGTTTCAGACGGACCCAAAGAAGACAACCATTACTGACTCGCCATCTTTTCTGGGCTGTAG
GATAATGAATGGGCGTCAGCTAGTCCCAAACCGTGATAGGATTCTCGCAGCTCTTGCCTACCACATGAAGGCGAATAATG
TTTCTGAGTACTACGCCTCCGCTGCTGCAATACTCATGGACAGTTGTGCTTGTCTGGAGTACGACCCTGAATGGTTTGAA
GAACTTGTGGTTGGAATGGCGCAATGCGCCCGCAAGGACGGCTATAGCTTCCCCGGCCCGCCGTTCTTCTTATCCATGTG
GGAGAAACTCAGGTCCAATTATGAGGGGAAGAAGTCAAGGGTGTGTGGGTACTGCGGAGCTTCGGCCCCGTATGCCACTG
CCTGTGGTCTTGACGTCTGTGTTTACCACACTCACTTTCACCAGCATTGTCCAGTCATAATCTGRTGTGGCCACCCTGCA
GGTTCCAGGTCCTGTGATGAGTGCAAATCCCCCATAGGGAAAGGTACAAGCCCTCTGGATGAGGTTTTAAGACAAGTCCC
GTATAAGCCTCCACGGACCGTCCTCATGCATGTGGAGCAGGGCCTCACCCCCCTTGACCCAGGCAGATATCAGACCCGCC
GTGGGTTGGTTGCCGTTAGGCGCGGGATCAGGGGAAATGAAGTTGACCTACCAGATGGTGATTATGCTAGCACCGCCTTA
CTCCCAACCTGTAAAGAGATCAACATGGTTGCTGTTGCTTCTAATGTGTTGCGCAGCAGATTTATCATCGGTCCACCCGG
TGCTGGGAAAACATACTGGCTCCTTCAACAGGTCCAGGATGGTGATGTCATATACACACCGACCCATCAGACCATGCTTG
ACATGATCAAAGCTTTGGGGACGTGCCGGTTTAACGTCCCGGCAGGCACAACGCTGCAATTCCCCGCCCCTTCCCGCACT
GGCCCGTGGGTTCGCATCCTGGCCGGCGGGTGGTGTCCTGGCAAAAACTCCTTCCTGGACGAAGCTGCGTATTGTAATCA
TCTTGATGTCTTGAGGCTTCTTAGCAAAACCACTCTCACCTGTTTAGGGGACTTCAAACAACTCCACCCAGTGGGTTTTG
ATTCTCATTGCTATGTCTTTGACATTATGCCTCAGACTCAACTGAAGACCATCTGGAGATTTGGACAGAACATCTGTGAT
GCCATCCAACCAGACTACAGAGACAAGCTTATGTCCATGGTCAACACAACTCGTGTAACTTATGTGGAAAAACCTGTCAA
ACATGGGCAAGTCCTCACCCCTTACCATAGGGACCGAGAGGATAGCGCCATTACCATTGACTCCAGTCAAGGCGCCACAT
TTGATGTGGTTACACTGCATTTGCCCACGAAAGATTCACTCAACAAACAAAGGGCCCTTGTTGCTATTRCCAGGGCAAGA
CATGCCATCTTTGTGTATGACCCACATAGGCAACTGCAGAGCCTATTTGATCTTCCTGCAAAAAGCACGCCCGTCAACTT
GGCCGTGCACCACGATGGRCAACTGATTGTGCTAGATAGAAATAACAAAGAATGCACGGTTGCCCAAGCTCTGGGTAATG
GTGACAAATTTAGGGCCACAGACAAGCGCGTTGTGGATTCTCTCCGCGCCATTTGTGCTGACCTAGAAGGGTCGAGCTCT
CCACTCCCCAAGGTTGCACATAATTTGGGGTTTTATTTCTCACCTGATTTGACACAGTTTGCCAAGCTTCCAATAGAACT
TGCGCCACACTGGCCAGTAGTGACGACCCAAGACAATAAAAACTGGCCAGATCGGCTGGTTGCCAGCCTGCGCCCTATTC
ACAAACATAGCCGTGCGTGCATCGGTGCCGGCTATATGGTGGGCCCTCGGTGTTTTTAGGCACCCCTGGGGTTGTGTCA
TACTATCTTACAAAATTTGTTAAGGGCGAGGCTCAAGTGCTTCCGGAAACGGTCTTCAGTACTGGCCGAATTGAGGTAGA
TTGCCGGGAATATCTTGACGACCGGGAGCGGGAAGTTGCAGCGTCCCTCCCACACGCCTTTATCGGCGACGTCAAAGGCA
CTACCGTCGGAGGGTGTCATCACATCACCTCCAAATACCTTCCGCGCTTCCTCCCCAAGGAATCAGTTGCGGTAGTCGGG
GTTTCAAGCCCCGGAAAAGCAGCGAAAGCAGTGTGTACATTGACAGATGTGTACCTCCCAGACCTTGAAGCTTACCTCCA
TCCTAAGACCCTGTCCAAGTGCTGGAAAATGATGTTGGACTTCAAAGAAGTTCGGCTGATGGTCTGGAAGGACAAGACGG
CCTATTTCCAACTCGAAGGTCGCCATTTCACCTGGTATCAACTTGCTAGCTATGCCTCGTACATCCGTGTTCCTTTAAAC
TCCACGGTGTACCTGGACCCCTGCATGGGCCCCGCCCTTTGCAACAGAAAAGTCGTTGGGTCCACTCATTGGGAGCTGA
CCTCGCAGTCACCCCTTATGATTATGGGGCAAGAATTATTTTGTCTAGTGCGTACCATGGTGAGATGCCTCCTGGGTACA
```

*Fig. 1F-4*

```
AGATTCTGGCGTGCGCGGAGTTCTCGCTGGACGACCCAGTCAGATACAAGCACACTTGGGGGTTTGAGTCGGATACAGCG
TACTTGTACGAGTTCACTGGAAACGGTGAGGACTGGGAGGATTATAACGACGCGTTTCGTGCGCGACAGAAAGGAAAGAT
TTACAAGGCCACTGCCACCAGCCTGAAGTTCCATTTTCCTCCGGGTCATACCGTTGAACCAACTTTGGGCTTAGACTGAA
ATGAAATGGGGGCTGTGCAGAGCCTATTTGATAAAATTGGCCAACTGTTTGTGGACGCTTTCACGGAGTTCTTGGTATCC
ATTGTTGATATCATCATATTTTTGGCCATTTTGTTCGGCTTCACAATCGCCGGTTGGCTGGTGGTCTTTTGCATCAGATT
GGTTTGCTCCGCGATACTCCGTTCGCGCTCTGCCGTTCACCCTGAGCAATTACAGAAGATCCTATGAGGCATTTCTCTCC
CAGTGCCGGACGGACATTCCCACCTGGGGAACTAAACATCCCTTGGGGATGCTCTGGCACCACAAGGTGTCGACCCTAAT
TGATGAAATGGTGTCGCGTCGAATGTACCGCACCATGGAACAAGCAGGGCAGGCTGCCTGGAGACAGGTGGTGACCGAGG
CAACGTTGTCTCGTATTAGTAACTTGGATGTGGTGGCTCATTTCCAGCACCTTGCCGCCATAGAAGCCGAGACTTGTAAA
TACTTGGCCTCCCGGCTGCCAATGCTGCACAACCTGCGCATGACAGGGTCAAATGTAACCATAGTGTATAATAGCTCTCT
AGAACAGGTGTTTGCTATTTTCCCGACCCTCGATTCCCGGCCAAAGCTTCATGATTTTCGGCAATGGCTAATAGCTGTGC
ATTCCTCCATATTCTCTTCTGTTGCGGCTTCCTGTACCCTTTTCGTCGTGCTGTGGTTGCGGCTTCCAATAATACGTACT
GTTTTTGGTTTCCACTGGTCAGGGGCAATTTTTTCCTTCGAGCTCACAGTGAACTACACGGTGTGTCCTCCCTGCCTCACC
CGGCAGGCGGCCGCAGAGATCTACGAACCTGGTGGGTCTCTTTGGTGCAGGATAGGGCACGATCGATGCTCGGAGGACGA
TCACGACGAGCTAGGATTTCTGGTGCCGCCTGGCCTCTCCAGCGAAGGCCACTTGACCAGTGTTTACGCCTGGTTGGCGT
TCTTGTCCTTCAGTTACACGGCCCAGTTTCACCCCGAGATATTCGGAATAGGGAATGTGAGCCAAGTTTATGTTGACATC
AAGCATCAATTTATTTGTGCTGTTCATGACGGGCAAAACACCACCTTGCCTCGCCATGACAACGTCTCAGCCGTGTTCCA
GACTTATTACCAGCATCAGGTCGACGGCGGCAATTGGTTTCACCTGGAATGGCTGCGCCCCTTCTTCTCCTCCTGGTTGG
TTTTGAACGTCTCTTGGTTTCTCAGGCGTTCGCCTGTAAGCCGTGTTTCAGTTCGAGTCTTTCAGACATTAAGACCAACA
CCACCGCAGCTGCAGGCTTTGCTGTCCTCCAAGACATCAGCTGTCTTAGGCATGGCCACTCGTCCTCTGAGGCGACTCGC
AAAGGCCGCCAATGCCGCACGGCGATAGGAACGCCCGTATACATTACTGTCACAGCCAATGTAACAGATGAGAATTATTT
GCATTCCTCTGACCTTCTCATGCTTTCCTCTTGCCTTTTCTACGCTTCCGAGATGAGTGAAAAGGGATTTGAGGTGATAT
TTGGCAATGTGTCAGGCATAGTGGCTGTGTGTGTCAACTTTACCAGCTATGTCCAACATGTTAAGGAGTTCACCCAGCGC
TCCTTGGTGGTTGACCATGTGCGGTTACTTCATTTTGTGACACCTGAGACTATGAGGTGGGCGACCGTTTTAGCCTGTCT
TTTTGCCATTCTGTTGGCCATTTGAATGTTCAGATATGTTGGGGAAATGCTTGACCGCGGGCTATTGCTCGCAATTGCCT
TTTTTGTGGTGTATCGTGCCGTTCTGTCTTGCTGCGCTCGTCAACGCCAGCAGCAACAGCAGCTCCCACTTACAGTTGAT
TTATAACTTAACGATATGTGAGCTGAATGGCACAGACTGGCTGAATGATCATTTTAGTTGGGCAGTGGAGACTTTCGTTA
TCTTTCCTGTGTTGACTCACATTGTTTCCTACGGCGCCCTCACTACCAGCCACTTCCTTGACACGGTCGGCCTGATCACT
GTGTCCACCGCCGGATACTACCATGCGCGGTATGTCTTGAGTAGCATCTATGCCGTCTGCGCCCTGGCTGCGCTGATTTG
CTTCGTCATCAGGTTGACGAAAAATTGTATGTCCTGGCGCTACTCATGTACCAGATATACCAACTTTCTTCTGGACACCA
AGGGCAGACTCTATCGCTGGCGGTCACCCGTCATCATAGAGAAAAGGGGTAAAATTGAGGTTGGAGGTGACCTGATCGAC
CTCAAGAGAGTTGTGCTTGATGGCTCCGCGGCAACCCCTGTAACCAAAGTTTCAGCGGAACAATGGGGTCGTCCTTAGAC
GACTTCTGCAATGACAGCACGGCTCCACAAAAGGTGATCTTGGCATTTTCTATCACCTACACTCCAGTGATGATATATGC
CCTAAAGGTGAGTCGTGGCCGGCTGCTAGGGCTTTTACACCTTTTGATTTTTCTAAACTGTGCTTTTACCTTCGGGTATA
TGACATTTGTGCACTTTCAGAGCACAAACAGAGTTGCACTCACTATGGGAGCAGTAGTCGCGCTCCTTTGGGGGGTGTAC
TCAGCTATAGAAACCTGGAAATTCATCACTTCCAGATGCCGTTTGTGCTTGCTAGGCCGCAAGTACATTCTGGCCCCTGC
CCACCACGTTGAGAGTGCCGCAGGCTTTCATCCGATTGCGGCAAGTGATAACCACGCATTTGTCGTCCGGCGTCCCGGTT
CCACTACGGTTAACGGCACATTGGTTCCCGGGTTGAAAAGCCTCGTGTTGGGTGGCAGAAGAGCTGTCAAACGGGGAGTG
GTAAACCTCGTTAAATATGCCAAATAACAACGGCAGGCAGCAGAAGAAGAAGAAAGGGGACGGCCAGCCAGTCAATCAGC
TGTGCCAAATGTTGGGCAGGATCATCGCCCAGCAAAACCAGTCCAGAGGTAAGGGACCGGGGAAGAAAAGTAAGAAGAAA
AGCCTGGAGAAGCCCCATTTTCCTCTCGCGACTGAAGATGACGTTAGACATCACTTCACCCCTAGTGAGCGGCAATTGTG
TCTGTCGTCAATCCAGACTGCCTTTAACCAAGGCGCTGGAACTTGTACCCTGTCGGATTCAGGGAGAATAAGTTACACTG
CGGAGTTTAGTTTGCCTACGCATCATACTGTGCGCCTAATTCGCGTCACAGCATCACCCTCAGCATGATGAGCTGGCATT
CTTGAGACATCCCAGTGTTTGAATTGGAAGGATGTGTGGTGAATGGCACTGATTGATATTGTGCCTYTAAGTCACCTATT
CAATTAGGGCGACCGTATGGGGGTAATATTTAATTGGCGTGAACCATGCGGCCGAAAYT
```

Fig. 1G-1

\>V7-Nsp2d324-434.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGCCAAAAGTTCAGCCTC
GAAAAACGAAGCCTGTCAAGAGCTTGCCGGAGAGAAAGCCTGTCCCCGCCCCGCGCAGGAAGGTTGGGTCCGATTGTGGC
AGCCCGGTTTCATTAGGCGGCGATGTCCCTAACAGTTGGGAAGATTTGGCTGTTAGTAGCCCCTTTGATCTCCCGACCCC
ACCTGAGCCGGCAACACCTTCAAGTGAGCTGGTGATTGTGTCCTCACCGCAATGCATCTTCAGGCCGGCGACACCCTTGA
GTGAGCCGGCTCCAATTCCCGCACCTCGCGGAACTGTGTCTCGACCGGTGACACCCTTGAGTGAGCCGATCCCTGTGCCC
GCACCGCGGCGTAAGTTTCAGCAGGTGAAAAGATTGAGTTCGGCGGCGGCAATCCCACCGTACCAGGACGAGCCCCTGGA
TTTGTCTGCTTCCTCACAGACTGAATATGAGGCCTCTCCCCCAGCACCGCCGCAGAGCGGGGGCGTTCTGGGAGTAGAGG
GGCATGAAGCTGAGGAAACCCTGAGTGAAATCTCGGACATGTCGGGTAACATTAAACCTGCGTCCGTGTCATCAAGCAGC
TCCTTGTCCAGCGTGAGAATCACACGCCCAAAATACTCAGCTCAAGCCATCATCGACTCGGGCGGGCCCTGCAGTGGGCA
TCTCCAAGAGGTAAAGGAAACATGCCTTAGTGTCATGCGCGAGGCATGTGATGCGACTAAGCTTGATGACCCTGCTACGC
AGGAATGGCTTTCTCGCATGTGGGATCGGGTGGACATGCTGACTTGGCGCAACACGTCTGTTTACCAGGCGATTTGCACC
TTAGATGGCAGGTTAAAGTTCCTCCCAAAAATGATACTCGAGACACCGCCGCCCTATCCGTGTGAGTTTGTGATGATGCC
TCACACGCCTGCACCTTCCGTAGGTGCGGAGAGCGACCTTACCATTGGCTCAGTTGCTACTGAAGATGTTCCACGCATCC
TCGAGAAAATAGAAATGTCGGCGAGATGGCCAACCAGGGACCCTTGGCCTTCTCCGAGGATAAACCGGTAGATGACCAA
CTTGTCAACGACCCCCGGATATCGTCGCGGAGGCCTGACGAGAGCACATCAGCTCCGTCCGCAGGCACAGGTGGCGCCGG
CTCTTTTACCGATTTGCCGCCTTCAGATGGCGCGGATGCGGACGGGGGGGGCCGTTTCGGACGGTAAAAAGAAAAGCTG
AAAGGCTCTTTGACCAACTGAGCCGTCAGGTTTTTGACCTCGTCTCCCATCTCCCTGTTTTCTTCTCACGCCTTTTCTAC
CCTGGCGGTGGTTATTCTCCGGGTGATTGGGGTTTTGCAGCTTTTACTCTATTGTGCCTCTTTTTATGTTACAGTTACCC
AGCCTTTGGTATTGCTCCCCTCTTGGGTGTGTTTTCTGGGTCTTCTCGGCGCGTTCGAATGGGGGTTTTTGGCTGCTGGT
TGGCTTTTGCTGTTGGTCTGTTCAAGCCTGTGTCCGACCCAGTCGGCGCTGCTTGTGAGTTTGACTCGCCAGAGTGTAGA
AACATCCTTCATTCTTTTGAGCTTCTCAAACCTTGGGACCCTGTTCGCAGCCTTGTTGTGGGCCCCGTCGGTCTCGGTCT

Fig. 1G-2

```
TGCCATTCTTGGCAGGTTACTGGGCGGGGCACGCTGCATCTGGCACTTTTTGCTTAGGCTTGGCATTGTTGCAGACTGTA
TCTTGGCTGGAGCTTACGTGCTTTCTCAAGGTAGGTGTAAAAAGTGCTGGGGATCTTGTATAAGAACTGCTCCCAATGAG
GTCGCTTTTAACGTGTTTCCTTTCACACGTGCGACCAGGTCGTCACTTATCGACCTGTGCGATCGGTTTTGTGCGCCAAA
AGGAATGGACCCCATTTTTCTCGCCACTGGGTGGCGCGGGTGCTGGGCCGGCCGAAGCCCCATTGAGCAACCCTCTGAAA
AACCCATCGCGTTTGCCCAGTTGGATGAAAAGAAGATTACGGCTAGGACTGTGGTCGCCCAGCCTTATGACCCCAACCAA
GCCGTAAAGTGCTTGCGGGTATTGCAGGCGGGTGGGGCGATGGTGGCTAAGGCGGTCCCAAAAGTGGTCAAGGTTTCCGC
TGTTCCATTCCGAGCCCCCTTCTTTCCCACTGGAGTGAAAGTTGACCCTGATTGCAGGGTCGTGGTTGACCCTGACACTT
TCACTGCAGCTCTCCGGTCTGGCTACTCCACCACAAACCTCGTCCTTGGTGTGGGGGACTTTGCCCAGCTGAATGGATTA
AAAATCAGGCAAATTTCCAAGCCTTCAGGGGGAGGCCCACATCTCATGGCTGCCCTGCATGTTGCCTGCTCGATGGCTCT
GCACATGCTTGCTGGATTTATGTGACTGCGGTGGGTTCTTGCGGCACCGGCACCAACGACCCGTGGTGCGCTAACCCGT
TTGCCGTCCCTGGCTACGGACCTGGCTCTCTCTGCACGTCCAGATTGTGCATTTCCCAACACGGCCTTACCCTGCCCTTG
ACAGCACTTGTGGCGGGATTCGGTATTCAAGAAATTGCCTTGGTCGTTTTGATTTTTGTTTCCATCGGAGGCATGGCTCA
TAGGTTGAGCTGTAAGGCTGACATGCTGTGTGTCTTGCTTGCAATTGCCAGCTATGTTTGGGTACCTCTTACCTGGTTGC
TTTGTGTGTTTCCTTGCTGGTTGCGCTGTTTTTCTTTGCACCCCCTCACCATCCTATGGTTGGTGTTTTTCTTGATTTCT
GTGAATATGCCTTCAGGAATCTTGGCCATGGTGTTGTTGGTTTCTCTTTGGCTTCTTGGTCGTTATACTAATGTTGCTGG
CCTTGTCACCCCCTACGACATTCATCATTACACCAGTGGCCCCCGCGGTGTTGCCGCCTTGGCTACCGCACCAGATGGGA
CCTACTTGGCCGCTGTCCGCCGCGCTGCGTTGACTGGCCGCACCATGCTGTTTACCCCGTCCCAGCTTGGGTCTCTTCTT
GAGGGTGCTTTCAGAACTCGAAAGCCCTCACTGAACACCGTCAATGTGATCGGGTCCTCCATGGGCTCTGGCGGGGTGTT
TACCATCGACGGGAAAGTCAAGTGCGTAACTGCCGCACATGTCCTTACGGGCAATTCAGCTCGGGTTTCCGGGGTCGGCT
TCAATCAAATGCTTGACTTTGACGTAAAGGGAGATTTCGCTATAGCTGATTGCCCGAATTGGCAAGGGGCTGCCCCCAAG
ACCCAATTCTGCACGGATGGATGGACTGGCCGTGCCTATTGGCTAACATCCTCTGGCGTCGAACCCGGCGTCATTGGAAA
AGGATTCGCCTTCTGCTTCACCGCATGTGGCGATTCCGGGTCCCCAGTGATCACCGAGGCCGGTGAGCTTGTCGGCGTTC
ACACGGGATCGAATAAACAAGGGGGGGGCATTGTTACGCGCCCCTCAGGCCAGTTTTGTAATGTGGCACCCATCAAGCTA
AGCGAATTAAGTGAATTCTTTGCTGGGCCTAAGGTCCCGCTCGGTGATGTGAAGGTCGGCAGCCACATAATTAAAGACAT
AAGCGAGGTGCCTTCAGATCTTTGTGCCTTGCTTGCTGCCAAACCTGAACTGGAAGGAGGCCTCTCCACCGTCCAACTTC
TTTGTGTGTTTTTTCTCCTGTGGAGAATGATGGGACATGCCTGGACGCCCTTGGTTGCTGTGAGTTTCTTTATTTTGAAT
GAGGTTCTCCCAGCCGTCCTGGTCCGGAGTGTTTTCTCCTTTGGAATGTTTGTGCTATCCTGGCTCACGCCATGGTCTGC
GCAAGTTCTGATGATCAGGCTTCTGACAGCAGCTCTTAACAGGAACAGATGGTCACTTGCCTTTTTCAGCCTCGGTGCAG
TGACCGGTTTTGTCGCAGATCTTGCGGCCACTCAGGGGCATCCGTTGCAGGCAGTGATGAATTTGAGCACCTATGCATTC
CTGCCTCGGATGATGGTTGTGACCTCACCAGTCCCAGTGATCACGTGTGGTGTCGTGCACCTACTTGCCATCATTTTGTA
CTTGTTTAAGTACCGTGGCCTGCACCATATCCTTGTTGGCGATGGAGTGTTCTCTGCGGCTTTCTTCTTGAGATACTTTG
CCGAGGGAAAGTTGAGGGAAGGGGTGTCGCAATCCTGCGGAATGAATCATGAGTCTCTGACTGGTGCCCTCGCTATGAGA
CTCAATGACGAGGACTTGGATTTCCTTATGAAATGGACTGATTTTAAGTGCTTTGTTTCTGCGTCCAACATGAGGAATGC
AGCGGGTCAATTTATCGAGGCTGCCTATGCTAAAGCACTTAGAGTAGAACTGGCCCAGTTGGTGCAGGTTGATAAAGTTC
GAGGTACTTTGGCCAAACTTGAAGCTTTTGCTGATACCGTGGCACCTCAACTCTCGCCCGGTGACATTGTTGTCGCTCTC
GGCCACACGCCTGTTGGCAGTATCTTCGACCTAAAGGTTGGTAGCACCAAGCATACCCTCCAAGCCATTGAGACCAGAGT
CCTTGCTGGGTCCAAAATGACCGTGGCGCGCGTCGTCGACCCGACCCCCACGCCCCACCCGCACCCGTGCCCATCCCCC
TCCCACCGAAAGTTCTGGAGAATGGCCCCAACGCTTGGGGGATGAGGACCGTTTGAATAAGAAGAAGAGGCGCAGGATG
GAAGCCCTCGGCATCTATGTTATGGGCGGGAAAAAATACCAGAAATTTTGGGACAAGAATTCCGGTGATGTGTTTTATGA
GGAGGTCCATAATAACACAGATGAGTGGGAGTGTCTCAGAGTTGGCGACCCTGCCGACTTTGACCCTGAGAAGGGAACTC
TGTGTGGACATGTCACCATTGAAAACAAGGCTTACCATGTTTACACCTCCCCATCTGGTAAGAAGTTCTTGGTCCCCGTC
AACCCAGAGAATGGAAGAGTCCAATGGGAAGCTGCAAAGCTTTCCGTGGAGCAGGCCCTAGGTATGATGAATGTCGACGG
CGAACTGACTGCCAAAGAACTGGAGAAACTGAAAAGAATAATTGACAAACTCCAGGGCCTGACTAAGGAGCAGTGTTTAA
ACTGCTAGCCGCCAGCGACTTGACCCGCTGTGGTCGCGGCGGCTTGGTTGTTACTGAAACAGCGGTAAAAATAGTCAAAT
TTCACAACCGGACCTTCACCCTGGGACCTGTGAATTTAAAAGTGGCCAGTGAGGTTGAGCTAAAAGACGCGGTTGAGCAC
AACCAACACCCGGTTGCGAGACCGATCGATGGTGGAGTTGTGCTCCTGCGTTCCGCGGTTCCTTCGCTTATAGACGTCTT
GATCTCCGGTGCTGATGCATCTCCCAAGTTACTTGCCCATCACGGGCCGGGAAACACTGGGATCGATGGCACGCTCTGGG
ATTTTGAGTCCGAAGCCACTAAAGAGGAAGTCGCACTCAGTGCGCAAATAATACAGGCTTGTGACATTAGGCGCGGCGAC
GCTCCTGAAATTGGTCTCCCTTACAAGCTGTACCCTGTTAGGGGTAACCCTGAGCGGGTGAAAGGAGTTCTGCAGAATAC
AAGGTTTGGAGACATACCTTACAAAACCCCCAGTGACACTGGAAGCCCAGTGCACGCGGCTGCCTGCCTTACGCCCAACG
```

*Fig. 1G-3*

```
CCACTCCGGTGACTGATGGGCGCTCCGTCTTGGCCACGACCATGCCCCCCGGGTTTGAGTTATATGTACCGACCATACCA
GCGTCTGTCCTTGATTACCTTGACTCTAGGCCTGACTGCCCTAAACAGCTGACAGAGCACGGCTGCGAAGATGCCGCACT
GAAAGACCTCTCTAAATATGACTTGTCCACCCAAGGCTTTGTTTTACCTGGAGTTCTTCGCCTTGTGCGGAAATACCTGT
TTGCCCATGTAGGTAAGTGCCCACCCGTTCATCGGCCTTCTACTTACCCTGCTAAGAATTCTATGGCTGGAATAAATGGG
AACAGGTTCCCAACCAAGGACATTCAGAGCGTCCCTGAAATCGACGTTCTGTGCGCACAGGCTGTGCGAGAAAACTGGCA
AACTGTCACCCCTTGTACTCTTAAGAAACAGTATTGCGGGAAGAAGAAGACTAGGACCATACTCGGCACCAATAACTTCA
TCGCACTAGCCCACCGAGCAGTGTTGAGTGGTGTTACCCAGGGCTTCATGAAAAAGGCGTTTAACTCGCCCATCGCCCTC
GGAAAGAACAAGTTTAAGGAGCTACAGACTCCGGTCCTGGGCAGGTGCCTTGAAGCTGATCTCGCATCCTGCGATCGATC
CACGCCTGCAATTGTCCGCTGGTTTGCCGCCAACCTTCTTTATGAACTTGCCTGTGCTGAAGAGCATCTACCGTCGTACG
TGCTGAACTGCTGCCACGACTTACTGGTCACGCAGTCCGGCGCAGTGACTAAGAGAGGTGGCCTGTCGTCTGGCGACCCG
ATCACCTCTGTGTCTAACACCATTTATAGTTTGGTGATCTATGCACAGCATATGGTGCTTAGTTACTTCAAAAGTGGTCA
CCCCCATGGCCTTCTGTTCTTACAAGACCAGCTAAAGTTTGAGGACATGCTCAAGGTTCAACCCCTGATCGTCTATTCGG
ACGACCTCGTGCTGTATGCCGAGTCTCCCACCATGCCAAACTATCACTGGTGGGTTGAACATCTGAATTTGATGCTGGGG
TTTCAGACGGACCCAAAGAAGACAGCAATAACAGACTCGCCATCATTTCTAGGCTGTAGAATAATAAATGGGCGCCAGCT
AGTCCCCAACCGTGACAGGATCCTCGCGGCCCTCGCCTATCACATGAAGGCGAGTAATGTTTCTGAATACTATGCCTCAG
CGGCTGCAATACTCATGGACAGCTGTGCTTGTTTGGAGTATGATCCTGAATGGTTTGAAGAACTTGTAGTTGGAATAGCG
CAGTGCGCCCGCAAGGACGGCTACAGCTTTCCCGGCACGCCGTTCTTCATGTCCATGTGGGAAAAACTCAGGTCCAATTA
TGAGGGGAAGAAGTCGAGAGTGTGCGGGTACTGCGGGGCCCCGGCCCCGTACGCTACTGCCTGTGGCCTCGACGTCTGCA
TTTACCACACCCACTTCCACCAGCATTGTCCAGTCACAATCTGGTGTGGCCATCCAGCGGGTTCTGGTTCTTGTAGTGAG
TGCAAATCCCCTGTAGGGAAAGGCACAAGCCCTTTAGACGAGGTGCTGGAACAAGTCCCGTATAAGCCCCCACGGACCGT
TATCATGCATGTGGAGCAGGGTCTCACCCCCCTTGATCCAGGTAGATACCAAACTCGCCGCGGATTAGTCTCTGTCAGGC
GTGGAATTAGGGGAAATGAAGTTGGACTACCAGACGGTGATTATGCTAGCACCGCCTTGCTCCCTACCTGCAAAGAGATC
AACATGGTCGCTGTCGCTTCCAATGTATTGCGCAGCAGGTTCATCATCGGCCCACCCGGTGCTGGGAAAACATACTGGCT
CCTTCAACAGGTCCAGGATGGTGATGTTATTTACACACCAACTCACCAGACCATGCTTGACATGATTAGGGCTTTGGGGA
CGTGCCGGTTCAACGTCCCGGCAGGCACAACGCTGCAATTCCCCGTCCCCTCCCGCACCGGTCCGTGGGTTCGCATCCTA
GCCGGCGGTTGGTGTCCTGGCAAGAATTCCTTCCTAGATGAAGCAGCGTATTGCAATCACCTTGATGTTTTGAGGCTTCT
TAGTAAAACTACCCTCACCTGTCTAGGAGACTTCAAGCAACTCCACCCAGTGGGTTTTGATTCTCATTGCTATGTTTTTG
ACATCATGCCTCAAACTCAACTGAAGACCATCTGGAGGTTTGGACAGAATATCTGTGATGCCATTCAGCCAGATTACAGG
GACAAACTCATGTCCATGGTCAACACAACCCGTGTGACCTACGTGGAAAAACCTGTCAGGTATGGGCAGGTCCTCACCCC
CTACCACAGGGACCGAGAGGACGACGCCATCACTATTGACTCCAGTCAAGGCGCCACATTCGATGTGGTTACATTGCATT
TGCCCACTAAAGATTCACTCAACAGGCAAAGAGCCCTTGTTGCTATCACCAGGGCAAGACACGCTATCTTTGTGTATGAC
CCACACAGGCAGCTGCAGGGCTTGTTTGATCTTCCTGCAAAAGGCACGCCCGTCAACCTCGCAGTGCACTGCGACGGGCA
GCTGATCGTGCTGGATAGAAATAACAAAGAATGCACGGTTGCTCAGGCTCTAGGCAACGGGGATAAATTTAGGGCCACAG
ACAAGCGTGTTGTAGATTCTCTCCGCGCCATTTGTGCTGATCTAGAAGGGTCGAGCTCTCCGCTCCCCAAGGTCGCACAC
AACTTGGGATTTTATTTCTCACCTGATTTAACACAGTTTGCTAAACTCCCAGTAGAACTTGCACCTCACTGGCCCGTGGT
GTCAACCCAGAACAATGAAAAGTGGCCGGATCGGCTGGTTGCCAGCCTTCGCCCTATCCATAAATACAGCCGCGCGTGCA
TCGGTGCCGGCTATATGGTGGGCCCTTCGGTGTTTCTAGGCACTCCTGGGGTCGTGTCATACTATCTCACAAAATTTGTT
AAGGGCGGGGCTCAAGTGCTTCCGGAGACGGTTTTCAGCACCGGCCGAATTGAGGTAGACTGCCGGGAATATCTTGATGA
TCGGGAGCGAGAAGTTGCTGCGTCCCTCCCACACGCTTTCATTGGCGACGTCAAAGGCACTACCGTTGGAGGATGTCATC
ATGTCACCTCCAGATACCTCCCGCGCGTCCTTCCCAAGGAATCAGTTGCGGTAGTCGGGGTTTCAAGCCCCGGAAAAGCC
GCGAAAGCATTGTGCACACTGACAGATGTGTACCTCCCAGATCTTGAAGCCTATCTCCACCCGGAGACCCAGTCCAAGTG
CTGGAAAATGATGTTGGACTTCAAAGAAGTTCGACTAATGGTCTGGAAAGACAAAACAGCCTATTTCCAACTTGAAGGTC
GCTATTTCACCTGGTATCAGCTTGCCAGCTATGCCTCGTACATCCGTGTTCCCGTCAACTCTACGGTGTACTTGGACCCC
TGCATGGGCCCCGCCCTTTGCAACAGGAGAGTCGTCGGGTCCACCCACTGGGGGCTGACCTCGCGGTCACCCCTTATGA
TTACGGCGCTAAAATTATCCTGTCTAGCGCGTACCATGGTGAAATGCCCCCCGGATACAAAATTCTGGCGTGCGCGGAGT
TCTCGTTGGATGACCCAGTTAAGTACAAACATACCTGGGGGTTTGAATCGGATACAGCGTATCTGTATGAGTTCACCGGA
AACGGTGAGGACTGGGAGGATTACAATGATGCGTTTCGTGCGCGCCAGGAAGGGAAATTTATAAGGCCACTGCCACCAG
CTTGAAGTTTTATTTTCCCCCGGGCCCTGTCATTGAACCAACTTTAGGCCTGAATTGAAATGAAATGGGGTCCATGCAAA
GCCTTTTTGACAAAATTGGCCAACTTTTTGTGGATGCTTTCACGGAGTTCTTGGTGTCCATTGTTGATATCATTATATTT
TTGGCCATTTTGTTTGGCTTCACCATCGCCGGTTGGCTGGTGGTCTTTTGCATCAGATTGGTTTGCTCCGCGATACTCCG
```

Fig. 1G-4

```
TACGCGCCCTGCCATTCACTCTGAGCAATTACAGAAGATCTTATGAGGCCTTTCTTTCCCAGTGCCAAGTGGACATTCCC
ACCTGGGGAACTAAACATCCTTTGGGGATGCTTTGGCACCATAAGGTGTCAACCCTGATTGATGAAATGGTGTCGCGTCG
AATGTACCGCATCATGGAAAAAGCAGGGCAGGCTGCCTGGAAACAGGTGGTGAGCGAGGCTACGCTGTCTCGCATTAGTA
GTTTGGATGTGGTGGCTCATTTTCAGCATCTAGCCGCCATTGAAGCCGAGACCTGTAAATATTTGGCCTCCCGGCTGCCC
ATGCTACACAACCTGCGCATGACAGGGTCAAATGTAACCATAGTGTATAATAGCACTTTGAATCAGGTGTTTGCTATTTT
TCCAACCCCTGGTTCCCGGCCAAAGCTTCATGATTTTCAGCAATGGTTAATAGCTGTACATTCCTCCATATTTTCCTCTG
TTGCAGCTTCTTGTACTCTTTTTGTTGTGCTGTGGTTGCGGGTTCCAATACTACGTACTGTTTTTGGTTTCCGCTGGTTA
GGGGCAATTTTTCTTTCGAACTCACAGTGAATTACACGGTGTGTCCACCTTGCCTCACCCGGCAAGCAGCCACAGAGATC
TACGAACCCGGTAGGTCTCTTTGGTGCAGGATAGGGTATGACCGATGTGGGGAGGACGATCATGACGAGCTAGGGTTTAT
GATACCGCCTGGCCTCTCCAGCGAAGGCCACTTGACTGGTGTTTACGCCTGGTTGGCGTTCTTGTCCTTCAGCTACACGG
CCCAGTTCCATCCCGAGATATTCGGGATAGGGAATGTGAGTCGAGTTTATGTTGACATCAAACATCAACTCATCTGCGCC
GAACATGACGGGCAGAACACCACCTTGCCTCGTCATGACAACATTTCAGCCGTGTTTCAGACCTATTACCAACATCAAGT
CGACGGCGGCAATTGGTTTCACCTAGAATGGCTTCGTCCCTTCTTTTCCTCGTGGTTGGTTTTAAATGTCTCTTGGTTTC
TCAGGCGTTCGCCTGCAAACCATGTTTCAGTTCGAGTCTTGCAGATATTAAGACCAACACCACCGCAGCGGCAAGCTTTG
CTGTCCTCCAAGACATCAGTTGCCTTAGGCATCGCGACTCGGCCTCTGAGGCGATTCGCAAAATCCCTCAGTGCCGTACG
GCGATAGGGACACCCGTGTATGTTACCATCACAGCCAATGTGACAGATGAGAATTATTTACATTCTTCTGATCTCCTCAT
GCTTTCTTCTTGCCTTTTCTATGCTTCTGAGATGAGTGAAAAGGGATTTAAGGTGGTATTTGGCAATGTGTCAGGCATCG
TGGCTGTGTGTGTCAATTTTACCAGCTACGTCCAACATGTCAAGGAGTTTACCCAACGCTCCCTGGTGGTCGACCATGTG
CGGTTGCTCCATTTCATGACACCTGAGACCATGAGGTGGGCAACTGTTTTAGCCTGTCTTTTTGCCATTCTGTTGGCAAT
TTGAATGTTTAAGTATGTTGGAGAAATGCTTGACCGCGGGCTGTTGCTCGCGATTGCTTTCTTTGTGGTGTATCGTGCCG
TTCTGTTTTGCTGTGCTCGCCAACGCCAGCAACGACAGCAGCTCCCATCTACAGCTGATTTACAACTTGACGCTATGTGA
GCTGAATGGCACAGATTGGCTAGCTAACAAATTTGATTGGGCAGTGGAGAGTTTTGTCATCTTTCCCGTTTTGACTCACA
TTGTCTCCTATGGTGCCCTCACTACCAGCCATTTCCTTGACACAGTCGCTTTAGTCACTGTGTCTACCGCCGGGTTTGTT
CACGGGCGGTATGTCCTAAGTAGCATCTACGCGGTCTGTGCCCTGGCTGCGTTGACTTGCTTCGTCATTAGGTTTGCAAA
GAATTGCATGTCCTGGCGCTACGCGTGTACCAGATATACCAACTTTCTTCTGGACACTAAGGGCAGACTCTATCGTTGGC
GGTCGCCTGTCATCATAGAGAAAAGGGGCAAAGTTGAGGTCGAAGGTCATCTGATCGACCTCAAAAGAGTTGTGCTTGAT
GGCTCCGTGGCAACCCCTATAACCAGAGTTTCAGCGGAACAATGGGGTCGTCCTTAGATGACTTCTGTCACGATAGCACG
GCTCCACAAAAGGTGCTTTTGGCGTTTTCTATTACCTACACGCCAGTGATGATATATGCCCTAAAGGTGAGTCGCGGCCG
ACTGCTAGGGCTTCTGCACCTTTTGATCTTCCTGAATTGTGCTTTCACCTTCGGGTACATGACTTTCGCGCACTTTCAGA
GTACAAATAAGGTCGCGCTCACTATGGGAGCAGTAGTTGCACTCCTTTGGGGGGTGTACTCAGCCATAGAAACCTGGAAA
TTCATCACCTCCAGATGCCGTTTGTGCTTGCTAGGCCGCAAGTACATTCTGGCCCCTGCCCACCACGTTGAAAGTGCCGC
AGGCTTTCATCCGATTGCGGCAAATGATAACCACGCATTTGTCGTCCGGCGTCCCGGCTCCACTACGGTCAACGGCACAT
TGGTGCCCGGGTTAAAAAGCCTCGTGTTGGGTGGCAGAAAAGCTGTTAAACAGGGAGTGGTAAACCTTGTCAAATATGCC
AAATAACAACGGCAAGCAGCAGAAGAGAAAGAAGGGGGATGGCCAGCCAGTCAATCAGCTGTGCCAGATGCTGGGTAAGA
TCATCGCTCAGCAAAACCAGTCCAGAGGCAAGGGACCGGGAAAGAAAAATAAGAAGAAAAACCCGGAGAAGCCCCATTTT
CCTCTAGCGACTGAAGATGATGTCAGACATCACTTTACCCCTAGTGAGCGGCAATTGTGTCTGTCGTCAATCCAGACCGC
CTTTAATCAAGGCGCTGGGACTTGCACCCTGTCAGATTCAGGGAGGATAAGTTACACTGTGGAGTTTAGTTTGCCTACGC
ATCATACTGTGCGCCTGATCCGCGTCACAGCATCACCCTCAGCATGATGGGCTGGCATTCTTGAGGCATCTCAGTGTTTG
AATTGGAAGAATGTGTGGTGAATGGCACTGATTGACATTGTGCCTCTAAGTCACCTATTCAATTAGGGCGACCGTGTGGG
GGTGAGATTTAATTGGCGAGAACCATGCGGCCGAAATTAAAAAAAA
```

*Fig. 1H-1*

```
>V7-Nsp2d324-523.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGCCAATTCCCGCACCTC
GCGGAACTGTGTCTCGACCGGTGACACCCTTGAGTGAGCCGATCCCTGTGCCCGCACCGCGGCGTAAGTTTCAGCAGGTG
AAAAGATTGAGTTCGGCGGCGGCAATCCCACCGTACCAGGACGAGCCCCTGGATTTGTCTGCTTCCTCACAGACTGAATA
TGAGGCCTCTCCCCCAGCACCGCCGCAGAGCGGGGGCGTTCTGGGAGTAGAGGGGCATGAAGCTGAGGAAACCCTGAGTG
AAATCTCGGACATGTCGGGTAACATTAAACCTGCGTCCGTGTCATCAAGCAGCTCCTTGTCCAGCGTGAGAATCACACGC
CCAAAATACTCAGCTCAAGCCATCATCGACTCGGGCGGGCCCTGCAGTGGGCATCTCCAAGAGGTAAAGGAAACATGCCT
TAGTGTCATGCGCGAGGCATGTGATGCGACTAAGCTTGATGACCCTGCTACGCAGGAATGGCTTTCTCGCATGTGGGATC
GGGTGGACATGCTGACTTGGCGCAACACGTCTGTTTACCAGGCGATTTGCACCTTAGATGGCAGGTTAAAGTTCCTCCCA
AAAATGATACTCGAGACACCGCCGCCCTATCCGTGTGAGTTTGTGATGATGCCTCACACGCCTGCACCTTCCGTAGGTGC
GGAGAGCGACCTTACCATTGGCTCAGTTGCTACTGAAGATGTTCCACGCATCCTCGAGAAAATAGAAAATGTCGGCGAGA
TGGCCAACCAGGGACCCTTGGCCTTCTCCGAGGATAAACCGGTAGATGACCAACTTGTCAACGACCCCCGGATATCGTCG
CGGAGGCCTGACGAGAGCACATCAGCTCCGTCCGCAGGCACAGGTGGCGCCGGCTCTTTTACCGATTTGCCGCCTTCAGA
TGGCGCGGATGCGGACGGGGGGGGGGCCGTTTCGGACGGTAAAAAGAAAAGCTGAAAGGCTCTTTGACCAACTGAGCCGTC
AGGTTTTTGACCTCGTCTCCCATCTCCCTGTTTTCTTCTCACGCCTTTTCTACCCTGGCGGTGGTTATTCTCCGGGTGAT
TGGGGTTTTGCAGCTTTTACTCTATTGTGCCTCTTTTTATGTTACAGTTACCCAGCCTTTGGTATTGCTCCCCTCTTGGG
TGTGTTTTCTGGGTCTTCTCGGCGCGTTCGAATGGGGGTTTTTGGCTGCTGGTTGGCTTTTGCTGTTGGTCTGTTCAAGC
CTGTGTCCGACCCAGTCGGCGCTGCTTGTGAGTTTGACTCGCCAGAGTGTAGAAACATCCTTCATTCTTTTGAGCTTCTC
AAACCTTGGGACCCTGTTCGCAGCCTTGTTGTGGGCCCCGTCGGTCTCGGTCTTGCCATTCTTGGCAGGTTACTGGGCGG
GGCACGCTGCATCTGGCACTTTTTGCTTAGGCTTGGCATTGTTGCAGACTGTATCTTGGCTGGAGCTTACGTGCTTTCTC
AAGGTAGGTGTAAAAAGTGCTGGGGATCTTGTATAAGAACTGCTCCCAATGAGGTCGCTTTTAACGTGTTTCCTTTCACA
CGTGCGACCAGGTCGTCACTTATCGACCTGTGCGATCGGTTTTGTGCGCCAAAAGGAATGGACCCCATTTTTCTCGCCAC
```

Fig. 1H-2

```
TGGGTGGCGCGGGTGCTGGGCCGGCCGAAGCCCCATTGAGCAACCCTCTGAAAAACCCATCGCGTTTGCCCAGTTGGATG
AAAAGAAGATTACGGCTAGGACTGTGGTCGCCCAGCCTTATGACCCCAACCAAGCCGTAAAGTGCTTGCGGGTATTGCAG
GCGGGTGGGGCGATGGTGGCTAAGGCGGTCCCAAAAGTGGTCAAGGTTTCCGCTGTTCCATTCCGAGCCCCCTTCTTTCC
CACTGGAGTGAAAGTTGACCCTGATTGCAGGGTCGTGGTTGACCCTGACACTTTCACTGCAGCTCTCCGGTCTGGCTACT
CCACCACAAACCTCGTCCTTGGTGTGGGGGACTTTGCCCAGCTGAATGGATTAAAAATCAGGCAAATTTCCAAGCCTTCA
GGGGGAGGCCCACATCTCATGGCTGCCCTGCATGTTGCCTGCTCGATGGCTCTGCACATGCTTGCTGGGATTTATGTGAC
TGCGGTGGGTTCTTGCGGCACCGGCACCAACGACCCGTGGTGCGCTAACCCGTTTGCCGTCCCTGGCTACGGACCTGGCT
CTCTCTGCACGTCCAGATTGTGCATTTCCCAACACGGCCTTACCCTGCCCTTGACAGCACTTGTGGCGGGATTCGGTATT
CAAGAAATTGCCTTGGTCGTTTTGATTTTTGTTTCCATCGGAGGCATGGCTCATAGGTTGAGCTGTAAGGCTGACATGCT
GTGTGTCTTGCTTGCAATTGCCAGCTATGTTTGGGTACCTCTTACCTGGTTGCTTTGTGTGTTTCCTTGCTGGTTGCGCT
GTTTTTCTTTGCACCCCCTCACCATCCTATGGTTGGTGTTTTTCTTGATTTCTGTGAATATGCCTTCAGGAATCTTGGCC
ATGGTGTTGTTGGTTTCTCTTTGGCTTCTTGGTCGTTATACTAATGTTGCTGGCCTTGTCACCCCCTACGACATTCATCA
TTACACCAGTGGCCCCCGCGGTGTTGCCGCCTTGGCTACCGCACCAGATGGGACCTACTTGGCCGCTGTCCGCCGCGCTG
CGTTGACTGGCCGCACCATGCTGTTTACCCCGTCCCAGCTTGGGTCTCTTCTTGAGGGTGCTTTCAGAACTCGAAAGCCC
TCACTGAACACCGTCAATGTGATCGGGTCCTCCATGGGCTCTGGCGGGGTGTTTACCATCGACGGGAAAGTCAAGTGCGT
AACTGCCGCACATGTCCTTACGGGCAATTCAGCTCGGGTTTCCGGGGTCGGCTTCAATCAAATGCTTGACTTTGACGTAA
AGGGAGATTTCGCTATAGCTGATTGCCCGAATTGGCAAGGGGCTGCCCCCAAGACCCAATTCTGCACGGATGGATGGACT
GGCCGTGCCTATTGGCTAACATCCTCTGGCGTCGAACCCGGCGTCATTGGAAAAGGATTCGCCTTCTGCTTCACCGCATG
TGGCGATTCCGGGTCCCCAGTGATCACCGAGGCCGGTGAGCTTGTCGGCGTTCACACGGGATCGAATAAACAAGGGGGGG
GCATTGTTACGCGCCCCTCAGGCCAGTTTTGTAATGTGGCACCCATCAAGCTAAGCGAATTAAGTGAATTCTTTGCTGGG
CCTAAGGTCCCGCTCGGTGATGTGAAGGTCGGCAGCCACATAATTAAAGACATAAGCGAGGTGCCTTCAGATCTTTGTGC
CTTGCTTGCTGCCAAACCTGAACTGGAAGGAGGCCTCTCCACCGTCCAACTTCTTTGTGTGTTTTTTCTCCTGTGGAGAA
TGATGGGACATGCCTGGACGCCCTTGGTTGCTGTGAGTTTCTTTATTTTGAATGAGGTTCTCCCAGCCGTCCTGGTCCGG
AGTGTTTTCTCCTTTGGAATGTTTGTGCTATCCTGGCTCACGCCATGGTCTGCGCAAGTTCTGATGATCAGGCTTCTGAC
AGCAGCTCTTAACAGGAACAGATGGTCACTTGCCTTTTTCAGCCTCGGTGCAGTGACCGGTTTTGTCGCAGATCTTGCGG
CCACTCAGGGGCATCCGTTGCAGGCAGTGATGAATTTGAGCACCTATGCATTCCTGCCTCGGATGATGGTTGTGACCTCA
CCAGTCCCAGTGATCACGTGTGGTGTCGTGCACCTACTTGCCATCATTTTGTACTTGTTTAAGTACCGTGGCCTGCACCA
TATCCTTGTTGGCGATGGAGTGTTCTCTGCGGCTTTCTTCTTGAGATACTTTGCCGAGGGAAAGTTGAGGGAAGGGGTGT
CGCAATCCTGCGGAATGAATCATGAGTCTCTGACTGGTGCCCTCGCTATGAGACTCAATGACGAGGACTTGGATTTCCTT
ATGAAATGGACTGATTTTAAGTGCTTTGTTTCTGCGTCCAACATGAGGAATGCAGCGGGTCAATTTATCGAGGCTGCCTA
TGCTAAAGCACTTAGAGTAGAACTGGCCCAGTTGGTGCAGGTTGATAAAGTTCGAGGTACTTTGGCCAAACTTGAAGCTT
TTGCTGATACCGTGGCACCTCAACTCTCGCCCGGTGACATTGTTGTCGCTCTCGGCCACACGCCTGTTGGCAGTATCTTC
GACCTAAAGGTTGGTAGCACCAAGCATACCCTCCAAGCCATTGAGACCAGAGTCCTTGCTGGGTCCAAAATGACCGTGGC
GCGCGTCGTCGACCCGACCCCCACGCCCCCACCCGCACCCGTGCCCATCCCCCTCCCACCGAAAGTTCTGGAGAATGGCC
CCAACGCTTGGGGGGATGAGGACCGTTTGAATAAGAAGAAGAGGCGCAGGATGGAAGCCCTCGGCATCTATGTTATGGGC
GGGAAAAAATACCAGAAATTTTGGGACAAGAATTCCGGTGATGTGTTTTATGAGGAGGTCCATAATAACACAGATGAGTG
GGAGTGTCTCAGAGTTGGCGACCCTGCCGACTTTGACCCTGAGAAGGGAACTCTGTGTGGACATGTCACCATTGAAAACA
AGGCTTACCATGTTTACACCTCCCCATCTGGTAAGAAGTTCTTGGTCCCCGTCAACCCAGAGAATGGAAGAGTCCAATGG
GAAGCTGCAAAGCTTTCCGTGGAGCAGGCCCTAGGTATGATGAATGTCGACGGCGAACTGACTGCCAAAGAACTGGAGAA
ACTGAAAAGAATAATTGACAAACTCCAGGGCCTGACTAAGGAGCAGTGTTTAAACTGCTAGCCGCCAGCGACTTGACCCG
CTGTGGTCGCGGCGGCTTGGTTGTTACTGAAACAGCGGTAAAAATAGTCAAATTTCACAACCGGACCTTCACCCTGGGAC
CTGTGAATTTAAAAGTGGCCAGTGAGGTTGAGCTAAAAGACGCGGTTGAGCACAACCAACACCCGGTTGCGAGACCGATC
GATGGTGGAGTTGTGCTCCTGCGTTCCGCGGTTCCTTCGCTTATAGACGTCTTGATCTCCGGTGCTGATGCATCTCCCAA
GTTACTTGCCCATCACGGGCCGGGAAACACTGGGATCGATGGCACGCTCTGGGATTTTGAGTCCGAAGCCACTAAAGAGG
AAGTCGCACTCAGTGCGCAAATAATACAGGCTTGTGACATTAGGCGCGGCGACGCTCCTGAAATTGGTCTCCCTTACAAG
CTGTACCCTGTTAGGGGTAACCCTGAGCGGGTGAAAGGAGTTCTGCAGAATACAAGGTTTGGAGACATACCTTACAAAAC
CCCCAGTGACACTGGAAGCCCAGTGCACGCGGCTGCCTGCCTTACGCCCAACGCCACTCCGGTGACTGATGGGCGCTCCG
TCTTGGCCACGACCATGCCCCCCGGGTTTGAGTTATATGTACCGACCATACCAGCGTCTGTCCTTGATTACCTTGACTCT
AGGCCTGACTGCCCTAAACAGCTGACAGAGCACGGCTGCGAAGATGCCGCACTGAAAGACCTCTCTAAATATGACTTGTC
CACCCAAGGCTTTGTTTTTACCTGGAGTTCTTCGCCTTGTGCGGAAATACCTGTTTGCCCATGTAGGTAAGTGCCCACCCG
```

Fig. 1H-3

```
TTCATCGGCCTTCTACTTACCCTGCTAAGAATTCTATGGCTGGAATAAATGGGAACAGGTTCCCAACCAAGGACATTCAG
AGCGTCCCTGAAATCGACGTTCTGTGCGCACAGGCTGTGCGAGAAAACTGGCAAACTGTCACCCCTTGTACTCTTAAGAA
ACAGTATTGCGGGAAGAAGAAGACTAGGACCATACTCGGCACCAATAACTTCATCGCACTAGCCCACCGAGCAGTGTTGA
GTGGTGTTACCCAGGGCTTCATGAAAAAGGCGTTTAACTCGCCCATCGCCCTCGGAAAGAACAAGTTTAAGGAGCTACAG
ACTCCGGTCCTGGGCAGGTGCCTTGAAGCTGATCTCGCATCCTGCGATCGATCCACGCCTGCAATTGTCCGCTGGTTTGC
CGCCAACCTTCTTTATGAACTTGCCTGTGCTGAAGAGCATCTACCGTCGTACGTGCTGAACTGCTGCCACGACTTACTGG
TCACGCAGTCCGGCGCAGTGACTAAGAGAGGTGGCCTGTCGTCTGGCGACCCGATCACCTCTGTGTCTAACACCATTTAT
AGTTTGGTGATCTATGCACAGCATATGGTGCTTAGTTACTTCAAAAGTGGTCACCCCCATGGCCTTCTGTTCTTACAAGA
CCAGCTAAAGTTTGAGGACATGCTCAAGGTTCAACCCCTGATCGTCTATTCGGACGACCTCGTGCTGTATGCCGAGTCTC
CCACCATGCCAAACTATCACTGGTGGGTTGAACATCTGAATTTGATGCTGGGGTTTCAGACGGACCCAAAGAAGACAGCA
ATAACAGACTCGCCATCATTTCTAGGCTGTAGAATAATAAATGGGCGCCAGCTAGTCCCCAACCGTGACAGGATCCTCGC
GGCCCTCGCCTATCACATGAAGGCGAGTAATGTTTCTGAATACTATGCCTCAGCGGCTGCAATACTCATGGACAGCTGTG
CTTGTTTGGAGTATGATCCTGAATGGTTTGAAGAACTTGTAGTTGGAATAGCGCAGTGCGCCCGCAAGGACGGCTACAGC
TTTCCCGGCACGCCGTTCTTCATGTCCATGTGGGAAAAACTCAGGTCCAATTATGAGGGGAAGAAGTCGAGAGTGTGCGG
GTACTGCGGGGCCCCGGCCCCGTACGCTACTGCCTGTGGCCTCGACGTCTGCATTTACCACACCCACTTCCACCAGCATT
GTCCAGTCACAATCTGGTGTGGCCATCCAGCGGGTTCTGGTTCTTGTAGTGAGTGCAAATCCCCTGTAGGGAAAGGCACA
AGCCCTTTAGACGAGGTGCTGGAACAAGTCCCGTATAAGCCCCCACGGACCGTTATCATGCATGTGGAGCAGGGTCTCAC
CCCCCTTGATCCAGGTAGATACCAAACTCGCCGCGGATTAGTCTCTGTCAGGCGTGGAATTAGGGGAAATGAAGTTGGAC
TACCAGACGGTGATTATGCTAGCACCGCCTTGCTCCCTACCTGCAAAGAGATCAACATGGTCGCTGTCGCTTCCAATGTA
TTGCGCAGCAGGTTCATCATCGGCCCACCCGGTGCTGGGAAAACATACTGGCTCCTTCAACAGGTCCAGGATGGTGATGT
TATTTACACACCAACTCACCAGACCATGCTTGACATGATTAGGGCTTTGGGGACGTGCCGGTTCAACGTCCCGGCAGGCA
CAACGCTGCAATTCCCCGTCCCTCCCGCACCGGTCCGTGGGTTCGCATCCTAGCCGGCGGTTGGTGTCCTGGCAAGAAT
TCCTTCCTAGATGAAGCAGCGTATTGCAATCACCTTGATGTTTTGAGGCTTCTTAGTAAAACTACCCTCACCTGTCTAGG
AGACTTCAAGCAACTCCACCCAGTGGGTTTTGATTCTCATTGCTATGTTTTTGACATCATGCCTCAAACTCAACTGAAGA
CCATCTGGAGGTTTGGACAGAATATCTGTGATGCCATTCAGCCAGATTACAGGGACAAACTCATGTCCATGGTCAACACA
ACCCGTGTGACCTACGTGGAAAAACCTGTCAGGTATGGGCAGGTCCTCACCCCCTACCACAGGGACCGAGAGGACGACGC
CATCACTATTGACTCCAGTCAAGGCGCCACATTCGATGTGGTTACATTGCATTTGCCCACTAAAGATTCACTCAACAGGC
AAAGAGCCCTTGTTGCTATCACCAGGGCAAGACACGCTATCTTTGTGTATGACCCACACAGGCAGCTGCAGGGCTTGTTT
GATCTTCCTGCAAAAGGCACGCCCGTCAACCTCGCAGTGCACTGCGACGGGCAGCTGATCGTGCTGGATAGAAATAACAA
AGAATGCACGGTTGCTCAGGCTCTAGGCAACGGGGATAAATTTAGGGCCACAGACAAGCGTGTTGTAGATTCTCTCCGCG
CCATTTGTGCTGATCTAGAAGGGTCGAGCTCTCCGCTCCCCAAGGTCGCACACAACTTGGGATTTTATTTCTCACCTGAT
TTAACACAGTTTGCTAAACTCCCAGTAGAACTTGCACCTCACTGGCCCGTGGTGTCAACCCAGAACAATGAAAAGTGGCC
GGATCGGCTGGTTGCCAGCCTTCGCCCTATCCATAAATACAGCCGCGCGTGCATCGGTGCCGGCTATATGGTGGGCCCTT
CGGTGTTTCTAGGCACTCCTGGGGTCGTGTCATACTATCTCACAAAATTTGTTAAGGGCGGGGCTCAAGTGCTTCCGGAG
ACGGTTTTCAGCACCGGCCGAATTGAGGTAGACTGCCGGGAATATCTTGATGATCGGGAGCGAGAAGTTGCTGCGTCCCT
CCCACACGCTTTCATTGGCGACGTCAAAGGCACTACCGTTGGAGGATGTCATCATGTCACCTCCAGATACCTCCCGCGCG
TCCTTCCCAAGGAATCAGTTGCGGTAGTCGGGGTTTCAAGCCCCGGAAAAGCCGCGAAAGCATTGTGCACACTGACAGAT
GTGTACCTCCCAGATCTTGAAGCCTATCTCCACCCGGAGACCCAGTCCAAGTGCTGGAAAATGATGTTGGACTTCAAAGA
AGTTCGACTAATGGTCTGGAAAGACAAAACAGCCTATTTCCAACTTGAAGGTCGCTATTTCACCTGGTATCAGCTTGCCA
GCTATGCCTCGTACATCCGTGTTCCCGTCAACTCTACGGTGTACTTGGACCCCTGCATGGGCCCCGCCCTTTGCAACAGG
AGAGTCGTCGGGTCCACCCACTGGGGGCTGACCTCGCGGTCACCCCTTATGATTACGGCGCTAAAATTATCCTGTCTAG
CGCGTACCATGGTGAAATGCCCCCCGGATACAAAATTCTGGCGTGCGCGGAGTTCTCGTTGGATGACCCAGTTAAGTACA
AACATACCTGGGGGTTTGAATCGGATACAGCGTATCTGTATGAGTTCACCGGAAACGGTGAGGACTGGGAGGATTACAAT
GATGCGTTTCGTGCGCGCCAGGAAGGGAAAATTTATAAGGCCACTGCCACCAGCTTGAAGTTTTATTTTCCCCGGGCCC
TGTCATTGAACCAACTTTAGGCCTGAATTGAAATGAAATGGGGTCCATGCAAAGCCTTTTTGACAAAATTGGCCAACTTT
TTGTGGATGCTTTCACGGAGTTCTTGGTGTCCATTGTTGATATCATTATATTTTTGGCCATTTTGTTTGGCTTCACCATC
GCCGGTTGGCTGGTGGTCTTTTGCATCAGATTGGTTTGCTCCGCGATACTCCGTACGCGCCCTGCCATTCACTCTGAGCA
ATTACAGAAGATCTTATGAGGCCTTTCTTTCCCAGTGCCAAGTGGACATTCCCACCTGGGGAACTAAACATCCTTTGGGG
ATGCTTTGGCACCATAAGGTGTCAACCCTGATTGATGAAATGGTGTCGCGTCGAATGTACCGCATCATGGAAAAAGCAGG
GCAGGCTGCCTGGAAACAGGTGGTGAGCGAGGCTACGCTGTCTCGCATTAGTAGTTTGGATGTGGTGGCTCATTTTCAGC
```

Fig. 1H-4

ATCTAGCCGCCATTGAAGCCGAGACCTGTAAATATTTGGCCTCCCGGCTGCCCATGCTACACAACCTGCGCATGACAGGG
TCAAATGTAACCATAGTGTATAATAGCACTTTGAATCAGGTGTTTGCTATTTTTCCAACCCCTGGTTCCCGGCCAAAGCT
TCATGATTTTCAGCAATGGTTAATAGCTGTACATTCCTCCATATTTTCCTCTGTTGCAGCTTCTTGTACTCTTTTTGTTG
TGCTGTGGTTGCGGGTTCCAATACTACGTACTGTTTTTGGTTTCCGCTGGTTAGGGGCAATTTTTCTTTCGAACTCACAG
TGAATTACACGGTGTGTCCACCTTGCCTCACCCGGCAAGCAGCCACAGAGATCTACGAACCCGGTAGGTCTCTTTGGTGC
AGGATAGGGTATGACCGATGTGGGGAGGACGATCATGACGAGCTAGGGTTTATGATACCGCCTGGCCTCTCCAGCGAAGG
CCACTTGACTGGTGTTTACGCCTGGTTGGCGTTCTTGTCCTTCAGCTACACGGCCCAGTTCCATCCCGAGATATTCGGGA
TAGGGAATGTGAGTCGAGTTTATGTTGACATCAAACATCAACTCATCTGCGCCGAACATGACGGGCAGAACACCACCTTG
CCTCGTCATGACAACATTTCAGCCGTGTTTCAGACCTATTACCAACATCAAGTCGACGGCGGCAATTGGTTTCACCTAGA
ATGGCTTCGTCCCTTCTTTTCCTCGTGGTTGGTTTTAAATGTCTCTTGGTTTCTCAGGCGTTCGCCTGCAAACCATGTTT
CAGTTCGAGTCTTGCAGATATTAAGACCAACACCACCGCAGCGGCAAGCTTTGCTGTCCTCCAAGACATCAGTTGCCTTA
GGCATCGCGACTCGGCCTCTGAGGCGATTCGCAAAATCCCTCAGTGCCGTACGGCGATAGGGACACCCGTGTATGTTACC
ATCACAGCCAATGTGACAGATGAGAATTATTTACATTCTTCTGATCTCCTCATGCTTTCTTCTTGCCTTTTCTATGCTTC
TGAGATGAGTGAAAAGGGATTTAAGGTGGTATTTGGCAATGTGTCAGGCATCGTGGCTGTGTGTGTCAATTTTACCAGCT
ACGTCCAACATGTCAAGGAGTTTACCCAACGCTCCCTGGTGGTCGACCATGTGCGGTTGCTCCATTTCATGACACCTGAG
ACCATGAGGTGGGCAACTGTTTTAGCCTGTCTTTTTGCCATTCTGTTGGCAATTTGAATGTTTAAGTATGTTGGAGAAAT
GCTTGACCGCGGGCTGTTGCTCGCGATTGCTTTCTTTGTGGTGTATCGTGCCGTTCTGTTTTGCTGTGCTCGCCAACGCC
AGCAACGACAGCAGCTCCCATCTACAGCTGATTTACAACTTGACGCTATGTGAGCTGAATGGCACAGATTGGCTAGCTAA
CAAATTTGATTGGGCAGTGGAGAGTTTTGTCATCTTTCCCGTTTTGACTCACATTGTCTCCTATGGTGCCCTCACTACCA
GCCATTTCCTTGACACAGTCGCTTTAGTCACTGTGTCTACCGCCGGGTTTGTTCACGGGCGGTATGTCCTAAGTAGCATC
TACGCGGTCTGTGCCCTGGCTGCGTTGACTTGCTTCGTCATTAGGTTTGCAAAGAATTGCATGTCCTGGCGCTACGCGTG
TACCAGATATACCAACTTTCTTCTGGACACTAAGGGCAGACTCTATCGTTGGCGGTCGCCTGTCATCATAGAGAAAAGGG
GCAAAGTTGAGGTCGAAGGTCATCTGATCGACCTCAAAAGAGTTGTGCTTGATGGCTCCGTGGCAACCCCTATAACCAGA
GTTTCAGCGGAACAATGGGTCGTCCTTAGATGACTTCTGTCACGATAGCACGGCTCCACAAAAGGTGCTTTTGGCGTTT
TCTATTACCTACACGCCAGTGATGATATATGCCCTAAAGGTGAGTCGCGGCCGACTGCTAGGGCTTCTGCACCTTTTGAT
CTTCCTGAATTGTGCTTTCACCTTCGGGTACATGACTTTCGCGCACTTTCAGAGTACAAATAAGGTCGCGCTCACTATGG
GAGCAGTAGTTGCACTCCTTTGGGGGGTGTACTCAGCCATAGAAACCTGGAAATTCATCACCTCCAGATGCCGTTTGTGC
TTGCTAGGCCGCAAGTACATTCTGGCCCCTGCCCACCACGTTGAAAGTGCCGCAGGCTTTCATCCGATTGCGGCAAATGA
TAACCACGCATTTGTCGTCCGGCGTCCCGGCTCCACTACGGTCAACGGCACATTGGTGCCCGGGTTAAAAAGCCTCGTGT
TGGGTGGCAGAAAAGCTGTTAAACAGGGAGTGGTAAACCTTGTCAAATATGCCAAATAACAACGGCAAGCAGCAGAAGAG
AAAGAAGGGGGATGGCCAGCCAGTCAATCAGCTGTGCCAGATGCTGGGTAAGATCATCGCTCAGCAAAACCAGTCCAGAG
GCAAGGGACCGGGAAAGAAAAATAAGAAGAAAAACCCGGAGAAGCCCCATTTTCCTCTAGCGACTGAAGATGATGTCAGA
CATCACTTTACCCCTAGTGAGCGGCAATTGTGTCTGTCGTCAATCCAGACCGCCTTTAATCAAGGCGCTGGGACTTGCAC
CCTGTCAGATTCAGGGAGGATAAGTTACACTGTGGAGTTTAGTTTGCCTACGCATCATACTGTGCGCCTGATCCGCGTCA
CAGCATCACCCTCAGCATGATGGGCTGGCATTCTTGAGGCATCTCAGTGTTTGAATTGGAAGAATGTGTGGTGAATGGCA
CTGATTGACATTGTGCCTCTAAGTCACCTATTCAATTAGGGCGACCGTGTGGGGGTGAGATTTAATTGGCGAGAACCATG
CGGCCGAAATTAAAAAAAA

Fig. 1I-1

```
>V7-Nsp2d543-632.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCACACGCCCAAAATACTCAGCTCAAGCCATCATCGACTCGGGCGGGCCCTGCAGTGGGCATCTCCAAGAGGTAAAGG
AAACATGCCTTAGTGTCATGCGCGAGGCATGTGATGCGACTAAGCTTGATGACCCTGCTACGCAGGAATGGCTTTCTCGC
ATGTGGGATCGGGTGGACATGCTGACTTGGCGCAACACGTCTGTTTACCAGGCGATTTGCACCTTAGATGGCAGGTTAAA
GTTCCTCCCAAAAATGATACTCGAGACACCGCCGCCCTATCCGTGTGAGTTTGTGATGATGCCTCACACGCCTGCACCTT
CCGTAGGTGCGGAGAGCGACCTTACCATTGGCTCAGTTGCTACTGAAGATGTTCCACGCATCCTCGAGAAAATAGAAAAT
GTCGGCGAGATGGCCAACCAGGGACCCTTGGCCTTCTCCGAGGATAAACCGGTAGATGACCAACTTGTCAACGACCCCCG
GATATCGTCGCGGAGGCCTGACGAGAGCACATCAGCTCCGTCCGCAGGCACAGGTGGCGCCGGCTCTTTTACCGATTTGC
CGCCTTCAGATGGCGCGGATGCGGACGGGGGGGGCCGTTTCGGACGGTAAAAAGAAAAGCTGAAAGGCTCTTTGACCAA
CTGAGCCGTCAGGTTTTTGACCTCGTCTCCCATCTCCCTGTTTTCTTCTCACGCCTTTTCTACCCTGGCGGTGGTTATTC
TCCGGGTGATTGGGGTTTTGCAGCTTTTACTCTATTGTGCCTCTTTTTATGTTACAGTTACCCAGCCTTTGGTATTGCTC
CCCTCTTGGGTGTGTTTTCTGGGTCTTCTCGGCGCGTTCGAATGGGGGTTTTGGCTGCTGGTTGGCTTTTGCTGTTGGT
CTGTTCAAGCCTGTGTCCGACCCAGTCGGCGCTGCTTGTGAGTTTGACTCGCCAGAGTGTAGAAACATCCTTCATTCTTT
```

Fig. 1I-2

```
TGAGCTTCTCAAACCTTGGGACCCTGTTCGCAGCCTTGTTGTGGGCCCCGTCGGTCTCGGTCTTGCCATTCTTGGCAGGT
TACTGGGCGGGGCACGCTGCATCTGGCACTTTTTGCTTAGGCTTGGCATTGTTGCAGACTGTATCTTGGCTGGAGCTTAC
GTGCTTTCTCAAGGTAGGTGTAAAAAGTGCTGGGGATCTTGTATAAGAACTGCTCCCAATGAGGTCGCTTTTAACGTGTT
TCCTTTCACACGTGCGACCAGGTCGTCACTTATCGACCTGTGCGATCGGTTTTGTGCGCCAAAAGGAATGGACCCCATTT
TTCTCGCCACTGGGTGGCGCGGGTGCTGGGCCGGCCGAAGCCCCATTGAGCAACCCTCTGAAAAACCCATCGCGTTTGCC
CAGTTGGATGAAAAGAAGATTACGGCTAGGACTGTGGTCGCCCAGCCTTATGACCCCAACCAAGCCGTAAAGTGCTTGCG
GGTATTGCAGGCGGGTGGGGCGATGGTGGCTAAGGCGGTCCCAAAAGTGGTCAAGGTTTCCGCTGTTCCATTCCGAGCCC
CCTTCTTTCCCACTGGAGTGAAAGTTGACCCTGATTGCAGGGTCGTGGTTGACCCTGACACTTTCACTGCAGCTCTCCGG
TCTGGCTACTCCACCACAAACCTCGTCCTTGGTGTGGGGGACTTTGCCCAGCTGAATGGATTAAAAATCAGGCAAATTTC
CAAGCCTTCAGGGGGAGGCCCACATCTCATGGCTGCCCTGCATGTTGCCTGCTCGATGGCTCTGCACATGCTTGCTGGGA
TTTATGTGACTGCGGTGGGTTCTTGCGGCACCGGCACCAACGACCCGTGGTGCGCTAACCCGTTTGCCGTCCCTGGCTAC
GGACCTGGCTCTCTCTGCACGTCCAGATTGTGCATTTCCCAACACGGCCTTACCCTGCCCTTGACAGCACTTGTGGCGGG
ATTCGGTATTCAAGAAATTGCCTTGGTCGTTTTGATTTTTGTTTCCATCGGAGGCATGGCTCATAGGTTGAGCTGTAAGG
CTGACATGCTGTGTGTCTTGCTTGCAATTGCCAGCTATGTTTGGGTACCTCTTACCTGGTTGCTTTGTGTGTTTCCTTGC
TGGTTGCGCTGTTTTTCTTTGCACCCCCTCACCATCCTATGGTTGGTGTTTTTCTTGATTTCTGTGAATATGCCTTCAGG
AATCTTGGCCATGGTGTTGTTGGTTTCTCTTTGGCTTCTTGGTCGTTATACTAATGTTGCTGGCCTTGTCACCCCCTACG
ACATTCATCATTACACCAGTGGCCCCCGCGGTGTTGCCGCCTTGGCTACCGCACCAGATGGGACCTACTTGGCCGCTGTC
CGCCGCGCTGCGTTGACTGGCCGCACCATGCTGTTTACCCCGTCCCAGCTTGGGTCTCTTCTTGAGGGTGCTTTCAGAAC
TCGAAAGCCCTCACTGAACACCGTCAATGTGATCGGGTCCTCCATGGGCTCTGGCGGGGTGTTTACCATCGACGGGAAAG
TCAAGTGCGTAACTGCCGCACATGTCCTTACGGGCAATTCAGCTCGGGTTTCCGGGGTCGGCTTCAATCAAATGCTTGAC
TTTGACGTAAAGGGAGATTTCGCTATAGCTGATTGCCCGAATTGGCAAGGGGCTGCCCCCAAGACCCAATTCTGCACGGA
TGGATGGACTGGCCGTGCCTATTGGCTAACATCCTCTGGCGTCGAACCCGGCGTCATTGGAAAAGGATTCGCCTTCTGCT
TCACCGCATGTGGCGATTCCGGGTCCCCAGTGATCACCGAGGCCGGTGAGCTTGTCGGCGTTCACACGGGATCGAATAAA
CAAGGGGGGGGCATTGTTACGCGCCCCTCAGGCCAGTTTTGTAATGTGGCACCCATCAAGCTAAGCGAATTAAGTGAATT
CTTTGCTGGGCCTAAGGTCCCGCTCGGTGATGTGAAGGTCGGCAGCCACATAATTAAAGACATAAGCGAGGTGCCTTCAG
ATCTTTGTGCCTTGCTTGCTGCCAAACCTGAACTGGAAGGAGGCCTCTCCACCGTCCAACTTCTTTGTGTGTTTTTTCTC
CTGTGGAGAATGATGGGACATGCCTGGACGCCCTTGGTTGCTGTGAGTTTCTTTATTTTGAATGAGGTTCTCCCAGCCGT
CCTGGTCCGGAGTGTTTTCTCCTTTGGAATGTTTGTGCTATCCTGGCTCACGCCATGGTCTGCGCAAGTTCTGATGATCA
GGCTTCTGACAGCAGCTCTTAACAGGAACAGATGGTCACTTGCCTTTTTCAGCCTCGGTGCAGTGACCGGTTTTGTCGCA
GATCTTGCGGCCACTCAGGGGCATCCGTTGCAGGCAGTGATGAATTTGAGCACCTATGCATTCCTGCCTCGGATGATGGT
TGTGACCTCACCAGTCCCAGTGATCACGTGTGGTGTCGTGCACCTACTTGCCATCATTTTGTACTTGTTTAAGTACCGTG
GCCTGCACCATATCCTTGTTGGCGATGGAGTGTTCTCTGCGGCTTTCTTCTTGAGATACTTTGCCGAGGGAAAGTTGAGG
GAAGGGGTGTCGCAATCCTGCGGAATGAATCATGAGTCTCTGACTGGTGCCCTCGCTATGAGACTCAATGACGAGGACTT
GGATTTCCTTATGAAATGGACTGATTTTAAGTGCTTTGTTTCTGCGTCCAACATGAGGAATGCAGCGGGTCAATTTATCG
AGGCTGCCTATGCTAAAGCACTTAGAGTAGAACTGGCCCAGTTGGTGCAGGTTGATAAAGTTCGAGGTACTTTGGCCAAA
CTTGAAGCTTTTGCTGATACCGTGGCACCTCAACTCTCGCCCGGTGACATTGTTGTCGCTCTCGGCCACACGCCTGTTGG
CAGTATCTTCGACCTAAAGGTTGGTAGCACCAAGCATACCCTCCAAGCCATTGAGACCAGAGTCCTTGCTGGGTCCAAAA
TGACCGTGGCGCGCGTCGTCGACCCGACCCCCACGCCCCCACCCGCACCCGTGCCCATCCCCCTCCCACCGAAAGTTCTG
GAGAATGGCCCCAACGCTTGGGGGGATGAGGACCGTTTGAATAAGAAGAAGAGGCGCAGGATGGAAGCCCTCGGCATCTA
TGTTATGGGCGGGAAAAAATACCAGAAATTTTGGGACAAGAATTCCGGTGATGTGTTTTATGAGGAGGTCCATAATAACA
CAGATGAGTGGGAGTGTCTCAGAGTTGGCGACCCTGCCGACTTTGACCCTGAGAAGGGAACTCTGTGTGGACATGTCACC
ATTGAAAACAAGGCTTACCATGTTTACACCTCCCCATCTGGTAAGAAGTTCTTGGTCCCCGTCAACCCAGAGAATGGAAG
AGTCCAATGGGAAGCTGCAAAGCTTTCCGTGGAGCAGGCCCTAGGTATGATGAATGTCGACGGCGAACTGACTGCCAAAG
AACTGGAGAAACTGAAAAGAATAATTGACAAACTCCAGGGCCTGACTAAGGAGCAGTGTTTAAACTGCTAGCCGCCAGCG
ACTTGACCCGCTGTGGTCGCGGCGGCTTGGTTGTTACTGAAACAGCGGTAAAAATAGTCAAATTTCACAACCGGACCTTC
ACCCTGGGACCTGTGAATTTAAAAGTGGCCAGTGAGGTTGAGCTAAAAGACGCGGTTGAGCACAACCAACACCCGGTTGC
GAGACCGATCGATGGTGGAGTTGTGCTCCTGCGTTCCGCGGTTCCTTCGCTTATAGACGTCTTGATCTCCGGTGCTGATG
CATCTCCCAAGTTACTTGCCCATCACGGGCCGGGAAACACTGGGATCGATGGCACGCTCTGGGATTTTGAGTCCGAAGCC
ACTAAAGAGGAAGTCGCACTCAGTGCGCAAATAATACAGGCTTGTGACATTAGGCGCGGCGACGCTCCTGAAATTGGTCT
CCCTTACAAGCTGTACCCTGTTAGGGGTAACCCTGAGCGGGTGAAAGGAGTTCTGCAGAATACAAGGTTTGGAGACATAC
```

Fig. 1I-3

```
CTTACAAAACCCCCAGTGACACTGGAAGCCCAGTGCACGCGGCTGCCTGCCTTACGCCCAACGCCACTCCGGTGACTGAT
GGGCGCTCCGTCTTGGCCACGACCATGCCCCCCGGGTTTGAGTTATATGTACCGACCATACCAGCGTCTGTCCTTGATTA
CCTTGACTCTAGGCCTGACTGCCCTAAACAGCTGACAGAGCACGGCTGCGAAGATGCCGCACTGAAAGACCTCTCTAAAT
ATGACTTGTCCACCCAAGGCTTTGTTTTACCTGGAGTTCTTCGCCTTGTGCGGAAATACCTGTTTGCCCATGTAGGTAAG
TGCCCACCCGTTCATCGGCCTTCTACTTACCCTGCTAAGAATTCTATGGCTGGAATAAATGGGAACAGGTTCCCAACCAA
GGACATTCAGAGCGTCCCTGAAATCGACGTTCTGTGCGCACAGGCTGTGCGAGAAAACTGGCAAACTGTCACCCCTTGTA
CTCTTAAGAAACAGTATTGCGGGAAGAAGAAGACTAGGACCATACTCGGCACCAATAACTTCATCGCACTAGCCCACCGA
GCAGTGTTGAGTGGTGTTACCCAGGGCTTCATGAAAAAGGCGTTTAACTCGCCCATCGCCCTCGGAAAGAACAAGTTTAA
GGAGCTACAGACTCCGGTCCTGGGCAGGTGCCTTGAAGCTGATCTCGCATCCTGCGATCGATCCACGCCTGCAATTGTCC
GCTGGTTTGCCGCCAACCTTCTTTATGAACTTGCCTGTGCTGAAGAGCATCTACCGTCGTACGTGCTGAACTGCTGCCAC
GACTTACTGGTCACGCAGTCCGGCGCAGTGACTAAGAGAGGTGGCCTGTCGTCTGGCGACCCGATCACCTCTGTGTCTAA
CACCATTTATAGTTTGGTGATCTATGCACAGCATATGGTGCTTAGTTACTTCAAAAGTGGTCACCCCCATGGCCTTCTGT
TCTTACAAGACCAGCTAAAGTTTGAGGACATGCTCAAGGTTCAACCCCTGATCGTCTATTCGGACGACCTCGTGCTGTAT
GCCGAGTCTCCCACCATGCCAAACTATCACTGGTGGGTTGAACATCTGAATTTGATGCTGGGGTTTCAGACGGACCCAAA
GAAGACAGCAATAACAGACTCGCCATCATTTCTAGGCTGTAGAATAATAAATGGGCGCCAGCTAGTCCCCAACCGTGACA
GGATCCTCGCGGCCCTCGCCTATCACATGAAGGCGAGTAATGTTTCTGAATACTATGCCTCAGCGGCTGCAATACTCATG
GACAGCTGTGCTTGTTTGGAGTATGATCCTGAATGGTTTGAAGAACTTGTAGTTGGAATAGCGCAGTGCGCCCGCAAGGA
CGGCTACAGCTTTCCCGGCACGCCGTTCTTCATGTCCATGTGGGAAAAACTCAGGTCCAATTATGAGGGGAAGAAGTCGA
GAGTGTGCGGGTACTGCGGGGCCCCGGCCCCGTACGCTACTGCCTGTGGCCTCGACGTCTGCATTTACCACACCCACTTC
CACCAGCATTGTCCAGTCACAATCTGGTGTGGCCATCCAGCGGGTTCTGGTTCTTGTAGTGAGTGCAAATCCCCTGTAGG
GAAAGGCACAAGCCCTTTAGACGAGGTGCTGGAACAAGTCCCGTATAAGCCCCCACGGACCGTTATCATGCATGTGGAGC
AGGGTCTCACCCCCCTTGATCCAGGTAGATACCAAACTCGCCGCGGATTAGTCTCTGTCAGGCGTGGAATTAGGGGAAAT
GAAGTTGGACTACCAGACGGTGATTATGCTAGCACCGCCTTGCTCCCTACCTGCAAAGAGATCAACATGGTCGCTGTCGC
TTCCAATGTATTGCGCAGCAGGTTCATCATCGGCCCACCCGGTGCTGGGAAAACATACTGGCTCCTTCAACAGGTCCAGG
ATGGTGATGTTATTTACACACCAACTCACCAGACCATGCTTGACATGATTAGGGCTTTGGGGACGTGCCGGTTCAACGTC
CCGGCAGGCACAACGCTGCAATTCCCCGTCCCCTCCCGCACCGGTCCGTGGGTTCGCATCCTAGCCGGCGGTTGGTGTCC
TGGCAAGAATTCCTTCCTAGATGAAGCAGCGTATTGCAATCACCTTGATGTTTTGAGGCTTCTTAGTAAAACTACCCTCA
CCTGTCTAGGAGACTTCAAGCAACTCCACCCAGTGGGTTTTGATTCTCATTGCTATGTTTTGACATCATGCCTCAAACT
CAACTGAAGACCATCTGGAGGTTTGGACAGAATATCTGTGATGCCATTCAGCCAGATTACAGGGACAAACTCATGTCCAT
GGTCAACACAACCCGTGTGACCTACGTGGAAAAACCTGTCAGGTATGGGCAGGTCCTCACCCCCTACCACAGGGACCGAG
AGGACGACGCCATCACTATTGACTCCAGTCAAGGCGCCACATTCGATGTGGTTACATTGCATTTGCCCACTAAAGATTCA
CTCAACAGGCAAAGAGCCCTTGTTGCTATCACCAGGGCAAGACACGCTATCTTTGTGTATGACCCACACAGGCAGCTGCA
GGGCTTGTTTGATCTTCCTGCAAAAGGCACGCCCGTCAACCTCGCAGTGCACTGCGACGGGCAGCTGATCGTGCTGGATA
GAAATAACAAAGAATGCACGGTTGCTCAGGCTCTAGGCAACGGGGATAAATTTAGGGCCACAGACAAGCGTGTTGTAGAT
TCTCTCCGCGCCATTTGTGCTGATCTAGAAGGGTCGAGCTCTCCGCTCCCAAGGTCGCACACAACTTGGGATTTTATTT
CTCACCTGATTTAACACAGTTTGCTAAACTCCCAGTAGAACTTGCACCTCACTGGCCCGTGGTGTCAACCCAGAACAATG
AAAAGTGGCCGGATCGGCTGGTTGCCAGCCTTCGCCCTATCCATAAATACAGCCGCGCGTGCATCGGTGCCGGCTATATG
GTGGGCCCTTCGGTGTTTCTAGGCACTCCTGGGGTCGTGTCATACTATCTCACAAAATTTGTTAAGGGCGGGGCTCAAGT
GCTTCCGGAGACGGTTTTCAGCACCGGCCGAATTGAGGTAGACTGCCGGGAATATCTTGATGATCGGGAGCGAGAAGTTG
CTGCGTCCCTCCCACACGCTTTCATTGGCGACGTCAAAGGCACTACCGTTGGAGGATGTCATCATGTCACCTCCAGATAC
CTCCCGCGCGTCCTTCCCAAGGAATCAGTTGCGGTAGTCGGGGTTTCAAGCCCCGGAAAAGCCGCGAAAGCATTGTGCAC
ACTGACAGATGTGTACCTCCCAGATCTTGAAGCCTATCTCCACCCGGAGACCCAGTCCAAGTGCTGGAAAATGATGTTGG
ACTTCAAAGAAGTTCGACTAATGGTCTGGAAAGACAAAACAGCCTATTTCCAACTTGAAGGTCGCTATTTCACCTGGTAT
CAGCTTGCCAGCTATGCCTCGTACATCCGTGTTCCCGTCAACTCTACGGTGTACTTGGACCCCTGCATGGGCCCCGCCCT
TTGCAACAGGAGAGTCGTCGGGTCCACCCACTGGGGGCTGACCTCGCGGTCACCCCTTATGATTACGGCGCTAAAATTA
TCCTGTCTAGCGCGTACCATGGTGAAATGCCCCCGGATACAAAATTCTGGCGTGCGCGGAGTTCTCGTTGGATGACCCA
GTTAAGTACAAACATACCTGGGGGTTTGAATCGGATACAGCGTATCTGTATGAGTTCACCGGAAACGGTGAGGACTGGGA
GGATTACAATGATGCGTTTCGTGCGCGCCAGGAAGGGAAAATTTATAAGGCCACTGCCACCAGCTTGAAGTTTTATTTTC
CCCCGGGCCCTGTCATTGAACCAACTTTAGGCCTGAATTGAAATGAAATGGGGTCCATGCAAAGCCTTTTTGACAAAATT
GGCCAACTTTTTGTGGATGCTTTCACGGAGTTCTTGGTGTCCATTGTTGATATCATTATATTTTTGGCCATTTTGTTTGG
```

Fig. 1I-4

```
CTTCACCATCGCCGGTTGGCTGGTGGTCTTTTGCATCAGATTGGTTTGCTCCGCGATACTCCGTACGCGCCCTGCCATTC
ACTCTGAGCAATTACAGAAGATCTTATGAGGCCTTTCTTTCCCAGTGCCAAGTGGACATTCCCACCTGGGGAACTAAACA
TCCTTTGGGGATGCTTTGGCACCATAAGGTGTCAACCCTGATTGATGAAATGGTGTCGCGTCGAATGTACCGCATCATGG
AAAAAGCAGGGCAGGCTGCCTGGAAACAGGTGGTGAGCGAGGCTACGCTGTCTCGCATTAGTAGTTTGGATGTGGTGGCT
CATTTTCAGCATCTAGCCGCCATTGAAGCCGAGACCTGTAAATATTTGGCCTCCCGGCTGCCCATGCTACACAACCTGCG
CATGACAGGGTCAAATGTAACCATAGTGTATAATAGCACTTTGAATCAGGTGTTTGCTATTTTTCCAACCCCTGGTTCCC
GGCCAAAGCTTCATGATTTTCAGCAATGGTTAATAGCTGTACATTCCTCCATATTTTCCTCTGTTGCAGCTTCTTGTACT
CTTTTTGTTGTGCTGTGGTTGCGGGTTCCAATACTACGTACTGTTTTTGGTTTCCGCTGGTTAGGGGCAATTTTTCTTTC
GAACTCACAGTGAATTACACGGTGTGTCCACCTTGCCTCACCCGGCAAGCAGCCACAGAGATCTACGAACCCGGTAGGTC
TCTTTGGTGCAGGATAGGGTATGACCGATGTGGGGAGGACGATCATGACGAGCTAGGGTTTATGATACCGCCTGGCCTCT
CCAGCGAAGGCCACTTGACTGGTGTTTACGCCTGGTTGGCGTTCTTGTCCTTCAGCTACACGGCCCAGTTCCATCCCGAG
ATATTCGGGATAGGGAATGTGAGTCGAGTTTATGTTGACATCAAACATCAACTCATCTGCGCCGAACATGACGGGCAGAA
CACCACCTTGCCTCGTCATGACAACATTTCAGCCGTGTTTCAGACCTATTACCAACATCAAGTCGACGGCGGCAATTGGT
TTCACCTAGAATGGCTTCGTCCCTTCTTTTCCTCGTGGTTGGTTTTAAATGTCTCTTGGTTTCTCAGGCGTTCGCCTGCA
AACCATGTTTCAGTTCGAGTCTTGCAGATATTAAGACCAACACCACCGCAGCGGCAAGCTTTGCTGTCCTCCAAGACATC
AGTTGCCTTAGGCATCGCGACTCGGCCTCTGAGGCGATTCGCAAAATCCCTCAGTGCCGTACGGCGATAGGGACACCCGT
GTATGTTACCATCACAGCCAATGTGACAGATGAGAATTATTTACATTCTTCTGATCTCCTCATGCTTTCTTCTTGCCTTT
TCTATGCTTCTGAGATGAGTGAAAAGGGATTTAAGGTGGTATTTGGCAATGTGTCAGGCATCGTGGCTGTGTGTGTCAAT
TTTACCAGCTACGTCCAACATGTCAAGGAGTTTACCCAACGCTCCCTGGTGGTCGACCATGTGCGGTTGCTCCATTTCAT
GACACCTGAGACCATGAGGTGGGCAACTGTTTTAGCCTGTCTTTTTGCCATTCTGTTGGCAATTTGAATGTTTAAGTATG
TTGGAGAAATGCTTGACCGCGGGCTGTTGCTCGCGATTGCTTTCTTTGTGGTGTATCGTGCCGTTCTGTTTTGCTGTGCT
CGCCAACGCCAGCAACGACAGCAGCTCCCATCTACAGCTGATTTACAACTTGACGCTATGTGAGCTGAATGGCACAGATT
GGCTAGCTAACAAATTTGATTGGGCAGTGGAGAGTTTTGTCATCTTTCCCGTTTTGACTCACATTGTCTCCTATGGTGCC
CTCACTACCAGCCATTTCCTTGACACAGTCGCTTTAGTCACTGTGTCTACCGCCGGGTTTGTTCACGGCGGTATGTCCT
AAGTAGCATCTACGCGGTCTGTGCCCTGGCTGCGTTGACTTGCTTCGTCATTAGGTTTGCAAAGAATTGCATGTCCTGGC
GCTACGCGTGTACCAGATATACCAACTTTCTTCTGGACACTAAGGGCAGACTCTATCGTTGGCGGTCGCCTGTCATCATA
GAGAAAAGGGGCAAAGTTGAGGTCGAAGGTCATCTGATCGACCTCAAAAGAGTTGTGCTTGATGGCTCCGTGGCAACCCC
TATAACCAGAGTTTCAGCGGAACAATGGGGTCGTCCTTAGATGACTTCTGTCACGATAGCACGGCTCCACAAAAGGTGCT
TTTGGCGTTTTCTATTACCTACACGCCAGTGATGATATATGCCCTAAAGGTGAGTCGCGGCCGACTGCTAGGGCTTCTGC
ACCTTTTGATCTTCCTGAATTGTGCTTTCACCTTCGGGTACATGACTTTCGCGCACTTTCAGAGTACAAATAAGGTCGCG
CTCACTATGGGAGCAGTAGTTGCACTCCTTTGGGGGGTGTACTCAGCCATAGAAACCTGGAAATTCATCACCTCCAGATG
CCGTTTGTGCTTGCTAGGCCGCAAGTACATTCTGGCCCCTGCCCACCACGTTGAAAGTGCCGCAGGCTTTCATCCGATTG
CGGCAAATGATAACCACGCATTTGTCGTCCGGCGTCCCGGCTCCACTACGGTCAACGGCACATTGGTGCCCGGGTTAAAA
AGCCTCGTGTTGGGTGGCAGAAAAGCTGTTAAACAGGGAGTGGTAAACCTTGTCAAATATGCCAAATAACAACGGCAAGC
AGCAGAAGAGAAAGAAGGGGGATGGCCAGCCAGTCAATCAGCTGTGCCAGATGCTGGGTAAGATCATCGCTCAGCAAAAC
CAGTCCAGAGGCAAGGGACCGGGAAAGAAAAATAAGAAGAAAAACCCGGAGAAGCCCCATTTTCCTCTAGCGACTGAAGA
TGATGTCAGACATCACTTTACCCCTAGTGAGCGGCAATTGTGTCTGTCGTCAATCCAGACCGCCTTTAATCAAGGCGCTG
GGACTTGCACCCTGTCAGATTCAGGGAGGATAAGTTACACTGTGGAGTTTAGTTTGCCTACGCATCATACTGTGCGCCTG
ATCCGCGTCACAGCATCACCCTCAGCATGATGGGCTGGCATTCTTGAGGCATCTCAGTGTTTGAATTGGAAGAATGTGTG
GTGAATGGCACTGATTGACATTGTGCCTCTAAGTCACCTATTCAATTAGGGCGACCGTGTGGGGGTGAGATTTAATTGGC
GAGAACCATGCGGCCGAAATTAAAAAAAA
```

Fig. 1J-1

```
>V7-Nsp2d633-726.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCCAGCACCGCCGCAGAGCGGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGATGTGAGTTTGTGATGATGCCTCACACGCCTGCACCTTCCGTAGGTGCGG
AGAGCGACCTTACCATTGGCTCAGTTGCTACTGAAGATGTTCCACGCATCCTCGAGAAAATAGAAATGTCGGCGAGATG
GCCAACCAGGGACCCTTGGCCTTCTCCGAGGATAAACCGGTAGATGACCAACTTGTCAACGACCCCCGGATATCGTCGCG
GAGGCCTGACGAGAGCACATCAGCTCCGTCCGCAGGCACAGGTGGCGCCGGCTCTTTTACCGATTTGCCGCCTTCAGATG
GCGCGGATGCGGACGGGGGGGGGCCGTTTCGGACGGTAAAAAGAAAAGCTGAAAGGCTCTTTTGACCAACTGAGCCGTCAG
GTTTTTGACCTCGTCTCCCATCTCCCTGTTTTCTTCTCACGCCTTTTCTACCCTGGCGGTGGTTATTCTCCGGGTGATTG
GGGTTTTGCAGCTTTTACTCTATTGTGCCTCTTTTTATGTTACAGTTACCCAGCCTTTGGTATTGCTCCCCTCTTGGGTG
```

Fig. 1J-2

```
TGTTTTCTGGGTCTTCTCGGCGCGTTCGAATGGGGGTTTTTGGCTGCTGGTTGGCTTTTGCTGTTGGTCTGTTCAAGCCT
GTGTCCGACCCAGTCGGCGCTGCTTGTGAGTTTGACTCGCCAGAGTGTAGAAACATCCTTCATTCTTTTGAGCTTCTCAA
ACCTTGGGACCCTGTTCGCAGCCTTGTTGTGGGCCCCGTCGGTCTCGGTCTTGCCATTCTTGGCAGGTTACTGGGCGGGG
CACGCTGCATCTGGCACTTTTTGCTTAGGCTTGGCATTGTTGCAGACTGTATCTTGGCTGGAGCTTACGTGCTTTCTCAA
GGTAGGTGTAAAAAGTGCTGGGGATCTTGTATAAGAACTGCTCCCAATGAGGTCGCTTTTAACGTGTTTCCTTTCACACG
TGCGACCAGGTCGTCACTTATCGACCTGTGCGATCGGTTTTGTGCGCCAAAAGGAATGGACCCCATTTTTCTCGCCACTG
GGTGGCGCGGGTGCTGGGCCGGCCGAAGCCCCATTGAGCAACCCTCTGAAAAACCCATCGCGTTTGCCCAGTTGGATGAA
AAGAAGATTACGGCTAGGACTGTGGTCGCCCAGCCTTATGACCCCAACCAAGCCGTAAAGTGCTTGCGGGTATTGCAGGC
GGGTGGGGCGATGGTGGCTAAGGCGGTCCCAAAAGTGGTCAAGGTTTCCGCTGTTCCATTCCGAGCCCCCTTCTTTCCCA
CTGGAGTGAAAGTTGACCCTGATTGCAGGGTCGTGGTTGACCCTGACACTTTCACTGCAGCTCTCCGGTCTGGCTACTCC
ACCACAAACCTCGTCCTTGGTGTGGGGGACTTTGCCCAGCTGAATGGATTAAAAATCAGGCAAATTTCCAAGCCTTCAGG
GGGAGGCCCACATCTCATGGCTGCCCTGCATGTTGCCTGCTCGATGGCTCTGCACATGCTTGCTGGGATTTATGTGACTG
CGGTGGGTTCTTGCGGCACCGGCACCAACGACCCGTGGTGCGCTAACCCGTTTGCCGTCCCTGGCTACGGACCTGGCTCT
CTCTGCACGTCCAGATTGTGCATTTCCCAACACGGCCTTACCCTGCCCTTGACAGCACTTGTGGCGGGATTCGGTATTCA
AGAAATTGCCTTGGTCGTTTTGATTTTTGTTTCCATCGGAGGCATGGCTCATAGGTTGAGCTGTAAGGCTGACATGCTGT
GTGTCTTGCTTGCAATTGCCAGCTATGTTTGGGTACCTCTTACCTGGTTGCTTTGTGTGTTTCCTTGCTGGTTGCGCTGT
TTTTCTTTGCACCCCCTCACCATCCTATGGTTGGTGTTTTTCTTGATTTCTGTGAATATGCCTTCAGGAATCTTGGCCAT
GGTGTTGTTGGTTTCTCTTTGGCTTCTTGGTCGTTATACTAATGTTGCTGGCCTTGTCACCCCCTACGACATTCATCATT
ACACCAGTGGCCCCCGCGGTGTTGCCGCCTTGGCTACCGCACCAGATGGGACCTACTTGGCCGCTGTCCGCCGCGCTGCG
TTGACTGGCCGCACCATGCTGTTTACCCCGTCCCAGCTTGGGTCTCTTCTTGAGGGTGCTTTCAGAACTCGAAAGCCCTC
ACTGAACACCGTCAATGTGATCGGGTCCTCCATGGGCTCTGGCGGGGTGTTTACCATCGACGGGAAAGTCAAGTGCGTAA
CTGCCGCACATGTCCTTACGGGCAATTCAGCTCGGGTTTCCGGGGTCGGCTTCAATCAAATGCTTGACTTTGACGTAAAG
GGAGATTTCGCTATAGCTGATTGCCCGAATTGGCAAGGGGCTGCCCCCAAGACCCAATTCTGCACGGATGGATGGACTGG
CCGTGCCTATTGGCTAACATCCTCTGGCGTCGAACCCGGCGTCATTGGAAAAGGATTCGCCTTCTGCTTCACCGCATGTG
GCGATTCCGGGTCCCCAGTGATCACCGAGGCCGGTGAGCTTGTCGGCGTTCACACGGGATCGAATAAACAAGGGGGGGGC
ATTGTTACGCGCCCCTCAGGCCAGTTTTGTAATGTGGCACCCATCAAGCTAAGCGAATTAAGTGAATTCTTTGCTGGGCC
TAAGGTCCCGCTCGGTGATGTGAAGGTCGGCAGCCACATAATTAAAGACATAAGCGAGGTGCCTTCAGATCTTTGTGCCT
TGCTTGCTGCCAAACCTGAACTGGAAGGAGGCCTCTCCACCGTCCAACTTCTTTGTGTGTTTTTTCTCCTGTGGAGAATG
ATGGGACATGCCTGGACGCCCTTGGTTGCTGTGAGTTTCTTTATTTTGAATGAGGTTCTCCCAGCCGTCCTGGTCCGGAG
TGTTTTCTCCTTTGGAATGTTTGTGCTATCCTGGCTCACGCCATGGTCTGCGCAAGTTCTGATGATCAGGCTTCTGACAG
CAGCTCTTAACAGGAACAGATGGTCACTTGCCTTTTTCAGCCTCGGTGCAGTGACCGGTTTTGTCGCAGATCTTGCGGCC
ACTCAGGGGCATCCGTTGCAGGCAGTGATGAATTTGAGCACCTATGCATTCCTGCCTCGGATGATGGTTGTGACCTCACC
AGTCCCAGTGATCACGTGTGGTGTCGTGCACCTACTTGCCATCATTTTGTACTTGTTTAAGTACCGTGGCCTGCACCATA
TCCTTGTTGGCGATGGAGTGTTCTCTGCGGCTTTCTTCTTGAGATACTTTGCCGAGGGAAAGTTGAGGGAAGGGGTGTCG
CAATCCTGCGGAATGAATCATGAGTCTCTGACTGGTGCCCTCGCTATGAGACTCAATGACGAGGACTTGGATTTCCTTAT
GAAATGGACTGATTTTAAGTGCTTTGTTTCTGCGTCCAACATGAGGAATGCAGCGGGTCAATTTATCGAGGCTGCCTATG
CTAAAGCACTTAGAGTAGAACTGGCCCAGTTGGTGCAGGTTGATAAAGTTCGAGGTACTTTGGCCAAACTTGAAGCTTTT
GCTGATACCGTGGCACCTCAACTCTCGCCCGGTGACATTGTTGTCGCTCTCGGCCACACGCCTGTTGGCAGTATCTTCGA
CCTAAAGGTTGGTAGCACCAAGCATACCCTCCAAGCCATTGAGACCAGAGTCCTTGCTGGGTCCAAAATGACCGTGGCGC
GCGTCGTCGACCCGACCCCCACGCCCCCACCCGCACCCGTGCCCATCCCCCTCCCACCGAAAGTTCTGGAGAATGGCCCC
AACGCTTGGGGGATGAGGACCGTTTGAATAAGAAGAAGAGGCGCAGGATGGAAGCCCTCGGCATCTATGTTATGGGCGG
GAAAAAATACCAGAAATTTTGGGACAAGAATTCCGGTGATGTGTTTTATGAGGAGGTCCATAATAACACAGATGAGTGGG
AGTGTCTCAGAGTTGGCGACCCTGCCGACTTTGACCCTGAGAAGGGAACTCTGTGTGGACATGTCACCATTGAAAACAAG
GCTTACCATGTTTACACCTCCCCATCTGGTAAGAAGTTCTTGGTCCCCGTCAACCCAGAGAATGGAAGAGTCCAATGGGA
AGCTGCAAAGCTTTCCGTGGAGCAGGCCCTAGGTATGATGAATGTCGACGGCGAACTGACTGCCAAAGAACTGGAGAAAC
TGAAAAGAATAATTGACAAACTCCAGGGCCTGACTAAGGAGCAGTGTTTAAACTGCTAGCCGCCAGCGACTTGACCCGCT
GTGGTCGCGGCGGCTTGGTTGTTACTGAAACAGCGGTAAAAATAGTCAAATTTCACAACCGGACCTTCACCCTGGGACCT
GTGAATTTAAAAGTGGCCAGTGAGGTTGAGCTAAAAGACGCGGTTGAGCACAACCAACACCCGGTTGCGAGACCGATCGA
```

Fig. 1J-3

```
TGGTGGAGTTGTGCTCCTGCGTTCCGCGGTTCCTTCGCTTATAGACGTCTTGATCTCCGGTGCTGATGCATCTCCCAAGT
TACTTGCCCATCACGGGCCGGGAAACACTGGGATCGATGGCACGCTCTGGGATTTTGAGTCCGAAGCCACTAAAGAGGAA
GTCGCACTCAGTGCGCAAATAATACAGGCTTGTGACATTAGGCGCGGCGACGCTCCTGAAATTGGTCTCCCTTACAAGCT
GTACCCTGTTAGGGGTAACCCTGAGCGGGTGAAAGGAGTTCTGCAGAATACAAGGTTTGGAGACATACCTTACAAAACCC
CCAGTGACACTGGAAGCCCAGTGCACGCGGCTGCCTGCCTTACGCCCAACGCCACTCCGGTGACTGATGGGCGCTCCGTC
TTGGCCACGACCATGCCCCCGGGTTTGAGTTATATGTACCGACCATACCAGCGTCTGTCCTTGATTACCTTGACTCTAG
GCCTGACTGCCCTAAACAGCTGACAGAGCACGGCTGCGAAGATGCCGCACTGAAAGACCTCTCTAAATATGACTTGTCCA
CCCAAGGCTTTGTTTTACCTGGAGTTCTTCGCCTTGTGCGGAAATACCTGTTTGCCCATGTAGGTAAGTGCCCACCCGTT
CATCGGCCTTCTACTTACCCTGCTAAGAATTCTATGGCTGGAATAAATGGGAACAGGTTCCCAACCAAGGACATTCAGAG
CGTCCCTGAAATCGACGTTCTGTGCGCACAGGCTGTGCGAGAAAACTGGCAAACTGTCACCCCTTGTACTCTTAAGAAAC
AGTATTGCGGGAAGAAGAAGACTAGGACCATACTCGGCACCAATAACTTCATCGCACTAGCCCACCGAGCAGTGTTGAGT
GGTGTTACCCAGGGCTTCATGAAAAAGGCGTTTAACTCGCCCATCGCCCTCGGAAAGAACAAGTTTAAGGAGCTACAGAC
TCCGGTCCTGGGCAGGTGCCTTGAAGCTGATCTCGCATCCTGCGATCGATCCACGCCTGCAATTGTCCGCTGGTTTGCCG
CCAACCTTCTTTATGAACTTGCCTGTGCTGAAGAGCATCTACCGTCGTACGTGCTGAACTGCTGCCACGACTTACTGGTC
ACGCAGTCCGGCGCAGTGACTAAGAGAGGTGGCCTGTCGTCTGGCGACCCGATCACCTCTGTGTCTAACACCATTTATAG
TTTGGTGATCTATGCACAGCATATGGTGCTTAGTTACTTCAAAAGTGGTCACCCCCATGGCCTTCTGTTCTTACAAGACC
AGCTAAAGTTTGAGGACATGCTCAAGGTTCAACCCCTGATCGTCTATTCGGACGACCTCGTGCTGTATGCCGAGTCTCCC
ACCATGCCAAACTATCACTGGTGGGTTGAACATCTGAATTTGATGCTGGGGTTTCAGACGGACCCAAAGAAGACAGCAAT
AACAGACTCGCCATCATTTCTAGGCTGTAGAATAATAAATGGGCGCCAGCTAGTCCCCAACCGTGACAGGATCCTCGCGG
CCCTCGCCTATCACATGAAGGCGAGTAATGTTTCTGAATACTATGCCTCAGCGGCTGCAATACTCATGGACAGCTGTGCT
TGTTTGGAGTATGATCCTGAATGGTTTGAAGAACTTGTAGTTGGAATAGCGCAGTGCGCCCGCAAGGACGGCTACAGCTT
TCCCGGCACGCCGTTCTTCATGTCCATGTGGGAAAAACTCAGGTCCAATTATGAGGGGAAGAAGTCGAGAGTGTGCGGGT
ACTGCGGGGCCCCGGCCCCGTACGCTACTGCCTGTGGCCTCGACGTCTGCATTTACCACACCCACTTCCACCAGCATTGT
CCAGTCACAATCTGGTGTGGCCATCCAGCGGGTTCTGGTTCTTGTAGTGAGTGCAAATCCCCTGTAGGGAAAGGCACAAG
CCCTTTAGACGAGGTGCTGGAACAAGTCCCGTATAAGCCCCCACGGACCGTTATCATGCATGTGGAGCAGGGTCTCACCC
CCCTTGATCCAGGTAGATACCAAACTCGCCGCGGATTAGTCTCTGTCAGGCGTGGAATTAGGGGAAATGAAGTTGGACTA
CCAGACGGTGATTATGCTAGCACCGCCTTGCTCCCTACCTGCAAAGAGATCAACATGGTCGCTGTCGCTTCCAATGTATT
GCGCAGCAGGTTCATCATCGGCCCACCCGGTGCTGGGAAAACATACTGGCTCCTTCAACAGGTCCAGGATGGTGATGTTA
TTTACACACCAACTCACCAGACCATGCTTGACATGATTAGGGCTTTGGGGACGTGCCGGTTCAACGTCCCGGCAGGCACA
ACGCTGCAATTCCCCGTCCCCTCCCGCACCGGTCCGTGGGTTCGCATCCTAGCCGGCGGTTGGTGTCCTGGCAAGAATTC
CTTCCTAGATGAAGCAGCGTATTGCAATCACCTTGATGTTTTGAGGCTTCTTAGTAAAACTACCCTCACCTGTCTAGGAG
ACTTCAAGCAACTCCACCCAGTGGGTTTTGATTCTCATTGCTATGTTTTTGACATCATGCCTCAAACTCAACTGAAGACC
ATCTGGAGGTTTGGACAGAATATCTGTGATGCCATTCAGCCAGATTACAGGGACAAACTCATGTCCATGGTCAACACAAC
CCGTGTGACCTACGTGGAAAAACCTGTCAGGTATGGGCAGGTCCTCACCCCCTACCACAGGGACCGAGAGGACGACGCCA
TCACTATTGACTCCAGTCAAGGCGCCACATTCGATGTGGTTACATTGCATTTGCCCACTAAAGATTCACTCAACAGGCAA
AGAGCCCTTGTTGCTATCACCAGGGCAAGACACGCTATCTTTGTGTATGACCCACACAGGCAGCTGCAGGGCTTGTTTGA
TCTTCCTGCAAAAGGCACGCCCGTCAACCTCGCAGTGCACTGCGACGGGCAGCTGATCGTGCTGGATAGAAATAACAAAG
AATGCACGGTTGCTCAGGCTCTAGGCAACGGGGATAAATTTAGGGCCACAGACAAGCGTGTTGTAGATTCTCTCCGCGCC
ATTTGTGCTGATCTAGAAGGGTCGAGCTCTCCGCTCCCCAAGGTCGCACACAACTTGGGATTTTATTTCTCACCTGATTT
AACACAGTTTGCTAAACTCCCAGTAGAACTTGCACCTCACTGGCCCGTGGTGTCAACCCAGAACAATGAAAAGTGGCCGG
ATCGGCTGGTTGCCAGCCTTCGCCCTATCCATAAATACAGCCGCGCGTGCATCGGTGCCGGCTATATGGTGGGCCCTTCG
GTGTTTCTAGGCACTCCTGGGGTCGTGTCATACTATCTCACAAAATTTGTTAAGGGCGGGGCTCAAGTGCTTCCGGAGAC
GGTTTTCAGCACCGGCCGAATTGAGGTAGACTGCCGGGAATATCTTGATGATCGGGAGCGAGAAGTTGCTGCGTCCCTCC
CACACGCTTTCATTGGCGACGTCAAAGGCACTACCGTTGGAGGATGTCATCATGTCACCTCCAGATACCTCCCGCGCGTC
CTTCCCAAGGAATCAGTTGCGGTAGTCGGGGTTTCAAGCCCCGGAAAAGCCGCGAAAGCATTGTGCACACTGACAGATGT
GTACCTCCCAGATCTTGAAGCCTATCTCCACCCGGAGACCCAGTCCAAGTGCTGGAAAATGATGTTGGACTTCAAAGAAG
TTCGACTAATGGTCTGGAAAGACAAAACAGCCTATTTCCAACTTGAAGGTCGCTATTTCACCTGGTATCAGCTTGCCAGC
TATGCCTCGTACATCCGTGTTCCCGTCAACTCTACGGTGTACTTGGACCCCTGCATGGGCCCCGCCCTTTGCAACAGGAG
```

*Fig. 1J-4*

```
AGTCGTCGGGTCCACCCACTGGGGGGCTGACCTCGCGGTCACCCCTTATGATTACGGCGCTAAAATTATCCTGTCTAGCG
CGTACCATGGTGAAATGCCCCCCGGATACAAAATTCTGGCGTGCGCGGAGTTCTCGTTGGATGACCCAGTTAAGTACAAA
CATACCTGGGGGTTTGAATCGGATACAGCGTATCTGTATGAGTTCACCGGAAACGGTGAGGACTGGGAGGATTACAATGA
TGCGTTTCGTGCGCGCCAGGAAGGGAAAATTTATAAGGCCACTGCCACCAGCTTGAAGTTTTATTTTCCCCCGGGCCCTG
TCATTGAACCAACTTTAGGCCTGAATTGAAATGAAATGGGGTCCATGCAAAGCCTTTTTGACAAAATTGGCCAACTTTTT
GTGGATGCTTTCACGGAGTTCTTGGTGTCCATTGTTGATATCATTATATTTTTGGCCATTTTGTTTGGCTTCACCATCGC
CGGTTGGCTGGTGGTCTTTTGCATCAGATTGGTTTGCTCCGCGATACTCCGTACGCGCCCTGCCATTCACTCTGAGCAAT
TACAGAAGATCTTATGAGGCCTTTCTTTCCCAGTGCCAAGTGGACATTCCCACCTGGGGAACTAAACATCCTTTGGGGAT
GCTTTGGCACCATAAGGTGTCAACCCTGATTGATGAAATGGTGTCGCGTCGAATGTACCGCATCATGGAAAAAGCAGGGC
AGGCTGCCTGGAAACAGGTGGTGAGCGAGGCTACGCTGTCTCGCATTAGTAGTTTGGATGTGGTGGCTCATTTTCAGCAT
CTAGCCGCCATTGAAGCCGAGACCTGTAAATATTTGGCCTCCCGGCTGCCCATGCTACACAACCTGCGCATGACAGGGTC
AAATGTAACCATAGTGTATAATAGCACTTTGAATCAGGTGTTTGCTATTTTTCCAACCCCTGGTTCCCGGCCAAAGCTTC
ATGATTTTCAGCAATGGTTAATAGCTGTACATTCCTCCATATTTTCCTCTGTTGCAGCTTCTTGTACTCTTTTTGTTGTG
CTGTGGTTGCGGGTTCCAATACTACGTACTGTTTTTGGTTTCCGCTGGTTAGGGGCAATTTTTCTTTCGAACTCACAGTG
AATTACACGGTGTGTCCACCTTGCCTCACCCGGCAAGCAGCCACAGAGATCTACGAACCCGGTAGGTCTCTTTGGTGCAG
GATAGGGTATGACCGATGTGGGGAGGACGATCATGACGAGCTAGGGTTTATGATACCGCCTGGCCTCTCCAGCGAAGGCC
ACTTGACTGGTGTTTACGCCTGGTTGGCGTTCTTGTCCTTCAGCTACACGGCCCAGTTCCATCCCGAGATATTCGGGATA
GGGAATGTGAGTCGAGTTTATGTTGACATCAAACATCAACTCATCTGCGCCGAACATGACGGGCAGAACACCACCTTGCC
TCGTCATGACAACATTTCAGCCGTGTTTCAGACCTATTACCAACATCAAGTCGACGGCGGCAATTGGTTTCACCTAGAAT
GGCTTCGTCCCTTCTTTTCCTCGTGGTTGGTTTTAAATGTCTCTTGGTTTCTCAGGCGTTCGCCTGCAAACCATGTTTCA
GTTCGAGTCTTGCAGATATTAAGACCAACACCACCGCAGCGGCAAGCTTTGCTGTCCTCCAAGACATCAGTTGCCTTAGG
CATCGCGACTCGGCCTCTGAGGCGATTCGCAAAATCCCTCAGTGCCGTACGGCGATAGGGACACCCGTGTATGTTACCAT
CACAGCCAATGTGACAGATGAGAATTATTTACATTCTTCTGATCTCCTCATGCTTTCTTCTTGCCTTTTCTATGCTTCTG
AGATGAGTGAAAAGGGATTTAAGGTGGTATTTGGCAATGTGTCAGGCATCGTGGCTGTGTGTGTCAATTTTACCAGCTAC
GTCCAACATGTCAAGGAGTTTACCCAACGCTCCCTGGTGGTCGACCATGTGCGGTTGCTCCATTTCATGACACCTGAGAC
CATGAGGTGGGCAACTGTTTTAGCCTGTCTTTTTGCCATTCTGTTGGCAATTTGAATGTTTAAGTATGTTGGAGAAATGC
TTGACCGCGGGCTGTTGCTCGCGATTGCTTTCTTTGTGGTGTATCGTGCCGTTCTGTTTTGCTGTGCTCGCCAACGCCAG
CAACGACAGCAGCTCCCATCTACAGCTGATTTACAACTTGACGCTATGTGAGCTGAATGGCACAGATTGGCTAGCTAACA
AATTTGATTGGGCAGTGGAGAGTTTTGTCATCTTTCCCGTTTTGACTCACATTGTCTCCTATGGTGCCCTCACTACCAGC
CATTTCCTTGACACAGTCGCTTTAGTCACTGTGTCTACCGCCGGGTTTGTTCACGGGCGGTATGTCCTAAGTAGCATCTA
CGCGGTCTGTGCCCTGGCTGCGTTGACTTGCTTCGTCATTAGGTTTGCAAAGAATTGCATGTCCTGGCGCTACGCGTGTA
CCAGATATACCAACTTTCTTCTGGACACTAAGGGCAGACTCTATCGTTGGCGGTCGCCTGTCATCATAGAGAAAAGGGGC
AAAGTTGAGGTCGAAGGTCATCTGATCGACCTCAAAAGAGTTGTGCTTGATGGCTCCGTGGCAACCCCTATAACCAGAGT
TTCAGCGGAACAATGGGGTCGTCCTTAGATGACTTCTGTCACGATAGCACGGCTCCACAAAAGGTGCTTTTGGCGTTTTC
TATTACCTACACGCCAGTGATGATATATGCCCTAAAGGTGAGTCGCGGCCGACTGCTAGGGCTTCTGCACCTTTTGATCT
TCCTGAATTGTGCTTTCACCTTCGGGTACATGACTTTCGCGCACTTTCAGAGTACAAATAAGGTCGCGCTCACTATGGGA
GCAGTAGTTGCACTCCTTTGGGGGTGTACTCAGCCATAGAAACCTGGAAATTCATCACCTCCAGATGCCGTTTGTGCTT
GCTAGGCCGCAAGTACATTCTGGCCCCTGCCCACCACGTTGAAAGTGCCGCAGGCTTTCATCCGATTGCGGCAAATGATA
ACCACGCATTTGTCGTCCGGCGTCCCGGCTCCACTACGGTCAACGGCACATTGGTGCCCGGGTTAAAAAGCCTCGTGTTG
GGTGGCAGAAAAGCTGTTAAACAGGGAGTGGTAAACCTTGTCAAATATGCCAAATAACAACGGCAAGCAGCAGAAGAGAA
AGAAGGGGGATGGCCAGCCAGTCAATCAGCTGTGCCAGATGCTGGGTAAGATCATCGCTCAGCAAAACCAGTCCAGAGGC
AAGGGACCGGGAAAGAAAAATAAGAAGAAAAACCCGGAGAAGCCCCATTTTCCTCTAGCGACTGAAGATGATGTCAGACA
TCACTTTACCCCTAGTGAGCGGCAATTGTGTCTGTCGTCAATCCAGACCGCCTTTAATCAAGGCGCTGGGACTTGCACCC
TGTCAGATTCAGGGAGGATAAGTTACACTGTGGAGTTTAGTTTGCCTACGCATCATACTGTGCGCCTGATCCGCGTCACA
GCATCACCCTCAGCATGATGGGCTGGCATTCTTGAGGCATCTCAGTGTTTGAATTGGAAGAATGTGTGGTGAATGGCACT
GATTGACATTGTGCCTCTAAGTCACCTATTCAATTAGGGCGACCGTGTGGGGGTGAGATTTAATTGGCGAGAACCATGCG
GCCGAAATTAAAAAAAA
```

Fig. 1K-1

```
>V7-Nsp2d543-726.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GTGTGAGTTTGTGATGATGCCTCACACGCCTGCACCTTCCGTAGGTGCGGAGAGCGACCTTACCATTGGCTCAGTTGCTA
CTGAAGATGTTCCACGCATCCTCGAGAAAATAGAAAATGTCGGCGAGATGGCCAACCAGGGACCCTTGGCCTTCTCCGAG
GATAAACCGGTAGATGACCAACTTGTCAACGACCCCCGGATATCGTCGCGGAGGCCTGACGAGAGCACATCAGCTCCGTC
CGCAGGCACAGGTGGCGCCGGCTCTTTTACCGATTTGCCGCCTTCAGATGGCGCGGATGCGGACGGGGGGGGCCGTTTC
GGACGGTAAAAAGAAAAGCTGAAAGGCTCTTTTGACCAACTGAGCCGTCAGGTTTTTGACCTCGTCTCCCATCTCCCTGTT
TTCTTCTCACGCCTTTTCTACCCTGGCGGTGGTTATTCTCCGGGTGATTGGGGTTTTGCAGCTTTTACTCTATTGTGCCT
CTTTTTATGTTACAGTTACCCAGCCTTTGGTATTGCTCCCCTCTTGGGTGTGTTTTCTGGGTCTTCTCGGCGCGTTCGAA
TGGGGGTTTTTGGCTGCTGGTTGGCTTTTGCTGTTGGTCTGTTCAAGCCTGTGTCCGACCCAGTCGGCGCTGCTTGTGAG
TTTGACTCGCCAGAGTGTAGAAACATCCTTCATTCTTTTGAGCTTCTCAAACCTTGGGACCCTGTTCGCAGCCTTGTTGT
GGGCCCCGTCGGTCTCGGTCTTGCCATTCTTGGCAGGTTACTGGGCGGGGCACGCTGCATCTGGCACTTTTTGCTTAGGC
```

Fig. 1K-2

```
TTGGCATTGTTGCAGACTGTATCTTGGCTGGAGCTTACGTGCTTTCTCAAGGTAGGTGTAAAAAGTGCTGGGGATCTTGT
ATAAGAACTGCTCCCAATGAGGTCGCTTTTAACGTGTTTCCTTTCACACGTGCGACCAGGTCGTCACTTATCGACCTGTG
CGATCGGTTTTGTGCGCCAAAAGGAATGGACCCCATTTTTCTCGCCACTGGGTGGCGCGGGTGCTGGGCCGGCCGAAGCC
CCATTGAGCAACCCTCTGAAAAACCCATCGCGTTTGCCCAGTTGGATGAAAAGAAGATTACGGCTAGGACTGTGGTCGCC
CAGCCTTATGACCCCAACCAAGCCGTAAAGTGCTTGCGGGTATTGCAGGCGGGTGGGGCGATGGTGGCTAAGGCGGTCCC
AAAAGTGGTCAAGGTTTCCGCTGTTCCATTCCGAGCCCCCTTCTTTCCCACTGGAGTGAAAGTTGACCCTGATTGCAGGG
TCGTGGTTGACCCTGACACTTTCACTGCAGCTCTCCGGTCTGGCTACTCCACCACAAACCTCGTCCTTGGTGTGGGGGAC
TTTGCCCAGCTGAATGGATTAAAAATCAGGCAAATTTCCAAGCCTTCAGGGGGAGGCCCACATCTCATGGCTGCCCTGCA
TGTTGCCTGCTCGATGGCTCTGCACATGCTTGCTGGATTTATGTGACTGCGGTGGGTTCTTGCGGCACCGGCACCAACG
ACCCGTGGTGCGCTAACCCGTTTGCCGTCCCTGGCTACGGACCTGGCTCTCTCTGCACGTCCAGATTGTGCATTTCCCAA
CACGGCCTTACCCTGCCCTTGACAGCACTTGTGGCGGGATTCGGTATTCAAGAAATTGCCTTGGTCGTTTTGATTTTTGT
TTCCATCGGAGGCATGGCTCATAGGTTGAGCTGTAAGGCTGACATGCTGTGTGTCTTGCTTGCAATTGCCAGCTATGTTT
GGGTACCTCTTACCTGGTTGCTTTGTGTGTTTCCTTGCTGGTTGCGCTGTTTTTCTTTGCACCCCCTCACCATCCTATGG
TTGGTGTTTTTCTTGATTTCTGTGAATATGCCTTCAGGAATCTTGGCCATGGTGTTGTTGGTTTCTCTTTGGCTTCTTGG
TCGTTATACTAATGTTGCTGGCCTTGTCACCCCCTACGACATTCATCATTACACCAGTGGCCCCCGCGGTGTTGCCGCCT
TGGCTACCGCACCAGATGGGACCTACTTGGCCGCTGTCCGCCGCGCTGCGTTGACTGGCCGCACCATGCTGTTTACCCCG
TCCCAGCTTGGGTCTCTTCTTGAGGGTGCTTTCAGAACTCGAAAGCCCTCACTGAACACCGTCAATGTGATCGGGTCCTC
CATGGGCTCTGGCGGGGTGTTTACCATCGACGGGAAAGTCAAGTGCGTAACTGCCGCACATGTCCTTACGGGCAATTCAG
CTCGGGTTTCCGGGGTCGGCTTCAATCAAATGCTTGACTTTGACGTAAAGGGAGATTTCGCTATAGCTGATTGCCCGAAT
TGGCAAGGGGCTGCCCCCAAGACCCAATTCTGCACGGATGGATGGACTGGCCGTGCCTATTGGCTAACATCCTCTGGCGT
CGAACCCGGCGTCATTGGAAAAGGATTCGCCTTCTGCTTCACCGCATGTGGCGATTCCGGGTCCCCAGTGATCACCGAGG
CCGGTGAGCTTGTCGGCGTTCACACGGGATCGAATAAACAAGGGGGGGGCATTGTTACGCGCCCCTCAGGCCAGTTTTGT
AATGTGGCACCCATCAAGCTAAGCGAATTAAGTGAATTCTTTGCTGGGCCTAAGGTCCCGCTCGGTGATGTGAAGGTCGG
CAGCCACATAATTAAAGACATAAGCGAGGTGCCTTCAGATCTTTGTGCCTTGCTTGCTGCCAAACCTGAACTGGAAGGAG
GCCTCTCCACCGTCCAACTTCTTTGTGTGTTTTTCTCCTGTGGAGAATGATGGGACATGCCTGGACGCCCTTGGTTGCT
GTGAGTTTCTTTATTTTGAATGAGGTTCTCCCAGCCGTCCTGGTCCGGAGTGTTTTCTCCTTTGGAATGTTTGTGCTATC
CTGGCTCACGCCATGGTCTGCGCAAGTTCTGATGATCAGGCTTCTGACAGCAGCTCTTAACAGGAACAGATGGTCACTTG
CCTTTTTCAGCCTCGGTGCAGTGACCGGTTTTGTCGCAGATCTTGCGGCCACTCAGGGGCATCCGTTGCAGGCAGTGATG
AATTTGAGCACCTATGCATTCCTGCCTCGGATGATGGTTGTGACCTCACCAGTCCCAGTGATCACGTGTGGTGTCGTGCA
CCTACTTGCCATCATTTTGTACTTGTTTAAGTACCGTGGCCTGCACCATATCCTTGTTGGCGATGGAGTGTTCTCTGCGG
CTTTCTTCTTGAGATACTTTGCCGAGGGAAAGTTGAGGGAAGGGGTGTCGCAATCCTGCGGAATGAATCATGAGTCTCTG
ACTGGTGCCCTCGCTATGAGACTCAATGACGAGGACTTGGATTTCCTTATGAAATGGACTGATTTTAAGTGCTTTGTTTC
TGCGTCCAACATGAGGAATGCAGCGGGTCAATTTATCGAGGCTGCCTATGCTAAAGCACTTAGAGTAGAACTGGCCCAGT
TGGTGCAGGTTGATAAAGTTCGAGGTACTTTGGCCAAACTTGAAGCTTTTGCTGATACCGTGGCACCTCAACTCTCGCCC
GGTGACATTGTTGTCGCTCTCGGCCACACGCCTGTTGGCAGTATCTTCGACCTAAAGGTTGGTAGCACCAAGCATACCCT
CCAAGCCATTGAGACCAGAGTCCTTGCTGGGTCCAAAATGACCGTGGCGCGCGTCGTCGACCCGACCCCCACGCCCCCAC
CCGCACCCGTGCCCATCCCCCTCCCACCGAAAGTTCTGGAGAATGGCCCCAACGCTTGGGGGGATGAGGACCGTTTGAAT
AAGAAGAAGAGGCGCAGGATGGAAGCCCTCGGCATCTATGTTATGGGCGGGAAAAAATACCAGAAATTTTGGGACAAGAA
TTCCGGTGATGTGTTTTATGAGGAGGTCCATAATAACACAGATGAGTGGGAGTGTCTCAGAGTTGGCGACCCTGCCGACT
TTGACCCTGAGAAGGGAACTCTGTGTGGACATGTCACCATTGAAAACAAGGCTTACCATGTTTACACCTCCCCATCTGGT
AAGAAGTTCTTGGTCCCCGTCAACCCAGAGAATGGAAGAGTCCAATGGGAAGCTGCAAAGCTTTCCGTGGAGCAGGCCCT
AGGTATGATGAATGTCGACGGCGAACTGACTGCCAAAGAACTGGAGAAACTGAAAAGAATAATTGACAAACTCCAGGGCC
TGACTAAGGAGCAGTGTTTAAACTGCTAGCCGCCAGCGACTTGACCCGCTGTGGTCGCGGCGGCTTGGTTGTTACTGAAA
CAGCGGTAAAAATAGTCAAATTTCACAACCGGACCTTCACCCTGGGACCTGTGAATTTAAAAGTGGCCAGTGAGGTTGAG
CTAAAAGACGCGGTTGAGCACAACCAACACCCGGTTGCGAGACCGATCGATGGTGGAGTTGTGCTCCTGCGTTCCGCGGT
TCCTTCGCTTATAGACGTCTTGATCTCCGGTGCTGATGCATCTCCCAAGTTACTTGCCCATCACGGGCCGGGAAACACTG
GGATCGATGGCACGCTCTGGGATTTTGAGTCCGAAGCCACTAAAGAGGAAGTCGCACTCAGTGCGCAAATAATACAGGCT
TGTGACATTAGGCGCGGCGACGCTCCTGAAATTGGTCTCCCTTACAAGCTGTACCCTGTTAGGGGTAACCCTGAGCGGGT
```

Fig. 1K-3

```
GAAAGGAGTTCTGCAGAATACAAGGTTTGGAGACATACCTTACAAAACCCCCAGTGACACTGGAAGCCCAGTGCACGCGG
CTGCCTGCCTTACGCCCAACGCCACTCCGGTGACTGATGGGCGCTCCGTCTTGGCCACGACCATGCCCCCCGGGTTTGAG
TTATATGTACCGACCATACCAGCGTCTGTCCTTGATTACCTTGACTCTAGGCCTGACTGCCCTAAACAGCTGACAGAGCA
CGGCTGCGAAGATGCCGCACTGAAAGACCTCTCTAAATATGACTTGTCCACCCAAGGCTTTGTTTTACCTGGAGTTCTTC
GCCTTGTGCGGAAATACCTGTTTGCCCATGTAGGTAAGTGCCCACCCGTTCATCGGCCTTCTACTTACCCTGCTAAGAAT
TCTATGGCTGGAATAAATGGGAACAGGTTCCCAACCAAGGACATTCAGAGCGTCCCTGAAATCGACGTTCTGTGCGCACA
GGCTGTGCGAGAAAACTGGCAAACTGTCACCCCTTGTACTCTTAAGAAACAGTATTGCGGGAAGAAGAAGACTAGGACCA
TACTCGGCACCAATAACTTCATCGCACTAGCCCACCGAGCAGTGTTGAGTGGTGTTACCCAGGGCTTCATGAAAAAGGCG
TTTAACTCGCCCATCGCCCTCGGAAAGAACAAGTTTAAGGAGCTACAGACTCCGGTCCTGGGCAGGTGCCTTGAAGCTGA
TCTCGCATCCTGCGATCGATCCACGCCTGCAATTGTCCGCTGGTTTGCCGCCAACCTTCTTTATGAACTTGCCTGTGCTG
AAGAGCATCTACCGTCGTACGTGCTGAACTGCTGCCACGACTTACTGGTCACGCAGTCCGGCGCAGTGACTAAGAGAGGT
GGCCTGTCGTCTGGCGACCCGATCACCTCTGTGTCTAACACCATTTATAGTTTGGTGATCTATGCACAGCATATGGTGCT
TAGTTACTTCAAAAGTGGTCACCCCCATGGCCTTCTGTTCTTACAAGACCAGCTAAAGTTTGAGGACATGCTCAAGGTTC
AACCCCTGATCGTCTATTCGGACGACCTCGTGCTGTATGCCGAGTCTCCCACCATGCCAAACTATCACTGGTGGGTTGAA
CATCTGAATTTGATGCTGGGGTTTCAGACGGACCCAAAGAAGACAGCAATAACAGACTCGCCATCATTTCTAGGCTGTAG
AATAATAAATGGGCGCCAGCTAGTCCCCAACCGTGACAGGATCCTCGCGGCCCTCGCCTATCACATGAAGGCGAGTAATG
TTTCTGAATACTATGCCTCAGCGGCTGCAATACTCATGGACAGCTGTGCTTGTTTGGAGTATGATCCTGAATGGTTTGAA
GAACTTGTAGTTGGAATAGCGCAGTGCGCCCGCAAGGACGGCTACAGCTTTCCCGGCACGCCGTTCTTCATGTCCATGTG
GGAAAAACTCAGGTCCAATTATGAGGGGAAGAAGTCGAGAGTGTGCGGGTACTGCGGGGCCCCGGCCCCGTACGCTACTG
CCTGTGGCCTCGACGTCTGCATTTACCACACCCACTTCCACCAGCATTGTCCAGTCACAATCTGGTGTGGCCATCCAGCG
GGTTCTGGTTCTTGTAGTGAGTGCAAATCCCCTGTAGGGAAAGGCACAAGCCCTTTAGACGAGGTGCTGGAACAAGTCCC
GTATAAGCCCCCACGGACCGTTATCATGCATGTGGAGCAGGGTCTCACCCCCCTTGATCCAGGTAGATACCAAACTCGCC
GCGGATTAGTCTCTGTCAGGCGTGGAATTAGGGGAAATGAAGTTGGACTACCAGACGGTGATTATGCTAGCACCGCCTTG
CTCCCTACCTGCAAAGAGATCAACATGGTCGCTGTCGCTTCCAATGTATTGCGCAGCAGGTTCATCATCGGCCCACCCGG
TGCTGGGAAAACATACTGGCTCCTTCAACAGGTCCAGGATGGTGATGTTATTTACACACCAACTCACCAGACCATGCTTG
ACATGATTAGGGCTTTGGGGACGTGCCGGTTCAACGTCCCGGCAGGCACAACGCTGCAATTCCCCGTCCCCTCCCGCACC
GGTCCGTGGGTTCGCATCCTAGCCGGCGGTTGGTGTCCTGGCAAGAATTCCTTCCTAGATGAAGCAGCGTATTGCAATCA
CCTTGATGTTTTGAGGCTTCTTAGTAAAACTACCCTCACCTGTCTAGGAGACTTCAAGCAACTCCACCCAGTGGGTTTTG
ATTCTCATTGCTATGTTTTTGACATCATGCCTCAAACTCAACTGAAGACCATCTGGAGGTTTGGACAGAATATCTGTGAT
GCCATTCAGCCAGATTACAGGGACAAACTCATGTCCATGGTCAACACAACCCGTGTGACCTACGTGGAAAAAACCTGTCAG
GTATGGGCAGGTCCTCACCCCCTACCACAGGGACCGAGAGGACGACGCCATCACTATTGACTCCAGTCAAGGCGCCACAT
TCGATGTGGTTACATTGCATTTGCCCACTAAAGATTCACTCAACAGGCAAAGAGCCCTTGTTGCTATCACCAGGGCAAGA
CACGCTATCTTTGTGTATGACCCACACAGGCAGCTGCAGGGCTTGTTTGATCTTCCTGCAAAAGGCACGCCCGTCAACCT
CGCAGTGCACTGCGACGGGCAGCTGATCGTGCTGGATAGAAATAACAAAGAATGCACGGTTGCTCAGGCTCTAGGCAACG
GGGATAAATTTAGGGCCACAGACAAGCGTGTTGTAGATTCTCTCCGCGCCATTTGTGCTGATCTAGAAGGGTCGAGCTCT
CCGCTCCCCAAGGTCGCACACAACTTGGGATTTTATTTCTCACCTGATTTAACACAGTTTGCTAAACTCCCAGTAGAACT
TGCACCTCACTGGCCCGTGGTGTCAACCCAGAACAATGAAAAGTGGCCGGATCGGCTGGTTGCCAGCCTTCGCCCTATCC
ATAAATACAGCCGCGCGTGCATCGGTGCCGGCTATATGGTGGGCCCTTCGGTGTTTCTAGGCACTCCTGGGGTCGTGTCA
TACTATCTCACAAAATTTGTTAAGGGCGGGGCTCAAGTGCTTCCGGAGACGGTTTTCAGCACCGGCCGAATTGAGGTAGA
CTGCCGGGAATATCTTGATGATCGGGAGCGAGAAGTTGCTGCGTCCCTCCCACACGCTTTCATTGGCGACGTCAAAGGCA
CTACCGTTGGAGGATGTCATCATGTCACCTCCAGATACCTCCCGCGCGTCCTTCCCAAGGAATCAGTTGCGGTAGTCGGG
GTTTCAAGCCCCGGAAAAGCCGCGAAAGCATTGTGCACACTGACAGATGTGTACCTCCCAGATCTTGAAGCCTATCTCCA
CCCGGAGACCCAGTCCAAGTGCTGGAAAATGATGTTGGACTTCAAAGAAGTTCGACTAATGGTCTGGAAAGACAAAACAG
CCTATTTCCAACTTGAAGGTCGCTATTTCACCTGGTATCAGCTTGCCAGCTATGCCTCGTACATCCGTGTTCCCGTCAAC
TCTACGGTGTACTTGGACCCCTGCATGGGCCCCGCCCTTTGCAACAGGAGAGTCGTCGGGTCCACCCACTGGGGGCTGA
CCTCGCGGTCACCCCTTATGATTACGGCGCTAAAATTATCCTGTCTAGCGCGTACCATGGTGAAATGCCCCCCGGATACA
AAATTCTGGCGTGCGCGGAGTTCTCGTTGGATGACCCAGTTAAGTACAAACATACCTGGGGGTTTGAATCGGATACAGCG
TATCTGTATGAGTTCACCGGAAACGGTGAGGACTGGGAGGATTACAATGATGCGTTTCGTGCGCGCCAGGAAGGGAAAAT
```

Fig. 1K-4

```
TTATAAGGCCACTGCCACCAGCTTGAAGTTTTATTTTCCCCCGGGCCCTGTCATTGAACCAACTTTAGGCCTGAATTGAA
ATGAAATGGGGTCCATGCAAAGCCTTTTTGACAAAATTGGCCAACTTTTTTGTGGATGCTTTCACGGAGTTCTTGGTGTCC
ATTGTTGATATCATTATATTTTTGGCCATTTTGTTTGGCTTCACCATCGCCGGTTGGCTGGTGGTCTTTTGCATCAGATT
GGTTTGCTCCGCGATACTCCGTACGCGCCCTGCCATTCACTCTGAGCAATTACAGAAGATCTTATGAGGCCTTTCTTTCC
CAGTGCCAAGTGGACATTCCCACCTGGGGAACTAAACATCCTTTGGGGATGCTTTGGCACCATAAGGTGTCAACCCTGAT
TGATGAAATGGTGTCGCGTCGAATGTACCGCATCATGGAAAAAGCAGGGCAGGCTGCCTGGAAACAGGTGGTGAGCGAGG
CTACGCTGTCTCGCATTAGTAGTTTGGATGTGGTGGCTCATTTTCAGCATCTAGCCGCCATTGAAGCCGAGACCTGTAAA
TATTTGGCCTCCCGGCTGCCCATGCTACACAACCTGCGCATGACAGGGTCAAATGTAACCATAGTGTATAATAGCACTTT
GAATCAGGTGTTTGCTATTTTTCCAACCCCTGGTTCCCGGCCAAAGCTTCATGATTTTCAGCAATGGTTAATAGCTGTAC
ATTCCTCCATATTTTCCTCTGTTGCAGCTTCTTGTACTCTTTTTGTTGTGCTGTGGTTGCGGGTTCCAATACTACGTACT
GTTTTTGGTTTCCGCTGGTTAGGGGCAATTTTTCTTTCGAACTCACAGTGAATTACACGGTGTGTCCACCTTGCCTCACC
CGGCAAGCAGCCACAGAGATCTACGAACCCGGTAGGTCTCTTTGGTGCAGGATAGGGTATGACCGATGTGGGGAGGACGA
TCATGACGAGCTAGGGTTTATGATACCGCCTGGCCTCTCCAGCGAAGGCCACTTGACTGGTGTTTACGCCTGGTTGGCGT
TCTTGTCCTTCAGCTACACGGCCCAGTTCCATCCCGAGATATTCGGGATAGGGAATGTGAGTCGAGTTTATGTTGACATC
AAACATCAACTCATCTGCGCCGAACATGACGGGCAGAACACCACCTTGCCTCGTCATGACAACATTTCAGCCGTGTTTCA
GACCTATTACCAACATCAAGTCGACGGCGGCAATTGGTTTCACCTAGAATGGCTTCGTCCCTTCTTTTCCTCGTGGTTGG
TTTTAAATGTCTCTTGGTTTCTCAGGCGTTCGCCTGCAAACCATGTTTCAGTTCGAGTCTTGCAGATATTAAGACCAACA
CCACCGCAGCGGCAAGCTTTGCTGTCCTCCAAGACATCAGTTGCCTTAGGCATCGCGACTCGGCCTCTGAGGCGATTCGC
AAAATCCCTCAGTGCCGTACGGCGATAGGGACACCCGTGTATGTTACCATCACAGCCAATGTGACAGATGAGAATTATTT
ACATTCTTCTGATCTCCTCATGCTTTCTTCTTGCCTTTTCTATGCTTCTGAGATGAGTGAAAAGGGATTTAAGGTGGTAT
TTGGCAATGTGTCAGGCATCGTGGCTGTGTGTGTCAATTTTACCAGCTACGTCCAACATGTCAAGGAGTTTACCCAACGC
TCCCTGGTGGTCGACCATGTGCGGTTGCTCCATTTCATGACACCTGAGACCATGAGGTGGGCAACTGTTTTAGCCTGTCT
TTTTGCCATTCTGTTGGCAATTTGAATGTTTAAGTATGTTGGAGAAATGCTTGACCGCGGGCTGTTGCTCGCGATTGCTT
TCTTTGTGGTGTATCGTGCCGTTCTGTTTTGCTGTGCTCGCCAACGCCAGCAACGACAGCAGCTCCCATCTACAGCTGAT
TTACAACTTGACGCTATGTGAGCTGAATGGCACAGATTGGCTAGCTAACAAATTTGATTGGGCAGTGGAGAGTTTTGTCA
TCTTTCCCGTTTTGACTCACATTGTCTCCTATGGTGCCCTCACTACCAGCCATTTCCTTGACACAGTCGCTTTAGTCACT
GTGTCTACCGCCGGGTTTGTTCACGGGCGGTATGTCCTAAGTAGCATCTACGCGGTCTGTGCCCTGGCTGCGTTGACTTG
CTTCGTCATTAGGTTTGCAAAGAATTGCATGTCCTGGCGCTACGCGTGTACCAGATATACCAACTTTCTTCTGGACACTA
AGGGCAGACTCTATCGTTGGCGGTCGCCTGTCATCATAGAGAAAAGGGGCAAAGTTGAGGTCGAAGGTCATCTGATCGAC
CTCAAAAGAGTTGTGCTTGATGGCTCCGTGGCAACCCCTATAACCAGAGTTTCAGCGGAACAATGGGGTCGTCCTTAGAT
GACTTCTGTCACGATAGCACGGCTCCACAAAAGGTGCTTTTGGCGTTTTCTATTACCTACACGCCAGTGATGATATATGC
CCTAAAGGTGAGTCGCGGCCGACTGCTAGGGCTTCTGCACCTTTTGATCTTCCTGAATTGTGCTTTCACCTTCGGGTACA
TGACTTTCGCGCACTTTCAGAGTACAAATAAGGTCGCGCTCACTATGGGAGCAGTAGTTGCACTCCTTTGGGGGGTGTAC
TCAGCCATAGAAACCTGGAAATTCATCACCTCCAGATGCCGTTTGTGCTTGCTAGGCCGCAAGTACATTCTGGCCCCTGC
CCACCACGTTGAAAGTGCCGCAGGCTTTCATCCGATTGCGGCAAATGATAACCACGCATTTGTCGTCCGGCGTCCCGGCT
CCACTACGGTCAACGGCACATTGGTGCCCGGGTTAAAAAGCCTCGTGTTGGGTGGCAGAAAAGCTGTTAAACAGGGAGTG
GTAAACCTTGTCAAATATGCCAAATAACAACGGCAAGCAGCAGAAGAGAAAGAAGGGGGATGGCCAGCCAGTCAATCAGC
TGTGCCAGATGCTGGGTAAGATCATCGCTCAGCAAAACCAGTCCAGAGGCAAGGGACCGGGAAAGAAAAATAAGAAGAAA
AACCCGGAGAAGCCCCATTTTCCTCTAGCGACTGAAGATGATGTCAGACATCACTTTACCCCTAGTGAGCGGCAATTGTG
TCTGTCGTCAATCCAGACCGCCTTTAATCAAGGCGCTGGGACTTGCACCCTGTCAGATTCAGGGAGGATAAGTTACACTG
TGGAGTTTAGTTTGCCTACGCATCATACTGTGCGCCTGATCCGCGTCACAGCATCACCCTCAGCATGATGGGCTGGCATT
CTTGAGGCATCTCAGTGTTTGAATTGGAAGAATGTGTGGTGAATGGCACTGATTGACATTGTGCCTCTAAGTCACCTATT
CAATTAGGGCGACCGTGTGGGGGTGAGATTTAATTGGCGAGAACCATGCGGCCGAAATTAAAAAAAA
```

Fig. 1L-1

```
>V7-Nsp2d727-813.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCCAGCACCGCCGCAGAGCGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGAATCACACGCCCAAAATACTCAGCTCAAGCCATCATCGACTCGGGCGGGC
CCTGCAGTGGGCATCTCCAAGAGGTAAAGGAAACATGCCTTAGTGTCATGCGCGAGGCATGTGATGCGACTAAGCTTGAT
GACCCTGCTACGCAGGAATGGCTTTCTCGCATGTGGGATCGGGTGGACATGCTGACTTGGCGCAACACGTCTGTTTACCA
GGCGATTTGCACCTTAGATGGCAGGTTAAAGTTCCTCCCAAAAATGATACTCGAGACACCGCCGCCCTATCCGTCTTTTA
CCGATTTGCCGCCTTCAGATGGCGCGGATGCGGACGGGGGGGGCCGTTTCGGACGGTAAAAAGAAAAGCTGAAAGGCTC
TTTGACCAACTGAGCCGTCAGGTTTTTGACCTCGTCTCCCATCTCCCTGTTTTCTTCTCACGCCTTTTCTACCCTGGCGG
TGGTTATTCTCCGGGTGATTGGGGTTTTGCAGCTTTTACTCTATTGTGCCTCTTTTTATGTTACAGTTACCCAGCCTTTG
GTATTGCTCCCCTCTTGGGTGTGTTTTCTGGGTCTTCTCGGCGCGTTCGAATGGGGGTTTTTGGCTGCTGGTTGGCTTTT
```

*Fig. 1L-2*

```
GCTGTTGGTCTGTTCAAGCCTGTGTCCGACCCAGTCGGCGCTGCTTGTGAGTTTGACTCGCCAGAGTGTAGAAACATCCT
TCATTCTTTTGAGCTTCTCAAACCTTGGGACCCTGTTCGCAGCCTTGTTGTGGGCCCCGTCGGTCTCGGTCTTGCCATTC
TTGGCAGGTTACTGGGCGGGGCACGCTGCATCTGGCACTTTTTTGCTTAGGCTTGGCATTGTTGCAGACTGTATCTTGGCT
GGAGCTTACGTGCTTTCTCAAGGTAGGTGTAAAAAGTGCTGGGGATCTTGTATAAGAACTGCTCCCAATGAGGTCGCTTT
TAACGTGTTTCCTTTCACACGTGCGACCAGGTCGTCACTTATCGACCTGTGCGATCGGTTTTGTGCGCCAAAAGGAATGG
ACCCCATTTTTCTCGCCACTGGGTGGCGCGGGTGCTGGGCCGGCCGAAGCCCCATTGAGCAACCCTCTGAAAAACCCATC
GCGTTTGCCCAGTTGGATGAAAAGAAGATTACGGCTAGGACTGTGGTCGCCCAGCCTTATGACCCCAACCAAGCCGTAAA
GTGCTTGCGGGTATTGCAGGCGGGTGGGGCGATGGTGGCTAAGGCGGTCCCAAAAGTGGTCAAGGTTTCCGCTGTTCCAT
TCCGAGCCCCCTTCTTTCCCACTGGAGTGAAAGTTGACCCTGATTGCAGGGTCGTGGTTGACCCTGACACTTTCACTGCA
GCTCTCCGGTCTGGCTACTCCACCACAAACCTCGTCCTTGGTGTGGGGACTTTGCCCAGCTGAATGGATTAAAAATCAG
GCAAATTTCCAAGCCTTCAGGGGGAGGCCCACATCTCATGGCTGCCCTGCATGTTGCCTGCTCGATGGCTCTGCACATGC
TTGCTGGGATTTATGTGACTGCGGTGGGTTCTTGCGGCACCGGCACCAACGACCCGTGGTGCGCTAACCCGTTTGCCGTC
CCTGGCTACGGACCTGGCTCTCTCTGCACGTCCAGATTGTGCATTTCCCAACACGGCCTTACCCTGCCCTTGACAGCACT
TGTGGCGGGATTCGGTATTCAAGAAATTGCCTTGGTCGTTTTGATTTTTGTTTCCATCGGAGGCATGGCTCATAGGTTGA
GCTGTAAGGCTGACATGCTGTGTGTCTTGCTTGCAATTGCCAGCTATGTTTGGGTACCTCTTACCTGGTTGCTTTGTGTG
TTTCCTTGCTGGTTGCGCTGTTTTTCTTTGCACCCCCTCACCATCCTATGGTTGGTGTTTTTCTTGATTTCTGTGAATAT
GCCTTCAGGAATCTTGGCCATGGTGTTGTTGGTTTCTCTTTGGCTTCTTGGTCGTTATACTAATGTTGCTGGCCTTGTCA
CCCCCTACGACATTCATCATTACACCAGTGGCCCCCGCGGTGTTGCCGCCTTGGCTACCGCACCAGATGGGACCTACTTG
GCCGCTGTCCGCCGCGCTGCGTTGACTGGCCGCACCATGCTGTTTACCCCGTCCCAGCTTGGGTCTCTTCTTGAGGGTGC
TTTCAGAACTCGAAAGCCCTCACTGAACACCGTCAATGTGATCGGGTCCTCCATGGGCTCTGGCGGGGTGTTTACCATCG
ACGGGAAAGTCAAGTGCGTAACTGCCGCACATGTCCTTACGGGCAATTCAGCTCGGGTTTCCGGGGTCGGCTTCAATCAA
ATGCTTGACTTTGACGTAAAGGGAGATTTCGCTATAGCTGATTGCCCGAATTGGCAAGGGGCTGCCCCCAAGACCCAATT
CTGCACGGATGGATGGACTGGCCGTGCCTATTGGCTAACATCCTCTGGCGTCGAACCCGGCGTCATTGGAAAAGGATTCG
CCTTCTGCTTCACCGCATGTGGCGATTCCGGGTCCCCAGTGATCACCGAGGCCGGTGAGCTTGTCGGCGTTCACACGGGA
TCGAATAAACAAGGGGGGGGCATTGTTACGCGCCCCTCAGGCCAGTTTTGTAATGTGGCACCCATCAAGCTAAGCGAATT
AAGTGAATTCTTTGCTGGGCCTAAGGTCCCGCTCGGTGATGTGAAGGTCGGCAGCCACATAATTAAAGACATAAGCGAGG
TGCCTTCAGATCTTTGTGCCTTGCTTGCTGCCAAACCTGAACTGGAAGGAGGCCTCTCCACCGTCCAACTTCTTTGTGTG
TTTTTTCTCCTGTGGAGAATGATGGGACATGCCTGGACGCCCTTGGTTGCTGTGAGTTTCTTTATTTTGAATGAGGTTCT
CCCAGCCGTCCTGGTCCGGAGTGTTTTCTCCTTTGGAATGTTTGTGCTATCCTGGCTCACGCCATGGTCTGCGCAAGTTC
TGATGATCAGGCTTCTGACAGCAGCTCTTAACAGGAACAGATGGTCACTTGCCTTTTTCAGCCTCGGTGCAGTGACCGGT
TTTGTCGCAGATCTTGCGGCCACTCAGGGGCATCCGTTGCAGGCAGTGATGAATTTGAGCACCTATGCATTCCTGCCTCG
GATGATGGTTGTGACCTCACCAGTCCCAGTGATCACGTGTGGTGTCGTGCACCTACTTGCCATCATTTTGTACTTGTTTA
AGTACCGTGGCCTGCACCATATCCTTGTTGGCGATGGAGTGTTCTCTGCGGCTTTCTTCTTGAGATACTTTGCCGAGGGA
AAGTTGAGGGAAGGGGTGTCGCAATCCTGCGGAATGAATCATGAGTCTCTGACTGGTGCCCTCGCTATGAGACTCAATGA
CGAGGACTTGGATTTCCTTATGAAATGGACTGATTTTAAGTGCTTTGTTTCTGCGTCCAACATGAGGAATGCAGCGGGTC
AATTTATCGAGGCTGCCTATGCTAAAGCACTTAGAGTAGAACTGGCCCAGTTGGTGCAGGTTGATAAAGTTCGAGGTACT
TTGGCCAAACTTGAAGCTTTTGCTGATACCGTGGCACCTCAACTCTCGCCCGGTGACATTGTTGTCGCTCTCGGCCACAC
GCCTGTTGGCAGTATCTTCGACCTAAAGGTTGGTAGCACCAAGCATACCCTCCAAGCCATTGAGACCAGAGTCCTTGCTG
GGTCCAAAATGACCGTGGCGCGCGTCGTCGACCCGACCCCCACGCCCCCACCCGCACCCGTGCCCATCCCCCTCCCACCG
AAAGTTCTGGAGAATGGCCCCAACGCTTGGGGGATGAGGACCGTTTGAATAAGAAGAAGAGGCGCAGGATGGAAGCCCT
CGGCATCTATGTTATGGGCGGGAAAAAATACCAGAAATTTTGGGACAAGAATTCCGGTGATGTGTTTTATGAGGAGGTCC
ATAATAACACAGATGAGTGGGAGTGTCTCAGAGTTGGCGACCCTGCCGACTTTGACCCTGAGAAGGGAACTCTGTGTGGA
CATGTCACCATTGAAAACAAGGCTTACCATGTTTACACCTCCCCATCTGGTAAGAAGTTCTTGGTCCCCGTCAACCCAGA
GAATGGAAGAGTCCAATGGGAAGCTGCAAAGCTTTCCGTGGAGCAGGCCCTAGGTATGATGAATGTCGACGGCGAACTGA
CTGCCAAAGAACTGGAGAAACTGAAAAGAATAATTGACAAACTCCAGGGCCTGACTAAGGAGCAGTGTTTAAACTGCTAG
CCGCCAGCGACTTGACCCGCTGTGGTCGCGGCGGCTTGGTTGTTACTGAAACAGCGGTAAAAATAGTCAAATTTCACAAC
CGGACCTTCACCCTGGGACCTGTGAATTTAAAAGTGGCCAGTGAGGTTGAGCTAAAAGACGCGGTTGAGCACAACCAACA
CCCGGTTGCGAGACCGATCGATGGTGGAGTTGTGCTCCTGCGTTCCGCGGTTCCTTCGCTTATAGACGTCTTGATCTCCG
GTGCTGATGCATCTCCCAAGTTACTTGCCCATCACGGGCCGGGAAACACTGGGATCGATGGCACGCTCTGGGATTTTGAG
```

Fig. 1L-3

```
TCCGAAGCCACTAAAGAGGAAGTCGCACTCAGTGCGCAAATAATACAGGCTTGTGACATTAGGCGCGGCGACGCTCCTGA
AATTGGTCTCCCTTACAAGCTGTACCCTGTTAGGGGTAACCCTGAGCGGGTGAAAGGAGTTCTGCAGAATACAAGGTTTG
GAGACATACCTTACAAAACCCCCAGTGACACTGGAAGCCCAGTGCACGCGGCTGCCTGCCTTACGCCCAACGCCACTCCG
GTGACTGATGGGCGCTCCGTCTTGGCCACGACCATGCCCCCCGGGTTTGAGTTATATGTACCGACCATACCAGCGTCTGT
CCTTGATTACCTTGACTCTAGGCCTGACTGCCCTAAACAGCTGACAGAGCACGGCTGCGAAGATGCCGCACTGAAAGACC
TCTCTAAATATGACTTGTCCACCCAAGGCTTTGTTTTACCTGGAGTTCTTCGCCTTGTGCGGAAATACCTGTTTGCCCAT
GTAGGTAAGTGCCCACCCGTTCATCGGCCTTCTACTTACCCTGCTAAGAATTCTATGGCTGGAATAAATGGGAACAGGTT
CCCAACCAAGGACATTCAGAGCGTCCCTGAAATCGACGTTCTGTGCGCACAGGCTGTGCGAGAAAACTGGCAAACTGTCA
CCCCTTGTACTCTTAAGAAACAGTATTGCGGGAAGAAGAAGACTAGGACCATACTCGGCACCAATAACTTCATCGCACTA
GCCCACCGAGCAGTGTTGAGTGGTGTTACCCAGGGCTTCATGAAAAAGGCGTTTAACTCGCCCATCGCCCTCGGAAAGAA
CAAGTTTAAGGAGCTACAGACTCCGGTCCTGGGCAGGTGCCTTGAAGCTGATCTCGCATCCTGCGATCGATCCACGCCTG
CAATTGTCCGCTGGTTTGCCGCCAACCTTCTTTATGAACTTGCCTGTGCTGAAGAGCATCTACCGTCGTACGTGCTGAAC
TGCTGCCACGACTTACTGGTCACGCAGTCCGGCGCAGTGACTAAGAGAGGTGGCCTGTCGTCTGGCGACCCGATCACCTC
TGTGTCTAACACCATTTATAGTTTGGTGATCTATGCACAGCATATGGTGCTTAGTTACTTCAAAAGTGGTCACCCCCATG
GCCTTCTGTTCTTACAAGACCAGCTAAAGTTTGAGGACATGCTCAAGGTTCAACCCCTGATCGTCTATTCGGACGACCTC
GTGCTGTATGCCGAGTCTCCCACCATGCCAAACTATCACTGGTGGGTTGAACATCTGAATTTGATGCTGGGGTTTCAGAC
GGACCCAAAGAAGACAGCAATAACAGACTCGCCATCATTTCTAGGCTGTAGAATAATAAATGGGCGCCAGCTAGTCCCCA
ACCGTGACAGGATCCTCGCGGCCCTCGCCTATCACATGAAGGCGAGTAATGTTTCTGAATACTATGCCTCAGCGGCTGCA
ATACTCATGGACAGCTGTGCTTGTTTGGAGTATGATCCTGAATGGTTTGAAGAACTTGTAGTTGGAATAGCGCAGTGCGC
CCGCAAGGACGGCTACAGCTTTCCCGGCACGCCGTTCTTCATGTCCATGTGGGAAAAACTCAGGTCCAATTATGAGGGGA
AGAAGTCGAGAGTGTGCGGGTACTGCGGGGCCCCGGCCCCGTACGCTACTGCCTGTGGCCTCGACGTCTGCATTTACCAC
ACCCACTTCCACCAGCATTGTCCAGTCACAATCTGGTGTGGCCATCCAGCGGGTTCTGGTTCTTGTAGTGAGTGCAAATC
CCCTGTAGGGAAAGGCACAAGCCCTTTAGACGAGGTGCTGGAACAAGTCCCGTATAAGCCCCCACGGACCGTTATCATGC
ATGTGGAGCAGGGTCTCACCCCCCTTGATCCAGGTAGATACCAAACTCGCCGCGGATTAGTCTCTGTCAGGCGTGGAATT
AGGGGAAATGAAGTTGGACTACCAGACGGTGATTATGCTAGCACCGCCTTGCTCCCTACCTGCAAAGAGATCAACATGGT
CGCTGTCGCTTCCAATGTATTGCGCAGCAGGTTCATCATCGGCCCACCCGGTGCTGGGAAAACATACTGGCTCCTTCAAC
AGGTCCAGGATGGTGATGTTATTTACACACCAACTCACCAGACCATGCTTGACATGATTAGGGCTTTGGGGACGTGCCGG
TTCAACGTCCCGGCAGGCACAACGCTGCAATTCCCCGTCCCCTCCCGCACCGGTCCGTGGGTTCGCATCCTAGCCGGCGG
TTGGTGTCCTGGCAAGAATTCCTTCCTAGATGAAGCAGCGTATTGCAATCACCTTGATGTTTTGAGGCTTCTTAGTAAAA
CTACCCTCACCTGTCTAGGAGACTTCAAGCAACTCCACCCAGTGGGTTTTGATTCTCATTGCTATGTTTTTGACATCATG
CCTCAAACTCAACTGAAGACCATCTGGAGGTTTGGACAGAATATCTGTGATGCCATTCAGCCAGATTACAGGGACAAACT
CATGTCCATGGTCAACACAACCCGTGTGACCTACGTGGAAAAACCTGTCAGGTATGGGCAGGTCCTCACCCCCTACCACA
GGGACCGAGAGGACGACGCCATCACTATTGACTCCAGTCAAGGCGCCACATTCGATGTGGTTACATTGCATTTGCCCACT
AAAGATTCACTCAACAGGCAAAGAGCCCTTGTTGCTATCACCAGGGCAAGACACGCTATCTTTGTGTATGACCCACACAG
GCAGCTGCAGGGCTTGTTTGATCTTCCTGCAAAAGGCACGCCCGTCAACCTCGCAGTGCACTGCGACGGGCAGCTGATCG
TGCTGGATAGAAATAACAAAGAATGCACGGTTGCTCAGGCTCTAGGCAACGGGGATAAATTTAGGGCCACAGACAAGCGT
GTTGTAGATTCTCTCCGCGCCATTTGTGCTGATCTAGAAGGGTCGAGCTCTCCGCTCCCCAAGGTCGCACACAACTTGGG
ATTTTATTTCTCACCTGATTTAACACAGTTTGCTAAACTCCAGTAGAACTTGCACCTCACTGGCCCGTGGTGTCAACCC
AGAACAATGAAAAGTGGCCGGATCGGCTGGTTGCCAGCCTTCGCCCTATCCATAAATACAGCCGCGCGTGCATCGGTGCC
GGCTATATGGTGGGCCCTTCGGTGTTTCTAGGCACTCCTGGGGTCGTGTCATACTATCTCACAAAATTTGTTAAGGGCGG
GGCTCAAGTGCTTCCGGAGACGGTTTTCAGCACCGGCCGAATTGAGGTAGACTGCCGGGAATATCTTGATGATCGGGAGC
GAGAAGTTGCTGCGTCCCTCCCACACGCTTTCATTGGCGACGTCAAAGGCACTACCGTTGGAGGATGTCATCATGTCACC
TCCAGATACCTCCCGCGCGTCCTTCCCAAGGAATCAGTTGCGGTAGTCGGGGTTTCAAGCCCCGGAAAAGCCGCGAAAGC
ATTGTGCACACTGACAGATGTGTACCTCCCAGATCTTGAAGCCTATCTCCACCCGGAGACCCAGTCCAAGTGCTGGAAAA
TGATGTTGGACTTCAAAGAAGTTCGACTAATGGTCTGGAAAGACAAAACAGCCTATTTCCAACTTGAAGGTCGCTATTTC
ACCTGGTATCAGCTTGCCAGCTATGCCTCGTACATCCGTGTTCCCGTCAACTCTACGGTGTACTTGGACCCCTGCATGGG
CCCCGCCCTTTGCAACAGGAGAGTCGTCGGGTCCACCCACTGGGGGGCTGACCTCGCGGTCACCCCTTATGATTACGGCG
CTAAAATTATCCTGTCTAGCGCGTACCATGGTGAAATGCCCCCCGGATACAAAATTCTGGCGTGCGCGGAGTTCTCGTTG
GATGACCCAGTTAAGTACAAACATACCTGGGGGTTTGAATCGGATACAGCGTATCTGTATGAGTTCACCGGAAACGGTGA
```

Fig. 1L-4

```
GGACTGGGAGGATTACAATGATGCGTTTCGTGCGCGCCAGGAAGGGAAAATTTATAAGGCCACTGCCACCAGCTTGAAGT
TTTATTTTCCCCCGGGCCCTGTCATTGAACCAACTTTAGGCCTGAATTGAAATGAAATGGGGTCCATGCAAAGCCTTTTT
GACAAAATTGGCCAACTTTTTTGTGGATGCTTTCACGGAGTTCTTGGTGTCCATTGTTGATATCATTATATTTTTGGCCAT
TTTGTTTGGCTTCACCATCGCCGGTTGGCTGGTGGTCTTTTGCATCAGATTGGTTTGCTCCGCGATACTCCGTACGCGCC
CTGCCATTCACTCTGAGCAATTACAGAAGATCTTATGAGGCCTTTCTTTCCCAGTGCCAAGTGGACATTCCCACCTGGGG
AACTAAACATCCTTTGGGGATGCTTTGGCACCATAAGGTGTCAACCCTGATTGATGAAATGGTGTCGCGTCGAATGTACC
GCATCATGGAAAAAGCAGGGCAGGCTGCCTGGAAACAGGTGGTGAGCGAGGCTACGCTGTCTCGCATTAGTAGTTTGGAT
GTGGTGGCTCATTTTCAGCATCTAGCCGCCATTGAAGCCGAGACCTGTAAATATTTGGCCTCCCGGCTGCCCATGCTACA
CAACCTGCGCATGACAGGGTCAAATGTAACCATAGTGTATAATAGCACTTTGAATCAGGTGTTTGCTATTTTTCCAACCC
CTGGTTCCCGGCCAAAGCTTCATGATTTTCAGCAATGGTTAATAGCTGTACATTCCTCCATATTTTCCTCTGTTGCAGCT
TCTTGTACTCTTTTTGTTGTGCTGTGGTTGCGGGTTCCAATACTACGTACTGTTTTTGGTTTCCGCTGGTTAGGGGCAAT
TTTTCTTTCGAACTCACAGTGAATTACACGGTGTGTCCACCTTGCCTCACCCGGCAAGCAGCCACAGAGATCTACGAACC
CGGTAGGTCTCTTTGGTGCAGGATAGGGTATGACCGATGTGGGGAGGACGATCATGACGAGCTAGGGTTTATGATACCGC
CTGGCCTCTCCAGCGAAGGCCACTTGACTGGTGTTTACGCCTGGTTGGCGTTCTTGTCCTTCAGCTACACGGCCCAGTTC
CATCCCGAGATATTCGGGATAGGGAATGTGAGTCGAGTTTATGTTGACATCAAACATCAACTCATCTGCGCCGAACATGA
CGGGCAGAACACCACCTTGCCTCGTCATGACAACATTTCAGCCGTGTTTCAGACCTATTACCAACATCAAGTCGACGGCG
GCAATTGGTTTCACCTAGAATGGCTTCGTCCCTTCTTTTCCTCGTGGTTGGTTTTAAATGTCTCTTGGTTTCTCAGGCGT
TCGCCTGCAAACCATGTTTCAGTTCGAGTCTTGCAGATATTAAGACCAACACCACCGCAGCGGCAAGCTTTGCTGTCCTC
CAAGACATCAGTTGCCTTAGGCATCGCGACTCGGCCTCTGAGGCGATTCGCAAAATCCCTCAGTGCCGTACGGCGATAGG
GACACCCGTGTATGTTACCATCACAGCCAATGTGACAGATGAGAATTATTTACATTCTTCTGATCTCCTCATGCTTTCTT
CTTGCCTTTTCTATGCTTCTGAGATGAGTGAAAAGGGATTTAAGGTGGTATTTGGCAATGTGTCAGGCATCGTGGCTGTG
TGTGTCAATTTTACCAGCTACGTCCAACATGTCAAGGAGTTTACCCAACGCTCCCTGGTGGTCGACCATGTGCGGTTGCT
CCATTTCATGACACCTGAGACCATGAGGTGGGCAACTGTTTTAGCCTGTCTTTTTGCCATTCTGTTGGCAATTTGAATGT
TTAAGTATGTTGGAGAAATGCTTGACCGCGGGCTGTTGCTCGCGATTGCTTTCTTTGTGGTGTATCGTGCCGTTCTGTTT
TGCTGTGCTCGCCAACGCCAGCAACGACAGCAGCTCCCATCTACAGCTGATTTACAACTTGACGCTATGTGAGCTGAATG
GCACAGATTGGCTAGCTAACAAATTTGATTGGGCAGTGGAGAGTTTTGTCATCTTTCCCGTTTTGACTCACATTGTCTCC
TATGGTGCCCTCACTACCAGCCATTTCCTTGACACAGTCGCTTTAGTCACTGTGTCTACCGCCGGGTTTGTTCACGGGCG
GTATGTCCTAAGTAGCATCTACGCGGTCTGTGCCCTGGCTGCGTTGACTTGCTTCGTCATTAGGTTTGCAAAGAATTGCA
TGTCCTGGCGCTACGCGTGTACCAGATATACCAACTTTCTTCTGGACACTAAGGGCAGACTCTATCGTTGGCGGTCGCCT
GTCATCATAGAGAAAAGGGGCAAAGTTGAGGTCGAAGGTCATCTGATCGACCTCAAAAGAGTTGTGCTTGATGGCTCCGT
GGCAACCCCTATAACCAGAGTTTCAGCGGAACAATGGGGTCGTCCTTAGATGACTTCTGTCACGATAGCACGGCTCCACA
AAAGGTGCTTTTGGCGTTTTCTATTACCTACACGCCAGTGATGATATATGCCCTAAAGGTGAGTCGCGGCCGACTGCTAG
GGCTTCTGCACCTTTTGATCTTCCTGAATTGTGCTTTCACCTTCGGGTACATGACTTTCGCGCACTTTCAGAGTACAAAT
AAGGTCGCGCTCACTATGGGAGCAGTAGTTGCACTCCTTTGGGGGTGTACTCAGCCATAGAAACCTGGAAATTCATCAC
CTCCAGATGCCGTTTGTGCTTGCTAGGCCGCAAGTACATTCTGGCCCCTGCCCACCACGTTGAAAGTGCCGCAGGCTTTC
ATCCGATTGCGGCAAATGATAACCACGCATTTGTCGTCCGGCGTCCCGGCTCCACTACGGTCAACGGCACATTGGTGCCC
GGGTTAAAAAGCCTCGTGTTGGGTGGCAGAAAAGCTGTTAAACAGGGAGTGGTAAACCTTGTCAAATATGCCAAATAACA
ACGGCAAGCAGCAGAAGAGAAAGAAGGGGGATGGCCAGCCAGTCAATCAGCTGTGCCAGATGCTGGGTAAGATCATCGCT
CAGCAAAACCAGTCCAGAGGCAAGGGACCGGGAAAGAAAAATAAGAAGAAAAACCCGGAGAAGCCCCATTTTCCTCTAGC
GACTGAAGATGATGTCAGACATCACTTTACCCCTAGTGAGCGGCAATTGTGTCTGTCGTCAATCCAGACCGCCTTTAATC
AAGGCGCTGGGACTTGCACCCTGTCAGATTCAGGGAGGATAAGTTACACTGTGGAGTTTAGTTTGCCTACGCATCATACT
GTGCGCCTGATCCGCGTCACAGCATCACCCTCAGCATGATGGGCTGGCATTCTTGAGGCATCTCAGTGTTTGAATTGGAA
GAATGTGTGGTGAATGGCACTGATTGACATTGTGCCTCTAAGTCACCTATTCAATTAGGGCGACCGTGTGGGGGTGAGAT
TTAATTGGCGAGAACCATGCGGCCGAAATTAAAAAAAA
```

Fig. 1M-1

```
>V7-Nsp2d324-726.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGTGTGAGTTTGTGATGA
TGCCTCACACGCCTGCACCTTCCGTAGGTGCGGAGAGCGACCTTACCATTGGCTCAGTTGCTACTGAAGATGTTCCACGC
ATCCTCGAGAAAATAGAAAATGTCGGCGAGATGGCCAACCAGGGACCCTTGGCCTTCTCCGAGGATAAACCGGTAGATGA
CCAACTTGTCAACGACCCCCGGATATCGTCGCGGAGGCCTGACGAGAGCACATCAGCTCCGTCCGCAGGCACAGGTGGCG
CCGGCTCTTTTACCGATTTGCCGCCTTCAGATGGCGCGGATGCGGACGGGGGGGGGCCGTTTCGGACGGTAAAAAGAAAA
GCTGAAAGGCTCTTTGACCAACTGAGCCGTCAGGTTTTTGACCTCGTCTCCCATCTCCCTGTTTTCTTCTCACGCCTTTT
CTACCCTGGCGGTGGTTATTCTCCGGGTGATTGGGGTTTTGCAGCTTTTACTCTATTGTGCCTCTTTTTATGTTACAGTT
ACCCAGCCTTTGGTATTGCTCCCCTCTTGGGTGTGTTTTCTGGGTCTTCTCGGCGCGTTCGAATGGGGGTTTTTGGCTGC
TGGTTGGCTTTTGCTGTTGGTCTGTTCAAGCCTGTGTCCGACCCAGTCGGCGCTGCTTGTGAGTTTGACTCGCCAGAGTG
TAGAAACATCCTTCATTCTTTTGAGCTTCTCAAACCTTGGGACCCTGTTCGCAGCCTTGTTGTGGGCCCCGTCGGTCTCG
GTCTTGCCATTCTTGGCAGGTTACTGGGCGGGGCACGCTGCATCTGGCACTTTTTGCTTAGGCTTGGCATTGTTGCAGAC
TGTATCTTGGCTGGAGCTTACGTGCTTTCTCAAGGTAGGTGTAAAAAGTGCTGGGGATCTTGTATAAGAACTGCTCCCAA
TGAGGTCGCTTTTAACGTGTTTCCTTTCACACGTGCGACCAGGTCGTCACTTATCGACCTGTGCGATCGGTTTTGTGCGC
CAAAAGGAATGGACCCCATTTTTCTCGCCACTGGGTGGCGCGGGTGCTGGGCCGGCCGAAGCCCCATTGAGCAACCCTCT
GAAAAACCCATCGCGTTTGCCCAGTTGGATGAAAAGAAGATTACGGCTAGGACTGTGGTCGCCCAGCCTTATGACCCCAA
CCAAGCCGTAAAGTGCTTGCGGGTATTGCAGGCGGGTGGGGCGATGGTGGCTAAGGCGGTCCCAAAAGTGGTCAAGGTTT
CCGCTGTTCCATTCCGAGCCCCCTTCTTTCCCACTGGAGTGAAAGTTGACCCTGATTGCAGGGTCGTGGTTGACCCTGAC
ACTTTCACTGCAGCTCTCCGGTCTGGCTACTCCACCACAAACCTCGTCCTTGGTGTGGGGGACTTTGCCCAGCTGAATGG
ATTAAAAATCAGGCAAATTTCCAAGCCTTCAGGGGGAGGCCCACATCTCATGGCTGCCCTGCATGTTGCCTGCTCGATGG
CTCTGCACATGCTTGCTGGGATTTATGTGACTGCGGTGGGTTCTTGCGGCACCGGCACCAACGACCCGTGGTGCGCTAAC
```

*Fig. 1M-2*

```
CCGTTTGCCGTCCCTGGCTACGGACCTGGCTCTCTCTGCACGTCCAGATTGTGCATTTCCCAACACGGCCTTACCCTGCC
CTTGACAGCACTTGTGGCGGGATTCGGTATTCAAGAAATTGCCTTGGTCGTTTTGATTTTTGTTTCCATCGGAGGCATGG
CTCATAGGTTGAGCTGTAAGGCTGACATGCTGTGTGTCTTGCTTGCAATTGCCAGCTATGTTTGGGTACCTCTTACCTGG
TTGCTTTGTGTGTTTCCTTGCTGGTTGCGCTGTTTTTCTTTGCACCCCCTCACCATCCTATGGTTGGTGTTTTTCTTGAT
TTCTGTGAATATGCCTTCAGGAATCTTGGCCATGGTGTTGTTGGTTTCTCTTTGGCTTCTTGGTCGTTATACTAATGTTG
CTGGCCTTGTCACCCCCTACGACATTCATCATTACACCAGTGGCCCCGCGGTGTTGCCGCCTTGGCTACCGCACCAGAT
GGGACCTACTTGGCCGCTGTCCGCCGCGCTGCGTTGACTGGCCGCACCATGCTGTTTACCCCGTCCCAGCTTGGGTCTCT
TCTTGAGGGTGCTTTCAGAACTCGAAAGCCCTCACTGAACACCGTCAATGTGATCGGGTCCTCCATGGGCTCTGGCGGGG
TGTTTACCATCGACGGGAAAGTCAAGTGCGTAACTGCCGCACATGTCCTTACGGGCAATTCAGCTCGGGTTTCCGGGGTC
GGCTTCAATCAAATGCTTGACTTTGACGTAAAGGGAGATTTCGCTATAGCTGATTGCCCGAATTGGCAAGGGGCTGCCCC
CAAGACCCAATTCTGCACGGATGGATGGACTGGCCGTGCCTATTGGCTAACATCCTCTGGCGTCGAACCCGGCGTCATTG
GAAAAGGATTCGCCTTCTGCTTCACCGCATGTGGCGATTCCGGGTCCCCAGTGATCACCGAGGCCGGTGAGCTTGTCGGC
GTTCACACGGGATCGAATAAACAAGGGGGGGCATTGTTACGCGCCCCTCAGGCCAGTTTTGTAATGTGGCACCCATCAA
GCTAAGCGAATTAAGTGAATTCTTTGCTGGGCCTAAGGTCCCGCTCGGTGATGTGAAGGTCGGCAGCCACATAATTAAAG
ACATAAGCGAGGTGCCTTCAGATCTTTGTGCCTTGCTTGCTGCCAAACCTGAACTGGAAGGAGGCCTCTCCACCGTCCAA
CTTCTTTGTGTGTTTTTTCTCCTGTGGAGAATGATGGGACATGCCTGGACGCCCTTGGTTGCTGTGAGTTTCTTTATTTT
GAATGAGGTTCTCCCAGCCGTCCTGGTCCGGAGTGTTTTCTCCTTTGGAATGTTTGTGCTATCCTGGCTCACGCCATGGT
CTGCGCAAGTTCTGATGATCAGGCTTCTGACAGCAGCTCTTAACAGGAACAGATGGTCACTTGCCTTTTTCAGCCTCGGT
GCAGTGACCGGTTTTGTCGCAGATCTTGCGGCCACTCAGGGGCATCCGTTGCAGGCAGTGATGAATTTGAGCACCTATGC
ATTCCTGCCTCGGATGATGGTTGTGACCTCACCAGTCCCAGTGATCACGTGTGGTGTCGTGCACCTACTTGCCATCATTT
TGTACTTGTTTAAGTACCGTGGCCTGCACCATATCCTTGTTGGCGATGGAGTGTTCTCTGCGGCTTTCTTCTTGAGATAC
TTTGCCGAGGGAAAGTTGAGGGAAGGGGTGTCGCAATCCTGCGGAATGAATCATGAGTCTCTGACTGGTGCCCTCGCTAT
GAGACTCAATGACGAGGACTTGGATTTCCTTATGAAATGGACTGATTTTAAGTGCTTTGTTTCTGCGTCCAACATGAGGA
ATGCAGCGGGTCAATTTATCGAGGCTGCCTATGCTAAAGCACTTAGAGTAGAACTGGCCCAGTTGGTGCAGGTTGATAAA
GTTCGAGGTACTTTGGCCAAACTTGAAGCTTTTGCTGATACCGTGGCACCTCAACTCTCGCCCGGTGACATTGTTGTCGC
TCTCGGCCACACGCCTGTTGGCAGTATCTTCGACCTAAAGGTTGGTAGCACCAAGCATACCCTCCAAGCCATTGAGACCA
GAGTCCTTGCTGGGTCCAAAATGACCGTGGCGCGCGTCGTCGACCCGACCCCCACGCCCCCACCCGCACCCGTGCCCATC
CCCCTCCCACCGAAAGTTCTGGAGAATGGCCCCAACGCTTGGGGGGATGAGGACCGTTTGAATAAGAAGAAGAGGCGCAG
GATGGAAGCCCTCGGCATCTATGTTATGGGCGGGAAAAAATACCAGAAATTTTGGGACAAGAATTCCGGTGATGTGTTTT
ATGAGGAGGTCCATAATAACACAGATGAGTGGGAGTGTCTCAGAGTTGGCGACCCTGCCGACTTTGACCCTGAGAAGGGA
ACTCTGTGTGGACATGTCACCATTGAAAACAAGGCTTACCATGTTTACACCTCCCCATCTGGTAAGAAGTTCTTGGTCCC
CGTCAACCCAGAGAATGGAAGAGTCCAATGGGAAGCTGCAAAGCTTTCCGTGGAGCAGGCCCTAGGTATGATGAATGTCG
ACGGCGAACTGACTGCCAAAGAACTGGAGAAACTGAAAAGAATAATTGACAAACTCCAGGGCCTGACTAAGGAGCAGTGT
TTAAACTGCTAGCCGCCAGCGACTTGACCCGCTGTGGTCGCGGCGGCTTGGTTGTTACTGAAACAGCGGTAAAAATAGTC
AAATTTCACAACCGGACCTTCACCCTGGGACCTGTGAATTTAAAAGTGGCCAGTGAGGTTGAGCTAAAAGACGCGGTTGA
GCACAACCAACACCCGGTTGCGAGACCGATCGATGGTGGAGTTGTGCTCCTGCGTTCCGCGGTTCCTTCGCTTATAGACG
TCTTGATCTCCGGTGCTGATGCATCTCCCAAGTTACTTGCCCATCACGGGCCGGGAAACACTGGGATCGATGGCACGCTC
TGGGATTTTGAGTCCGAAGCCACTAAAGAGGAAGTCGCACTCAGTGCGCAAATAATACAGGCTTGTGACATTAGGCGCGG
CGACGCTCCTGAAATTGGTCTCCCTTACAAGCTGTACCCTGTTAGGGGTAACCCTGAGCGGGTGAAAGGAGTTCTGCAGA
ATACAAGGTTTGGAGACATACCTTACAAAACCCCAGTGACACTGGAAGCCCAGTGCACGCGGCTGCCTGCCTTACGCCC
AACGCCACTCCGGTGACTGATGGGCGCTCCGTCTTGGCCACGACCATGCCCCCCGGGTTTGAGTTATATGTACCGACCAT
ACCAGCGTCTGTCCTTGATTACCTTGACTCTAGGCCTGACTGCCCTAAACAGCTGACAGAGCACGGCTGCGAAGATGCCG
CACTGAAAGACCTCTCTAAATATGACTTGTCCACCCAAGGCTTTGTTTTACCTGGAGTTCTTCGCCTTGTGCGGAAATAC
CTGTTTGCCCATGTAGGTAAGTGCCCACCCGTTCATCGGCCTTCTACTTACCCTGCTAAGAATTCTATGGCTGGAATAAA
TGGGAACAGGTTCCCAACCAAGGACATTCAGAGCGTCCCTGAAATCGACGTTCTGTGCGCACAGGCTGTGCGAGAAAACT
GGCAAACTGTCACCCCTTGTACTCTTAAGAAACAGTATTGCGGGAAGAAGAAGACTAGGACCATACTCGGCACCAATAAC
TTCATCGCACTAGCCCACCGAGCAGTGTTGAGTGGTGTTACCCAGGGCTTCATGAAAAAGGCGTTTAACTCGCCCATCGC
CCTCGGAAAGAACAAGTTTAAGGAGCTACAGACTCCGGTCCTGGGCAGGTGCCTTGAAGCTGATCTCGCATCCTGCGATC
GATCCACGCCTGCAATTGTCCGCTGGTTTGCCGCCAACCTTCTTTATGAACTTGCCTGTGCTGAAGAGCATCTACCGTCG
```

Fig. 1M-3

```
TACGTGCTGAACTGCTGCCACGACTTACTGGTCACGCAGTCCGGCGCAGTGACTAAGAGAGGTGGCCTGTCGTCTGGCGA
CCCGATCACCTCTGTGTCTAACACCATTTATAGTTTGGTGATCTATGCACAGCATATGGTGCTTAGTTACTTCAAAAGTG
GTCACCCCCATGGCCTTCTGTTCTTACAAGACCAGCTAAAGTTTGAGGACATGCTCAAGGTTCAACCCCTGATCGTCTAT
TCGGACGACCTCGTGCTGTATGCCGAGTCTCCCACCATGCCAAACTATCACTGGTGGGTTGAACATCTGAATTTGATGCT
GGGGTTTCAGACGGACCCAAAGAAGACAGCAATAACAGACTCGCCATCATTTCTAGGCTGTAGAATAATAAATGGGCGCC
AGCTAGTCCCCAACCGTGACAGGATCCTCGCGGCCCTCGCCTATCACATGAAGGCGAGTAATGTTTCTGAATACTATGCC
TCAGCGGCTGCAATACTCATGGACAGCTGTGCTTGTTTGGAGTATGATCCTGAATGGTTTGAAGAACTTGTAGTTGGAAT
AGCGCAGTGCGCCCGCAAGGACGGCTACAGCTTTCCCGGCACGCCGTTCTTCATGTCCATGTGGGAAAAACTCAGGTCCA
ATTATGAGGGGAAGAAGTCGAGAGTGTGCGGGTACTGCGGGGCCCCGGCCCCGTACGCTACTGCCTGTGGCCTCGACGTC
TGCATTTACCACACCCACTTCCACCAGCATTGTCCAGTCACAATCTGGTGTGGCCATCCAGCGGGTTCTGGTTCTTGTAG
TGAGTGCAAATCCCCTGTAGGGAAAGGCACAAGCCCTTTAGACGAGGTGCTGGAACAAGTCCCGTATAAGCCCCCACGGA
CCGTTATCATGCATGTGGAGCAGGGTCTCACCCCCCTTGATCCAGGTAGATACCAAACTCGCCGCGGATTAGTCTCTGTC
AGGCGTGGAATTAGGGGAAATGAAGTTGGACTACCAGACGGTGATTATGCTAGCACCGCCTTGCTCCCTACCTGCAAAGA
GATCAACATGGTCGCTGTCGCTTCCAATGTATTGCGCAGCAGGTTCATCATCGGCCCACCCGGTGCTGGGAAAACATACT
GGCTCCTTCAACAGGTCCAGGATGGTGATGTTATTTACACACCAACTCACCAGACCATGCTTGACATGATTAGGGCTTTG
GGGACGTGCCGGTTCAACGTCCCGGCAGGCACAACGCTGCAATTCCCCGTCCCCTCCCGCACCGGTCCGTGGGTTCGCAT
CCTAGCCGGCGGTTGGTGTCCTGGCAAGAATTCCTTCCTAGATGAAGCAGCGTATTGCAATCACCTTGATGTTTTGAGGC
TTCTTAGTAAAACTACCCTCACCTGTCTAGGAGACTTCAAGCAACTCCACCCAGTGGGTTTTGATTCTCATTGCTATGTT
TTTGACATCATGCCTCAAACTCAACTGAAGACCATCTGGAGGTTTGGACAGAATATCTGTGATGCCATTCAGCCAGATTA
CAGGGACAAACTCATGTCCATGGTCAACACAACCCGTGTGACCTACGTGGAAAAACCTGTCAGGTATGGGCAGGTCCTCA
CCCCCTACCACAGGGACCGAGAGGACGACGCCATCACTATTGACTCCAGTCAAGGCGCCACATTCGATGTGGTTACATTG
CATTTGCCCACTAAAGATTCACTCAACAGGCAAAGAGCCCTTGTTGCTATCACCAGGGCAAGACACGCTATCTTTGTGTA
TGACCCACACAGGCAGCTGCAGGGCTTGTTTGATCTTCCTGCAAAAGGCACGCCCGTCAACCTCGCAGTGCACTGCGACG
GGCAGCTGATCGTGCTGGATAGAAATAACAAAGAATGCACGGTTGCTCAGGCTCTAGGCAACGGGGATAAATTTAGGGCC
ACAGACAAGCGTGTTGTAGATTCTCTCCGCGCCATTTGTGCTGATCTAGAAGGGTCGAGCTCTCCGCTCCCCAAGGTCGC
ACACAACTTGGGATTTTATTTCTCACCTGATTTAACACAGTTTGCTAAACTCCCAGTAGAACTTGCACCTCACTGGCCCG
TGGTGTCAACCCAGAACAATGAAAAGTGGCCGGATCGGCTGGTTGCCAGCCTTCGCCCTATCCATAAATACAGCCGCGCG
TGCATCGGTGCCGGCTATATGGTGGGCCCTTCGGTGTTTCTAGGCACTCCTGGGGTCGTGTCATACTATCTCACAAAATT
TGTTAAGGGCGGGGCTCAAGTGCTTCCGGAGACGGTTTTCAGCACCGGCCGAATTGAGGTAGACTGCCGGGAATATCTTG
ATGATCGGGAGCGAGAAGTTGCTGCGTCCCTCCCACACGCTTTCATTGGCGACGTCAAAGGCACTACCGTTGGAGGATGT
CATCATGTCACCTCCAGATACCTCCCGCGCGTCCTTCCCAAGGAATCAGTTGCGGTAGTCGGGGTTTCAAGCCCCGGAAA
AGCCGCGAAAGCATTGTGCACACTGACAGATGTGTACCTCCCAGATCTTGAAGCCTATCTCCACCCGGAGACCCAGTCCA
AGTGCTGGAAAATGATGTTGGACTTCAAAGAAGTTCGACTAATGGTCTGGAAAGACAAAACAGCCTATTTCCAACTTGAA
GGTCGCTATTTCACCTGGTATCAGCTTGCCAGCTATGCCTCGTACATCCGTGTTCCCGTCAACTCTACGGTGTACTTGGA
CCCCTGCATGGGCCCCGCCCTTTGCAACAGGAGAGTCGTCGGGTCCACCCACTGGGGGCTGACCTCGCGGTCACCCCTT
ATGATTACGGCGCTAAAATTATCCTGTCTAGCGCGTACCATGGTGAAATGCCCCCCGGATACAAAATTCTGGCGTGCGCG
GAGTTCTCGTTGGATGACCCAGTTAAGTACAAACATACCTGGGGGTTTGAATCGGATACAGCGTATCTGTATGAGTTCAC
CGGAAACGGTGAGGACTGGGAGGATTACAATGATGCGTTTCGTGCGCGCCAGGAAGGGAAAATTTATAAGGCCACTGCCA
CCAGCTTGAAGTTTTATTTTCCCCCGGGCCCTGTCATTGAACCAACTTTAGGCCTGAATTGAAATGAAATGGGGTCCATG
CAAAGCCTTTTTGACAAAATTGGCCAACTTTTTGTGGATGCTTTCACGGAGTTCTTGGTGTCCATTGTTGATATCATTAT
ATTTTTGGCCATTTTGTTTGGCTTCACCATCGCCGGTTGGCTGGTGGTCTTTTGCATCAGATTGGTTTGCTCCGCGATAC
TCCGTACGCGCCCTGCCATTCACTCTGAGCAATTACAGAAGATCTTATGAGGCCTTTCTTTCCCAGTGCCAAGTGGACAT
TCCCACCTGGGGAACTAAACATCCTTTGGGGATGCTTTGGCACCATAAGGTGTCAACCCTGATTGATGAAATGGTGTCGC
GTCGAATGTACCGCATCATGGAAAAAGCAGGGCAGGCTGCCTGGAAACAGGTGGTGAGCGAGGCTACGCTGTCTCGCATT
AGTAGTTTGGATGTGGTGGCTCATTTTCAGCATCTAGCCGCCATTGAAGCCGAGACCTGTAAATATTTGGCCTCCCGGCT
GCCCATGCTACACAACCTGCGCATGACAGGGTCAAATGTAACCATAGTGTATAATAGCACTTTGAATCAGGTGTTTGCTA
TTTTTCCAACCCCTGGTTCCCGGCCAAAGCTTCATGATTTTCAGCAATGGTTAATAGCTGTACATTCCTCCATATTTTCC
TCTGTTGCAGCTTCTTGTACTCTTTTTTGTTGTGCTGTGGTTGCGGGTTCCAATACTACGTACTGTTTTTGGTTTCCGCTG
GTTAGGGGCAATTTTTCTTTCGAACTCACAGTGAATTACACGGTGTGTCCACCTTGCCTCACCCGGCAAGCAGCCACAGA
```

Fig. 1M-4

```
GATCTACGAACCCGGTAGGTCTCTTTGGTGCAGGATAGGGTATGACCGATGTGGGGAGGACGATCATGACGAGCTAGGGT
TTATGATACCGCCTGGCCTCTCCAGCGAAGGCCACTTGACTGGTGTTTACGCCTGGTTGGCGTTCTTGTCCTTCAGCTAC
ACGGCCCAGTTCCATCCCGAGATATTCGGGATAGGGAATGTGAGTCGAGTTTATGTTGACATCAAACATCAACTCATCTG
CGCCGAACATGACGGGCAGAACACCACCTTGCCTCGTCATGACAACATTTCAGCCGTGTTTCAGACCTATTACCAACATC
AAGTCGACGGCGGCAATTGGTTTTCACCTAGAATGGCTTCGTCCCTTCTTTTCCTCGTGGTTGGTTTTAAATGTCTCTTGG
TTTCTCAGGCGTTCGCCTGCAAACCATGTTTCAGTTCGAGTCTTGCAGATATTAAGACCAACACCACCGCAGCGGCAAGC
TTTGCTGTCCTCCAAGACATCAGTTGCCTTAGGCATCGCGACTCGGCCTCTGAGGCGATTCGCAAAATCCCTCAGTGCCG
TACGGCGATAGGGACACCCGTGTATGTTACCATCACAGCCAATGTGACAGATGAGAATTATTTACATTCTTCTGATCTCC
TCATGCTTTCTTCTTGCCTTTTCTATGCTTCTGAGATGAGTGAAAAGGGATTTAAGGTGGTATTTGGCAATGTGTCAGGC
ATCGTGGCTGTGTGTGTCAATTTTACCAGCTACGTCCAACATGTCAAGGAGTTTACCCAACGCTCCCTGGTGGTCGACCA
TGTGCGGTTGCTCCATTTCATGACACCTGAGACCATGAGGTGGGCAACTGTTTTAGCCTGTCTTTTTGCCATTCTGTTGG
CAATTTGAATGTTTAAGTATGTTGGAGAAATGCTTGACCGCGGGCTGTTGCTCGCGATTGCTTTCTTTGTGGTGTATCGT
GCCGTTCTGTTTTGCTGTGCTCGCCAACGCCAGCAACGACAGCAGCTCCCATCTACAGCTGATTTACAACTTGACGCTAT
GTGAGCTGAATGGCACAGATTGGCTAGCTAACAAATTTGATTGGGCAGTGGAGAGTTTTGTCATCTTTCCCGTTTTGACT
CACATTGTCTCCTATGGTGCCCTCACTACCAGCCATTTCCTTGACACAGTCGCTTTAGTCACTGTGTCTACCGCCGGGTT
TGTTCACGGGCGGTATGTCCTAAGTAGCATCTACGCGGTCTGTGCCCTGGCTGCGTTGACTTGCTTCGTCATTAGGTTTG
CAAAGAATTGCATGTCCTGGCGCTACGCGTGTACCAGATATACCAACTTTCTTCTGGACACTAAGGGCAGACTCTATCGT
TGGCGGTCGCCTGTCATCATAGAGAAAAGGGGCAAAGTTGAGGTCGAAGGTCATCTGATCGACCTCAAAAGAGTTGTGCT
TGATGGCTCCGTGGCAACCCCTATAACCAGAGTTTCAGCGGAACAATGGGGTCGTCCTTAGATGACTTCTGTCACGATAG
CACGGCTCCACAAAAGGTGCTTTTGGCGTTTTCTATTACCTACACGCCAGTGATGATATATGCCCTAAAGGTGAGTCGCG
GCCGACTGCTAGGGCTTCTGCACCTTTTGATCTTCCTGAATTGTGCTTTCACCTTCGGGTACATGACTTTCGCGCACTTT
CAGAGTACAAATAAGGTCGCGCTCACTATGGGAGCAGTAGTTGCACTCCTTTGGGGGGTGTACTCAGCCATAGAAACCTG
GAAATTCATCACCTCCAGATGCCGTTTGTGCTTGCTAGGCCGCAAGTACATTCTGGCCCCTGCCCACCACGTTGAAAGTG
CCGCAGGCTTTCATCCGATTGCGGCAAATGATAACCACGCATTTGTCGTCCGGCGTCCCGGCTCCACTACGGTCAACGGC
ACATTGGTGCCCGGGTTAAAAAGCCTCGTGTTGGGTGGCAGAAAAGCTGTTAAACAGGGAGTGGTAAACCTTGTCAAATA
TGCCAAATAACAACGGCAAGCAGCAGAAGAGAAAGAAGGGGGATGGCCAGCCAGTCAATCAGCTGTGCCAGATGCTGGGT
AAGATCATCGCTCAGCAAAACCAGTCCAGAGGCAAGGGACCGGGAAAGAAAAATAAGAAGAAAAACCCGGAGAAGCCCCA
TTTTCCTCTAGCGACTGAAGATGATGTCAGACATCACTTTACCCCTAGTGAGCGGCAATTGTGTCTGTCGTCAATCCAGA
CCGCCTTTAATCAAGGCGCTGGGACTTGCACCCTGTCAGATTCAGGGAGGATAAGTTACACTGTGGAGTTTAGTTTGCCT
ACGCATCATACTGTGCGCCTGATCCGCGTCACAGCATCACCCTCAGCATGATGGGCTGGCATTCTTGAGGCATCTCAGTG
TTTGAATTGGAAGAATGTGTGGTGAATGGCACTGATTGACATTGTGCCTCTAAGTCACCTATTCAATTAGGGCGACCGTG
TGGGGGTGAGATTTAATTGGCGAGAACCATGCGGCCGAAATTAAAAAAAA
```

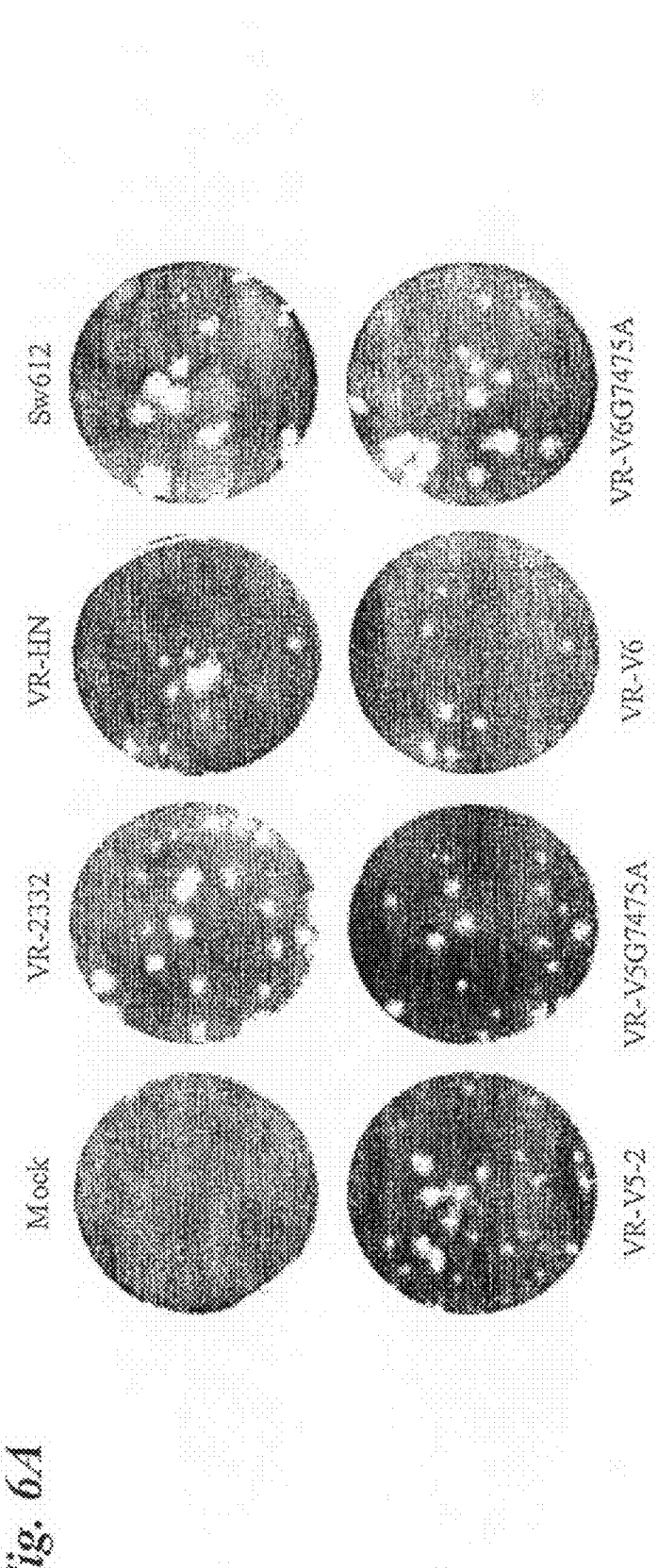

Fig. 7A

| | wt VR2332 | Sw612 | VR-HN | VR-V5 | VR-V5G7475A | VR-V6 | VR-V6G7475A | Mock |
|---|---|---|---|---|---|---|---|---|
| Viral Titer | 8.12 × 10⁴ | 2.0 × 10⁵ | 5.5 × 10³ | 5.0 × 10³ | 2.5 × 10⁴ | 4.4 × 10³ | 1.9 × 10⁴ | |

| | | |
|---|---|---|
| EuroPRRSV | IVDDRGVHRWKSPIVVELGRADIDGSLVTIKHVLEGVKAQPLIRTSAEQW--EA | 201 |
| Lelystad | IVDDRGVHRWKSPIVVELGRAHDGNLVTIKHVLEGVKAQLIRTSAEQW--EA | 201 |
| MN184A | LLDTKGRLTWRSPVIIERGRIEVGGDLIDLKRVIDGSAATEVTKVSAEQWGRP | 200 |
| MN184B | LLDTKGRLTWRSPVIIERGHIEWGGDLIDLKFVIDGSAATEVTKVSAEQWGRP | 200 |
| 98-3298 | LLDTKGRLTWRSPVIIERGKVEVGEHLIDLKRVIDGSAATEVTKVSAERWGRP | 200 |
| 98-3403 | LLDTKGRLTWRSPVIIEKGGKVEVGEHLIDLKFVIDGSAATEVTKVSAERWGRP | 200 |
| 99-3584 | LLDTKGRLTWRSPVIIEKGRVEVGEHLIDLKRVIDGSAATEVTKVSAERWGRP | 200 |
| IAF-93-653 | LLDTKGKLTWRSPVIIERQRVEVGEHLIDLKRVVIDGSAATEVTRVSAERWGRP | 200 |
| IAF-Klop | LLDSKGKITRRSPVIIEGGRVEYDGRLIDLKRVVIDGSVATPITRVSAEQWCRP | 200 |
| IngelVac | LLDTKGGLTWRSPVIIEKGRVEVEGKVEGAVATPITRVSAEQWGRP | 200 |

| | | |
|---|---|---|
| EuroPRRSV | ADWELTGSFNGFSNTSHSCGHFVRNSMFEDGKCWLICFLGQSVEVRCHEEHLANAFGIDTWGHTLQRLL | 150 |
| Lelystad | ADWELTESFNGFSNTSHSCGHFVQNPDVEDICWLSCFLGQSVEVRCHEEHLADAFGIDTWGHTLQRLL | 150 |
| MN184A | SKFTFT-ALDGSASMRVEKHTGCPAGT-VTDGNCWMSLFSSFPLIQTRHLTDFSFCTRKFCTAGHYLQRLL | 144 |
| MN184B | SKFTFT-ALDGSASMRVEKHTGCPAGT-VTDGNCWMSLFSSLPLEVQYKIRYATDPGVKRGVAGKYLQRLL | 144 |
| Ingelvac | SKFAFT-APGCGVSMRVERQHGCLPADT-VPEGNCWLSLFDLLPLEVQNKTRHANPGTTHGVSGHTLQRLL | 144 |
| VR-2332 | SKFAFT-APGCGVSMRVERQHGCLPADT-VPEGNCWLSLFDLLPLEVQNKTRHANPGYQTRHGVSGRTLQRLL | 144 |
| PL97-1 | SKFAFT-APGCGVSMRVERQHGCLPADT-VPEGNCWLSLFDLLPLEVQNKTRHANPGYQTHGVSGRTLQRLL | 144 |
| HN1 | SKFAFT-APGCGVSMRVERQHGCLPADT-VPEGNCWLSLFDLLPLEVQNKTRHANPGYQTHNSGRTLQRLL | 144 |
| 16244B | SKFAFT-ALGCGVSMRVERQHGCLPADT-VPEGNCWLSLFDLLPLEVQNKTRHANPGYQTHGVSGKYLQRLL | 144 |
| PA-8 | SKFAFT-APGCGVSMRVERQHGCLPADT-VPEGNCWLSLFDLLPLEVDKETRHANPGYQTKHGVSGKYLQRLL | 144 |
| SP | SKFTFT-APGRGVSMRVERQHGCLPADT-VPEGNCWLSLFDLLPLEVQNKETRHANPGYQTHGVSGKYLQRLL | 144 |
| JA142 | SKFVFI-APGSGVSMRVECPHGCPANT-VPEGNCWLRLPDSFLDVQNKETRHANPGYQTHGVAGRILQRLL | 144 |
| CH-1 | SKFAFI-APGSGVSLRVEHQHGCLPADI-VPEGNCWLRLFDLLPFVDKETRYANPGYQTHGVPGHTLQRLL | 144 |
| P129 | SEFAFI-APGSGVSLRVEHQHGCLPADI-VPEGNCWCLFDLLPFVDKETRYANPGYQTHGVPGHTLQRLL | 144 |
| HB-2 | SKFAFI-VPGSGVSLRVEHQHGCPADI-VFKGNCWCLFDLLPGVDNRETRYMDPGYQTHGVSGHTLQRLL | 144 |
|

| | | | |
|---|---|---|---|
| MN184A | GAGKRKRKSARKSAVTAVAGHAPVTAGHAPPTKSTQQAKKHELASANKAELLKPSPPAEGNCGWHCISAANRMVNSMKFTA | 75 |
| MN184B | GAGKRKRKARASAVTAVAGHAPPTKETQQAKKHELASANKAEXLXXSPPAEGNCGWHCISAANRMVNSKEFTX | 75 |
| VR-2332 | GAGKRKRKSRCATATVAGHAPVTAGHAGHAPPTKSTQQAKKHELASANKAENHTSPPAEGNCGWHCISAANRMVNSTETT | 75 |
| IngelVac | GAGKRKRKSRCATATVAGHAPVTAGHAGHAPPTKSTQQAKKHELASANKAENHTSPPAEGNCGWHCISAANRMVNSTETT | 75 |
| 01NP12 | GAGKRKRKSRCATATVAGHAPVTAGHAGHAPPTKSTQQAKKHELASANKAENHTSPPAEGNCGWHCISAANRMVNSTETT | 75 |
| PL97-1 | GAGKRKRKSAATATVAGHAPPTKSTQQAKKHELASANKAENHTSPPAEGNCGWHCISAANRMVNSKETT | 75 |
| SP | GAGKRKRKARSATATVAGRALPTKSTQVELEHE/ACANRAEHETSPPAEGRCGWHCISA.GMHLISMETT | 75 |
| PA-8 | GAGKRKRKSAATATVAGRALSVRETRQAKKHE/AGANRAEHERHSPPAEGNCGWHCISAANRMVNSKETT | 75 |
| BJ-4 | GAGKRKRKSCATATVAGRALSVCETRQAKKHE/AGTNAEHLKHYSPPAEGNCGWHCISAANRMVNSIETT | 75 |
| HN1 | GAGKRKRKSCATATVAGRALSAHETRQAKKHE/AGDRAEHLRHYSPPAEGNCGWHCISAANRMVNSIETT | 75 |
| 162443 | GAGKRKRKGATTWAHALSAHETROAKKHE/GVDANNAHEHHYSPPAEGNCGWHCISAITRMVRNSKETT | 75 |
| CH-1 | GAGKRKRKGATTWAHRASSAHETRQAKKHE/ASAMRAEHIRYISPPADSCGWHCISAVRMVNSMETT | 75 |
| HB-2 | GAGKRKRKGATTWAHRASSAHETRQAKKHEAGANRAEHLEAQDARKLE/ASAMRAEHIRYISPPADSCGWHCISAVRMVNSKETT | 75 |
| P129 | GAGKRKRKGATATVAGHIPAHEAQADARKLE/ASAMRAEHIRYISPPADSCGWHCISAVRMVNSKETT | 75 |
| JA142 | GAGKRKRKGSMTTVAHRELPAEHIQQAKKHEDAGADKVHLERHSPPADGCGWHCISAANRMVNSKETT | 75 |
| HB-1 | GAGKRKRKGATTWAHRASSAHETRQATKHEGAGANRAEHKL/SPPAEGNCGWHCISAVRMVNSMEFTT | 75 |
| SDPRRSV-01-08 | AKGRRRARKR------ATKSGKDSALAPKIAPPVPTCGITTSPFTDGSCGWHYLAVRMINGDETSP | 64 |
| EuroPRRSV | ASGRRRABAKR------ZAKGGKDSVFRALCVALPVFACGITTSPFTDGSCGMTVAAMGRRMDDETSP | 64 |
| Lelystad | AKGRRRAKR------AAKSGKDSAETFKGALPVFTCGITTSPFTKALPVFTCGITTSPFTDGSCGMMLAVRMINGDETSP | 64 |

| | | |
|---|---|---|
| MN184A | SKIISLCQVIESCCSSQNTNRVTPEEVTPEYTAKIDLTTQAASLEECLARLEKARPPSVLXTSFDNVPLPGVGAA | 300 |
| MN184B | XKIISLCQVIESCCSXNKTNRVTPEEVAAKIDQYLEGAASLEECLARLEKARPPSVLDTSFDNVLPGVGAA | 300 |
| VR-2332 | SRIISLCQVIEDCCCSQNTNRVTPEEVAAKIDLLEGATNLEECLARLEKARPPRVIDTSFDNVLPGVEAT | 300 |
| Ingelvac | SRIISLCQVIEDCCCSQNTNRVTPEEVAAKIDLYLEGATNLEECLARLEKARPPRVIDTFDNVLPGVEAT | 300 |
| 01NP1.2 | SRIISLCQVIEDCCCSQNTNRVTPEEVAAKIDLYLEGATNLEECLARLEKARPPRVIDTFDNVLPGVEAT | 300 |
| PL97-1 | SRIISLCQVIEDCCCSQNTNRVTPEEVAAKIDLYLEGATNLEECLARLEKARPPRVIDTFDNVLPGVEAT | 300 |
| SP | SRIISLCQVIEDCCCSQNTNRVTPEEVAAKIDLYLEGATNLEECLARLEKARPPRVIDTFDNVLPGVEAT | 300 |
| PA-8 | SRIISLCQVIEDCCCSQNTNRVTPEEVAAKIDLYLEGATNLEECLARLEKARPPRVMDTSFDNVLPGVEAT | 300 |
| BJ-4 | SRIISLCQVIEDCCCSQNTNRVTPEEVAAKIDLYLEGATNLEECLARLEKARPPRVIDTFDNVLPGVEAT | 300 |
| HN1 | SRIISLCQVIEDCCCSQNTNRVTPEEVAAKIDLYLEGATNLEECLARLEKARPPRVIDTFDNVLPGVEAT | 300 |
| 16244B | SRIISLCQVIEDCCCSQNTNRVTPEEVAAKIDLYLRGATNLEECLARLEKARPPRVIDTSPDNVLPGVEAT | 300 |
| CH-1 | SRIISLCQVIEDCCHQNTNRATPEEVAAKIDQLEGATSLEECLIKLERVSPPSAADTSDNVLPGVEAN | 300 |
| HB-2 | SRIISLCQVIEDCCHQNKTNRATPEEVAAKIDQYLEGATSLEECLIKLERVSPBSAADTSDNVVLPGVEALG | 300 |
| P129 | SRIMDCQVIEDCCCSRKAQNRATPEEVAAQVDQTLEGAASLGEECLAKLERARPPSAMDTSDNVVLPGVETAD | 300 |
| JA142 | SRIISLCQVVEDCCHQNKTNRATPEEVAARIDQYLEGATSLEECLIKLERVCPSSAADTFDNVVLPGVCAST | 300 |
| HB-1 | SRIISLCQVIEDCCHQNTNRATPEEVAAKIDQLEGATSLEECLARLERVSPGAADTSEDNVLPGVEAH | 300 |
| suiPRRS-01-08 | VVPQKCGATEGAFTYAVERMLKDCKSSPEQQMALLAKIRVPSSKAPSVSLDECFPAGTPADFEPAPQERPRSPGAA | 286 |
| EuroPRRSV | VVPQKCGVTEGAFTYAVERMLMDCPSSEQQMALLAKIRVPSSKAPSVSLDECFPADYPADFEPTSQRREQSSGAA | 286 |
| Lelystad | VVPQKCGATEGAFTYAVERMLKDCKSSRQQMALLAKIRVPSSKAPSVSLDECFTDVLADFEPASQRREQSSGAA | 286 |

| | | |
|---|---|---|
| MN184A | DPATQEHLSRMDHRVDMLTWRNTSIFQAPFTLADKFTSLPRMLLETPPYPCGFYMPRTPAPSVGAESDLTVGS | 619 |
| MN184B | DPATQEHLSRMDRVDMLTWRNTSIFQAPFTLADKFTSLPRMLLETPPYPCGFYMPRTPAPSVGAESDLTVGS | 619 |
| VR-2332 | DPATQEHLSRMDRVDMLTWRNTSVTQAICTIDGRLFTLPRMILETPPYPCGFYMPRTPAPSVGAESDLTIGS | 750 |
| IngeIvac | DPATQEHLSRMDRVDMLTWRNTSVTQAICTINGRLFTLPRMILETPPYPCGFYMPHTPAPSVGAESDLTIGS | 750 |
| 01NP1.2 | DPATQEHLSRMDRVDMLTWRNTSVTQAICTIDGRLFTLPRMILETPPYPCEFYMPHTPAPSVGAESDLTIGS | 750 |
| PL97-1 | DPATQEHLSRMDRVDMLTWRNTSVTQAICTIDGRLFTLPRMILETPPYPCEFYMPHTPAPSVGAESDLTIGS | 750 |
| SP | DPATQEHLSRMDRVDMLTWRNTSVHQASRLDDRFFTLPRMLLETPPYPCGFYMPRTPAPSVGAESDLTIGS | 750 |
| PA-8 | DPATQEHLSRMDRVDMLTWRNTSVIQVICTLDGMLFTLPRMITASTPPYPCEFYMPHTPAPSVGAESDLTIGS | 749 |
| BJ-4 | DPATQEHLSRMDRVDMLTCN-TSVTQAICTLDGRLFTLPKLILETPPYPCEFYMPHTPAPSVGAESDLTIGS | 750 |
| HN1 | DPATQEHLSRMDRVDMLTWRNTSAYQAICTLDGRLFTLPKMLETPPYPCEFYMPHTPAPSVGAESDLTIGS | 750 |
| 16244B | DPATQEHLSRMDRVDMLTWRNTSVCQAFRTLDGRLFTLPKMLETPPYPCEFYMPHTPAPSVGAESDLTIGS | 750 |
| CH-1 | DPATQEHLSHMDRVDVTTWRNTSVTQALHTLDGRSGTLPRMILETPPYPEHPCGFVMLPHTPTPSVSAESDLTIGS | 738 |
| HB-2 | DPATQEHLSRMDRVDMLTWRNTSVTQAFTLDGRFCFTLPDMILETPPYPCGFVMLPHTPTPSVSAESDLTIGS | 744 |
| P129 | DPATQEHLSRMDRVDMLTWRNTSAYQAFTILDGRFTLPKMILETPPYPCGFVMLPHTPAPSVGAESDLTIGS | 750 |
| JA142 | DPATQEHLSRMDRVDMLTWRNTSAYQAFTLNGRFFTLPRMILETPPYPHPCGFVMLPHTPAPSVAESDLTIGS | 750 |
| HB-1 | DPATQEHLSRMDRVDMLTWRNTSAYQAFTLNGRFFTLPRMILETPPYPHPCGFVMLPHTPAPSVSAESDLTIGS | 750 |
| SDPPRRS-01-08 | TPATRHMLDKMDRVDFLTWRCTSQFQAGRILAS--LHFLPDMIQDTPPPVPRKNRASDNAGLKQLVARWDKKLSV | 643 |
| EuroPRRSV | FPATKHMLDKMDRVDMKTWRCCTSQFQAGRILAS--LHFLPDMIQQDTPPPVPRKNRASDNADLKQLVAQWDRKLSM | 643 |
| Lelystad | TPATRHMLDRMDRVDMLTWRCTSQFQAGRILAS--LHFLPDMEQDTPPPVPRKNRASDNAGLKQLVAQWDRKLSV | 660 |

Figure 12 (continued)

| | | |
|---|---|---|
| MN184A | VATEDVPRILGKVQGVGETTDGPLAFADELADDFAREPRTQTPPASAGGAGLVLDSGGSP | 682 |
| MN184B | VATEDVPRILGNVQGVGETTDQGPLAFADELADDQLAREPRTQTPPASTGGAGLVSDSGRSP | 682 |
| VR-2332 | VATEDVPRILEKIENVGEMANQGPLAFSEDKPVDDQLVNDPRISSRRPDESTSAPSAGTGGAG | 813 |
| Ingelvac | VATEDVPRILEKIENVGEMANQGPLAFSEDKPVDDQLVNDPRISSRRPDESTSAPSAGTGGAG | 813 |
| 01NP1.2 | VATEDVPRILEKIENVGEMANQGPLAFSEDKPVDDQLVNDPRISSRRPDESTSAPSAGTGGAG | 813 |
| PL97-1 | VATEDVPRILEKIENVGEMANQGPLAFSEDKPVDDQLVNDPRISSRRPDESTSAPSAGTGGAG | 813 |
| SP | VATEDVPRILFGKVNDVCKMIDQPRLVLFENELADDGFARDPRTSQRFDGSTPAPPAGTDGTGLASGPGVPREVDS | 825 |
| PA-8 | VATEDVPRILEKIGNVGEMANQGPLAFSEDKPVDDQLVNDPRISSRRPDESTSAPSAGTGGAG | 813 |
| BJ-4 | VATEDVPRILEKIENVGEMANQGPLAFSEDKPVDDQLVNDPRISSRRPDESTSAPSAGTGGAG | 812 |
| HN1 | VATEDVPRILEKIEMENVGEMANQGPLAFSEDKPVDDQLVNDPRISSRRPDESTSAPSAGTGGAG | 813 |
| 16244B | VATEDVPRILEKIENVGEMANEGAPSEDKPVDDQLVNDPRIGSRRPDESTAAPGAGTGGAG | 813 |
| CH-1 | VATEDVPRILGKIENTGEMLANQGPLAFFEEEPVCDQFAKDSRISSRGSGESTTAPSADTGGAG | 813 |
| HB-2 | VATEDVPRILGKTENTGNVLNQKPLALFEEEPVCDQFAKDSRTLSRESGDSTTAPVGTGGAG | 801 |
| P129 | VATEDIPRILGKIENTGEMINQGPLASSEEEPVYNQPAKDSRISSGSDESTAAPSAGTGGAG | 807 |
| JA142 | VATEDVPRILGKIENACBMPNQGLITSFGEEPVCDQPVRDSWMSSRGFDESTTAPSAGTGGAD | 813 |
| HB-1 | VATEDVPRILGKIGDTGELLINGFSAPFKGGPVCDQPAKNSRMSPRESDESIIAPPADTGGAG | 813 |
| SDPRRS.01-08 | tPPPKSAGLVLDQTVPPPDIQQEDATPSDGLS | 676 |
| EuroPRRSV | tPPQKPVEPVLDQTVSPPTDTQQEDVTPSDGPP | 676 |
| Lelystad | tPPPKPVGPVLDQTVPPPDIQEDVTPSDGPP | 693 |

Figure 12 (continued)

| | | |
|---|---|---|
| MN184A | FKSDSHYSSGMSPAAFTLICLPLCISYPAFGVAPLLGVPSGSSRVRMGVFGCWLAPAVGLPKPAPDPVGAACE | 808 |
| MN184B | FKSDSHYSSGMSPAAFTLICLPLCISTPAFGVAPLLGVPSGSSRVRMGVPGCWLAPAVGLPKPAPDPVGAACE | 808 |
| VR-2332 | FYPGGGYSPGDWGFAAFTLLCLPLCISTPAFGIAPLLGVFSGSSRRVRMGVFGCWLAPAVGLPKPVSDPVGAACE | 939 |
| Ingelvac | FYPGGGYSPGDWGFAAFTLLCLPLCISTPAFGIAPLLGVFSGSSRRVRMGVFGCWLAPAVGLPKPVSDPVGAACE | 939 |
| 01NP1.2 | FYPGGGYSPGDWGFAAFTLLCLPLCISTPAFGIAPLLGVFSGSSRRVRMGVFGCWLAPAVGLPKPVSDPVGAACE | 939 |
| PL97-1 | FCRGGYSPGDWGFAALTLLCLPLCVSYPAFGVAPLLGVFSGSSRRVRMGVFGCWLAPAVGLPKPVSDPVGAACE | 975 |
| SP | FKSGDTSPGDWGFAAFTLLCLPLCVSYPAFGSAVFLGVPSGSSRRVRMGVFGCWLAPAISLRPVSDPVGAACE | 939 |
| PA-8 | FYPGGGYSPGDWGFAAFTLLCLPLCVSYPAFGIAPLLGVPSGSSRRVRMGVFGCWLAPAVGLPKPVSDPVGAACE | 938 |
| BJ-4 | FYPGGGYSPGDWGFAAFTLLCLPLCISTPAFGIAPLLGVFSGSSRRVRMGVFGCWLAPAVGLPKPVSDPVGAACE | 939 |
| HN1 | FHPGGGYSPGDWGFAAFTLLCLPLCISTPAFGIAPLLGVFSGSSRRVRMGVFGCWLAPAVGLPKPVSDPVGAACE | 939 |
| IG244B | FHPGGGYSPGDWGFAAFTLFCLPLCVSYPFTGFAPLLGVFSGSSRVRMGVFGCWLAPAVGLPKPVSDPVGTACE | 939 |
| CH-1 | FKSDSGGYSPGDWGFAAFTLFCLPLCVSYPFTGFLPLIGVFSGSSRVRMGVFGCWLAPAVGLPKPVSDPVGTACE | 927 |
| HB-2 | FKSDSGTSPGDWGFAAFTLFCLPLCVSYPFTGFVPIIGVFSGSSRVRMGVFGCWLAPAVGLPKPVSDPVGTACE | 833 |
| P129 | FKSDSGTSPGDWGFAAFTLFCLPLCVSYPFTGFLPLLGVFSGSSRVRMGVFGCWLAPAVGLPRPVSDPVGTACE | 939 |
| JA142 | FKSDSGTSPGDWGFAAFTLFCLPLCVSYPFTGFLPLLGVFSGSSRVRMGVFGCWLAPAVGLPRPVSDPVGTACE | 939 |
| HB-1 | FKSDSGTSPGDWGFAAFTLFCLPLCVSYPFTGFLPLLGVFSGSSRVRMGVFGCWLAPAVGLPRPVSDPVGTACE | 939 |
| SDPRRS-01-08 | FSPRGSMAPGWLAGVYLALLCRSYPILALLCHSTPILLGLPLLGVFSGLRVRLGVPGSMAPAVFLESTPSNPVGSSCD | 802 |
| EuroPRRSV | FSPRGSMAPGWLAGVYLALLCRSYPILALLCHSTPILLGLPLLGVFSGLRVRLGVPGSMAPAVFLESTPSNPVGSSCD | 802 |
| Lelystad | FSPRGSMAPGWLAGVYLALLCRSYPILLGLPLLGVFSGLRVRLGVPGSMAPAVFLESTPSNPVGSSCD | 821 |

| | | |
|---|---|---|
| MN184A | RSGYSTRLIIGVGDFAQLNGLKIRQ---ISKPSGG | 1068 |
| MN184B | RSGYSTRLIIGVGDFAQLNGLKIRQ---ISKPSGG | 1068 |
| VR-2332 | RSGYSTRLVLGVGDFAQLNGLKIRQ---ISKPSGG | 1197 |
| Ingelvac | RSGYSTRLVLGVGDFAQLNGLKIRQ---ISKPSGG | 1197 |
| 01NP1.2 | RSGYSTRLVLGVGDFAQLNGLKIRQ---ISKPSGG | 1197 |
| PL97-1 | RSGYSTRLVLGVGDFAQLNGLKIRQ---ISKPSGG | 1197 |
| SP | RSGYSTRLVLGVGDFAQLNGLKIRQ---ISKPSGG | 1233 |
| PA-8 | RSGYSTRLVLGVGDFAQLNGLKIRQ---ISKPSGG | 1197 |
| BJ-4 | RSGYSTRLVLGVGDFAQLNGLKIRQ---ISKPSGG | 1196 |
| HN1 | RSGYPTRLVLGVGDFAQLNGLKIRQ---ISKPSGG | 1197 |
| 16244B | RSGYSTRLVLGVGDFAQLNGLKIRQ---ISKPSGG | 1197 |
| CH-1 | RSGYSTRLVLGVGDFAQLNGLKIRQ---ISKPSGG | 1197 |
| HB-2 | RSGYSTRLVLGVGDFAQLNGLKIRQ---ISKPSGG | 1185 |
| P129 | RSGYSTRLVLGVGDFAQLNGLKIRQ---ISKPSGG | 1191 |
| JA142 | RSGYSTRLVLGVGDFAQLNGLKIRQ---ISKPSGG | 1197 |
| HB-1 | RSGYSTRLVVGVGDFAQLNGLKIRQ---ISKPSGG | 1197 |
| SDPRRS-01-08 | RSGYSTRLVLGVGDFAQLNGLKIRQ---ISKPSGG | 1061 |
| EuroPRRSV | RCGYSTAQLVLGRGNFAKLNQTPPPRNSTSTKTTGG | 1061 |
| Lelystad | RCGYSTAQLVLGRGNFAKLNQTPPPRNSISTRTTGG | 1078 |

```
                        SEQUENCE LISTING

<160> NUMBER OF SEQ ID NOS: 90

<210> SEQ ID NO 1
<211> LENGTH: 15419
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 1
atgacgtata ggtgttggct ctatgccttg gcatttgtat tgtcaggagc tgtgaccatt      60
ggcacagccc aaaacttgct gcacagaaac acccttctgt gatagcctcc ttcagggag     120 cttagggttt gtccctagca ccttgcttcc ggagttgcac tgctttacgg tctctccacc     180
cctttaacca tgtctgggat acttgatcgg tgcacgtgta cccccaatgc cagggtgttt     240
atggcggagg gccaagtcta ctgcacacga tgcctcagtg cacggtctct ccttcccctg     300
aacctccagg tttctgagct cggggtgcta ggcctattct acaggcccga agagccactc     360
cggtggacgt tgccacgtgc attccccact gttgagtgct ccccgccgg ggcctgctgg      420 ctttctgcaa tctttccaat cgcacgaatg accagtggaa acctgaactt ccaacaaaga     480
atggtacggg tcgcagctga gctttacaga gccggccagc tcaccctgc agtcttgaag      540 gctctacaag tttatgaacg gggttgccgc tggtacccca ttgttggacc tgtccctgga     600
```

```
gtggccgttt tcgccaattc cctacatgtg agtgataaac ccttcccggg agcaactcac      660
gtgttgacca acctgccgct cccgcagaga cccaagcctg aagacttttg cccctttgag      720
tgtgctatgg ctactgtcta tgacattggt catgacgccg tcatgtatgt ggccgaaagg      780
aaagtctcct gggcccctcg tggcggggat gaagtgaaat ttgaagctgt ccccggggag      840
ttgaagttga ttgcgaaccg gctccgcacc tccttcccgc ccaccacac agtggacatg       900 tctaagttcg ccttcacagc ccctgggtgt ggtgtttcta tgcgggtcga acgccaacac      960
ggctgccttc ccgctgacac tgtccctgaa ggcaactgct ggtggagctt gtttgacttg     1020
cttccactgg aagttcagaa caaagaaatt cgccatgcta accaatttgg ctaccagacc     1080
aagcatggtg tctctggcaa gtacctgcag cggaggctgc aagttaatgg tctccgagca     1140
gtaactgacc taaacggacc tatcgtcgta cagtacttct ccgttaagga gagttggatc     1200
cgccatttga aactggcggg agaacccagc tactctgggt ttgaggacct cctcagaata     1260
agggttgagc ctaacacgtc gccattggct gacaaggaag aaaaaatttt ccggtttggc     1320
agtcacaagt ggtacggcgc tggaaagaga gcaagaaaag cacgctcttg tgcgactgct     1380
acagtcgctg gccgcgcttt gtccgttcgt gaaacccggc aggccaagga gcacgaggtt     1440
gccggcgcca acaaggctga gcacctcaaa cactactccc cgcctgccga agggaattgt     1500
ggttggcact gcatttccgc catcgccaac cggatggtga attccaaatt tgaaaccacc     1560
cttcccgaaa gagtgagacc tccagatgac tgggctactg acgaggatct tgtgaatgcc     1620
atccaaatcc tcagactccc tgcggcctta gacaggaacg gtgcttgtac tagcgccaag     1680
tacgtactta agctggaagg tgagcattgg actgtcactg tgaccctgg gatgtcccct     1740 tctttgctcc ctcttgaatg tgttcagggc tgttgtgggc acaagggcgg tcttggttcc     1800
ccagatgcag tcgaggtctc cggatttgac cctgcctgcc ttgaccggct ggctgaggtg     1860
atgcacctgc ctagcagtgc tatcccagcc gctctggccg aaatgtctgg cgattccgat     1920
cgttcggctt ctccggtcac caccgtgtgg actgtttcgc agttctttgc ccgtcacagc     1980
ggagggaatc ccctgaccaa gtgcgcttta gggaaaatta tcagcctttg tcaggtgatt     2040
gaggactgct gctgttccca gaacaaaacc aaccgggtca ccccggagga ggtcgcagca     2100
aagattgacc tgtacctccg tggtgcaaca aatcttgaag aatgcttggc caggcttgag     2160
aaagcgcgcc cgccacgcgt aatcgacacc tcctttgatt gggatgttgt gctccctggg     2220
gttgaggcgg caacccagac gatcaagctg ccccaggtca accagtgtcg tgctctggtc     2280
cctgttgtga ctcaaaagtc cttggacaac aactcggtcc cctgaccgc ttttcactg      2340 gctaactact actaccgtgc gcaaggtgac gaagttcgtc accgtgaaag actaaccgcc     2400
gtgctctcca gttggaaaaa ggttgttcga gaagaatatg gctcatgcc aaccgagcct     2460 ggtccacggc ccacactgcc acgcgggctc gacgaactca agaccagat ggaggaggac      2520 ttgctgaaac tggctaacgc ccagacgact tcggacatga tggcctgggc agtcgagcag     2580
gttgacctaa aaacttgggt caagaactac ccgcggtgga caccaccacc ccctccgcca     2640
aaagttcagc ctcgaaaaac gaagcctgtc aagagcttgc cggagagaaa gcctgtcccc     2700
gccccgcgca ggaaggttgg gtccgattgt ggcagcccgg tttcattagg cggcgatgtc     2760
cctaacagtt gggaagattt ggctgttagt agcccctttg atctcccgac ccacctgag      2820 ccggcaacac cttcaagtga gctggtgatt gtgtcctcac cgcaatgcat cttcaggccg     2880
gcgacaccct tgagtgagcc ggctccaatt cccgcacctc gcggaactgt gtctcgaccg     2940
gtgacaccct tgagtgagcc gatccctgtg cccgcaccgc ggcgtaagtt tcagcaggtg     3000
```

```
aaaagattga gttcggcggc ggcaatccca ccgtaccagg acgagcccct ggatttgtct    3060
gcttcctcac agactgaata tgaggcctct cccccagcac cgccgcagag cggggggcgtt   3120 ctgggagtag aggggcatga agctgaggaa accctgagtg aaatctcgga catgtcgggt   3180
aacattaaac ctgcgtccgt gtcatcaagc agctccttgt ccagcgtgag aatcacacgc   3240
ccaaaatact cagctcaagc catcatcgac tcgggcgggc cctgcagtgg gcatctccaa   3300
gaggtaaagg aaacatgcct tagtgtcatg cgcgaggcat gtgatgcgac taagcttgat   3360
gaccctgcta cgcaggaatg gctttctcgc atgtgggatc gggtggacat gctgacttgg   3420
cgcaacacgt ctgtttacca ggcgatttgc accttagatg gcaggttaaa gttcctccca   3480
aaaatgatac tcgagacacc gccgccctat ccgtgtgagt ttgtgatgat gcctcacacg   3540
cctgcacctt ccgtaggtgc ggagagcgac cttaccattg gctcagttgc tactgaagat   3600
gttccacgca tcctcgagaa aatagaaaat gtcggcgaga tggccaacca gggacccttg   3660
gccttctccg aggataaacc ggtagatgac caacttgtca acgaccccg gatatcgtcg    3720 cggaggcctg acgagagcac atcagctccg tccgcaggca caggtggcgc cggctctttt   3780
accgatttgc cgccttcaga tggcgcggat gcggacgggg gggggccgtt tcggacggta   3840
aaaagaaaag ctgaaaggct ctttgaccaa ctgagccgtc aggtttttga cctcgtctcc   3900
catctccctg ttttcttctc acgccttttc taccctggcg gtggttattc tccgggtgat   3960
tggggttttg cagcttttac tctattgtgc ctcttttttat gttacagtta cccagccttt   4020
ggtattgctc ccctcttggg tgtgttttct gggtcttctc ggcgcgttcg aatgggggtt   4080
tttggctgct ggttggcttt tgctgttggt ctgttcaagc ctgtgtccga cccagtcggc   4140
gctgcttgtg agtttgactc gccagagtgt agaaacatcc ttcattcttt tgagcttctc   4200
aaaccttggg accctgttcg cagccttgtt gtgggccccg tcggtctcgg tcttgccatt   4260
cttggcaggt tactgggcgg ggcacgctgc atctggcact ttttgcttag gcttggcatt   4320
gttgcagact gtatcttggc tggagcttac gtgctttctc aaggtaggtg taaaaagtgc   4380
tggggatctt gtataagaac tgctcccaat gaggtcgctt ttaacgtgtt tccttttcaca   4440 cgtgcgacca ggtcgtcact tatcgacctg tgcgatcggt tttgtgcgcc aaaaggaatg   4500 gacccccattt ttctcgccac tgggtggcgc gggtgctggg ccggccgaag ccccattgag   4560
caaccctctg aaaaacccat cgcgtttgcc cagttggatg aaaagaagat tacggctagg   4620
actgtggtcg cccagcctta tgaccccaac caagccgtaa agtgcttgcg ggtattgcag   4680
gcgggtgggg cgatggtggc taaggcggtc ccaaaagtgg tcaaggtttc cgctgttcca   4740
ttccgagccc ccttctttcc cactggagtg aaagttgacc ctgattgcag ggtcgtggtt   4800
gaccctgaca ctttcactgc agctctccgg tctggctact ccaccacaaa cctcgtcctt   4860
ggtgtggggg actttgccca gctgaatgga ttaaaaatca ggcaaatttc caagccttca   4920
gggggaggcc cacatctcat ggctgccctg catgttgcct gctcgatggc tctgcacatg   4980
cttgctggga tttatgtgac tgcggtgggt tcttgcggca ccggcaccaa cgacccgtgg   5040
tgcgctaacc cgtttgccgt ccctggctac ggacctggct ctctctgcac gtccagattg   5100
tgcatttccc aacacggcct taccctgccc ttgacagcac ttgtggcggg attcggtatt   5160
caagaaattg ccttggtcgt tttgattttt gtttccatcg gaggcatggc tcataggttag   5220 agctgtaagg ctgacatgct gtgtgtcttg cttgcaattg ccagctatgt ttgggtacct   5280
cttacctggt tgctttgtgt gtttccttgc tggttgcgct ttttctcttt gcaccccctc   5340
accatcctat ggttggtgtt tttcttgatt tctgtgaata tgccttcagg aatcttggcc   5400
```

```
atggtgttgt tggtttctct ttggcttctt ggtcgttata ctaatgttgc tggccttgtc    5460 acccccctacg acattcatca ttacaccagt ggccccccgcg gtgttgccgc cttggctacc   5520
gcaccagatg ggacctactt ggccgctgtc cgccgcgctg cgttgactgg ccgcaccatg    5580
ctgtttaccc cgtcccagct tgggtctctt cttgagggtg ctttcagaac tcgaaagccc    5640
tcactgaaca ccgtcaatgt gatcgggtcc tccatgggct ctggcggggt gtttaccatc    5700
gacgggaaag tcaagtgcgt aactgccgca catgtcctta cgggcaattc agctcgggtt    5760
tccggggtcg gcttcaatca aatgcttgac tttgacgtaa agggagattt cgctatagct    5820
gattgcccga attggcaagg ggctgccccc aagacccaat tctgcacgga tggatggact    5880
ggccgtgcct attggctaac atcctctggc gtcgaacccg gcgtcattgg aaaaggattc    5940
gccttctgct tcaccgcatg tggcgattcc gggtccccag tgatcaccga ggccggtgag    6000
cttgtcggcg ttcacacggg atcgaataaa caagggggggg gcattgttac gcgcccctca    6060
ggccagtttt gtaatgtggc acccatcaag ctaagcgaat taagtgaatt ctttgctggg    6120
cctaaggtcc cgctcggtga tgtgaaggtc ggcagccaca taattaaaga cataagcgag    6180
gtgccttcag atctttgtgc cttgcttgct gccaaacctg aactgaagg aggcctctcc     6240 accgtccaac ttctttgtgt gttttttctc ctgtggagaa tgatgggaca tgcctggacg    6300
cccttggttg ctgtgagttt ctttattttg aatgaggttc tcccagccgt cctggtccgg    6360 agtgtttttct cctttggaat gtttgtgcta tcctggctca cgccatggtc tgcgcaagtt    6420
ctgatgatca ggcttctgac agcagctctt aacaggaaca gatggtcact tgccttttc    6480 agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gcctgcacca tatccttgtt ggcgatggag tgttctctgc ggcttttcttc    6720 ttgagatact ttgccgaggg aaagttgagg gaaggggtgt cgcaatcctg cggaatgaat    6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactgggccca gttggtgcag    6960 gttgataaag ttcgaggtac tttggccaaa cttgaagctt ttgctgatac cgtggcacct    7020
caactctcgc ccggtgacat tgttgtcgct ctcggccaca cgcctgttgg cagtatcttc    7080
gacctaaagg ttggtagcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc ccctcccacc gaaagttctg gagaatggcc ccaacgcttg gggggatgag    7260
gaccgtttga ataagaagaa gaggcgcagg atggaagccc tcggcatcta tgttatgggc    7320
gggaaaaaat accagaaatt ttgggacaag aattccggtg atgtgttta tgaggaggtc    7380 cataataaca cagatgagtg ggagtgtctc agagttggcg accctgccga ctttgacccct   7440 gagaagggaa ctctgtgtgg acatgtcacc attgaaaaca aggcttacca tgtttacacc    7500
tccccatctg gtaagaagtt cttggtcccc gtcaacccag agaatggaag agtccaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccacgc acttgacccg ctgtggtcgc ggcggcttgg    7740
ttgttactga aacagcggta aaaatagtca aatttcacaa ccggaccttc accctgggac    7800
```

```
ctgtgaattt aaaagtggcc agtgaggttg agctaaaaga cgcggttgag cacaaccaac   7860
acccggttgc gagaccgatc gatggtggag ttgtgctcct gcgttccgcg gttccttcgc   7920
ttatagacgt cttgatctcc ggtgctgatg catctcccaa gttacttgcc catcacgggc   7980
cgggaaacac tgggatcgat ggcacgctct gggattttga gtccgaagcc actaaagagg   8040
aagtcgcact cagtgcgcaa ataatacagg cttgtgacat taggcgcggc gacgctcctg   8100
aaattggtct cccttacaag ctgtaccctg ttaggggtaa ccctgagcgg gtgaaaggag   8160
ttctgcagaa tacaaggttt ggagacatac cttacaaaac ccccagtgac actgaaagcc   8220
cagtgcacgc ggctgcctgc cttacgccca acgccactcc ggtgactgat gggcgctccg   8280
tcttggccac gaccatgccc cccgggtttg agttatatgt accgaccata ccagcgtctg   8340
tccttgatta ccttgactct aggcctgact gccctaaaca gctgacagag cacggctgcg   8400
aagatgccgc actgaaagac ctctctaaat atgacttgtc cacccaaggc tttgttttac   8460
ctggagttct tcgccttgtg cggaaatacc tgtttgccca tgtaggtaag tgcccacccg   8520
ttcatcggcc ttctacttac cctgctaaga attctatggc tggaataaat gggaacaggt   8580
tcccaaccaa ggacattcag agcgtccctg aaatcgacgt tctgtgcgca caggctgtgc   8640
gagaaaactg gcaaactgtc accccttgta ctcttaagaa acagtattgc gggaagaaga   8700
agactaggac catactcggc accaataact tcatcgcact agcccaccga gcagtgttga   8760
gtggtgttac ccagggcttc atgaaaaagg cgtttaactc gcccatcgcc ctcggaaaga   8820
acaagtttaa ggagctacag actccggtcc tgggcaggtg ccttgaagct gatctcgcat   8880
cctgcgatcg atccacgcct gcaattgtcc gctggtttgc cgccaacctt ctttatgaac   8940
ttgcctgtgc tgaagagcat ctaccgtcgt acgtgctgaa ctgctgccac gacttactgg   9000
tcacgcagtc cggcgcagtg actaagagag gtggcctgtc gtctggcgac ccgatcacct   9060
ctgtgtctaa caccatttat agtttggtga tctatgcaca gcatatggtg cttagttact   9120
tcaaaagtgg tcaccccat ggccttctgt tcttacaaga ccagctaaag tttgaggaca   9180
tgctcaaggt tcaaccccctg atcgtctatt cggacgacct cgtgctgtat gccgagtctc   9240
ccaccatgcc aaactatcac tggtgggttg aacatctgaa tttgatgctg gggtttcaga   9300
cggacccaaa aagacagca ataacagact cgccatcatt tctaggctgt agaataataa   9360
atgggcgcca gctagtcccc aaccgtgaca ggatcctcgc ggccctcgcc tatcacatga   9420
aggcgagtaa tgtttctgaa tactatgcct cagcggctgc aatactcatg acagctgtg   9480 cttgttttgga gtatgatcct gaatggtttg aagaacttgt agttggaata gcgcagtgcg   9540
cccgcaagga cggctacagc tttcccggca cgccgttctt catgtccatg tgggaaaaac   9600
tcaggtccaa ttatgagggg aagaagtcga gagtgtgcgg gtactgcggg gccccggccc   9660
cgtacgctac tgcctgtggc ctcgacgtct gcatttacca cacccacttc caccagcatt   9720
gtccagtcac aatctggtgt ggccatccag cgggttctgg ttcttgtagt gagtgcaaat   9780
cccctgtagg gaaaggcaca agcccttag acgaggtgct ggaacaagtc ccgtataagc   9840
ccccacggac cgttatcatg catgtggagc agggtctcac cccccttgat ccaggtagat   9900
accaaactcg ccgcggatta gtctctgtca ggcgtggaat taggggaat gaagttggac   9960 taccagacgg tgattatgct agcaccgcct tgctccctac ctgcaaagag atcaacatgg  10020 tgctgtcgc ttccaatgta ttgcgcagca ggttcatcat cggcccaccc ggtgctggga  10080
aaacatactg gctccttcaa caggtccagg atggtgatgt tatttacaca ccaactcacc  10140
agaccatgct tgacatgatt agggctttgg ggacgtgccg gttcaacgtc ccggcaggca  10200
```

```
caacgctgca attccccgtc ccctcccgca ccggtccgtg ggttcgcatc ctagccggcg   10260
gttggtgtcc tggcaagaat tccttcctag atgaagcagc gtattgcaat caccttgatg   10320
ttttgaggct tcttagtaaa actaccctca cctgtctagg agacttcaag caactccacc   10380
cagtgggttt tgattctcat tgctatgttt ttgacatcat gcctcaaact caactgaaga   10440
ccatctggag gtttggacag aatatctgtg atgccattca gccagattac agggacaaac   10500
tcatgtccat ggtcaacaca acccgtgtga cctacgtgga aaaacctgtc aggtatgggc   10560
aggtcctcac cccctaccac agggaccgag aggacgacgc catcactatt gactccagtc   10620
aaggcgccac attcgatgtg gttacattgc atttgcccac taaagattca ctcaacaggc   10680
aaagagccct tgttgctatc accagggcaa gacacgctat ctttgtgtat gacccacaca   10740
ggcagctgca gggcttgttt gatcttcctg caaaaggcac gcccgtcaac ctcgcagtgc   10800
actgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttattt ctcacctgat ttaacacagt ttgctaaact cccagtagaa cttgcacctc   11040
actggcccgt ggtgtcaacc cagaacaatg aaaagtggcc ggatcggctg gttgccagcc   11100
ttcgccctat ccataaatac agccgcgcgt gcatcggtgc cggctatatg gtgggccctt   11160
cggtgtttct aggcactcct ggggtcgtgt catactatct cacaaaattt gttaagggcg   11220
gggctcaagt gcttccggag acggttttca gcaccggccg aattgaggta gactgccggg   11280
aatatcttga tgatcgggag cgagaagttg ctgcgtccct cccacacgct ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag ccccggaaaa gccgcgaaag   11460
cattgtgcac actgacagat gtgtacctcc cagatcttga agcctatctc cacccggaga   11520
cccagtccaa gtgctggaaa atgatgttgg acttcaaaga agttcgacta atggtctgga   11580
aagacaaaac agcctatttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggggct gacctcgcgg   11760
tcaccccttg tgattacggc gctaaaatta tcctgtctag cgcgtaccat ggtgaaatgc   11820
cccccggata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag ttttatttc ccccgggccc tgtcattgaa ccaactttag   12060
gcctgaattg aaatgaaatg gggtccatgc aaagccttt tgacaaaatt ggccaacttt   12120
ttgtggatgc tttcacggag ttcttggtgt ccattgttga tatcattata ttttggcca   12180
ttttgtttgg cttcaccatc gccggttggc tggtggtctt ttgcatcaga ttggtttgct   12240
ccgcgatact ccgtacgcgc cctgccattc actctgagca attacagaag atcttatgag   12300
gcctttcttt cccagtgcca agtggacatt cccacctggg gaactaaaca tcctttgggg   12360
atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct cattttcagc atctagccgc cattgaagcc   12540
gagacctgta aatatttggc ctcccggctg cccatgctac acaacctgcg catgacaggg   12600
```

```
tcaaatgtaa ccatagtgta taatagcact ttgaatcagg tgtttgctat ttttccaacc   12660
cctggttccc ggccaaagct tcatgatttt cagcaatggt taatagctgt acattcctcc   12720
atattttcct ctgttgcagc ttcttgtact cttttttgttg tgctgtggtt gcgggttcca   12780
atactacgta ctgttttttgg tttccgctgg ttaggggcaa tttttctttc gaactcacag   12840
tgaattacac ggtgtgtcca ccttgcctca cccggcaagc agccacagag atctacgaac   12900
ccggtaggtc tctttggtgc aggatagggt atgaccgatg tggggaggac gatcatgacg   12960
agctagggtt tatgataccg cctggcctct ccagcgaagg ccacttgact ggtgtttacg   13020
cctggttggc gttcttgtcc ttcagctaca cggcccagtt ccatcccgag atattcggga   13080
tagggaatgt gagtcgagtt tatgttgaca tcaaacatca actcatctgc gccgaacatg   13140
acgggcagaa caccaccttg cctcgtcatg acaacatttc agccgtgttt cagacctatt   13200
accaacatca agtcgacggc ggcaattggt ttcacctaga atggcttcgt cccttctttt   13260
cctcgtggtt ggttttaaat gtctcttggt ttctcaggcg ttcgcctgca aaccatgttt   13320
cagttcgagt cttgcagata ttaagaccaa caccaccgca gcggcaagct ttgctgtcct   13380
ccaagacatc agttgcctta ggcatcgcga ctcggcctct gaggcgattc gcaaaatccc   13440
tcagtgccgt acggcgatag ggacacccgt gtatgttacc atcacagcca atgtgacaga   13500
tgagaattat ttacattctt ctgatctcct catgctttct tcttgccttt tctatgcttc   13560
tgagatgagt gaaaagggat ttaaggtggt atttggcaat gtgtcaggca tcgtggctgt   13620
gtgtgtcaat tttaccagct acgtccaaca tgtcaaggag tttacccaac gctccctggt   13680
ggtcgaccat gtgcggttgc tccatttcat gacacctgag accatgaggt gggcaactgt   13740
tttagcctgt cttttttgcca ttctgttggc aatttgaatg tttaagtatg ttggagaaat   13800
gcttgaccgc gggctgttgc tcgcgattgc tttctttgtg gtgtatcgtg ccgttctgtt   13860
ttgctgtgct cgccaacgcc agcaacgaca gcagctccca tctacagctg atttacaact   13920
tgacgctatg tgagctgaat ggcacagatt ggctagctaa caaatttgat tgggcagtgg   13980
agagttttgt catctttccc gttttgactc acattgtctc ctatggtgcc ctcactacca   14040
gccatttcct tgacacagtc gctttagtca ctgtgtctac cgccgggttt gttcacgggc   14100
ggtatgtcct aagtagcatc tacgcggtct gtgccctggc tgcgttgact tgcttcgtca   14160
ttaggtttgc aaagaattgc atgtcctggc gctacgcgtg taccagatat accaactttc   14220
ttctggacac taagggcaga ctctatcgtt ggcggtcgcc tgtcatcata gagaaaaggg   14280
gcaaagttga ggtcgaaggt catctgatcg acctcaaaag agttgtgctt gatggctccg   14340
tggcaacccc tataaccaga gtttcagcgg aacaatgggg tcgtccttag atgacttctg   14400
tcacgatagc acggctccac aaaaggtgct tttggcgttt tctattaccct acacgccagt   14460 gatgatatat gccctaaagg tgagtcgcgg ccgactgcta gggcttctgc acctttttgat   14520 cttcctgaat tgtgctttca ccttcgggta catgactttc gcgcacttttc agagtacaaa   14580 taaggtcgcg ctcactatgg gagcagtagt tgcactcctt tgggggtgt actcagccat   14640 agaaacctgg aaattcatca cctccagatg ccgtttgtgc ttgctaggcc gcaagtacat   14700
tctggcccct gcccaccacg ttgaaagtgc cgcaggcttt catccgattg cggcaaatga   14760
taaccacgca tttgtcgtcc ggcgtcccgg ctccactacg gtcaacggca cattggtgcc   14820
cgggttaaaa agcctcgtgt tgggtggcag aaaagctgtt aaacagggag tggtaaacct   14880
tgtcaaatat gccaaataac aacggcaagc agcagaagag aaagaagggg gatggccagc   14940
cagtcaatca gctgtgccag atgctgggta agatcatcgc tcagcaaaac cagtccagag   15000
```

| | | | | |
|---|---|---|---|---|
| gcaagggacc | gggaaagaaa | aataagaaga | aaaacccgga | gaagccccat | tttcctctag | 15060 |
| cgactgaaga | tgatgtcaga | catcacttta | ccccctagtga | gcggcaattg | tgtctgtcgt | 15120 |
| caatccagac | cgcctttaat | caaggcgctg | ggacttgcac | cctgtcagat | tcagggagga | 15180 |
| taagttacac | tgtggagttt | agtttgccta | cgcatcatac | tgtgcgcctg | atccgcgtca | 15240 |
| cagcatcacc | ctcagcatga | tgggctggca | ttcttgaggc | atctcagtgt | ttgaattgga | 15300 |
| agaatgtgtg | gtgaatggca | ctgattgaca | ttgtgcctct | aagtcaccta | ttcaattagg | 15360 |
| gcgaccgtgt | gggggtgaga | tttaattggc | gagaaccatg | cggccgaaat | taaaaaaaaa | 15419 |

<210> SEQ ID NO 2
<211> LENGTH: 15458
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 2

| | | | | | |
|---|---|---|---|---|---|
| atgacgtata | ggtgttggct | ctatgccttg | gcatttgtat | tgtcaggagc | tgtgaccatt | 60 |
| ggcacagccc | aaaacttgct | gcacagaaac | acccttctgt | gatagcctcc | ttcaggggag | 120 |
| cttagggttt | gtccctagca | ccttgcttcc | ggagttgcac | tgctttacgg | tctctccacc | 180 |
| cctttaacca | tgtctgggat | acttgatcgg | tgcacgtgta | ccccccaatgc | cagggtgttt | 240 |
| atggcggagg | gccaagtcta | ctgcacacga | tgcctcagtg | cacggtctct | ccttcccctg | 300 |
| aacctccagg | tttctgagct | cggggtgcta | ggcctattct | acaggcccga | agagccactc | 360 |
| cggtggacgt | tgccacgtgc | attcccact | gttgagtgct | ccccgccgg | ggcctgctgg | 420 |
| ctttctgcaa | tctttccaat | cgcacgaatg | accagtggaa | acctgaactt | ccaacaaaga | 480 |
| atggtacggg | tcgcagctga | gctttacaga | gccggccagc | tcacccctgc | agtcttgaag | 540 |
| gctctacaag | tttatgaacg | gggttgccgc | tggtacccca | ttgttggacc | tgtccctgga | 600 |
| gtggccgttt | tcgccaattc | cctacatgtg | agtgataaac | ccttcccggg | agcaactcac | 660 |
| gtgttgacca | acctgccgct | cccgcagaga | cccaagcctg | aagacttttg | ccccttttgag | 720 |
| tgtgctatgg | ctactgtcta | tgacattggt | catgacgccg | tcatgtatgt | ggccgaaagg | 780 |
| aaagtctcct | gggcccctcg | tggcggggat | gaagtgaaat | ttgaagctgt | ccccggggag | 840 |
| ttgaagttga | ttgcgaaccg | gctccgcacc | tccttcccgc | ccaccacac | agtggacatg | 900 |
| tctaagttcg | ccttcacagc | ccctgggtgt | ggtgtttcta | gcgggtcga | acgccaacac | 960 |
| ggctgccttc | ccgctgacac | tgtccctgaa | ggcaactgct | ggtggagctt | gtttgacttg | 1020 |
| cttccactgg | aagttcagaa | caaagaaatt | cgccatgcta | accaatttgg | ctaccagacc | 1080 |
| aagcatggtg | tctctggcaa | gtacctgcag | cggaggctgc | aagttaatgg | tctccgagca | 1140 |
| gtaactgacc | taaacggacc | tatcgtcgta | cagtacttct | ccgttaagga | gagttggatc | 1200 |
| cgccatttga | aactggcggg | agaacccagc | tactctgggt | ttgaggacct | cctcagaata | 1260 |
| agggttgagc | ctaacacgtc | gccattggct | gacaaggaag | aaaaaatttt | ccggtttggc | 1320 |
| agtcacaagt | ggtacggcgc | tggaaagaga | gcaagaaaag | cacgctcttg | tgcgactgct | 1380 |
| acagtcgctg | gccgcgcttt | gtccgttcgt | gaaaccggc | aggccaagga | gcacgaggtt | 1440 |
| gccggcgcca | acaaggctga | gcacctcaaa | cactactccc | cgcctgccga | agggaattgt | 1500 |
| ggttggcact | gcatttccgc | catcgccaac | cggatggtga | attccaaatt | tgaaaccacc | 1560 |
| cttcccgaaa | gagtgagacc | tccagatgac | tgggctactg | acgaggatct | tgtgaatgcc | 1620 |

```
atccaaatcc tcagactccc tgcggcctta gacaggaacg gtgcttgtac tagcgccaag   1680
tacgtactta agctggaagg tgagcattgg actgtcactg tgacccctgg gatgtcccct   1740
tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc ccctgaccgc cttttcactg   2340
gctaactact actaccgtgc gcaaggtgac gaagttcgtc accgtgaaag actaaccgcc   2400
gtgctctcca agttggaaaa ggttgttcga gaagaatatg gctcatgcc aaccgagcct   2460 ggtccacggc ccacactgcc acgcgggctc gacgaactca agaccagat ggaggaggac   2520 ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agccccttgt atctcccgac cccacctgag   2820
ccggcaacac cttcaagtga gctggtgatt gtgtcctcac cgcaatgcat cttcaggccg   2880
gcgacaccct tgagtgagcc ggctccaatt cccgcacctc gcggaactgt gtctcgaccg   2940
gtgacaccct tgagtgagcc gatccctgtg cccgcaccgc ggcgtaagtt tcagcaggtg   3000
aaaagattga gttcggcggc ggcaatccca ccgtaccagg acgagcccct ggatttgtct   3060
gcttcctcac agactgaata tgaggcctct cccccagcac cgccgcagag cggggcgtt   3120 ctgggagtag aggggcatga agctgaggaa accctgagtg aaatctcgga catgtcgggt   3180
aacattaaac ctgcgtccgt gtcatcaagc agctccttgt ccagcgtgag aatcacacgc   3240
ccaaaatact cagctcaagc catcatcgac tcgggcgggc cctgcagtgg gcatctccaa   3300
gaggtaaagg aaacatgcct tagtgtcatg cgcgaggcat gtgatgcgac taagcttgat   3360
gaccctgcta cgcaggaatg gctttctcgc atgtgggatc gggtggacat gctgacttgg   3420
cgcaacacgt ctgtttacca ggcgatttgc accttagatg gcaggttaaa gttcctccca   3480
aaaatgatac tcgagacacc gccgccctat ccgtgtgagt ttgtgatgat gcctcacacg   3540
cctgcacctt ccgtaggtgc ggagagcgac cttaccattg gctcagttgc tactgaagat   3600
gttccacgca tcctcgagaa aatagaaaat gtcggcgaga tggccaacca gggacccttg   3660
gccttctccg aggataaacc ggtagatgac caacttgtca acgaccccg gatatcgtcg   3720 cggaggcctg acgagagcac atcagctccg tccgcaggca caggtggcgc cggctctttt   3780
accgatttgc cgccttcaga tgcgcggat cggacgggg ggggccgtt tcggacggta   3840 aaagaaaag ctgaaaggct ctttgaccaa ctgagccgtc aggttttga cctcgtctcc   3900 catctccctg ttttcttctc acgccttttc taccctggcg gtggttattc tccgggtgat   3960
tggggttttg cagcttttac tctattgtgc ctctttttat gttacagtta cccagccttt   4020
```

```
ggtattgctc ccctcttggg tgtgttttct gggtcttctc ggcgcgttcg aatgggggtt      4080
tttggctgct ggttggcttt tgctgttggt ctgttcaagc ctgtgtccga cccagtcggc      4140
gctgcttgtg agtttgactc gccagagtgt agaaacatcc ttcattcttt tgagcttctc      4200
aaaccttggg accctgttcg cagccttgtt gtgggcccg tcggtctcgg tcttgccatt       4260
cttggcaggt tactgggcgg ggcacgctgc atctggcact ttttgcttag gcttggcatt      4320
gttgcagact gtatcttggc tggagcttac gtgctttctc aaggtaggtg taaaaagtgc      4380
tggggatctt gtataagaac tgctcccaat gaggtcgctt ttaacgtgtt tcctttcaca      4440
cgtgcgacca ggtcgtcact tatcgacctg tgcgatcggt tttgtgcgcc aaaaggaatg      4500
gaccccattt ttctcgccac tgggtggcgc gggtgctggg ccggccgaag ccccattgag      4560
caaccctctg aaaaacccat cgcgtttgcc cagttggatg aaaagaagat tacgctagg       4620 actgtggtcg cccagcctta tgaccccaac caagccgtaa agtgcttgcg ggtattgcag      4680
gcgggtgggg cgatggtggc taaggcggtc ccaaaagtgg tcaaggtttc cgctgttcca      4740
ttccgagccc ccttctttcc cactggagtg aaagttgacc ctgattgcag ggtcgtggtt      4800
gaccctgaca ctttcactgc agctctccgg tctggctact ccaccacaaa cctcgtcctt      4860
ggtgtggggg actttgccca gctgaatgga ttaaaaatca ggcaaatttc caagccttca      4920
gggggaggcc cacatctcat ggctgccctg catgttgcct gctcgatggc tctgcacatg      4980
cttgctggga tttatgtgac tgcggtgggt tcttgcggca ccggcaccaa cgacccgtgg      5040
tgcgctaacc cgtttgccgt ccctggctac ggacctggct ctctctgcac gtccagattg      5100
tgcatttccc aacacggcct taccctgccc ttgacagcac ttgtggcggg attcggtatt      5160
caagaaattg ccttggtcgt tttgattttt gtttccatcg gaggcatggc tcataggttg      5220
agctgtaagg ctgacatgct gtgtgtcttg cttgcaattg ccagctatgt ttgggtacct      5280
cttacctggt tgctttgtgt gtttccttgc tggttgcgct gtttttcttt gcaccccctc      5340
accatcctat ggttggtgtt tttcttgatt tctgtgaata tgccttcagg aatcttggcc      5400
atggtgttgt tggtttctct ttggcttctt ggtcgttata ctaatgttgc tggccttgtc      5460 acccccctacg acattcatca ttacaccagt ggccccgcg tgttgccgc cttggctacc       5520 gcaccagatg ggacctactt ggccgctgtc cgccgcgctg cgttgactgg ccgcaccatg      5580
ctgtttaccc cgtcccagct tgggtctctt cttgagggtg ctttcagaac tcgaaagccc      5640
tcactgaaca ccgtcaatgt gatcgggtcc tccatgggct ctggcggggt gtttaccatc      5700
gacgggaaag tcaagtgcgt aactgccgca catgtcctta cggcaattc agctcgggtt       5760 tccggggtcg gcttcaatca aatgcttgac tttgacgtaa agggagattt cgctatagct      5820
gattgcccga attggcaagg ggctgccccc aagacccaat tctgcacgga tggatggact      5880
ggccgtgcct attggctaac atcctctggc gtcgaacccg gcgtcattgg aaaaggattc      5940
gccttctgct tcaccgcatg tggcgattcc ggtcccccag tgatcaccga ggccggtgag      6000
cttgtcggcg ttcacacggg atcgaataaa caaggggggg gcattgttac gcgcccctca      6060
ggccagtttt gtaatgtggc acccatcaag ctaagcgaat taagtgaatt ctttgctggg      6120
cctaaggtcc cgctcggtga tgtgaaggtc ggcagccaca taattaaaga cataagcgag      6180
gtgccttcag atctttgtgc cttgcttgct gccaaacctg aactggaagg aggcctctcc      6240
accgtccaac ttctttgtgt gttttttctc ctgtggagaa tgatgggaca tgcctggacg      6300
cccttggttg ctgtgagttt cttattttg aatgaggttc tcccagccgt cctggtccgg      6360
agtgttttct cctttggaat gtttgtgcta tcctggctca cgccatggtc tgcgcaagtt      6420
```

```
ctgatgatca ggcttctgac agcagctctt aacaggaaca gatggtcact tgcctttttc    6480
agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gcctgcacca tatccttgtt ggcgatggag tgttctctgc ggctttcttc    6720
ttgagatact ttgccgaggg aaagttgagg aaggggtgt cgcaatcctg cggaatgaat    6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt ttgctgatac cgtggcacct    7020
caactctcgc ccggtgacat tgttgtcgct ctcggccaca cgcctgttgg cagtatcttc    7080
gacctaaagg ttggtagcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc ccctcccacc gaaagttctg gagaatggcc ccaacgcttg ggggatgag    7260 gaccgtttga ataagaagaa gaggcgcagg atggaagccc tcggcatcta tgttatgggc    7320
gggaaaaaat accagaaatt ttgggacaag aattccggtg atgtgtttta tgaggaggtc    7380
cataataaca cagatgagtg ggagtgtctc agagttggcg accctgccga ctttgaccct    7440
gagaagggaa ctctgtgtgg acatgtcacc attggaaaca aggcttacca tgtttacacc    7500
tccccatctg gtaagaagtt cttggtcccc gtcaacccag agaatggaag agtccaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccagcg acttgacccg ctgtggtcgc ggcggcttgg    7740
ttgttactga aacagcggta aaaatagtca aatttcacaa ccggaccttc accctgggac    7800
ctgtgaattt aaaagtggcc agtgaggttg agctaaaaga cgcggttgag cacaaccaac    7860
acccggttgc gagaccgatc gatggtggag ttgtgctcct gcgttccgcg gttccttcgc    7920
ttatagacgt cttgatctcc ggtgctgatg catctcccaa gttacttgcc catcacgggc    7980
cgggaaacac tgggatcgat ggcacgctct gggattttga gtccgaagcc actaaagagg    8040
aagtcgcact cagtgcgcaa ataatacagg cttgtgacat taggcgcggc gacgctcctg    8100
aaattggtct cccttacaag ctgtaccctg ttaggggtaa ccctgagcgg gtgaaaggag    8160
ttctgcagaa tacaaggttt ggagacatac cttacaaaac ccccagtgac actggaagcc    8220
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc accccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
```

```
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat ggccttctgt tcttacaaga ccagctaaag tttgaggaca    9180
tgctcaaggt tcaaccccctg atcgtctatt cggacgacct cgtgctgtat gccgagtctc    9240
ccaccatgcc aaactatcac tggtgggttg aacatctgaa tttgatgctg gggtttcaga    9300
cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg acagctgtg     9480
cttgtttgga gtatgatcct gaatgggttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
cccctgtagg gaaaggcaca agcccttag acgaggtgct ggaacaagtc ccgtataagc     9840
ccccacggac cgttatcatg catgtggagc agggtctcac ccccccttgat ccaggtagat    9900
accaaactcg ccgcggatta gtctctgtca ggcgtggaat taggggaaat gaagttggac    9960
taccagacgg tgattatgct agcaccgcct gctccctac ctgcaaagag atcaacatgg     10020
tcgctgtcgc ttccaatgta ttgcgcagca ggttcatcat cggcccaccc ggtgctggga    10080
aaacatactg gctccttcaa caggtccagg atggtgatgt tatttacaca ccaactcacc    10140
agaccatgct tgacatgatt agggctttgg ggacgtgccg gttcaacgtc ccggcaggca    10200
caacgctgca attccccgtc ccctcccgca ccggtcgtg ggttcgcatc ctagccggcg      10260
gttggtgtcc tggcaagaat tccttcctag atgaagcagc gtattgcaat cacccttgatg    10320
ttttgaggct tcttagtaaa actaccctca cctgtctagg agacttcaag caactccacc    10380
cagtgggttt tgattctcat tgctatgttt ttgacatcat gcctcaaact caactgaaga    10440
ccatctggag gtttggacag aatatctgtg atgccattca gccagattac agggacaaac    10500
tcatgtccat ggtcaacaca acccgtgtga cctacgtgga aaaacctgtc aggtatgggc    10560
aggtcctcac cccctaccac agggaccgag aggacgacgc catcactatt gactccagtc    10620
aaggcgccac attcgatgtg gttacattgc atttgcccac taaagattca ctcaacaggc    10680
aaagagccct tgttgctatc accagggcaa gacacgctat cttttgtgtat gacccacaca    10740
ggcagctgca gggcttgttt gatcttcctg caaaaggcac gcccgtcaac ctcgcagtgc    10800
actgcgacgg gcagctgatc gtgctggata gaaataacaa gaatgcacg gttgctcagg     10860
ctctaggcaa cgggataaaa tttagggcca cagacaagcg tgttgtagat tctctccgcg    10920
ccatttgtgc tgatctagaa gggtcgagct ctccgctccc caaggtcgca cacaacttgg    10980
gattttattt ctcacctgat ttaacacagt ttgctaaact cccagtagaa cttgcacctc    11040
actggcccgt ggtgtcaacc cagaacaatg aaaagtggcc ggatcggctg gttgccagcc    11100
ttcgccctat ccataaatac agccgcgcgt gcatcggtgc cggctatatg gtgggccctt    11160
cggtgttct aggcactcct ggggtcgtgt catactatct cacaaaattt gttaagggcg     11220
```

```
gggctcaagt gcttccggag acggttttca gcaccggccg aattgaggta gactgccggg   11280
aatatcttga tgatcgggag cgagaagttg ctgcgtccct cccacacgct ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag ccccggaaaa gccgcgaaag   11460
cattgtgcac actgacagat gtgtacctcc cagatcttga agcctatctc cacccggaga   11520
cccagtccaa gtgctggaaa atgatgttgg acttcaaaga agttcgacta atggtctgga   11580
aagacaaaac agcctatttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggggct gacctcgcgg   11760
tcacccctta tgattacggc gctaaaatta tcctgtctag cgcgtaccat ggtgaaatgc   11820
ccccggata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag ttttatttc ccccggccc tgtcattgaa ccaactttag   12060
gcctgaattg aaatgaaatg gggtccatgc aaagccttt tgacaaaatt ggccaacttt   12120
ttgtggatgc tttcacggag ttcttggtgt ccattgttga tatcattata ttttggcca   12180
ttttgtttgg cttcaccatc gccggttggc tggtggtctt ttgcatcaga ttggttgct   12240
ccgcgatact ccgtacgcgc cctgccattc actctgagca attacagaag atcttatgag   12300
gcctttcttt cccagtgcca agtggacatt cccacctggg gaactaaaca tcctttgggg   12360
atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct cattttcagc atctagccgc cattgaagcc   12540
gagacctgta atatttggc ctcccggctg cccatgctac acaacctgcg catgacaggg   12600
tcaaatgtaa ccatagtgta taatagcact ttgaatcagg tgtttgctat ttttccaacc   12660
cctggttccc ggccaaagct tcatgatttt cagcaatggt taatagctgt acattcctcc   12720
atatttcct ctgttgcagc ttcttgtact ctttttgttg tgctgtggtt gcgggttcca   12780
atactacgta ctgttttgg tttccgctgg ttaggggcaa ttttctttc gaactcacag   12840
tgaattacac ggtgtgtcca ccttgcctca cccggcaagc agccacagag atctacgaac   12900
ccggtaggtc tctttggtgc aggatagggt atgaccgatg tggggaggac gatcatgacg   12960
agctagggtt tatgataccg cctggcctct ccagcgaagg ccacttgact ggtgtttacg   13020
cctggttggc gttcttgtcc ttcagctaca cggcccagtt ccatcccgag atattcggga   13080
tagggaatgt gagtcgagtt tatgttgaca tcaaacatca actcatctgc gccgaacatg   13140
acggcagaa caccaccttg cctcgtcatg acaacatttc agccgtgttt cagacctatt   13200
accaacatca agtcgacggc ggcaattggt ttcacctaga atggcttcgt cccttctttt   13260
cctcgtggtt ggttttaaat gtctcttggt ttctcaggcg ttcgcctgca aaccatgttt   13320
cagttcgagt cttgcagata ttaagaccaa caccaccgca gcggcaagct ttgctgtcct   13380
ccaagacatc agttgcctta ggcatcgcga ctcggcctct gaggcgattc gcaaaatccc   13440
tcagtgccgt acggcgatag ggacacccgt gtatgttacc atcacagcca atgtgacaga   13500
tgagaattat ttacattctt ctgatctcct catgctttct tcttgccttt tctatgcttc   13560
tgagatgagt gaaaagggat ttaaggtggt atttggcaat gtgtcaggca tcgtggctgt   13620
```

```
gtgtgtcaat tttaccagct acgtccaaca tgtcaaggag tttacccaac gctccctggt    13680
ggtcgaccat gtgcggttgc tccatttcat gacacctgag accatgaggt gggcaactgt    13740
tttagcctgt cttttttgcca ttctgttggc aatttgaatg tttaagtatg ttggagaaat    13800
gcttgaccgc gggctgttgc tcgcgattgc tttctttgtg gtgtatcgtg ccgttctgtc    13860
ttgctgtgct cgccaacgcc agcaacgaca gcagctccca tctacagctg atttacaact    13920
tgacgctatg tgagctgaat ggcacagatt ggctagctaa caaatttgat tgggcagtgg    13980
agagttttgt catctttccc gttttgactc acattgtctc ctatggtgcc ctcactacca    14040
gccatttcct tgacacagtc gctttagtca ctgtgtctac cgccgggttt gttcacgggc    14100
ggtatgtcct aagtagcatc tacgcggtct gtgccctggc tgcgttgact tgcttcgtca    14160
ttaggtttgc aaagaattgc atgtcctggc gctacgcgtg taccagatat accaactttc    14220
ttctggacac taagggcaga ctctatcgtt ggcggtcgcc tgtcatcata gagaaagggg    14280
gcaaagttga ggtcgaaggt catctgatcg acctcaaaag agttgtgctt gatggctccg    14340
tggcaacccc tataaccaga gtttcagcgg aacaatgggg tcgtccttag atgacttctg    14400
tcacgatagc acggctccac aaaaggtgct tttggcgttt tctattacct acacgccagt    14460
gatgatatat gccctaaagg tgagtcgcgg ccgactgcta gggcttctgc accttttgat    14520
cttcctgaat tgtgctttca ccttcgggta catgactttc gcgcactttc agagtacaaa    14580
taaggtcgcg ctcactatgg gagcagtagt tgcactcctt tggggggtgt actcagccat    14640
agaaacctgg aaattcatca cctccagatg ccgtttgtgc ttgctaggcc gcaagtacat    14700
tctggcccct gcccaccacg ttgaaagtgc cgcaggcttt catccgattg cggcaaatga    14760
taaccacgca tttgtcgtcc ggcgtcccgg ctccactacg gtcaacggca cattggtgcc    14820
cgggttaaaa agcctcgtgt tgggtggcag aaaagctgtt aaacagggag tggtaaacct    14880
tgtcaaatat gccaaataac aacggcaagc agcagaagag aaagaagggg gatggccagc    14940
cagtcaatca gctgtgccag atgctgggta agatcatcac tcagcaaaac cagtccagag    15000
gcaagggacc gggaaagaaa aataagaaga aaaacccgga gaagccccat tttcctctag    15060
cgactgaaga tgatgtcaga catcacttta ccccctagtga gcggcaattg tgtctgtcgt    15120
caatccagac cgccttttaat caaggcgctg ggacttgcac cctgtcagat tcagggagga    15180
taagttacac tgtggagttt agtttgccta cgcatcatac tgtgcgcctg atccgcgtca    15240
cagcatcacc ctcagcatga tgggctggca ttcttgaggc atctcagtgt ttgaattgga    15300
agaatgtgtg gtgaatggca ctgattgaca ttgtgcctct aagtcaccta ttcaattagg    15360
gcgaccgtgt gggggtgaga tttaattggc gagaaccatg cggccgaaat taaaaaaaaa    15420
aaaaaaaaaa aaaaaaaaaa aaaaaaaaaa aaaaaaa                             15458

<210> SEQ ID NO 3
<211> LENGTH: 15460
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 3
atgacgtata ggtgttggct ctatgccttg gcatttgtat tgtcaggagc tgtgaccatt      60
ggcacagccc aaaacttgct gcacagaaac accttctgt gatagcctcc ttcaggggag     120
cttagggttt gtccctagca ccttgcttcc ggagttgcac tgctttacgg tctctccacc     180
cctttaacca tgtctgggat acttgatcgg tgcacgtgta cccccaatgc cagggtgttt     240
```

```
atggcggagg gccaagtcta ctgcacacga tgcctcagtg cacggtctct ccttcccctg    300
aacctccagg tttctgagct cggggtgcta ggcctattct acaggcccga agagccactc    360
cggtggacgt tgccacgtgc attccccact gttgagtgct ccccgccgg ggcctgctgg     420 cttctgcaa tctttccaat cgcacgaatg accagtggaa acctgaactt ccaacaaaga     480
atggtacggg tcgcagctga gctttacaga gccggccagc tcaccctgc agtcttgaag     540 gctctacaag tttatgaacg gggttgccgc tggtacccca ttgttggacc tgtccctgga    600
gtggccgttt tcgccaattc cctacatgtg agtgataaac ccttcccggg agcaactcac    660
gtgttgacca acctgccgct cccgcagaga cccaagcctg aagacttttg ccccttgag    720 tgtgctatgg ctactgtcta tgacattggt catgacgccg tcatgtatgt ggccgaaagg    780
aaagtctcct gggcccctcg tggcggggat gaagtgaaat ttgaagctgt ccccggggag    840
ttgaagttga ttgcgaaccg gctccgcacc tccttcccgc cccaccacac agtggacatg    900
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caagaaatt cgccatgcta accaatttgg ctaccagacc    1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga aactggcggg agaacccagc tactctgggt ttgaggacct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg tgcttgtac tagcgccaag   1680 tacgtactta agctggaagg tgagcattgg actgtcactg tgaccctgg gatgtcccct    1740 tctttgctcc ctcttgaatg tgttcagggc tgttgtgggc gcaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca aacaaaacc aaccgggtca ccccggagga ggtcgcagca   2100
aagattgacc tgtacctccg tgtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc cctgaccgc cttttcactg    2340 gctaactact actaccgtgc gcaaggtgac gaagttcgtc accgtgaaag actaaccgcc   2400
gtgctctcca gttggaaaa ggttgttcga aagaatatg gctcatgcc aaccgagcct     2460 ggtccacggc ccacactgcc acgcgggctc gacgaactca agaccagat ggaggaggac    2520 ttgctgaaac tggctaacgc ccagacgact tcggacatga tggcctgggc agtcgagcag   2580
gttgacctaa aaacttgggt caagaactac ccgcggtgga caccaccacc ccctccgcca   2640
```

```
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agccccttg atctcccgac cccacctgag    2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct cccccagcac cgccgcagag cggggggcgtt   3120 ctggagtag aggggcatga agctgaggaa accctgagtg aaatctcgga catgtcgggt     3180
aacattaaac ctgcgtccgt gtcatcaagc agctccttgt ccagcgtgag aatcacacgc    3240
ccaaaatact cagctcaagc catcatcgac tcggcgggc cctgcagtgg gcatctccaa    3300
gaggtaaagg aaacatgcct tagtgtcatg cgcgaggcat gtgatgcgac taagcttgat    3360
gaccctgcta cgcaggaatg gctttctcgc atgtgggatc gggtggacat gctgacttgg    3420
cgcaacacgt ctgtttacca ggcgatttgc accttagatg gcaggttaaa gttcctccca    3480
aaaatgatac tcgagacacc gccgccctat ccgtgtgagt ttgtgatgat gcctcacacg    3540
cctgcacctt ccgtaggtgc ggagagcgac cttaccattg gctcagttgc tactgaagat    3600
gttccacgca cctcgagaa aatagaaaat gtcggcgaga tggccaacca gggacccttg     3660
gccttctccg aggataaacc ggtagatgac caacttgtca acgaccccg gatatcgtcg     3720 cggaggcctg acgagagcac atcagctccg tccgcaggca caggtggcgc cggctctttt    3780
accgatttgc cgccttcaga tggcgcggat gcggacgggg gggggccgtt tcggacggta    3840 aaagaaaag ctgaaaggct cttgaccaa ctgagccgtc aggtttttga cctcgtctcc     3900
catctccctg ttttcttctc acgccttttc taccctggcg gtggttattc tccgggtgat    3960
tggggttttg cagcttttac tctattgtgc ctcttttat gttacagtta cccagccttt     4020
ggtattgctc ccctcttggg tgtgttttct gggtcttctc ggcgcgttcg aatgggggtt    4080
tttggctgct ggttggcttt gctgttggt ctgttcaagc ctgtgtccga cccagtcggc     4140
gctgcttgtg agtttgactc gccagagtgt agaaacatcc ttcattcttt tgagcttctc    4200
aaaccttggg accctgttcg cagccttgtt gtgggccccg tcggtctcgg tcttgccatt    4260
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tggggatctt gtataagaac tgctcccaat gaggtcgctt ttaacgtgtt cctttcaca    4440 cgtgcgacca ggtcgtcact tatcgacctg tgcgatcggt tttgtgcgcc aaaaggaatg    4500
gaccccattt ttctcgccac tgggtggcgc gggtgctggg ccggccgaag ccccattgag    4560
caaccctctg aaaacccat cgcgtttgcc cagttggatg aaaagaagat tacggctagg    4620
actgtggtcg cccagcctta tgaccccaac caagccgtaa agtgcttgcg ggtattgcag    4680
gcgggtgggg cgatggtggc taaggcggtc ccaaaagtgg tcaaggtttc cgctgttcca    4740
ttccgagccc ccttctttcc cactggagtg aaagttgacc ctgattgcag gtcgtggtt    4800 gaccctgaca ctttcactgc agctctccgg tctggctact ccaccacaaa cctcgtcctt    4860
ggtgtggggg actttgccca gctgaatgga ttaaaaatca ggcaaatttc caagccttca    4920
gggggaggcc cacatctcat ggctgccctg catgttgcct gctcgatggc tctgcacatg    4980
cttgctggga tttatgtgac tgcggtgggt tcttgcggca ccggcaccaa cgacccgtgg    5040
```

-continued

| | |
|---|---|
| tgcgctaacc cgtttgccgt ccctggctac ggacctggct ctctctgcac gtccagattg | 5100 |
| tgcatttccc aacacggcct taccctgccc ttgacagcac ttgtggcggg attcggtatt | 5160 |
| caagaaattg ccttggtcgt tttgattttt gtttccatcg gaggcatggc tcataggttg | 5220 |
| agctgtaagg ctgacatgct gtgtgtcttg cttgcaattg ccagctatgt ttgggtacct | 5280 |
| cttacctggt tgctttgtgt gtttccttgc tggttcgct gttttcttt gcacccctc | 5340 |
| accatcctat ggttggtgtt tttcttgatt tctgtgaata tgccttcagg aatcttggcc | 5400 |
| atggtgttgt tggtttctct ttggcttctt ggtcgttata ctaatgttgc tggccttgtc | 5460 |
| accccctacg acattcatca ttacaccagt ggccccgcg gtgttgccgc cttggctacc | 5520 |
| gcaccagatg ggacctactt ggccgctgtc cgccgcgctg cgttgactgg ccgcaccatg | 5580 |
| ctgtttaccc cgtcccagct tgggtctctt cttgaggggtg ctttcagaac tcgaaagccc | 5640 |
| tcactgaaca ccgtcaatgt gatcgggtcc tccatgggct ctggcggggt gtttaccatc | 5700 |
| gacgggaaag tcaagtgcgt aactgccgca catgtcctta cgggcaattc agctcgggtt | 5760 |
| tccggggtcg gcttcaatca aatgcttgac tttgacgtaa agggagattt cgctatagct | 5820 |
| gattgcccga attggcaagg ggctgccccc aagacccaat tctgcacgga tggatggact | 5880 |
| ggccgtgcct attggctaac atcctctggc gtcgaacccg cgtcattgg aaaaggattc | 5940 |
| gccttctgct tcaccgcatg tggcgattcc gggtccccag tgatcaccga ggccggtgag | 6000 |
| cttgtcggcg ttcacacggg atcgaataaa caaggggggg gcattgttac gcgcccctca | 6060 |
| ggccagtttt gtaatgtggc acccatcaag ctaagcgaat taagtgaatt ctttgctggg | 6120 |
| cctaaggtcc cgctcggtga tgtgaaggtc ggcagccaca taattaaaga cataagcgag | 6180 |
| gtgccttcag atctttgtgc cttgcttgct gccaaacctg aactggaagg aggcctctcc | 6240 |
| accgtccaac ttcttttgtgt gtttttctc ctgtggagaa tgatgggaca tgcctggacg | 6300 |
| cccttggttg ctgtgagttt ctttatttg aatgaggttc tcccagccgt cctggtccgg | 6360 |
| agtgttttct cctttggaat gtttgtgcta tcctggctca cgccatggtc tgcgcaagtt | 6420 |
| ctgatgatca ggcttctgac agcagctctt aacaggaaca gatggtcact tgccttttc | 6480 |
| agcctcggtg cagtgaccgg ttttgtcgca gatcttgcgg ccactcaggg gcatccgttg | 6540 |
| caggcagtga tgaatttgag cacctatgca ttcctgcctc ggatgatggt tgtgacctca | 6600 |
| ccagtcccag tgatcacgtg tggtgtcgtg cacctacttg ccatcatttt gtacttgttt | 6660 |
| aagtaccgtg gcctgcacca tatccttgtt ggcgatggag tgttctctgc ggcttcttc | 6720 |
| ttgagatact tgccgagggg aaagttgagg gaagggtgt cgcaatcctg cggaatgaat | 6780 |
| catgagtctc tgactggtgc cctcgctatg agactcaatg acgaggactt ggatttcctt | 6840 |
| atgaaatgga ctgattttaa gtgctttgtt tctgcgtcca acatgaggaa tgcagcgggt | 6900 |
| caatttatcg aggctgccta tgctaaagca cttagagtag aactggccca gttggtgcag | 6960 |
| gttgataaag ttcgaggtac tttggccaaa cttgaagctt tgctgatac cgtggcacct | 7020 |
| caactctcgc ccggtgacat tgttgtcgct ctcggccaca cgcctgttgg cagtatcttc | 7080 |
| gacctaaagg ttggtagcac caagcatacc ctccaagcca ttgagaccag agtccttgct | 7140 |
| gggtccaaaa tgaccgtggc gcgcgtcgtc gacccgaccc ccacgccccc acccgcaccc | 7200 |
| gtgcccatcc ccctcccacc gaaagttctg agaatggcc caacgcttg gggggatgag | 7260 |
| gaccgtttga ataagaagaa gaggcgcagg atggaagccc tcggcatcta tgttatgggc | 7320 |
| gggaaaaaat accagaaatt ttgggacaag aattccggtg atgtgtttta tgaggaggtc | 7380 |
| cataataaca cagatgagtg ggagtgtctc agagttggcg accctgccga ctttgaccct | 7440 |

```
gagaagggaa ctctgtgtgg acatgtcacc attgaaaaca aggcttacca tgtttacacc   7500
tccccatctg gtaagaagtt cttggtcccc gtcaacccag agaatggaag agtccaatgg   7560
gaagctgcaa agctttccgt ggagcaggcc ctaggtatga tgaatgtcga cggcgaactg   7620
actgccaaag aactggagaa actgaaaaga ataattgaca aactccaggg cctgactaag   7680
gagcagtgtt taaactgcta gccgccagcg acttgacccg ctgtggtcgc ggcggcttgg   7740
ttgttactga aacagcggta aaaatagtca aatttcacaa ccggaccttc accctgggac   7800
ctgtgaattt aaaagtggcc agtgaggttg agctaaaaga cgcggttgag cacaaccaac   7860
acccggttgc gagaccgatc gatggtggag ttgtgctcct gcgttccgcg gttccttcgc   7920
ttatagacgt cttgatctcc ggtgctgatg catctcccaa gttacttgcc catcacgggc   7980
cgggaaacac tgggatcgat ggcacgctct gggattttga gtccgaagcc actaaagagg   8040
aagtcgcact cagtgcgcaa ataatacagg cttgtgacat taggcgcggc gacgctcctg   8100
aaattggtct cccttacaag ctgtaccctg ttaggggtaa ccctgagcgg gtgaaaggag   8160
ttctgcagaa tacaaggttt ggagacatac cttacaaaac ccccagtgac actggaagcc   8220
cagtgcacgc ggctgcctgc cttacgccca acgccactcc ggtgactgat gggcgctccg   8280
tcttggccac gaccatgccc cccgggtttg agttatatgt accgaccata ccagcgtctg   8340
tccttgatta ccttgactct aggcctgact gccctaaaca gctgacagag cacggctgcg   8400
aagatgccgc actgaaagac ctctctaaat atgacttgtc cacccaaggc tttgttttac   8460
ctggagttct tcgccttgtg cggaaatacc tgtttgccca tgtaggtaag tgcccacccg   8520
ttcatcggcc ttctacttac cctgctaaga attctatggc tggaataaat gggaacaggt   8580
tcccaaccaa ggacattcag agcgtccctg aaatcgacgt tctgtgcgca caggctgtgc   8640
gagaaaactg gcaaactgtc accccttgta ctcttaagaa acagtattgc gggaagaaga   8700
agactaggac catactcggc accaataact tcatcgcact agcccaccga gcagtgttga   8760
gtggtgttac ccagggcttc atgaaaaagg cgtttaactc gcccatcgcc ctcggaaaga   8820
acaagtttaa ggagctacag actccggtcc tgggcaggtg ccttgaagct gatctcgcat   8880
cctgcgatcg atccacgcct gcaattgtcc gctggtttgc cgccaacctt ctttatgaac   8940
ttgcctgtgc tgaagagcat ctaccgtcgt acgtgctgaa ctgctgccac gacttactgg   9000
tcacgcagtc cggcgcagtg actaagagag gtggcctgtc gtctggcgac ccgatcacct   9060
ctgtgtctaa caccatttat agtttggtga tctatgcaca gcatatggtg cttagttact   9120
tcaaaagtgg tcacccccat ggccttctgt tcttacaaga ccagctaaag tttgaggaca   9180
tgctcaaggt tcaaccccctg atcgtctatt cggacgacct cgtgctgtat gccgagtctc   9240
ccaccatgcc aaactatcac tggtgggttg aacatctgaa tttgatgctg gggtttcaga   9300
cggacccaaa gaagacagca ataacagact cgccatcatt tctaggctgt agaataataa   9360
atgggcgcca gctagtcccc aaccgtgaca ggatcctcgc ggccctcgcc tatcacatga   9420
aggcgagtaa tgtttctgaa tactatgcct cagcggctgc aatactcatg gacagctgtg   9480
cttgtttgga gtatgatcct gaatggtttg aagaacttgt agttgaata gcgcagtgcg   9540 cccgcaagga cggctacagc tttcccggca cgccgttctt catgtccatg tgggaaaaac   9600
tcaggtccaa ttatgagggg aagaagtcga gagtgtgcgg gtactgcggg gccccggccc   9660
cgtacgctac tgcctgtggc ctcgacgtct gcatttacca cacccacttc caccagcatt   9720
gtccagtcac aatctggtgt ggccatccag cgggttctgg ttcttgtagt gagtgcaaat   9780
cccctgtagg gaaaggcaca agcccttag acgaggtgct ggaacaagtc ccgtataagc   9840
```

```
ccccacggac cgttatcatg catgtggagc agggtctcac cccccttgat ccaggtagat    9900
accaaactcg ccgcggatta gtctctgtca ggcgtggaat taggggaaat gaagttggac    9960
taccagacgg tgattatgct agcaccgcct tgctccctac ctgcaaagag atcaacatgg   10020
tcgctgtcgc ttccaatgta ttgcgcagca ggttcatcat cggcccaccc ggtgctggga   10080
aaacatactg gctccttcaa caggtccagg atggtgatgt tatttacaca ccaactcacc   10140
agaccatgct tgacatgatt agggctttgg ggacgtgccg gttcaacgtc ccggcaggca   10200
caacgctgca attccccgtc ccctcccgca ccggtccgtg ggttcgcatc ctagccggcg   10260
gttggtgtcc tggcaagaat tccttcctag atgaagcagc gtattgcaat caccttgatg   10320
ttttgaggct tcttagtaaa actaccctca cctgtctagg agacttcaag caactccacc   10380
cagtgggttt tgattctcat tgctatgttt ttgacatcat gcctcaaact caactgaaga   10440
ccatctggag gtttggacag aatatctgtg atgccattca gccagattac agggacaaac   10500
tcatgtccat ggtcaacaca acccgtgtga cctacgtgga aaaacctgtc aggtatgggc   10560
aggtcctcac cccctaccac agggaccgag aggacgacgc catcactatt gactccagtc   10620
aaggcgccac attcgatgtg gttacattgc atttgcccac taaagattca ctcaacaggc   10680
aaagagccct tgttgctatc accagggcaa gacacgctat ctttgtgtat gacccacaca   10740
ggcagctgca gggcttgttt gatcttcctg caaaaggcac gcccgtcaac ctcgcagtgc   10800
actgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttatt ctcacctgat ttaacacagt ttgctaaact cccagtagaa cttgcacctc   11040
actggcccgt ggtgtcaacc cagaacaatg aaaagtggcc ggatcggctg gttgccagcc   11100
ttcgccctat ccataaatac agccgcgcgt gcatcggtgc cggctatatg gtgggccctt   11160
cggtgtttct aggcactcct gggggtcgtgt catactatct cacaaaatt gttaagggcg   11220
gggctcaagt gcttccggag acggttttca gcaccggccg aattgaggta gactgccggg   11280
aatatcttga tgatcgggag cgagaagttg ctgcgtccct cccacacgct ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag ccccggaaaa gccgcgaaag   11460
cattgtgcac actgacagat gtgtacctcc cagatcttga agcctatctc cacccggaga   11520
cccagtccaa gtgctggaaa atgatgttgg acttcaaaga agttcgacta atggtctgga   11580
aagacaaaac agcctatttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggggct gacctcgcgg   11760
tcaccccttta tgattacggc gctaaaatta tcctgtctag cgcgtaccat ggtgaaatgc   11820
ccccccggata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag tttttatttt ccccgggccc tgtcattgaa ccaactttag   12060
gcctgaattg aaatgaaatg gggtccatgc aaagccttt tgacaaaatt ggccaacttt   12120
ttgtggatgc tttcacggag ttcttggtgt ccattgttga tatcattata tttttggcca   12180
ttttgtttgg cttcaccatc gccggttggc tggtggtctt ttgcatcaga ttggtttgct   12240
```

```
ccgcgatact ccgtacgcgc cctgccattc actctgagca attacagaag atcttatgag    12300
gcctttcttt cccagtgcca agtggacatt cccacctggg gaactaaaca tcctttgggg    12360
atgctttggc accataaggt gtcaaccctg attgatgaaa tggtgtcgcg tcgaatgtac    12420
cgcatcatgg aaaaagcagg gcaggctgcc tggaaacagg tggtgagcga ggctacgctg    12480
tctcgcatta gtagtttgga tgtggtggct cattttcagc atctagccgc cattgaagcc    12540
gagacctgta atatttggc ctcccggctg cccatgctac acaacctgcg catgacaggg    12600
tcaaatgtaa ccatagtgta taatagcact ttgaatcagg tgtttgctat ttttccaacc    12660
cctggttccc ggccaaagct tcatgatttt cagcaatggt taatagctgt acattcctcc    12720
atatttccct ctgttgcagc ttcttgtact ctttttgttg tgctgtggtt gcgggttcca    12780
atactacgta ctgttttgg tttccgctgg ttagggcaa ttttctttc gaactcacag    12840 tgaattacac ggtgtgtcca ccttgcctca cccggcaagc agccacagag atctacgaac    12900
ccggtaggtc tctttggtgc aggataggt atgaccgatg tggggaggac gatcatgacg    12960
agctagggtt tatgataccg cctggcctct ccagcgaagg ccacttgact ggtgtttacg    13020
cctggttggc gttcttgtcc ttcagctaca cggcccagtt ccatcccgag atattcggga    13080
tagggaatgt gagtcgagtt tatgttgaca tcaaacatca actcatctgc gccgaacatg    13140
acgggcagaa caccaccttg cctcgtcatg acaacatttc agccgtgttt cagacctatt    13200
accaacatca agtcgacggc ggcaattggt ttcacctaga atggcttcgt cccttctttt    13260
cctcgtggtt ggttttaaat gtctcttggt ttctcaggcg ttcgcctgca aaccatgttt    13320
cagttcgagt cttgcaaata ttaagaccaa caccaccgca gcggcaagct ttgctgtcct    13380
ccaagacatc agttgcctta ggcatcgcga ctcggcctct gaggcgattc gcaaaatccc    13440
tcagtgccgt acggcgatag ggacacccgt gtatgttacc atcacagcca atgggacaga    13500
tgagaattat ctacattctt ctgatctcct catgctttct tcttgccttt tctatgcttc    13560
tgagatgagt gaaaagggat ttaaggtggt atttggcaat gtgtcaggca tcgtggctgt    13620
gtgtgtcaat tttaccagct acgtccaaca tgtcaaggag tttacccaac gctccctggt    13680
ggtcgaccat gtgcggttgc tccatttcat gacacctgag accatgaggt gggcaactgt    13740
tttagcctgt cttttgcca ttctgttggc aatttgaatg tttaagtatg ttggagaaat    13800
gcttgaccgc gggctgttgc tcgcgattgc tttctttgtg gtgtatcgtg ccgttctgtc    13860
ttgctgtgct cgccaacgcc agcaacgaca gcagctccca tctacagctg atttacaact    13920
tgacgctatg tgagctgaat ggcacagatt ggctagctaa caaatttgat tgggcagtgg    13980 agagtttgt catctttccc gttttgactc acattgtctc ctatggtgcc ctcactacca    14040
gccatttcct tgacacagtc gctttagtca ctgtgtctac cgccgggttt gttcacgggc    14100
ggtatgtcct aagtagcatc tacgcggtct gtgccctggc tgcgttgact tgcttcgtca    14160
ttaggtttgc aaagaattgc atgtcctggc gctacgcgtg taccagatat accaactttc    14220
ttctggacac taagggcaga ctctatcgtt ggcggtcgcc tgtcatcata gagaaaaggg    14280
gcaaagttga ggtcgaaggt catctgatcg acctcaaaag agttgtgctt gatggctccg    14340
tggcaacccc tataaccaga gtttcagcgg aacaatgggg tcgtccttag atgacttctg    14400
tcacgatagc acggctccac aaaaggtgct tttggcgttt tctattacct acacgccagt    14460
gatgatatat gccctaaagg tgagtcgcgg ccgactgcta gggcttctgc acctttgat    14520 cttcctgaat tgtgctttca ccttcgggta catgactttc gcgcactttc agagtacaaa    14580
taaggtcgcg ctcactatgg agcagtagt tgcactcctt tggggggtgt actcagccat    14640
```

```
agaaacctgg aaattcatca cctccagatg ccgtttgtgc ttgctaggcc gcaagtacat    14700
tctggcccct gcccaccacg ttgaaagtgc cgcaggcttt catccgattg cggcaaatga    14760
taaccacgca tttgtcgtcc ggcgtcccgg ctccactacg gtcaacggca cattggtgcc    14820
cgggttaaaa agcctcgtgt tgggtggcag aaaagctgtt aaacagggag tggtaaacct    14880
tgtcaaatat gccaaataac aacggcaagc agcagaagag aaagaagggg gatggccagc    14940
cagtcaatca gctgtgccag atgctgggta agatcatcac tcagcaaaac cagtccagag    15000
gcaagggacc gggaaagaaa aataagaaga aaaacccgga gaagccccat tttcctctag    15060
cgactgaaga tgatgtcaga catcacttta cccctagtga gcggcaattg tgtctgtcgt    15120
caatccagac cgcctttaat caaggcgctg gaacttgcac cctgtcagat tcagggagga    15180
taagttacac tgtggagttt agtttgccta cgcatcatac tgtgcgcctg atccgcgtca    15240
cagcatcacc ctcagcatga tgggctggca ttcttgaggc atctcagtgt ttgaattgga    15300
agaatgtgtg gtgaatggca ctgattgaca ttgtgcctct aagtcaccta ttcaattagg    15360
gcgaccgtgt gggggtgaga tttaattggc gagaaccatg cggccgaaat taaaaaaaaa    15420
aaaaaaaaaa aaaaaaaaaa aaaaaaaaaa aaaaaaccc                           15460

<210> SEQ ID NO 4
<211> LENGTH: 15456
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 4
atgacgtata ggtgttggct ctatgccttg gcatttgtat tgtcaggagc tgtgaccatt      60
ggcacagccc aaaacttgct gcacagaaac acccttctgt gatagcctcc ttcaggggag     120
cttagggttt gtccctagca ccttgcttcc ggagttcac tgctttacgg tctctccacc      180
cctttaacca tgtctgggat acttgatcgg tgcacgtgta ccccaatgc cagggtgttt      240 atggcggagg gccaagtcta ctgcacacga tgcctcagtg cacggtctct ccttcccctg     300
aacctccagg tttctgagct cggggtgcta ggcctattct acaggcccga agagccactc     360
cggtggacgt tgccacgtgc attccccact gttgagtgct ccccgccgg ggcctgctgg     420 ctttctgcaa tctttccaat cgcacgaatg accagtggaa acctgaactt ccaacaaaga     480
atggtacggg tcgcagctga gctttacaga gccggccagc tcacccctgc agtcttgaag     540
gctctacaag tttatgaacg gggttgccgc tggtacccca ttgttggacc tgtccctgga     600
gtggccgttt tcgccaattc cctacatgtg agtgataaac ccttcccggg agcaactcac     660
gtgttgacca acctgccgct cccgcagaga cccaagcctg aagactttg ccccttttgag      720 tgtgctatgg ctactgtcta tgacattggt catgacgccg tcatgtatgt ggccgaaagg      780
aaagtctcct gggcccctcg tggcgggat gaagtgaaat ttgaagctgt ccccggggag      840
ttgaagttga ttgcgaaccg gctccgcacc tccttcccgc ccaccacac agtggacatg      900 tctaagttcg ccttcacagc ccctgggtgt ggtgtttcta tgcgggtcga acgccaacac     960
ggctgccttc ccgctgacac tgtccctgaa ggcaactgct ggtggagctt gtttgacttg    1020
cttccactgg aagttcagaa caaagaaatt cgccatgcta accaatttgg ctaccagacc    1080
aagcatggtg tctctggcaa gtacctgcag cggaggctgc aagttaatgg tctccgagca    1140
gtaactgacc taaacggacc tatcgtcgta cagtacttct ccgttaagga gagttggatc    1200
```

-continued

```
cgccatttga aactggcggg agaacccagc tactctgggt ttgaggacct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcattccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctggaagg tgagcattgg actgtcactg tgaccccctgg gatgtcccct   1740 tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc cctgaccgc cttttcactg   2340 gctaactact actaccgtgc gcaaggtgac gaagttcgtc accgtgaaag actaaccgcc   2400
gtgctctcca agttggaaaa ggttgttcga gaagaatatg ggctcatgcc aaccgagcct   2460
ggtccacggc ccacactgcc acgcgggctc gacgaactca aagaccagat ggaggaggac   2520
ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agccccttg atctcccgac ccacctgag   2820 ccggcaacac cttcaagtga gctggtgatt gtgtcctcac cgcaatgcat cttcaggccg   2880
gcgacaccct tgagtgagcc ggctccaatt cccgcacctc gcggaactgt gtctcgaccg   2940
gtgacaccct tgagtgagcc gatcctgtg cccgcaccgc ggcgtaagtt tcagcaggtg   3000
aaaagattga gttcggcggc ggcaatccca ccgtaccagg acgagcccct ggatttgtct   3060
gcttcctcac agactgaata tgaggcctct cccccagcac cgccgcagag cggggcgtt    3120 ctgggagtag aggggcatga agctgaggaa accctgagtg aaatctcgga catgtcgggt   3180
aacattaaac ctgcgtccgt gtcatcaagc agctccttgt ccagcgtgag aatcacacgc   3240
ccaaaatact cagctcaagc catcatcgac tcgggcgggc cctgcagtgg gcatctccaa   3300
gaggtaaagg aaacatgcct tagtgtcatg cgcgaggcat gtgatgcgac taagcttgat   3360
gaccctgcta cgcaggaatg gctttctcgc atgtgggatc gggtggacat gctgacttgg   3420
cgcaacacgt ctgtttacca ggcgattttgc accttagatg gcaggttaaa gttcctccca   3480
aaaatgatac tcgagacacc gccgcccctat ccgtgtgagt ttgtgatgat gcctcacacg   3540
cctgcacctt ccgtaggtgc ggagagcgac cttaccattg gctcagttgc tactgaagat   3600
```

```
gttccacgca tcctcgagaa aatagaaaat gtcggcgaga tggccaacca gggacccttg    3660
gccttctccg aggataaacc ggtagatgac caacttgtca acgaccccg gatatcgtcg     3720
cggaggcctg acgagagcac atcagctccg tccgcaggca caggtggcgc cggctctttt    3780
accgatttgc cgccttcaga tggcgcggat gcggacgggg gggggccgtt tcggacggta    3840
aaagaaaag ctgaaaggct ctttgaccaa ctgagccgtc aggttttga cctcgtctcc      3900
catctccctg ttttcttctc acgccttttc taccctggcg gtggttattc tccgggtgat    3960
tgggttttg cagcttttac tctattgtgc ctctttttat gttacagtta cccagccttt     4020
ggtattgctc ccctcttggg tgtgttttct gggtcttctc ggcgcgttcg aatgggggtt    4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggccccg tcggtctcgg tcttgccatt    4260
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tggggatctt gtataagaac tgctcccaat gaggtcgctt ttaacgtgtt tcctttcaca    4440
cgtgcgacca ggtcgtcact tatcgacctg tgcgatcggt tttgtgcgcc aaaaggaatg    4500
gacccccattt ttctcgccac tgggtggcgc gggtgctggg ccggccgaag ccccattgag   4560
caaccctctg aaaaacccat cgcgtttgcc cagttggatg aaaagaagat tacggctagg    4620
actgtggtcg cccagcctta tgaccccaac caagccgtaa agtgcttgcg ggtattgcag    4680
gcgggtgggg cgatggtggc taaggcggtc ccaaaagtgg tcaaggtttc cgctgttcca    4740
ttccgagccc ccttctttcc cactggagtg aaagttgacc ctgattgcag ggtcgtggtt    4800
gaccctgaca ctttcactgc agctctccgg tctggctact ccaccacaaa cctcgtcctt    4860
ggtgtggggg actttgccca gctgaatgga ttaaaaatca ggcaaatttc caagccttca    4920
gggggaggcc cacatctcat ggctgccctg catgttgcct gctcgatggc tctgcacatg    4980
cttgctggga tttatgtgac tgcggtgggt tcttgcggca ccggcaccaa cgacccgtgg    5040
tgcgctaacc cgtttgccgt ccctggctac ggacctggct ctctctgcac gtccagattg    5100
tgcatttccc aacacggcct taccctgccc ttgacagcac ttgtggcggg attcggtatt    5160
caagaaattg ccttggtcgt tttgattttt gtttccatcg gaggcatggc tcataggttg    5220
agctgtaagg ctgacatgct gtgtgtcttg cttgcaattg ccagctatgt ttgggtacct    5280
cttacctggt tgctttgtgt gtttccttgc tggttgcgct gtttttcttt gcaccccctc    5340
accatcctat ggttggtgtt tttcttgatt tctgtgaata tgccttcagg aatcttggcc    5400
atggtgttgt tggtttctct ttggcttctt ggtcgttata ctaatgttgc tggccttgtc    5460
acccctacg acattcatca ttacaccagt ggccccgcg tgttgccgc cttggctacc       5520
gcaccagatg ggacctactt ggccgctgtc cgccgcgctg cgttgactgg ccgcaccatg    5580
ctgtttaccc cgtcccagct tgggtctctt cttgagggtg ctttcagaac tcgaaagccc    5640
tcactgaaca ccgtcaatgt gatcgggtcc tccatgggct ctgcggggt gtttaccatc    5700
gacgggaaag tcaagtgcgt aactgccgca catgtcctta cggcaattc agctcgggtt    5760
tccgggtcg gcttcaatca aatgcttgac tttgacgtaa agggagattt cgctatagct    5820
gattgcccga attggcaagg ggctgccccc aagacccaat tctgcacgga tggatggact    5880
ggccgtgcct attggctaac atcctctggc gtcgaacccg cgtcattgg aaaaggattc    5940
gccttctgct tcaccgcatg tggcgattcc gggtccccag tgatcaccga ggccggtgag    6000
```

```
cttgtcggcg ttcacacggg atcgaataaa caaggggggg gcattgttac gcgcccctca    6060
ggccagtttt gtaatgtggc acccatcaag ctaagcgaat taagtgaatt ctttgctggg    6120
cctaaggtcc cgctcggtga tgtgaaggtc ggcagccaca taattaaaga cataagcgag    6180
gtgccttcag atctttgtgc cttgcttgct gccaaacctg aactggaagg aggcctctcc    6240
accgtccaac ttctttgtgt gttttttctc ctgtggagaa tgatgggaca tgcctggacg    6300
cccttggttc tgtgagtttc ttttattttg aatgaggttc tcccagccgt cctggtccgg    6360
agtgttttct cctttggaat gtttgtgcta tcctggctca cgccatggtc tgcgcaagtt    6420
ctgatgatca ggcttctgac agcagctctt aacaggaaca gatggtcact tgccttttc    6480
agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gcctgcacca tatccttgtt ggcgatggag tgttctctgc ggctttcttc    6720
ttgagatact ttgccgaggg aaagttgagg gaagggtgt cgcaatcctg cggaatgaat    6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt ttgctgatac cgtggcacct    7020
caactctcgc ccggtgacat tgttgtcgct ctcggccaca cgcctgttgg cagtatcttc    7080
gacctaaagg ttggtagcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc ccctcccacc gaaagttctg gagaatggcc caacgcttg gggggatgag    7260
gaccgtttga ataagaagaa gaggcgcagg atggaagccc tcggcatcta tgttatgggc    7320
gggaaaaaat accagaaatt ttgggacaag aattccggtg atgtgttta tgaggaggtc    7380
cataataaca cagatgagtg ggagtgtctc agagttggcg accctgccga ctttgacccc    7440
gagaagggaa ctctgtgtgg acatgtcacc attggaaaca aggcttacca tgtttacacc    7500
tccccatctg gtaagaagtt cttggtcccc gtcaacccag agaatggaag agtccaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccagcg acttgacccg ctgtggtcgc ggcggcttgg    7740
ttgttactga acagcggta aaaatagtca aatttcacaa ccggaccttc accctgggac    7800
ctgtgaattt aaaagtggcc agtgaggttg agctaaaaga cgcggttgag cacaaccaac    7860
acccggttgc gagaccgatc gatggtggag ttgtgctcct gcgttccgcg gttccttcgc    7920
ttatagacgt cttgatctcc ggtgctgatg catctcccaa gttacttgcc catcacgggc    7980
cgggaaacac tgggatcgat ggcacgctct gggattttga gtccgaagcc actaaagagg    8040
aagtcgcact cagtgcgcaa ataatacagg cttgtgacat taggcgcggc gacgctcctg    8100
aaattggtct cccttacaag ctgtaccctg ttaggggtaa ccctgagcgg gtgaaaggag    8160
ttctgcagaa tacaaggttt ggagacatac cttacaaaac ccccagtgac actgaagcc    8220
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gccctaaaca gctgacagag cacggctgcg    8400
```

```
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc accccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcacccccat ggccttctgt tcttacaaga ccagctaaag tttgaggaca    9180
tgctcaaggt tcaaccccctg atcgtctatt cggacgacct cgtgctgtat gccgagtctc    9240
ccaccatgcc aaactatcac tggtgggttg aacatctgaa tttgatgctg gggtttcaga    9300
cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg acagctgtg    9480
cttgttttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
cccctgtagg gaaaggcaca agcccttttag acgaggtgct ggaacaagtc ccgtataagc    9840
ccccacggac cgttatcatg catgtggagc agggtctcac cccccttgat ccaggtagat    9900
accaaactcg ccgcggatta gtctctgtca ggcgtggaat taggggaaat gaagttggac    9960
taccagacgg tgattatgct agcaccgcct tgctccctac ctgcaaagag atcaacatgg    10020
tcgctgtcgc ttccaatgta ttgcgcagca ggttcatcat cggcccaccc ggtgctggga    10080
aaacatactg gctccttcaa caggtccagg atggtgatgt tatttacaca ccaactcacc    10140
agaccatgct tgacatgatt agggctttgg ggacgtgccg gttcaacgtc ccggcaggca    10200
caacgctgca attccccgtc ccctcccgca ccggtccgtg ggttcgcatc ctagccggcg    10260
gttggtgtcc tggcaagaat tccttcctag atgaagcagc gtattgcaat cacccttgatg    10320
ttttgaggct tcttagtaaa actaccctca cctgtctagg agacttcaag caactccacc    10380
cagtgggttt tgattctcat tgctatgttt ttgacatcat gcctcaaact caactgaaga    10440
ccatctggag gttggacagc aatatctgtg atgccattca gccagattac agggacaaac    10500
tcatgtccat ggtcaacaca acccgtgtga cctacgtgga aaaacctgtc aggtatgggc    10560
aggtcctcac cccctaccac agggaccgag aggacgacgc catcactatt gactccagtc    10620
aaggcgccac attcgatgtg gttacattgc atttgcccac taaagattca ctcaacaggc    10680
aaagagccct tgttgctatc accagggcaa gacacgctat ctttgtgtat gacccacaca    10740
ggcagctgca gggcttgttt gatcttcctg caaaaggcac gccccgtcaac ctcgcagtgc    10800
```

```
actgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttattt ctcacctgat ttaacacagt ttgctaaact cccagtagaa cttgcacctc   11040
actggcccgt ggtgtcaacc cagaacaatg aaaagtggcc ggatcggctg gttgccagcc   11100
ttcgccctat ccataaatac agccgcgcgt gcatcggtgc cggctatatg gtgggccctt   11160
cggtgtttct aggcactcct ggggtcgtgt catactatct cacaaaattt gttaagggcg   11220
gggctcaagt gcttccggag acggttttca gcaccggccg aattgaggta gactgccggg   11280
aatatcttga tgatcgggag cgagaagttg ctgcgtccct cccacacgct ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag ccccggaaaa gccgcgaaag   11460
cattgtgcac actgacagat gtgtacctcc cagatcttga agcctatctc cacccggaga   11520
cccagtccaa gtgctggaaa atgatgttgg acttcaaaga agttcgacta atggtctgga   11580
aagacaaaac agcctatttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggggct gacctcgcgg   11760 tcacccctta tgattacggc gctaaaatta tcctgtctag cgcgtaccat ggtgaaatgc   11820 cccccgata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag ttttattttc ccccgggccc tgtcattgaa ccaactttag   12060
gcctgaattg aaatgaaatg gggtccatgc aaagcctttt tgacaaaatt ggccaacttt   12120
ttgtggatgc tttcacggag ttcttggtgt ccattgttga tatcattata ttttttggcca   12180 ttttgtttgg cttcaccatc gccggttggc tggtggtctt ttgcatcaga ttggtttgct   12240
ccgcgatact ccgtacgcgc cctgccattc actctgagca attacagaag atcttatgag   12300
gcctttcttt cccagtgcca agtggacatt cccacctggg gaactaaaca tccttttgggg   12360 atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct cattttcagc atctagccgc cattgaagcc   12540
gagacctgta aatatttggc ctcccggctg cccatgctac acaacctgcg catgacaggg   12600
tcaaatgtaa ccatagtgta taatagcact ttgaatcagg tgtttgctat ttttccaacc   12660
cctggttccc ggccaaagct tcatgatttt cagcaatggt taatagctgt acattcctcc   12720
atattttcct ctgttgcagc ttcttgtact cttttttgttg tgctgtggtt gcgggttcca   12780
atactacgta ctgttttttgg tttccgctgg ttaggggcaa ttttttctttc gaactcacag   12840 tgaattacac ggtgtgtcca ccttgcctca cccggcaagc agccacagag atctacgaac   12900
ccggtaggtc tctttggtgc aggataggggt atgaccgatg tggggaggac gatcatgacg   12960
agctagggtt tatgataccg cctggcctct ccagcgaagg ccacttgact ggtgtttacg   13020
cctggttggc gttcttgtcc ttcagctaca cggcccagtt ccatcccgag atattcggga   13080
tagggaatgt gagtcgagtt tatgttgaca tcaaacatca actcatctgc gccgaacatg   13140
acgggcagaa caccaccttg cctcgtcatg acaacatttc agccgtgttt cagacctatt   13200
```

```
accaacatca agtcgacggc ggcaattggt ttcacctaga atggcttcgt cccttctttt    13260
cctcgtggtt ggttttaaat gtctcttggt ttctcaggcg ttcgcctgca aaccatgttt    13320
cagttcgagt cttgcagata ttaagaccaa caccaccgca gcggcaagct ttgctgtcct    13380
ccaagacatc agttgcctta ggcatcgcga ctcggcctct gaggcgattc gcaaaatccc    13440
tcagtgccgt acggcgatag ggacacccgt gtatgttacc atcacagcca atgtgacaga    13500
tgagaattat ttacattctt ctgatctcct catgcttcct tcttgccttt tctatgcttc    13560
tgagatgagt gaaaagggat ttaaggtggt atttggcaat gtgtcaggca tcgtggctgt    13620
gtgtgtcaat tttaccagct acgtccaaca tgtcaaggag tttacccaac gctccctggt    13680
ggtcgaccat gtgcggttgc tccatttcat gacacctgag accatgaggt gggcaactgt    13740
tttagcctgc cttttgcca ttctgttggc aatttgaatg tttaagtatg ttggagaaat    13800
gcttgaccgc gggctgttgc tcgcgattgc tttctttgtg gtgtatcgtg ccgttctgtt    13860
ttgctgtgct cgccaacgcc agcaacgaca gcagctccca tctacagctg atttacaact    13920
tgacgctatg tgagctgaat ggcacagatt ggctagctaa caaatttgat tgggcagtgg    13980
agagttttgt catcttttccc gttttgactc acattgtctc ctatggtgcc ctcactacca    14040
gccatttcct tgacacagtc gctttagtca ctgtgtctac cgccgggttt gttcacgggc    14100
ggtatgtcct aagtagcatc tacgcggtct gtgccctggc tgcgttgact tgcttcgtca    14160
ttaggtttgc aaagaattgc atgtcctggc gctacgcgtg taccagatat accaactttc    14220
ttctggacac taagggcaga ctctatcgtt ggcggtcgcc tgtcatcata gagaaaaggg    14280
gcaaagttga ggtcgaaggt catctgatcg acctcaaaag agttgtgctt gatggctccg    14340 tggcaaccc tataaccaga gtttcagcgg aacaatgggg tcgtccttag atgacttctg    14400
tcacgatagc acggctccac aaaaggtgct tttggcgttt tctattacct acacgccagt    14460
gatgatatat gccctaaagg tgagtcgcgg ccgactgcta gggcttctgc acctttgat    14520 cttcctgaat tgtgctttca ccttcgggta catgactttc gcgcactttc agagtacaaa    14580
taaggtcgcg ctcactatgg gagcagtagt tgcactcctt tgggggtgt actcagccat    14640 agaaacctgg aaattcatca cctccagatg ccgtttgtgc ttgctaggcc gcaagtacat    14700
tctggcccct gcccaccacg ttgaaagtgc cgcaggcttt catccgattg cggcaaatga    14760
taaccacgca tttgtcgtcc ggcgtcccgg ctccactacg gtcaacggca cattggtgcc    14820
cgggttaaaa agcctcgtgt tgggtggcag aaaagctgtt aaacagggag tggtaaacct    14880
tgtcaaatat gccaaataac aacggcaagc agcagaagag aaagaagggg gatgccagc    14940 cagtcaatca gctgtgccag atgctgggta agatcatcgc tcagcaaaac cagtccagag    15000
gcaagggacc gggaaagaaa aataagaaga aaaacccgga gaagcccat tttcctctag    15060 cgactgaaga tgatgtcaga catcacttta cccctagtga gcggcaattg tgtctgtcgt    15120
caatccagac cgcctttaat caaggcgctg ggacttgcac cctgtcagat tcagggagga    15180
taagttacac tgtggagttt agtttgccta cgcatcatac tgtgcgcctg atccgcgtca    15240
cagcatcacc ctcagcatga tgggctggca ttcttgaggc atctcagtgt ttgaattgga    15300
agaatgtgtg gtgaatggca ctgattgaca ttgtgcctct aagtcaccta ttcaattagg    15360
gcgaccgtgt gggggtgaga tttaattggc gagaaccatg cggccgaaat taaaaaaaa    15420 aaaaaaaaaa aaaaaaaaaa aaaaaaaaaa aaaaaa                              15456
```

<210> SEQ ID NO 5
<211> LENGTH: 15019
<212> TYPE: DNA

```
<213> ORGANISM: Artificial Sequence
<220> FEATURE:
<223> OTHER INFORMATION: Porcine reproductive and respiratory syndrome
      virus, strain MN184A
<220> FEATURE:
<221> NAME/KEY: misc_feature
<222> LOCATION: (654)..(654)
<223> OTHER INFORMATION: S = C or G
<220> FEATURE:
<221> NAME/KEY: misc_feature
<222> LOCATION: (735)..(735)
<223> OTHER INFORMATION: M = A or C
<220> FEATURE:
<221> NAME/KEY: misc_feature
<222> LOCATION: (745)..(745)
<223> OTHER INFORMATION: Y = C or T
<220> FEATURE:
<221> NAME/KEY: misc_feature
<222> LOCATION: (1627)..(1627)
<223> OTHER INFORMATION: R = A or G
<220> FEATURE:
<221> NAME/KEY: misc_feature
<222> LOCATION: (1642)..(1642)
<223> OTHER INFORMATION: Y = C or T
<220> FEATURE:
<221> NAME/KEY: misc_feature
<222> LOCATION: (1736)..(1736)
<223> OTHER INFORMATION: Y = C or T
<220> FEATURE:
<221> NAME/KEY: misc_feature
<222> LOCATION: (1987)..(1987)
<223> OTHER INFORMATION: R = A or G
<220> FEATURE:
<221> NAME/KEY: misc_feature
<222> LOCATION: (2061)..(2061)
<223> OTHER INFORMATION: R = A or G
<220> FEATURE:
<221> NAME/KEY: misc_feature
<222> LOCATION: (2161)..(2161)
<223> OTHER INFORMATION: R = A or G
<220> FEATURE:
<221> NAME/KEY: misc_feature
<222> LOCATION: (2186)..(2186)
<223> OTHER INFORMATION: R = A or G
<220> FEATURE:
<221> NAME/KEY: misc_feature
<222> LOCATION: (2228)..(2228)
<223> OTHER INFORMATION: R = A or G
<220> FEATURE:
<221> NAME/KEY: misc_feature
<222> LOCATION: (2293)..(2293)
<223> OTHER INFORMATION: Y = C or T
<220> FEATURE:
<221> NAME/KEY: misc_feature
<222> LOCATION: (3407)..(3407)
<223> OTHER INFORMATION: R = A or G
<220> FEATURE:
<221> NAME/KEY: misc_feature
<222> LOCATION: (5992)..(5992)
<223> OTHER INFORMATION: Y = C or T
<220> FEATURE:
<221> NAME/KEY: misc_feature
<222> LOCATION: (5994)..(5994)
<223> OTHER INFORMATION: Y = C or T
      R = A or G
<220> FEATURE:
<221> NAME/KEY: misc_feature
<222> LOCATION: (5995)..(5995)
<223> OTHER INFORMATION: K= G or T
<220> FEATURE:
<221> NAME/KEY: misc_feature
<222> LOCATION: (5998)..(5998)
<223> OTHER INFORMATION: R = A or G
<220> FEATURE:
<221> NAME/KEY: misc_feature
<222> LOCATION: (6001)..(6001)
<223> OTHER INFORMATION: Y = C or T
<220> FEATURE:
<221> NAME/KEY: misc_feature
<222> LOCATION: (6704)..(6704)
```

```
<223> OTHER INFORMATION: R = A or G
<220> FEATURE:
<221> NAME/KEY: misc_feature
<222> LOCATION: (8811)..(8811)
<223> OTHER INFORMATION: Y = C or T
<220> FEATURE:
<221> NAME/KEY: misc_feature
<222> LOCATION: (9777)..(9777)
<223> OTHER INFORMATION: R = A or G
<220> FEATURE:
<221> NAME/KEY: misc_feature
<222> LOCATION: (11935)..(11935)
<223> OTHER INFORMATION: Y = C or T
<220> FEATURE:
<221> NAME/KEY: misc_feature
<222> LOCATION: (13527)..(13527)
<223> OTHER INFORMATION: M = A or C
<220> FEATURE:
<221> NAME/KEY: misc_feature
<222> LOCATION: (14133)..(14133)
<223> OTHER INFORMATION: Y = C or T
<220> FEATURE:
<221> NAME/KEY: misc_feature
<222> LOCATION: (14947)..(14947)
<223> OTHER INFORMATION: Y = C or T

<400> SEQUENCE: 5
atgacgtata ggtgttggct ctatgccacg acatttgtat tgtcaggagc tgtgaccact      60
ggcacagccc aaagcttgct gcacagaaac acccttctgt gacggcctcc ttcaggggag     120
tttaggggtt tatccctagc accttgtttc tggagttgca ctgctttacg gtctctccac     180 cccttaacc atgtctggga ttcttgatcg gtgcacgtgc accccaatg ccagggtgtt       240 tatggcagag ggccaagtct actgcacacg atgtctcagt gcacggtccc tccttcccct     300
gaatctccaa gtccctgagc tcggagtgtt gggcttgttt tataggcccg aagagccgct     360
ccggtggacg ttgccacgcg cattccccac tgttgagtgc tcccctgctg gggcttgttg     420
gctttctgca atttttccaa ttgcacgaat gaccagtgga aacctgaact ttcaacaaag     480
attagtgcgg gtcgcagctg agctttacaa agccggctgc ctcaccccta tagtcctaaa     540
gaatctacaa gtctatgaac ggggttgccg atggtacccc atcgttggac ctgtccctgg     600
agttgccgtt ttcgccaact ccctacatgt gagtgataga cctttcccag gggstactca     660
cgtgctaacc aacctgccgc tcccgcagag acctaagcct gaagattttt gccccttttga    720 gtgtgctatg gctgmcgtct atgayattgg tcatgacgcc gttatgttcg tggccgaagg     780
gagagtctcc tgggctccgc gtggtggggg aaaaggaaaa tttgaaactg ttccccgagga    840 gttgaggttg attgcagagc aactttatac ctccttcccg ccccaccacg tggtggacat     900
gtcgaaattc accttttacgg cccctgagtg tggtgcttcc atgcgagtcg aacgccatta    960
tggctgcctc cccgccggca ctgtccctga cggcaattgc tggtggagtt tgtttagctc    1020
gctcccattg gaaatccagt acaaagaaat tcgccacgcc acccaatttg ctatcaaac    1080 taagcatggc gttgctggca agtacctaca gcggaggctg caagttaatg gtctccgagc    1140
agtggttgac tcgaatggac ctatcgtcat acagtacttc tctgttaagg agagctggat   1200
ccgccacgtg aaactggcgg aagagtttga ctaccctggg tttgaggatc tcctcaggat    1260
aagagtcgag cccaacacgt tgccattgtc caacaaggac gagaaaatct tccggtttgg    1320
tgggtgcaag tggtacggtg ctgggaagag ggcaaggagg gcacgtgcaa gtgcagtcac   1380
cgcagtcgcc ggtcacgctc cgcctactcg tgaaacccag caagccaaga acacgaggc    1440 tgctagtgcc aacaaggctg agcttcttga acgctactcc ccgcctgctg aagggaattg   1500
cggctggcac tgtatttccg ccatcgccaa tcggatggta aattctaagt ttgagactgc   1560
```

```
ccttcccgaa agagtgagat ccccagaaga ctgggctact gatgaggatc ttgtgaatac    1620
tatccaratc ctcaggctcc cygcggcctt agacaggaac ggcgcctgtg caagcgccaa    1680
gtacatcctt aagctggaag gtgagcactg gactgtttca gtgattcccg gaatgycccc    1740
ttccttgctc ccccttgaat gcgttcaggg ttgctgtgag cataagggta atcttggttc    1800
tccgaacgcg gtcgggtttt ttggattcga ccctgccagc cttgaccgac ttgctggggt    1860
gatgcacctg cccagcagtg ccatcccagc cgctctggcc gagttgtctg gcgaccttga    1920
tcgtccaact tccccggccg ccactgtgtg gactgtctcg cagttttatg ctcgtcatag    1980
tggaggrgag catcctgatc aaaagtgttt aaaaaaaatt atcagtctct gtgaggtgat    2040
cgagagttgt tgctgttctc rgaacaaaac taaccgggtc accccggaag aggtcacagc    2100
aaagattgat ctgtaccttt ttggtgcagc aagtcttgaa gaatgcttgg ccaggcttga    2160
raaagctcgc ccgccaagcg tattaracac ctcctttgat tgggatgttg tgctccctgg    2220
tgttgggrcg gctgctcaag cagcaaaact gcccctcacc aaccagcgtc acgctctagc    2280
cactgttgtg acycaaaggt cttttgccgaa atttcaacct cgaaaagcgg agtctgtcaa    2340
gagcctacca gagagcaggc cactccctgc ccgcgcaaa aagattaggt ccaggtgtgg    2400
tagtccgatt tcattgggcg gcaatctccc tgacagccag gaagacttgg ccggtggttc    2460
ctttgatttc ccaaccctac ctgagttggt ggtaagctcg agtgagtctg tgcctgtccc    2520
tgcaccgcgc agggttgtgt cccgattagt gtcgtctccg atagtgtcga cccctgtgcc    2580
cgcaccacga cgtgggcttc ggcaggtgga gggaatgaat ttggcggcag tgactctagc    2640
gtgccaggac gagcccctcg atttgtctgc gtcctcgcag actgaatatg aggcgtcccc    2700
cttggcattg ccgctgagtg aggatgtcct ggcggtggag agacgagaag ttgaagaagt    2760
cctgagcgga atatcgggca tgtcagatga catcaggttg gcgcccgtgt catcaagtag    2820
ctccctgtca agcatagaga tcacacgtcc aaagtactca gctcaagcca tcattaactc    2880
aggtgggccc tgttgtgggc acctccagga ggtgaaagag aaataccctta atgtgatgcg    2940
tgaggcatgt gatgcgacca agcttgatga ccctgccacg caagaatggc tttcccgtat    3000
gtgggatagg gtagacatgc taacctggcg caacacgtcc atttttcagg cgcctttcac    3060
cttggctgac aagtttaagt ccctcccgaa gatgatactc gaaacaccgc cgccctaccc    3120
ttgtgggttt gtgatgatgc cccgcacgcc tgcaccttct gtaggtgcgg agagcgacct    3180
caccgttggc tcagttgcta ctgaagatgt cccgcgcatt ctcgggaagg tacaaggtgt    3240
tggcgaaacg accgaccagg gacccttggc actcttcgca gatgaattgg cagatgacca    3300
acctgctaga gaaccccgga cacaaacccc tcctgcaagc gcaggtggcg ccggcttagt    3360
tttggattct ggagggtcgc cggagctcac tgacctgccg cttccaracg gtacagacgc    3420
gggcggaggg ggaccgttac acacggtcaa gaagaaagct gagaggtgct tgaccagct    3480
gagccgtcgg gttttgaca ttgtctccca tctccctgtc ttcttctcac gccttttcaa    3540
gcctgacagt cactactctt cgggtgactg gagttttgca gcttttactt tattgtgcct    3600
cttttctatgt tacagttacc cggcctttgg tgttgctccc ctattgggtg tattttctgg    3660
gtcttctcgg cgcgttcgca tggggttttt tggctgctgg ttggctttcg ctgttggttt    3720
gttcaagcct gcaccgacc cagtcggtgc tgcttgtgag tttgattcgc cagagtgtag    3780
agacatcctt cattcttttg agctcctgca accttgggat cctgttcgca gccttgtggt    3840
gggacccgtc ggtctcggtc ttgccattat tggcaggtta ctgggcgggg cacgctacgt    3900
ctggctgctt ttgcttaggc ttggcatcgt ttcagactgt atcttggctg gagcttacgt    3960
```

```
gctttcgcaa ggtaggtgta aaaagtgttg gggatcttgt ataagaactg cccccagtga   4020
ggtcgccttc aatgtgtttc ccttcacacg tgcaaccaga tcgtcacttg tcgacctgtg   4080
cgaccggttt tgtgcgccca agggcatgga ccccatcttc ctcgccactg gatggcgcgg   4140
atgctggtcc ggccagagcc ccgttgagca acccactgag aaacccattg cattcgccca   4200
gttggatgag aagaaaatca cggcaaggac tgtggttgcc caaccttatg accccaacca   4260
agctgtgaag tgcttacgag tcttgcaggc gggtggggcg atggtggctg aggcgattcc   4320
aaaagtggtt aaggtctctg ctgtcccatt tcgagccccc ttcttcccca ccggagtgaa   4380
agttgatcct gaatgcaggg tcgtggttga cccagacacc ttcacaactg ctctccggtc   4440
cggctactcc accacaaacc tcattcttgg tgtgggggat tttgcccagc tgaatgggtt   4500
gaaaatcaga caaatttcca agccttcagg aggaggccca tacctcatgg cggccttaca   4560
tgtcgcttgc tcgatggcct tgcacatgct cgttgggatt tatgttaccg cggtgggttc   4620
ttgtggttct ggcactaacg atccgtggtg cactaacccg tttgccgtcc ctgtctacgg   4680
gcctggctct cttttgcacgt ccaggttgtg catctcccag catggcctta ctctgccttt   4740
aacagcgctt gtggcggggt ttggtattca ggaagttgct ttggttgttt taatctttgc   4800
ttccatcggg ggtatggctc acaggttgag ttgcaaggcc gatgtgctgt gcattctgct   4860
tgcaattgcc agctatgttt gggtacccctt cacctggttg ctttgtgtgt tccttgctg   4920
gttgcgctgg ttttctttgc atcccctcac cattctatgg ttggtgtttt tttgatttc   4980
tgtgaacatg ccctcaggaa tcttggcttt agtgttgttg atctctctct ggctccttgg   5040
tcgctatacc aatgtcgctg gccttgtcac cccttatgac attcaccatt acaccaacgg   5100
ccccccgcggc gttgccgcct tggccactgc cccggatggg acctatttgg ctgctgtccg   5160
ccgcgctgcg ttgactggcc gtaccatgct gtttacccccg tctcaacttg ggtcactcct   5220
tgagggcgcc tttagaaccc aaaagccttc actgaatacc gtcaatgtgg ttgggtcctc   5280
catgggctcc ggcggggtgt tcaccattga cgggaaaatt aaatgcgtga ccgccgcaca   5340
tatcctcacg ggtaactctg ctagggtctc tggggttggc ttcaatcaaa tgttggattt   5400
tgatgtaaaa ggggattttg ccatagccga ttgtccgggt tggcaaggag tcgctcccaa   5460
gtcccagatc tgcaaggatg ggtggactgg ccgcgcttat tggctaacgt cctctggcgt   5520
cgaacccggc gtcattggta ggggattcgc ctttttgtttc accgcgtgcg gcgattccgg   5580
gtccccagtg atcaccgagg ccggagagct tgtcggagtc cacacgggat caaacaaaca   5640
aggaggaggc attgtcacgc gcccttcagg ccagttttgt aatgtgacac ccaccaaact   5700
aagtgaattg agtgaattct cgccggacc cagggtcccg cttggtgatg tgaaggttgg   5760
caaccacata atcaaagata cagatgaggt gccctcagat ctttgcgcct tgcttgctgc   5820
caagcccgag ttggaaggag gcctctccac cgttcaactt ctgtgcgtgt tttttctcct   5880
atggagaatg atgggacatg cctggacgcc cttggttgct gttggttttt tcatcttgaa   5940
tgaratcctc ccagcggtcc tggtccggag tgttttctcc tttggaatgt tygykctrtc   6000
ytggctcacg ccatggtctg cgcaagttct gatgatcagg cttctgacag cagctcttaa   6060
caggaacaga tggtcacttg cctttttcag cctcggtgca gtgaccggtt ttgtcgcaga   6120
tcttgcggcc actcagggc atccgttgca ggcagtgatg aatttgagca cctatgcatt   6180
cctgcctcgg atgatggttg tgacctcacc agtcccagtg atcacgtgtg tgtcgtgca   6240
cctacttgcc atcattttgt acttgttaa gtaccgtggc ctgcaccata tccttgttgg   6300
cgatggagtg ttctctgcgg cttttcttctt gagatacttt gccgagggaa agttgaggga   6360
```

```
agggggtgtcg caatcctgcg gaatgaatca tgagtctctg actggtgccc tcgctatgag    6420
actcaatgac gaggacttgg atttccttat gaaatggact gattttaagt gctttgtttc    6480
tgcgtccaac atgaggaatg cggcgggtca gtttatcgag gccgcttatg cgaaagcgat    6540
cagggtggaa cttgcccagt tagtgcaggt cgacaaggtt cggggtgttt tagccaaact    6600
tgaagctttt gctgacaccg tggcgcccca tctttcaccc ggcgacattg ttgttgttct    6660
tggtcatacg cccgttggca gcatctttga cttaaagatt ggcratgcca agcacaccct    6720
acaagccatc gagaccagag tccttgctgg gtccaggatg accgtggcgc gtgtcgttga    6780
tccgactccc gcgccgccac ccgtacccgt gcccgttcct ctcccaccga agttttaga    6840 gaacggcccc agtgcctggg gggatgaaga ccgcctgaac aaaagaagc ggcgcaagat    6900 ggaagccgtt ggcgtttacg tcatgggcgg gaaaaagtac cagaaatttt gggataagaa    6960
ttctggtgat gtgttctatg aggaagtcca cgacaacaca gatgcgtggg aatgccttag    7020
agctgacgac cctgccgact tggatcctga gaggggaacc ttgtgtggac acgtcaccat    7080
agagaatagg ccttaccatg tttacgcctc cccgtctggt aggaagttcc tggtccctgc    7140
cgacccagag aatgggaaag cccagtggga agctgcaaag ctttccatag agcaggccct    7200
tggtatgatg aacgttgacg gcgagctgac cgccaaagaa ctggagaaat tgaagagaat    7260
aattgacaaa ctccagggcc tgactaagga gcagtgttta aactgttagc cgccagcggc    7320
ttgacccgct gtggtcgcgg cggcttggtt attactgaga cagcggtaaa aatagtcaga    7380
ttccacaatc ggaccttcac cctggggcct gtgaatttga aagtggccag cgaagttgag    7440
ttgaaagacg ccgtcgagca caaccaacac ccggttgcaa gaccagttga cggtggcgtt    7500
gtgctcctgc gctctgcagt tccttcgctt atagacgtct tgatctccgg tgccgacgca    7560
tctccccagt tgctcgccca tcacggtcca ggaaacactg ggattgatgg cacgctctgg    7620
gattttgagt ccgtagccac taagaggaa gtcgcactta gtgcacaaat aatacaggct    7680
tgtggcatta ggcgtggcga tgctcctgag attggcctcc cttacaagct gcaccctgtt    7740
agggacaacc ctgaacgtgt aaagggggtt ttgaaaaaca caaggtttgg agacatacct    7800
tacaagaccc ctagcgacac tgggagccca gtacatgcgg ccgcctgcct tacgcctaat    7860
gccaccccgg tgactgatgg gcgctccgtc ttggccacga ctatgccctc cgggtttgag    7920
ttgtatgtgc cgaccattcc agcgtctgtc cttgattacc ttgattccag gccagactgc    7980
cctaaacagt tgacggagca cgggtgtgaa aatgctgcat tgagagacct ctccaaatat    8040
gacttgtcca cccaaggttt tgttttgccc ggagtcctcc gcctcgtgcg gaaatacttg    8100
tttgcccacg tgggcaagtg cccacctgtc catcggccct ccacctaccc ggccaagaat    8160
tccatggctg gaataaacgg gaataggttc ccgaccaagg acattcagag catccctgag    8220
atcgacgttc tgtgtgcaca ggctgtacga gagaactggc agaccgttac cccttgcacc    8280
ctcaagaagc agtattgcgg gaagaagaaa accaggacca tactcggtac caataacttc    8340
attgcgctgg cccaccgggc agcactgagt ggtgtcaccc agggcttcat gaaaaaggcg    8400
tttaactcgc ccatcgccct cgggaagaac aaattcaagg agctacagac tccggtcctg    8460
ggcagatgtc ttgaggctga tcttgcctct tgcgatcggt ccactcccgc gattgtccgc    8520
tggtttgccg cccatctcct ttatgaactt gcctgcgctg aggagcacct accgtcgtat    8580
gtgctgaatt gctgccatga cctattggtc acgcagtccg gtgcggtgac taagagaggt    8640
ggcctgtcat ctggtgatcc gatcacctct gtatccaaca ccatttacag tctggtaatt    8700
tatgcgcagc acatggtgct cagttacttc aaaagtggtc acccacatgg tctcctgtat    8760
```

```
ctccaggacc agctaaagtt tgaggacatg cttaaggttc agcccctgat ygtctactcg   8820
gatgatcttg tgctgtatgc cgagtccccc accatgccaa actaccactg gtgggttgag   8880
catctgaact tgatgctagg gtttcagacg gacccaaaga agacaaccat tactgactcg   8940
ccatcttttc tgggctgtag gataatgaat gggcgtcagc tagtcccaaa ccgtgacagg   9000
attctcgcag ctcttgccta ccacatgaag gcgaataatg tttctgagta ctacgcctcc   9060
gctgctgcaa tactcatgga cagttgtgct tgtctggagt acgaccctga atggtttgaa   9120
gaacttgtgg ttggaatggc gctatgcgcc cgcaaggacg gctatagctt ccccggcccg   9180
ccgttcttct tatccatgtg ggagaaactt aagtccaatt atgaggggaa gaagtcaagg   9240
gtatgtgggt actgcggagc ttcggccccg tatgccactg cctgtggtct tgacgtctgt   9300
gtttaccaca ctcactttca ccagcattgt ccagtcataa tctggtgtgg ccaccctgca   9360
ggttccaggt cctgtgatga gtgcaaatcc cccatagga aaggcacaag ccctctggat    9420
gaggttttga gacaagtccc gtataagcct ccacggaccg tcctcatgca tgtggagcag   9480
ggcctcaccc cccttgaccc aggcagatat cagacccgcc gtgggttggt tgccgttagg   9540
cgcgggatca ggggaaatga agttgaccta ccagatggtg attatgctag caccgcctta   9600
ctcccaacct gtaaagagat caacatggtt gctgttgctt ctaatgtgtt gcgcagcaga   9660
tttatcatcg gtccacccgg tgctgggaaa acatactggc tccttcaaca ggtccaggat   9720
ggtgatgtca tatacacacc gacccatcag accatgcttg acatgatcaa agctttrggg   9780
acgtgccggt ttaacgtccc ggcaggcaca acgctgcaat tccccgtccc ctcccgcacc   9840
ggtccgtggg ttcgcatcct ggccggcggg tggtgtcctg gcaaaaactc cttcctggac   9900
gaagctgcgt attgtaatca tcttgatgtc ttgaggcttc ttagcaaaac cactctcacc   9960
tgtttggggg acttcaaaca actccaccca gtgggttttg attctcattg ctatgtcttt  10020
gacattatgc ctcagactca attgaagacc atctggagat ttggacagaa catctgtgat  10080
gccatccaac cagactacag agacaagctt atgtccatgg tcaacacaac tcgtgtaact  10140
tatgtgaaaa aacctgtcaa atatgggcaa gtcctcaccc cttaccatag ggaccgagag  10200
gatagcgcca ttaccattga ctccagtcaa ggcgccacat ttgatgtggt tacactgcat  10260
ttgcccacga aagattcact caacaaacaa agggcccttg ttgctattac cagggcaaga  10320
catgccatct ttgtgtatga cccatatagg caactgcaga gcctatttga tcttcctgca  10380
aaaagcacgc ccgtcaactt ggccgtgcac cacgatgggc aactgattgt gctagataga  10440
aataacaaag aatgcacggt tgcccaagct ctgggtaatg gtgacaaatt tagggccaca  10500
gacaagcgcg ttgtggattc tctccgcgcc atttgtgctg acctagaagg gtcgagctct  10560
ccactcccca aggttgcaca taatttgggg ttttatttct cacctgattt gatacagttt  10620
gccaagcttc aatagaact tgcgccacac tggccagtag tgacgaccca agacaataaa   10680
aactggccag atcggctggt tgccagccta cgccctattc acaaacatag ccgtgcgtgt  10740
atcggtgccg gctatatggt gggcccctcg gtgttttag gcacccctgg ggttgtgtca   10800
tactatctta caaatttgt taagggcgag gctcaagtgc ttccggaaac ggtcttcagt   10860
accggccgaa ttgaggtgga ttgccgggaa tatcttgacg accgggagcg ggaagttgca  10920
gcgtccctcc cacacgcctt tatcggcgac gtcaaaggca ctaccgtcgg agggtgtcat  10980
cacatcacct ccaaataccta tccgcgcttc ctccccaagg aatcagttgc ggtagtcggg  11040
gtttcaagcc ccggaaaagc agcgaaagca gtgtgtacat tgacagatgt gtacctccca  11100
gaccttgaag cttacctcca tcctaagacc ctgtccaagt gctggaaaat gatgttggac  11160
```

```
ttcaaagaag ttcggctgat ggtctggaag gacaagacgg cctatttcca actcgaaggt    11220
cgccatttca cctggtatca acttgctagc tatgcctcgt acatccgtgt tcctttaaac    11280
tccacggtgt acctggaccc ctgcatgggc cccgcccttt gcaacagaaa agttgttggg    11340
tccactcatt ggggagctga cctcgcagtc accccttatg attatggggc aagaattatt    11400
ttgtctagtg cgtaccatgg tgagatgcct cctgggtaca agattctggc gtgcgcggag    11460
ttctcgctgg acgacccagt cagatacaag cacacttggg ggtttgagtc ggatacagcg    11520
tacttgtacg agttcactgg aaacggtgag gactgggagg attataacga cgcgtttcgt    11580
gcgcgacaga aaggaaagat ttacaaggcc actgccacca gcctgaagtt ccattttcct    11640
ccgggtcata ccgttgaacc aactttgggc ctagactgaa atgaaatggg ggctgtgcag    11700
agcctatttg ataaaattgg ccaactgttt gtggacgctt tcacggagtt cttggtgtcc    11760
attgttgata tcatcatatt tttggccatt ttgttcggct tcacaatcgc cggttggctg    11820
gtggtctttt gcatcagatt ggtttgctcc gcgatactcc gttcgcgctc tgccgttcac    11880
cctgagcaat tacagaagat cctatgaggc atttctctcc cagtgccgga cggayattcc    11940
cacctgggga actaaacatc ccttggggat gctctggcac cacaaggtgt cgaccctaat    12000
tgatgaaatg gtgtcgcgtc gaatgtaccg catcatggaa caagcagggc aggctgcctg    12060
gaaacaggtg gtgaccgagg caacgttgtc tcgtattagt agcttggatg tggtggctca    12120
tttccagcac cttgccgcca tagaagccga gacttgtaaa tacttggcct cccggctgcc    12180
aatgctgcac aacctgcgca tgacagggtc aaatgtaacc atagtgtata atagctctct    12240
agaacaggtg tttgctgttt tcccgaccct cagttcccgg ccaaagcttc atgattttcg    12300
gcaatggcta atagctgtgc attcctccat attctcttct gttgcggctt cctgtaccct    12360
tttcgtcgtg ctgtggttgc ggcttccaat aatacgtact gttttggtt tccactggtt     12420 agggcaatt tttccttcga gctcacagtg aactacacgg tgtgtcctcc ctgcctcacc      12480
cggcaggcgg ccgcagagat ctacgaacct agtgggtctc tttggtgcag gatagggcac    12540
gatcgatgct cggaggacga tcacgacgag ctaggatttc tggtgccgcc tggcctctcc    12600
agcgaaggcc acttgaccag tgtttacgcc tggttggcgt tcttgtcctt cagttacacg    12660
gcccagtttc accccgagat attcgggata gggaatgtga gtaaagttta tgttgacatc    12720
aagcatcaat ttatttgcgc tgttcatgac gggcaaaaca ccaccttgcc tcgccatgac    12780
aacgtctcag ccgtgttcca gacttattac cagcatcagg tcgacggcgg caattggttt    12840
cacctggaat ggctgcgccc cttcttctcc tcctggttgg ttttgaacgt ctcttggttt    12900
ctcaggcgtt cgcctgtaag ccgtgtttca gttcgagtct ctcagacatt aagaccaaca    12960
ccaccgcagc tgcaggcttt gctgtcctcc aagacatcag ttgtcttagg catggccact    13020
cgtcctctga ggcgactcgc aaaagccgtc aatgtcgcac ggcgatagga acgcccgtat    13080
acattactgt cacagccaat gtaacagatg agaattattt gcattcctct gaccttctca    13140
tgctttcctc ttgcctttc tacgcttccg agatgagtga aaagggatt gaagtgatat      13200 ttggcaatgt gtcaggcata gtggctgtgt gtgtcaactt taccagctat gtccaacatg    13260
tcaaggagtt cacccagcgc tccttggtgg ttgaccatgt gcggttactt cattttatga    13320
cacctgagac tatgaggtgg gcgaccgttt tagcctgtct ttttgccatt ctgttggcca    13380
tttgaatgtt cagatatgtt ggggaaatgc ttgaccgcgg gctattgctc gcaattgctt    13440 ttttttgtggt gtatcgtgcc gttctgtctt gctgcgctcg tcaacgccga cagcaacagc    13500
agctcccatt tacagttgat ttataamtta acgatatgtg agctgaatgg cacagactgg    13560
```

-continued

```
ctgaacaatc attttagttg ggcagtggag actttcgtta tctttcctgt gttgactcat  13620
attgtttcct acggcgccct cactaccagc cacctccttg acacggtcgg cctgatcact  13680
gtgtccaccg ccggatactg ccataagcgg tatgtcttga gtagcatcta tgctgtctgc  13740
gccctggctg cgctgatttg cttcgtcatc aggttgacga aaaattgtat gtcctggcgc  13800
tactcatgta ccagatatac caactttctt ctggacacca agggcagact ctatcgctgg  13860
cggtcacccg tcatcataga gaaaaggggt aaaattgagg ttggaggtga cctgatcgac  13920
ctcaagagag ttgtgcttga tggttccgcg gcaacccctg taaccaaagt ttcagcggaa  13980
caatggggtc gtccttagac gacttctgca atgacagcac ggctccacaa aaggtgatct  14040
tggcattttc tatcacctac acaccagtga tgatatatgc cctaaaggtg agtcgtggcc  14100
ggctgctagg gcttttacac cttttgattt ttytaaactg tgcttttacc ttcgggtata  14160
tgacatttgt gcactttcag agcacaaaca gagttgcact cactatggga gcagtagtcg  14220
cgctcctttg gggggtgtac tcagctatag aaacctggaa attcatcact tccagatgcc  14280
gtttgtgctt gctaggccgc aagtacattc tggcccctgc ccaccacgtt gagagtgccg  14340
caggctttca tccgattgcg gcaagtgata accacgcatt tgtcgtccgg cgtcccggtt  14400
ccactacggt taacggcaca ttggtgcccg ggttgaaaag cctcgtgttg ggtggcagaa  14460
gagctgtcaa acggggagtg gtaaacctcg ttaaatatgc caaataacaa cggcaggcag  14520
cagaagaaaa agaaagggga cggccagcca gtcaatcagc tgtgccaaat gttgggcagg  14580
atcatcgccc agcaaaacca gtccagaggt aagggaccgg ggaagaaaag taagaagaaa  14640
agcccggaga agccccattt tcctctcgcg actgaagatg acgttagaca tcacttcacc  14700
cctagtgagc ggcaattgtg tctgtcgtca atccagactg cctttaacca aggcgctgga  14760
acttgtaccc tgtcggattc agggagaata agttacgctg tggagtttag tttgcctacg  14820
catcatactg tgcgcctaat tcgcgtcaca gcatcaccct cagcatgatg agctggcatt  14880
cttgagacat cccagtgttt gaattggaag gatgtgtggt gaatggcact gattgatatt  14940
gtgcctytaa gtcacctatt caattagggc gaccgtatgg gggtaatatt taattggcgt  15000
gaaccatgcg gccgaaatt                                                15019
```

```

<210> SEQ ID NO 6
<211> LENGTH: 15019
<212> TYPE: DNA
<213> ORGANISM: Artificial Sequence
<220> FEATURE:
<223> OTHER INFORMATION: Porcine reproductive and respiratory syndrome
      virus, strain MN184B
<220> FEATURE:
<221> NAME/KEY: misc_feature
<222> LOCATION: (1540)..(1540)
<223> OTHER INFORMATION: R = A or G
<220> FEATURE:
<221> NAME/KEY: misc_feature
<222> LOCATION: (1546)..(1546)
<223> OTHER INFORMATION: Y = C or T
<220> FEATURE:
<221> NAME/KEY: misc_feature
<222> LOCATION: (1549)..(1549)
<223> OTHER INFORMATION: R = C or A
<220> FEATURE:
<221> NAME/KEY: misc_feature
<222> LOCATION: (1558)..(1558)
<223> OTHER INFORMATION: Y = C or T
<220> FEATURE:
<221> NAME/KEY: misc_feature
<222> LOCATION: (1559)..(1559)
<223> OTHER INFORMATION: R = C or A
<220> FEATURE:
<221> NAME/KEY: misc_feature
```

```
<222> LOCATION: (2110)..(2110)
<223> OTHER INFORMATION: Y = C or T
<220> FEATURE:
<221> NAME/KEY: misc_feature
<222> LOCATION: (2161)..(2161)
<223> OTHER INFORMATION: R = C or A
<220> FEATURE:
<221> NAME/KEY: misc_feature
<222> LOCATION: (2186)..(2186)
<223> OTHER INFORMATION: R = C or A
<220> FEATURE:
<221> NAME/KEY: misc_feature
<222> LOCATION: (5389)..(5389)
<223> OTHER INFORMATION: R = C or A
<220> FEATURE:
<221> NAME/KEY: misc_feature
<222> LOCATION: (5687)..(5687)
<223> OTHER INFORMATION: R = C or A
<220> FEATURE:
<221> NAME/KEY: misc_feature
<222> LOCATION: (5694)..(5694)
<223> OTHER INFORMATION: Y = C or T
<220> FEATURE:
<221> NAME/KEY: misc_feature
<222> LOCATION: (5698)..(5698)
<223> OTHER INFORMATION: R = C or A
<220> FEATURE:
<221> NAME/KEY: misc_feature
<222> LOCATION: (5699)..(5699)
<223> OTHER INFORMATION: Y = C or T
<220> FEATURE:
<221> NAME/KEY: misc_feature
<222> LOCATION: (5704)..(5704)
<223> OTHER INFORMATION: Y = C or T
<220> FEATURE:
<221> NAME/KEY: misc_feature
<222> LOCATION: (5710)..(5710)
<223> OTHER INFORMATION: R = C or A
<220> FEATURE:
<221> NAME/KEY: misc_feature
<222> LOCATION: (5722)..(5722)
<223> OTHER INFORMATION: Y = C or T
<220> FEATURE:
<221> NAME/KEY: misc_feature
<222> LOCATION: (5724)..(5724)
<223> OTHER INFORMATION: Y = C or T
<220> FEATURE:
<221> NAME/KEY: misc_feature
<222> LOCATION: (5728)..(5728)
<223> OTHER INFORMATION: R = C or A
<220> FEATURE:
<221> NAME/KEY: misc_feature
<222> LOCATION: (5733)..(5733)
<223> OTHER INFORMATION: R = C or A
<220> FEATURE:
<221> NAME/KEY: misc_feature
<222> LOCATION: (5743)..(5743)
<223> OTHER INFORMATION: Y = C or T
<220> FEATURE:
<221> NAME/KEY: misc_feature
<222> LOCATION: (5749)..(5749)
<223> OTHER INFORMATION: Y = C or T
<220> FEATURE:
<221> NAME/KEY: misc_feature
<222> LOCATION: (6511)..(6511)
<223> OTHER INFORMATION: R = C or A
<220> FEATURE:
<221> NAME/KEY: misc_feature
<222> LOCATION: (6523)..(6523)
<223> OTHER INFORMATION: Y = C or T
<220> FEATURE:
<221> NAME/KEY: misc_feature
<222> LOCATION: (8050)..(8050)
<223> OTHER INFORMATION: R = C or A
<220> FEATURE:
<221> NAME/KEY: misc_feature
<222> LOCATION: (9345)..(9345)
<223> OTHER INFORMATION: R = C or A
<220> FEATURE:
<221> NAME/KEY: misc_feature
```

```
<222> LOCATION: (10309)..(10309)
<223> OTHER INFORMATION: R = C or A
<220> FEATURE:
<221> NAME/KEY: misc_feature
<222> LOCATION: (10419)..(10419)
<223> OTHER INFORMATION: R = C or A
<220> FEATURE:
<221> NAME/KEY: misc_feature
<222> LOCATION: (14947)..(14947)
<223> OTHER INFORMATION: Y = C or T
<220> FEATURE:
<221> NAME/KEY: misc_feature
<222> LOCATION: (15018)..(15018)
<223> OTHER INFORMATION: Y = C or T

<400> SEQUENCE: 6
```

| | | | | | |
|---|---|---|---|---|---|
| atgacgtata | ggtgttggct | ctatgccacg | acatttgtat | tgtcaggagc | tgtgaccact | 60 |
| ggcacagccc | aaagcttgct | gcacagaaac | acccttctgt | gacggcctcc | ttcaggggag | 120 |
| tttaggggtt | tgtccctagc | accttgtttc | tggagttgca | ctgctttacg | gtctctccac | 180 |
| cccttaacc | atgtctggga | ttcttgatcg | gtgcacgtgc | accccaatg | ccagggtgtt | 240 |
| tatggcagag | ggccaagtct | actgcacacg | atgtctcagt | gcacggtccc | tccttcccct | 300 |
| gaatctccaa | gtctctgagc | tcggagtgtt | gggcttgttt | tataggcctg | aagagccgct | 360 |
| ccggtggacg | ttgccacgcg | cattccccac | tgttgagtgc | tcccctgctg | gggcttgttg | 420 |
| gctttctgca | attttccaa | ttgcacgaat | gaccagtgga | aacctgaact | ttcaacaaag | 480 |
| attagtgcgg | gtcgcagctg | agctttacaa | agccggctgc | ctcaccccta | cagtcctaaa | 540 |
| gagtctacaa | gtctatgaac | ggggttgccg | ctggtacccc | atcgttggac | ctgtccctgg | 600 |
| agttgccgtt | ttcgccaact | ccctacatgt | gagtgataga | cctttcccag | gtgctactca | 660 |
| cgtgctaacc | aacctgccgc | tcccgcagag | acctaagcct | gaagattttt | gccccttga | 720 |
| gtgtgctatg | gctgccgtct | atgacattgg | tcatgacgcc | gttatgttcg | tggccgaagg | 780 |
| gagagtctct | tgggctccgc | gtggtgggga | aaaaggaaaa | tttgaaactg | ttcccgagga | 840 |
| gttggggttg | attgcagagc | aactttatac | ctccttcccg | ccccaccact | tggtggacat | 900 |
| gtcgaaattc | accttacgg | cccctgagtg | tggtgcttcc | atgcgagtcg | aacgccagta | 960 |
| tggctgcctc | cccgctggca | ctgtccctga | cggcaattgc | tggtggagct | tgtttagctc | 1020 |
| gctcccattg | gaagtccagt | ataaagaaat | tcgctacgcc | acccaatttg | gctatcaaac | 1080 |
| taagcatggc | gttgctggca | agtacctaca | gcggaggctg | caaattaatg | gtctccgagc | 1140 |
| agtggttgac | tcgaatggac | ccatcgtcat | acagtactc | tctgttaagg | agagctggat | 1200 |
| ccgccacgtg | aaactggcgg | aagagtttga | ctaccctggg | tttgaggatc | tcctcaggat | 1260 |
| aagagtcgag | cccaacacgt | tgccattgtc | caacaaggac | gagaaaatct | tccggtttgg | 1320 |
| tgggtgcaag | tggtacggtg | ctgggaagag | ggcaaggagg | gcacgtgcaa | gtgcagtcac | 1380 |
| cgcagtcgcc | ggtcacgctc | cgcctactcg | tgaaacccag | caagccaaga | aacacgaagc | 1440 |
| tgctagtgcc | aacaaggctg | agcttcttga | acgctactcc | ccgcctgctg | aagggaattg | 1500 |
| cggctggcac | tgtatctccg | ccatcgccaa | ccggatggtr | aattcyaart | ttgaaacyrc | 1560 |
| ccttcccgaa | agagtgagac | ctccagatga | ctgggctact | gacgaggatc | ttgtgaatgc | 1620 |
| catccaaatc | ctcagactcc | ctgcggcctt | agacaggaac | ggtgcttgta | ctagcgccaa | 1680 |
| gtacgtactt | aagctggaag | gtgagcattg | gactgtcact | gtgaccctg | ggatgtcccc | 1740 |
| ttctttgctc | cctcttgaat | gtgttcaggg | ctgttgtggg | cacaagggcg | gtcttggttc | 1800 |
| cccagatgca | gtcgaggtct | ccggatttga | ccctgcctgc | cttgaccggc | tggctgaggt | 1860 |
| gatgcacctg | cctagcagtg | ctatcccagc | cgctctggcc | gaaatgtctg | gcgattccga | 1920 |

```
tcgttcggct ctctccggtca ccaccgtgtg gactgtttcg cagttctttg cccgtcacag    1980
cggagggaat caccctgacc aagtgcgctt agggaaaatt atcagccttt gtcaggtgat    2040
tgaggactgc tgctgttccc agaacaaaac caaccgggtc accccggagg aggtcgcagc    2100
aaagattgay cagtaccttt ttggtgcagc aagtcttgaa gaatgcttgg ccaggcttga    2160
raaagctcgc ccgccaagcg tattaracac ctcctttgat tgggatgttg tgctccctgg    2220
tgtcggggcg gctgctcaag cagcaaaact gcccctcacc aaccagcgtc acgctctagc    2280
cactgttgtg actcaaaggt cttttgccgaa atttcaacct cgaaaagcgg agtctgtcaa    2340
gagcctacca gagagcaggc ccctccctgc cccgcgcaaa aagattgggt ccaggtgtgg    2400
tagtccgatt tcattgggcg gcaatctccc tgacagccgg gaagacttgg ccggtggttc    2460
ctttgatttc ccaaccctac ctgagttggt ggcaagctcg agcgagcctg tgcctgtccc    2520
tgcaccgcgc agggttgtgt cccgattagt gtcgtctccg atagtgtcga cccctgtgcc    2580
cgcaccacga cgtgggcttc ggcaggtgga gggaatgaat ttggcggcgg tgactctagc    2640
gtgccaggac gagcccctcg atttgtctgc gtcctcgcag actgaatatg aggcgtcccc    2700
cttggcattg ccgctgagtg aggatgtcct ggcggtggag agacgagaag ttgaagaagt    2760
cctgagcgga atatcgggca tgccagatga catcaggttg gcgcccgtgt catcaagtag    2820
ctccctgtca agcatagaga tcacgcgtcc aaagtactca gctcaagcca tcattaactc    2880
aggtgggccc tgttgtgggc acctccagga ggtaaaagag aaataccttta atgtgatgcg    2940
tgaggcatgt gatgcgacca gcttgatga ccctgccacg caagaatggc tttcccgcat     3000
gtgggatagg gtagacatgc taacctggcg caacacgtcc attttttcagg cgccttttcac   3060
cttggctgac aagtttaaga ccctcccgaa gatgatactc gaaacaccgc cgccctaccc    3120
ttgtgggttt gtgatgatgc cccgcacgcc tgcaccttct gtaggtgcgg agagcgacct    3180
caccgttggc tcagttgcta ctgaggatgt cccgcgcatt ctcgggaatg tacaaggtgt    3240
tggcgaaacg accgaccagg gaccccttggc acccttcgca gacgaattgg cagatgacca    3300
acttgctaga gaaccccgga cacaaacccc tcctgcaagc acaggtggcg ccggcttggt    3360
ttcggattct ggaaggtcgc cggagctcac tgacctgccg ctttcaaacg gtacagacgc    3420
gggcggaggg gggccgttac acacggtcaa gaagaaagct gagaggtgct ttgaccagct    3480
gagccgtcgg gttttttgaca ttgtctccca tctccctgtt ttcttctcac gccttttcaa    3540
gcctgacagt cactactctt cgggtgactg gagttttgca gcttttactt tattgtgcct    3600
cttttctatgt tacagttacc cagcctttgg tgttgctccc ctattgggtg tatttttctgg   3660
gtcttctcgg cgcgttcgca tgggggtttt tggctgctgg ttggcttttcg ctgttggttt    3720
gttcaagcct gcacccgacc cagtcggtgc tgcttgtgag tttgattcgc cagagtgtag    3780
agacatcctt cattcttttg agcttctgca accttgggac cctgttcgca gccttgtggt    3840
ggggcccgtc ggtctcggtc ttgccattat tggcaggtta ctgggcgggg cacgctacgt    3900
ctggctgctt ttgcttaggc ttggcatcgt ttcagactgt atcttggctg agcttatgt     3960
gctttcgcaa ggtaggtgta aaagtgttg gggatcttgt ataagaactg ctcccagtga    4020
ggtcgccttc aatgtgtttc ccttcacacg tgcaaccaga tcgtcacttg tcgacctgtg    4080
cgaccggttt tgtgcgccca agggcatgga ccccatcttc ctcgccactg gatggcgcgg    4140
atgttggtcc ggccagagcc ccattgagca acccactgag aaacccattg cgttcgccca    4200
gttggatgaa aagaaaatca cggcaaggac tgtggttgcc caaccttatg accccaacca    4260
agctgtgaag tgcttacgag tcttgcaggc gggtggggcg atggtggctg aggcggttcc    4320
```

```
aaaagtggtt aaggtctctg ctgtcccatt tcgagccccc ttcttccccg ccggagtgaa    4380
agttgatcct gaatgcaggg tcgtggttga cccagacacc ttcacaactg ctctccggtc    4440
cggctactcc accacaaacc tcattcttgg tatgggggat tttgcccaac tgaatgggtt    4500
gaaaatcaga caaatttcca agccttcagg aggtggtcca tacctcatgg cggccttaca    4560
tgtcgcttgc tcgatggcct tgcacatgct cgttgggatt tatgttaccg cggtgggttc    4620
ttgtggttct ggcactaacg atccgtggtg cactaacccg tttgccgtcc ctgtctacgg    4680
gcctggctct ctttgcacgt ccaggttgtg catctcccag catggcctta ctctgccttt    4740
aacagcgctt gtggcggggt ttggcattca ggaagttgct ttggttgttt taatctttac    4800
ttccatcggg ggtatggctc acaggttgag ctgcaaggcc gatgtgctgt gtattctgct    4860
tgcaattgcc agctatgttt gggtacccct cacctggttg ctttgtgtgt ttccttgctg    4920
gttgcgctgg ttttctttgc atcccctcac cattctatgg ttggtgtttt tcttgatttc    4980
tgtgaacatg ccctcaggaa tcttggcttt agtgttgttg atctctctct ggctccttgg    5040
tcgctatacc aatgtcgctg gccttgtcac cccttatgac attcaccatt acaccaacgg    5100
cccccgcggc gttgccgcct tggccactgc cccggatggg acctatttgg ctgctgtccg    5160
ccgcgctgcg ttgactggcc gcaccatgct gtttaccccg tctcaacttg ggtcactcct    5220
tgagggcgcc tttagaaccc aaaagccttc actgaatacc gtcaatgtgg ttgggtcctc    5280
catgggctcc ggcggggtgt tcaccattga cgggaaaatt aagtgcgtga ccgccgcaca    5340
tatcctcacg ggtaactctg ctagggtctc tggggttggc ttcaatcara tgttggattt    5400
tgatgtaaaa ggggattttg ccatagccga ttgtccgggt tggcagggag tcgctcccaa    5460
gtcccagttc tgcaaggatg ggtggactgg ccgcgcttat tggctaacgt cctctggcgt    5520
cgaacccggc gtcattggta ggggattcgc cttttgtttc accgcgtgcg gcgattccgg    5580 gtcccccagtg atcaccgagg ccggagagct tgtcggagtc cacacgggat caaacaaaca    5640
aggaggaggc attgtcacgc gcccttcagg ccagttttgt aatgtgrcac ccaycaaryt    5700
aagygaattr agtgaattct tygcyggrcc targgtcccg ctyggtgayg tgaaggtcgg    5760
cagccacata attaaagaca taagcgaggt gccttcagat ctttgtgcct tgcttgctgc    5820
caaacctgaa ctggaaggag gcctctccac cgtccaactt ctttgtgtgt ttttctcct    5880 gtggagaatg atgggacatg cctggacgcc cttggttgct gtgagtttct ttattttgaa    5940
tgaggttctc ccagccgtcc tggtccggag tgttttctcc tttggaatgt tgtgctatc    6000 ctggctcacg ccatggtctg cgcaagttct gatgatcagg cttctgacag cagctcttaa    6060
caggaacaga tggtcacttg cctttttcag cctcggtgca gtgaccggtt ttgtcgcaga    6120
tcttgcggcc actcaggggc atccgttgca ggcagtgatg aatttgagca cctatgcatt    6180
cctgcctcgg atgatggttg tgacctcacc agtcccagtg atcacgtgtg gtgtcgtgca    6240
cctacttgcc atcattttgt acttgtttaa gtaccgtggc ctgcaccata tccttgttgg    6300
cgatggagtg ttctctgcgg cttttcttctt gagatacttt gccgagggaa agttgaggga    6360
aggggtgtcg caatcctgcg gaatgaatca tgagtctctg actggtgccc tcgctatgag    6420
actcaatgac gaggacttgg atttccttat gaaatggact gattttaagt gctttgtttc    6480
tgcgtccaac atgaggaatg cagcgggtca rtttatcgag gcygcctatg cgaaagcgat    6540
cagggtggaa cttgcccagt tagtgcaggt cgacaaggtt cggggtgttt tagccaaact    6600
tgaagctttt gctgacaccg tggcgcccca tctttcaccc ggcgacattg ttgttgttct    6660
tggtcatacg cccgttggca gcatctttga cttaaagatt ggcaatgcca agcacaccct    6720
```

```
acaagccatc gagaccagag tccttgctgg gtccaggatg accgtggcgc gtgtcgttga   6780
tccgactccc gcgccgccac ccgtacccgt gcccgttcct ctcccaccga aagttttaga   6840
gaacggcccc agtgcctggg gggatgaaga ccgcctgaac aaaaagaagc ggcgcaagat   6900
ggaagccgtt ggcatttacg ttatgggcgg gaaaaagtac cagaaatttt gggataagaa   6960
ttctggtgat gtgttctatg aggaagtcca cgacaacaca gatgcgtggg aatgccttag   7020
agctgacgac cccgccgact tggatcctga gaggggaacc ttgtgtggac acgtcaccat   7080
agagaatagg ccttaccatg tttatgcctc cccgtctggt aggaagttcc tggtccctgc   7140
cgacccagag aatgggaaag cccagtggga agctgcaaag ctttccatgg agcaggccct   7200
tggtatgatg aacgttgacg gcgagctgac cgccaaagaa ctggagaaat tgaagagaat   7260
aattgacaaa ctccagggcc tgactaagga gcagtgttta aactgttagc cgccagcggc   7320
ttgacccgct gtggtcgcgg cggcttggtt attactgaga cagcggtaaa aatagtcaga   7380
ttccacaatc ggaccttcac cctggggcct gtgaatttga aagtggccag cgaagttgag   7440
ttgaaagacg ccgtcgagca caaccaacac ccggttgcaa gaccagttga cggtggcgtt   7500
gtgctcctgc gctctgcagt tccttcgctt atagacgtct tgatctccgg tgccgacgca   7560
tctccccagt tgctcgccca tcacgggcca ggaaacactg ggattgatgg cacgctctgg   7620
gattttgagt ccgtagccac taaagaggaa gtcgcactta gtgcacaaat aatacaggct   7680
tgtggcatta ggcgtggcga tgctcctgag attggcctcc cttacaagct gcaccctgtt   7740
aggggcaacc ctgaacgtgt gaaggggtt ttgaaaaaca caaggtttgg agacataccc   7800
tacaggaccc ctagcgacac tgggagccca gtacatgcgg ccgcctgcct tacgcctaac   7860
gccacccegg tgactgatgg gcgctccgtc ttggccacga ctatgccctc cgggtttgag   7920
ttgtatgtgc cgaccattcc agcatctgtc cttgattacc ttgattccag gccagactgc   7980
cctaaacagt tgacggagca cggggtgtgaa gatgctgcat tgagagacct ctccaaatat   8040
gacttgtccr cccaaggttt tgttttgccc ggagtcctcc gcctcgtgcg gaaatacttg   8100
tttgcccacg tgggcaagtg cccacctgtc catcggccct ccacctaccc ggccaagaat   8160
tccatggctg aataaacgg gaataggttc ccaaccaagg acattcagag catccctgag   8220
atcgacgttc tgtgtgcaca ggctgtacga gagaactggc agaccgttac cccttgcacc   8280
ctcaagaagc agtattgcgg gaagaagaaa accaggacca tactcggtac caataacttc   8340
attgcgctgg cccaccggc agcactgagt ggtgtcaccc agggcttcat gaaaaaggcg   8400
tttaactcgc ccatcgccct cgggaagaac aaattcaagg agctacagac tccggtcctg   8460
ggcagatgcc ttgaggctga tcttgcctct tgcgatcgat ccactcccgc gattgtccgc   8520
tggtttgccg cccatctcct ttatgaactt gcctgcgctg aggaacacct accgtcgtat   8580
gtgctgaatt gctgccatga cctattggtc acgcagtccg gtgcggtgac taagagaggt   8640
ggcctgtcat ctggtgatcc gatcacctcg gtatccaaca ccatttacag tctggtgatt   8700
tatgcgcagc acatggtgct cagttatttc aaaagtggtc acccacatgg tctcctgttt   8760
ctccaggacc agctaaagtt tgaggacatg cttaaggttc agcccctgat tgtctactcg   8820
gatgatcttg tgctgtatgc cgagtctccc accatgccaa actatcactg gtgggttgag   8880
catctgaact tgatgctagg gtttcagacg gacccaaaga agacaaccat tactgactcg   8940
ccatcttttc tgggctgtag gataatgaat gggcgtcagc tagtcccaaa ccgtgatagg   9000
attctcgcag ctcttgccta ccacatgaag gcgaataatg tttctgagta ctacgcctcc   9060
gctgctgcaa tactcatgga cagttgtgct tgtctggagt acgaccctga atggtttgaa   9120
```

```
gaacttgtgg ttggaatggc gcaatgcgcc cgcaaggacg gctatagctt ccccggcccg   9180
ccgttcttct tatccatgtg ggagaaactc aggtccaatt atgaggggaa gaagtcaagg   9240
gtgtgtgggt actgcggagc ttcggccccg tatgccactg cctgtggtct tgacgtctgt   9300
gtttaccaca ctcactttca ccagcattgt ccagtcataa tctgrtgtgg ccaccctgca   9360
ggttccaggt cctgtgatga gtgcaaatcc cccataggga aaggtacaag ccctctggat   9420
gaggttttaa dacaagtccc gtataagcct ccacggaccg tcctcatgca tgtggagcag   9480
ggcctcaccc cccttgaccc aggcagatat cagacccgcc gtgggttggt tgccgttagg   9540
cgcgggatca ggggaaatga agttgaccta ccagatggtg attatgctag caccgcctta   9600
ctcccaacct gtaaagagat caacatggtt gctgttgctt ctaatgtgtt gcgcagcaga   9660
tttatcatcg gtccacccgg tgctgggaaa acatactggc tccttcaaca ggtccaggat   9720
ggtgatgtca tatacacacc gacccatcag accatgcttg acatgatcaa agctttgggg   9780
acgtgccggt ttaacgtccc ggcaggcaca acgctgcaat tccccgcccc ttcccgcact   9840
ggcccgtggg ttcgcatcct ggccggcggg tggtgtcctg gcaaaaactc cttcctggac   9900
gaagctgcgt attgtaatca tcttgatgtc ttgaggcttc ttagcaaaac cactctcacc   9960
tgtttagggg acttcaaaca actccaccca gtgggttttg attctcattg ctatgtcttt  10020
gacattatgc ctcagactca actgaagacc atctggagat ttggacagaa catctgtgat  10080
gccatccaac cagactacag agacaagctt atgtccatgg tcaacacaac tcgtgtaact  10140
tatgtggaaa aacctgtcaa acatgggcaa gtcctcaccc cttaccatag ggaccgagag  10200
gatagcgcca ttaccattga ctccagtcaa ggcgccacat ttgatgtggt tacactgcat  10260
ttgcccacga aagattcact caacaaacaa agggcccttg ttgctattrc cagggcaaga  10320
catgccatct ttgtgtatga cccacatagg caactgcaga gcctatttga tcttcctgca  10380
aaaagcacgc ccgtcaactt ggccgtgcac cacgatggrc aactgattgt gctagataga  10440
aataacaaag aatgcacggt tgcccaagct ctgggtaatg gtgacaaatt tagggccaca  10500
gacaagcgcg ttgtggattc tctccgcgcc atttgtgctg acctagaagg gtcgagctct  10560
ccactcccca aggttgcaca taatttgggg ttttatttct cacctgattt gacacagttt  10620
gccaagcttc caatagaact tgcgccacac tggccagtag tgacgaccca agacaataaa  10680
aactggccag atcggctggt tgccagcctg cgccctattc acaaacatag ccgtgcgtgc  10740
atcggtgccg gctatatggt gggcccctcg gtgttttttag gcaccctggg ggttgtgtca  10800
tactatctta caaaatttgt taagggcgag gctcaagtgc ttccggaaac ggtcttcagt  10860
actggccgaa ttgaggtaga ttgccggaa tatcttgacg accgggagcg ggaagttgca  10920
gcgtccctcc cacacgcctt tatcggcgac gtcaaaggca ctaccgtcgg agggtgtcat  10980
cacatcacct ccaaatacct tccgcgcttc ctccccaagg aatcagttgc ggtagtcggg  11040
gtttcaagcc ccggaaaagc agcgaaagca gtgtgtacat tgacagatgt gtacctccca  11100
gaccttgaag cttacctcca tcctaagacc ctgtccaagt gctggaaaat gatgttggac  11160
ttcaaagaag ttcggctgat ggtctggaag gacaagacgg cctatttcca actcgaaggt  11220
cgccatttca cctggtatca acttgctagc tatgcctcgt acatccgtgt tccttaaac  11280 tccacggtgt acctggaccc ctgcatgggc cccgcccttt gcaacagaaa agtcgttggg  11340
tccactcatt ggggagctga cctcgcagtc acccccttatg attatggggc aagaattatt  11400
ttgtctagtg cgtaccatgg tgagatgcct cctgggtaca agattctggc gtgcgcggag  11460
ttctcgctgg acgacccagt cagatacaag cacacttggg ggtttgagtc ggatacagcg  11520
```

```
tacttgtacg agttcactgg aaacggtgag gactgggagg attataacga cgcgtttcgt   11580
gcgcgacaga aaggaaagat ttacaaggcc actgccacca gcctgaagtt ccattttcct   11640
ccgggtcata ccgttgaacc aactttgggc ttagactgaa atgaaatggg ggctgtgcag   11700
agcctatttg ataaaattgg ccaactgttt gtggacgctt tcacggagtt cttggtatcc   11760
attgttgata tcatcatatt tttggccatt ttgttcggct tcacaatcgc cggttggctg   11820
gtggtctttt gcatcagatt ggtttgctcc gcgatactcc gttcgcgctc tgccgttcac   11880
cctgagcaat tacagaagat cctatgaggc atttctctcc cagtgccgga cggacattcc   11940
cacctgggga actaaacatc ccttggggat gctctggcac cacaaggtgt cgaccctaat   12000
tgatgaaatg gtgtcgcgtc gaatgtaccg caccatggaa caagcagggc aggctgcctg   12060
gagacaggtg gtgaccgagg caacgttgtc tcgtattagt aacttggatg tggtggctca   12120
tttccagcac cttgccgcca tagaagccga gacttgtaaa tacttggcct cccggctgcc   12180
aatgctgcac aacctgcgca tgacagggtc aaatgtaacc atagtgtata atagctctct   12240
agaacaggtg tttgctattt tcccgaccct cgattcccgg ccaaagcttc atgattttcg   12300
gcaatggcta atagctgtgc attcctccat attctcttct gttgcggctt cctgtaccct   12360
tttcgtcgtg ctgtggttgc ggcttccaat aatacgtact gttttggtt tccactggtc    12420 aggggcaatt tttccttcga gctcacagtg aactacacgg tgtgtcctcc ctgcctcacc   12480
cggcaggcgg ccgcagagat ctacgaacct ggtgggtctc tttggtgcag gatagggcac   12540
gatcgatgct cggaggacga tcacgacgag ctaggatttc tggtgccgcc tggcctctcc   12600
agcgaaggcc acttgaccag tgtttacgcc tggttggcgt tcttgtcctt cagttacacg   12660
gcccagtttc accccgagat attcggaata gggaatgtga ccaagtttta tgttgacatc   12720
aagcatcaat ttatttgtgc tgttcatgac gggcaaaaca ccaccttgcc tcgccatgac   12780
aacgtctcag ccgtgttcca gacttattac cagcatcagg tcgacggcgg caattggttt   12840
cacctggaat ggctgcgccc cttcttctcc tcctggttgg ttttgaacgt ctcttggttt   12900
ctcaggcgtt cgcctgtaag ccgtgtttca gttcgagtct ttcagacatt aagaccaaca   12960
ccaccgcagc tgcaggcttt gctgtcctcc aagacatcag ctgtcttagg catggccact   13020
cgtcctctga ggcgactcgc aaaggccgcc aatgccgcac ggcgatagga acgcccgtat   13080
acattactgt cacagccaat gtaacagatg agaattattt gcattcctct gaccttctca   13140
tgctttcctc ttgccttttc tacgcttccg agatgagtga aaagggattt gaggtgtatat   13200 ttggcaatgt gtcaggcata gtggctgtgt gtgtcaactt taccagctat gtccaacatg   13260
ttaaggagtt cacccagcgc tccttggtgg ttgaccatgt gcggttactt cattttgtga   13320
cacctgagac tatgaggtgg gcgaccgttt tagcctgtct ttttgccatt ctgttggcca   13380
tttgaatgtt cagatatgtt ggggaaatgc ttgaccgcgg gctattgctc gcaattgcct   13440
tttttgtggt gtatcgtgcc gttctgtctt gctgcgctcg tcaacgccag cagcaacagc   13500
agctcccact tacagttgat ttataactta acgatatgtg agctgaatgg cacagactgg   13560
ctgaatgatc attttagttg ggcagtggag actttcgtta tctttcctgt gttgactcac   13620 attgttcct acggcgccct cactaccagc cacttccttg acacggtcgg cctgatcact   13680
gtgtccaccg ccggatacta ccatgcgcgg tatgtcttga gtagcatcta tgccgtctgc   13740
gccctggctg cgctgatttg cttcgtcatc aggttgacga aaaattgtat gtcctggcgc   13800
tactcatgta ccagatatac caactttctt ctggacacca agggcagact ctatcgctgg   13860
cggtcacccg tcatcataga gaaaagggt aaaattgagg ttggaggtga cctgatcgac   13920
```

```
ctcaagagag ttgtgcttga tggctccgcg gcaaccctg taaccaaagt ttcagcggaa   13980
caatggggtc gtccttagac gacttctgca atgacagcac ggctccacaa aaggtgatct   14040
tggcattttc tatcacctac actccagtga tgatatatgc cctaaaggtg agtcgtggcc   14100
ggctgctagg gcttttacac cttttgattt ttctaaactg tgcttttacc ttcgggtata   14160
tgacatttgt gcactttcag agcacaaaca gagttgcact cactatggga gcagtagtcg   14220
cgctcctttg gggggtgtac tcagctatag aaacctggaa attcatcact tccagatgcc   14280
gtttgtgctt gctaggccgc aagtacattc tggcccctgc ccaccacgtt gagagtgccg   14340
caggctttca tccgattgcg gcaagtgata accacgcatt tgtcgtccgg cgtcccggtt   14400
ccactacggt taacggcaca ttggttcccg ggttgaaaag cctcgtgttg ggtggcagaa   14460
gagctgtcaa acggggagtg gtaaacctcg ttaaatatgc caaataacaa cggcaggcag   14520
cagaagaaga agaaggggga cggccagcca gtcaatcagc tgtgccaaat gttgggcagg   14580
atcatcgccc agcaaaacca gtccagaggt aagggaccgg ggaagaaaag taagaagaaa   14640
agcctggaga agccccattt tcctctcgcg actgaagatg acgttagaca tcacttcacc   14700
cctagtgagc ggcaattgtg tctgtcgtca atccagactg cctttaacca aggcgctgga   14760
acttgtaccc tgtcggattc agggagaata agttacactg cggagtttag tttgcctacg   14820
catcatactg tgcgcctaat tcgcgtcaca gcatcaccct cagcatgatg agctggcatt   14880
cttgagacat cccagtgttt gaattggaag gatgtgtggt gaatggcact gattgatatt   14940
gtgcctytaa gtcacctatt caattagggc gaccgtatgg gggtaatatt taattggcgt   15000
gaaccatgcg gccgaaayt                                                15019
```

<210> SEQ ID NO 7  
<211> LENGTH: 15086  
<212> TYPE: DNA  
<213> ORGANISM: Artificial Sequence  
<220> FEATURE:  
<223> OTHER INFORMATION: Porcine reproductive and respiratory syndrome virus

<400> SEQUENCE: 7

```
atgacgtata ggtgttggct ctatgccttg gcatttgtat tgtcaggagc tgtgaccatt    60
ggcacagccc aaaacttgct gcacagaaac acccttctgt gatagcctcc ttcaggggag   120
cttagggttt gtccctagca ccttgcttcc ggagttgcac tgctttacgg tctctccacc   180
cctttaacca tgtctgggat acttgatcgg tgcacgtgta ccccaatgc cagggtgttt   240 atggcggagg gccaagtcta ctgcacacga tgcctcagtg cacggtctct ccttcccctg   300
aacctccagg tttctgagct cggggtgcta ggcctattct acaggcccga agagccactc   360
cggtggacgt tgccacgtgc attccccact gttgagtgct ccccgccgg ggcctgctgg   420 ctttctgcaa tctttccaat cgcacgaatg accagtggaa acctgaactt ccaacaaaga   480
atggtacggg tcgcagctga gctttacaga gccggccagc tcacccctgc agtcttgaag   540
gctctacaag tttatgaacg gggttgccgc tggtacccca ttgttggacc tgtccctgga   600
gtggccgttt tcgccaattc cctacatgtg agtgataaac ccttcccggg agcaactcac   660
gtgttgacca acctgccgct cccgcagaga cccaagcctg aagactttgg ccccttgag   720 tgtgctatgg ctactgtcta tgacattggt catgacgccg tcatgtatgt ggccgaaagg   780
aaagtctcct gggcccctcg tggcgggat gaagtgaaat ttgaagctgt ccccggggag   840
ttgaagttga ttgcgaaccg gctccgcacc tccttcccgc cccaccacac agtggacatg   900
```

```
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga aactggcggg agaacccagc tactctgggt tgaggacct cctcagaata    1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctggaagg tgagcattgg actgtcactg tgaccctgg  gatgtcccct    1740
tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca gtgcgcttta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttgccaaaa gttcagcctc gaaaaacgaa gcctgtcaag   2340
agcttgccgg agagaaagcc tgtccccgcc ccgcgcagga aggttgggtc cgattgtggc   2400
agcccggttt cattaggcgg cgatgtccct aacagttggg aagatttggc tgttagtagc   2460
cccttgatc  tcccgacccc acctgagccg gcaacacctt caagtgagct ggtgattgtg    2520
tcctcaccgc aatgcatctt caggccggcg acacccttga gtgagccggc tccaattccc   2580
gcacctcgcg gaactgtgtc tcgaccggtg acacccttga gtgagccgat ccctgtgccc   2640
gcaccgcggc gtaagtttca gcaggtgaaa agattgagtt cggcggcggc aatcccaccg   2700
taccaggacg agcccctgga tttgtctgct tcctcacaga ctgaatatga ggcctctccc   2760
ccagcaccgc cgcagagcgg gggcgttctg ggagtagagg ggcatgaagc tgaggaaacc   2820
ctgagtgaaa tctcggacat gtcgggtaac attaaacctg cgtccgtgtc atcaagcagc   2880
tccttgtcca gcgtgagaat cacacgccca aaatactcag ctcaagccat catcgactcg   2940
ggcgggccct gcagtgggca tctccaagag gtaaaggaaa catgccttag tgtcatgcgc   3000
gaggcatgtg atgcgactaa gcttgatgac cctgctacgc aggaatggct ttctcgcatg   3060
tgggatcggg tggacatgct gacttggcgc aacacgtctg tttaccaggc gatttgcacc   3120
ttagatggca ggttaaagtt cctcccaaaa atgatactcg agacaccgcc gcccctatccg  3180
tgtgagtttg tgatgatgcc tcacacgcct gcaccttccg taggtgcgga gagcgacctt   3240
accattggct cagttgctac tgaagatgtt ccacgcatcc tcgagaaaat agaaaatgtc   3300
```

```
ggcgagatgg ccaaccaggg acccttggcc ttctccgagg ataaaccggt agatgaccaa    3360
cttgtcaacg acccccggat atcgtcgcgg aggcctgacg agagcacatc agctccgtcc    3420
gcaggcacag gtggcgccgg ctcttttacc gatttgccgc cttcagatgg cgcggatgcg    3480 gacgggggggg ggccgtttcg gacggtaaaa agaaaagctg aaaggctctt tgaccaactg    3540
agccgtcagg tttttgacct cgtctcccat ctccctgttt tcttctcacg ccttttctac    3600
cctggcggtg gttattctcc gggtgattgg ggttttgcag cttttactct attgtgcctc    3660
tttttatgtt acagttaccc agcctttggt attgctcccc tcttgggtgt gttttctggg    3720
tcttctcggc gcgttcgaat gggggttttt ggctgctggt tggcttttgc tgttggtctg    3780
ttcaagcctg tgtccgaccc agtcggcgct gcttgtgagt ttgactcgcc agagtgtaga    3840
aacatccttc attcttttga gcttctcaaa ccttgggacc ctgttcgcag ccttgttgtg    3900
ggccccgtcg gtctcggtct tgccattctt ggcaggttac tgggcggggc acgctgcatc    3960
tggcactttt tgcttaggct tggcattgtt gcagactgta tcttggctgg agcttacgtg    4020 cttctcaag gtaggtgtaa aaagtgctgg ggatcttgta taagaactgc tcccaatgag    4080
gtcgctttta acgtgtttcc tttcacacgt gcgaccaggt cgtcacttat cgacctgtgc    4140
gatcggtttt gtgcgccaaa aggaatggac cccattttc tcgccactgg gtggcgcggg    4200
tgctgggccg gccgaagccc cattgagcaa ccctctgaaa aacccatcgc gtttgcccag    4260
ttggatgaaa agaagattac ggctaggact gtggtcgccc agccttatga ccccaaccaa    4320
gccgtaaagt gcttgcgggt attgcaggcg ggtggggcga tggtggctaa ggcggtccca    4380
aaagtggtca aggtttccgc tgttccattc cgagccccct tctttcccac tggagtgaaa    4440
gttgaccctg attgcagggt cgtggttgac cctgacactt tcactgcagc tctccggtct    4500
ggctactcca ccacaaacct cgtccttggt gtggggact ttgcccagct gaatggatta    4560
aaaatcaggc aaatttccaa gccttcaggg ggaggcccac atctcatggc tgccctgcat    4620
gttgcctgct cgatggctct gcacatgctt gctgggattt atgtgactgc ggtgggttct    4680
tgcggcaccg gcaccaacga cccgtggtgc gctaacccgt ttgccgtccc tggctacgga    4740
cctggctctc tctgcacgtc cagattgtgc atttcccaac acggcttac cctgcccttg    4800 acagcacttg tggcgggatt cggtattcaa gaaattgcct tggtcgtttt gattttgtt    4860 tccatcggag gcatggctca taggttgagc tgtaaggctg acatgctgtg tgtcttgctt    4920
gcaattgcca gctatgtttg ggtacctctt acctggttgc tttgtgtgtt ccttgctgg    4980 ttgcgctgtt tttctttgca cccctcacc atcctatggt tggtgttttt cttgatttct    5040
gtgaatatgc cttcaggaat cttggccatg gtgttgttgg tttctctttg gcttcttggt    5100
cgttatacta atgttgctgg ccttgtcacc ccctacgaca ttcatcatta caccagtggc    5160
ccccgcggtg ttgccgcctt ggctaccgca ccagatggga cctacttggc cgctgtccgc    5220
cgcgctgcgt tgactggccg caccatgctg tttaccccgt cccagcttgg gtctcttctt    5280
gagggtgctt tcagaactcg aaagccctca ctgaacaccg tcaatgtgat cgggtcctcc    5340
atgggctctg gcgggtgtt taccatcgac gggaaagtca agtgcgtaac tgccgcacat    5400
gtccttacgg gcaattcagc tcgggtttcc ggggtcggct tcaatcaaat gcttgacttt    5460
gacgtaaagg gagatttcgc tatagctgat tgcccgaatt ggcaagggc tgcccccaag    5520 acccaattct gcacggatgg atggactggc cgtgcctatt ggctaacatc ctctggcgtc    5580
gaacccggcg tcattggaaa aggattcgcc ttctgcttca ccgcatgtgg cgattccggg    5640
tccccagtga tcaccgaggc cggtgagctt gtcggcgttc acacgggatc gaataaacaa    5700
```

```
ggggggggca ttgttacgcg cccctcaggc cagttttgta atgtggcacc catcaagcta    5760
agcgaattaa gtgaattctt tgctgggcct aaggtcccgc tcggtgatgt gaaggtcggc    5820
agccacataa ttaaagacat aagcgaggtg ccttcagatc tttgtgcctt gcttgctgcc    5880
aaacctgaac tggaaggagg cctctccacc gtccaacttc tttgtgtgtt ttttctcctg    5940
tggagaatga tgggacatgc ctggacgccc ttggttgctg tgagtttctt tattttgaat    6000
gaggttctcc cagccgtcct ggtccggagt gttttctcct ttggaatgtt tgtgctatcc    6060
tggctcacgc catggtctgc gcaagttctg atgatcaggc ttctgacagc agctcttaac    6120
aggaacagat ggtcacttgc ctttttcagc ctcggtgcag tgaccggttt tgtcgcagat    6180
cttgcggcca ctcaggggca tccgttgcag gcagtgatga atttgagcac ctatgcattc    6240
ctgcctcgga tgatggttgt gacctcacca gtcccagtga tcacgtgtgg tgtcgtgcac    6300
ctacttgcca tcattttgta cttgtttaag taccgtggcc tgcaccatat ccttgttggc    6360
gatggagtgt tctctgcggc tttcttcttg agatactttg ccgagggaaa gttgagggaa    6420
ggggtgtcgc aatcctgcgg aatgaatcat gagtctctga ctggtgccct cgctatgaga    6480
ctcaatgacg aggacttgga tttccttatg aaatggactg attttaagtg ctttgtttct    6540
gcgtccaaca tgaggaatgc agcgggtcaa tttatcgagg ctgcctatgc taaagcactt    6600
agagtagaac tggcccagtt ggtgcaggtt gataaagttc gaggtacttt ggccaaactt    6660
gaagcttttg ctgataccgt ggcacctcaa ctctcgcccg gtgacattgt tgtcgctctc    6720
ggccacacgc ctgttggcag tatcttcgac ctaaaggttg gtagcaccaa gcataccctc    6780
caagccattg agaccagagt ccttgctggg tccaaaatga ccgtggcgcg cgtcgtcgac    6840
ccgacccca cgcccccacc cgcacccgtg cccatccccc tcccaccgaa agttctggag    6900
aatggcccca acgcttgggg ggatgaggac cgtttgaata agaagaagag gcgcaggatg    6960
gaagccctcg gcatctatgt tatgggcggg aaaaaatacc agaaattttg ggacaagaat    7020
tccggtgatg tgttttatga ggaggtccat aataacacag atgagtggga gtgtctcaga    7080
gttggcgacc ctgccgactt tgaccctgag aagggaactc tgtgtggaca tgtcaccatt    7140
gaaaacaagg cttaccatgt ttacacctcc ccatctggta agaagttctt ggtccccgtc    7200
aacccagaga atggaagagt ccaatgggaa gctgcaaagc tttccgtgga gcaggcccta    7260
ggtatgatga atgtcgacgg cgaactgact gccaaagaac tggagaaact gaaaagaata    7320
attgacaaac tccagggcct gactaaggag cagtgtttaa actgctagcc gccagcgact    7380
tgaccccgctg tggtcgcggc ggcttggttg ttactgaaac agcggtaaaa atagtcaaat    7440
ttcacaaccg gaccttcacc ctgggacctg tgaatttaaa agtggccagt gaggttgagc    7500
taaaagacgc ggttgagcac aaccaacacc cggttgcgag accgatcgat ggtggagttg    7560
tgctcctgcg ttccgcggtt ccttcgctta tagacgtctt gatctccggt gctgatgcat    7620
ctcccaagtt acttgcccat cacgggccgg gaaacactgg gatcgatggc acgtctgggg    7680
attttgagtc cgaagccact aaagaggaag tcgcactcag tgcgcaaata atacaggctt    7740
gtgacattag gcgcggcgac gctcctgaaa ttggtctccc ttacaagctg tacccgttta    7800
ggggtaaccc tgagcgggtg aaaggagttc tgcagaatac aaggtttgga gacatacctt    7860
acaaaacccc cagtgacact ggaagcccag tgcacgcggc tgcctgcctt acgcccaacg    7920
ccactccggt gactgatggg cgctccgtct tggccacgac catgccccc gggtttgagt    7980
tatatgtacc gaccatacca gcgtctgtcc ttgattacct tgactctagg cctgactgcc    8040
ctaaacagct gacagagcac ggctgcgaag atgccgcact gaaagacctc tctaaatatg    8100
```

```
acttgtccac ccaaggcttt gttttacctg gagttcttcg ccttgtgcgg aaatacctgt   8160
ttgcccatgt aggtaagtgc ccacccgttc atcggccttc tacttaccct gctaagaatt   8220
ctatggctgg aataaatggg aacaggttcc caaccaagga cattcagagc gtccctgaaa   8280
tcgacgttct gtgcgcacag gctgtgcgag aaaactggca aactgtcacc ccttgtactc   8340
ttaagaaaca gtattgcggg aagaagaaga ctaggaccat actcggcacc aataacttca   8400
tcgcactagc ccaccgagca gtgttgagtg gtgttaccca gggcttcatg aaaaaggcgt   8460
ttaactcgcc catcgccctc ggaaagaaca gtttaaggga gctacagact ccggtcctgg   8520
gcaggtgcct tgaagctgat ctcgcatcct gcgatcgatc cacgcctgca attgtccgct   8580
ggtttgccgc caaccttctt tatgaacttg cctgtgctga agagcatcta ccgtcgtacg   8640
tgctgaactg ctgccacgac ttactggtca cgcagtccgg cgcagtgact aagagaggtg   8700
gcctgtcgtc tggcgacccg atcacctctg tgtctaacac catttatagt ttggtgatct   8760
atgcacagca tatggtgctt agttacttca aaagtggtca ccccccatggc cttctgttct   8820 tacaagacca gctaaagttt gaggacatgc tcaaggttca acccctgatc gtctattcgg   8880
acgacctcgt gctgtatgcc gagtctccca ccatgccaaa ctatcactgg tgggttgaac   8940
atctgaattt gatgctgggg tttcagacgg acccaaagaa gacagcaata acagactcgc   9000
catcatttct aggctgtaga ataataaatg ggcgccagct agtccccaac cgtgacagga   9060
tcctcgcggc cctcgcctat cacatgaagg cgagtaatgt ttctgaatac tatgcctcag   9120
cggctgcaat actcatggac agctgtgctt gtttggagta tgatcctgaa tggtttgaag   9180
aacttgtagt tggaatagcg cagtgcgccc gcaaggacgg ctacagcttt cccggcacgc   9240
cgttcttcat gtccatgtgg gaaaaactca ggtccaatta tgaggggaag aagtcgagag   9300
tgtgcgggta ctgcggggcc ccggccccgt acgctactgc ctgtggcctc gacgtctgca   9360
tttaccacac ccacttccac cagcattgtc cagtcacaat ctggtgtggc catccagcgg   9420
gttctggttc ttgtagtgag tgcaaatccc ctgtagggaa aggcacaagc cctttagacg   9480
aggtgctgga acaagtcccg tataagcccc cacggaccgt tatcatgcat gtggagcagg   9540
gtctcacccc ccttgatcca ggtagatacc aaactcgccg cggattagtc tctgtcaggc   9600
gtggaattag gggaaatgaa gttggactac cagacggtga ttatgctagc accgccttgc   9660
tccctacctg caaagagatc aacatggtcg ctgtcgcttc caatgtattg cgcagcaggt   9720
tcatcatcgg cccacccggt gctgggaaaa cactggct ccttcaacag gtccaggatg   9780
gtgatgttat ttacacacca actcaccaga ccatgcttga catgattagg ctttggggga   9840
cgtgccggtt caacgtcccg gcaggcacaa cgctgcaatt ccccgtcccc tcccgcaccg   9900
gtccgtgggt tcgcatccta gccggcggtt ggtgtcctgg caagaattcc ttcctagatg   9960
aagcagcgta ttgcaatcac cttgatgttt tgaggcttct tagtaaaact accctcacct  10020
gtctaggaga cttcaagcaa ctccacccag tgggttttga ttctcattgc tatgtttttg  10080
acatcatgcc tcaaactcaa ctgaagacca tctggaggtt tggacagaat atctgtgatg  10140
ccattcagcc agattacagg gacaaactca tgtccatggt caacacaacc cgtgtgacct  10200
acgtggaaaa acctgtcagg tatgggcagg tcctcacccc ctaccacagg gaccgagagg  10260
acgacgccat cactattgac tccagtcaag gcgccacatt cgatgtggtt acattgcatt  10320
tgcccactaa agattcactc aacaggcaaa gagcccttgt tgctatcacc agggcaagac  10380
acgctatctt tgtgtatgac ccacacaggc agctgcaggg cttgtttgat cttcctgcaa  10440
aaggcacgcc cgtcaacctc gcagtgcact gcgacgggca gctgatcgtg ctggatagaa  10500
```

```
ataacaaaga atgcacggtt gctcaggctc taggcaacgg ggataaattt agggccacag   10560
acaagcgtgt tgtagattct ctccgcgcca tttgtgctga tctagaaggg tcgagctctc   10620
cgctccccaa ggtcgcacac aacttgggat tttatttctc acctgattta acacagtttg   10680
ctaaactccc agtagaactt gcacctcact ggcccgtggt gtcaacccag aacaatgaaa   10740
agtggccgga tcggctggtt gccagccttc gccctatcca taaatacagc cgcgcgtgca   10800
tcggtgccgg ctatatggtg ggcccttcgg tgtttctagg cactcctggg gtcgtgtcat   10860
actatctcac aaaatttgtt aagggcgggg ctcaagtgct tccggagacg gttttcagca   10920
ccggccgaat tgaggtagac tgccgggaat atcttgatga tcgggagcga aagttgctg    10980 cgtccctccc acacgctttc attggcgacg tcaaaggcac taccgttgga ggatgtcatc   11040
atgtcacctc cagatacctc ccgcgcgtcc ttcccaagga atcagttgcg gtagtcgggg   11100
tttcaagccc cggaaaagcc gcgaaagcat tgtgcacact gacagatgtg tacctcccag   11160
atcttgaagc ctatctccac ccggagaccc agtccaagtg ctggaaaatg atgttggact   11220
tcaaagaagt tcgactaatg gtctggaaag acaaaacagc ctatttccaa cttgaaggtc   11280
gctatttcac ctggtatcag cttgccagct atgcctcgta catccgtgtt cccgtcaact   11340
ctacggtgta cttggacccc tgcatgggcc ccgccctttg caacaggaga gtcgtcgggt   11400
ccacccactg gggggctgac ctcgcggtca cccctatga ttacggcgct aaaattatcc    11460
tgtctagcgc gtaccatggt gaaatgcccc ccggatacaa aattctggcg tgcgcggagt   11520
tctcgttgga tgacccagtt aagtacaaac atcctgggg gtttaatcg gatacagcgt     11580 atctgtatga gttcaccgga aacggtgagg actgggagga ttacaatgat gcgtttcgtg   11640
cgcgccagga agggaaaatt tataaggcca ctgccaccag cttgaagttt tattttcccc   11700
cgggccctgt cattgaacca actttaggcc tgaattgaaa tgaaatgggg tccatgcaaa   11760 gccttttga caaaattggc caactttttg tggatgcttt cacggagttc ttggtgtcca    11820
ttgttgatat cattatattt ttggccattt tgtttggctt caccatcgcc ggttggctgg   11880
tggtcttttg catcagattg gtttgctccg cgatactccg tacgcgccct gccattcact   11940
ctgagcaatt acagaagatc ttatgaggcc ttctttccc agtgccaagt ggacattccc    12000
acctggggaa ctaaacatcc tttggggatg ctttggcacc ataaggtgtc aaccctgatt   12060
gatgaaatgg tgtcgcgtcg aatgtaccgc atcatggaaa aagcagggca ggctgcctgg   12120
aaacaggtgg tgagcgaggc tacgctgtct cgcattagta gtttggatgt ggtggctcat   12180
tttcagcatc tagccgccat tgaagccgag acctgtaaat atttggcctc ccggctgccc   12240
atgctacaca acctgcgcat gacagggtca aatgtaacca tagtgtataa tagcactttg   12300
aatcaggtgt ttgctatttt tccaaccct ggttccgcg caaagcttca tgattttcag     12360
caatggttaa tagctgtaca ttcctccata ttttcctctg ttgcagcttc ttgtactctt   12420
tttgttgtgc tgtggttgcg ggttccaata ctacgtactg tttttggttt ccgctggtta   12480
ggggcaattt ttctttcgaa ctcacagtga attacacggt gtgtccacct tgcctcaccc   12540
ggcaagcagc cacagagatc tacgaacccg gtaggtctct ttggtgcagg atagggtatg   12600
accgatgtgg ggaggacgat catgacgagc tagggtttat gataccgcct ggcctctcca   12660
gcgaaggcca cttgactggt gtttacgcct ggttggcgtt cttgtccttc agctacacgg   12720
cccagttcca tcccgagata ttcgggatag ggaatgtgag tcgagtttat gttgacatca   12780
aacatcaact catctgcgcc gaacatgacg ggcagaacac caccttgcct cgtcatgaca   12840
acatttcagc cgtgtttcag acctattacc aacatcaagt cgacgcggc aattggtttc     12900
```

```
acctagaatg gcttcgtccc ttcttttcct cgtggttggt tttaaatgtc tcttggtttc   12960
tcaggcgttc gcctgcaaac catgtttcag ttcgagtctt gcagatatta agaccaacac   13020
caccgcagcg gcaagctttg ctgtcctcca agacatcagt tgccttaggc atcgcgactc   13080
ggcctctgag gcgattcgca aaatccctca gtgccgtacg gcgatagggca cacccgtgta   13140 tgttaccatc acagccaatg tgacagatga gaattattta cattcttctg atctcctcat   13200
gctttcttct tgccttttct atgcttctga gatgagtgaa aagggattta aggtggtatt   13260
tggcaatgtg tcaggcatcg tggctgtgtg tgtcaatttt accagctacg tccaacatgt   13320
caaggagttt acccaacgct ccctggtggt cgaccatgtg cggttgctcc atttcatgac   13380
acctgagacc atgaggtggg caactgtttt agcctgtctt tttgccattc tgttggcaat   13440
ttgaatgttt aagtatgttg gagaaatgct tgaccgcggg ctgttgctcg cgattgcttt   13500
ctttgtggtg tatcgtgccg ttctgttttg ctgtgctcgc caacgccagc aacgacagca   13560
gctcccatct acagctgatt tacaacttga cgctatgtga gctgaatggc acagattggc   13620
tagctaacaa atttgattgg gcagtggaga gttttgtcat cttccccgtt ttgactcaca   13680
ttgtctccta tggtgccctc actaccagcc atttccttga cacagtcgct ttagtcactg   13740
tgtctaccgc cgggtttgtt cacgggcggt atgtcctaag tagcatctac gcggtctgtg   13800
ccctggctgc gttgacttgc ttcgtcatta ggttttgcaaa gaattgcatg tcctggcgct   13860
acgcgtgtac cagatatacc aactttcttc tggacactaa gggcagactc tatcgttggc   13920
ggtcgcctgt catcatagag aaaagggca aagttgaggt cgaaggtcat ctgatcgacc   13980
tcaaaagagt tgtgcttgat ggctccgtgg caaccccta t aaccagagtt tcagcggaac   14040
aatggggtcg tccttagatg acttctgtca cgatagcacg gctccacaaa aggtgctttt   14100
ggcgttttct attacctaca cgccagtgat gatatatgcc ctaaaggtga gtcgcggccg   14160
actgctaggg cttctgcacc ttttgatctt cctgaattgt gctttcacct tcgggtacat   14220
gactttcgcg cactttcaga gtacaaataa ggtcgcgctc actatgggag cagtagttgc   14280
actcctttgg ggggtgtact cagccataga aacctggaaa ttcatcacct ccagatgccg   14340
tttgtgcttg ctaggccgca agtacattct ggcccctgcc caccacgttg aaagtgccgc   14400
aggctttcat ccgattgcgg caaatgataa ccacgcattt gtcgtccggc gtcccggctc   14460
cactacggtc aacggcacat tggtgcccgg gttaaaaagc ctcgtgttgg gtggcagaaa   14520
agctgttaaa cagggagtgg taaaccttgt caaatatgcc aaataacaac ggcaagcagc   14580
agaagagaaa gaagggggat ggccagccag tcaatcagct gtgccagatg ctgggtaaga   14640
tcatcgctca gcaaaaccag tccagaggca agggaccggg aaagaaaaat aagaagaaaa   14700
acccggagaa gccccatttt cctctagcga ctgaagatga tgtcagacat cactttaccc   14760
ctagtgagcg gcaattgtgt ctgtcgtcaa tccagaccgc ctttaatcaa ggcgctggga   14820 cttgcacccct gtcagattca ggaggataa gttacactgt ggagtttagt ttgcctacgc   14880
atcatactgt gcgcctgatc cgcgtcacag catcacccctc agcatgatgg gctggcattc   14940
ttgaggcatc tcagtgtttg aattggaaga atgtgtggtg aatggcactg attgacattg   15000
tgcctctaag tcacctattc aattagggcg accgtgtggg ggtgagattt aattggcgag   15060
aaccatgcgg ccgaaattaa aaaaaa                                         15086
```

<210> SEQ ID NO 8
<211> LENGTH: 14819
<212> TYPE: DNA
<213> ORGANISM: Artificial Sequence
<220> FEATURE:

<223> OTHER INFORMATION: Porcine reproductive and respiratory syndrome virus

<400> SEQUENCE: 8

```
atgacgtata ggtgttggct ctatgccttg gcatttgtat tgtcaggagc tgtgaccatt      60
ggcacagccc aaaacttgct gcacagaaac acccttctgt gatagcctcc ttcaggggag     120
cttagggttt gtccctagca ccttgcttcc ggagttgcac tgctttacgg tctctccacc     180
cctttaacca tgtctgggat acttgatcgg tgcacgtgta cccccaatgc cagggtgttt     240
atggcggagg gccaagtcta ctgcacacga tgcctcagtg cacggtctct ccttcccctg     300
aacctccagg tttctgagct cggggtgcta ggcctattct acaggcccga agagccactc     360
cggtggacgt tgccacgtgc attccccact gttgagtgct ccccgccgg ggcctgctgg      420
cttctgcaa tctttccaat cgcacgaatg accagtggaa acctgaactt ccaacaaaga      480
atggtacggg tcgcagctga gctttacaga gccggccagc tcaccctgc agtcttgaag       540
gctctacaag tttatgaacg ggttgccgc tggtacccca ttgttggacc tgtccctgga       600
gtggccgttt cgccaattc cctacatgtg agtgataaac ccttcccggg agcaactcac       660
gtgttgacca acctgccgct cccgcagaga cccaagcctg aagacttttg ccccttgag      720
tgtgctatgg ctactgtcta tgacattggt catgacgccg tcatgtatgt ggccgaaagg      780
aaagtctcct gggcccctcg tggcggggat gaagtgaaat tgaagctgt ccccggggag       840
ttgaagttga ttgcgaaccg gctccgcacc tccttcccgc ccaccacac agtggacatg      900
tctaagttcg ccttcacagc ccctgggtgt ggtgtttcta tgcgggtcga acgccaacac      960
ggctgccttc ccgctgacac tgtccctgaa gcaactgct ggtggagctt gtttgacttg     1020
cttccactgg aagttcagaa caaagaaatt cgccatgcta accaatttgg ctaccagacc     1080
aagcatggtg tctctggcaa gtacctgcag cggaggctgc aagttaatgg tctccgagca     1140
gtaactgacc taaacggacc tatcgtcgta cagtacttct ccgttaagga gagttggatc     1200
cgccatttga aactggcggg agaacccagc tactctgggt ttgaggacct cctcagaata     1260
agggttgagc ctaacacgtc gccattggct gacaaggaag aaaaaatttt ccggtttggc     1320
agtcacaagt ggtacggcgc tggaaagaga gcaagaaaag cacgctcttg tgcgactgct     1380
acagtcgctg gccgcgcttt gtccgttcgt gaaacccggc aggccaagga gcacgaggtt     1440
gccggcgcca acaaggctga gcacctcaaa cactactccc gcctgccga agggaattgt      1500
ggttggcact gcatttccgc catcgccaac cggatggtga attccaaatt tgaaaccacc     1560
cttcccgaaa gagtgagacc tccagatgac tgggctactg acgaggatct tgtgaatgcc     1620
atccaaatcc tcagactccc tgcggcctta gacaggaacg tgcttgtac tagcgccaag     1680
tacgtactta agctggaagg tgagcattgg actgtcactg tgaccctgg gatgtcccct     1740
tctttgctcc ctcttgaatg tgttcagggc tgttgtgggc acaagggcgg tcttggttcc     1800
ccagatgcag tcgaggtctc cggatttgac cctgcctgcc ttgaccggct ggctgaggtg     1860
atgcacctgc ctagcagtgc tatcccagcc gctctggccg aaatgtctgg cgattccgat     1920
cgttcggctt ctcccgtcac caccgtgtgg actgtttcgc agttcttgc ccgtcacagc     1980
ggagggaatc accctgacca agtgcgctta gggaaaatta tcagccttg tcaggtgatt     2040
gaggactgct gctgttccca gaacaaaacc aaccgggtca cccggagga ggtcgcagca     2100
aagattgacc tgtacctccg tggtgcaaca atcttgaag aatgcttggc caggcttgag     2160
aaagcgcgcc cgcacgcgt aatcgacacc tcctttgatt gggatgttgt gctccctggg     2220
gttgaggcgg caacccagac gatcaagctg ccccaggtca ccagtgtcg tgctctggtc     2280
```

```
cctgttgtga ctcaaaagtc cttgccaatt cccgcacctc gcggaactgt gtctcgaccg   2340
gtgacaccct tgagtgagcc gatccctgtg cccgcaccgc ggcgtaagtt tcagcaggtg   2400
aaaagattga gttcggcggc ggcaatccca ccgtaccagg acgagcccct ggatttgtct   2460
gcttcctcac agactgaata tgaggcctct cccccagcac cgccgcagag cggggggcgtt  2520 ctgggagtag aggggcatga agctgaggaa accctgagtg aaatctcgga catgtcgggt   2580
aacattaaac ctgcgtccgt gtcatcaagc agctccttgt ccagcgtgag aatcacacgc   2640
ccaaaatact cagctcaagc catcatcgac tcgggcgggc cctgcagtgg gcatctccaa   2700
gaggtaaagg aaacatgcct tagtgtcatg cgcgaggcat gtgatgcgac taagcttgat   2760
gaccctgcta cgcaggaatg gctttctcgc atgtgggatc gggtggacat gctgacttgg   2820
cgcaacacgt ctgtttacca ggcgatttgc accttagatg gcaggttaaa gttcctccca   2880
aaaatgatac tcgagacacc gccgcccctat ccgtgtgagt ttgtgatgat gcctcacacg   2940
cctgcacctt ccgtaggtgc ggagagcgac cttaccattg gctcagttgc tactgaagat   3000
gttccacgca tcctcgagaa aatagaaaat gtcggcgaga tggccaacca gggacccttg   3060
gccttctccg aggataaacc ggtagatgac caacttgtca cgaccccgg atatcgtcg    3120 cggaggcctg acgagagcac atcagctccg tccgcaggca caggtggcgc cggctctttt   3180
accgatttgc cgccttcaga tggcgcggat gcggacgggg gggggccgtt tcggacggta   3240 aaagaaaag ctgaaaggct ctttgaccaa ctgagccgtc aggttttga cctcgtctcc    3300 catctccctg ttttcttctc acgccttttc taccctggcg gtggttattc tccgggtgat   3360
tggggttttg cagcttttac tctattgtgc ctcttttat gttacagtta cccagccttt    3420
ggtattgctc ccctcttggg tgtgttttct gggtcttctc ggcgcgttcg aatgggggtt   3480
tttggctgct ggttggcttt tgctgttggt ctgttcaagc ctgtgtccga cccagtcggc   3540
gctgcttgtg agtttgactc gccagagtgt agaaacatcc ttcattcttt tgagcttctc   3600
aaaccttggg accctgttcg cagccttgtt gtgggccccg tcggtctcgg tcttgccatt   3660
cttggcaggt tactgggcgg ggcacgctgc atctggcact ttttgcttag gcttggcatt   3720
gttgcagact gtatcttggc tggagcttac gtgctttctc aaggtaggtg taaaaagtgc   3780
tggggatctt gtataagaac tgctcccaat gaggtcgctt ttaacgtgtt tccttcaca   3840 cgtgcgacca ggtcgtcact tatcgacctg tgcgatcggt tttgtgcgcc aaaaggaatg   3900
gaccccattt ttctcgccac tgggtggcgc gggtgctggg ccggccgaag ccccattgag   3960
caaccctctg aaaaacccat cgcgtttgcc cagttggatg aaaagaagat tacggctagg   4020
actgtggtcg cccagcctta tgaccccaac caagccgtaa agtgcttgcg ggtattgcag   4080
gcgggtgggg cgatggtggc taaggcggtc ccaaaagtgg tcaaggtttc cgctgttcca   4140
ttccgagccc ccttctttcc cactggagtg aaagttgacc ctgattgcag ggtcgtggtt   4200
gaccctgaca ctttcactgc agctctccgg tctggctact ccaccacaaa cctcgtcctt   4260
ggtgtggggg actttgccca gctgaatgga ttaaaaatca ggcaaatttc caagccttca   4320
gggggaggcc cacatctcat ggctgccctg catgttgcct gctcgatggc tctgcacatg   4380
cttgctggga tttatgtgac tgcggtgggt tcttgcggca ccggcaccaa cgacccgtgg   4440
tgcgctaacc cgtttgccgt ccctggctac ggacctggct ctctctgcac gtccagattg   4500
tgcatttccc aacacggcct taccctgccc ttgacagcac ttgtggcggg attcggtatt   4560
caagaaattg ccttggtcgt tttgattttt gtttccatcg gaggcatggc tcataggttt   4620
agctgtaagg ctgacatgct gtgtgtcttg cttgcaattg ccagctatgt ttgggtacct   4680
```

```
cttacctggt tgctttgtgt gtttccttgc tggttgcgct gttttctttt gcaccccctc    4740
accatcctat ggttggtgtt tttcttgatt tctgtgaata tgccttcagg aatcttggcc    4800
atggtgttgt tggtttctct ttggcttctt ggtcgttata ctaatgttgc tggccttgtc    4860 acccccctacg acattcatca ttacaccagt ggcccccgcg gtgttgccgc cttggctacc    4920
```
(Note: line at 4920 as transcribed may contain OCR artifact; verify original)
```
gcaccagatg ggacctactt ggccgctgtc cgccgcgctg cgttgactgg ccgcaccatg    4980
ctgtttaccc cgtcccagct tgggtctctt cttgagggtg ctttcagaac tcgaaagccc    5040
tcactgaaca ccgtcaatgt gatcgggtcc tccatgggct ctggcggggt gtttaccatc    5100
gacgggaaag tcaagtgcgt aactgccgca catgtcctta cgggcaattc agctcgggtt    5160
tccggggtcg gcttcaatca aatgcttgac tttgacgtaa agggagattt cgctatagct    5220
gattgcccga attggcaagg ggctgccccc aagacccaat tctgcacgga tggatggact    5280
ggccgtgcct attggctaac atcctctggc gtcgaacccg gcgtcattgg aaaaggattc    5340
gccttctgct tcaccgcatg tggcgattcc gggtccccag tgatcaccga ggccggtgag    5400
cttgtcggcg ttcacacggg atcgaataaa caaggggggg gcattgttac gcgcccctca    5460
ggccagtttt gtaatgtggc acccatcaag ctaagcgaat taagtgaatt ctttgctggg    5520
cctaaggtcc cgctcggtga tgtgaaggtc ggcagccaca taattaaaga cataagcgag    5580
gtgccttcag atctttgtgc cttgcttgct gccaaacctg aactgaagg aggcctctcc    5640
```
(Note: one line appears to have a minor OCR inconsistency)
```
accgtccaac ttctttgtgt gttttttctc ctgtggagaa tgatgggaca tgcctggacg    5700
cccttggttg ctgtgagttt ctttattttg aatgaggttc tcccagccgt cctggtccgg    5760
agtgttttct cctttggaat gtttgtgcta tcctggctca cgccatggtc tgcgcaagtt    5820
ctgatgatca ggcttctgac agcagctctt aacaggaaca gatggtcact tgccttttc    5880 agcctcggtg cagtgaccgg ttttgtcgca gatcttgcgg ccactcaggg gcatccgttg    5940
caggcagtga tgaatttgag cacctatgca ttcctgcctc ggatgatggt tgtgacctca    6000
ccagtcccag tgatcacgtg tggtgtcgtg cacctacttg ccatcatttt gtacttgttt    6060
aagtaccgtg gcctgcacca tatccttgtt ggcgatggag tgttctctgc ggctttcttc    6120
ttgagatact ttgccgaggg aaagttgagg gaagggtgt cgcaatcctg cggaatgaat    6180
```
(note: one column possibly off)
```
catgagtctc tgactggtgc cctcgctatg agactcaatg acgaggactt ggatttcctt    6240
atgaaatgga ctgattttaa gtgctttgtt tctgcgtcca acatgaggaa tgcagcgggt    6300
caatttatcg aggctgccta tgctaaagca cttagagtag aactggccca gttggtgcag    6360
gttgataaag ttcgaggtac tttggccaaa cttgaagctt ttgctgatac cgtggcacct    6420
caactctcgc ccggtgacat tgttgtcgct ctcggccaca cgcctgttgg cagtatcttc    6480
gacctaaagg ttggtagcac caagcatacc ctccaagcca ttgagaccag agtccttgct    6540
gggtccaaaa tgaccgtggc gcgcgtcgtc gacccgaccc ccacgccccc acccgcaccc    6600
gtgcccatcc ccctcccacc gaaagttctg gagaatggcc ccaacgcttg ggggatgag    6660 gaccgtttga ataagaagaa gaggcgcagg atgaagccc tcggcatcta tgttatgggc    6720
gggaaaaaat accagaaatt ttgggacaag aattccggtg atgtgtttta tgaggaggtc    6780
cataataaca cagatgagtg ggagtgtctc agagttggcg accctgccga ctttgacc    6840
```
(note: possible OCR variance on final column)
```
gagaagggaa ctctgtgtgg acatgtcacc attgaaaaca aggcttacca tgtttacacc    6900
tccccatctg gtaagaagtt cttggtcccc gtcaacccag agaatggaag agtccaatgg    6960
gaagctgcaa agctttccgt ggagcaggcc ctaggtatga tgaatgtcga cggcgaactg    7020
actgccaaag aactggagaa actgaaaaga ataattgaca aactccaggg cctgactaag    7080
```

```
gagcagtgtt taaactgcta gccgccagcg acttgacccg ctgtggtcgc ggcggcttgg    7140
ttgttactga aacagcggta aaatagtca aatttcacaa ccggaccttc accctgggac    7200
ctgtgaattt aaaagtggcc agtgaggttg agctaaaaga cgcggttgag cacaaccaac    7260
acccggttgc gagaccgatc gatggtggag ttgtgctcct gcgttccgcg gttccttcgc    7320
ttatagacgt cttgatctcc ggtgctgatg catctcccaa gttacttgcc catcacgggc    7380
cgggaaacac tgggatcgat ggcacgctct gggattttga gtccgaagcc actaaagagg    7440
aagtcgcact cagtgcgcaa ataatacagg cttgtgacat taggcgcggc gacgctcctg    7500
aaattggtct cccttacaag ctgtaccctg ttaggggtaa ccctgagcgg gtgaaaggag    7560
ttctgcagaa tacaaggttt ggagacatac cttacaaaac ccccagtgac actggaagcc    7620
cagtgcacgc ggctgcctgc cttacgccca acgccactcc ggtgactgat gggcgctccg    7680
tcttggccac gaccatgccc cccgggtttg agttatatgt accgaccata ccagcgtctg    7740
tccttgatta ccttgactct aggcctgact gccctaaaca gctgacagag cacggctgcg    7800
aagatgccgc actgaaagac ctctctaaat atgacttgtc cacccaaggc tttgttttac    7860
ctggagttct tcgccttgtg cggaaatacc tgtttgccca tgtaggtaag tgcccacccg    7920
ttcatcggcc ttctacttac cctgctaaga attctatggc tggaataaat gggaacaggt    7980
tcccaaccaa ggacattcag agcgtccctg aaatcgacgt tctgtgcgca caggctgtgc    8040
gagaaaactg gcaaactgtc accccttgta ctcttaagaa acagtattgc gggaagaaga    8100
agactaggac catactcggc accaataact tcatcgcact agcccaccga gcagtgttga    8160
gtggtgttac ccagggcttc atgaaaaagg cgtttaactc gcccatcgcc ctcggaaaga    8220
acaagtttaa ggagctacag actccggtcc tgggcaggtg ccttgaagct gatctcgcat    8280
cctgcgatcg atccacgcct gcaattgtcc gctggtttgc cgccaacctt ctttatgaac    8340
ttgcctgtgc tgaagagcat ctaccgtcgt acgtgctgaa ctgctgccac gacttactgg    8400
tcacgcagtc cggcgcagtg actaagagag gtggcctgtc gtctggcgac ccgatcacct    8460
ctgtgtctaa caccatttat agtttggtga tctatgcaca gcatatggtg cttagttact    8520
tcaaaagtgg tcaccccat ggccttctgt tcttacaaga ccagctaaag tttgaggaca    8580
tgctcaaggt tcaaccctg atcgtctatt cggacgacct cgtgctgtat gccgagtctc    8640
ccaccatgcc aaactatcac tggtgggttg aacatctgaa tttgatgctg gggtttcaga    8700
cggacccaaa aagacagca ataacagact cgccatcatt tctaggctgt agaataataa    8760
atgggcgcca gctagtcccc aaccgtgaca ggatcctcgc ggccctcgcc tatcacatga    8820
aggcgagtaa tgtttctgaa tactatgcct cagcggctgc aatactcatg acagctgtg    8880 cttgttttgga gtatgatcct gaatggtttg aagaacttgt agttggaata gcgcagtgcg    8940
cccgcaagga cggctacagc tttcccggca cgccgttctt catgtccatg tgggaaaaac    9000
tcaggtccaa ttatgagggg aagaagtcga gagtgtgcgg gtactgcggg gccccggccc    9060
cgtacgctac tgcctgtggc ctcgacgtct gcatttacca cacccacttc caccagcatt    9120
gtccagtcac aatctggtgt ggccatccag cgggttctgg ttcttgtagt gagtgcaaat    9180
cccctgtagg gaaaggcaca agccctttag acgaggtgct ggaacaagtc cgtataagc    9240 ccccacggac cgttatcatg catgtggagc agggtctcac cccccttgat ccaggtagat    9300
accaaactcg ccgcggatta gtctctgtca ggcgtggaat taggggaaat gaagttggac    9360
taccagacgg tgattatgct agcaccgcct tgctccctac ctgcaaagag atcaacatgg    9420
tcgctgtcgc ttccaatgta ttgcgcagca ggttcatcat cggcccaccc ggtgctggga    9480
```

| | |
|---|---|
| aaacatactg gctccttcaa caggtccagg atggtgatgt tatttacaca ccaactcacc | 9540 |
| agaccatgct tgacatgatt agggctttgg ggacgtgccg gttcaacgtc ccggcaggca | 9600 |
| caacgctgca attccccgtc ccctcccgca ccggtccgtg ggttcgcatc ctagccggcg | 9660 |
| gttggtgtcc tggcaagaat tccttcctag atgaagcagc gtattgcaat caccttgatg | 9720 |
| ttttgaggct tcttagtaaa actaccctca cctgtctagg agacttcaag caactccacc | 9780 |
| cagtgggttt tgattctcat tgctatgttt ttgacatcat gcctcaaact caactgaaga | 9840 |
| ccatctggag gttttggacag aatatctgtg atgccattca gccagattac agggacaaac | 9900 |
| tcatgtccat ggtcaacaca acccgtgtga cctacgtgga aaaacctgtc aggtatgggc | 9960 |
| aggtcctcac cccctaccac agggaccgag aggacgacgc catcactatt gactccagtc | 10020 |
| aaggcgccac attcgatgtg gttacattgc atttgcccac taaagattca ctcaacaggc | 10080 |
| aaagagccct tgttgctatc accagggcaa gacacgctat cttgtgtat gacccacaca | 10140 |
| ggcagctgca gggcttgttt gatcttcctg caaaaggcac gcccgtcaac ctcgcagtgc | 10200 |
| actgcgacgg gcagctgatc gtgctggata gaaataacaa agaatgcacg gttgctcagg | 10260 |
| ctctaggcaa cggggataaa tttagggcca cagacaagcg tgttgtagat tctctccgcg | 10320 |
| ccatttgtgc tgatctagaa gggtcgagct ctccgctccc caaggtcgca cacaacttgg | 10380 |
| gattttattt ctcacctgat ttaacacagt ttgctaaact cccagtagaa cttgcacctc | 10440 |
| actggcccgt ggtgtcaacc cagaacaatg aaaagtggcc ggatcggctg gttgccagcc | 10500 |
| ttcgccctat ccataaatac agccgcgcgt gcatcggtgc cggctatatg gtgggcctt | 10560 |
| cggtgtttct aggcactcct ggggtcgtgt catactatct cacaaaattt gttaagggcg | 10620 |
| gggctcaagt gcttccggag acggttttca gcaccggccg aattgaggta gactgccggg | 10680 |
| aatatcttga tgatcgggag cgagaagttg ctgcgtccct cccacacgct ttcattggcg | 10740 |
| acgtcaaagg cactaccgtt ggaggatgtc atcatgtcac ctccagatac ctcccgcgcg | 10800 |
| tccttcccaa ggaatcagtt gcggtagtcg gggtttcaag ccccggaaaa gccgcgaaag | 10860 |
| cattgtgcac actgacagat gtgtacctcc cagatcttga agcctatctc cacccggaga | 10920 |
| cccagtccaa gtgctggaaa atgatgttgg acttcaaaga agttcgacta atggtctgga | 10980 |
| aagacaaaac agcctatttc caacttgaag gtcgctattt cacctggtat cagcttgcca | 11040 |
| gctatgcctc gtacatccgt gttcccgtca actctacggt gtacttggac ccctgcatgg | 11100 |
| gcccgccct ttgcaacagg agagtcgtcg ggtccaccca ctgggggct gacctcgcgg | 11160 |
| tcaccccta tgattacggc gctaaaatta tcctgtctag cgcgtaccat ggtgaaatgc | 11220 |
| cccccggata caaattctg gcgtgcgcgg agttctcgtt ggatgaccca gttaagtaca | 11280 |
| aacatacctg ggggtttgaa tcggatacag cgtatctgta tgagttcacc ggaaacggtg | 11340 |
| aggactggga ggattacaat gatgcgtttc gtgcgcgcca ggaagggaaa atttataagg | 11400 |
| ccactgccac cagcttgaag ttttattttc ccccgggccc tgtcattgaa ccaactttag | 11460 |
| gcctgaattg aaatgaaatg gggtccatgc aaagccttt tgacaaaatt ggccaacttt | 11520 |
| ttgtggatgc tttcacggag ttcttggtgt ccattgttga tatcattata tttttggcca | 11580 |
| ttttgtttgg cttcaccatc gccggttggc tggtggtctt ttgcatcaga ttggtttgct | 11640 |
| ccgcgatact ccgtacgcgc cctgccattc actctgagca attacagaag atcttatgag | 11700 |
| gcctttcttt cccagtgcca agtggacatt cccacctggg gaactaaaca tcctttgggg | 11760 |
| atgctttggc accataaggt gtcaaccctg attgatgaaa tggtgtcgcg tcgaatgtac | 11820 |
| cgcatcatgg aaaaagcagg gcaggctgcc tggaaacagg tggtgagcga ggctacgctg | 11880 |

```
tctcgcatta gtagtttgga tgtggtggct cattttcagc atctagccgc cattgaagcc   11940
gagacctgta aatatttggc ctcccggctg cccatgctac acaacctgcg catgacaggg   12000
tcaaatgtaa ccatagtgta taatagcact ttgaatcagg tgtttgctat ttttccaacc   12060
cctggttccc ggccaaagct tcatgatttt cagcaatggt taatagctgt acattcctcc   12120
atattttcct ctgttgcagc ttcttgtact ctttttgttg tgctgtggtt gcgggttcca   12180
atactacgta ctgtttttgg tttccgctgg ttagggggcaa ttttttcttc gaactcacag   12240
tgaattacac ggtgtgtcca ccttgcctca cccggcaagc agccacagag atctacgaac   12300
ccggtaggtc tctttggtgc aggatagggt atgaccgatg tggggaggac gatcatgacg   12360
agctagggtt tatgataccg cctggcctct ccagcgaagg ccacttgact ggtgtttacg   12420
cctggttggc gttcttgtcc ttcagctaca cggcccagtt ccatcccgag atattcggga   12480
tagggaatgt gagtcgagtt tatgttgaca tcaaacatca actcatctgc gccgaacatg   12540
acgggcagaa caccaccttg cctcgtcatg acaacatttc agccgtgttt cagacctatt   12600
accaacatca agtcgacggc ggcaattggt ttcacctaga atggcttcgt cccttctttt   12660
cctcgtggtt ggttttaaat gtctcttggt ttctcaggcg ttcgcctgca aaccatgttt   12720
cagttcgagt cttgcagata ttaagaccaa caccaccgca gcggcaagct ttgctgtcct   12780
ccaagacatc agttgcctta ggcatcgcga ctcggcctct gaggcgattc gcaaaatccc   12840
tcagtgccgt acggcgatag ggacacccgt gtatgttacc atcacagcca atgtgacaga   12900
tgagaattat ttacattctt ctgatctcct catgctttct tcttgccttt tctatgcttc   12960
tgagatgagt gaaaagggat ttaaggtggt atttggcaat gtgtcaggca tcgtggctgt   13020
gtgtgtcaat tttaccagct acgtccaaca tgtcaaggag tttacccaac gctccctggt   13080
ggtcgaccat gtgcggttgc tccatttcat gacacctgag accatgaggt gggcaactgt   13140
tttagcctgt cttttttgcca ttctgttggc aatttgaatg tttaagtatg ttggagaaat   13200
gcttgaccgc gggctgttgc tcgcgattgc tttctttgtg gtgtatcgtg ccgttctgtt   13260
ttgctgtgct cgccaacgcc agcaacgaca gcagctccca tctacagctg atttacaact   13320
tgacgctatg tgagctgaat ggcacagatt ggctagctaa caaatttgat tgggcagtgg   13380
agagttttgt catctttccc gttttgactc acattgtctc ctatggtgcc ctcactacca   13440
gccatttcct tgacacagtc gctttagtca ctgtgtctac cgccgggttt gttcacgggc   13500
ggtatgtcct aagtagcatc tacgcggtct gtgccctggc tgcgttgact tgcttcgtca   13560
ttaggtttgc aaagaattgc atgtcctggc gctacgcgtg taccagatat accaactttc   13620
ttctggacac taagggcaga ctctatcgtt ggcggtcgcc tgtcatcata gagaaagggg   13680
gcaaagttga ggtcgaaggt catctgatcg acctcaaaag agttgtgctt gatggctccg   13740
tggcaacccc tataaccaga gtttcagcgg aacaatgggg tcgtccttag atgacttctg   13800
tcacgatagc acggctccac aaaaggtgct tttggcgttt tctattacct acacgccagt   13860
gatgatatat gccctaaagg tgagtcgcgg ccgactgcta gggcttctgc acctttttgat   13920 cttcctgaat tgtgctttca ccttcgggta catgactttc gcgcactttc agagtacaaa   13980
taaggtcgcg ctcactatgg gagcagtagt tgcactcctt tggggggtgt actcagccat   14040
agaaacctgg aaattcatca cctccagatg ccgtttgtgc ttgctaggcc gcaagtacat   14100
tctggcccct gcccaccacg ttgaaagtgc cgcaggcttt catccgattg cggcaaatga   14160
taaccacgca tttgtcgtcc ggcgtccgg ctccactacg gtcaacggca cattggtgcc   14220
cgggttaaaa agcctcgtgt tgggtggcag aaaagctgtt aaacagggag tggtaaacct   14280
```

```
tgtcaaatat gccaaataac aacggcaagc agcagaagag aaagaagggg gatggccagc    14340
cagtcaatca gctgtgccag atgctgggta agatcatcgc tcagcaaaac cagtccagag    14400
gcaagggacc gggaaagaaa aataagaaga aaaacccgga gaagccccat tttcctctag    14460
cgactgaaga tgatgtcaga catcacttta ccccctagtga gcggcaattg tgtctgtcgt    14520
caatccagac cgcctttaat caaggcgctg gacttgcac cctgtcagat tcagggagga    14580
taagttacac tgtggagttt agtttgccta cgcatcatac tgtgcgcctg atccgcgtca    14640
cagcatcacc ctcagcatga tgggctggca ttcttgaggc atctcagtgt ttgaattgga    14700
agaatgtgtg gtgaatggca ctgattgaca ttgtgcctct aagtcaccta ttcaattagg    14760
gcgaccgtgt gggggtgaga tttaattggc gagaaccatg cggccgaaat taaaaaaaa    14819

<210> SEQ ID NO 9
<211> LENGTH: 15149
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 9
atgacgtata ggtgttggct ctatgccttg gcatttgtat tgtcaggagc tgtgaccatt      60
ggcacagccc aaaacttgct gcacagaaac acccttctgt gatagcctcc ttcaggggag     120
cttagggttt gtccctagca ccttgcttcc ggagttgcac tgctttacgg tctctccacc     180
cctttaacca tgtctgggat acttgatcgg tgcacgtgta cccccaatgc cagggtgttt     240
atggcggagg ccaagtcta ctgcacacga tgcctcagtg cacggtctct ccttcccctg     300
aacctccagg tttctgagct cggggtgcta ggcctattct acaggcccga agagccactc     360
cggtggacgt tgccacgtgc attccccact gttgagtgct ccccgccgg ggcctgctgg     420 cttttctgcaa tctttccaat cgcacgaatg accagtggaa acctgaactt ccaacaaaga     480
atggtacggg tcgcagctga gctttacaga gccggccagc tcacccctgc agtcttgaag     540
gctctacaag tttatgaacg gggttgccgc tggtacccca ttgttggacc tgtccctgga     600
gtggccgttt tcgccaattc cctacatgtg agtgataaac ccttcccggg agcaactcac     660
gtgttgacca acctgccgct cccgcagaga cccaagcctg aagacttttg ccccttgag     720 tgtgctatgg ctactgtcta tgacattggt catgacgccg tcatgtatgt ggccgaaagg     780
aaagtctcct gggcccctcg tggcggggat gaagtgaaat ttgaagctgt ccccggggag     840
ttgaagttga ttgcgaaccg gctccgcacc tccttcccgc ccaccacac agtggacatg     900 tctaagttcg ccttcacagc ccctgggtgt ggtgtttcta tgcgggtcga acgccaacac     960
ggctgccttc ccgctgacac tgtccctgaa ggcaactgct ggtggagctt gtttgacttg    1020
cttccactgg aagttcagaa caaagaaatt cgccatgcta accaatttgg ctaccagacc    1080
aagcatggtg tctctggcaa gtacctgcag cggaggctgc aagttaatgg tctccgagca    1140
gtaactgacc taaacggacc tatcgtcgta cagtacttct ccgttaagga gagttggatc    1200
cgccatttga aactggcggg agaacccagc tactctgggt ttgaggacct cctcagaata    1260
agggttgagc ctaacacgtc gccattggct gacaaggaag aaaaaatttt ccggtttggc    1320
agtcacaagt ggtacggcgc tggaaagaga gcaagaaaag cacgctcttg tgcgactgct    1380
acagtcgctg gccgcgcttt gtccgttcgt gaaacccgc aggccaagga gcacgaggtt    1440
gccggcgcca acaaggctga gcacctcaaa cactactccc cgcctgccga agggaattgt    1500
```

```
ggttggcact gcatttccgc catcgccaac cggatggtga attccaaatt tgaaaccacc    1560
cttcccgaaa gagtgagacc tccagatgac tgggctactg acgaggatct tgtgaatgcc    1620
atccaaatcc tcagactccc tgcggcctta gacaggaacg gtgcttgtac tagcgccaag    1680
tacgtactta agctggaagg tgagcattgg actgtcactg tgacccctgg gatgtccctt    1740
tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat    1920
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caacccagac gatcaagctg ccccaggtca accagtgtcg tgctctggtc    2280
cctgttgtga ctcaaaagtc cttggacaac aactcggtcc ccctgaccgc cttttcactg    2340
gctaactact actaccgtgc gcaaggtgac gaagttcgtc accgtgaaag actaaccgcc    2400
gtgctctcca gttggaaaa ggttgttcga gaagaatatg ggctcatgcc aaccgagcct    2460
ggtccacggc ccacactgcc acgcgggctc gacgaactca agaccagat ggaggaggac    2520 ttgctgaaac tggctaacgc ccagacgact tcggacatga tggcctgggc agtcgagcag    2580
gttgacctaa aaacttgggt caagaactac ccgcggtgga caccaccacc ccctccgcca    2640
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agcccctttg atctcccgac cccacctgag    2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatcacacgc ccaaaatact cagctcaagc catcatcgac    3000
tcgggcgggc cctgcagtgg gcatctccaa gaggtaaagg aaacatgcct tagtgtcatg    3060
cgcgaggcat gtgatcgac taagcttgat gaccctgcta cgcaggaatg cttttctcgc    3120
atgtgggatc gggtggacat gctgacttgg cgcaacacgt ctgtttacca ggcgatttgc    3180
accttagatg gcaggttaaa gttcctccca aaaatgatac tcgagacacc gccgccctat    3240
ccgtgtgagt ttgtgatgat gcctcacacg cctgcacctt ccgtaggtgc ggagagcgac    3300
cttaccattg gctcagttgc tactgaagat gttccacgca tcctcgagaa aatagaaaat    3360
gtcggcgaga tggccaacca gggacccttg gccttctccg aggataaacc ggtagatgac    3420
caacttgtca acgaccccg gatatcgtcg cggaggcctg acgagagcac atcagctccg    3480
tccgcaggca caggtggcgc cggctctttt accgatttgc cgccttcaga tggcgcggat    3540
gcggacgggg ggggccgtt tcggacggta aaaagaaaag ctgaaaggct cttttgaccaa    3600 ctgagccgtc aggttttga cctcgtctcc catctccctg ttttcttctc acgccttttc    3660
taccctggcg gtggttattc tccgggtgat tggggttttg cagcttttac tctattgtgc    3720
ctctttttat gttacagtta cccagccttt ggtattgctc ccctcttggg tgtgttttct    3780
gggtcttctc ggcgcgttcg aatgggggtt tttggctgct ggttggcttt tgctgttggt    3840
ctgttcaagc ctgtgtccga cccagtcggc gctgcttgtg agtttgactc gccagagtgt    3900
```

-continued

```
agaaacatcc ttcattcttt tgagcttctc aaaccttggg accctgttcg cagccttgtt    3960
gtgggccccg tcggtctcgg tcttgccatt cttggcaggt tactgggcgg ggcacgctgc    4020
atctggcact ttttgcttag gcttggcatt gttgcagact gtatcttggc tggagcttac    4080
gtgctttctc aaggtaggtg taaaaagtgc tggggatctt gtataagaac tgctcccaat    4140
gaggtcgctt ttaacgtgtt tcctttcaca cgtgcgacca ggtcgtcact tatcgacctg    4200
tgcgatcggt tttgtgcgcc aaaaggaatg daccccattt ttctcgccac tgggtggcgc    4260
gggtgctggg ccggccgaag ccccattgag caaccctctg aaaaacccat cgcgtttgcc    4320
cagttggatg aaaagaagat tacggctagg actgtggtcg cccagcctta tgaccccaac    4380
caagccgtaa agtgcttgcg ggtattgcag gcgggtgggg cgatggtggc taaggcggtc    4440
ccaaaagtgg tcaaggtttc cgctgttcca ttccgagccc ccttctttcc cactggagtg    4500
aaagttgacc ctgattgcag ggtcgtggtt daccctgaca ctttcactgc agctctccgg    4560
tctggctact ccaccacaaa cctcgtcctt ggtgtggggg actttgccca gctgaatgga    4620
ttaaaaatca ggcaaatttc caagccttca ggggaggcc cacatctcat ggctgccctg    4680
catgttgcct gctcgatggc tctgcacatg cttgctggga tttatgtgac tgcggtgggt    4740
tcttgcggca ccggcaccaa cgacccgtgg tgcgctaacc cgtttgccgt ccctggctac    4800
ggacctggct ctctctgcac gtccagattg tgcatttccc aacacggcct taccctgccc    4860
ttgacagcac ttgtggcggg attcggtatt caagaaattg ccttggtcgt tttgattttt    4920
gtttccatcg gaggcatggc tcataggttg agctgtaagg ctgacatgct gtgtgtcttg    4980
cttgcaattg ccagctatgt ttgggtacct cttacctggt tgctttgtgt gtttccttgc    5040
tggttgcgct gtttttcttt gcaccccctc accatcctat ggttggtgtt tttcttgatt    5100
tctgtgaata tgccttcagg aatcttggcc atggtgttgt tggtttctct ttggcttctt    5160
ggtcgttata ctaatgttgc tggccttgtc acccctacg acattcatca ttacaccagt    5220
ggccccgcg gtgttgccgc cttggctacc gcaccagatg ggacctactt ggccgctgtc    5280
cgccgcgctg cgttgactgg ccgcaccatg ctgtttaccc cgtcccagct gggtctctt    5340
cttgagggtg ctttcagaac tcgaaagccc tcactgaaca ccgtcaatgt gatcgggtcc    5400
tccatgggct ctggcggggt gtttaccatc gacgggaaag tcaagtgcgt aactgccgca    5460
catgtcctta cgggcaattc agctcgggtt tccggggtcg gcttcaatca aatgcttgac    5520
tttgacgtaa agggagattt cgctatagct gattgcccga attggcaagg ggctgccccc    5580
aagacccaat tctgcacgga tggatggact ggccgtgcct attggctaac atcctctggc    5640
gtcgaacccg gcgtcattgg aaaaggattc gccttctgct tcaccgcatg tggcgattcc    5700
gggtccccag tgatcaccga ggccggtgag cttgtcggcg ttcacacggg atcgaataaa    5760
caagggggg gcattgttac gcgccctca ggccagtttt gtaatgtggc acccatcaag    5820
ctaagcgaat taagtgaatt cttttgctggg cctaaggtcc cgctcggtga tgtgaaggtc    5880
ggcagccaca taattaaaga cataagcgag gtgccttcag atctttgtgc cttgcttgct    5940
gccaaacctg aactgaagg aggcctctcc accgtccaac ttctttgtgt gttttttctc    6000
ctgtggagaa tgatgggaca tgcctggacg cccttggttg ctgtgagttt ctttattttg    6060
aatgaggttc tcccagccgt cctggtccgg agtgttttct cctttggaat gtttgtgcta    6120
tcctggctca cgccatggtc tgcgcaagtt ctgatgatca ggcttctgac agcagctctt    6180
aacaggaaca gatggtcact tgcctttttc agctcggtg cagtgaccgg ttttgtcgca    6240
gatcttgcgg ccactcaggg gcatccgttg caggcagtga tgaatttgag cacctatgca    6300
```

```
ttcctgcctc ggatgatggt tgtgacctca ccagtcccag tgatcacgtg tggtgtcgtg    6360
cacctacttg ccatcatttt gtacttgttt aagtaccgtg gcctgcacca tatccttgtt    6420
ggcgatggag tgttctctgc ggcttcttc ttgagatact ttgccgaggg aaagttgagg     6480 gaagggtgt cgcaatcctg cggaatgaat catgagtctc tgactggtgc cctcgctatg     6540
agactcaatg acgaggactt ggatttcctt atgaaatgga ctgattttaa gtgctttgtt    6600
tctgcgtcca acatgaggaa tgcagcgggt caatttatcg aggctgccta tgctaaagca    6660
cttagagtag aactggccca gttggtgcag gttgataaag ttcgaggtac tttggccaaa    6720
cttgaagctt ttgctgatac cgtggcacct caactctcgc ccggtgacat tgttgtcgct    6780
ctcggccaca cgcctgttgg cagtatcttc gacctaaagg ttggtagcac caagcatacc    6840
ctccaagcca ttgagaccag agtccttgct gggtccaaaa tgaccgtggc gcgcgtcgtc    6900
gacccgaccc ccacgccccc acccgcaccc gtgcccatcc cctcccacc gaaagttctg     6960 gagaatggcc ccaacgcttg gggggatgag gaccgtttga ataagaagaa gaggcgcagg    7020
atggaagccc tcggcatcta tgttatgggc gggaaaaaat accagaaatt tgggacaag    7080 aattccggtg atgtgttta tgaggaggtc cataataaca cagatgagtg ggagtgtctc     7140
agagttggcg accctgccga cttgacccct gagaagggaa ctctgtgtgg acatgtcacc    7200
attgaaaaca aggcttacca tgtttacacc tccccatctg gtaagaagtt cttggtcccc    7260
gtcaacccag agaatggaag agtccaatgg gaagctgcaa agctttccgt ggagcaggcc    7320
ctaggtatga tgaatgtcga cggcgaactg actgccaaag aactggagaa actgaaaaga    7380
ataattgaca aactccaggg cctgactaag gagcagtgtt taaactgcta gccgccagcg    7440
acttgacccg ctgtggtcgc ggcggcttgg ttgttactga acagcggta aaaatagtca    7500 aatttcacaa ccggaccttc accctgggac ctgtgaattt aaaagtggcc agtgaggttg    7560
agctaaaaga cgcggttgag cacaaccaac accccggttgc gagaccgatc gatggtggag    7620
ttgtgctcct gcgttccgcg gttccttcgc ttatagacgt cttgatctcc ggtgctgatg    7680
catctcccaa gttacttgcc catcacgggc cgggaaacac tgggatcgat ggcacgctct    7740 gggatttttga gtccgaagcc actaaagagg aagtcgcact cagtgcgcaa ataatacagg    7800
cttgtgacat taggcgcggc gacgctcctg aaattggtct cccttacaag ctgtaccctg    7860
ttaggggtaa ccctgagcgg gtgaaaggag ttctgcagaa tacaaggttt ggagacatac    7920
cttacaaaac ccccagtgac actggaagcc cagtgcacgc ggctgcctgc cttacgccca    7980
acgccactcc ggtgactgat gggcgctccg tcttggccac gaccatgccc cgggttttg    8040 agttatatgt accgaccata ccagcgtctg tccttgatta ccttgactct aggcctgact    8100
gccctaaaca gctgacagag cacggctgcg aagatgccgc actgaaagac ctctctaaat    8160
atgacttgtc cacccaaggc tttgttttac ctggagttct tcgccttgtg cggaaatacc    8220 tgttttgccca tgtaggtaag tgcccacccg ttcatcggcc ttctacttac cctgctaaga    8280
attctatggc tggaataaat gggaacaggt tcccaaccaa ggacattcag agcgtccctg    8340
aaatcgacgt tctgtgcgca caggctgtgc gagaaaactg gcaaactgtc accccttgta    8400
ctcttaagaa acagtattgc gggaagaaga agactaggac catactcggc accaataact    8460
tcatcgcact agcccaccga gcagtgttga gtggtgttac ccaggggcttc atgaaaaagg    8520 cgtttaactc gcccatcgcc ctcggaaaga acaagtttaa ggagctacag actccggtcc    8580
tgggcaggtg ccttgaagct gatctcgcat cctgcgatcg atccacgcct gcaattgtcc    8640 gctggttgc cgccaaccttt cttatgaac ttgcctgtgc tgaagagcat ctaccgtcgt     8700
```

```
acgtgctgaa ctgctgccac gacttactgg tcacgcagtc cggcgcagtg actaagagag    8760
gtggcctgtc gtctggcgac ccgatcacct ctgtgtctaa caccatttat agtttggtga    8820
tctatgcaca gcatatggtg cttagttact tcaaaagtgg tcaccccat ggccttctgt     8880 tcttacaaga ccagctaaag tttgaggaca tgctcaaggt tcaacccctg atcgtctatt    8940
cggacgacct cgtgctgtat gccgagtctc ccaccatgcc aaactatcac tggtgggttg    9000
aacatctgaa tttgatgctg gggtttcaga cggacccaaa gaagacagca ataacagact    9060
cgccatcatt tctaggctgt agaataataa atgggcgcca gctagtcccc aaccgtgaca    9120
ggatcctcgc ggccctcgcc tatcacatga aggcgagtaa tgtttctgaa tactatgcct    9180
cagcggctgc aatactcatg gacagctgtg cttgtttgga gtatgatcct gaatggtttg    9240
aagaacttgt agttggaata gcgcagtgcg cccgcaagga cggctacagc tttcccggca    9300
cgccgttctt catgtccatg tgggaaaaac tcaggtccaa ttatgagggg aagaagtcga    9360
gagtgtgcgg gtactgcggg gccccggccc cgtacgctac tgcctgtggc ctcgacgtct    9420
gcatttacca cacccacttc caccagcatt gtccagtcac aatctggtgt ggccatccag    9480
cgggttctgg ttcttgtagt gagtgcaaat cccctgtagg gaaaggcaca agccctttag    9540
acgaggtgct ggaacaagtc ccgtataagc ccccacggac cgttatcatg catgtggagc    9600
agggtctcac ccccccttgat ccaggtagat accaaactcg ccgcggatta gtctctgtca    9660
ggcgtggaat taggggaaat gaagttggac taccagacgg tgattatgct agcaccgcct    9720
tgctccctac ctgcaaagag atcaacatgg tcgctgtcgc ttccaatgta ttgcgcagca    9780
ggttcatcat cggcccaccc ggtgctggga aaacatactg gctccttcaa caggtccagg    9840
atggtgatgt tatttacaca ccaactcacc agaccatgct tgacatgatt agggctttgg    9900
ggacgtgccg gttcaacgtc ccggcaggca caacgctgca attccccgtc ccctcccgca    9960
ccggtccgtg ggttcgcatc ctagccggcg gttggtgtcc tggcaagaat tccttcctag   10020
atgaagcagc gtattgcaat caccttgatg ttttgaggct tcttagtaaa actaccctca   10080
cctgtctagg agacttcaag caactccacc cagtgggttt tgattctcat tgctatgttt   10140
ttgacatcat gcctcaaact caactgaaga ccatctggag gtttggacag aatatctgtg   10200
atgccattca gccagattac agggacaaac tcatgtccat ggtcaacaca acccgtgtga   10260
cctacgtgga aaaacctgtc aggtatgggc aggtcctcac cccctaccac agggaccgag   10320
aggacgacgc catcactatt gactccagtc aaggcgccac attcgatgtg gttacattgc   10380
atttgcccac taaagattca ctcaacaggc aaagagccct tgttgctatc accagggcaa   10440
gacacgctat ctttgtgtat gacccacaca ggcagctgca gggcttgttt gatcttcctg   10500
caaaaggcac gcccgtcaac ctcgcagtgc actgcgacgg gcagctgatc gtgctggata   10560
gaaataacaa agaatgcacg gttgctcagg ctctaggcaa cgggataaa tttagggcca    10620 cagacaagcg tgttgtagat tctctccgcg ccatttgtgc tgatctagaa gggtcgagct   10680
ctccgctccc caaggtcgca cacaacttgg gatttatttt ctcacctgat ttaacacagt   10740
ttgctaaact cccagtagaa cttgcacctc actggcccgt ggtgtcaacc cagaacaatg   10800
aaaagtggcc ggatcggctg gttgccagcc ttcgccctat ccataaatac agccgcgcgt   10860
gcatcggtgc cggctatatg gtgggccctt cggtgttttc taggcactcc ggggtcgtgt   10920
catactatct cacaaaattt gttaagggcg gggctcaagt gcttccggag acggttttca   10980
gcaccggccg aattgaggta gactgccggg aatatcttga tgatcgggag cgagaagttg   11040
ctgcgtccct cccacacgct ttcattggcg acgtcaaagg cactaccgtt ggaggatgtc   11100
```

```
atcatgtcac ctccagatac ctcccgcgcg tccttcccaa ggaatcagtt gcggtagtcg   11160
gggtttcaag ccccggaaaa gccgcgaaag cattgtgcac actgacagat gtgtacctcc   11220
cagatcttga agcctatctc cacccggaga cccagtccaa gtgctggaaa atgatgttgg   11280
acttcaaaga agttcgacta atggtctgga aagacaaaac agcctatttc caacttgaag   11340
gtcgctattt cacctggtat cagcttgcca gctatgcctc gtacatccgt gttcccgtca   11400
actctacggt gtacttggac ccctgcatgg gccccgccct ttgcaacagg agagtcgtcg   11460
ggtccaccca ctgggggct gacctcgcgg tcaccccta tgattacggc gctaaaatta   11520
tcctgtctag cgcgtaccat ggtgaaatgc ccccggata caaaattctg gcgtgcgcgg   11580
agttctcgtt ggatgaccca gttaagtaca acatacctg gggtttgaa tcggatacag   11640
cgtatctgta tgagttcacc ggaaacggtg aggactggga ggattacaat gatgcgtttc   11700
gtgcgcgcca ggaagggaaa atttataagg ccactgccac cagcttgaag ttttattttc   11760
ccccgggccc tgtcattgaa ccaactttag gcctgaattg aaatgaaatg gggtccatgc   11820
aaagcctttt tgacaaaatt ggccaacttt ttgtggatgc tttcacggag ttcttggtgt   11880
ccattgttga tatcattata ttttttggcca ttttgtttgg cttccaccat gccggttggc   11940
tggtggtctt ttgcatcaga ttggtttgct ccgcgatact ccgtacgcgc cctgccattc   12000
actctgagca attacagaag atcttatgag gcctttcttt cccagtgcca agtggacatt   12060
cccacctggg gaactaaaca tcctttgggg atgctttggc accataaggt gtcaaccctg   12120
attgatgaaa tggtgtcgcg tcgaatgtac cgcatcatgg aaaaagcagg gcaggctgcc   12180
tggaaacagg tggtgagcga ggctacgctg tctcgcatta gtagtttgga tgtggtggct   12240
cattttcagc atctagccgc cattgaagcc gagacctgta aatatttggc ctcccggctg   12300
cccatgctac acaacctgcg catgacaggg tcaaatgtaa ccatagtgta aatagcact   12360
ttgaatcagg tgttgctat ttttccaacc cctggttccc ggccaaagct tcatgatttt   12420
cagcaatggt taatagctgt acattcctcc atatttcct ctgttgcagc ttcttgtact   12480
cttttttgttg tgctgtggtt gcgggttcca atactacgta ctgttttttgg tttccgctgg   12540
ttaggggcaa tttttctttc gaactcacag tgaattacac ggtgtgtcca ccttgcctca   12600
cccggcaagc agccacagag atctacgaac ccggtaggtc tctttggtgc aggatagggt   12660
atgaccgatg tggggaggac gatcatgacg agctagggtt tatgataccg cctggcctct   12720
ccagcgaagg ccacttgact ggtgtttacg cctggttggc gttcttgtcc ttcagctaca   12780
cggcccagtt ccatcccgag atattcggga tagggaatgt gagtcgagtt tatgttgaca   12840
tcaaacatca actcatctgc gccgaacatg acgggcagaa caccaccttg cctcgtcatg   12900
acaacatttc agccgtgttt cagacctatt accaacatca agtcgacggc ggcaattggt   12960
ttcacctaga atggcttcgt cccttctttt cctcgtggtt ggttttaaat gtctcttggt   13020
ttctcaggcg ttcgcctgca aaccatgttt cagttcgagt cttgcagata ttaagaccaa   13080
caccaccgca gcggcaagct ttgctgtcct ccaagacatc agttgcctta ggcatcgcga   13140
ctcggcctct gaggcgattc gcaaaatccc tcagtgccgt acggcgatag gacacccgt    13200
gtatgttacc atcacagcca atgtgacaga tgagaattat ttacattctt ctgatctcct   13260
catgctttct tcttgccttt tctatgcttc tgagatgagt gaaaagggat ttaaggtggt   13320
atttggcaat gtgtcaggca tcgtggctgt gtgtgtcaat tttaccagct acgtccaaca   13380
tgtcaaggag tttacccaac gctccctggt ggtcgaccat gtgcggttgc tccatttcat   13440
gacacctgag accatgaggt gggcaactgt tttagcctgt ctttttgcca ttctgttggc   13500
```

-continued

```
aatttgaatg tttaagtatg ttggagaaat gcttgaccgc gggctgttgc tcgcgattgc    13560
tttctttgtg gtgtatcgtg ccgttctgtt ttgctgtgct cgccaacgcc agcaacgaca    13620
gcagctccca tctacagctg atttacaact tgacgctatg tgagctgaat ggcacagatt    13680
ggctagctaa caaatttgat tgggcagtgg agagttttgt catctttccc gttttgactc    13740
acattgtctc ctatggtgcc ctcactacca gccatttcct tgacacagtc gctttagtca    13800
ctgtgtctac cgccgggttt gttcacgggc ggtatgtcct aagtagcatc tacgcggtct    13860
gtgccctggc tgcgttgact tgcttcgtca ttaggtttgc aaagaattgc atgtcctggc    13920
gctacgcgtg taccagatat accaactttc ttctggacac taagggcaga ctctatcgtt    13980
ggcggtcgcc tgtcatcata gagaaaaggg gcaaagttga ggtcgaaggt catctgatcg    14040
acctcaaaag agttgtgctt gatggctccg tggcaacccc tataaccaga gtttcagcgg    14100
aacaatgggg tcgtccttag atgacttctg tcacgatagc acggctccac aaaaggtgct    14160
tttggcgttt tctattacct acacgccagt gatgatatat gccctaaagg tgagtcgcgg    14220
ccgactgcta gggcttctgc accttttgat cttcctgaat tgtgctttca ccttcgggta    14280
catgactttc gcgcactttc agagtacaaa taaggtcgcg ctcactatgg gagcagtagt    14340
tgcactcctt tgggggtgt actcagccat agaaacctgg aaattcatca cctccagatg    14400
ccgtttgtgc ttgctaggcc gcaagtacat tctggcccct gccccaccac gttgaaagtgc    14460 cgcaggcttt catccgattg cggcaaatga taaccacgca tttgtcgtcc ggcgtcccgg    14520
ctccactacg gtcaacggca cattggtgcc cgggttaaaa agcctcgtgt tgggtggcag    14580
aaaagctgtt aaacagggag tggtaaacct tgtcaaatat gccaaataac aacggcaagc    14640
agcagaagag aaagaagggg gatggccagc cagtcaatca gctgtgccag atgctgggta    14700
agatcatcgc tcagcaaaac cagtccagag gcaagggacc gggaaagaaa aataagaaga    14760 aaacccgga gaagccccat tttcctctag cgactgaaga tgatgtcaga catcactttta    14820 cccctagtga gcggcaattg tgtctgtcgt caatccagac cgcctttaat caaggcgctg    14880
ggacttgcac cctgtcagat tcagggagga taagttacac tgtggagttt agtttgccta    14940
cgcatcatac tgtgcgcctg atccgcgtca cagcatcacc ctcagcatga tgggctggca    15000
ttcttgaggc atctcagtgt ttgaattgga agaatgtgtg gtgaatggca ctgattgaca    15060
ttgtgcctct aagtcaccta ttcaattagg gcgaccgtgt gggggtgaga tttaattggc    15120
gagaaccatg cggccgaaat taaaaaaaa                                      15149
```

<210> SEQ ID NO 10
<211> LENGTH: 15137
<212> TYPE: DNA
<213> ORGANISM: Artificial Sequence
<220> FEATURE:
<223> OTHER INFORMATION: Porcine reproductive and respiratory syndrome virus

<400> SEQUENCE: 10

```
atgacgtata ggtgttggct ctatgccttg gcatttgtat tgtcaggagc tgtgaccatt      60
ggcacagccc aaaacttgct gcacagaaac acccttctgt gatagcctcc ttcaggggag     120
cttagggttt gtccctagca ccttgcttcc ggagttgcac tgctttacgg tctctccacc     180
cctttaacca tgtctgggat acttgatcgg tgcacggtgt accccaatgc cagggtgttt     240
atggcggagg ccaagtctac tgcacacga tgcctcagtg cacggtctct ccttcccctg      300
aacctccagg tttctgagct cggggtgcta ggcctattct acaggcccga agagccactc     360
cggtggacgt tgccacgtgc attccccact gttgagtgct ccccgccgg ggcctgctgg      420
```

```
ctttctgcaa tctttccaat cgcacgaatg accagtggaa acctgaactt ccaacaaaga    480
atggtacggg tcgcagctga gctttacaga gccggccagc tcacccctgc agtcttgaag    540
gctctacaag tttatgaacg gggttgccgc tggtacccca ttgttggacc tgtccctgga    600
gtggccgttt tcgccaattc cctacatgtg agtgataaac ccttcccggg agcaactcac    660
gtgttgacca acctgccgct cccgcagaga cccaagcctg aagacttttg ccccttgag    720
tgtgctatgg ctactgtcta tgacattggt catgacgccg tcatgtatgt ggccgaaagg    780
aaagtctcct gggcccctcg tggcggggat gaagtgaaat ttgaagctgt ccccggggag    840
ttgaagttga ttgcgaaccg gctccgcacc tccttcccgc cccaccacac agtggacatg    900
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga aactggcggg agaacccagc tactctgggt tgaggaccct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctggaagg tgagcattgg actgtcactg tgaccctgg gatgtcccct   1740
tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagccttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc cctgaccgc ttttcactg   2340
gctaactact actaccgtgc gcaaggtgac gaagttcgtc accgtgaaag actaaccgcc   2400
gtgctctcca gttggaaaa ggttgttcga gaagaatatg gctcatgcc aaccgagcct   2460
ggtccacggc ccacactgcc acgcgggctc gacgaactca agaccagat ggaggaggac   2520
ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agcccctttg atctcccgac cccacctgag   2820
```

```
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct cccccagcac cgccgcagag cgggggcgtt    3120
ctgggagtag aggggcatga agctgaggaa accctgagtg aaatctcgga catgtcgggt    3180
aacattaaac ctgcgtccgt gtcatcaagc agctccttgt ccagcgtgag atgtgagttt    3240
gtgatgatgc ctcacacgcc tgcaccttcc gtaggtgcgg agagcgacct taccattggc    3300
tcagttgcta ctgaagatgt tccacgcatc ctcgagaaaa tagaaaatgt cggcgagatg    3360
gccaaccagg gacccttggc cttctccgag ataaaccgg tagatgacca acttgtcaac    3420 gaccccccgga tatcgtcgcg gaggcctgac gagagcacat cagctccgtc cgcaggcaca    3480
ggtggcgccg gctcttttac cgatttgccg ccttcagatg gcgcggatgc ggacgggggg    3540
gggccgtttc ggacggtaaa aagaaaagct gaaaggctct ttgaccaact gagccgtcag    3600
gtttttgacc tcgtctccca tctccctgtt ttcttctcac gccttttcta ccctggcggt    3660
ggttattctc cgggtgattg gggttttgca gcttttactc tattgtgcct cttttatgt    3720 tacagttacc cagcctttgg tattgctccc ctcttgggtg tgttttctgg gtcttctcgg    3780
cgcgttcgaa tgggggtttt tggctgctgg ttggcttttg ctgttggtct gttcaagcct    3840
gtgtccgacc cagtcggcgc tgcttgtgag tttgactcgc cagagtgtag aaacatcctt    3900
cattcttttg agcttctcaa accttgggac cctgttcgca gccttgttgt gggccccgtc    3960
ggtctcggtc ttgccattct tggcaggtta ctgggcgggg cacgctgcat ctggcacttt    4020
ttgcttaggc ttggcattgt tgcagactgt atcttggctg gagcttacgt gctttctcaa    4080
ggtaggtgta aaaagtgctg gggatcttgt ataagaactg ctcccaatga ggtcgctttt    4140
aacgtgtttc ctttcacacg tgcgaccagg tcgtcactta tcgacctgtg cgatcggttt    4200
tgtgcgccaa aaggaatgga ccccatttttt ctcgccactg ggtggcgcgg gtgctgggcc    4260
ggccgaagcc ccattgagca accctctgaa aaacccatcg cgtttgccca gttggatgaa    4320
aagaagatta cggctaggac tgtggtcgcc cagccttatg accccaacca agccgtaaag    4380
tgcttgcggg tattgcaggc gggtggggcg atggtggcta aggcggtccc aaaagtggtc    4440
aaggtttccg ctgttccatt ccgagccccc ttctttccca ctggagtgaa agttgaccct    4500
gattgcaggg tcgtggttga ccctgacact ttcactgcag ctctccggtc tggctactcc    4560
accacaaacc tcgtccttgg tgtgggggac tttgcccagc tgaatggatt aaaaaatcagg    4620 caaatttcca agccttcagg gggaggccca catctcatgg ctgccctgca tgttgcctgc    4680
tcgatggctc tgcacatgct tgctgggatt tatgtgactg cggtgggttc ttgcggcacc    4740
ggcaccaacg accccgtggtg cgctaacccg tttgccgtcc ctggctacgg acctggctct    4800
ctctgcacgt ccagattgtg catttcccaa cacggcctta ccctgccctt gacagcactt    4860
gtggcgggat tcggtattca agaaattgcc ttggtcgttt tgattttttgt ttccatcgga    4920 ggcatggctc ataggttgag ctgtaaggct gacatgctgt gtgtcttgct tgcaattgcc    4980
agctatgttt gggtacctct tacctggttg ctttgtgtgt ttccttgctg gttgcgctgt    5040
ttttctttgc acccctcac catcctatgg ttggtgtttt tcttgatttc tgtgaatatg    5100
ccttcaggaa tcttggccat ggtgttgttg gtttctcttt ggcttcttgg tcgttatact    5160
aatgttgctg gccttgtcac cccctacgac attcatcatt acaccagtgg ccccgcggt    5220
```

```
gttgccgcct tggctaccgc accagatggg acctacttgg ccgctgtccg ccgcgctgcg   5280
ttgactggcc gcaccatgct gtttaccccg tcccagcttg ggtctcttct tgagggtgct   5340
ttcagaactc gaaagccctc actgaacacc gtcaatgtga tcgggtcctc catgggctct   5400
ggcggggtgt ttaccatcga cgggaaagtc aagtgcgtaa ctgccgcaca tgtccttacg   5460
ggcaattcag ctcgggtttc cggggtcggc ttcaatcaaa tgcttgactt tgacgtaaag   5520
ggagatttcg ctatagctga ttgcccgaat tggcaagggg ctgcccccaa gacccaattc   5580
tgcacggatg gatggactgg ccgtgcctat tggctaacat cctctggcgt cgaacccggc   5640
gtcattggaa aaggattcgc cttctgcttc accgcatgtg gcgattccgg gtccccagtg   5700
atcaccgagg ccggtgagct tgtcggcgtt cacacgggat cgaataaaca agggggggc   5760 attgttacgc gcccctcagg ccagttttgt aatgtggcac ccatcaagct aagcgaatta   5820
agtgaattct tgctgggcc taaggtcccg ctcggtgatg tgaaggtcgg cagccacata   5880
attaaagaca taagcgaggt gccttcagat cttgtgcct tgcttgctgc caaacctgaa   5940
ctggaaggag gcctctccac cgtccaactt cttgtgtgt tttttctcct gtggagaatg   6000
atgggacatg cctggacgcc cttggttgct gtgagtttct ttattttgaa tgaggttctc   6060
ccagccgtcc tggtccggag tgttttctcc tttggaatgt tgtgctatc ctggctcacg   6120 ccatggtctg cgcaagttct gatgatcagg cttctgacag cagctcttaa caggaacaga   6180
tggtcacttg ccttttcag cctcggtgca gtgaccggtt ttgtcgcaga tcttgcggcc   6240 actcagggc atccgttgca ggcagtgatg aatttgagca cctatgcatt cctgcctcgg   6300
atgatggttg tgacctcacc agtcccagtg atcacgtgtg gtgtcgtgca cctacttgcc   6360 atcatttgt acttgtttaa gtaccgtggc ctgcaccata tccttgttgg cgatggagtg   6420
ttctctgcgg ctttcttctt gagatacttt gccgagggaa agttgaggga aggggtgtcg   6480
caatcctgcg gaatgaatca tgagtctctg actggtgccc tcgctatgag actcaatgac   6540
gaggacttgg atttccttat gaaatggact gatttttaagt gctttgtttc tgcgtccaac   6600
atgaggaatg cagcgggtca atttatcgag gctgcctatg ctaaagcact tagagtagaa   6660
ctggcccagt tggtgcaggt tgataaagtt cgaggtactt tggccaaact tgaagctttt   6720
gctgataccg tggcacctca actctcgccc ggtgacattg ttgtcgctct cggccacacg   6780
cctgttggca gtatcttcga cctaaaggtt ggtagcacca agcataccct ccaagccatt   6840
gagaccagag tccttgctgg gtccaaaatg accgtggcgc gcgtcgtcga cccgacccc   6900 acgcccccac ccgcacccgt gcccatcccc ctcccaccga aagttctgga gaatggcccc   6960
aacgcttggg gggatgagga ccgtttgaat aagaagaaga ggcgcaggat ggaagccctc   7020
ggcatctatg ttatgggcgg gaaaaaatac cagaaatttt gggacaagaa ttccggtgat   7080
gtgttttatg aggaggtcca taataacaca gatgagtggg agtgtctcag agttggcgac   7140
cctgccgact ttgaccctga agggaact ctgtgtggac atgtcaccat gaaaacaag   7200 gcttaccatg tttacacctc cccatctggt aagaagttct tggtcccgt caacccagag   7260 aatggaagag tccaatggga agctgcaaag ctttccgtgg agcaggccct aggtatgatg   7320
aatgtcgacg gcgaactgac tgccaaagaa ctggagaaac tgaaaagaat aattgacaaa   7380
ctccagggcc tgactaagga gcagtgttta aactgctagc cgccagcgac ttgacccgct   7440
gtggtcgcgg cggcttggtt gttactgaaa cagcggtaaa aatagtcaaa tttcacaacc   7500
ggaccttcac cctgggacct gtgaatttaa aagtggccag tgaggttgag ctaaaagacg   7560
cggttgagca caaccaacac ccggttgcga gaccgatcga tggtggagtt gtgctcctgc   7620
```

```
gttccgcggt tccttcgctt atagacgtct tgatctccgg tgctgatgca tctcccaagt   7680
tacttgccca tcacgggccg ggaaacactg ggatcgatgg cacgctctgg gattttgagt   7740
ccgaagccac taaagaggaa gtcgcactca gtgcgcaaat aatacaggct tgtgacatta   7800
ggcgcggcga cgctcctgaa attggtctcc cttacaagct gtaccctgtt aggggtaacc   7860
ctgagcgggt gaaggagtt ctgcagaata caaggtttgg agacatacct tacaaaaccc    7920
ccagtgacac tggaagccca gtgcacgcgg ctgcctgcct tacgcccaac gccactccgg   7980
tgactgatgg gcgctccgtc ttggccacga ccatgccccc cgggtttgag ttatatgtac   8040
cgaccatacc agcgtctgtc cttgattacc ttgactctag gcctgactgc cctaaacagc   8100
tgacagagca cggctgcgaa gatgccgcac tgaaagacct ctctaaatat gacttgtcca   8160
cccaaggctt tgttttacct ggagttcttc gccttgtgcg gaaatacctg tttgcccatg   8220
taggtaagtg cccacccgtt catcggcctt ctacttaccc tgctaagaat tctatggctg   8280
gaataaatgg gaacaggttc ccaaccaagg acattcagag cgtccctgaa atcgacgttc   8340
tgtgcgcaca ggctgtgcga gaaaactggc aaactgtcac cccttgtact cttaagaaac   8400
agtattgcgg gaagaagaag actaggacca tactcggcac caataacttc atcgcactag   8460
cccaccgagc agtgttgagt ggtgttaccc agggcttcat gaaaaaggcg tttaactcgc   8520
ccatcgccct cggaaagaac aagtttaagg agctacagac tccggtcctg ggcaggtgcc   8580
ttgaagctga tctcgcatcc tgcgatcgat ccacgcctgc aattgtccgc tggtttgccg   8640
ccaaccttct ttatgaactt gcctgtgctg aagagcatct accgtcgtac gtgctgaact   8700
gctgccacga cttactggtc acgcagtccg gcgcagtgac taagagaggt ggcctgtcgt   8760
ctggcgaccc gatcacctct gtgtctaaca ccatttatag tttggtgatc tatgcacagc   8820
atatggtgct tagttacttc aaaagtggtc accccatgg ccttctgttc ttacaagacc    8880
agctaaagtt tgaggacatg ctcaaggttc aaccctgat cgtctattcg gacgacctcg    8940
tgctgtatgc cgagtctccc accatgccaa actatcactg gtgggttgaa catctgaatt   9000
tgatgctggg gtttcagacg gacccaaaga agacagcaat aacagactcg ccatcatttc   9060
taggctgtag aataataaat gggcgccagc tagtccccaa ccgtgacagg atcctcgcgg   9120
ccctcgccta tcacatgaag gcgagtaatg tttctgaata ctatgcctca gcggctgcaa   9180
tactcatgga cagctgtgct tgtttggagt atgatcctga atggtttgaa gaacttgtag   9240
ttggaatagc gcagtgcgcc cgcaaggacg gctacagctt tcccggcacg ccgttcttca   9300
tgtccatgtg ggaaaaactc aggtccaatt atgagggaa gaagtcgaga gtgtgcgggt    9360
actgcggggc cccggccccg tacgctactg cctgtggcct cgacgtctgc atttaccaca   9420
cccacttcca ccagcattgt ccagtcacaa tctggtgtgg ccatccagcg ggttctggtt   9480
cttgtagtga gtgcaaatcc cctgtaggga aaggcacaag ccctttagac gaggtgctgg   9540
aacaagtccc gtataagccc ccacggaccg ttatcatgca tgtggagcag ggtctcaccc   9600
cccttgatcc aggtagatac caaactcgcc gcggattagt ctctgtcagg cgtgaatta    9660 ggggaaatga agttggacta ccagacggtg attatgctag caccgccttg ctccctacct   9720
gcaaagagat caacatggtc gctgtcgctt ccaatgtatt gcgcagcagg ttcatcatcg   9780 gcccaccccgg tgctgggaaa acatactggc tccttcaaca ggtccaggat ggtgatgtta   9840
tttacacacc aactcaccag accatgcttg acatgattag ggctttgggg acgtgccggt   9900
tcaacgtccc ggcaggcaca acgctgcaat tccccgtccc ctcccgcacc ggtccgtggg   9960
ttcgcatcct agccggcggt tggtgtcctg gcaagaattc cttcctagat gaagcagcgt   10020
```

```
attgcaatca ccttgatgtt ttgaggcttc ttagtaaaac taccctcacc tgtctaggag    10080
acttcaagca actccaccca gtgggttttg attctcattg ctatgttttt gacatcatgc    10140
ctcaaactca actgaagacc atctggaggt tggacagaa tatctgtgat gccattcagc     10200
cagattacag ggacaaactc atgtccatgg tcaacacaac ccgtgtgacc tacgtggaaa    10260
aacctgtcag gtatgggcag gtcctcaccc cctaccacag ggaccgagag gacgacgcca    10320
tcactattga ctccagtcaa ggcgccacat tcgatgtggt tacattgcat ttgcccacta    10380
aagattcact caacaggcaa agagcccttg ttgctatcac cagggcaaga cacgctatct    10440
ttgtgtatga cccacacagg cagctgcagg gcttgtttga tcttcctgca aaaggcacgc    10500
ccgtcaacct cgcagtgcac tgcgacgggc agctgatcgt gctggataga aataacaaag    10560
aatgcacggt tgctcaggct ctaggcaacg gggataaatt tagggccaca gacaagcgtg    10620
ttgtagattc tctccgcgcc atttgtgctg atctagaagg gtcgagctct ccgctcccca    10680
aggtcgcaca caacttggga tttttatttct cacctgattt aacacagttt gctaaactcc    10740
cagtagaact tgcacctcac tggcccgtgg tgtcaaccca gaacaatgaa agtggccgg    10800 atcggctggt tgccagcctt cgccctatcc ataaatacag ccgcgcgtgc atcggtgccg    10860
gctatatggt gggcccttcg gtgtttctag gcactcctgg ggtcgtgtca tactatctca    10920
caaaatttgt taagggcggg gctcaagtgc ttccggagac ggttttcagc accggccgaa    10980
ttgaggtaga ctgccgggaa tatcttgatg atcgggagcg agaagttgct gcgtccctcc    11040
cacacgcttt cattggcgac gtcaaaggca ctaccgttgg aggatgtcat catgtcacct    11100
ccagatacct cccgcgcgtc cttcccaagg aatcagttgc ggtagtcggg gtttcaagcc    11160
ccggaaaagc cgcgaaagca ttgtgcacac tgacagatgt gtacctccca gatcttgaag    11220
cctatctcca cccggagacc cagtccaagt gctggaaaat gatgttggac ttcaaagaag    11280
ttcgactaat ggtctggaaa gacaaaacag cctatttcca acttgaaggt cgctatttca    11340
cctggtatca gcttgccagc tatgcctcgt acatccgtgt tcccgtcaac tctacggtgt    11400
acttggaccc ctgcatgggc cccgcccttt gcaacaggag agtcgtcggg tccacccact    11460 gggggggctga cctcgcggtc accccttatg attacggcgc taaaattatc ctgtctagcg    11520
cgtaccatgg tgaaatgccc cccggataca aaattctggc gtgcgcggag ttctcgttgg    11580
atgacccagt taagtacaaa catacctggg ggtttgaatc ggatacagcg tatctgtatg    11640
agttcaccgg aaacggtgag gactgggagg attacaatga tgcgtttcgt gcgcgccagg    11700
aagggaaaat ttataaggcc actgccacca gcttgaagtt ttatttttccc ccgggccctg    11760 tcattgaacc aactttaggc ctgaattgaa atgaaatggg gtccatgcaa agccttttg    11820 acaaaattgg ccaacttttt gtggatgctt tcacggagtt cttggtgtcc attgttgata    11880
tcattatatt tttggccatt ttgtttggct tcaccatcgc cggttggctg gtggtctttt    11940
gcatcagatt ggtttgctcc gcgatactcc gtacgcgccc tgccattcac tctgagcaat    12000
tacagaagat cttatgaggc ctttctttcc cagtgccaag tggacattcc cacctgggga    12060
actaaacatc ctttggggat gctttggcac cataaggtgt caaccctgat tgatgaaatg    12120
gtgtcgcgtc gaatgtaccg catcatggaa aaagcagggc aggctgcctg gaaacaggtg    12180
gtgagcgagg ctacgctgtc tcgcattagt agtttggatg tggtggctca ttttcagcat    12240
ctagccgcca ttgaagccga gacctgtaaa tatttggcct cccggctgcc catgctacac    12300
aacctgcgca tgacagggtc aaatgtaacc atagtgtata atagcacttt gaatcaggtg    12360
tttgctattt ttccaacccc tggttcccgg ccaaagcttc atgattttca gcaatggtta    12420
```

```
atagctgtac attcctccat attttcctct gttgcagctt cttgtactct ttttgttgtg   12480
ctgtggttgc gggttccaat actacgtact gttttggtt tccgctggtt aggggcaatt    12540
tttctttcga actcacagtg aattacacgg tgtgtccacc ttgcctcacc cggcaagcag   12600
ccacagagat ctacgaaccc ggtaggtctc tttggtgcag atagggtat gaccgatgtg    12660 gggaggacga tcatgacgag ctagggttta tgataccgcc tggcctctcc agcgaaggcc   12720
acttgactgg tgtttacgcc tggttggcgt tcttgtcctt cagctacacg gcccagttcc   12780
atcccgagat attcgggata gggaatgtga gtcgagttta tgttgacatc aaacatcaac   12840
tcatctgcgc cgaacatgac gggcagaaca ccaccttgcc tcgtcatgac aacatttcag   12900
ccgtgtttca gacctattac caacatcaag tcgacggcgg caattggttt cacctagaat   12960
ggcttcgtcc cttctttttcc tcgtggttgg ttttaaatgt ctcttggttt ctcaggcgtt   13020
cgcctgcaaa ccatgtttca gttcgagtct tgcagatatt aagaccaaca ccaccgcagc   13080
ggcaagcttt gctgtcctcc aagacatcag ttgccttagg catcgcgact cggcctctga   13140
ggcgattcgc aaaatccctc agtgccgtac ggcgataggg acaccgtgt atgttaccat    13200 cacagccaat gtgacagatg agaattattt acattcttct gatctcctca tgctttcttc   13260
ttgccttttc tatgcttctg agatgagtga aaagggattt aaggtggtat ttggcaatgt   13320
gtcaggcatc gtggctgtgt gtgtcaattt taccagctac gtccaacatg tcaaggagtt   13380
tacccaacgc tccctggtgg tcgaccatgt gcggttgctc catttcatga cacctgagac   13440
catgaggtgg gcaactgttt tagcctgtct ttttgccatt ctgttggcaa tttgaatgtt   13500
taagtatgtt ggagaaatgc ttgaccgcgg gctgttgctc gcgattgctt tctttgtggt   13560
gtatcgtgcc gttctgtttt gctgtgctcg ccaacgccag caacgacagc agctcccatc   13620
tacagctgat ttacaacttg acgctatgtg agctgaatgg cacagattgg ctagctaaca   13680
aatttgattg ggcagtggag agttttgtca tcttttcccgt tttgactcac attgtctcct   13740
atggtgccct cactaccagc catttccttg acacagtcgc tttagtcact gtgtctaccg   13800 ccgggttgt tcacgggcgg tatgtcctaa gtagcatcta cgcggtctgt gccctggctg    13860
cgttgacttg cttcgtcatt aggtttgcaa agaattgcat gtcctggcgc tacgcgtgta   13920
ccagatatac caactttctt ctggacacta agggcagact ctatcgttgg cggtcgcctg   13980
tcatcataga gaaaaggggc aaagttgagg tcgaaggtca tctgatcgac ctcaaaagag   14040
ttgtgcttga tggctccgtg gcaaccccta taaccagagt ttcagcggaa caatggggtc   14100
gtccttagat gacttctgtc acgatagcac ggctccacaa aagttgcttt tggcgttttc   14160
tattacctac acgccagtga tgatatatgc cctaaaggtg agtcgcggcc gactgctagg   14220
gcttctgcac cttttgatct tcctgaattg tgctttcacc ttcgggtaca tgactttcgc   14280
gcactttcag agtacaaata aggtcgcgct cactatggga gcagtagttg cactccttg    14340 gggggtgtac tcagccatag aaacctggaa attcatcacc tccagatgcc gtttgtgctt   14400
gctaggccgc aagtacattc tggccctgc ccaccacgtt gaaagtgccg caggctttca    14460
tccgattgcg gcaaatgata accacgcatt tgtcgtccgg cgtcccggct ccactacggt   14520
caacggcaca ttggtgcccg ggttaaaaag cctcgtgttg ggtggcagaa aagctgttaa   14580
acagggagtg gtaaaccttg tcaaatatgc caaataacaa cggcaagcag cagaagagaa   14640
agaaggggga tggccagcca gtcaatcagc tgtgccagat gctgggtaag atcatcgctc   14700
agcaaaacca gtccagaggc aagggaccgg gaaagaaaaa taagaagaaa acccgggaga   14760
agccccattt tcctctagcg actgaagatg atgtcagaca tcactttacc cctagtgagc   14820
```

```
ggcaattgtg tctgtcgtca atccagaccg cctttaatca aggcgctggg acttgcaccc   14880
tgtcagattc agggaggata agttacactg tggagtttag tttgcctacg catcatactg   14940
tgcgcctgat ccgcgtcaca gcatcaccct cagcatgatg ggctggcatt cttgaggcat   15000
ctcagtgttt gaattggaag aatgtgtggt gaatggcact gattgacatt gtgcctctaa   15060
gtcacctatt caattagggc gaccgtgtgg gggtgagatt taattggcga gaaccatgcg   15120
gccgaaatta aaaaaaa                                                 15137
```

<210> SEQ ID NO 11
<211> LENGTH: 14867
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 11

```
atgacgtata ggtgttggct ctatgccttg gcatttgtat tgtcaggagc tgtgaccatt     60
ggcacagccc aaaacttgct gcacagaaac acccttctgt gatagcctcc ttcaggggag    120
cttagggttt gtccctagca ccttgcttcc ggagttgcac tgctttacgg tctctccacc    180
cctttaacca tgtctgggat acttgatcgg tgcacgtgta cccccaatgc cagggtgttt    240
atggcggagg ccaagtctac tgcacacga tgcctcagtg cacggtctct ccttcccctg     300
aacctccagg tttctgagct cggggtgcta ggcctattct acaggcccga agagccactc    360
cggtggacgt tgccacgtgc attccccact gttgagtgct ccccgccgg ggcctgctgg     420 cttttctgcaa tctttccaat cgcacgaatg accagtggaa acctgaactt ccaacaaaga    480
atggtacggg tcgcagctga gctttacaga gccggccagc tcacccctgc agtcttgaag    540
gctctacaag tttatgaacg gggttgccgc tggtacccca ttgttggacc tgtccctgga    600
gtggccgttt tcgccaattc cctacatgtg agtgataaac ccttcccggg agcaactcac    660
gtgttgacca acctgccgct cccgcagaga cccaagcctg aagactttttg ccccttggag    720 tgtgctatgg ctactgtcta tgacattggt catgacgccg tcatgtatgt ggccgaaagg    780
aaagtctcct gggccccctcg tggcggggat gaagtgaaat ttgaagctgt ccccggggag    840
ttgaagttga ttgcgaaccg gctccgcacc tccttcccgc ccaccacac agtggacatg    900 tctaagttcg ccttcacagc ccctgggtgt ggtgtttcta gcgggtcga acgccaacac    960 ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga actggcggg agaacccagc tactctgggt tgaggacct cctcagaata   1260 agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg tgcttgtac tagcgccaag   1680
```

```
tacgtactta agctggaagg tgagcattgg actgtcactg tgaccoctgg gatgtccct    1740
tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat    1920
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caaccagac gatcaagctg ccccaggtca accagtgtcg tgctctggtc    2280
cctgttgtga ctcaaaagtc cttggacaac aactcggtcc cctgaccgc cttttcactg    2340
gctaactact actaccgtgc gcaaggtgac gaagttcgtc accgtgaaag actaaccgcc    2400
gtgctctcca agttggaaaa ggttgttcga gaagaatatg ggctcatgcc aaccgagcct    2460
ggtccacggc ccacactgcc acgcgggctc gacgaactca aagaccagat ggaggaggac    2520
ttgctgaaac tggctaacgc ccagacgact tcggacatga tggcctgggc agtcgagcag    2580
gttgacctaa aaacttgggt caagaactac ccgcggtgga caccaccacc ccctccgcca    2640
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agcccctttg atctcccgac cccacctgag    2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gtgtgagttt gtgatgatgc ctcacacgcc tgcaccttcc    3000
gtaggtgcgg agagcgacct taccattggc tcagttgcta ctgaagatgt tccacgcatc    3060
ctcgagaaaa tagaaaatgt cggcgagatg gccaaccagg gaccccttggc cttctccgag    3120
gataaaccgg tagatgacca acttgtcaac gaccccgga tatcgtcgcg gaggcctgac    3180
gagagcacat cagctccgtc cgcaggcaca ggtggcgccg gctcttttac cgatttgccg    3240
ccttcagatg gcgcggatgc ggacgggggg gggccgtttc ggacggtaaa aagaaaagct    3300
gaaaggctct ttgaccaact gagccgtcag gttttttgacc tcgtctccca tctccctgtt    3360
ttcttctcac gccttttcta ccctggcggt ggttattctc cgggtgattg gggttttgca    3420
gcttttactc tattgtgcct ctttttatgt tacagttacc cagcctttgg tattgctccc    3480
ctcttgggtg tgttttctgg gtcttctcgg gcgttcgaa tgggggtttt tggctgctgg    3540
ttggcttttg ctgttggtct gttcaagcct gtgtccgacc cagtcggcgc tgcttgtgag    3600
tttgactcgc cagagtgtag aaacatcctt cattcttttg agcttctcaa acctgggac    3660
cctgttcgca gccttgttgt gggccccgtc ggtctcggtc ttgccattct tggcaggtta    3720
ctgggcgggg cacgctgcat ctggcacttt ttgcttaggc ttggcattgt tgcagactgt    3780
atcttggctg gagcttacgt gctttctcaa ggtaggtgta aaaagtgctg gggatcttgt    3840
ataagaactg ctcccaatga ggtcgctttt aacgtgtttc cttcacacg tgcgaccagg    3900
tcgtcactta tcgacctgtg cgatcggttt tgtgcgccaa aaggaatgga ccccatttttt    3960
ctcgccactg ggtggcgcgg gtgctgggcc ggccgaagcc ccattgagca accctctgaa    4020
aaacccatcg cgtttgccca gttggatgaa aagaagatta cggctaggac tgtggtcgcc    4080
```

```
cagccttatg accccaacca agccgtaaag tgcttgcggg tattgcaggc gggtggggcg    4140
atggtggcta aggcggtccc aaaagtggtc aaggtttccg ctgttccatt ccagccccc     4200 ttctttccca ctggagtgaa agttgaccct gattgcaggg tcgtggttga ccctgacact    4260
ttcactgcag ctctccggtc tggctactcc accacaaacc tcgtccttgg tgtgggggac    4320
tttgcccagc tgaatggatt aaaaatcagg caaatttcca agccttcagg gggaggccca    4380
catctcatgg ctgccctgca tgttgcctgc tcgatggctc tgcacatgct tgctgggatt    4440
tatgtgactg cggtgggttc ttgcggcacc ggcaccaacg acccgtggtg cgctaacccg    4500
tttgccgtcc ctggctacgg acctggctct ctctgcacgt ccagattgtg catttcccaa    4560
cacggcctta ccctgccctt gacagcactt gtggcgggat tcggtattca agaaattgcc    4620
ttggtcgttt tgattttgt ttccatcgga ggcatggctc ataggttgag ctgtaaggct     4680
gacatgctgt gtgtcttgct tgcaattgcc agctatgttt gggtacctct tacctggttg    4740
ctttgtgtgt ttccttgctg gttgcgctgt ttttctttgc acccctcac catcctatgg     4800 ttggtgtttt tcttgatttc tgtgaatatg ccttcaggaa tcttggccat ggtgttgttg    4860
gtttctcttt ggcttcttgg tcgttatact aatgttgctg gccttgtcac cccctacgac    4920
attcatcatt acaccagtgg cccccgcggt gttgccgcct ggctaccgc accagatggg     4980 acctacttgg ccgctgtccg ccgcgctgcg ttgactggcc gcaccatgct gtttaccccg    5040
tcccagcttg ggtctcttct tgagggtgct ttcagaactc gaaagccctc actgaacacc    5100
gtcaatgtga tcgggtcctc catgggctct ggcggggtgt ttaccatcga cgggaaagtc    5160
aagtgcgtaa ctgccgcaca tgtccttacg ggcaattcag ctcgggtttc cggggtcggc    5220
ttcaatcaaa tgcttgactt tgacgtaaag ggagatttcg ctatagctga ttgcccgaat    5280
tggcaagggg ctgcccccaa gacccaattc tgcacggatg gatggactgg ccgtgcctat    5340
tggctaacat cctctggcgt cgaacccggc gtcattggaa aaggattcgc cttctgcttc    5400
accgcatgtg gcgattccgg gtccccagtg atcaccgagg ccggtgagct tgtcggcgtt    5460
cacacgggat cgaataaaca agggggggc attgttacgc gcccctcagg ccagttttgt    5520
aatgtggcac ccatcaagct aagcgaatta agtgaattct ttgctgggcc taaggtcccg    5580
ctcggtgatg tgaaggtcgg cagccacata attaaagaca taagcgaggt gccttcagat    5640 cttttgtgcct tgcttgctgc caaacctgaa ctggaaggag gctctccac cgtccaactt    5700 ctttgtgtgt tttttctcct gtggagaatg atgggacatg cctggacgcc cttggttgct    5760
gtgagtttct ttattttgaa tgaggttctc ccagccgtcc tggtccggag tgttttctcc    5820
tttggaatgt ttgtgctatc ctggctcacg ccatggtctg cgcaagttct gatgatcagg    5880
cttctgacag cagctcttaa caggaacaga tggtcacttg ccttttttcag cctcggtgca    5940 gtgaccggtt ttgtcgcaga tcttgcggcc actcaggggc atccgttgca ggcagtgatg    6000
aatttgagca cctatgcatt cctgcctcgg atgatggttg tgacctcacc agtcccagtg    6060
atcacgtgtg gtgtcgtgca cctacttgcc atcattttgt acttgtttaa gtaccgtggc    6120
ctgcaccata tccttgttgg cgatggagtg ttctctgcgg cttcttctt gagatacttt    6180 gccgagggaa agttgaggga aggggtgtcg caatcctgcg gaatgaatca tgagtctctg    6240
actggtgccc tcgctatgag actcaatgac gaggacttgg attccttat gaatggact     6300 gattttaagt gctttgtttc tgcgtccaac atgaggaatg cagcgggtca atttatcgag    6360
gctgcctatg ctaaagcact tagagtagaa ctggcccagt tggtgcaggt tgataaagtt    6420
cgaggtactt tggccaaact tgaagctttt gctgataccg tggcacctca actctcgccc    6480
```

```
ggtgacattg ttgtcgctct cggccacacg cctgttggca gtatcttcga cctaaaggtt    6540
ggtagcacca agcatacct ccaagccatt gagaccagag tccttgctgg gtccaaaatg     6600
accgtggcgc gcgtcgtcga cccgaccccc acgccccac ccgcacccgt gcccatcccc     6660
ctcccaccga aagttctgga gaatggcccc aacgcttggg gggatgagga ccgtttgaat    6720
aagaagaaga ggcgcaggat ggaagccctc ggcatctatg ttatgggcgg gaaaaaatac    6780
cagaaatttt gggacaagaa ttccggtgat gtgttttatg aggaggtcca taataacaca    6840
gatgagtggg agtgtctcag agttggcgac cctgccgact ttgaccctga agggaact     6900 ctgtgtggac atgtcaccat tgaaaacaag gcttaccatg tttacacctc cccatctggt    6960
aagaagttct tggtccccgt caacccagag aatggaagag tccaatggga agctgcaaag    7020 cttccgtgg agcaggccct aggtatgatg aatgtcgacg gcgaactgac tgccaaagaa     7080
ctggagaaac tgaaaagaat aattgacaaa ctccagggcc tgactaagga gcagtgttta    7140
aactgctagc cgccagcgac ttgacccgct gtggtcgcgg cggcttggtt gttactgaaa    7200
cagcggtaaa aatagtcaaa tttcacaacc ggaccttcac cctgggacct gtgaatttaa    7260
aagtggccag tgaggttgag ctaaaagacg cggttgagca caaccaacac ccggttgcga    7320
gaccgatcga tggtggagtt gtgctcctgc gttccgcggt tccttcgctt atagacgtct    7380
tgatctccgg tgctgatgca tctcccaagt tacttgccca tcacgggccg ggaaacactg    7440
ggatcgatgg cacgctctgg gattttgagt ccgaagccac taaagaggaa gtcgcactca    7500
gtgcgcaaat aatacaggct tgtgacatta ggcgcggcga cgctcctgaa attggtctcc    7560
cttacaagct gtaccctgtt aggggtaacc ctgagcgggt gaaggagtt ctgcagaata     7620 caaggtttgg agacatacct tacaaaaccc ccagtgacac tggaagccca gtgcacgcgg    7680
ctgcctgcct tacgcccaac gccactccgg tgactgatgg gcgctccgtc ttggccacga    7740
ccatgccccc cgggtttgag ttatatgtac cgaccatacc agcgtctgtc cttgattacc    7800
ttgactctag gcctgactgc cctaaacagc tgacagagca cggctgcgaa gatgccgcac    7860
tgaaagacct ctctaaatat gacttgtcca cccaaggctt tgttttacct ggagttcttc    7920
gccttgtgcg gaaatacctg tttgcccatg taggtaagtg cccacccgtt catcggcctt    7980
ctacttaccc tgctaagaat tctatggctg gaataaatgg gaacaggttc ccaaccaagg    8040
acattcagag cgtccctgaa atcgacgttc tgtgcgcaca ggctgtgcga gaaaactggc    8100
aaactgtcac cccttgtact cttaagaaac agtattgcgg gaagaagaag actaggacca    8160
tactcggcac caataacttc atcgcactag cccaccgagc agtgttgagt ggtgttaccc    8220
agggcttcat gaaaaaggcg tttaactcgc ccatcgccct cggaaagaac aagtttaagg    8280
agctacagac tccggtcctg gcaggtgcc ttgaagctga tctcgcatcc tgcgatcgat     8340
ccacgcctgc aattgtccgc tggtttgccg ccaaccttct ttatgaactt gcctgtgctg    8400
aagagcatct accgtcgtac gtgctgaact gctgccacga cttactggtc acgcagtccg    8460
gcgcagtgac taagagaggt ggcctgtcgt ctggcgaccc gatcacctct gtgtctaaca    8520
ccatttatag tttggtgatc tatgcacagc atatggtgct tagttacttc aaaagtggtc    8580
acccccatgg ccttctgttc ttacaagacc agctaaagtt tgaggacatg ctcaaggttc    8640
aacccctgat cgtctattcg gacgacctcg tgctgtatgc cgagtctccc accatgccaa    8700
actatcactg gtgggttgaa catctgaatt tgatgctggg gtttcagacg acccaaaga    8760 agacagcaat aacagactcg ccatcatttc taggctgtag aataataaat gggcgccagc    8820
tagtccccaa ccgtgacagg atcctcgcgg ccctcgccta tcacatgaag gcgagtaatg    8880
```

-continued

```
tttctgaata ctatgcctca gcggctgcaa tactcatgga cagctgtgct tgtttggagt    8940
atgatcctga atggtttgaa gaacttgtag ttggaatagc gcagtgcgcc cgcaaggacg    9000
gctacagctt tcccggcacg ccgttcttca tgtccatgtg ggaaaaactc aggtccaatt    9060
atgagggaa gaagtcgaga gtgtgcgggt actgcgggc cccggcccg tacgctactg      9120
cctgtggcct cgacgtctgc atttaccaca cccacttcca ccagcattgt ccagtcacaa   9180
tctggtgtgg ccatccagcg ggttctggtt cttgtagtga gtgcaaatcc cctgtaggga   9240
aaggcacaag cctttagac gaggtgctgg aacaagtccc gtataagccc ccacggaccg    9300
ttatcatgca tgtggagcag ggtctcaccc cccttgatcc aggtagatac caaactcgcc   9360
gcggattagt ctctgtcagg cgtggaatta ggggaaatga agttggacta ccagacggtg   9420
attatgctag caccgccttg ctccctacct gcaaagagat caacatggtc gctgtcgctt   9480
ccaatgtatt gcgcagcagg ttcatcatcg gcccacccgg tgctgggaaa acatactggc   9540
tccttcaaca ggtccaggat ggtgatgtta tttacacacc aactcaccag accatgcttg   9600
acatgattag ggctttgggg acgtgccggt tcaacgtccc ggcaggcaca acgctgcaat   9660
tccccgtccc ctcccgcacc ggtccgtggg ttcgcatcct agccggcggt tggtgtcctg   9720
gcaagaattc cttcctagat gaagcagcgt attgcaatca ccttgatgtt ttgaggcttc   9780
ttagtaaaac taccctcacc tgtctaggag acttcaagca actccaccca gtgggttttg   9840
attctcattg ctatgttttt gacatcatgc ctcaaactca actgaagacc atctggaggt   9900
ttggacagaa tatctgtgat gccattcagc cagattacag ggacaaactc atgtccatgg   9960
tcaacacaac ccgtgtgacc tacgtggaaa aacctgtcag gtatgggcag gtcctcaccc   10020
cctaccacag ggaccgagag gacgacgcca tcactattga ctccagtcaa ggcgccacat   10080
tcgatgtggt tacattgcat ttgcccacta agattcact caacaggcaa agagcccttg    10140
ttgctatcac cagggcaaga cacgctatct ttgtgtatga cccacacagg cagctgcagg   10200
gcttgtttga tcttcctgca aaaggcacgc ccgtcaacct cgcagtgcac tgcgacgggc   10260
agctgatcgt gctggataga aataacaaag aatgcacggt tgctcaggct ctaggcaacg   10320
gggataaatt tagggccaca gacaagcgtg ttgtagattc tctccgcgcc atttgtgctg   10380
atctagaagg gtcgagctct ccgctcccca aggtcgcaca caacttggga tttatttct    10440
cacctgattt aacacagttt gctaaactcc cagtagaact tgcacctcac tggcccgtgg   10500
tgtcaaccca gaacaatgaa aagtggccgg atcggctggt tgccagcctt cgccctatcc   10560
ataaatacag ccgcgcgtgc atcggtgccg gctatatggt gggcccttcg gtgtttctag   10620
gcactcctgg ggtcgtgtca tactatctca caaaatttgt taagggcggg gctcaagtgc   10680
ttccggagac ggttttcagc accggccgaa ttgaggtaga ctgccgggaa tatcttgatg   10740
atcgggagcg agaagttgct gcgtccctcc cacacgcttt cattggcgac gtcaaaggca   10800
ctaccgttgg aggatgtcat catgtcacct ccagatacct cccgcgcgtc cttcccaagg   10860
aatcagttgc ggtagtcggg gtttcaagcc ccggaaaagc cgcgaaagca ttgtgcacac   10920
tgacagatgt gtacctccca gatcttgaag cctatctcca cccggagacc cagtccaagt   10980
gctggaaaat gatgttggac ttcaaagaag ttcgactaat ggtctggaaa gacaaaacag   11040
cctatttcca acttgaaggt cgctatttca cctggtatca gcttgccagc tatgcctcgt   11100
acatccgtgt tcccgtcaac tctacggtgt acttggaccc ctgcatgggc cccgccttt    11160
gcaacaggag agtcgtcggg tccacccact gggggctga cctcgcggtc accccttatg    11220
attacggcgc taaaattatc ctgtctagcg cgtaccatgg tgaaatgccc cccggataca   11280
```

```
aaattctggc gtgcgcggag ttctcgttgg atgacccagt taagtacaaa catacctggg   11340
ggtttgaatc ggatacagcg tatctgtatg agttcaccgg aaacggtgag gactgggagg   11400
attacaatga tgcgtttcgt gcgcgccagg aagggaaaat ttataaggcc actgccacca   11460
gcttgaagtt ttattttccc ccgggccctg tcattgaacc aactttaggc ctgaattgaa   11520
atgaaatggg gtccatgcaa agccttttg acaaaattgg ccaacttttt gtggatgctt   11580
tcacggagtt cttggtgtcc attgttgata tcattatatt tttggccatt ttgtttggct   11640
tcaccatcgc cggttggctg gtggtctttt gcatcagatt ggtttgctcc gcgatactcc   11700
gtacgcgccc tgccattcac tctgagcaat tacagaagat cttatgaggc ctttctttcc   11760
cagtgccaag tggacattcc cacctgggga actaaacatc ctttggggat gctttggcac   11820
cataaggtgt caaccctgat tgatgaaatg gtgtcgcgtc gaatgtaccg catcatggaa   11880
aaagcagggc aggctgcctg gaaacaggtg gtgagcgagg ctacgctgtc tcgcattagt   11940
agtttggatg tggtggctca ttttcagcat ctagccgcca ttgaagccga gacctgtaaa   12000
tatttggcct cccggctgcc catgctacac aacctgcgca tgacagggtc aaatgtaacc   12060
atagtgtata atagcacttt gaatcaggtg tttgctattt ttccaaccce tggttcccgg   12120 ccaaagcttc atgattttca gcaatggtta atagctgtac attcctccat attttcctct   12180
gttgcagctt cttgtactct ttttgttgtg ctgtggttgc gggttccaat actacgtact   12240
gtttttggtt tccgctggtt aggggcaatt tttctttcga actcacagtg aattacacgg   12300
tgtgtccacc ttgcctcacc cggcaagcag ccacagagat ctacgaaccc ggtaggtctc   12360
tttggtgcag atagggtat gaccgatgtg gggaggacga tcatgacgag ctagggttta   12420
tgataccgcc tggcctctcc agcgaaggcc acttgactgg tgtttacgcc tggttggcgt   12480
tcttgtcctt cagctacacg gcccagttcc atcccgagat attcgggata gggaatgtga   12540
gtcgagttta tgttgacatc aaacatcaac tcatctgcgc cgaacatgac gggcagaaca   12600
ccaccttgcc tcgtcatgac aacatttcag ccgtgtttca gacctattac caacatcaag   12660
tcgacggcgg caattggttt cacctagaat ggcttcgtcc cttcttttcc tcgtggttgg   12720
ttttaaatgt ctcttggttt ctcaggcgtt cgcctgcaaa ccatgtttca gttcgagtct   12780
tgcagatatt aagaccaaca ccaccgcagc ggcaagcttt gctgtcctcc aagacatcag   12840
ttgccttagg catcgcgact cggcctctga ggcgattcgc aaaatccctc agtgccgtac   12900
ggcgataggg acacccgtgt atgttaccat cacagccaat gtgacagatg agaattattt   12960
acattcttct gatctcctca tgctttcttc ttgccttttc tatgcttctg agatgagtga   13020
aaagggattt aaggtggtat ttggcaatgt gtcaggcatc gtggctgtgt gtgtcaattt   13080
taccagctac gtccaacatg tcaaggagtt tacccaacgc tccctggtgg tcgaccatgt   13140
gcggttgctc catttcatga cacctgagac catgaggtgg gcaactgttt tagcctgtct   13200
ttttgccatt ctgttggcaa tttgaatgtt taagtatgtt ggagaaatgc ttgaccgcgg   13260
gctgttgctc gcgattgctt ctttgtggt gtatcgtgcc gttctgtttt gctgtgctcg   13320
ccaacgccag caacgacagc agctcccatc tacagctgat ttacaacttg acgctatgtg   13380
agctgaatgg cacagattgg ctagctaaca aatttgattg ggcagtggag agttttgtca   13440
tctttcccgt tttgactcac attgtctcct atggtgccct cactaccagc catttccttg   13500
acacagtcgc tttagtcact gtgtctaccg ccgggtttgt tcacgggcgg tatgtcctaa   13560
gtagcatcta cgcggtctgt gccctggctg cgttgacttg cttcgtcatt aggtttgcaa   13620
agaattgcat gtcctggcgc tacgcgtgta ccagatatac caactttctt ctggacacta   13680
```

```
agggcagact ctatcgttgg cggtcgcctg tcatcataga gaaaaggggc aaagttgagg    13740
tcgaaggtca tctgatcgac ctcaaaagag ttgtgcttga tggctccgtg caacccta    13800 taaccagagt ttcagcggaa caatggggtc gtccttagat gacttctgtc acgatagcac    13860
ggctccacaa aaggtgcttt tggcgttttc tattacctac acgccagtga tgatatatgc    13920
cctaaaggtg agtcgcggcc gactgctagg gcttctgcac cttttgatct tcctgaattg    13980
tgctttcacc ttcgggtaca tgactttcgc gcactttcag agtacaaata aggtcgcgct    14040
cactatggga gcagtagttg cactccttg ggggtgtac tcagccatag aaacctggaa    14100
attcatcacc tccagatgcc gtttgtgctt gctaggccgc aagtacattc tggcccctgc    14160
ccaccacgtt gaaagtgccg caggctttca tccgattgcg gcaaatgata accacgcatt    14220
tgtcgtccgg cgtcccggct ccactacggt caacggcaca ttggtgcccg ggttaaaaag    14280
cctcgtgttg ggtggcagaa aagctgttaa acagggagtg gtaaaccttg tcaaatatgc    14340
caaataacaa cggcaagcag cagaagagaa agaaggggga tggccagcca gtcaatcagc    14400
tgtgccagat gctgggtaag atcatcgctc agcaaaacca gtccagaggc aagggaccgg    14460
gaaagaaaaa taagaagaaa aacccggaga agccccattt tcctctagcg actgaagatg    14520
atgtcagaca tcactttacc cctagtgagc ggcaattgtg tctgtcgtca atccagaccg    14580
cctttaatca aggcgctggg acttgcaccc tgtcagattc agggaggata agttacactg    14640
tggagtttag tttgcctacg catcatactg tgcgcctgat ccgcgtcaca gcatcaccct    14700
cagcatgatg ggctggcatt cttgaggcat ctcagtgttt gaattggaag aatgtgtggt    14760
gaatggcact gattgacatt gtgcctctaa gtcacctatt caattagggc gaccgtgtgg    14820
gggtgagatt taattggcga gaaccatgcg gccgaaatta aaaaaaa    14867
```

<210> SEQ ID NO 12
<211> LENGTH: 15158
<212> TYPE: DNA
<213> ORGANISM: Artificial Sequence
<220> FEATURE:
<223> OTHER INFORMATION: Porcine reproductive and respiratory syndrome virus

<400> SEQUENCE: 12

```
atgacgtata ggtgttggct ctatgccttg gcatttgtat tgtcaggagc tgtgaccatt      60
ggcacagccc aaaacttgct gcacagaaac acccttctgt gatagcctcc ttcaggggag     120
cttagggttt gtccctagca ccttgcttcc ggagttgcac tgcttacgg tctctccacc     180 cctttaacca tgtctgggat acttgatcgg tgcacgtgta cccccaatgc cagggtgttt     240
atggcggagg gccaagtcta ctgcacacga tgcctcagtg cacggtctct ccttcccctg     300
aacctccagg tttctgagct cggggtgcta ggcctattct acaggcccga agagccactc     360
cggtggacgt tgccacgtgc attccccact gttgagtgct ccccgcgg ggcctgctgg     420 ctttctgcaa tctttccaat cgcacgaatg accagtggaa acctgaactt ccaacaaaga     480
atggtacggg tcgcagctga gctttacaga gccggccagc tcacccctgc agtcttgaag     540
gctctacaag tttatgaacg gggttgccgc tggtaccca ttgttggacc tgtccctgga     600
gtggccgttt tcgccaattc cctacatgtg agtgataaac ccttcccggg agcaactcac     660
gtgttgacca acctgccgct cccgcagaga cccaagcctg aagactttg cccctttgag     720 tgtgctatgg ctactgtcta tgacattggt catgacgccg tcatgtatgt ggccgaaagg     780
aaagtctcct gggccctcg tggcgggat gaagtgaaat ttgaagctgt ccccgggga    840 ttgaagttga ttgcgaaccg gctccgcacc tccttcccgc cccaccacac agtggacatg    900
```

```
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga aactggcggg agaacccagc tactctgggt ttgaggacct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctggaagg tgagcattgg actgtcactg tgaccccggg gatgtcccct   1740
tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc ccctgaccgc cttttcactg   2340
gctaactact actaccgtgc gcaaggtgac gaagttcgtc accgtgaaag actaaccgcc   2400
gtgctctcca agttggaaaa ggttgttcga gaagaatatg ggctcatgcc aaccgagcct   2460
ggtccacggc ccacactgcc acgcgggctc gacgaactca aagaccagat ggaggaggac   2520
ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agcccctttg atctcccgac cccacctgag   2820
ccggcaacac cttcaagtga gctggtgatt gtgtcctcac cgcaatgcat cttcaggccg   2880
gcgacaccct tgagtgagcc ggctccaatt cccgcacctc gcggaactgt gtctcgaccg   2940
gtgacaccct tgagtgagcc gatccctgtg cccgcaccgc ggcgtaagtt tcagcaggtg   3000
aaaagattga gttcggcggc ggcaatccca ccgtaccagg acgagcccct ggatttgtct   3060
gcttcctcac agactgaata tgaggcctct cccccagcac cgccgcagag cggggcgtt    3120
ctggagtag aggggcatga agctgaggaa accctgagtg aaatctcgga catgtcgggt   3180
aacattaaac ctgcgtccgt gtcatcaagc agctccttgt ccagcgtgag aatcacacgc   3240
ccaaaatact cagctcaagc catcatcgac tcgggcgggc cctgcagtgg gcatctccaa   3300
```

```
gaggtaaagg aaacatgcct tagtgtcatg cgcgaggcat gtgatgcgac taagcttgat   3360
gaccctgcta cgcaggaatg gctttctcgc atgtgggatc gggtggacat gctgacttgg   3420
cgcaacacgt ctgtttacca ggcgatttgc accttagatg gcaggttaaa gttcctccca   3480
aaaatgatac tcgagacacc gccgccctat ccgtctttta ccgatttgcc gccttcagat   3540
ggcgcggatg cggacggggg ggggccgttt cggacggtaa aaagaaaagc tgaaaggctc   3600
tttgaccaac tgagccgtca ggttttttgac ctcgtctccc atctccctgt tttcttctca   3660
cgccttttct accctggcgg tggttattct ccgggtgatt ggggttttgc agcttttact   3720
ctattgtgcc tctttttatg ttacagttac ccagcctttg gtattgctcc cctcttgggt   3780 gtgtttctg gtcttctcg gcgcgttcga atggggtttt ttggctgctg gttggctttt    3840
gctgttggtc tgttcaagcc tgtgtccgac ccagtcggcg ctgcttgtga gtttgactcg   3900
ccagagtgta gaaacatcct tcattctttt gagcttctca aaccttggga ccctgttcgc   3960
agccttgttg tgggccccgt cggtctcggt cttgccattc ttggcaggtt actgggcggg   4020
gcacgctgca tctggcactt tttgcttagg cttggcattg ttgcagactg tatcttggct   4080
ggagcttacg tgctttctca aggtaggtgt aaaaagtgct ggggatcttg tataagaact   4140
gctcccaatg aggtcgcttt taacgtgttt cctttcacac gtgcgaccag gtcgtcactt   4200
atcgacctgt gcgatcggtt ttgtgcgcca aaaggaatgg accccatttt tctcgccact   4260
gggtggcgcg ggtgctgggc cggccgaagc cccattgagc aaccctctga aaaacccatc   4320
gcgtttgccc agttggatga aaagaagatt acggctagga ctgtggtcgc ccagccttat   4380
gaccccaacc aagccgtaaa gtgcttgcgg gtattgcagg cgggtgggc gatggtggct   4440 aaggcggtcc caaagtggt caaggtttcc gctgttccat tccgagcccc cttcttttccc   4500 actggagtga agttgacccc tgattgcagg gtcgtggttg accctgacac tttcactgca   4560
gctctccggt ctggctactc caccacaaac ctcgtccttg gtgtgggga cttttgcccag   4620 ctgaatggat taaaaatcag gcaaatttcc aagccttcag ggggaggccc acatctcatg   4680
gctgccctgc atgttgcctg ctcgatggct ctgcacatgc ttgctgggat ttatgtgact   4740
gcggtgggtt cttgcggcac cggcaccaac gacccgtggt gcgctaaccc gtttgccgtc   4800
cctggctacg gacctggctc tctctgcacg tccagattgt gcatttccca acacggcctt   4860
accctgccct tgacagcact tgtggcggga ttcggtattc aagaaattgc cttggtcgtt   4920 ttgattttg tttccatcgg aggcatggct cataggttga gctgtaaggc tgacatgctg   4980
tgtgtcttgc ttgcaattgc cagctatgtt tgggtaccctc ttacctggtt gctttgtgtg   5040
tttccttgct ggttgcgctg ttttttcttttg cacccccctca ccatcctatg gttggtgttt   5100
ttcttgattt ctgtgaatat gccttcagga atcttggcca tggtgttgtt ggtttctctt   5160
tggcttcttg gtcgttatac taatgttgct ggccttgtca cccctacga cattcatcat   5220 tacaccagtg gcccccgcgg tgttgccgcc ttggctaccg caccagatgg gacctacttg   5280
gccgctgtcc gccgcgctgc gttgactggc cgcaccatgc tgtttacccc gtcccagctt   5340
gggtctcttc ttgagggtgc tttcagaact cgaaagccct cactgaacac cgtcaatgtg   5400
atcgggtcct ccatgggctc tggcggggtg tttaccatcg acgggaaagt caagtgcgta   5460
actgccgcac atgtccttac gggcaattca gctcggtttt ccggggtcgg cttcaatcaa   5520
atgcttgact ttgacgtaaa gggagatttc gctatagctg attgcccgaa ttggcaaggg   5580
gctgccccca gacccaatt ctgcacggat ggatggactg gccgtgccta ttggctaaca   5640
tcctctggcg tcgaacccgg cgtcattgga aaaggattcg ccttctgctt caccgcatgt   5700
```

```
ggcgattccg ggtccccagt gatcaccgag gccggtgagc ttgtcggcgt tcacacggga    5760
tcgaataaac aagggggggg cattgttacg cgcccctcag gccagttttg taatgtggca    5820
cccatcaagc taagcgaatt aagtgaattc tttgctgggc ctaaggtccc gctcggtgat    5880
gtgaaggtcg gcagccacat aattaaagac ataagcgagg tgccttcaga tctttgtgcc    5940
ttgcttgctg ccaaacctga actgaaggag ggcctctcca ccgtccaact tctttgtgtg    6000 tttttttctcc tgtggagaat gatgggacat gcctggacgc ccttggttgc tgtgagtttc    6060
tttattttga atgaggttct cccagccgtc ctggtccgga gtgttttctc ctttggaatg    6120
tttgtgctat cctggctcac gccatggtct gcgcaagttc tgatgatcag gcttctgaca    6180
gcagctctta acaggaacag atggtcactt gccttttca gcctcggtgc agtgaccggt    6240
tttgtcgcag atcttgcggc cactcagggg catccgttgc aggcagtgat gaatttgagc    6300
acctatgcat tcctgcctcg gatgatggtt gtgacctcac cagtcccagt gatcacgtgt    6360
ggtgtcgtgc acctacttgc catcattttg tacttgttta agtaccgtgg cctgcaccat    6420
atccttgttg gcgatggagt gttctctgcg gctttcttct tgagatactt gccgaggga    6480 aagttgaggg aaggggtgtc gcaatcctgc ggaatgaatc atgagtctct gactggtgcc    6540
ctcgctatga gactcaatga cgaggacttg gatttcctta tgaaatggac tgattttaag    6600
tgctttgttt ctgcgtccaa catgaggaat gcagcgggtc aatttatcga ggctgcctat    6660
gctaaagcac ttagagtaga actggcccag ttggtgcagg ttgataaagt tcgaggtact    6720
ttggccaaac ttgaagcttt tgctgatacc gtggcacctc aactctcgcc cggtgacatt    6780
gttgtcgctc tcggccacac gcctgttggc agtatcttcg acctaaaggt tggtagcacc    6840
aagcataccc tccaagccat tgagaccaga gtccttgctg ggtccaaaat gaccgtggcg    6900
cgcgtcgtcg acccgacccc cacgccccca cccgcacccg tgcccatccc cctcccaccg    6960
aaagttctgg agaatggccc caacgcttgg ggggatgagg accgtttgaa taagaagaag    7020
aggcgcagga tggaagccct cggcatctat gttatgggcg ggaaaaaata ccagaaattt    7080
tgggacaaga attccggtga tgtgttttat gaggaggtcc ataataacac agatgagtgg    7140
gagtgtctca gagttggcga ccctgccgac tttgaccctg agaagggaac tctgtgtgga    7200
catgtcacca ttgaaaacaa ggcttaccat gtttacacct ccccatctgg taagaagttc    7260
ttggtccccg tcaacccaga gaatggaaga gtccaatggg aagctgcaaa gctttccgtg    7320
gagcaggccc taggtatgat gaatgtcgac ggcgaactga ctgccaaaga actggagaaa    7380
ctgaaaagaa taattgacaa actccagggc ctgactaagg agcagtgttt aaactgctag    7440
ccgccagcga cttgacccgc tgtggtcgcg gcggcttggt tgttactgaa acagcggtaa    7500
aaatagtcaa atttcacaac cggaccttca ccctgggacc tgtgaattta aaagtggcca    7560
gtgaggttga gctaaaagac gcggttgagc acaaccaaca cccggttgcg agaccgatcg    7620
atggtggagt tgtgctcctg cgttccgcgg ttccttcgct tatagacgtc ttgatctccg    7680
gtgctgatgc atctcccaag ttacttgccc atcacgggcc gggaaacact gggatcgatg    7740
gcacgctctg ggattttgag tccgaagcca ctaaagagga agtcgcactc agtgcgcaaa    7800
taatacaggc ttgtgacatt aggcgcggcg acgctcctga aattggtctc ccttacaagc    7860
tgtaccctgt taggggtaac cctgagcggg tgaaggagt tctgcagaat acaaggtttg    7920
gagacatacc ttacaaaacc cccagtgaca ctggaagccc agtgcacgcg gctgcctgcc    7980
ttacgcccaa cgccactccg gtgactgatg gcgctccgt cttggccacg accatgcccc    8040
ccgggtttga gttatatgta ccgaccatac cagcgtctgt ccttgattac cttgactcta    8100
```

```
ggcctgactg ccctaaacag ctgacagagc acggctgcga agatgccgca ctgaaagacc    8160
tctctaaata tgacttgtcc acccaaggct ttgttttacc tggagttctt cgccttgtgc    8220
ggaaatacct gtttgcccat gtaggtaagt gcccacccgt tcatcggcct tctacttacc    8280
ctgctaagaa ttctatggct ggaataaatg ggaacaggtt cccaaccaag gacattcaga    8340
gcgtccctga aatcgacgtt ctgtgcgcac aggctgtgcg agaaaactgg caaactgtca    8400 cccccttgtac tcttaagaaa cagtattgcg ggaagaagaa gactaggacc atactcggca    8460
ccaataactt catcgcacta gcccaccgag cagtgttgag tggtgttacc cagggcttca    8520
tgaaaaaggc gtttaactcg cccatcgccc tcggaaagaa caagtttaag gagctacaga    8580
ctccggtcct gggcaggtgc cttgaagctg atctcgcatc ctgcgatcga tccacgcctg    8640
caattgtccg ctggtttgcc gccaaccttc tttatgaact tgcctgtgct gaagagcatc    8700
taccgtcgta cgtgctgaac tgctgccacg acttactggt cacgcagtcc ggcgcagtga    8760
ctaagagagg tggcctgtcg tctggcgacc cgatcacctc tgtgtctaac accatttata    8820
gtttggtgat ctatgcacag catatggtgc ttagttactt caaaagtggt caccccatg    8880 gccttctgtt cttacaagac cagctaaagt ttgaggacat gctcaaggtt caacccctga    8940
tcgtctattc ggacgacctc gtgctgtatg ccgagtctcc caccatgcca aactatcact    9000
ggtgggttga acatctgaat ttgatgctgg ggtttcagac ggacccaaag aagacagcaa    9060
taacagactc gccatcattt ctaggctgta gaataataaa tgggcgccag ctagtcccca    9120
accgtgacag gatcctcgcg gccctcgcct atcacatgaa ggcgagtaat gtttctgaat    9180
actatgcctc agcggctgca atactcatgg acagctgtgc ttgtttggag tatgatcctg    9240
aatggtttga agaacttgta gttggaatag cgcagtgcgc ccgcaaggac ggctacagct    9300
ttcccggcac gccgttcttc atgtccatgt gggaaaaact caggtccaat tatgagggga    9360
agaagtcgag agtgtgcggg tactgcgggg ccccggcccc gtacgctact gcctgtggcc    9420
tcgacgtctg catttaccac acccacttcc accagcattg tccagtcaca atctggtgtg    9480
gccatccagc gggttctggt tcttgtagtg agtgcaaatc ccctgtaggg aaaggcacaa    9540 gcccctttaga cgaggtgctg aacaagtcc cgtataagcc cccacggacc gttatcatgc    9600
atgtggagca gggtctcacc cccttgatc caggtagata ccaaactcgc cgcggattag    9660
tctctgtcag gcgtggaatt aggggaaatg aagttggact accagacggt gattatgcta    9720
gcaccgcctt gctccctacc tgcaaagaga tcaacatggt cgctgtcgct tccaatgtat    9780
tgcgcagcag gttcatcatc ggcccacccg gtgctgggaa aacatactgg ctccttcaac    9840
aggtccagga tggtgatgtt atttacacac caactcacca gaccatgctt gacatgatta    9900
gggctttggg gacgtgccgg ttcaacgtcc cggcaggcac aacgctgcaa ttccccgtcc    9960
cctcccgcac cggtccgtgg gttcgcatcc tagccggcgg ttggtgtcct ggcaagaatt   10020
ccttcctaga tgaagcagcg tattgcaatc accttgatgt tttgaggctt cttagtaaaa   10080 ctacccctcac ctgtctagga gacttcaagc aactccaccc agtgggtttt gattctcatt   10140
gctatgtttt tgacatcatg cctcaaactc aactgaagac catctggagg tttgacagaa   10200
atatctgtga tgccattcag ccagattaca gggacaaact catgtccatg gtcaacacaa   10260
cccgtgtgac ctacgtggaa aaacctgtca ggtatgggca ggtcctcacc cctaccaca   10320 gggaccgaga ggacgacgcc atcactattg actccagtca aggcgccaca ttcgatgtgg   10380
ttacattgca tttgcccact aaagattcac tcaacaggca aagagccctt gttgctatca   10440
ccagggcaag acacgctatc tttgtgtatg acccacacag gcagctgcag gcttgttttg   10500
```

```
atcttcctgc aaaaggcacg cccgtcaacc tcgcagtgca ctgcgacggg cagctgatcg   10560
tgctggatag aaataacaaa gaatgcacgg ttgctcaggc tctaggcaac ggggataaat   10620
ttagggccac agacaagcgt gttgtagatt ctctccgcgc catttgtgct gatctagaag   10680
ggtcgagctc tccgctcccc aaggtcgcac acaacttggg attttatttc tcacctgatt   10740
taacacagtt tgctaaactc ccagtagaac ttgcacctca ctggcccgtg gtgtcaaccc   10800
agaacaatga aaagtggccg gatcggctgg ttgccagcct tcgccctatc cataaataca   10860
gccgcgcgtg catcggtgcc ggctatatgg tgggcccttc ggtgtttcta ggcactcctg   10920
gggtcgtgtc atactatctc acaaaatttg ttaagggcgg ggctcaagtg cttccggaga   10980
cggttttcag caccgccga attgaggtag actgccggga atatcttgat gatcgggagc   11040
gagaagttgc tgcgtccctc ccacacgctt tcattggcga cgtcaaaggc actaccgttg   11100
gaggatgtca tcatgtcacc tccagatacc tcccgcgcgt ccttcccaag gaatcagttg   11160
cggtagtcgg ggtttcaagc cccggaaaag ccgcgaaagc attgtgcaca ctgacagatg   11220
tgtacctccc agatcttgaa gcctatctcc acccggagac ccagtccaag tgctggaaaa   11280
tgatgttgga cttcaaagaa gttcgactaa tggtctggaa agacaaaaca gcctatttcc   11340
aacttgaagg tcgctatttc acctggtatc agcttgccag ctatgcctcg tacatccgtg   11400
ttcccgtcaa ctctacggtg tacttggacc cctgcatggg ccccgccctt tgcaacagga   11460
gagtcgtcgg gtccacccac tgggggggctg acctcgcggt cacccccttat gattacggcg   11520 ctaaaattat cctgtctagc gcgtaccatg gtgaaatgcc ccccggatac aaaattctgg   11580
cgtgcgcgga gttctcgttg gatgacccag ttaagtacaa acatacctgg gggtttgaat   11640
cggatacagc gtatctgtat gagttcaccg gaaacggtga ggactgggag gattacaatg   11700
atgcgtttcg tgcgcgccag gaagggaaaa tttataaggc cactgccacc agcttgaagt   11760
tttattttcc cccggggccct gtcattgaac caactttagg cctgaattga aatgaaatgg   11820
ggtccatgca aagccttttt gacaaaattg gccaactttt tgtggatgct ttcacggagt   11880
tcttggtgtc cattgttgat atcattatat ttttggccat tttgtttggc ttcaccatcg   11940
ccggttggct ggtggtctttt tgcatcagat tggtttgctc cgcgatactc cgtacgcgcc   12000
ctgccattca ctctgagcaa ttacagaaga tcttatgagg cctttctttc ccagtgccaa   12060
gtggacattc ccacctgggg aactaaacat cctttgggga tgctttggca ccataaggtg   12120
tcaaccctga ttgatgaaat ggtgtcgcgt cgaatgtacc gcatcatgga aaaagcaggg   12180
caggctgcct ggaaacaggt ggtgagcgag gctacgctgt ctcgcattag tagtttggat   12240
gtggtggctc attttcagca tctagccgcc attgaagccg agacctgtaa atatttggcc   12300
tcccggctgc ccatgctaca caacctgcgc atgacagggt caaatgtaac catagtgtat   12360
aatagcactt tgaatcaggt gttttgctatt ttttccaaccc ctggttcccg gccaaagctt   12420
catgattttc agcaatggtt aatagctgta cattcctcca tattttcctc tgttgcagct   12480
tcttgtactc ttttttgttgt gctgtggttg cgggttccaa tactacgtac tgttttggt   12540 ttccgctggt taggggcaat ttttctttcg aactcacagt gaattacacg gtgtgtccac   12600
cttgcctcac ccggcaagca gccacagaga tctacgaacc cggtaggtct ctttggtgca   12660 ggataggta tgaccgatgt ggggaggacg atcatgacga gctaggggtttt atgataccgc   12720 ctggcctctc cagcgaaggc cacttgactg gtgtttacgc ctggttggcg ttcttgtcct   12780
tcagctacac ggcccagttc catcccgaga tattcgggat agggaatgtg agtcgagttt   12840
atgttgacat caaacatcaa ctcatctgcg ccgaacatga cgggcagaac accaccttgc   12900
```

```
ctcgtcatga caacatttca gccgtgtttc agacctatta ccaacatcaa gtcgacggcg    12960
gcaattggtt tcacctagaa tggcttcgtc ccttctttc ctcgtggttg gtttaaatg    13020
tctcttggtt tctcaggcgt tcgcctgcaa accatgttc agttcgagtc ttgcagatat    13080
taagaccaac accaccgcag cggcaagctt tgctgtcctc aagacatca gttgccttag    13140
gcatcgcgac tcggcctctg aggcgattcg caaaatccct cagtgccgta cggcgatagg    13200
gacacccgtg tatgttacca tcacagccaa tgtgacagat gagaattatt tacattcttc    13260
tgatctcctc atgctttctt cttgcctttt ctatgcttct gagatgagtg aaaagggatt    13320
taaggtggta tttggcaatg tgtcaggcat cgtggctgtg tgtgtcaatt ttaccagcta    13380
cgtccaacat gtcaaggagt ttacccaacg ctccctggtg gtcgaccatg tgcggttgct    13440
ccatttcatg acacctgaga ccatgaggtg ggcaactgtt ttagcctgtc ttttttgccat    13500
tctgttggca atttgaatgt ttaagtatgt tggagaaatg cttgaccgcg ggctgttgct    13560
cgcgattgct ttctttgtgg tgtatcgtgc cgttctgttt tgctgtgctc gccaacgcca    13620
gcaacgacag cagctcccat ctacagctga tttacaactt gacgctatgt gagctgaatg    13680
gcacagattg gctagctaac aaatttgatt gggcagtgga gagttttgtc atctttcccg    13740
ttttgactca cattgtctcc tatggtgccc tcactaccag ccatttcctt gacacagtcg    13800
ctttagtcac tgtgtctacc gccgggtttg ttcacgggcg gtatgtccta agtagcatct    13860
acgcggtctg tgccctggct gcgttgactt gcttcgtcat taggtttgca aagaattgca    13920
tgtcctggcg ctacgcgtgt accagatata ccaactttct tctggacact aagggcagac    13980
tctatcgttg gcggtcgcct gtcatcatag agaaagggg caaagttgag gtcgaaggtc    14040
atctgatcga cctcaaaaga gttgtgcttg atggctccgt ggcaaccct ataaccgag    14100
tttcagcgga acaatggggt cgtccttaga tgacttctgt cacgatagca cggctccaca    14160
aaaggtgctt ttggcgtttt ctattaccta cacgccagtg atgatatatg ccctaaaggt    14220
gagtcgcggc cgactgctag ggcttctgca cctttgatc ttcctgaatt gtgctttcac    14280
cttcgggtac atgactttcg cgcactttca gagtacaaat aaggtcgcgc tcactatggg    14340
agcagtagtt gcactccttt gggggtgta ctcagccata gaaacctgga aattcatcac    14400
ctccagatgc cgtttgtgct tgctaggccg caagtacatt ctggcccctg cccaccacgt    14460
tgaaagtgcc gcaggctttc atccgattgc ggcaaatgat aaccacgcat ttgtcgtccg    14520
gcgtcccggc tccactacgg tcaacggcac attggtgccc gggttaaaaa gcctcgtgtt    14580
gggtggcaga aaagctgtta acagggagt ggtaaacctt gtcaaatatg ccaaataaca    14640
acggcaagca gcagaagaga agaaggggg atggccagcc agtcaatcag ctgtgccaga    14700
tgctgggtaa gatcatcgct cagcaaaacc agtccagagg caagggaccg ggaaagaaaa    14760
ataagaagaa aaacccggag aagcccatt ttcctctagc gactgaagat gatgtcagac    14820
atcactttac ccctagtgag cggcaattgt gtctgtcgtc aatccagacc gcctttaatc    14880
aaggcgctgg gacttgcacc ctgtcagatt cagggaggat aagttacact gtggagttta    14940
gtttgcctac gcatcatact gtgcgcctga tccgcgtcac agcatcaccc tcagcatgat    15000
gggctggcat tcttgaggca tctcagtgtt tgaattggaa gaatgtgtgg tgaatggcac    15060
tgattgacat tgtgcctcta agtcacctat tcaattaggg cgaccgtgtg ggggtgagat    15120
ttaattggcg agaaccatgc ggccgaaatt aaaaaaaa                           15158

<210> SEQ ID NO 13
<211> LENGTH: 14210
```

<212> TYPE: DNA
<213> ORGANISM: Artificial Sequence
<220> FEATURE:
<223> OTHER INFORMATION: Porcine reproductive and respiratory syndrome virus

<400> SEQUENCE: 13

```
atgacgtata ggtgttggct ctatgccttg catttgtat tgtcaggagc tgtgaccatt      60
ggcacagccc aaaacttgct gcacagaaac acccttctgt gatagcctcc ttcaggggag    120
cttagggttt gtccctagca ccttgcttcc ggagttgcac tgctttacgg tctctccacc    180
cctttaacca tgtctgggat acttgatcgg tgcacgtgta ccccaatgc cagggtgttt     240
atggcggagg gccaagtcta ctgcacacga tgcctcagtg cacggtctct ccttcccctg    300
aacctccagg tttctgagct cggggtgcta ggcctattct acaggcccga agagccactc    360
cggtggacgt tgccacgtgc attccccact gttgagtgct ccccgccgg ggcctgctgg     420
ctttctgcaa tctttccaat cgcacgaatg accagtggaa acctgaactt ccaacaaaga    480
atggtacggg tcgcagctga gctttacaga gccggccagc tcaccccctgc agtcttgaag   540
gctctacaag tttatgaacg gggttgccgc tggtacccca ttgttggacc tgtccctgga    600
gtggccgttt tcgccaattc cctacatgtg agtgataaac ccttcccggg agcaactcac    660
gtgttgacca acctgccgct cccgcagaga cccaagcctg aagacttttg ccccttgag    720
tgtgctatgg ctactgtcta tgacattggt catgacgccg tcatgtatgt ggccgaaagg    780
aaagtctcct gggcccctcg tggcggggat gaagtgaaat ttgaagctgt ccccggggag    840
ttgaagttga ttgcgaaccg gctccgcacc tccttcccgc ccaccacac agtggacatg    900
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga aactggcggg agaacccagc tactctgggt tgaggaccct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccgcgcca acaaggctga gcacctcaaa cactactccc cgcctgccga agggaattgt   1500
ggttggcact gcatttccgc catcgccaac cggatggtga attccaaatt tgaaaccacc   1560
cttccgaaa gagtgagacc tccagatgac tgggctactg acgaggatct tgtgaatgcc   1620
atccaaatcc tcagactccc tgcggcctta gacaggaacg tgcttgtac tagcgccaag   1680
tacgtactta agctggaagg tgagcattgg actgtcactg tgaccctgg gatgtcccct    1740
tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aacggggtca ccccgaggga ggtcgcagca   2100
aagattgacc tgtacctccg tggtgcaaca aatcttgaag aatgcttggc caggcttgag   2160
```

```
aaagcgcgcc cgccacgcgt aatcgacacc tcctttgatt gggatgttgt gctccctggg    2220
gttgaggcgg caacccagac gatcaagctg ccccaggtca accagtgtcg tgctctggtc    2280
cctgttgtga ctcaaaagtc cttgtgtgag tttgtgatga tgcctcacac gcctgcacct    2340
tccgtaggtg cggagagcga ccttaccatt ggctcagttg ctactgaaga tgttccacgc    2400
atcctcgaga aaatagaaaa tgtcggcgag atggccaacc agggacccct tggccttctcc    2460 gaggataaac cggtagatga ccaacttgtc aacgaccccc ggatatcgtc gcggaggcct    2520
gacgagagca catcagctcc gtccgcaggc acaggtggcg ccggctcttt taccgatttg    2580
ccgccttcag atggcgcgga tgcggacggg ggggggccgt ttcggacggt aaaaagaaaa    2640
gctgaaaggc tctttgacca actgagccgt caggttttg acctcgtctc ccatctccct     2700
gttttcttct cacgccttt ctaccctggc ggtggttatt ctccgggtga ttggggtttt     2760
gcagctttta ctctattgtg cctcttttta tgttacagtt acccagcctt tggtattgct    2820
cccctcttgg gtgtgttttc tgggtcttct cggcgcgttc gaatgggggt ttttggctgc    2880
tggttggctt ttgctgttgg tctgttcaag cctgtgtccg acccagtcgg cgctgcttgt    2940
gagtttgact cgccagagtg tagaaacatc cttcattctt ttgagcttct caaaccttgg    3000
gaccctgttc gcagccttgt tgtgggcccc gtcggtctcg gtcttgccat tcttggcagg    3060
ttactgggcg gggcacgctg catctggcac ttttttgctta ggcttggcat tgttgcagac   3120
tgtatcttgg ctggagctta cgtgctttct caaggtaggt gtaaaagtg ctggggatct     3180 tgtataagaa ctgctcccaa tgaggtcgct tttaacgtgt ttcctttcac acgtgcgacc    3240
aggtcgtcac ttatcgacct gtgcgatcgg ttttgtgcgc caaaaggaat ggaccccatt    3300
tttctcgcca ctgggtggcg cgggtgctgg gccggccgaa gccccattga gcaaccctct    3360
gaaaaaccca tcgcgtttgc ccagttggat gaaaagaaga ttacggctag gactgtggtc    3420
gcccagcctt atgaccccaa ccaagccgta aagtgcttgc gggtattgca ggcgggtggg    3480
gcgatggtgg ctaaggcggt cccaaaagtg gtcaaggttt ccgctgttcc attccgagcc    3540
cccttctttc ccactggagt gaaagttgac cctgattgca gggtcgtggt tgaccctgac    3600
actttcactg cagctctccg gtctggctac tccaccacaa acctcgtcct tggtgtgggg    3660
gactttgccc agctgaatgg attaaaaatc aggcaaattt ccaagccttc aggggaggc    3720 ccacatctca tggctgccct gcatgttgcc tgctcgatgg ctctgcacat gcttgctggg    3780
atttatgtga ctgcggtggg ttcttgcggc accggcacca acgacccgtg gtgcgctaac    3840
ccgtttgccg tccctggcta cggacctggc tctctctgca cgtccagatt gtgcatttcc    3900
caacacggcc ttaccctgcc cttgacagca cttgtggcgg gattcggtat tcaagaaatt    3960
gccttggtcg ttttgatttt tgtttccatc ggaggcatgg ctcataggtt gagctgtaag    4020
gctgacatgc tgtgtgtctt gcttgcaatt gccagctatg tttgggtacc tcttacctgg    4080
ttgctttgtg tgtttccttg ctggttgcgc tgttttttctt tgcacccct caccatccta   4140 tggttggtgt ttttcttgat ttctgtgaat atgccttcag gaatcttggc catggtgttg    4200
ttggtttctc tttggcttct tggtcgttat actaatgttg ctggccttgt cacccccac    4260 gacattcatc attacaccag tggccccgc ggtgttgccg ccttggctac cgcaccagat     4320
gggacctact tggccgctgt ccgccgcgct gcgttgactg gccgcaccat gctgtttacc    4380
ccgtcccagc ttgggtctct tcttgagggt gctttcagaa ctcgaaagcc ctcactgaac    4440
accgtcaatg tgatcgggtc ctccatgggc tctggcgggg tgtttaccat cgacgggaaa    4500
gtcaagtgcg taactgccgc acatgtcctt acgggcaatt cagctcgggt ttccggggtc    4560
```

-continued

```
ggcttcaatc aaatgcttga ctttgacgta aagggagatt tcgctatagc tgattgcccg    4620
aattggcaag gggctgcccc caagacccaa ttctgcacgg atggatggac tggccgtgcc    4680
tattggctaa catcctctgg cgtcgaaccc ggcgtcattg gaaaaggatt cgccttctgc    4740
ttcaccgcat gtggcgattc cgggtcccca gtgatcaccg aggccggtga gcttgtcggc    4800
gttcacacgg atcgaataa acaagggggg ggcattgtta cgcgcccctc aggccagttt    4860
tgtaatgtgg cacccatcaa gctaagcgaa ttaagtgaat tctttgctgg gcctaaggtc    4920
ccgctcggtg atgtgaaggt cggcagccac ataattaaag acataagcga ggtgccttca    4980
gatctttgtg ccttgcttgc tgccaaacct gaactggaag gaggcctctc caccgtccaa    5040
cttctttgtg tgtttttttct cctgtggaga atgatgggac atgcctggac gcccttggtt    5100
gctgtgagtt tctttatttt gaatgaggtt ctcccagccg tcctggtccg gagtgttttc    5160
tcctttggaa tgtttgtgct atcctggctc acgccatggt ctgcgcaagt tctgatgatc    5220
aggcttctga cagcagctct taacaggaac agatggtcac ttgccttttt cagcctcggt    5280
gcagtgaccg gttttgtcgc agatcttgcg gccactcagg ggcatccgtt gcaggcagtg    5340
atgaatttga gcacctatgc attcctgcct cggatgatgg ttgtgacctc accagtccca    5400
gtgatcacgt gtggtgtcgt gcacctactt gccatcattt tgtacttgtt taagtaccgt    5460
ggcctgcacc atatccttgt tggcgatgga gtgttctctg cggctttctt cttgagatac    5520
tttgccgagg gaaagttgag ggaagggggtg tcgcaatcct gcggaatgaa tcatgagtct    5580
ctgactggtg ccctcgctat gagactcaat gacgaggact tggatttcct tatgaaatgg    5640
actgattta agtgctttgt ttctgcgtcc aacatgagga atgcagcggg tcaatttatc    5700
gaggctgcct atgctaaagc acttagagta gaactggccc agttggtgca ggttgataaa    5760
gttcgaggta ctttggccaa acttgaagct tttgctgata ccgtggcacc tcaactctcg    5820
cccggtgaca ttgttgtcgc tctcggccac acgcctgttg gcagtatctt cgacctaaag    5880
gttggtagca ccaagcatac cctccaagcc attgagacca gagtccttgc tgggtccaaa    5940
atgaccgtgg cgcgcgtcgt cgaccccgacc cccacgcccc caccgccacc cgtgcccatc    6000
cccctcccac cgaaagttct ggagaatggc cccaacgctt gggggggatga ggaccgtttg    6060
aataagaaga gaggcgcag atggaagcc ctcggcatct atgttatggg cgggaaaaaa    6120
taccagaaat tttgggacaa gaattccggt gatgtgtttt atgaggaggt ccataataac    6180
acagatgagt gggagtgtct cagagttggc gaccctgccg actttgaccc tgagaaggga    6240
actctgtgtg gacatgtcac cattgaaaac aaggcttacc atgtttacac ctccccatct    6300
ggtaagaagt tcttggtccc cgtcaaccca gagaatggaa gagtccaatg ggaagctgca    6360
aagctttccg tggagcaggc cctaggtatg atgaatgtcg acggcgaact gactgccaaa    6420
gaactggaga aactgaaaag aataattgac aaactccagg gcctgactaa ggagcagtgt    6480
ttaaactgct agccgccagc gacttgaccc gctgtggtcg cggcggcttg gttgttactg    6540
aaacagcggt aaaaatagtc aaatttcaca accggacctt caccctggga cctgtgaatt    6600
taaaagtggc cagtgaggtt gagctaaaag acgcggttga gcacaaccaa cacccggttg    6660
cgagaccgat cgatggtgga gttgtgctcc tgcgttccgc ggttccttcg cttatagacg    6720
tcttgatctc cggtgctgat gcatctccca agttacttgc ccatcacggg ccgggaaaca    6780
ctgggatcga tggcacgctc tgggattttg agtccgaagc cactaaagag gaagtcgcac    6840
tcagtgcgca ataatacag gcttgtgaca ttaggcgcgg cgacgctcct gaaattggtc    6900
tcccttacaa gctgtaccct gttaggggta accctgagcg ggtgaaagga gttctgcaga    6960
```

```
atacaaggtt tggagacata ccttacaaaa cccccagtga cactggaagc ccagtgcacg    7020
cggctgcctg ccttacgccc aacgccactc cggtgactga tgggcgctcc gtcttggcca    7080
cgaccatgcc ccccgggttt gagttatatg taccgaccat accagcgtct gtccttgatt    7140
accttgactc taggcctgac tgccctaaac agctgacaga gcacggctgc gaagatgccg    7200
cactgaaaga cctctctaaa tatgacttgt ccacccaagg ctttgtttta cctggagttc    7260
ttcgccttgt gcggaaatac ctgtttgccc atgtaggtaa gtgcccaccc gttcatcggc    7320
cttctactta ccctgctaag aattctatgg ctggaataaa tgggaacagg ttcccaacca    7380
aggacattca gagcgtccct gaaatcgacg ttctgtgcgc acaggctgtg cgagaaaact    7440
ggcaaactgt caccccttgt actcttaaga aacagtattg cgggaagaag aagactagga    7500
ccatactcgg caccaataac ttcatcgcac tagcccaccg agcagtgttg agtggtgtta    7560
cccagggctt catgaaaaag gcgtttaact cgcccatcgc cctcggaaag aacaagttta    7620
aggagctaca gactccggtc ctgggcaggt gccttgaagc tgatctcgca tcctgcgatc    7680
gatccacgcc tgcaattgtc cgctggtttg ccgccaacct tctttatgaa cttgcctgtg    7740
ctgaagagca tctaccgtcg tacgtgctga actgctgcca cgacttactg gtcacgcagt    7800
ccggcgcagt gactaagaga ggtggcctgt cgtctggcga cccgatcacc tctgtgtcta    7860
acaccattta tagtttggtg atctatgcac agcatatggt gcttagttac ttcaaaagtg    7920
gtcaccccca tggccttctg ttcttacaag accagctaaa gtttgaggac atgctcaagg    7980
ttcaacccct gatcgtctat tcggacgacc tcgtgctgta tgccgagtct cccaccatgc    8040
caaactatca ctggtgggtt gaacatctga atttgatgct ggggtttcag acggacccaa    8100
agaagacagc aataacagac tcgccatcat ttctaggctg tagaataata aatgggcgcc    8160
agctagtccc caaccgtgac aggatcctcg cggccctcgc ctatcacatg aaggcgagta    8220
atgtttctga atactatgcc tcagcggctg caatactcat ggacagctgt gcttgttttgg   8280 agtatgatcc tgaatggttt gaagaacttg tagttggaat agcgcagtgc gcccgcaagg    8340
acggctacag cttcccggc acgccgttct tcatgtccat gtgggaaaaa ctcaggtcca    8400
attatgaggg gaagaagtcg agagtgtgcg ggtactgcgg ggccccggcc ccgtacgcta    8460
ctgcctgtgg cctcgacgtc tgcatttacc acacccactt ccaccagcat tgtccagtca    8520
caatctggtg tggccatcca gcgggttctg gttcttgtag tgagtgcaaa tccctgtag     8580 ggaaaggcac aagcccttta gacgaggtgc tggaacaagt cccgtataag cccccacgga    8640
ccgttatcat gcatgtggag cagggtctca ccccccttga tccaggtaga taccaaactc    8700
gccgcggatt agtctctgtc aggcgtggaa ttaggggaaa tgaagttgga ctaccagacg    8760
gtgattatgc tagcaccgcc ttgctcccta cctgcaaaga gatcaacatg gtcgctgtcg    8820
cttccaatgt attgcgcagc aggttcatca tcggcccacc cggtgctggg aaaacatact    8880
ggctccttca acaggtccag gatggtgatg ttattacac accaactcac cagaccatgc     8940
ttgacatgat tagggctttg gggacgtgcc ggttcaacgt cccggcaggc acaacgctgc    9000
aattccccgt ccctccccgc accggtccgt gggttcgcat cctagccggc ggttggtgtc    9060
ctggcaagaa ttccttccta gatgaagcag cgtattgcaa tcaccttgat gttttgaggc    9120
ttcttagtaa aactaccctc acctgtctag gagacttcaa gcaactccac ccagtgggtt    9180
ttgattctca ttgctatgtt tttgacatca tgcctcaaac tcaactgaag accatctgga    9240
ggtttggaca gaatatctgt gatgccattc agccagatta cagggacaaa ctcatgtcca    9300
tggtcaacac aaccgtgtg acctacgtgg aaaaacctgt caggtatggg caggtcctca    9360
```

```
ccccctacca cagggaccga gaggacgacg ccatcactat tgactccagt caaggcgcca    9420
cattcgatgt ggttacattg catttgccca ctaaagattc actcaacagg caaagagccc    9480
ttgttgctat caccagggca agacacgcta tctttgtgta tgacccacac aggcagctgc    9540
agggcttgtt tgatcttcct gcaaaaggca cgcccgtcaa cctcgcagtg cactgcgacg    9600
ggcagctgat cgtgctggat agaaataaca aagaatgcac ggttgctcag gctctaggca    9660
acggggataa atttagggcc acagacaagc gtgttgtaga ttctctccgc gccatttgtg    9720
ctgatctaga agggtcgagc tctccgctcc ccaaggtcgc acacaacttg ggattttatt    9780
tctcacctga tttaacacag tttgctaaac tcccagtaga acttgcacct cactggcccg    9840
tggtgtcaac ccagaacaat gaaaagtggc cggatcggct ggttgccagc cttcgcccta    9900
tccataaata cagccgcgcg tgcatcggtg ccggctatat ggtgggccct tcggtgtttc    9960
taggcactcc tggggtcgtg tcatactatc tcacaaaatt tgttaagggc ggggctcaag   10020
tgcttccgga gacggttttc agcaccggcc gaattgaggt agactgccgg gaatatcttg   10080
atgatcggga gcgagaagtt gctgcgtccc tcccacacgc tttcattggc gacgtcaaag   10140
gcactaccgt tggaggatgt catcatgtca cctccagata cctcccgcgc gtccttccca   10200
aggaatcagt tgcggtagtc gggtttcaa gccccggaaa agccgcgaaa gcattgtgca    10260
cactgacaga tgtgtacctc ccagatcttg aagcctatct ccaccggag acccagtcca    10320 agtgctggaa aatgatgttg gacttcaaag aagttcgact aatggtctgg aaagacaaaa   10380
cagcctattt ccaacttgaa ggtcgctatt tcacctggta tcagcttgcc agctatgcct   10440
cgtacatccg tgttcccgtc aactctacgg tgtacttgga cccctgcatg ggccccgccc   10500
tttgcaacag gagagtcgtc gggtccaccc actgggggc tgacctcgcg gtcaccccett   10560 atgattacgg cgctaaaatt atcctgtcta gcgcgtacca tggtgaaatg ccccccggat   10620
acaaaattct ggcgtgcgcg gagttctcgt tggatgaccc agttaagtac aaacatacct   10680
gggggtttga atcggataca gcgtatctgt atgagttcac cggaaacggt gaggactggg   10740
aggattacaa tgatgcgttt cgtgcgcgcg aggaagggaa aatttataag gccactgcca   10800
ccagcttgaa gttttatttt ccccccgggcc ctgtcattga accaacttta ggcctgaatt   10860
gaaatgaaat ggggtccatg caaagccttt ttgacaaaat tggccaactt tttgtggatg   10920 cttttcacgga gttcttggtg tccattgttg atatcattat atttttggcc atttttgtttg   10980 gcttcaccat cgccggttgg ctggtggtct tttgcatcag attggtttgc tccgcgatac   11040
tccgtacgcg ccctgccatt cactctgagc aattacagaa gatcttatga ggcctttctt   11100
tcccagtgcc aagtggacat tcccacctgg ggaactaaac atcctttggg gatgctttgg   11160
caccataagg tgtcaaccct gattgatgaa atggtgtcgc gtcgaatgta ccgcatcatg   11220
gaaaaagcag ggcaggctgc ctggaaacag gtggtgagcg aggctacgct gtctcgcatt   11280
agtagtttgg atgtggtggc tcattttcag catctagccg ccattgaagc cgagacctgt   11340
aaatatttgg cctcccggct gcccatgcta cacaacctgc gcatgacagg gtcaaatgta   11400
accatagtgt ataatagcac tttgaatcag gtgtttgcta ttttccaac ccctggttcc   11460 cggccaaagc ttcatgattt tcagcaatgg ttaatagctg tacattcctc catattttcc   11520
tctgttgcag cttcttgtac tcttttttgtt gtgctgtggt tgcgggttcc aatactacgt   11580 actgttttttg gtttccgctg gttagggca atttttcttt cgaactcaca gtgaattaca   11640
cggtgtgtcc accttgcctc acccggcaag cagccacaga gatctacgaa cccggtaggt   11700 ctcttttggtg caggataggg tatgaccgat gtggggagga cgatcatgac gagctagggt   11760
```

```
ttatgatacc gcctggcctc tccagcgaag gccacttgac tggtgtttac gcctggttgg   11820
cgttcttgtc cttcagctac acggcccagt tccatcccga gatattcggg atagggaatg   11880
tgagtcgagt ttatgttgac atcaaacatc aactcatctg cgccgaacat gacgggcaga   11940
acaccacctt gcctcgtcat gacaacattt cagccgtgtt tcagacctat taccaacatc   12000
aagtcgacgg cggcaattgg tttcacctag aatggcttcg tcccttcttt tcctcgtggt   12060
tggttttaaa tgtctcttgg tttctcaggc gttcgcctgc aaaccatgtt tcagttcgag   12120
tcttgcagat attaagacca acaccaccgc agcggcaagc tttgctgtcc tccaagacat   12180
cagttgcctt aggcatcgcg actcggcctc tgaggcgatt cgcaaaatcc ctcagtgccg   12240
tacggcgata gggacacccg tgtatgttac catcacagcc aatgtgacag atgagaatta   12300
tttacattct tctgatctcc tcatgctttc ttcttgcctt ttctatgctt ctgagatgag   12360
tgaaaaggga tttaaggtgg tatttggcaa tgtgtcaggc atcgtggctg tgtgtgtcaa   12420
ttttaccagc tacgtccaac atgtcaagga gtttacccaa cgctccctgg tggtcgacca   12480
tgtgcggttg ctccatttca tgacacctga gaccatgagg tgggcaactg ttttagcctg   12540 tcttttgcc attctgttgg caatttgaat gtttaagtat gttggagaaa tgcttgaccg   12600
cgggctgttg ctcgcgattg ctttctttgt ggtgtatcgt gccgttctgt tttgctgtgc   12660
tcgccaacgc cagcaacgac agcagctccc atctacagct gatttacaac ttgacgctat   12720
gtgagctgaa tggcacagat tggctagcta acaaatttga ttgggcagtg gagagttttg   12780 tcatcttttcc cgttttgact cacattgtct cctatggtgc cctcactacc agccatttcc   12840
ttgacacagt cgctttagtc actgtgtcta ccgccgggtt tgttcacggg cggtatgtcc   12900
taagtagcat ctacgcggtc tgtgcccctgg ctgcgttgac ttgcttcgtc attaggtttg   12960
caaagaattg catgtcctgg cgctacgcgt gtaccagata taccaacttt cttctggaca   13020
ctaagggcag actctatcgt tggcggtcgc ctgtcatcat agagaaaagg ggcaaagttg   13080
aggtcgaagg tcatctgatc gacctcaaaa gagttgtgct tgatggctcc gtggcaaccc   13140
ctataaccag agtttcagcg gaacaatggg gtcgtcctta gatgacttct gtcacgatag   13200
cacggctcca caaaaggtgc ttttggcgtt ttctattacc tacacgccag tgatgatata   13260
tgccctaaag gtgagtcgcg gccgactgct agggcttctg cacctttga tcttcctgaa   13320 ttgtgctttc accttcgggt acatgacttt cgcgcacttt cagagtacaa ataaggtcgc   13380
gctcactatg ggagcagtag ttgcactcct ttgggggtg tactcagcca tagaaacctg   13440
gaaattcatc acctccagat gccgtttgtg cttgctaggc cgcaagtaca ttctggcccc   13500 tgccccaccac gttgaaagtg ccgcaggctt tcatccgatt gcggcaaatg ataaccacgc   13560
atttgtcgtc cggcgtcccg gctccactac ggtcaacggc acattggtgc ccgggttaaa   13620
aagcctcgtg ttgggtggca gaaaagctgt taaacaggga gtggtaaacc ttgtcaaata   13680
tgccaaataa caacggcaag cagcagaaga gaaagaaggg ggatggccag ccagtcaatc   13740
agctgtgcca gatgctgggt aagatcatcg ctcagcaaaa ccagtccaga ggcaagggac   13800
cgggaaagaa aaataagaag aaaaacccgg agaagcccca ttttcctcta gcgactgaag   13860
atgatgtcag acatcacttt accctagtg agcggcaatt gtgtctgtcg tcaatccaga   13920
ccgcctttaa tcaaggcgct gggacttgca ccctgtcaga ttcagggagg ataagttaca   13980
ctgtggagtt tagtttgcct acgcatcata ctgtgcgcct gatccgcgtc acagcatcac   14040
cctcagcatg atgggctggc attcttgagg catctcagtg tttgaattgg aagaatgtgt   14100
ggtgaatggc actgattgac attgtgcctc taagtcacct attcaattag ggcgaccgtg   14160
```
tgggggtgag atttaattgg cgagaaccat gcggccgaaa ttaaaaaaaa        14210

<210> SEQ ID NO 14
<211> LENGTH: 15111
<212> TYPE: DNA
<213> ORGANISM: Porcine Reproductive and Respiratory Syndrome Virus
<220> FEATURE:
<221> NAME/KEY: misc_feature
<223> OTHER INFORMATION: Lelystad strain
<300> PUBLICATION INFORMATION:
<308> DATABASE ACCESSION NUMBER: Genbank/M96262.2
<309> DATABASE ENTRY DATE: 2000-11-08
<313> RELEVANT RESIDUES IN SEQ ID NO: (1)..(15111)

<400> SEQUENCE: 14
atgatgtgta gggtattccc cctacataca cgacacttct agtgtttgtg taccttggag        60
gcgtgggtac agccccgccc cacccccttgg cccctgttct agcccaacag gtatccttct        120 ctctcgggc gagtgcgccg cctgctgctc ccttgcagcg ggaaggacct cccgagtatt        180
tccggagagc acctgcttta cgggatctcc accctttaac catgtctggg acgttctccc        240
ggtgcatgtg caccccggct gcccgggtat tttggaacgc cggccaagtc ttttgcacac        300
ggtgtctcag tgcgcggtct cttctctctc cagagcttca ggacactgac ctcggtgcag        360
ttggcttgtt ttacaagcct agggacaagc ttcactggaa agtccctatc ggcatccctc        420
aggtggaatg tactccatcc gggtgctgtt ggctctcagc tgtttccct ttggcgcgta        480 tgacctccgg caatcacaac ttcctccaac gacttgtgaa ggttgctgat gttttgtacc        540
gtgacggttg cttggcacct cgacaccttc gtgaactcca gtttacgag cgcggctgca        600 actggtaccc gatcacgggg cccgtgcccg ggatgggttt gtttgcgaac tccatgcacg        660
tatccgacca gccgttccct ggtgccaccc atgtgttgac taactcgcct ttgcctcaac        720
aggcttgtcg gcagccgttc tgtccatttg aggaggctca ttctagcgtg tacaggtgga        780
agaaatttgt ggttttcacg gactcctccc tcaacggtcg atctcgcatg atgtggacgc        840
cggaatccga tgattcagcc gccctggagg tactaccgcc tgagttagaa cgtcaggtcg        900
aaatcctcat tcggagtttt cctgctcatc ccctgtcga cctggccgac tgggagctca        960
ctgagtcccc tgagaacggt ttttccttca acacgtctca ttcttgcggt caccttgtcc        1020 agaacccga cgtgtttgat ggcaagtgct ggctctcctg ctttttgggc cagtcggtcg        1080
aagtgcgctg ccatgaggaa catctagctg acgccttcgg ttaccaaacc aagtggggcg        1140
tgcatggtaa gtacctccag cgcaggcttc aagttcgcgg cattcgtgct gtagtcgatc        1200
ctgatggtcc cattcacgtt gaagcgctgt cttgccccca gtcttggatc aggcacctga        1260
ctctggatga tgatgtcacc ccaggattcg ttcgcctgac atcccttcgc attgtgccga        1320
acacagagcc taccacttcc cggatctttc ggtttggagc gcataagtgg tatggcgctg        1380
ccggcaaacg ggctcgtgct aagcgtgccg ctaaaagtga aaggattcg gctcccaccc        1440 ccaaggttgc cctgccggtc cccacctgtg gaattaccac ctactctcca ccgacagacg        1500
ggtcttgtgg ttggcatgtc cttgccgcca taatgaaccg gatgataaat ggtgacttca        1560 cgtccctct gactcagtac aacagaccag aggatgattg gcttctgat tatgatcttg        1620 ttcaggcgat tcaatgtcta cgactgcctg ctaccgtggt tcggaatcgc gcctgtccta        1680
acgccaagta ccttataaaa cttaacggag ttcactggga ggtagaggtg aggtctgaa        1740 tggctcctcg ctcccttct cgtgaatgtg tggttggcgt ttgctctgaa ggctgtgtcg        1800
caccgcctta tccagcagac gggctaccta acgtgcact cgaggcctg gcgtctgctt        1860 acagactacc ctccgattgt gttagctctg gtattgctga cttcttgct aatccacctc        1920

```
ctcaggaatt ctggaccctc gacaaaatgt tgacctcccc gtcaccgagg cggtccggct    1980
tctctagttt gtataaatta ctattagagg ttgttccgca aaaatgcggt gccacggaag    2040
gggctttcat ctatgctgtt gagaggatgt tgaaggattg tccgagctcc aaacaggcca    2100
tggcccttct ggcaaaaatt aaagttccat cctcaaaggc cccgtctgtg tccctggacg    2160
agtgtttccc tacgatgtt ttagccgact tcgagccagc atctcaggaa aggccccaaa    2220
gttccggcgc tgctgttgtc ctgtgttcac cggatgcaaa agagttcgag gaagcagccc    2280
cggaagaagt tcaagagagt ggccacaagg ccgtccactc tgcactcctt gccgagggtc    2340
ctaacaatga gcaggtacag gtggttgccg gtgagcaact gaagctcggc ggttgtggtt    2400
tggcagtcgg gaatgctcat gaaggtgctc tggtctcagc tggtctaatt aacctggtag    2460
gcgggaattt gtccccctca gacccatga aagaaaacat gctcaatagc cgggaagacg    2520
aaccactgga tttgtcccaa ccagcaccag cttccacaac gacccttgtg agagagcaaa    2580
cacccgacaa cccaggttct gatgccgtg ccctccccgt caccgttcga gaatttgtcc    2640
cgacggggcc tatactctgt catgttgagc actgcggcac ggagtcgggc gacagcagtt    2700
cgcctttgga tctatctgat gcgcaaaccc tggaccagcc tttaaatcta tccctggccg    2760
cttggccagt gagggccacc gcgtctgacc ctggctgggt ccacggtagg cgcgagcctg    2820
tctttgtaaa gcctcgaaat gctttctctg atggcgattc agcccttcag ttcggggagc    2880
tttctgaatc cagctctgtc atcgagtttg accggacaaa agatgctccg gtggttgacg    2940
cccctgtcga cttgacgact tcgaacgagg ccctctctgt agtcgatcct ttcgaatttg    3000
ccgaactcaa gcgcccgcgt ttctccgcac aagccttaat tgaccgaggc ggtccacttg    3060
ccgatgtcca tgcaaaaata aagaaccggg tatatgaaca gtgcctccaa gcttgtgagc    3120
ccggtagtcg tgcaaccccca gccaccaggg agtggctcga caaaatgtgg gatagggtgg    3180
acatgaaaac ttggcgctgc acctcgcagt tccaagctgg tcgcattctt gcgtccctca    3240
aattcctccc tgacatgatt caagacacac cgcctcctgt tcccaggaag aaccgagcta    3300
gtgacaatgc cggcctgaag caactggtgg cacagtggga taggaaattg agtgtgaccc    3360 ccccccaaa accggttggg ccagtgcttg accagatcgt ccctccgcct acggatatcc    3420
agcaagaaga tgtcaccccc tccgatgggc cacccatgc gccggatttt cctagtcgag    3480
tgagcacggg cgggagttgg aaaggcctta tgctttccgg cacccgtctc gcggggtcta    3540
tcagccagcg ccttatgaca tgggttttttg aagttttctc ccacctccca gcttttatgc    3600 tcacacttttt ctcgccgcgg ggctctatgg ctccaggtga ttggttgttt gcaggtgtcg    3660
ttttacttgc tctcttgctc tgtcgttctt acccgatact cggatgcctt cccttattgg    3720 gtgtctttc tggttctttg cggcgtgttc gtctgggtgt ttttggttct tggatggctt    3780
ttgctgtatt tttattctcg actccatcca acccagtcgg ttcttcttgt gaccacgatt    3840
cgccggagtg tcatgctgag cttttggctc ttgagcagcg ccaactttgg gaacctgtgc    3900
gcggccttgt ggtcggcccc tcaggcctct tatgtgtcat tcttggcaag ttactcggtg    3960
ggtcacgtta tctctggcat gttctcctac gtttatgcat gcttgcagat ttggcccttt    4020
ctcttgttta tgtggtgtcc cagggcgtt gtcacaagtg ttggggaaag tgtataagga    4080
cagctcctgc ggaggtggct cttaatgtat tccttttctc gcgcgccacc cgtgtctctc    4140
ttgtatcctt gtgtgatcga ttccaaacgc caaaggggt tgatcctgtg cacttggcaa    4200
cgggttggcg cgggtgctgg cgtggtgaga gcccatcca tcaaccacac caaaagccca    4260
tagcttatgc caatttggat gaaaagaaaa tgtctgccca acggtggtt gctgtcccat    4320
```

```
acgatcccag tcaggctatc aaatgcctga aagttctgca ggcgggaggg gccatcgtgg    4380
accagcctac acctgaggtc gttcgtgtgt ccgagatccc cttctcagcc ccattttttcc   4440 caaaagttcc agtcaaccca gattgcaggg ttgtggtaga ttcggacact tttgtggctg    4500
cggttcgctg cggttactcg acagcacaac tggttctggg ccggggcaac tttgccaagt    4560
taaatcagac ccccccccagg aactctatct ccaccaaaac gactggtggg gcctcttaca   4620
cccttgctgt ggctcaagtg tctgcgtgga ctcttgttca tttcatcctc ggtcttttggt  4680 tcacatcacc tcaagtgtgt ggccgaggaa ccgctgaccc atggtgttca aatccttttt    4740
catatcctac ctatggcccc ggagttgtgt gctcctctcg actttgtgtg tctgccgacg    4800
gggtcaccct gccattgttc tcagccgtgg cacaactctc cggtagagag gtggggattt    4860
ttattttggt gctcgtctcc ttgactgctt tggcccaccg catggctctt aaggcagaca    4920
tgttagtggt cttttcggct ttttgtgctt acgcctggcc catgagctcc tggttaatct    4980 gcttcttttcc tatactcttg aagtgggtta cccttcaccc tcttactatg ctttgggtgc   5040
actcattctt ggtgttttgt ctgccagcag ccggcatcct ctcactaggg ataactggcc    5100
ttctttgggc aattggccgc tttacccagg ttgccggaat tattcacacct tatgacatcc   5160 accagtacac ctctgggcca cgtggtgcag ctgctgtggc cacagcccca gaaggcactt    5220
atatggccgc cgtccggaga gctgcttttaa ctgggcgaac tttaatcttc accccgtctg   5280
cagttggatc ccttctcgaa ggtgctttca ggactcataa accctgcctt aacaccgtga    5340
atgttgtagg ctcttccctt ggttccgag ggttttcac cattgatggc agaagaactg      5400
tcgtcactgc tgcccatgtg ttgaacggcg acacagctag agtcaccggc gactcctaca   5460
accgcatgca ctctttcaag accaatggtg attatgcctg gtcccatgct gatgactggc    5520
agggcgttgc ccctgtggtc aaggttgcga aggggtaccg cggtcgtgcc tactggcaaa    5580
catcaactgg tgtcgaaccc ggtatcattg gggaagggtt cgccttctgt tttactaact    5640
gcggcgattc ggggtcaccc gtcatctcag aatctggtga tcttattgga atccacaccg    5700
gttcaaacaa acttggttct ggtcttgtga caacccctga aggggagacc tgcaccatca   5760
aagaaaccaa gctctctgac cttttccagac attttgcagg cccaagcgtt cctcttgggg   5820
acattaaatt gagtccggcc atcatccctg atgtaacatc cattccgagt gacttggcat    5880
cgctcctagc ctccgtccct gtagtggaag gcggcctctc gaccgttcaa cttttgtgtg   5940 tcttttttcct tctctggcgc atgatgggcc atgcctggac acccattgtt gccgtgggct   6000 tcttttttgct gaatgaaatt cttccagcag ttttggtccg agccgtgttt tcttttgcac    6060
tctttgtgct tgcatgggcc acccccttggt ctgcacaggt gttgatgatt agactcctca    6120
cggcatctct caaccgcaac aagctttctc tggcgttcta cgcactcggg ggtgtcgtcg    6180
gtttggcagc tgaaatcggg actttttgctg gcagattgtc tgaattgtct caagctcttt    6240
cgacatactg cttcttacct agggtccttg ctatgaccag ttgtgttccc accatcatca   6300
ttggtggact ccatacccctc ggtgtgattc tgtggttatt caaataccgg tgcctccaca    6360
acatgctggt tggtgatggg agttttttcaa gcgccttctt cctacggtat tttgcagagg    6420
gtaatctcag aaaaggtgtt tcacagtcct gtggcatgaa taacgagtcc ctaacggctg    6480
ctttagcttg caagttgtca caggctgacc ttgatttttt gtccagctta acgaacttca    6540
agtgctttgt atctgcttca aacatgaaaa atgctgccgg ccagtacatt gaagcagcgt    6600
atgccaaggc cctgcgccaa gagttggcct ctctagttca gattgacaaa atgaaaggag    6660
ttttgtccaa gctcgaggcc tttgctgaaa cagccacccc gtcccttgac ataggtgacg    6720
```

```
tgattgttct gcttgggcaa catcctcacg gatccatcct cgatattaat gtggggactg    6780
aaaggaaaac tgtgtccgtg caagagaccc ggagcctagg cggctccaaa ttcagtgttt    6840
gtactgtcgt gtccaacaca cccgtggacg ccttgaccgg catcccactc cagacaccaa    6900
cccctctttt tgagaatggt ccgcgtcatc gcagcgagga agacgatctt aaagtcgaga    6960
ggatgaagaa acactgtgta tccctcggct tccacaacat caatggcaaa gtttactgca    7020
aaatttggga caagtctacc ggtgacacct tttacacgga tgattcccgg tacacccaag    7080
accatgcttt tcaggacagg tcagccgact acagagacag ggactatgag ggtgtgcaaa    7140
ccacccccca acagggattt gatccaaagt ctgaaacccc tgttggcact gttgtgatcg    7200
gcggtattac gtataacagg tatctgatca aaggtaagga ggttctggtc cccaagcctg    7260
acaactgcct tgaagctgcc aagctgtccc ttgagcaagc tctcgctggg atgggccaaa    7320
cttgcgacct tacagctgcc gaggtggaaa agctaaagcg catcattagt caactccaag    7380
gtttgaccac tgaacaggct ttaaactgtt agccgccagc ggcttgaccc gctgtggccg    7440
cggcggccta gttgtgactg aaacggcggt aaaaattata aaataccaca gcagaacttt    7500
caccttaggc ccctttagacc taaaagtcac ttccgaggtg gaggtaaaga aatcaactga    7560
gcagggccac gctgttgtgg caaacttatg ttccggtgtc atcttgatga gacctcaccc    7620 accgtcccctt gtcgacgttc ttctgaaacc cggacttgac acaatacccg gcattcaacc    7680
agggcatggg gccgggaata tgggcgtgga cggttctatt tgggattttg aaaccgcacc    7740
cacaaaggca gaactcgagt tatccaagca aataatccaa gcatgtgaag ttaggcgcgg    7800
ggacgccccg aacctccaac tcccttacaa gctctatcct gttaggggggg atcctgagcg    7860 gcataaaggc cgccttatca ataccaggtt tggagattta ccttacaaaa ctcctcaaga    7920
caccaagtcc gcaatccacg cggcttgttg cctgcacccc aacggggccc ccgtgtctga    7980
tggtaaatcc acactaggta ccactcttca acatggtttc gagctttatg tccctactgt    8040
gccctatagt gtcatggagt accttgattc acgccctgac accccttta tgtgtactaa    8100 acatggcact tccaaggctg ctgcagagga cctccaaaaa tacgacctat ccacccaagg    8160
atttgtcctg cctggggtcc tacgcctagt acgcagattc atctttggcc atattggtaa    8220
ggcgccgcca ttgttcctcc catcaaccta tcccgccaag aactctatgg cagggatcaa    8280
tggccagagg ttcccaacaa aggacgttca gagcatacct gaaattgatg aaatgtgtgc    8340
ccgcgctgtc aaggagaatt ggcaaactgt gacaccttgc accctcaaga aacagtactg    8400
ttccaagccc aaaaccagga ccatcctggg caccaacaac tttattgcct tggctcacag    8460
atcggcgctc agtggtgtca cccaggcatt catgaagaag gcttggaagt ccccaattgc    8520
cttggggaaa aacaaattca aggagctgca ttgcactgtc gccggcaggt gtcttgaggc    8580
cgacttggcc tcctgtgacc gcagcacccc cgccattgta agatggtttg ttgccaacct    8640
cctgtatgaa cttgcaggat gtgaagagta cttgcctagc tatgtgctta attgctgcca    8700
tgacctcgtg gcaacacagg atggtgcctt cacaaaacgc ggtggccttg tcgtccggga    8760
ccccgtcacc agtgtgtcca acaccgtata ttcactggta atttatgccc agcacatggt    8820
attgtcggcc ttgaaaatgg gtcatgaaat tggtcttaag ttcctcgagg aacagctcaa    8880
gttcgaggac ctccttgaaa ttcagccat gttggtatac tctgatgatc ttgtcttgta    8940
cgctgaaaga cccacatttc ccaattacca ctggtgggtc gagcaccttg acctgatgct    9000
gggtttcaga acggacccaa agaaaaccgt cataactgat aaacccagct tcctcggctg    9060
cagaattgag gcagggcgac agctagtccc caatcgcgac cgcatcctgg ctgctcttgc    9120
```

```
atatcacatg aaggcgcaga acgcctcaga gtattatgcg tctgctgccg caatcctgat    9180
ggattcatgt gcttgcattg accatgaccc tgagtggtat gaggacctca tctgcggtat    9240
tgcccggtgc gcccgccagg atggttatag cttcccaggt ccggcatttt tcatgtccat    9300
gtgggagaag ctgagaagtc ataatgaagg gaagaaattc cgccactgcg gcatctgcga    9360
cgccaaagcc gactatgcgt ccgcctgtgg gcttgatttg tgtttgttcc attcgcactt    9420
tcatcaacac tgccctgtca ctctgagctg cggtcaccat gccggttcaa aggaatgttc    9480
gcagtgtcag tcacctgttg gggctggcag atcccctctt gatgccgtgc taaaacaaat    9540
tccatacaaa cctcctcgta ctgtcatcat gaaggtgggt aataaaacaa cggccctcga    9600
tccggggagg taccagtccc gtcgaggtct cgttgcagtc aagaggggta ttgcaggcaa    9660
tgaagttgat ctttctgatg gggactacca agtggtgcct cttttgccga cttgcaaaga    9720
cataaacatg gtgaaggtgg cttgcaatgt actactcagc aagttcatag tagggccacc    9780
aggttccgga aagaccacct ggctactgag tcaagtccag gacgatgatg tcatttacac    9840
acccacccat cagactatgt ttgatatagt cagtgctctc aaagtttgca ggtattccat    9900
tccaggagcc tcaggactcc cttttcccacc acctgccagg tccgggccgt gggttaggct    9960
tattgccagc gggcacgtcc ctggccgagt atcatacctc gatgaggctg gatattgtaa   10020
tcatctggac attcttagac tgcttttccaa acaccccctt gtgtgtttgg gtgaccttca   10080
gcaacttcac cctgtcggct ttgattccta ctgttatgtg ttcgatcaga tgcctcagaa   10140
gcagctgacc actatttaca gatttggccc taacatctgc gcagccatcc agccttgtta   10200
cagggagaaa cttgaatcta aggctaggaa cactagggtg ttttttacca cccggcctgt   10260
ggcctttggt caggtgctga caccatacca taaagatcgc atcggctctg cgataaccat   10320
agattcatcc caggggggcca ccttttgatat tgtgacattg catctaccat cgccaaagtc   10380
cctaaataaa tcccgagcac ttgtagccat cactcgggca agacacgggt tgttcattta   10440
tgaccctcat aaccagctcc aggagttttt caacttaacc cctgagcgca ctgattgtaa   10500
ccttgtgttc agccgtgggg atgagctggt agttctgaat gcggataatg cagtcacaac   10560
tgtagcgaag gcccttgaga caggtccatc tcgatttcga gtatcagacc cgaggtgcaa   10620
gtctctctta gccgcttgtt cggccagtct ggaagggagc tgtatgccac taccgcaagt   10680
ggcacataac ctgggggtttt acttttcccc ggacagtcca acatttgcac ctctgccaaa   10740
agagttggcg ccacattggc cagtggttac ccaccagaat aatcgggcgt ggcctgatcg   10800
acttgtcgct agtatgcgcc caattgatgc ccgctacagc aagccaatgg tcggtgcagg   10860
gtatgtggtc gggccgtcca cctttcttgg tactcctggt gtggtgtcat actatctcac   10920
actatacatc aggggtgagc cccaggcctt gccagaaaca ctcgtttcaa cagggcgtat   10980
agccacagat tgtcgggagt atctcgacgc ggctgaggaa gaggcagcaa aagaactccc   11040
ccacgcattc attggcgatg tcaaaggtac cacggttggg gggtgtcatc acattacatc   11100
aaaatacctta cctaggtccc tgcctaagga ctctgttgcc gtagttggag taagttcgcc   11160
cggcagggct gctaaagccg tgtgcactct caccgatgtg tacctcccccg aactccggcc   11220
atatctgcaa cctgagacgg catcaaaatg ctggaaactc aaattagact tcagggacgt   11280
ccgactaatg gtctggaaag gagccaccgc ctatttccag ttggaagggc ttacatggtc   11340
ggcgctgccc gactatgcca ggtttattca gctgcccaag gatgccgttg tatacattga   11400
tccgtgtata ggaccggcaa cagccaaccg taaggtcgtg cgaaccacag actggcgggc   11460
cgacctggca gtgacaccgt atgattacgg tgcccagaac attttgacaa cagcctggtt   11520
```

```
cgaggacctc gggccgcagt ggaagatttt ggggttgcag cccttaggc gagcatttgg   11580 ctttgaaaac actgaggatt gggcaatcct tgcacgccgt atgaatgacg gcaaggacta   11640
cactgactat aactggaact gtgttcgaga acgcccacac gccatctacg ggcgtgctcg   11700
tgaccatacg tatcattttg ccctggcac agaattgcag gtagagctag gtaaaccccg   11760
gctgccgcct gggcaagtgc cgtgaattcg gggtgatgca atgggggtcac tgtggagtaa   11820 aatcagccag ctgttcgtgg acgccttcac tgagttcctt gttagtgtgg ttgatattgc   11880
cattttcctt gccatactgt ttgggttcac cgtcgcagga tggttactgg tcttctttct   11940
cagagtggtt tgctccgcgc ttctccgttc gcgctctgcc attcactctc ccgaactatc   12000
gaaggtccta tgaaggcttg ttgcccaact gcagaccgga tgtcccacaa tttgcagtca   12060
agcacccatt gggtatgttt tggcacatgc gagtttccca cttgattgat gagatggtct   12120
ctcgtcgcat ttaccagacc atggaacatt caggtcaagc ggcctggaag caggtggttg   12180
gtgaggccac tctcacgaag ctgtcaggc tcgatatagt tactcatttc caacacctgg   12240
ccgcagtgga ggcggattct tgccgctttc tcagctcacg actcgtgatg ctaaaaaatc   12300
ttgccgttgg caatgtgagc ctacagtaca acaccacgtt ggaccgcgtt gagctcatct   12360
tccccacgcc aggtacgagg cccaagttga ccgatttcag acaatggctc atcagtgtgc   12420
acgcttccat tttttcctct gtggcttcat ctgttacctt gttcatagtg ctttggcttc   12480
gaattccagc tctacgctat gttttttggtt ccattggcc cacggcaaca catcattcga   12540
gctgaccatc aactcaccca tatgcatgcc ctgttctacc agtcaagcgg ctcgccaaag   12600
gctcgagccc ggtcgtaaca tgtggtgcaa ataggggcat gacaggtgtg aggagcgtga   12660
ccatgatgag ttgttaatgt ccatcccgtc cgggtacgac aacctcaaac ttgagggtta   12720
ttatgcttgg ctggctttt tgtccttttc ctacgcggcc caattccatc cggagttgtt   12780
cgggataggg aatgtgtcgc gcgtcttcgt ggacaagcga caccagttca tttgtgccga   12840
gcatgatgga cacaattcaa ccgtatctac cggacacaac atctccgcat tatatgcggc   12900
atattaccac caccaaatag acgggggcaa ttggttccat ttggaatggc tgcggccact   12960
cttttcttcc tggctggtgc tcaacatatc atggtttctg aggcgttcgc ctgtaagccc   13020 tgttctcga cgcatctatc agatattgag accaacacga ccgcggctgc cggtttcatg   13080
gtccttcagg acatcaattg tttccgacct cacgggtct cagcagcgca agagaaaatt   13140
tccttcggaa agtcgtccca atgtcgtgaa gccgtcggta ctcccagta catcacgata   13200 acggctaacg tgaccgacga atcatacttg tacaacgcgg acctgctgat gctttctgcg   13260
tgccttttct acgcctcaga aatgagcgag aaaggcttca aagtcatctt tgggaatgtc   13320
tctggcgttg tttctgcttg tgtcaatttc acagattatg tggcccatgt gacccaacat   13380
acccagcagc atcatctggt aattgatcac attcggttgc tgcatttcct gacaccatct   13440
gcaatgaggt gggctacaac cattgcttgt ttgttcgcca ttctcttggc aatatgagat   13500
gttctcacaa attggggcgt ttcttgactc cgcactcttg cttctggtgg cttttttgc   13560 tgtgtaccgg cttgtcctgg tcctttgccg atggcaacgg cgacagctcg atacccaat   13620 acatatataa cttgacgata tgcgagctga atgggaccga ctggttgtcc agccattttg   13680
gttgggcagt cgagaccttt gtgctttacc cggttgccac tcatatcctc tcactgggtt   13740
ttctcacaac aagccatttt tttgacgcgc tcggtctcgg cgctgtatcc actgcaggat   13800
ttgttggcgg gcggtacgta ctctgcagcg tctacgcgc ttgtgctttc gcagcgttcg   13860
tatgttttgt catccgtgct gctaaaaatt gcatggcctg ccgctatgcc cgtacccggt   13920
```
ttaccaactt cattgtggac gaccggggga gagttcatcg atggaagtct ccaatagtgg   13980
tagaaaaatt gggcaaagcc gaagtcgatg gcaacctcgt caccatcaaa catgtcgtcc   14040 tcgaagggggt taaagctcaa cccttgacga ggacttcggc tgagcaatgg gaggcctaga   14100 cgattttttgc aacgatccta tcgccgcaca aaagctcgtg ctagccttta gcatcacata   14160
cacacctata atgatatacg cccttaaggt gtcacgcggc cgactcctgg ggctgttgca   14220
catcctaata tttctgaact gttcctttac attcggatac atgacatatg tgcattttca   14280
atccaccaac cgtgtcgcac ttaccctggg ggctgttgtc gcccttctgt ggggtgttta   14340
cagcttcaca gagtcatgga agtttatcac ttccagatgc agattgtgtt gccttggccg   14400
gcgatacatt ctggcccctg cccatcacgt agaaagtgct gcaggtctcc attcaatctc   14460
agcgtctggt aaccgagcat acgctgtgag aaagcccgga ctaacatcag tgaacggcac   14520
tctagtacca ggacttcgga gcctcgtgct gggcggcaaa cgagctgtta acgaggagt   14580 ggttaacctc gtcaagtatg gccggtaaaa accagagcca gaagaaaaag aaaagtacag   14640
ctccgatggg gaatggccag ccagtcaatc aactgtgcca gttgctgggt gcaatgataa   14700
agtcccagcg ccagcaacct aggggaggac aggccaaaaa gaaaaagcct gagaagccac   14760
attttcccct ggctgctgaa gatgacatcc ggcaccacct cacccagact gaacgctccc   14820
tctgcttgca atcgatccag acggctttca atcaaggcgc aggaactgcg tcgctttcat   14880
ccagcgggaa ggtcagtttt caggttgagt ttatgctgcc ggttgctcat acagtgcgcc   14940
tgattcgcgt gacttctaca tccgccagtc agggtgcaag ttaatttgac agtcaggtga   15000
atggccgcga ttggcgtgtg gcctctgagt cacctattca attagggcga tcacatgggg   15060
gtcatactta atcaggcagg aaccatgtga ccgaaattaa aaaaaaaaa a             15111

<210> SEQ ID NO 15
<211> LENGTH: 15411
<212> TYPE: DNA
<213> ORGANISM: Porcine Reproductive and Respiratory Syndrome Virus
<220> FEATURE:
<221> NAME/KEY: misc_feature
<223> OTHER INFORMATION: Strain VR-2332
<300> PUBLICATION INFORMATION:
<308> DATABASE ACCESSION NUMBER: Genbank/U87392.3
<309> DATABASE ENTRY DATE: 2000-11-17
<313> RELEVANT RESIDUES IN SEQ ID NO: (1)..(15411)

<400> SEQUENCE: 15
atgacgtata ggtgttggct ctatgccttg gcatttgtat tgtcaggagc tgtgaccatt     60
ggcacagccc aaaacttgct gcacagaaac acccttctgt gatagcctcc ttcaggggag    120
cttagggttt gtccctagca ccttgcttcc ggagttgcac tgctttacgg tctctccacc    180 ccttttaacca tgtctgggat acttgatcgg tgcacgtgta cccccaatgc cagggtgttt    240
atggcggagg ccaagtcta ctgcacacga tgcctcagtg cacggtctct ccttcccctg     300
aacctccaag tttctgagct cggggtgcta ggcctattct acaggcccga agagccactc     360
cggtggacgt tgccacgtgc attccccact gttgagtgct ccccgccgg ggcctgctgg     420 ctttctgcaa tctttccaat cgcacgaatg accagtggaa acctgaactt ccaacaaaga    480
atggtacggg tcgcagctga gctttacaga gccggccagc tcacccctgc agtcttgaag    540
gctctacaag tttatgaacg gggttgccgc tggtacccca ttgttggacc tgtccctgga    600
gtggccgttt tcgccaattc cctacatgtg agtgataaac cttttcccgg agcaactcac    660
gtgttgacca acctgccgct cccgcagaga cccaagcctg aagactttg ccccctttgag    720

-continued

```
tgtgctatgg ctactgtcta tgacattggt catgacgccg tcatgtatgt ggccgaaagg   780
aaagtctcct gggcccctcg tggcgggat gaagtgaaat ttgaagctgt ccccggggag    840
ttgaagttga ttgcgaaccg gctccgcacc tccttcccgc cccaccacac agtggacatg   900
tctaagttcg ccttcacagc ccctgggtgt ggtgtttcta tgcgggtcga acgccaacac   960
ggctgccttc ccgctgacac tgtccctgaa ggcaactgct ggtggagctt gtttgacttg  1020
cttccactgg aagttcagaa caaagaaatt cgccatgcta accaatttgg ctaccagacc  1080
aagcatggtg tctctggcaa gtacctacag cggaggctgc aagttaatgg tctccgagca  1140
gtaactgacc taaacggacc tatcgtcgta cagtacttct ccgttaagga gagttggatc  1200
cgccatttga aactggcggg agaacccagc tactctgggt ttgaggacct cctcagaata  1260
agggttgagc ctaacacgtc gccattggct gacaaggaag aaaaaatttt ccggtttggc  1320
agtcacaagt ggtacggcgc tggaaagaga gcaagaaaag cacgctcttg tgcgactgct  1380
acagtcgctg gccgcgcttt gtccgttcgt gaaacccggc aggccaagga gcacgaggtt  1440
gccggcgcca acaaggctga gcacctcaaa cactactccc cgcctgccga agggaattgt  1500
ggttggcact gcatttccgc catcgccaac cggatggtga attccaaatt tgaaaccacc  1560
cttcccgaaa gagtgagacc tccagatgac tgggctactg acgaggatct tgtgaatgcc  1620
atccaaatcc tcagactccc tgcggcctta gacaggaacg gtgcttgtac tagcgccaag  1680
tacgtactta agctggaagg tgagcattgg actgtcactg tgaccctggg gatgtcccct  1740
tctttgctcc ctcttgaatg tgttcagggc tgttgtgggc acaagggcgg tcttggttcc  1800
ccagatgcag tcgaggtctc cggatttgac cctgcctgcc ttgaccggct ggctgaggtg  1860
atgcacctgc ctagcagtgc tatcccagcc gctctggccg aaatgtctgg cgattccgat  1920
cgttcggctt ctccggtcac caccgtgtgg actgtttcgc agttctttgc ccgtcacagc  1980
ggagggaatc accctgacca agtgcgctta gggaaaatta tcagcctttg tcaggtgatt  2040
gaggactgct gctgttccca gaacaaaacc aaccgggtca ccccggagga ggtcgcagca  2100
aagattgacc tgtacctccg tggtgcaaca aatcttgaag aatgcttggc caggcttgag  2160 aaaagcgcgcc cgccacgcgt aatcgacacc tcctttgatt gggatgttgt gctccctggg  2220
gttgaggcgg caacccagac gatcaagctg ccccaggtca accagtgtcg tgctctggtc  2280
cctgttgtga ctcaaaagtc cttggacaac aactcggtcc cctgaccgc cttttcactg   2340 gctaactact actaccgtgc gcaaggtgac gaagttcgtc accgtgaaag actaaccgcc  2400
gtgctctcca agttggaaaa ggttgttcga gaagaatatg ggctcatgcc aaccgagcct  2460
ggtccacggc ccacactgcc acgcgggctc gacgaactca agaccagat ggaggaggac   2520 ttgctgaaac tggctaacgc ccagacgact tcggacatga tggcctgggc agtcgagcag  2580
gttgacctaa aaacttgggt caagaactac ccgcggtgga caccaccacc ccctccgcca  2640
aaagttcagc ctcgaaaaac gaagcctgtc aagagcttgc cggagagaaa gcctgtcccc  2700
gccccgcgca ggaaggttgg gtccgattgt ggcagcccgg tttcattagg cggcgatgtc  2760
cctaacagtt gggaagattt ggctgttagt agccccttg atctcccgac cccacctgag  2820
ccggcaacac cttcaagtga gctggtgatt gtgtcctcac cgcaatgcat cttcaggccg  2880
gcgacaccct tgagtgagcc ggctccaatt cccgcacctc gcggaactgt gtctcgaccg  2940
gtgacaccct tgagtgagcc gatccctgtg cccgcaccgc ggcgtaagtt tcagcaggtg  3000
aaaagattga gttcggcggc ggcaatccca ccgtaccagg acgagcccct ggatttgtct  3060
gcttcctcac agactgaata tgaggcctct cccccagcac cgccgcagag cggggggcgtt 3120
```

```
ctgggagtag aggggcatga agctgaggaa accctgagtg aaatctcgga catgtcgggt   3180
aacattaaac ctgcgtccgt gtcatcaagc agctccttgt ccagcgtgag aatcacacgc   3240
ccaaaatact cagctcaagc catcatcgac tcgggcgggc cctgcagtgg gcatctccaa   3300
gaggtaaagg aaacatgcct tagtgtcatg cgcgaggcat gtgatgcgac taagcttgat   3360
gaccctgcta cgcaggaatg gctttctcgc atgtgggatc gggtggacat gctgacttgg   3420
cgcaacacgt ctgtttacca ggcgatttgc accttagatg gcaggttaaa gttcctccca   3480
aaaatgatac tcgagacacc gccgccctat ccgtgtgagt ttgtgatgat gcctcacacg   3540
cctgcacctt ccgtaggtgc ggagagcgac cttaccattg gctcagttgc tactgaagat   3600
gttccacgca tcctcgagaa aatagaaaat gtcggcgaga tggccaacca gggacccttg   3660
gccttctccg aggataaacc ggtagatgac caacttgtca cgaccccccg gatatcgtcg   3720
cggaggcctg acgagagcac atcagctccg tccgcaggca caggtggcgc cggctctttt   3780
accgatttgc cgccttcaga tggcgcggat gcggacgggg gggggccgtt tcggacggta   3840
aaagaaaag ctgaaaggct cttttgaccaa ctgagccgtc aggttttga cctcgtctcc   3900
catctccctg ttttcttctc acgccttttc taccctggcg gtggttattc tccgggtgat   3960
tggggttttg cagcttttac tctattgtgc ctctttttat gttacagtta cccagccttt   4020
ggtattgctc ccctcttggg tgtgttttct gggtcttctc ggcgcgttcg aatgggggtt   4080
tttggctgct ggttggcttt gctgttggt ctgttcaagc ctgtgtccga cccagtcggc   4140
gctgcttgtg agtttgactc gccagagtgt agaaacatcc ttcattcttt tgagcttctc   4200
aaaccttggg accctgttcg cagccttgtt gtgggccccg tcggtctcgg tcttgccatt   4260
cttggcaggt tactgggcgg ggcacgctgc atctggcact ttttgcttag gcttggcatt   4320
gttgcagact gtatcttggc tggagcttac gtgctttctc aaggtaggtg taaaaagtgc   4380
tgggatctt gtataagaac tgctcctaat gaggtcgctt ttaacgtgtt tcctttcaca   4440
cgtgcgacca ggtcgtcact tatcgacctg tgcgatcggt tttgtgcgcc aaaaggaatg   4500
gaccccattt ttctcgccac tgggtggcgc gggtgctggg ccggccgaag ccccattgag   4560
caaccctctg aaaaacccat cgcgtttgcc caattggatg aaaagaagat tacggctagg   4620
actgtggtcg cccagcctta tgaccccaac caagccgtaa agtgcttgcg ggtattgcag   4680
tcgggtgggg cgatggtggc taaggcggtc ccaaaagtgg tcaaggtttc cgctgttcca   4740
ttccgagccc ccttctttcc cactggagtg aaagttgacc ctgattgcag ggtcgtggtt   4800
gaccctgaca ctttcactgc agctctccgg tctggctact ccaccacaaa cctcgtcctt   4860
ggtgtagggg actttgccca gctgaatgga ttaaaaatca ggcaaatttc caagccttca   4920
gggggaggcc cacatctcat ggctgccctg catgttgcct gctcgatggc tctgcacatg   4980
cttgctggga tttatgtgac tgcggtgggt tcttgcggca ccggcaccaa cgacccgtgg   5040
tgcgctaacc cgtttgccgt ccctggctac ggacctggct ctctctgcac gtccaggttg   5100
tgcatttccc aacacggcct taccctgccc ttgacagcac ttgtggcggg attcggtatt   5160
caagaaattg ccttggtcgt tttgattttt gtttccatcg gaggcatggc tcataggttg   5220
agctgtaagg ctgacatgct gtgtgttttg cttgcaattg ccagctatgt ttgggtacct   5280
cttacctggt tgctttgtgt gtttccttgc tggttgcgct gttttctttt gcaccccctc   5340
accatcctat ggttggtgtt tttcttgatt tctgtgaata tgccttcagg aatcttggcc   5400
atggtgttgt tggtttctct ttggcttctt ggtcgttata ctaatgttgc tggccttgtc   5460
accccctacg acattcatca ttacaccagt ggccccccgcg tgttgccgc cttggctacc   5520
```

```
gcaccagatg ggacctactt ggccgctgtc cgccgcgctg cgttgactgg ccgcaccatg    5580
ctgtttaccc cgtcccagct tgggtctctt cttgagggtg ctttcagaac tcgaaagccc    5640
tcactgaaca ccgtcaatgt gatcgggtcc tccatgggct ctggcggggt gtttaccatc    5700
gacgggaaag tcaagtgcgt aactgccgca catgtcctta cgggcaattc agctcgggtt    5760
tccggggtcg gcttcaatca aatgcttgac tttgacgtaa agggagattt cgctatagct    5820
gattgcccga attggcaagg ggctgccccc aagacccaat tctgcacgga tggatggact    5880
ggccgtgcct attggctaac atcctctggc gtcgaacccg cgtcattgg aaaaggattc     5940 gccttctgct tcaccgcatg tggcgattcc gggtccccag tgatcaccga ggccggtgag    6000
cttgtcggcg ttcacacggg atcgaataaa caaggggggg gcattgttac gcgcccctca    6060
ggccagtttt gtaatgtggc acccatcaag ctaagcgaat taagtgaatt ctttgctggg    6120
cctaaggtcc cgctcggtga tgtgaaggtc ggcagccaca taattaaaga cataagcgag    6180
gtgccttcag atctttgtgc cttgcttgct gccaaacctg aactggaagg aggcctctcc    6240
accgtccaac ttctttgtgt gttttttctc ctgtggagaa tgatgggaca tgcctggacg    6300
cccttggttg ctgtgagttt ctttattttg aatgaggttc tcccagccgt cctggtccgg    6360
agtgttttct cctttggaat gtttgtgcta tcctggctca cgccatggtc tgcgcaagtt    6420
ctgatgatca ggcttctgac agcagctctt aacaggaaca gatggtcact tgccttttc     6480 agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gccgcacca tatccttgtt ggcgatggag tgttctctgc ggctttcttc    6720
ttgagatact ttgccgaggg aaagttgagg gaagggtgt cgcaatcctg cggaatgaat    6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt tgctgatac cgtggcacct     7020 caactctcgc ccggtgacat tgttgtcgct ctcggccaca cgcctgttgg cagtatcttc    7080
gacctaaagg ttggtagcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc cctcccacc gaaagttctg agaatggcc caacgcttg ggggatgag       7260 gaccgtttga ataagaagaa gaggcgcagg atggaagccc tcggcatcta tgttatgggc    7320
gggaaaaagt accagaaatt tgggacaag aattccggtg atgtgtttta tgaggaggtc     7380
cataataaca cagatgagtg ggagtgtctc agagttggcg accctgccga ctttgaccct    7440
gagaagggaa ctctgtgtgg acatgtcacc attgaaaaca aggcttacca tgtttacacc    7500
tccccatctg gtaagaagtt cttggtcccc gtcaacccag agaatggaag agttcaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccacgc acttgacccg ctgtggtcgc ggcggcttgg    7740
ttgttactga aacagcggta aaaatagtca aatttcacaa ccggaccttc accctgggac    7800
ctgtgaattt aaaagtggcc agtgaggttg agctaaaaga cgcggttgag cacaaccaac    7860
acccggttgc gagaccgatc gatggtggag ttgtgctcct gcgttccgcg gttccttcgc    7920
```

```
ttatagacgt cttgatctcc ggtgctgatg catctcccaa gttacttgcc catcacgggc    7980
cgggaaacac tgggatcgat ggcacgctct gggattttga gtccgaagcc actaaagagg    8040
aagtcgcact cagtgcgcaa ataatacagg cttgtgacat taggcgcggc gacgctcctg    8100
aaattggtct cccttacaag ctgtaccctg ttagggtaa ccctgagcgg gtgaaaggag      8160
ttctgcagaa tacaaggttt ggagacatac cttacaaaac ccccagtgac actggaagcc    8220
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc accccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat ggccttctgt tcttacaaga ccagctaaag tttgaggaca     9180
tgctcaaggt tcaaccctg atcgtctatt cggacgacct cgtgctgtat gccgagtctc     9240
ccaccatgcc aaactatcac tggtgggttg aacatctgaa tttgatgctg gggtttcaga    9300
cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg gacagctgtg    9480
cttgtttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
cccctgtagg gaaaggcaca agcccttag acgaggtgct ggaacaagtc ccgtataagc      9840
ccccacggac cgttatcatg catgtggagc agggtctcac ccccttgat ccaggtagat      9900 accaaactcg ccgcggatta gtctctgtca ggcgtggaat tagggaaat gaagttggac      9960 taccagacgt tgattatgct agcaccgcct tgctccctac ctgcaaagag atcaacatgg   10020
tcgctgtcgc ttccaatgta ttgcgcagca ggttcatcat cggcccaccc ggtgctggga   10080
aaacatactg gctccttcaa caggtccagg atggtgatgt tatttacaca ccaactcacc   10140
agaccatgct tgacatgatt agggctttgg ggacgtgccg gttcaacgtc ccggcaggca   10200
caacgctgca attccccgtc ccctcccgca ccggtccgtg ggttcgcatc ctagccggcg   10260
gttggtgtcc tggcaagaat tccttcctag atgaagcagc gtattgcaat caccttgatg   10320
```

```
ttttgaggct tcttagtaaa actaccctca cctgtctagg agacttcaag caactccacc   10380
cagtgggttt tgattctcat tgctatgttt ttgacatcat gcctcaaact caactgaaga   10440
ccatctggag gtttggacag aatatctgtg atgccattca gccagattac agggacaaac   10500
tcatgtccat ggtcaacaca acccgtgtga cctacgtgga aaaacctgtc aggtatgggc   10560
aggtcctcac cccctaccac agggaccgag aggacgacgc catcactatt gactccagtc   10620
aaggcgccat attcgatgtg gttacattgc atttgcccac taagattca ctcaacaggc   10680
aaagagccct tgttgctatc accagggcaa gacacgctat cttgtgtat gacccacaca   10740
ggcagctgca gggcttgttt gatcttcctg caaaaggcac gcccgtcaac ctcgcagtgc   10800
actgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttattt ctcacctgat ttaacacagt ttgctaaact cccagtagaa cttgcacctc   11040
actggcccgt ggtgtcaacc cagaacaatg aaaagtggcc ggatcggctg gttgccagcc   11100
ttcgccctat ccataaatac agccgcgcgt gcatcggtgc cggctatatg gtgggccctt   11160
cggtgtttct aggcactcct ggggtcgtgt catactatct cacaaaattt gttaagggcg   11220
gggctcaagt gcttccggag acggttttca gcaccggccg aattgaggta gactgccggg   11280
aatatcttga tgatcgggag cgagaagttg ctgcgtccct cccacacggt ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag ccccggaaaa gccgcgaaag   11460
cattgtgcac actgacagat gtgtacctcc cagatcttga agcctatctc cacccggaga   11520
cccagtccaa gtgctggaaa atgatgttgg acttcaaaga agttcgacta atggtctgga   11580
aagacaaaac agcctatttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggggct gacctcgcgg   11760
tcaccccttta tgattacggc gctaaaatta tcctgtctag cgcgtaccat ggtgaaatgc   11820
cccccggata caaaattctg gcgtgcgcgg agttctcgtt ggatgaccca gttaagtaca   11880
aacataccctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag ttttattttc ccccgggccc tgtcattgaa ccaactttag   12060
gcctgaattg aaatgaaatg gggtccatgc aaagccttttt tgacaaaatt ggccaacttt   12120
ttgtggatgc tttcacggag ttcttggtgt ccattgttga tatcattata ttttggcca   12180
ttttgtttgg cttcaccatc gccggttggc tggtggtctt ttgcatcaga ttggtttgct   12240
ccgcgatact ccgtacgcgc cctgccattc actctgagca attacagaag atcttatgag   12300
gcctttcttt cccagtgcca agtggacatt cccacctggg gaactaaaca tcctttgggg   12360
atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct catttttcagc atctagccgc cattgaagcc   12540
gagacctgta aatatttggc ctcccggctg ccatgctac acaacctgcg catgacaggg   12600
tcaaatgtaa ccatagtgta taatagcact ttgaatcagg tgtttgctat ttttccaacc   12660
cctggttccc ggccaaagct tcatgatttt cagcaatggt taatagctgt acattcctcc   12720
```

```
atattttcct ctgttgcagc ttcttgtact ctttttgttg tgctgtggtt gcgggttcca    12780
atactacgta ctgtttttgg tttccgctgg ttagggcaa ttttctttc gaactcacag     12840 tgaattacac ggtgtgtcca ccttgcctca cccggcaagc agccacagag atctacgaac    12900
ccggtaggtc tctttggtgc aggatagggt atgaccgatg tggggaggac gatcatgacg    12960
agctagggtt tatgataccg cctggcctct ccagcgaagg ccacttgact ggtgtttacg    13020
cctggttggc gttcttgtcc ttcagctaca cggcccagtt ccatcccgag atattcggga    13080
tagggaatgt gagtcgagtt tatgttgaca tcaaacatca actcatctgc gccgaacatg    13140
acgggcagaa caccaccttg cctcgtcatg acaacatttc agccgtgttt cagacctatt    13200
accaacatca agtcgacggc ggcaattggt ttcacctaga atggcttcgt cccttctttt    13260
cctcgtggtt ggttttaaat gtctcttggt ttctcaggcg ttcgcctgca aaccatgttt    13320
cagttcgagt cttgcagata ttaagaccaa caccaccgca gcggcaagct ttgctgtcct    13380
ccaagacatc agttgcctta ggcatcgcga ctcggcctct gaggcgattc gcaaaatccc    13440
tcagtgccgt acggcgatag ggacacccgt gtatgttacc atcacagcca atgtgacaga    13500
tgagaattat ttacattctt ctgatctcct catgctttct tcttgccttt tctatgcttc    13560
tgagatgagt gaaaagggat ttaaggtggt atttggcaat gtgtcaggca tcgtggctgt    13620
gtgtgtcaat tttaccagct acgtccaaca tgtcaaggag tttacccaac gctccctggt    13680
ggtcgaccat gtgcggttgc tccatttcat gacacctgag accatgaggt gggcaactgt    13740
tttagcctgt cttttttgcca ttctgttggc aatttgaatg tttaagtatg ttggagaaat    13800
gcttgaccgc gggctgttgc tcgcgattgc tttctttgtg gtgtatcgtg ccgttctgtt    13860
ttgctgtgct cgccaacgcc agcaacgaca gcagctccca tctacagctg atttacaact    13920
tgacgctatg tgagctgaat ggcacagatt ggctagctaa caaatttgat tgggcagtgg    13980
agagttttgt catctttccc gttttgactc acattgtctc ctatggtgcc ctcactacca    14040
gccatttcct tgacacagtc gctttagtca ctgtgtctac cgccgggttt gttcacgggc    14100
ggtatgtcct aagtagcatc tacgcggtct gtgccctggc tgcgttgact tgcttcgtca    14160 ttaggttttgc aaagaattgc atgtcctggc gctacgcgtg taccagatat accaactttc    14220
ttctggacac taagggcaga ctctatcgtt ggcggtcgcc tgtcatcata gagaaaggg    14280 gcaaagttga ggtcgaaggt catctgatcg acctcaaaag agttgtgctt gatggttccg    14340
tggcaacccc tataaccaga gtttcagcgg aacaatgggg tcgtccttag atgacttctg    14400
tcatgatagc acggctccac aaaaggtgct tttggcgttt tctattacct acacgccagt    14460
gatgatatat gccctaaagg tgagtcgcgg ccgactgcta gggcttctgc accttttgat    14520
cttcctgaat tgtgctttca ccttcgggta catgactttc gcgcacttc agagtacaaa    14580 taaggtcgcg ctcactatgg gagcagtagt tgcactcctt tgggggtgt actcagccat    14640 agaaacctgg aaattcatca cctccagatg ccgtttgtgc ttgctaggcc gcaagtacat    14700
tctggcccct gcccaccacg ttgaaagtgc cgcacggttt catccgattg cggcaaatga    14760
taaccacgca tttgtcgtcc ggcgtccgg ctccactacg gtcaacggca cattggtgcc    14820
cgggttaaaa agcctcgtgt tgggtggcag aaaagctgtt aaacagggag tggtaaacct    14880
tgtcaaatat gccaaataac aacggcaagc agcagaagag aaagaagggg gatggccagc    14940
cagtcaatca gctgtgccag atgctgggta agatcatcgc tcagcaaaac cagtccagag    15000
gcaagggacc gggaaagaaa aataagaaga aaaacccgga gaagcccccat tttcctctag    15060 cgactgaaga tgatgtcaga catcacttta cccctagtga gcggcaattg tgtctgtcgt    15120
```

```
caatccagac cgcctttaat caaggcgctg ggacttgcac cctgtcagat tcagggagga    15180
taagttacac tgtggagttt agtttgccta cgcatcatac tgtgcgcctg atccgcgtca    15240
cagcatcacc ctcagcatga tgggctggca ttcttgaggc atctcagtgt ttgaattgga    15300
agaatgtgtg gtgaatggca ctgattgaca ttgtgcctct aagtcaccta ttcaattagg    15360
gcgaccgtgt gggggtgaga tttaattggc gagaaccatg cggccgaaat t             15411

<210> SEQ ID NO 16
<211> LENGTH: 17
<212> TYPE: DNA
<213> ORGANISM: Artificial Sequence
<220> FEATURE:
<223> OTHER INFORMATION: Synthetic Promoter

<400> SEQUENCE: 16
taatacgact cactata                                                      17

<210> SEQ ID NO 17
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 17

Glu Gln Lys Leu Ile Ser Glu Glu Asp Leu
1               5                   10

<210> SEQ ID NO 18
<211> LENGTH: 61
<212> TYPE: DNA
<213> ORGANISM: Artificial Sequence
<220> FEATURE:
<223> OTHER INFORMATION: Synthetic Primer

<400> SEQUENCE: 18
acatgcatgc ttaatacgac tcactatagt atgacgtata ggtgttggct ctatgccttg      60
g                                                                       61

<210> SEQ ID NO 19
<211> LENGTH: 19
<212> TYPE: DNA
<213> ORGANISM: Artificial Sequence
<220> FEATURE:
<223> OTHER INFORMATION: Synthetic Primer

<400> SEQUENCE: 19
ctgggcgacc acagtccta                                                    19

<210> SEQ ID NO 20
<211> LENGTH: 25
<212> TYPE: DNA
<213> ORGANISM: Artificial Sequence
<220> FEATURE:
<223> OTHER INFORMATION: Synthetic Primer

<400> SEQUENCE: 20
cttctcggcg cgcccgaatg ggagt                                             25

<210> SEQ ID NO 21
<211> LENGTH: 26
<212> TYPE: DNA
<213> ORGANISM: Artificial Sequence
<220> FEATURE:
<223> OTHER INFORMATION: Synthetic Primer
```

```
<400> SEQUENCE: 21
tcatcatacc tagggcctgc tccacg                                              26

<210> SEQ ID NO 22
<211> LENGTH: 26
<212> TYPE: DNA
<213> ORGANISM: Artificial Sequence
<220> FEATURE:
<223> OTHER INFORMATION: Synthetic Primer

<400> SEQUENCE: 22
cgtggagcag gccctaggta tgatga                                              26

<210> SEQ ID NO 23
<211> LENGTH: 18
<212> TYPE: DNA
<213> ORGANISM: Artificial Sequence
<220> FEATURE:
<223> OTHER INFORMATION: Synthetic Primer

<400> SEQUENCE: 23
tgcaggcgaa cgcctgag                                                       18

<210> SEQ ID NO 24
<211> LENGTH: 21
<212> TYPE: DNA
<213> ORGANISM: Artificial Sequence
<220> FEATURE:
<223> OTHER INFORMATION: Synthetic Primer

<400> SEQUENCE: 24
gtgaggactg ggaggattac a                                                   21

<210> SEQ ID NO 25
<211> LENGTH: 53
<212> TYPE: DNA
<213> ORGANISM: Artificial Sequence
<220> FEATURE:
<223> OTHER INFORMATION: Synthetic Primer

<400> SEQUENCE: 25
gtctttaatt aactagtttt tttttttttt tttttttttt tttttttaatt tcg               53

<210> SEQ ID NO 26
<211> LENGTH: 27
<212> TYPE: DNA
<213> ORGANISM: Artificial Sequence
<220> FEATURE:
<223> OTHER INFORMATION: Synthetic Primer

<400> SEQUENCE: 26
gatgcatgcc attaattaag ggtcggc                                             27

<210> SEQ ID NO 27
<211> LENGTH: 27
<212> TYPE: DNA
<213> ORGANISM: Artificial Sequence
<220> FEATURE:
<223> OTHER INFORMATION: Synthetic Primer

<400> SEQUENCE: 27
gccgaccctt aattaatggc atgcatc                                             27

<210> SEQ ID NO 28
<211> LENGTH: 36
```

```
<212> TYPE: DNA
<213> ORGANISM: Artificial Sequence
<220> FEATURE:
<223> OTHER INFORMATION: Synthetic Primer

<400> SEQUENCE: 28
acatgcatgc ttaatacgac tcactatagg tatgac                                36

<210> SEQ ID NO 29
<211> LENGTH: 25
<212> TYPE: DNA
<213> ORGANISM: Artificial Sequence
<220> FEATURE:
<223> OTHER INFORMATION: Synthetic Primer

<400> SEQUENCE: 29
ctgtgtggac atgtcaccat tgaaa                                            25

<210> SEQ ID NO 30
<211> LENGTH: 25
<212> TYPE: DNA
<213> ORGANISM: Artificial Sequence
<220> FEATURE:
<223> OTHER INFORMATION: Synthetic Primer

<400> SEQUENCE: 30
gtgtatcgtg ccgttctgtt ttgct                                            25

<210> SEQ ID NO 31
<211> LENGTH: 25
<212> TYPE: DNA
<213> ORGANISM: Artificial Sequence
<220> FEATURE:
<223> OTHER INFORMATION: Synthetic Primer

<400> SEQUENCE: 31
cagatgctgg gtaagatcat cgctc                                            25

<210> SEQ ID NO 32
<211> LENGTH: 39
<212> TYPE: DNA
<213> ORGANISM: Artificial Sequence
<220> FEATURE:
<223> OTHER INFORMATION: Synthetic Primer

<400> SEQUENCE: 32
gcacaatgtc aatcagtgcc attcaccaca cattcttcc                             39

<210> SEQ ID NO 33
<211> LENGTH: 41
<212> TYPE: DNA
<213> ORGANISM: Artificial Sequence
<220> FEATURE:
<223> OTHER INFORMATION: Synthetic Primer

<400> SEQUENCE: 33
tagacttggc cctccgccat aaacaccctg gcattggggg t                          41

<210> SEQ ID NO 34
<211> LENGTH: 201
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENC

```
Met Arg Cys Ser Tyr Lys Leu Gly Arg Ser Leu Ile Leu His Ser Cys
1               5                   10                  15

Ser Trp Trp Phe Phe Leu Leu Cys Thr Gly Leu Ser Trp Ser Phe Ala
                20                  25                  30

Asp Gly Asn Gly Asn Asn Ser Thr Tyr Gln Tyr Ile Tyr Asn Leu Thr
            35                  40                  45

Ile Cys Glu Leu Asn Gly Thr Asn Trp Leu Ser Gly His Phe Asp Trp
    50                  55                  60

Ala Val Glu Thr Phe Val Leu Tyr Pro Val Val Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Ile Asp Gly Arg Tyr Val Leu Ser Ser
                100                 105                 110

Ile Tyr Gly Ala Cys Ala Phe Ala Ala Phe Val Cys Phe Val Ile Arg
            115                 120                 125

Ala Ala Lys Asn Cys Met Ala Cys Arg Tyr Ala Arg Thr Arg Phe Thr
130                 135                 140

Asn Phe Ile Val Asp Asp Arg Gly Gly Val His Arg Trp Lys Ser Pro
145                 150                 155                 160

Ile Val Val Glu Lys Leu Gly Lys Ala Asp Ile Asp Gly Ser Leu Val
            165                 170                 175

Thr Ile Lys His Val Val Leu Glu Gly Val Lys Ala Gln Pro Leu Thr
                180                 185                 190

Arg Thr Ser Ala Glu Gln Trp Glu Ala
            195                 200

<210> SEQ ID NO 35
<211> LENGTH: 201
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 35

Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
                20                  25                  30

Asp Gly Asn Gly Asp Ser Ser Thr Tyr Gln Tyr Ile Tyr Asn Leu Thr
            35                  40                  45

Ile Cys Glu Leu Asn Gly Thr Asp Trp Leu Ser Ser His Phe Gly Trp
    50                  55                  60

Ala Val Glu Thr Phe Val Leu Tyr Pro Val Ala Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Val Gly Gly Arg Tyr Val Leu Cys Ser
                100                 105                 110

Val Tyr Gly Ala Cys Ala Phe Ala Ala Phe Val Cys Phe Val Ile Arg
            115                 120                 125

Ala Ala Lys Asn Cys Met Ala Cys Arg Tyr Ala Arg Thr Arg Phe Thr
130                 135                 140

Asn Phe Ile Val Asp Asp Arg Gly Arg Val His Arg Trp Lys Ser Pro
145                 150                 155                 160
```

```
Ile Val Val Glu Lys Leu Gly Lys Ala Glu Val Asp Gly Asn Leu Val
            165                 170                 175

Thr Ile Lys His Val Val Leu Glu Gly Val Lys Ala Gln Pro Leu Thr
        180                 185                 190

Arg Thr Ser Ala Glu Gln Trp Glu Ala
        195                 200

<210> SEQ ID NO 36
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)
<220> FEATURE:
<221> NAME/KEY: MISC_FEATURE
<222> LOCATION: (44)..(44)
<223> OTHER INFORMATION: X = Xaa
<220> FEATURE:
<221> NAME/KEY: MISC_FEATURE
<222> LOCATION: (44)..(44)
<223> OTHER INFORMATION: Xaa = variable or unknown amino acid

<400> SEQUENCE: 36

Met Leu Gly Lys Cys Leu Thr Ala Gly Tyr Cys Ser Gln Leu Leu Phe
1               5                   10                  15

Leu Trp Cys Ile Val Pro Phe Cys Leu Ala Ala Leu Val Asn Ala Asp
            20                  25                  30

Ser Asn Ser Ser Ser His Leu Gln Leu Ile Tyr Xaa Leu Thr Ile Cys
        35                  40                  45

Glu Leu Asn Gly Thr Asp Trp Leu Asn Asn His Phe Ser Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Leu Leu Asp Thr Val Gly Leu Ile Thr Val
            85                  90                  95

Ser Thr Ala Gly Tyr Cys His Lys Arg Tyr Val Leu Ser Ser Ile Tyr
        100                 105                 110

Ala Val Cys Ala Leu Ala Ala Leu Ile Cys Phe Val Ile Arg Leu Thr
    115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Ile Glu Val Gly Gly Asp Leu Ile Asp Leu
            165                 170                 175

Lys Arg Val Val Leu Asp Gly Ser Ala Ala Thr Pro Val Thr Lys Val
        180                 185                 190

Ser Ala Glu Gln Trp Gly Arg Pro
        195                 200

<210> SEQ ID NO 37
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 37

Met Leu Gly Lys Cys Leu Thr Ala Gly Tyr Cys Ser Gln Leu Pro Phe
1               5                   10                  15
```

Leu Trp Cys Ile Val Pro Phe Cys Leu Ala Ala Leu Val Asn Ala Ser
            20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Asp His Phe Ser Trp Ala Val
 50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Ile Thr Val
                85                  90                  95

Ser Thr Ala Gly Tyr Tyr His Ala Arg Tyr Val Leu Ser Ser Ile Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Ile Glu Val Gly Gly Asp Leu Ile Asp Leu
                165                 170                 175

Lys Arg Val Val Leu Asp Gly Ser Ala Ala Thr Pro Val Thr Lys Val
            180                 185                 190

Ser Ala Glu Gln Trp Gly Arg Pro
        195                 200

<210> SEQ ID NO 38
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 38

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
            20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Asp Lys Phe Asp Trp Ala Val
 50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Tyr Tyr His Gly Arg Tyr Val Leu Ser Ser Ile Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

```
Lys Arg Val Val Leu Asp Gly Ser Ala Ala Thr Pro Val Thr Lys Val
            180                 185                 190

Ser Ala Glu Arg Trp Gly Arg Pro
        195                 200

<210> SEQ ID NO 39
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 39

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asp Ala Ser
            20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Lys Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Tyr Tyr His Gly Arg Tyr Val Leu Ser Ser Ile Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Ala Ala Thr Pro Val Thr Lys Val
            180                 185                 190

Ser Ala Glu Arg Trp Gly Arg Pro
        195                 200

<210> SEQ ID NO 40
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 40

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Gly
            20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Asp Lys Phe Asp Trp Ala Val
50                  55                  60
```

```
Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Tyr Tyr His Arg Arg Tyr Val Leu Ser Ser Ile Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Ala Ala Thr Pro Val Thr Lys Val
                180                 185                 190

Ser Ala Glu Arg Trp Gly Arg Pro
            195                 200

<210> SEQ ID NO 41
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 41

Met Leu Gly Lys Cys Leu Thr Ala Gly Cys Cys Ser Gln Leu Pro Phe
  1               5                  10                  15

Leu Trp Cys Ile Val Pro Phe Cys Phe Val Ala Leu Val Asn Ala Asn
                 20                  25                  30

Thr Asp Ser Ser Ser His Leu Gln Leu Ile Tyr Asn Leu Thr Ile Cys
            35                  40                  45

Glu Leu Asn Gly Thr Asp Trp Leu Asn Asp Lys Phe Asp Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Ile Thr Val
                 85                  90                  95

Ser Thr Ala Gly Tyr Tyr His Gly Arg Tyr Val Leu Ser Ser Ile Tyr
            100                 105                 110

Ala Val Cys Ala Leu Ala Ala Leu Ile Cys Phe Ala Ile Arg Leu Thr
        115                 120                 125

Lys Asn Cys Met Ser Trp Arg Tyr Ser Cys Thr Arg Tyr Thr Asn Phe
130                 135                 140

Leu Leu Asp Thr Lys Gly Lys Leu Tyr Arg Trp Arg Ser Pro Val Ile
145                 150                 155                 160

Ile Glu Arg Gln Gly Lys Val Glu Val Glu Gly His Leu Ile Asp Leu
                165                 170                 175

Lys Arg Val Val Leu Asp Gly Ser Ala Ala Thr Pro Val Thr Arg Val
                180                 185                 190

Ser Ala Glu Arg Trp Gly Arg Pro
            195                 200

<210> SEQ ID NO 42
<211> LENGTH: 200
```

<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 42

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
            20                  25                  30

Ser Ser Ser Ser Ser Gln Leu Gln Ser Ile Tyr Asn Leu Thr Ile Cys
        35                  40                  45

Glu Leu Asn Gly Thr Asp Trp Leu Asn Lys Asn Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Ala Val Gly Leu Ile Thr Val
                85                  90                  95

Ser Thr Ala Gly Tyr Tyr His Gly Arg Tyr Val Leu Ser Ser Val Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
    130                 135                 140

Leu Leu Asp Ser Lys Gly Lys Leu Tyr Arg Trp Arg Ser Pro Val Ile
145                 150                 155                 160

Ile Glu Lys Gly Gly Lys Val Glu Val Asp Gly His Leu Ile Asp Leu
                165                 170                 175

Lys Arg Val Val Leu Asp Gly Ser Ala Ala Thr Pro Val Thr Lys Val
            180                 185                 190

Ser Ala Glu Gln Trp Cys Arg Pro
        195                 200

<210> SEQ ID NO 43
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 43

Met Leu Glu Lys Cys Leu Thr Ala Gly Cys Cys Ser Gln Leu Leu Ser
1               5                   10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala

```
                115             120                 125

Lys Asn Cys Met Ser Trp Arg Tyr Ala Cys Thr Arg Tyr Thr Asn Phe
        130                 135                 140

Leu Leu Asp Thr Lys Gly Gly Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
                180                 185                 190

Ser Ala Glu Gln Trp Gly Arg Pro
        195                 200

<210> SEQ ID NO 44
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 44

Met Leu Glu Lys Cys Leu Thr Ala Gly Cys Cys Ser Gln Leu Leu Ser
1               5                   10                  15

Leu Trp Cys Ile Val Pro Phe Cys Phe Ala Ala Leu Ala Asn Ala Ser
                20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Cys Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
        130                 135                 140

Leu Leu Asp Thr Lys Gly Gly Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
                180                 185                 190

Ser Ala Glu Gln Trp Gly Arg Pro
        195                 200

<210> SEQ ID NO 45
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 45

Met Leu Glu Lys Cys Leu Thr Ala Gly Cys Cys Ser Arg Leu Leu Ser
1               5                   10                  15
```

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
         35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 46
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 46

Met Leu Glu Lys Cys Leu Thr Ala Gly Cys Cys Ser Gln Leu Leu Ser
1               5                  10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
         35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

```
Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 47
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 47

Met Leu Glu Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
            20                  25                  30

Asn Ser Ser Ser His Leu Gln Leu Ile Tyr Asn Leu Thr Leu Cys
            35                  40                  45

Glu Leu Asn Gly Thr Asp Trp Leu Ala Asn Arg Phe Asp Trp Ala Val
50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
            85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
            115                 120                 125

Lys Asn Cys Met Ser Trp Arg Tyr Ala Cys Thr Arg Tyr Thr Asn Phe
            130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 48
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 48

Met Leu Glu Lys Cys Leu Thr Ala Gly Cys Cys Ser Gln Leu Leu Ser
1               5                   10                  15

Leu Trp Cys Ile Val Pro Phe Cys Phe Val Ala Leu Ala Asn Ala Asn
            20                  25                  30

Asn Asp Ser Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
50                  55                  60
```

```
Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
                100                 105                 110

Ala Ala Cys Ala Leu Ala Ala Leu Thr Cys Phe Val Ile Arg Leu Ala
            115                 120                 125

Lys Asn Cys Met Ser Trp Arg Tyr Ala Cys Thr Arg Tyr Thr Asn Phe
        130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
            195                 200

<210> SEQ ID NO 49
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 49

Met Leu Gly Lys Cys Leu Thr Ala Gly Trp Cys Ser Gln Leu Leu Ser
  1               5                  10                  15

Leu Gly Cys Ile Val Pro Ph

```
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 50

Met Leu Gly Arg Cys Leu Thr Ala Gly Cys Cys Ser Arg Leu Leu Ser
1               5                   10                  15

Leu Trp Cys Ile Val Pro Phe Cys Phe Ala Ala Leu Val Asn Ala Asn
                20                  25                  30

Ser Asn Ser Ser Ser His Leu Gln Leu Ile Tyr Asn Leu Thr Leu Cys
            35                  40                  45

Glu Leu Asn Gly Thr Asp Trp Leu Lys Asp Lys Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 51
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 51

Met Leu Gly Lys Cys Leu Thr Thr Gly Cys Cys Ser Arg Leu Leu Ser
1               5                   10                  15

Leu Trp Cys Ile Val Pro Phe Cys Phe Ala Val Leu Val Asn Ala Asn
                20                  25                  30

Ser Asn Ser Ser Ser His Phe Gln Leu Ile Tyr Asn Leu Thr Leu Cys
            35                  40                  45

Glu Leu Asn Gly Thr Asp Trp Leu Ala Asn Lys Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
```

```
                115                 120                 125
Lys Asn Cys Met Ser Trp Arg Tyr Ser Cys Thr Arg Tyr Thr Asn Phe
        130                 135                 140

Leu Leu Asp Thr Lys Gly Arg Leu Tyr Arg Trp Arg Ser Pro Val Ile
145                 150                 155                 160

Val Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 52
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 52

Met Leu Gly Lys Cys Leu Thr Ala Gly Cys Cys Ser Arg Leu Leu Ser
1               5                   10                  15

Leu Trp Cys Ile Val Pro Phe Cys Phe Ala Val Leu Gly Ser Ala Asn
            20                  25                  30

Ser Ser Ser Ser Ser His Phe Gln Leu Ile Tyr Asn Leu Thr Leu Cys
        35                  40                  45

Glu Leu Asn Gly Thr Asp Trp Leu Ala Glu Lys Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 53
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 53

Met Leu Gly Lys Cys Leu Thr Ala Gly Cys Cys Ser Arg Leu Leu Ser
1               5                   10                  15
```

```
Phe Trp Cys Ile Val Pro Phe Cys Phe Ala Val Leu Val Asn Ala Ser
            20                  25                  30

Tyr Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
                100                 105                 110

Ala Val Cys Ala Leu Ala Ala Leu Ile Cys Phe Val Ile Arg Leu Ala
                115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Ser His Leu Ile Asp Leu
                165                 170                 175

Lys Arg Val Val Leu Asp Gly Ser Ala Ala Thr Pro Leu Thr Arg Val
                180                 185                 190

Ser Ala Glu Gln Trp Gly Arg Pro
                195                 200

<210> SEQ ID NO 54
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 54

Met Leu Gly Lys Cys Leu Thr Ala Gly Cys Tyr Ser Gln Leu Leu Ser
1               5                   10                  15

Leu Trp Cys Ile Val Pro Phe Cys Phe Ala Val Leu Val Asn Ala Ser
            20                  25                  30

Ser Asn Ser Ser Pro His Phe Gln Leu Ile Tyr Asn Leu Thr Leu Cys
        35                  40                  45

Glu Leu Asn Gly Thr Asp Trp Leu Ala Glu Arg Phe Asp Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Ile Thr Val
                85                  90                  95

Ser Thr Ala Gly Phe Tyr His Arg Arg Tyr Val Leu Ser Ser Ile Tyr
                100                 105                 110

Ala Val Cys Ala Leu Ala Ala Leu Ile Cys Phe Val Ile Arg Leu Ala
                115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Pro Pro Val Ile
145                 150                 155                 160

Val Glu Lys Gly Gly Lys Val Glu Val Glu Gly His Leu Ile Asp Leu
                165                 170                 175
```

```
Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 55
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 55

Met Leu Gly Lys Cys Leu Thr Ala Gly Cys Cys Ser Arg Leu Leu Ser
1               5                   10                  15

Leu Trp Cys Ile Val Pro Phe Tyr Leu Ala Val Leu Val Asn Ala Ser
            20                  25                  30

Asn Asn Ser Ser Ser His Ile Gln Leu Ile Tyr Asn Leu Thr Leu Cys
        35                  40                  45

Glu Leu Asn Gly Thr Asp Trp Leu Ala Lys Asn Phe Asn Arg Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Tyr Tyr His Arg Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
130                 135                 140

Leu Leu Asp Thr Lys Gly Lys Leu Tyr Arg Trp Arg Ser Pro Val Ile
145                 150                 155                 160

Val Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 56
<211> LENGTH: 219
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 56

Gln Ala Cys Arg Gln Pro Phe Cys Pro Phe Glu Glu Ala His Ser Gly
1               5                   10                  15

Val Tyr Arg Trp Lys Lys Phe Val Ile Phe Ser Asp Ser Pro Leu Asn
            20                  25                  30

Gly Gln Ser Arg Ile Met Trp Thr Pro Lys Ser Asp Asp Ser Ala Ala
        35                  40                  45

Leu Glu Glu Leu Pro Pro Glu Leu Glu Arg Gln Val Glu Ile Leu Ile
50                  55                  60
```

```
Arg Ser Phe Pro Ala His His Pro Val Asn Leu Ala Asp Trp Glu Leu
 65                  70                  75                  80

Thr Gly Ser Pro Glu Asn Gly Phe Ser Phe Asn Thr Ser His Ser Cys
                 85                  90                  95

Gly His Leu Val Arg Asn Ser Asn Val Phe Asp Gly Lys Cys Trp Leu
            100                 105                 110

Thr Cys Phe Leu Gly Gln Ser Val Glu Val Arg Cys His Glu Glu His
        115                 120                 125

Leu Ala Asn Ala Phe Gly Tyr Gln Thr Lys Trp Gly Val His Gly Lys
    130                 135                 140

Tyr Leu Gln Arg Arg Leu Gln Val Arg Gly Ile Arg Ala Val Val Asp
145                 150                 155                 160

Pro Asp Gly Pro Ile His Val Glu Ala Leu Ser Cys Ser Gln Ser Trp
                165                 170                 175

Ile Arg His Leu Thr Leu Asn Asp Asp Val Thr Pro Gly Phe Val Arg
            180                 185                 190

Leu Thr Ser Ile Arg Ile Val Pro Asn Thr Glu Pro Thr Thr Ser Gln
        195                 200                 205

Ile Phe Arg Phe Gly Ala His Lys Trp Tyr Gly
    210                 215

<210> SEQ ID NO 57
<211> LENGTH: 219
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 57

Gln Ala Cys Arg Gln Pro Phe Cys Pro Phe Glu Glu Ala His Ser Ser
 1               5                  10                  15

Val Tyr Arg Trp Lys Lys Phe Val Phe Thr Asp Ser Ser Leu Asn
                 20                  25                  30

Gly Arg Ser Arg Met Met Trp Thr Pro Glu Ser Asp Asp Ser Ala Ala
             35                  40                  45

Leu Glu Val Leu Pro Pro Glu Leu Glu Arg Gln Val Glu Ile Leu Ile
 50                  55                  60

Arg Ser Phe Pro Ala His His Pro Val Asp Leu Ala Asp Trp Glu Leu
 65                  70                  75                  80

Thr Glu Ser Pro Glu Asn Gly Phe Ser Phe Asn Thr Ser His Ser Cys
                 85                  90                  95

Gly His Leu Val Gln Asn Pro Asp Val Phe Asp Gly Lys Cys Trp Leu
            100                 105                 110

Ser Cys Phe Leu Gly Gln Ser Val Glu Val Arg Cys His Glu Glu His
        115                 120                 125

Leu Ala Asp Ala Phe Gly Tyr Gln Thr Lys Trp Gly Val His Gly Lys
    130                 135                 140

Tyr Leu Gln Arg Arg Leu Gln Val Arg Gly Ile Arg Ala Val Val Asp
145                 150                 155                 160

Pro Asp Gly Pro Ile His Val Glu Ala Leu Ser Cys Pro Gln Ser Trp
                165                 170                 175

Ile Arg His Leu Thr Leu Asp Asp Val Thr Pro Gly Phe Val Arg
            180                 185                 190

Leu Thr Ser Leu Arg Ile Val Pro Asn Thr Glu Pro Thr Thr Ser Arg
        195                 200                 205
```

```
Ile Phe Arg Phe Gly Ala His Lys Trp Tyr Gly
    210                 215
```

<210> SEQ ID NO 58
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta
<220> FEATURE:
<221> NAME/KEY: MOD_RES
<222> LOCATION: (16)..(16)
<223> OTHER INFORMATION: Xaa = variable or unknown amino acid

<400> SEQUENCE: 58

```
Arg Pro Lys Pro Glu Asp Phe Cys Pro Phe Glu Cys Ala Met Ala Xaa
1               5                   10                  15

Val Tyr Asp Ile Gly His Asp Ala Val Met Phe Val Ala Glu Gly Arg
            20                  25                  30

Val Ser Trp Ala Pro Arg Gly Gly Lys Gly Lys Phe Glu Thr Val
        35                  40                  45

Pro Glu Glu Leu Arg Leu Ile Ala Glu Gln Leu Tyr Thr Ser Phe Pro
    50                  55                  60

Pro His His Val Val Asp Met Ser Lys Phe Thr Phe Thr Ala Pro Glu
65                  70                  75                  80

Cys Gly Ala Ser Met Arg Val Glu Arg His Tyr Gly Cys Leu Pro Ala
                85                  90                  95

Gly Thr Val Pro Asp Gly Asn Cys Trp Trp Ser Leu Phe Ser Ser Leu
            100                 105                 110

Pro Leu Glu Ile Gln Tyr Lys Glu Ile Arg His Ala Thr Gln Phe Gly
        115                 120                 125

Tyr Gln Thr Lys His Gly Val Ala Gly Lys Tyr Leu Gln Arg Arg Leu
    130                 135                 140

Gln Val Asn Gly Leu Arg Ala Val Val Asp Ser Asn Gly Pro Ile Val
145                 150                 155                 160

Ile Gln Tyr Phe Ser Val Lys Glu Ser Trp Ile Arg His Val Lys Leu
                165                 170                 175

Ala Glu Glu Phe Asp Tyr Pro Gly Phe Glu Asp Leu Leu Arg Ile Arg
            180                 185                 190

Val Glu Pro Asn Thr Leu Pro Leu Ser Asn Lys Asp Glu Lys Ile Phe
        195                 200                 205

Arg Phe Gly Gly Cys Lys Trp Tyr Gly
    210                 215
```

<210> SEQ ID NO 59
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta
<220> FEATURE:
<221> NAME/KEY: MOD_RES
<222> LOCATION: (53)..(53)
<223> OTHER INFORMATION: Xaa = variable or unknown amino acid
<220> FEATURE:
<221> NAME/KEY: MOD_RES
<222> LOCATION: (198)..(198)
<223> OTHER INFORMATION: Xaa = variable or unknown amino acid

<400> SEQUENCE: 59

```
Arg Pro Lys Pro Glu Asp Phe Cys Pro Phe Glu Cys Ala Met Ala Ala
```

```
                1               5                  10                 15
Val Tyr Asp Ile Gly His Asp Ala Val Met Phe Val Ala Glu Gly Arg
                20                  25                 30

Val Ser Trp Ala Pro Arg Gly Gly Glu Lys Gly Lys Phe Glu Thr Val
                35                  40                 45

Pro Glu Glu Leu Xaa Leu Ile Ala Glu Gln Leu Tyr Thr Ser Phe Pro
            50                  55                 60

Pro His His Leu Val Asp Met Ser Lys Phe Thr Phe Thr Ala Pro Glu
65                  70                  75                 80

Cys Gly Ala Ser Met Arg Val Glu Arg Gln Tyr Gly Cys Leu Pro Ala
                85                  90                 95

Gly Thr Val Pro Asp Gly Asn Cys Trp Trp Ser Leu Phe Ser Ser Leu
                100                 105                110

Pro Leu Glu Val Gln Tyr Lys Glu Ile Arg Tyr Ala Thr Gln Phe Gly
            115                 120                125

Tyr Gln Thr Lys His Gly Val Ala Gly Lys Tyr Leu Gln Arg Arg Leu
            130                 135                140

Gln Ile Asn Gly Leu Arg Ala Val Val Asp Ser Asn Gly Pro Ile Val
145                 150                 155                160

Ile Gln Tyr Phe Ser Val Lys Glu Ser Trp Ile Arg His Val Lys Leu
                165                 170                175

Ala Glu Glu Phe Asp Tyr Pro Gly Phe Glu Asp Leu Leu Arg Ile Arg
                180                 185                190

Val Glu Pro Asn Thr Xaa Pro Leu Ser Asn Lys Asp Glu Lys Ile Phe
            195                 200                205

Arg Phe Gly Gly Cys Lys Trp Tyr Gly
            210                 215

<210> SEQ ID NO 60
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 60

Arg Pro Lys Pro Glu Asp Phe Cys Pro Phe Glu Cys Ala Met Ala Thr
1               5                   10                 15

Val Tyr Asp Ile Gly His Asp Ala Val Met Tyr Val Ala Glu Arg Lys
                20                  25                 30

Ile Ser Trp Ala Pro Arg Gly Gly Asp Glu Val Lys Phe Glu Ala Val
                35                  40                 45

Pro Gly Glu Leu Lys Leu Ile Ala Asn Arg Leu Arg Thr Ser Phe Pro
            50                  55                 60

Pro His His Thr Val Asp Met Ser Lys Phe Ala Phe Thr Ala Pro Gly
65                  70                  75                 80

Cys Gly Val Ser Met Arg Val Glu Arg Gln His Gly Cys Leu Pro Ala
                85                  90                 95

Asp Thr Val Pro Glu Gly Asn Cys Trp Trp Ser Leu Phe Asp Leu Leu
                100                 105                110

Pro Leu Glu Val Gln Asn Lys Glu Ile Arg His Ala Asn Gln Phe Gly
            115                 120                125

Tyr Gln Thr Lys His Gly Val Ser Gly Lys Tyr Leu Gln Arg Arg Leu
            130                 135                140

Gln Val Asn Gly Leu Arg Ala Val Thr Asp Leu Asn Gly Pro Ile Val
```

```
                145                 150                 155                 160
Val Gln Tyr Phe Phe Val Lys Glu Ser Trp Ile Arg His Leu Lys Leu
                165                 170                 175

Ala Gly Glu Pro Ser Tyr Ser Gly Phe Glu Asp Leu Leu Arg Ile Arg
            180                 185                 190

Val Glu Pro Asn Thr Ser Pro Leu Ala Asp Lys Glu Glu Lys Ile Phe
        195                 200                 205

Arg Phe Gly Ser His Lys Trp Tyr Gly
    210                 215

<210> SEQ ID NO 61
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 61

Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Glu Arg Lys
            20                  25                  30

Val Ser Trp Ala Pro Arg Gly Gly Asp Glu Val Lys Phe Glu Ala Val
        35                  40                  45

Pro Gly Glu Leu Lys Leu Ile Ala Asn Arg Leu Arg Thr Ser Phe Pro
    50                  55                  60

Pro His His Thr Val Asp Met Ser Lys Phe Ala Phe Thr Ala Pro Gly
65                  70                  75                  80

Cys Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asp Leu Leu
            100                 105                 110

Pro Leu Glu Val Gln Asn Lys Glu Ile Arg His Ala Asn Gln Phe Gly
        115                 120                 125

Tyr Gln Thr Lys His Gly Val Ser Gly Lys Tyr Leu Gln Arg Arg Leu
    130                 135                 140

Gln Val Asn Gly Leu Arg Ala Val Thr Asp Leu Asn Gly Pro Ile Val
145                 150                 155                 160

Val Gln Tyr Phe Ser Val Lys Glu Ser Trp Ile Arg His Leu Lys Leu
                165                 170                 175

Ala Gly Glu Pro Ser Tyr Ser Gly Phe Glu Asp Leu Leu Arg Ile Arg
            180                 185                 190

Val Glu Pro Asn Thr Ser Pro Leu Ala Asp Lys Glu Glu Lys Ile Phe
        195                 200                 205

Arg Phe Gly Ser His Lys Trp Tyr Gly
    210                 215

<210> SEQ ID NO 62
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 62

Arg Pro Lys Pro Glu Asp Phe Cys Pro Phe Glu Cys Ala Met Ala Thr
1               5                   10                  15
```

Val Tyr Asp Ile Gly His Asp Ala Val Met Tyr Val Ala Glu Arg Lys
            20                  25                  30

Ile Ser Trp Ala Pro Arg Gly Gly Asp Glu Val Lys Phe Glu Ala Val
        35                  40                  45

Pro Gly Glu Leu Lys Leu Ile Ala Asn Arg Leu Arg Thr Ser Phe Pro
 50                  55                  60

Pro His His Thr Val Asp Met Ser Lys Phe Ala Phe Thr Ala Pro Gly
 65                  70                  75                  80

Cys Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asp Leu Leu
            100                 105                 110

Pro Leu Glu Val Gln Asn Lys Glu Ile Arg His Ala Asn Gln Phe Gly
        115                 120                 125

Tyr Gln Thr Lys His Gly Val Ser Gly Lys Tyr Leu Gln Arg Arg Leu
130                 135                 140

Gln Val Asn Gly Leu Arg Ala Val Thr Asp Pro Asn Gly Pro Ile Val
145                 150                 155                 160

Val Gln Tyr Phe Ser Val Lys Glu Ser Trp Ile Arg His Leu Lys Leu
                165                 170                 175

Ala Gly Glu Pro Ser Tyr Pro Gly Phe Glu Asp Leu Leu Arg Ile Arg
            180                 185                 190

Val Glu His Asn Thr Ser Pro Leu Ala Asp Lys Glu Glu Lys Ile Phe
        195                 200                 205

Arg Phe Gly Ser His Lys Trp Tyr Gly
        210                 215

<210> SEQ ID NO 63
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 63

Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Glu Arg Lys
            20                  25                  30

Ile Ser Trp Ala Pro Arg Gly Gly Asp Glu Val Lys Phe Glu Ala Val
        35                  40                  45

Pro Gly Glu Leu Lys Leu Ile Ala Asp Gln Leu Arg Thr Ser Phe Pro
 50                  55                  60

Pro His His Thr Val Asp Val Ser Lys Phe Ala Phe Thr Ala Pro Gly
 65                  70                  75                  80

Cys Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asp Leu Leu
            100                 105                 110

Pro Leu Glu Val Lys Asn Lys Glu Ile Arg His Ala Asn Gln Phe Gly
        115                 120                 125

Tyr Gln Thr Lys His Gly Val Ser Gly Lys Tyr Leu Gln Arg Arg Leu
130                 135                 140

Gln Val Asn Gly Leu Arg Ala Val Thr Asp Pro Asn Gly Pro Ile Val
145                 150                 155                 160

Val Gln Tyr Phe Ser Val Lys Glu Ser Trp Ile Arg His Leu Arg Leu
            165                 170                 175

Ala Gly Glu Pro Ser Tyr Pro Gly Phe Glu Asp Leu Leu Arg Ile Arg
            180                 185                 190

Val Glu Pro Asn Thr Ser Pro Leu Ala Asp Lys Glu Lys Ile Phe
            195                 200                 205

Arg Phe Gly Ser His Lys Trp Tyr Gly
            210                 215

<210> SEQ ID NO 64
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 64

Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Glu Gly Lys
            20                  25                  30

Ile Ser Trp Ala Pro Arg Gly Gly Asp Glu Val Lys Phe Glu Ala Val
            35                  40                  45

Pro Gly Glu Leu Lys Leu Ile Ala Asn Arg Leu Arg Thr Ser Phe Pro
50                  55                  60

Pro His His Ala Val Asp Met Ser Lys Phe Ala Phe Thr Ala Pro Gly
65                  70                  75                  80

Cys Gly Val Ser Met Arg Val Glu Arg Gln His Gly Cys Leu Pro Ala
            85                  90                  95

Asp Thr Val Pro Glu Gly Asn Cys Trp Trp Ser Leu Phe Asp Leu Leu
            100                 105                 110

Pro Leu Glu Val Gln Asp Lys Glu Ile Arg His Ala Asn Gln Phe Gly
            115                 120                 125

Tyr Gln Thr Lys His Gly Val Ser Gly Lys Tyr Leu Gln Arg Arg Leu
            130                 135                 140

Gln Val Asn Gly Leu Arg Ala Val Thr Asp Ser Asn Gly Pro Ile Val
145                 150                 155                 160

Val Gln Tyr Phe Ser Val Lys Glu Ser Trp Ile Arg His Leu Lys Leu
            165                 170                 175

Ala Gly Glu Pro Ser Tyr Ser Gly Phe Glu Asp Leu Leu Arg Ile Arg
            180                 185                 190

Val Glu Pro Asn Thr Ser Pro Leu Ala Asn Thr Glu Gly Lys Ile Phe
            195                 200                 205

Arg Phe Gly Ser His Lys Trp Tyr Gly
            210                 215

<210> SEQ ID NO 65
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 65

Arg Pro Lys Pro Glu Asp Phe Cys Pro Phe Glu Cys Ala Met Ala Thr
1               5                   10                  15

```
Val Tyr Asp Ile Gly His Asp Ala Val Met Tyr Val Ala Gly Met Lys
            20                  25                  30

Ile Ser Trp Ala Pro Arg Gly Gly Asp Glu Val Lys Phe Glu Ala Val
        35                  40                  45

Pro Gly Glu Leu Lys Leu Ile Ala Asn Arg Leu Arg Thr Ser Phe Pro
 50                  55                  60

Pro His His Thr Val Asp Met Ser Lys Phe Ala Phe Thr Ala Leu Gly
 65                  70                  75                  80

Cys Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asp Leu Leu
            100                 105                 110

Pro Leu Glu Val Gln Asn Lys Glu Ile Arg Tyr Ala Asn Gln Phe Gly
        115                 120                 125

Tyr Gln Thr Lys His Gly Val Ser Gly Lys Tyr Leu Gln Arg Arg Leu
130                 135                 140

Gln Val Asn Gly Leu Arg Ala Val Thr Asp Leu Asn Gly Pro Ile Val
145                 150                 155                 160

Val Gln Tyr Phe Ser Val Lys Glu Ser Trp Ile Arg His Leu Lys Leu
                165                 170                 175

Ala Gly Glu Pro Ser Tyr Ser Gly Phe Glu Asp Leu Leu Arg Ile Arg
            180                 185                 190

Val Glu Pro Asn Thr Ser Pro Leu Ala Asp Lys Glu Glu Lys Ile Phe
        195                 200                 205

Arg Phe Gly Ser His Lys Trp Tyr Gly
        210                 215

<210> SEQ ID NO 66
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 66

Arg Pro Lys Pro Asp Asp Phe Cys Pro Phe Glu Cys Ala Met Ala Thr
1               5                   10                  15

Val Tyr Asp Ile Gly His Asp Ala Val Met Tyr Val Ala Glu Lys
            20                  25                  30

Val Ser Trp Ala Pro Arg Gly Gly Asp Glu Val Lys Phe Glu Pro Val
        35                  40                  45

Pro Gly Glu Leu Lys Leu Ile Ala Asn Arg Leu Arg Thr Ser Phe Pro
 50                  55                  60

Pro His His Ala Val Asp Met Ser Lys Phe Thr Phe Thr Ala Pro Gly
 65                  70                  75                  80

Arg Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asn Leu Leu
            100                 105                 110

Pro Leu Glu Val Gln Asn Lys Glu Ile Arg His Ala Gly Gln Phe Gly
        115                 120                 125

Tyr Gln Thr Lys His Gly Val Ser Gly Lys Tyr Leu Gln Arg Arg Leu
130                 135                 140

Gln Val Asn Gly Leu Arg Ala Val Thr Asp Leu Asn Gly Pro Ile Val
145                 150                 155                 160
```

```
Val Gln Cys Phe Ser Val Lys Glu Ser Trp Ile Arg His Leu Lys Leu
                165                 170                 175

Ala Glu Glu Pro Ser Tyr Pro Gly Phe Glu Asp Leu Leu Arg Ile Arg
            180                 185                 190

Val Glu Pro Asn Thr Ser Pro Leu Ala Asp Lys Asp Glu Lys Ile Phe
        195                 200                 205

Arg Phe Gly Asn His Lys Trp Tyr Gly
        210                 215

<210> SEQ ID NO 67
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 67

Arg Pro Lys Pro Glu Asp Phe Cys Pro Phe Glu Cys Ala Met Ala Asp
1               5                   10                  15

Val Tyr Asp Ile Gly His Gly Ala Val Met Tyr Val Ala Lys Gly Lys
            20                  25                  30

Val Ser Trp Ala Pro Arg Gly Gly Asp Glu Ala Lys Phe Glu Thr Val
        35                  40                  45

Pro Arg Glu Leu Lys Leu Ile Ala Asn Gln Leu His Ile Ser Phe Pro
    50                  55                  60

Pro His His Ala Val Asp Met Ser Lys Phe Val Phe Ile Ala Pro Gly
65                  70                  75                  80

Ser Gly Val Ser Met Arg Val Glu Cys Pro His Gly Cys Leu Pro Ala
                85                  90                  95

Asn Thr Val Pro Glu Gly Asn Cys Trp Trp Arg Leu Phe Asp Ser Leu
            100                 105                 110

Pro Leu Asp Val Gln Asn Lys Glu Ile Arg Arg Ala Asn Gln Phe Gly
        115                 120                 125

Tyr Gln Thr Lys His Gly Val Ala Gly Lys Tyr Leu Gln Arg Arg Leu
    130                 135                 140

Gln Ala Asn Gly Leu Arg Ala Val Thr Asp Thr Asp Gly Pro Ile Val
145                 150                 155                 160

Val Gln Tyr Phe Ser Val Arg Glu Ser Trp Ile Arg His Phe Arg Leu
                165                 170                 175

Ala Glu Glu Pro Ser Leu Pro Gly Phe Glu Asp Leu Leu Arg Ile Arg
            180                 185                 190

Val Glu Pro Asn Thr Ser Pro Leu Ser Asp Lys Gly Gly Lys Ile Phe
        195                 200                 205

Arg Phe Gly Ser His Lys Trp Tyr Gly
        210                 215

<210> SEQ ID NO 68
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 68

Arg Pro Lys Pro Glu Asp Phe Cys Pro Phe Glu Cys Ala Met Ala Asp
1               5                   10                  15

Val Tyr Asp Ile Gly Arg Asp Ala Val Met Tyr Val Ala Arg Gly Lys
```

-continued

```
                    20                  25                  30
Val Ser Trp Ala Pro Arg Gly Gly Asp Glu Val Lys Phe Glu Thr Val
            35                  40                  45
Pro Glu Glu Leu Lys Leu Ile Ala Asn Arg Leu His Ile Ser Phe Pro
        50                  55                  60
Pro Tyr His Ala Val Asp Met Ser Lys Phe Ala Phe Ile Ala Pro Gly
65                  70                  75                  80
Ser Gly Val Ser Leu Arg Val Glu Tyr Gln His Gly Cys Leu Pro Ala
                85                  90                  95
Asp Thr Val Pro Glu Gly Asn Cys Trp Trp Arg Leu Phe Asp Leu Leu
            100                 105                 110
Pro Pro Glu Val Gln Asn Lys Glu Ile Arg Tyr Ala Asn Gln Phe Gly
        115                 120                 125
Tyr Gln Thr Lys His Gly Val Pro Gly Lys Tyr Leu Gln Arg Arg Leu
    130                 135                 140
Gln Val Asn Gly Leu Arg Ala Val Thr Asp Thr His Gly Pro Ile Val
145                 150                 155                 160
Ile Gln Tyr Phe Ser Val Glu Glu Ser Trp Ile Arg His Phe Arg Leu
                165                 170                 175
Ala Gly Glu Pro Ser Leu Pro Gly Phe Glu Asp Leu Leu Arg Ile Arg
            180                 185                 190
Val Glu Pro Asn Thr Ser Pro Leu Ala Glu Lys Asp Gly Lys Ile Phe
        195                 200                 205
Arg Phe Gly Ser His Lys Trp Tyr Gly
    210                 215

<210> SEQ ID NO 69
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 69

Arg Pro Lys Pro Glu Asp Phe Cys Pro Phe Glu Cys Ala Met Ala Asp
1               5                   10                  15
Val Tyr Asp Ile Ser His Asp Ala Val Met Tyr Val Ala Arg Gly Lys
            20                  25                  30
Val Ser Trp Ala Pro Arg Gly Gly Asp Glu Val Lys Phe Glu Thr Val
        35                  40                  45
Pro Glu Glu Leu Lys Leu Ile Ala Asn Arg Leu His Ile Ser Phe Pro
    50                  55                  60
Pro His His Ala Val Asp Met Ser Glu Phe Ala Phe Ile Ala Pro Gly
65                  70                  75                  80
Ser Gly Val Ser Leu Arg Val Glu His Gln His Gly Cys Leu Pro Ala
                85                  90                  95
Asp Thr Val Pro Glu Gly Asn Cys Trp Trp Cys Leu Phe Asp Leu Leu
            100                 105                 110
Pro Pro Glu Val Gln Asn Lys Glu Ile Arg Arg Ala Asn Gln Phe Gly
        115                 120                 125
Tyr Gln Thr Lys His Gly Val Pro Gly Lys Tyr Leu Gln Arg Arg Leu
    130                 135                 140
Gln Val Asn Gly Leu Arg Ala Val Thr Asp Thr Asp Gly Pro Ile Val
145                 150                 155                 160
Val Gln Tyr Phe Ser Val Arg Glu Ser Trp Ile Arg His Phe Arg Leu
```

165                 170                 175
Ala Glu Glu Pro Ser Leu Pro Gly Phe Glu Asp Leu Leu Arg Ile Arg
            180                 185                 190

Val Glu Pro Asn Thr Ser Pro Leu Gly Gly Lys Gly Glu Lys Ile Phe
        195                 200                 205

Arg Phe Gly Ser His Lys Trp Tyr Gly
    210                 215

<210> SEQ ID NO 70
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 70

Arg Pro Lys Pro Glu Asp Phe Cys Pro Phe Glu Cys Ala Met Ala Asp
1               5                   10                  15

Val Tyr Asp Ile Gly His Gly Ala Val Met Phe Val Ala Gly Gly Lys
            20                  25                  30

Val Ser Trp Ala Pro Arg Gly Gly Asp Glu Val Arg Phe Glu Thr Val
        35                  40                  45

Pro Glu Glu Leu Lys Leu Ile Ala Asn Arg Leu His Ile Ser Phe Pro
    50                  55                  60

Pro His His Leu Val Asp Met Ser Lys Phe Ala Phe Ile Val Pro Gly
65                  70                  75                  80

Ser Gly Val Ser Leu Arg Val Glu His Gln His Gly Cys Leu Pro Ala
                85                  90                  95

Asp Ile Val Pro Lys Gly Asn Cys Trp Trp Cys Leu Phe Asp Leu Leu
            100                 105                 110

Pro Pro Gly Val Gln Asn Arg Glu Ile Arg Tyr Ala Asn Gln Phe Gly
        115                 120                 125

Tyr Gln Thr Lys His Gly Val Ser Gly Lys Tyr Leu Gln Arg Arg Leu
    130                 135                 140

Gln Ile Asn Gly Leu Arg Ala Val Thr Asp Thr His Gly Pro Ile Val
145                 150                 155                 160

Val Gln Tyr Phe Ser Val Lys Glu Ser Trp Ile Arg His Phe Arg Leu
                165                 170                 175

Ala Gly Glu Pro Ser Leu Pro Gly Phe Glu Asp Leu Leu Arg Ile Arg
            180                 185                 190

Val Glu Ser Asn Thr Ser Pro Leu Ala Asp Lys Asp Glu Lys Ile Phe
        195                 200                 205

Arg Phe Gly Ser His Lys Trp Tyr Gly
    210                 215

<210> SEQ ID NO 71
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 71

Arg Pro Lys Pro Glu Asp Phe Cys Pro Phe Glu Cys Ala Met Ala Asp
1               5                   10                  15

Val Tyr Asp Ile Gly Arg Gly Ala Val Met Tyr Val Ala Gly Gly Lys
            20                  25                  30

```
Val Ser Trp Ala Pro Arg Gly Gly Asp Glu Val Lys Phe Glu Pro Val
         35                  40                  45

Pro Lys Glu Leu Lys Leu Val Ala Asn Arg Leu His Thr Ser Phe Pro
 50                  55                  60

Pro His His Val Val Asp Met Ser Lys Phe Thr Phe Met Thr Pro Gly
 65                  70                  75                  80

Ser Gly Val Ser Met Arg Val Glu Tyr Gln Tyr Gly Cys Leu Pro Ala
                 85                  90                  95

Asp Thr Val Pro Glu Gly Asn Cys Trp Trp Arg Leu Phe Asp Leu Leu
                100                 105                 110

Pro Pro Glu Val Gln Asn Lys Glu Ile Arg His Ala Asn Gln Phe Gly
                115                 120                 125

Tyr Gln Thr Lys His Gly Val Pro Gly Lys Tyr Leu Gln Arg Arg Leu
        130                 135                 140

Gln Val Asn Gly Leu Arg Ala Val Thr Asp Thr His Gly Pro Ile Val
145                 150                 155                 160

Ile Gln Tyr Phe Ser Val Lys Glu Ser Trp Ile Arg His Leu Lys Pro
                165                 170                 175

Val Glu Glu Pro Ser Leu Pro Gly Phe Glu Asp Leu Leu Arg Ile Arg
                180                 185                 190

Val Glu Pro Asn Thr Ser Pro Leu Ala Gly Lys Asn Glu Lys Ile Phe
        195                 200                 205

Arg Phe Gly Ser His Lys Trp Tyr Gly
    210                 215

<210> SEQ ID NO 72
<211> LENGTH: 1066
<212> TYPE: PRT
<213> ORGANISM: Artificial Sequence
<220> FEATURE:
<223> OTHER INFORMATION: Porcine reproductive and respiratory syndrome
      virus; Nsp2
<220> FEATURE:
<221> NAME/KEY: MOD_RES
<222> LOCATION: (134)..(134)
<223> OTHER INFORMATION: Xaa = variable or unknown amino acid
<220> FEATURE:
<221> NAME/KEY: MOD_RES
<222> LOCATION: (242)..(242)
<223> OTHER INFORMATION: Xaa = variable or unknown amino acid
<220> FEATURE:
<221> NAME/KEY: MOD_RES
<222> LOCATION: (284)..(284)
<223> OTHER INFORMATION: Xaa = variable or unknown amino acid
<220> FEATURE:
<221> NAME/KEY: MOD_RES
<222> LOCATION: (298)..(298)
<223> OTHER INFORMATION: Xaa = variable or unknown amino acid
<220> FEATURE:
<221> NAME/KEY: MOD_RES
<222> LOCATION: (691)..(691)
<223> OTHER INFORMATION: Xaa = variable or unknown amino acid

<400> SEQUENCE: 72

Gly Ala Gly Lys Arg Ala Arg Arg Ala Arg Ala Ser Ala Val Thr Ala
 1               5                  10                  15

Val Ala Gly His Ala Pro Pro Thr Arg Glu Thr Gln Gln Ala Lys Lys
                20                  25                  30

His Glu Ala Ala Ser Ala Asn Lys Ala Glu Leu Leu Glu Arg Tyr Ser
        35                  40                  45

Pro Pro Ala Glu Gly Asn Cys Gly Trp His Cys Ile Ser Ala Ile Ala
 50                  55                  60
```

```
Asn Arg Met Val Asn Ser Lys Phe Glu Thr Ala Leu Pro Glu Arg Val
 65                  70                  75                  80

Arg Ser Pro Glu Asp Trp Ala Thr Asp Glu Asp Leu Val Asn Thr Ile
                 85                  90                  95

Gln Ile Leu Arg Leu Pro Ala Ala Leu Asp Arg Asn Gly Ala Cys Ala
                100                 105                 110

Ser Ala Lys Tyr Ile Leu Lys Leu Glu Gly Glu His Trp Thr Val Ser
                115                 120                 125

Val Ile Pro Gly Met Xaa Pro Ser Leu Leu Pro Leu Glu Cys Val Gln
                130                 135                 140

Gly Cys Cys Glu His Lys Gly Asn Leu Gly Ser Pro Asn Ala Val Gly
145                 150                 155                 160

Val Phe Gly Phe Asp Pro Ala Ser Leu Asp Arg Leu Ala Gly Val Met
                165                 170                 175

His Leu Pro Ser Ser Ala Ile Pro Ala Ala Leu Ala Glu Leu Ser Gly
                180                 185                 190

Asp Leu Asp Arg Pro Thr Ser Pro Ala Ala Thr Val Trp Thr Val Ser
                195                 200                 205

Gln Phe Tyr Ala Arg His Ser Gly Gly Glu His Pro Asp Gln Lys Cys
                210                 215                 220

Leu Lys Lys Ile Ile Ser Leu Cys Glu Val Ile Glu Ser Cys Cys Cys
225                 230                 235                 240

Ser Xaa Asn Lys Thr Asn Arg Val Thr Pro Glu Val Thr Ala Lys
                245                 250                 255

Ile Asp Leu Tyr Leu Phe Gly Ala Ala Ser Leu Glu Glu Cys Leu Ala
                260                 265                 270

Arg Leu Glu Lys Ala Arg Pro Pro Ser Val Leu Xaa Thr Ser Phe Asp
                275                 280                 285

Trp Asp Val Val Leu Pro Gly Val Gly Xaa Ala Ala Gln Ala Ala Lys
290                 295                 300

Leu Pro Leu Thr Asn Gln Arg His Ala Leu Ala Thr Val Val Thr Gln
305                 310                 315                 320

Arg Ser Leu Pro Lys Phe Gln Pro Arg Lys Ala Glu Ser Val Lys Ser
                325                 330                 335

Leu Pro Glu Ser Arg Pro Leu Pro Ala Pro Arg Lys Lys Ile Arg Ser
                340                 345                 350

Arg Cys Gly Ser Pro Ile Ser Leu Gly Gly Asn Leu Pro Asp Ser Gln
                355                 360                 365

Glu Asp Leu Ala Gly Gly Ser Phe Asp Phe Pro Thr Leu Pro Glu Leu
                370                 375                 380

Val Val Ser Ser Ser Glu Ser Val Pro Val Pro Ala Pro Arg Arg Val
385                 390                 395                 400

Val Ser Arg Leu Val Ser Ser Pro Ile Val Ser Thr Pro Val Pro Ala
                405                 410                 415

Pro Arg Arg Gly Leu Arg Gln Val Glu Gly Met Asn Leu Ala Ala Val
                420                 425                 430

Thr Leu Ala Cys Gln Asp Glu Pro Leu Asp Leu Ser Ala Ser Ser Gln
                435                 440                 445

Thr Glu Tyr Glu Ala Ser Pro Leu Ala Leu Pro Leu Ser Glu Asp Val
                450                 455                 460

Leu Ala Val Glu Arg Arg Glu Val Glu Val Leu Ser Gly Ile Ser
465                 470                 475                 480

Gly Met Ser Asp Asp Ile Arg Leu Ala Pro Val Ser Ser Ser Ser Ser
                485                 490                 495
```

```
Leu Ser Ser Ile Glu Ile Thr Arg Pro Lys Tyr Ser Ala Gln Ala Ile
            500                 505                 510
Ile Asn Ser Gly Gly Pro Cys Cys Gly His Leu Gln Glu Val Lys Glu
            515                 520                 525
Lys Tyr Leu Asn Val Met Arg Glu Ala Cys Asp Ala Thr Lys Leu Asp
            530                 535                 540
Asp Pro Ala Thr Gln Glu Trp Leu Ser Arg Met Trp Asp Arg Val Asp
545                 550                 555                 560
Met Leu Thr Trp Arg Asn Thr Ser Ile Phe Gln Ala Pro Phe Thr Leu
                565                 570                 575
Ala Asp Lys Phe Lys Ser Leu Pro Lys Met Ile Leu Glu Thr Pro Pro
            580                 585                 590
Pro Tyr Pro Cys Gly Phe Val Met Met Pro Arg Thr Pro Ala Pro Ser
            595                 600                 605
Val Gly Ala Glu Ser Asp Leu Thr Val Gly Ser Val Ala Thr Glu Asp
            610                 615                 620
Val Pro Arg Ile Leu Gly Lys Val Gln Gly Val Gly Glu Thr Thr Asp
625                 630                 635                 640
Gln Gly Pro Leu Ala Leu Phe Ala Asp Glu Leu Ala Asp Asp Gln Pro
                645                 650                 655
Ala Arg Glu Pro Arg Thr Gln Thr Pro Pro Ala Ser Ala Gly Gly Ala
            660                 665                 670
Gly Leu Val Leu Asp Ser Gly Gly Ser Pro Glu Leu Thr Asp Leu Pro
            675                 680                 685
Leu Pro Xaa Gly Thr Asp Ala Gly Gly Gly Pro Leu His Thr Val
            690                 695                 700
Lys Lys Lys Ala Glu Arg Cys Phe Asp Gln Leu Ser Arg Arg Val Phe
705                 710                 715                 720
Asp Ile Val Ser His Leu Pro Val Phe Phe Ser Arg Leu Phe Lys Pro
                725                 730                 735
Asp Ser His Tyr Ser Ser Gly Asp Trp Ser Phe Ala Ala Phe Thr Leu
            740                 745                 750
Leu Cys Leu Phe Leu Cys Tyr Ser Tyr Pro Ala Phe Gly Val Ala Pro
            755                 760                 765
Leu Leu Gly Val Phe Ser Gly Ser Arg Arg Val Arg Met Gly Val
            770                 775                 780
Phe Gly Cys Trp Leu Ala Phe Ala Val Gly Leu Phe Lys Pro Ala Pro
785                 790                 795                 800
Asp Pro Val Gly Ala Ala Cys Glu Phe Asp Ser Pro Glu Cys Arg Asp
            805                 810                 815
Ile Leu His Ser Phe Glu Leu Leu Gln Pro Trp Asp Pro Val Arg Ser
            820                 825                 830
Leu Val Val Gly Pro Val Gly Leu Gly Leu Ala Ile Ile Gly Arg Leu
            835                 840                 845
Leu Gly Gly Ala Arg Tyr Val Trp Leu Leu Leu Arg Leu Gly Ile
            850                 855                 860
Val Ser Asp Cys Ile Leu Ala Gly Ala Tyr Val Leu Ser Gln Gly Arg
865                 870                 875                 880
Cys Lys Lys Cys Trp Gly Ser Cys Ile Arg Thr Ala Pro Ser Glu Val
                885                 890                 895
Ala Phe Asn Val Phe Pro Phe Thr Arg Ala Thr Arg Ser Ser Leu Val
            900                 905                 910
Asp Leu Cys Asp Arg Phe Cys Ala Pro Lys Gly Met Asp Pro Ile Phe
```

```
                915                 920                 925
Leu Ala Thr Gly Trp Arg Gly Cys Trp Ser Gln Ser Pro Val Glu
    930                 935                 940

Gln Pro Thr Glu Lys Pro Ile Ala Phe Ala Gln Leu Asp Glu Lys Lys
945                 950                 955                 960

Ile Thr Ala Arg Thr Val Val Ala Gln Pro Tyr Asp Pro Asn Gln Ala
                965                 970                 975

Val Lys Cys Leu Arg Val Leu Gln Ala Gly Ala Met Val Ala Glu
            980                 985                 990

Ala Ile Pro Lys Val Val Lys Val Ser Ala Val Pro Phe Arg Ala Pro
        995                 1000                1005

Phe Phe Pro Thr Gly Val Lys Val Asp Pro Glu Cys Arg Val Val
    1010                1015                1020

Val Asp Pro Asp Thr Phe Thr Thr Ala Leu Arg Ser Gly Tyr Ser
    1025                1030                1035

Thr Thr Asn Leu Ile Leu Gly Val Gly Asp Phe Ala Gln Leu Asn
    1040                1045                1050

Gly Leu Lys Ile Arg Gln Ile Ser Lys Pro Ser Gly Gly
    1055                1060                1065

<210> SEQ ID NO 73
<211> LENGTH: 1066
<212> TYPE: PRT
<213> ORGANISM: Artificial Sequence
<220> FEATURE:
<223> OTHER INFORMATION: Porcine reproductive and respiratory syndrome
      virus; Nsp2
<220> FEATURE:
<221> NAME/KEY: MOD_RES
<222> LOCATION: (43)..(43)
<223> OTHER INFORMATION: Xaa = variable or unknown amino acid
<220> FEATURE:
<221> NAME/KEY: MOD_RES
<222> LOCATION: (45)..(46)
<223> OTHER INFORMATION: Xaa = variable or unknown amino acid
<220> FEATURE:
<221> NAME/KEY: MOD_RES
<222> LOCATION: (75)..(75)
<223> OTHER INFORMATION: Xaa = variable or unknown amino acid
<220> FEATURE:
<221> NAME/KEY: MOD_RES
<222> LOCATION: (82)..(82)
<223> OTHER INFORMATION: Xaa = variable or unknown amino acid
<220> FEATURE:
<221> NAME/KEY: MOD_RES
<222> LOCATION: (84)..(84)
<223> OTHER INFORMATION: Xaa = variable or unknown amino acid
<220> FEATURE:
<221> NAME/KEY: MOD_RES
<222> LOCATION: (95)..(95)
<223> OTHER INFORMATION: Xaa = variable or unknown amino acid
<220> FEATURE:
<221> NAME/KEY: MOD_RES
<222> LOCATION: (112)..(112)
<223> OTHER INFORMATION: Xaa = variable or unknown amino acid
<220> FEATURE:
<221> NAME/KEY: MOD_RES
<222> LOCATION: (117)..(117)
<223> OTHER INFORMATION: Xaa = variable or unknown amino acid
<220> FEATURE:
<221> NAME/KEY: MOD_RES
<222> LOCATION: (128)..(128)
<223> OTHER INFORMATION: Xaa = variable or unknown amino acid
<220> FEATURE:
<221> NAME/KEY: MOD_RES
<222> LOCATION: (130)..(130)
<223> OTHER INFORMATION: Xaa = variable or unknown amino acid
<220> FEATURE:
<221> NAME/KEY: MOD_RES
<222> LOCATION: (174)..(174)
```

-continued

```
<223> OTHER INFORMATION: Xaa = variable or unknown amino acid
<220> FEATURE:
<221> NAME/KEY: MOD_RES
<222> LOCATION: (190)..(190)
<223> OTHER INFORMATION: Xaa = variable or unknown amino acid
<220> FEATURE:
<221> NAME/KEY: MOD_RES
<222> LOCATION: (194)..(194)
<223> OTHER INFORMATION: Xaa = variable or unknown amino acid
<220> FEATURE:
<221> NAME/KEY: MOD_RES
<222> LOCATION: (197)..(198)
<223> OTHER INFORMATION: Xaa = variable or unknown amino acid
<220> FEATURE:
<221> NAME/KEY: MOD_RES
<222> LOCATION: (201)..(202)
<223> OTHER INFORMATION: Xaa = variable or unknown amino acid
<220> FEATURE:
<221> NAME/KEY: MOD_RES
<222> LOCATION: (218)..(218)
<223> OTHER INFORMATION: Xaa = variable or unknown amino acid
<220> FEATURE:
<221> NAME/KEY: MOD_RES
<222> LOCATION: (223)..(224)
<223> OTHER INFORMATION: Xaa = variable or unknown amino acid
<220> FEATURE:
<221> NAME/KEY: MOD_RES
<222> LOCATION: (226)..(226)
<223> OTHER INFORMATION: Xaa = variable or unknown amino acid
<220> FEATURE:
<221> NAME/KEY: MOD_RES
<222> LOCATION: (233)..(233)
<223> OTHER INFORMATION: Xaa = variable or unknown amino acid
<220> FEATURE:
<221> NAME/KEY: MOD_RES
<222> LOCATION: (237)..(237)
<223> OTHER INFORMATION: Xaa = variable or unknown amino acid
<220> FEATURE:
<221> NAME/KEY: MOD_RES
<222> LOCATION: (242)..(242)
<223> OTHER INFORMATION: Xaa = variable or unknown amino acid
<220> FEATURE:
<221> NAME/KEY: MOD_RES
<222> LOCATION: (254)..(254)
<223> OTHER INFORMATION: Xaa = variable or unknown amino acid

<400> SEQUENCE: 73

Gly Ala Gly Lys Arg Ala Arg Arg Ala Arg Ala Ser Ala Val Thr Ala
1               5                   10                  15

Val Ala Gly His Ala Pro Pro Thr Arg Glu Thr Gln Gln Ala Lys Lys
            20                  25                  30

His Glu Ala Ala Ser Ala Asn Lys Ala Glu Xaa Leu Xaa Xaa Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Xaa Leu Pro Glu Arg Val
65                  70                  75                  80

Arg Xaa Pro Xaa Asp Trp Ala Thr Asp Glu Asp Leu Val Asn Xaa Ile
                85                  90                  95

Gln Ile Leu Arg Leu Pro Ala Ala Leu Asp Arg Asn Gly Ala Cys Xaa
            100                 105                 110

Ser Ala Lys Tyr Xaa Leu Lys Leu Glu Gly Glu His Trp Thr Val Xaa
        115                 120                 125

Val Xaa Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Xaa Val Met
                165                 170                 175
```

```
His Leu Pro Ser Ser Ala Ile Pro Ala Ala Leu Ala Glu Xaa Ser Gly
            180                 185                 190

Asp Xaa Asp Arg Xaa Xaa Ser Pro Xaa Xaa Thr Val Trp Thr Val Ser
        195                 200                 205

Gln Phe Tyr Ala Arg His Ser Gly Gly Xaa His Pro Asp Gln Xaa Xaa
    210                 215                 220

Leu Xaa Lys Ile Ile Ser Leu Cys Xaa Val Ile Glu Xaa Cys Cys Cys
225                 230                 235                 240

Ser Xaa Asn Lys Thr Asn Arg Val Thr Pro Glu Glu Val Xaa Ala Lys
            245                 250                 255

Ile Asp Gln Tyr Leu Phe Gly Ala Ala Ser Leu Glu Glu Cys Leu Ala
            260                 265                 270

Arg Leu Glu Lys Ala Arg Pro Pro Ser Val Leu Asp Thr Ser Phe Asp
            275                 280                 285

Trp Asp Val Val Leu Pro Gly Val Gly Ala Ala Gln Ala Ala Lys
290                 295                 300

Leu Pro Leu Thr Asn Gln Arg His Ala Leu Ala Thr Val Val Thr Gln
305                 310                 315                 320

Arg Ser Leu Pro Lys Phe Gln Pro Arg Lys Ala Glu Ser Val Lys Ser
            325                 330                 335

Leu Pro Glu Ser Arg Pro Leu Pro Ala Pro Arg Lys Lys Ile Gly Ser
            340                 345                 350

Arg Cys Gly Ser Pro Ile Ser Leu Gly Gly Asn Leu Pro Asp Ser Arg
            355                 360                 365

Glu Asp Leu Ala Gly Gly Ser Phe Asp Phe Pro Thr Leu Pro Glu Leu
            370                 375                 380

Val Ala Ser Ser Ser Glu Pro Val Pro Val Pro Ala Pro Arg Arg Val
385                 390                 395                 400

Val Ser Arg Leu Val Ser Ser Pro Ile Val Ser Thr Pro Val Pro Ala
            405                 410                 415

Pro Arg Arg Gly Leu Arg Gln Val Glu Gly Met Asn Leu Ala Ala Val
            420                 425                 430

Thr Leu Ala Cys Gln Asp Glu Pro Leu Asp Leu Ser Ala Ser Ser Gln
            435                 440                 445

Thr Glu Tyr Glu Ala Ser Pro Leu Ala Leu Pro Leu Ser Glu Asp Val
            450                 455                 460

Leu Ala Val Glu Arg Arg Glu Val Glu Val Leu Ser Gly Ile Ser
465                 470                 475                 480

Gly Met Pro Asp Asp Ile Arg Leu Ala Pro Val Ser Ser Ser Ser
                485                 490                 495

Leu Ser Ser Ile Glu Ile Thr Arg Pro Lys Tyr Ser Ala Gln Ala Ile
            500                 505                 510

Ile Asn Ser Gly Gly Pro Cys Cys Gly His Leu Gln Glu Val Lys Glu
            515                 520                 525

Lys Tyr Leu Asn Val Met Arg Glu Ala Cys Asp Ala Thr Lys Leu Asp
            530                 535                 540

Asp Pro Ala Thr Gln Glu Trp Leu Ser Arg Met Trp Asp Arg Val Asp
545                 550                 555                 560

Met Leu Thr Trp Arg Asn Thr Ser Ile Phe Gln Ala Pro Phe Thr Leu
                565                 570                 575

Ala Asp Lys Phe Lys Thr Leu Pro Lys Met Ile Leu Glu Thr Pro Pro
            580                 585                 590

Pro Tyr Pro Cys Gly Phe Val Met Met Pro Arg Thr Pro Ala Pro Ser
```

```
                    595                 600                 605
Val Gly Ala Glu Ser Asp Leu Thr Val Gly Ser Val Ala Thr Glu Asp
    610                 615                 620

Val Pro Arg Ile Leu Gly Asn Val Gln Gly Val Gly Glu Thr Thr Asp
625                 630                 635                 640

Gln Gly Pro Leu Ala Pro Phe Ala Asp Glu Leu Ala Asp Asp Gln Leu
                    645                 650                 655

Ala Arg Glu Pro Arg Thr Gln Thr Pro Pro Ala Ser Thr Gly Gly Ala
                660                 665                 670

Gly Leu Val Ser Asp Ser Gly Arg Ser Pro Glu Leu Thr Asp Leu Pro
            675                 680                 685

Leu Ser Asn Gly Thr Asp Ala Gly Gly Gly Pro Leu His Thr Val
        690                 695                 700

Lys Lys Lys Ala Glu Arg Cys Phe Asp Gln Leu Ser Arg Arg Val Phe
705                 710                 715                 720

Asp Ile Val Ser His Leu Pro Val Phe Phe Ser Arg Leu Phe Lys Pro
                    725                 730                 735

Asp Ser His Tyr Ser Ser Gly Asp Trp Ser Phe Ala Ala Phe Thr Leu
                740                 745                 750

Leu Cys Leu Phe Leu Cys Tyr Ser Tyr Pro Ala Phe Gly Val Ala Pro
            755                 760                 765

Leu Leu Gly Val Phe Ser Ser Ser Arg Arg Val Arg Met Gly Val
        770                 775                 780

Phe Gly Cys Trp Leu Ala Phe Ala Val Gly Leu Phe Lys Pro Ala Pro
785                 790                 795                 800

Asp Pro Val Gly Ala Ala Cys Glu Phe Asp Ser Pro Glu Cys Arg Asp
                    805                 810                 815

Ile Leu His Ser Phe Glu Leu Leu Gln Pro Trp Asp Pro Val Arg Ser
                820                 825                 830

Leu Val Val Gly Pro Val Gly Leu Gly Leu Ala Ile Ile Gly Arg Leu
            835                 840                 845

Leu Gly Gly Ala Arg Tyr Val Trp Leu Leu Leu Arg Leu Gly Ile
        850                 855                 860

Val Ser Asp Cys Ile Leu Ala Gly Ala Tyr Val Leu Ser Gln Gly Arg
865                 870                 875                 880

Cys Lys Lys Cys Trp Gly Ser Cys Ile Arg Thr Ala Pro Ser Glu Val
                    885                 890                 895

Ala Phe Asn Val Phe Pro Phe Thr Arg Ala Thr Arg Ser Ser Leu Val
                900                 905                 910

Asp Leu Cys Asp Arg Phe Cys Ala Pro Lys Gly Met Asp Pro Ile Phe
            915                 920                 925

Leu Ala Thr Gly Trp Arg Gly Cys Trp Ser Gly Gln Ser Pro Ile Glu
        930                 935                 940

Gln Pro Thr Glu Lys Pro Ile Ala Phe Ala Gln Leu Asp Glu Lys Lys
945                 950                 955                 960

Ile Thr Ala Arg Thr Val Val Ala Gln Pro Tyr Asp Pro Asn Gln Ala
                    965                 970                 975

Val Lys Cys Leu Arg Val Leu Gln Ala Gly Gly Ala Met Val Ala Glu
                980                 985                 990

Ala Val Pro Lys Val Val Lys Val  Ser Ala Val Pro Phe  Arg Ala Pro
            995                 1000                1005

Phe Phe  Pro Ala Gly Val Lys  Val Asp Pro Glu Cys  Arg Val Val
    1010                1015                1020
```

-continued

Val Asp Pro Asp Thr Phe Thr Thr Ala Leu Arg Ser Gly Tyr Ser
1025                1030                1035

Thr Thr Asn Leu Ile Leu Gly Met Gly Asp Phe Ala Gln Leu Asn
     1040                1045                1050

Gly Leu Lys Ile Arg Gln Ile Ser Lys Pro Ser Gly Gly
     1055                1060                1065

<210> SEQ ID NO 74
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 74

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
        195                 200                 205

Gln Phe Phe Ala Arg His Ser Gly Gly Asn His Pro Asp Gln Val Arg
    210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Ser Phe Asp
        275                 280                 285

Trp Asp Val Val Leu Pro Gly Val Glu Ala Ala Thr Gln Thr Ile Lys
    290                 295                 300

Leu Pro Gln Val Asn Gln Cys Arg Ala Leu Val Pro Val Val Thr Gln
305                 310                 315                 320

```
Lys Ser Leu Asp Asn Asn Ser Val Pro Leu Thr Ala Phe Ser Leu Ala
            325                 330                 335

Asn Tyr Tyr Arg Ala Gln Gly Asp Glu Val Arg His Arg Glu Arg
            340                 345                 350

Leu Thr Ala Val Leu Ser Lys Leu Glu Lys Val Arg Glu Glu Tyr
            355                 360                 365

Gly Leu Met Pro Thr Glu Pro Gly Pro Arg Pro Thr Leu Pro Arg Gly
370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
            405                 410                 415

Asp Leu Lys Thr Trp Val Lys Asn Tyr Pro Arg Trp Thr Pro Pro Pro
            420                 425                 430

Pro Pro Pro Lys Val Gln Pro Arg Lys Thr Lys Pro Val Lys Ser Leu
            435                 440                 445

Pro Glu Arg Lys Pro Val Pro Ala Pro Arg Arg Lys Val Gly Ser Asp
            450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Pro
            485                 490                 495

Ala Thr Pro Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
            515                 520                 525

Arg Gly Thr Val Ser Arg Pro Val Thr Pro Leu Ser Glu Pro Ile Pro
            530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asp Glu Pro Leu Asp Leu Ser Ala
            565                 570                 575

Ser Ser Gln Thr Glu Tyr Glu Ala Ser Pro Pro Ala Pro Pro Gln Ser
            580                 585                 590

Gly Gly Val Leu Gly Val Glu Gly His Glu Ala Glu Glu Thr Leu Ser
            595                 600                 605

Glu Ile Ser Asp Met Ser Gly Asn Ile Lys Pro Ala Ser Val Ser Ser
            610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Gly Pro Cys Ser Gly His Leu Gln Glu
            645                 650                 655

Val Lys Glu Thr Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
            675                 680                 685

Arg Val Asp Met Leu Thr Trp Arg Asn Thr Ser Val Tyr Gln Ala Ile
            690                 695                 700

Cys Thr Leu Asp Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
            725                 730                 735

Ala Pro Ser Val Gly Ala Glu Ser Asp Leu Thr Ile Gly Ser Val Ala
            740                 745                 750
```

```
Thr Glu Asp Val Pro Arg Ile Leu Glu Lys Ile Glu Asn Val Gly Glu
        755                 760                 765
Met Ala Asn Gln Gly Pro Leu Ala Phe Ser Glu Asp Lys Pro Val Asp
        770                 775                 780
Asp Gln Leu Val Asn Asp Pro Arg Ile Ser Arg Arg Pro Asp Glu
785                 790                 795                 800
Ser Thr Ser Ala Pro Ser Ala Gly Thr Gly Gly Ala Gly Ser Phe Thr
                805                 810                 815
Asp Leu Pro Pro Ser Asp Gly Ala Asp Ala Asp Gly Gly Pro Phe
                820                 825                 830
Arg Thr Val Lys Arg Lys Ala Glu Arg Leu Phe Asp Gln Leu Ser Arg
                835                 840                 845
Gln Val Phe Asp Leu Val Ser His Leu Pro Val Phe Phe Ser Arg Leu
        850                 855                 860
Phe Tyr Pro Gly Gly Gly Tyr Ser Pro Gly Asp Trp Gly Phe Ala Ala
865                 870                 875                 880
Phe Thr Leu Leu Cys Leu Phe Leu Cys Tyr Ser Tyr Pro Ala Phe Gly
                885                 890                 895
Ile Ala Pro Leu Leu Gly Val Phe Gly Ser Ser Arg Arg Val Arg
                900                 905                 910
Met Gly Val Phe Gly Cys Trp Leu Ala Phe Ala Val Gly Leu Phe Lys
        915                 920                 925
Pro Val Ser Asp Pro Val Gly Ala Ala Cys Glu Phe Asp Ser Pro Glu
        930                 935                 940
Cys Arg Asn Ile Leu His Ser Phe Glu Leu Leu Lys Pro Trp Asp Pro
945                 950                 955                 960
Val Arg Ser Leu Val Val Gly Pro Val Gly Leu Ala Ile Leu
                965                 970                 975
Gly Arg Leu Leu Gly Gly Ala Arg Cys Ile Trp His Phe Leu Leu Arg
                980                 985                 990
Leu Gly Ile Val Ala Asp Cys Ile  Leu Ala Gly Ala Tyr Val Leu Ser
        995                1000                1005
Gln Gly Arg Cys Lys Lys Cys Trp Gly Ser Cys Ile Arg Thr Ala
       1010                1015                1020
Pro Asn Glu Val Ala Phe Asn Val Phe Pro Phe Thr Arg Ala Thr
       1025                1030                1035
Arg Ser Ser Leu Ile Asp Leu Cys Asp Arg Phe Cys Ala Pro Lys
       1040                1045                1050
Gly Met Asp Pro Ile Phe Leu Ala Thr Gly Trp Arg Gly Cys Trp
       1055                1060                1065
Ala Gly Arg Ser Pro Ile Glu Gln Pro Ser Glu Lys Pro Ile Ala
       1070                1075                1080
Phe Ala Gln Leu Asp Glu Lys Lys Ile Thr Ala Arg Thr Val Val
       1085                1090                1095
Ala Gln Pro Tyr Asp Pro Asn Gln Ala Val Lys Cys Leu Arg Val
       1100                1105                1110
Leu Gln Ser Gly Gly Ala Met Val Ala Lys Ala Val Pro Lys Val
       1115                1120                1125
Val Lys Val Ser Ala Val Pro Phe Arg Ala Pro Phe Phe Pro Thr
       1130                1135                1140
Gly Val Lys Val Asp Pro Asp Cys Arg Val Val Val Asp Pro Asp
       1145                1150                1155
Thr Phe Thr Ala Ala Leu Arg Ser Gly Tyr Ser Thr Thr Asn Leu
```

Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 75
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 75

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
        195                 200                 205

Gln Phe Phe Ala Arg His Ser Gly Gly Asn His Pro Asp Gln Val Arg
    210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Phe Phe Asp
        275                 280                 285

Trp Asp Val Val Leu Pro Gly Val Glu Ala Ala Thr Gln Thr Ile Lys
    290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala

```
                    325                 330                 335
Asn Tyr Tyr Tyr Arg Ala Gln Gly Asp Glu Val Arg His Arg Glu Arg
                340                 345                 350

Leu Thr Ala Val Leu Ser Lys Leu Glu Lys Val Val Arg Glu Glu Tyr
            355                 360                 365

Gly Leu Met Pro Thr Glu Pro Gly Pro Arg Pro Thr Leu Pro Arg Gly
        370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
                420                 425                 430

Pro Pro Pro Lys Val Gln Pro Arg Lys Thr Lys Pro Val Lys Ser Leu
            435                 440                 445

Pro Glu Arg Lys Pro Val Pro Ala Pro Arg Arg Lys Val Gly Ser Asp
        450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Pro
                485                 490                 495

Ala Thr Pro Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
        515                 520                 525

Arg Gly Thr Val Ser Arg Pro Val Thr Pro Leu Ser Glu Pro Ile Pro
        530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asn Glu Pro Leu Asp Leu Ser Ala
                565                 570                 575

Ser Ser Gln Thr Glu Tyr Glu Ala Ser Pro Ala Pro Pro Gln Ser
            580                 585                 590

Gly Gly Val Leu Gly Val Glu Gly His Glu Ala Glu Glu Thr Leu Ser
        595                 600                 605

Glu Ile Ser Asp Met Ser Gly Asn Ile Lys Pro Ala Ser Val Ser Ser
    610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Gly Pro Cys Ser Gly His Leu Gln Glu
                645                 650                 655

Val Lys Glu Thr Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
        675                 680                 685

Arg Val Asp Met Leu Thr Trp Arg Asn Thr Ser Val Tyr Gln Ala Ile
        690                 695                 700

Cys Thr Leu Asn Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
                725                 730                 735

Ala Pro Ser Val Gly Ala Glu Ser Asp Leu Thr Ile Gly Ser Val Ala
            740                 745                 750
```

```
Thr Glu Asp Val Pro Arg Ile Leu Glu Lys Ile Glu Asn Val Gly Glu
        755                 760                 765

Met Ala Asn Gln Gly Pro Leu Ala Phe Ser Glu Asp Lys Pro Val Asp
    770                 775                 780

Asp Gln Leu Val Asn Asp Pro Arg Ile Ser Ser Arg Arg Pro Asp Glu
785                 790                 795                 800

Ser Thr Ser Ala Pro Ser Ala Gly Thr Gly Gly Ala Gly Ser Phe Thr
                805                 810                 815

Asp Leu Pro Pro Ser Asp Gly Ala Asp Ala Asp Gly Gly Gly Pro Phe
                820                 825                 830

Arg Thr Val Lys Arg Lys Ala Glu Arg Leu Phe Asp Gln Leu Ser Arg
                835                 840                 845

Gln Val Phe Asp Leu Val Ser His Leu Pro Val Phe Phe Ser Arg Leu
    850                 855                 860

Phe Tyr Pro Gly Gly Gly Tyr Ser Pro Gly Asp Trp Gly Phe Ala Ala
865                 870                 875                 880

Phe Thr Leu Leu Cys Leu Phe Leu Cys Tyr Ser Tyr Pro Ala Phe Gly
                885                 890                 895

Ile Ala Pro Leu Leu Gly Val Phe Ser Gly Ser Ser Arg Arg Val Arg
                900                 905                 910

Met Gly Val Phe Gly Cys Trp Leu Ala Phe Ala Val Gly Leu Phe Lys
                915                 920                 925

Pro Val Ser Asp Pro Val Gly Ala Ala Cys Glu Phe Asp Ser Pro Glu
    930                 935                 940

Cys Arg Asn Ile Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
                980                 985                 990

Leu Gly Ile Val Ala Asp Cys Ile Leu Ala Gly Ala Tyr Val Leu Ser
                995                 1000                1005

Gln Gly Arg Cys Lys Lys Cys Trp Gly Ser Cys Ile Arg Thr Ala
    1010                1015                1020

Pro Asn Glu Val Ala Phe Asn Val Phe Pro Phe Thr Arg Ala Thr
    1025                1030                1035

Arg Ser Ser Leu Ile Asp Leu Cys Asp Arg Phe Cys Ala Pro Lys
    1040                1045                1050

Gly Met Asp Pro Ile Phe Leu Ala Thr Gly Trp Arg Gly Cys Trp
    1055                1060                1065

Ala Gly Arg Ser Pro Ile Glu Gln Pro Ser Glu Lys Pro Ile Ala
    1070                1075                1080

Phe Ala Gln Leu Asp Glu Lys Ile Thr Ala Arg Thr Val Val
    1085                1090                1095

Ala Gln Pro Tyr Asp Pro Asn Gln Ala Val Lys Cys Leu Arg Val
    1100                1105                1110

Leu Gln Ala Gly Gly Ala Met Val Ala Lys Ala Val Pro Lys Val
    1115                1120                1125

Val Lys Val Ser Ala Val Pro Phe Arg Ala Pro Phe Phe Pro Thr
    1130                1135                1140

Gly Val Lys Val Asp Pro Asp Cys Arg Val Val Asp Pro Asp
    1145                1150                1155

Thr Phe Thr Ala Ala Leu Arg Ser Gly Tyr Ser Thr Thr Asn Leu
    1160                1165                1170
```

Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 76
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 76

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
        195                 200                 205

Gln Phe Phe Ala Arg His Ser Gly Gly Asn His Pro Asp Gln Val Arg
    210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Phe Phe Asp
        275                 280                 285

Trp Asp Val Val Leu Pro Gly Val Glu Ala Ala Thr Gln Thr Ile Lys
    290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335

```
Asn Tyr Tyr Tyr Arg Ala Gln Gly Asp Glu Val Arg His Arg Glu Arg
                340                 345                 350

Leu Thr Ala Val Leu Ser Lys Leu Glu Lys Val Val Arg Glu Glu Tyr
            355                 360                 365

Gly Leu Met Pro Thr Glu Pro Gly Pro Arg Pro Thr Leu Pro Arg Gly
        370                 375                 380

Leu Asp Glu Leu Lys Ala Gln Met Glu Asp Leu Leu Lys Leu Ala
385                 390                 395                 400

Asn Ala Gln Thr Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
            420                 425                 430

Pro Pro Pro Lys Val Gln Pro Arg Lys Thr Lys Pro Val Lys Ser Leu
        435                 440                 445

Pro Glu Arg Lys Pro Val Pro Ala Pro Arg Arg Lys Val Gly Ser Asp
    450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Pro
                485                 490                 495

Ala Thr Pro Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
        515                 520                 525

Arg Gly Thr Val Ser Arg Pro Val Thr Pro Leu Ser Glu Pro Ile Pro
    530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asn Glu Pro Leu Asp Leu Ser Ala
                565                 570                 575

Ser Ser Gln Thr Glu Tyr Glu Ala Ser Pro Ala Pro Pro Gln Ser
            580                 585                 590

Gly Gly Val Leu Gly Val Glu Gly His Glu Ala Glu Glu Thr Leu Ser
        595                 600                 605

Glu Ile Ser Asp Met Ser Gly Asn Ile Lys Pro Ala Ser Val Ser Ser
    610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Gly Pro Cys Ser Gly His Leu Gln Glu
                645                 650                 655

Val Lys Glu Thr Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
        675                 680                 685

Arg Val Asp Met Leu Thr Trp Arg Asn Thr Ser Val Tyr Gln Ala Ile
    690                 695                 700

Cys Thr Leu Asp Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
                725                 730                 735

Ala Pro Ser Val Gly Ala Glu Ser Asp Leu Thr Ile Gly Ser Val Ala
            740                 745                 750

Thr Glu Asp Val Pro Arg Ile Leu Glu Lys Ile Glu Asn Val Gly Glu
```

```
                  755                 760                 765
Met Ala Asn Gln Gly Pro Leu Ala Phe Ser Glu Asp Lys Pro Val Asp
770                 775                 780

Asp Gln Leu Val Asn Asp Pro Arg Ile Ser Arg Arg Pro Asp Glu
785                 790                 795                 800

Ser Thr Ser Ala Pro Ser Ala Gly Thr Gly Gly Ala Gly Ser Phe Thr
                805                 810                 815

Asp Leu Pro Pro Ser Asp Gly Ala Asp Ala Asp Gly Gly Gly Pro Phe
                820                 825                 830

Arg Thr Val Lys Arg Lys Ala Glu Arg Leu Phe Asp Gln Leu Ser Arg
                835                 840                 845

Gln Val Phe Asp Leu Val Ser His Leu Pro Val Phe Phe Ser Arg Leu
850                 855                 860

Phe Tyr Pro Gly Gly Gly Tyr Ser Pro Gly Asp Trp Gly Phe Ala Ala
865                 870                 875                 880

Phe Thr Leu Leu Cys Leu Phe Leu Cys Tyr Ser Tyr Pro Ala Phe Gly
                885                 890                 895

Ile Ala Pro Leu Leu Gly Val Phe Ser Gly Ser Ser Arg Arg Val Arg
                900                 905                 910

Met Gly Val Phe Gly Cys Trp Leu Ala Phe Ala Val Gly Leu Phe Lys
                915                 920                 925

Pro Val Ser Asp Pro Val Gly Ala Ala Cys Glu Phe Asp Ser Pro Glu
                930                 935                 940

Cys Arg Asn Ile Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
                980                 985                 990

Leu Gly Ile Val Ala Asp Cys Ile  Leu Ala Gly Ala Tyr  Val Leu Ser
                995                 1000                1005

Gln Gly  Arg Cys Lys Lys Cys  Trp Gly Ser Cys Ile  Arg Thr Ala
     1010                1015                1020

Pro Asn  Glu Val Ala Phe Asn  Val Phe Pro Phe Thr  Arg Ala Thr
     1025                1030                1035

Arg Ser  Ser Leu Ile Asp Leu  Cys Asp Arg Phe Cys  Ala Pro Lys
     1040                1045                1050

Gly Met  Asp Pro Ile Phe Leu  Ala Thr Gly Trp Arg  Gly Cys Trp
     1055                1060                1065

Ala Gly  Arg Ser Pro Ile Glu  Gln Pro Ser Glu Lys  Pro Ile Ala
     1070                1075                1080

Phe Ala  Gln Leu Asp Glu Lys  Lys Ile Thr Ala Arg  Thr Val Val
     1085                1090                1095

Ala Gln  Pro Tyr Asp Pro Asn  Gln Ala Val Lys Cys  Leu Arg Val
     1100                1105                1110

Leu Gln  Ala Gly Gly Ala Met  Val Ala Lys Ala Val  Pro Lys Val
     1115                1120                1125

Val Lys  Val Ser Ala Val Pro  Phe Arg Ala Pro Phe  Phe Pro Thr
     1130                1135                1140

Gly Val  Lys Val Asp Pro Asp  Cys Arg Val Val Val  Asp Pro Asp
     1145                1150                1155

Thr Phe  Thr Ala Ala Leu Arg  Ser Gly Tyr Ser Thr  Thr Asn Leu
     1160                1165                1170
```

```
Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 77
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 77

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
        195                 200                 205

Gln Phe Phe Ala Arg His Ser Gly Gly Asn His Pro Asp Gln Val Arg
    210                 215                 220

Leu Gly Lys Ile Leu Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Phe Phe Asp
        275                 280                 285

Trp Asp Val Val Leu Pro Gly Val Glu Ala Ala Thr Gln Thr Ile Lys
    290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335
```

-continued

```
Asn His Tyr Tyr Arg Ala Gln Gly Asp Glu Val Arg His Arg Glu Arg
            340                 345                 350

Leu Thr Ala Val Leu Ser Asn Leu Glu Lys Val Val Arg Glu Glu Tyr
            355                 360                 365

Gly Leu Met Pro Thr Glu Pro Gly Pro Arg Pro Thr Leu Pro Arg Gly
        370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
            405                 410                 415

Asp Leu Lys Thr Trp Val Lys Asn Tyr Pro Arg Trp Thr Pro Pro Pro
        420                 425                 430

Pro Pro Pro Lys Val Gln Pro Arg Lys Thr Lys Pro Val Lys Ser Leu
        435                 440                 445

Pro Glu Arg Lys Pro Val Pro Ala Pro Arg Arg Lys Val Gly Ser Asp
        450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Pro
            485                 490                 495

Ala Thr Pro Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
        515                 520                 525

Arg Gly Thr Val Ser Arg Pro Val Thr Pro Leu Ser Glu Pro Ile Pro
        530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asn Glu Pro Leu Asp Leu Ser Ala
            565                 570                 575

Ser Ser Gln Thr Glu Tyr Glu Ala Ser Pro Ala Pro Pro Gln Ser
            580                 585                 590

Gly Gly Val Leu Gly Val Glu Gly His Glu Ala Glu Glu Thr Leu Ser
        595                 600                 605

Glu Ile Ser Asp Met Ser Gly Asn Ile Lys Pro Ala Ser Val Ser Ser
        610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Pro Cys Ser Gly His Leu Gln Glu
            645                 650                 655

Val Lys Glu Ala Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
        675                 680                 685

Arg Val Asp Met Leu Thr Trp Arg Asn Thr Ser Val Tyr Gln Ala Ile
        690                 695                 700

Cys Thr Leu Asp Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
            725                 730                 735

Ala Pro Ser Val Gly Ala Glu Ser Asp Leu Thr Ile Gly Ser Val Ala
            740                 745                 750

Thr Glu Asp Val Pro Arg Ile Leu Glu Lys Ile Glu Asn Val Gly Glu
        755                 760                 765
```

```
Met Ala Asn Gln Gly Pro Leu Ala Phe Ser Glu Asp Lys Pro Val Asp
    770             775                 780
Asp Gln Leu Val Asn Asp Pro Arg Ile Ser Arg Arg Pro Asp Glu
785             790                 795                 800
Ser Thr Ser Ala Pro Ser Ala Gly Thr Gly Gly Ala Gly Phe Phe Thr
                805                 810                 815
Asp Leu Pro Pro Ser Asp Gly Ala Asp Ala Asp Gly Gly Pro Phe
        820                 825                 830
Arg Thr Val Lys Arg Lys Ala Glu Arg Leu Phe Asp Gln Leu Ser Arg
        835                 840                 845
Gln Val Phe Asp Leu Val Ser His Leu Pro Val Phe Phe Ser Arg Leu
    850                 855                 860
Phe Cys Pro Gly Gly Gly Tyr Ser Pro Gly Asp Trp Gly Phe Ala Ala
865                 870                 875                 880
Leu Thr Leu Leu Cys Leu Phe Leu Cys Tyr Ser Tyr Pro Ala Phe Gly
                885                 890                 895
Ile Ala Pro Leu Leu Gly Val Phe Ser Gly Ser Ser Arg Arg Val Arg
            900                 905                 910
Met Gly Val Phe Gly Cys Trp Leu Ala Phe Ala Val Gly Leu Phe Lys
            915                 920                 925
Pro Val Ser Asp Pro Val Gly Ala Ala Cys Glu Phe Asp Ser Pro Glu
    930                 935                 940
Cys Arg Asn Ile Leu His Ser Phe Glu Leu Leu Lys Pro Trp Asp Pro
945                 950                 955                 960
Val Arg Ser Leu Val Val Gly Pro Val Gly Leu Gly Leu Ala Ile Leu
                965                 970                 975
Gly Arg Leu Leu Gly Gly Ala Arg Cys Ile Trp His Phe Leu Leu Arg
            980                 985                 990
Leu Gly Ile Val Ala Asp Cys Ile Leu Ala Gly Ala Tyr Val Leu Ser
            995                 1000                1005
Gln Gly Arg Cys Lys Lys Cys Trp Gly Ser Cys Ile Arg Thr Ala
    1010                1015                1020
Pro Asn Glu Val Ala Phe Asn Val Phe Pro Phe Thr Arg Ala Thr
    1025                1030                1035
Arg Ser Ser Leu Ile Asp Leu Cys Asp Arg Phe Cys Ala Pro Lys
    1040                1045                1050
Gly Met Asp Pro Ile Phe Leu Ala Thr Gly Trp Arg Gly Cys Trp
    1055                1060                1065
Ala Gly Arg Ser Pro Ile Glu Gln Pro Ser Glu Lys Pro Ile Ala
    1070                1075                1080
Phe Ala Gln Leu Asp Glu Lys Lys Ile Thr Ala Arg Thr Val Val
    1085                1090                1095
Ala Gln Pro Tyr Asp Pro Asn Gln Ala Val Lys Cys Leu Arg Val
    1100                1105                1110
Leu Gln Ala Gly Gly Ala Met Val Ala Lys Ala Val Pro Lys Val
    1115                1120                1125
Val Lys Val Ser Ala Val Pro Phe Arg Ala Pro Phe Phe Pro Thr
    1130                1135                1140
Gly Val Lys Val Asp Pro Asp Cys Arg Val Val Val Asp Pro Asp
    1145                1150                1155
Thr Phe Thr Ala Ala Leu Arg Ser Gly Tyr Ser Thr Thr Asn Leu
    1160                1165                1170
Val Leu Gly Val Gly Asp Phe Ala Gln Leu Asn Gly Leu Lys Ile
```

<210> SEQ ID NO 78
<211> LENGTH: 1233
<212> TYPE: PRT
<213> ORGANISM: Artificial Sequence
<220> FEATURE:
<223> OTHER INFORMATION: Porcine reproductive and respiratory syndrome virus; Nsp2

<400> SEQUENCE: 78

```
Gly Ala Gly Lys Arg Ala Arg Lys Ala Arg Ser Ser Ala Thr Ala Thr
1               5                   10                  15

Val Ala Gly Arg Ala Leu Pro Val Arg Glu Thr Arg Gln Val Glu Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Gly
    50                  55                  60

Asn Arg Met Leu Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Ala
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Glu His Lys Gly Gly Leu Gly Ser Pro Asp Ala Val Glu
145                 150                 155                 160

Val Phe Gly Phe Asp Pro Ala Cys Leu Asp Trp Leu Ala Glu Val Met
                165                 170                 175

His Leu Pro Ser Asn Ala Ile Pro Ala Ala Leu Ala Glu Met Ser Gly
            180                 185                 190

Asp Ser Asn Arg Pro Ala Ser Pro Val Thr Thr Val Trp Thr Val Ser
        195                 200                 205

Gln Phe Leu Ala Arg His Asn Gly Gly Asn His Pro Asp Gln Ile Arg
    210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Met Asp Thr Ser Phe Asp
        275                 280                 285

Trp Asp Val Val Leu Pro Gly Val Glu Ala Ala Thr Gln Thr Thr Glu
    290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335

Asn Tyr Tyr Tyr Arg Ala Gln Gly Asp Glu Val Arg His Arg Glu Arg
```

```
                  340                 345                 350
Leu Thr Ala Val Leu Ser Lys Leu Glu Gly Val Val Arg Glu Glu Tyr
            355                 360                 365
Gly Leu Met Pro Thr Gly Pro Gly Pro Arg Pro Thr Leu Pro Arg Gly
        370                 375                 380
Leu Asp Glu Leu Lys Asp Gln Met Glu Val Asp Leu Leu Lys Leu Ala
385                 390                 395                 400
Asn Ala Gln Met Thr Ser Asp Met Met Ala Trp Ala Val Glu Gln Val
                405                 410                 415
Asp Leu Lys Thr Trp Val Lys Asn Tyr Pro Arg Trp Thr Pro Pro Pro
            420                 425                 430
Pro Pro Pro Ile Val Gln Pro Arg Lys Thr Lys Leu Val Lys Ser Leu
        435                 440                 445
Pro Glu Ser Lys Pro Val Pro Ala Pro Arg Arg Lys Val Arg Ser Asp
    450                 455                 460
Cys Asp Cys Pro Thr Leu Ser Gly Asn Asn Leu Pro Asp Ser Trp Glu
465                 470                 475                 480
Asp Leu Ala Val Gly Cys Pro Ser Asp Leu Pro Thr Ser Pro Glu Pro
                485                 490                 495
Val Thr Pro Leu Ser Glu Pro Ala Ser Val Ser Ala Pro Arg Arg Ser
            500                 505                 510
Phe Arg Pro Val Lys Pro Leu Ser Glu Pro Val Pro Val Pro Ala Pro
        515                 520                 525
Arg Lys Thr Val Ser Arg Pro Ala Thr Pro Leu Ser Glu Pro Ile Pro
    530                 535                 540
Val Pro Ala Pro Arg Arg Lys Phe Gln Gln Val Glu Lys Val Asn Pro
545                 550                 555                 560
Ala Ala Ala Thr Leu Gly Cys Gln Asp Glu Phe Pro Asp Leu Ser Ala
                565                 570                 575
Ser Ser His Thr Glu Tyr Glu Ala Ser Pro Leu Val Leu Pro Gln Asn
            580                 585                 590
Gly Asp Val Leu Glu Val Glu Arg Glu Ala Glu Glu Ile Leu Ser
        595                 600                 605
Gly Ile Ser Asp Ile Leu Asp Ala Ile Lys Pro Ala Ser Ala Ser Ser
    610                 615                 620
Ser Ser Ser Leu Ser Ser Val Ala Ile Thr Arg Pro Lys Tyr Ser Ala
625                 630                 635                 640
Gln Ala Ile Ile Asp Ser Gly Gly Pro Tyr Ser Gly His Leu Gln Glu
                645                 650                 655
Val Lys Glu Thr Cys Leu Ser Ile Met Ser Glu Ala Cys Asp Val Thr
            660                 665                 670
Lys Leu Asp Asp Pro Ala Thr Gln Glu Trp Leu Ser Arg Met Trp Asp
        675                 680                 685
Arg Val Asp Met Leu Thr Trp Arg Asn Thr Ser Val His Gln Ala Ser
    690                 695                 700
Arg Thr Leu Asp Asp Phe Lys Phe Leu Pro Lys Met Ile Leu Glu
705                 710                 715                 720
Thr Pro Pro Pro Tyr Pro Cys Gly Phe Val Met Met Pro Arg Thr Pro
                725                 730                 735
Ala Pro Ser Val Gly Ala Glu Ser Asp Leu Thr Ile Gly Ser Val Ala
            740                 745                 750
Thr Glu Asp Val Pro Arg Ile Phe Gly Lys Val Asn Asp Val Cys Lys
        755                 760                 765
```

-continued

```
Met Ile Asp Gln Arg Pro Leu Val Leu Phe Glu Asn Glu Leu Ala Asp
770                 775                 780

Asp Gln Pro Ala Arg Asp Pro Arg Thr Ser Ser Gln Arg Phe Asp Gly
785                 790                 795                 800

Ser Thr Pro Ala Pro Pro Ala Gly Thr Asp Gly Thr Gly Leu Ala Ser
                805                 810                 815

Gly Pro Gly Val Arg Glu Val Asp Ser Cys Glu Ala Ser Ser Thr Glu
                820                 825                 830

Lys Ile Glu Gln Pro Phe Val Leu Asn Gly Gly Ala Ser Thr Gln Ala
                835                 840                 845

Ser Thr Phe Thr Asn Leu Pro Pro Gly Gly Ile Asp Ala Gly Gly
850                 855                 860

Ser Gly Pro Leu Gln Thr Val Arg Lys Ala Glu Arg Phe Asp
865                 870                 875                 880

Leu Leu Ser Arg Gln Val Phe Asn Leu Val Ser His Leu Pro Val Phe
                885                 890                 895

Phe Ser Arg Leu Phe Lys Pro Gly Gly Asp Tyr Ser Pro Gly Asp Trp
                900                 905                 910

Gly Phe Ala Ala Phe Thr Leu Leu Cys Leu Phe Leu Cys Tyr Ser Tyr
                915                 920                 925

Pro Ala Phe Gly Ala Val Pro Leu Leu Gly Val Phe Ser Gly Ser Ser
930                 935                 940

Arg Arg Val Arg Met Gly Phe Phe Gly Cys Trp Leu Ala Phe Ala Val
945                 950                 955                 960

Ser Leu Phe Lys Pro Val Ser Asp Pro Val Gly Ala Ala Cys Glu Phe
                965                 970                 975

Asp Ser Pro Glu Cys Arg Asn Ile Leu His Ser Phe Glu Leu Leu Lys
                980                 985                 990

Pro Trp Asp Pro Val Arg Gly Leu Val Val Gly Pro Val Gly Leu Ser
                995                 1000                1005

Leu Ala Ile Phe Gly Arg Leu Leu Gly Gly Ala Arg His Ile Trp
         1010                1015                1020

His Phe Leu Leu Arg Phe Gly Ile Val Ala Asp Cys Ile Leu Ala
         1025                1030                1035

Gly Ala Tyr Val Leu Ser Gln Gly Arg Cys Lys Lys Cys Trp Gly
         1040                1045                1050

Ser Cys Ile Arg Thr Ala Pro Asn Glu Val Ala Phe Asn Val Phe
         1055                1060                1065

Pro Phe Thr Arg Ala Thr Arg Ser Ser Leu Ile Asp Leu Cys Asn
         1070                1075                1080

Arg Phe Cys Ala Pro Lys Gly Met Asp Pro Ile Phe Phe Ala Thr
         1085                1090                1095

Gly Trp Arg Gly Cys Trp Thr Gly Arg Ser Pro Ile Glu Gln Pro
         1100                1105                1110

Ser Glu Lys Pro Ile Ala Phe Ala Gln Leu Asp Glu Lys Lys Ile
         1115                1120                1125

Thr Ala Arg Thr Val Val Ala Gln Pro Tyr Asp Pro Asn Gln Ala
         1130                1135                1140

Val Lys Cys Leu Arg Val Leu Gln Ala Gly Gly Val Met Val Ala
         1145                1150                1155

Glu Ala Val Pro Lys Val Val Lys Val Ser Ala Val Pro Phe Arg
         1160                1165                1170

Ala Pro Phe Phe Pro Thr Gly Val Lys Val Asp Pro Glu Cys Arg
         1175                1180                1185
```

```
Ile Val Val Asp Pro Asp Thr Phe Thr Ala Ala Leu Arg Ser Gly
    1190                1195                1200

Tyr Ser Thr Thr Asn Leu Val Leu Gly Val Gly Asp Phe Ala Gln
    1205                1210                1215

Leu Asn Gly Leu Lys Ile Arg Gln Ile Ser Lys Pro Ser Gly Gly
    1220                1225                1230

<210> SEQ ID NO 79
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 79

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
                20                  25                  30

His Glu Val Ala Gly Ala Asn Lys Ala Glu His Leu Lys His Tyr Ser
                35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
                100                 105                 110

Ser Ala Lys Tyr Val Leu Lys Leu Glu Gly Glu His Trp Thr Val Thr
            115                 120                 125

Val Thr Pro Gly Met Ser Pro Ser Leu Leu Pro Leu Glu Cys Val Gln
        130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
                180                 185                 190

Asp Ser Asp Arg Ser Ala Ser Pro Val Thr Thr Val Trp Thr Val Ser
            195                 200                 205

Gln Phe Phe Ala Arg His Ser Gly Gly Asn His Pro Asp Gln Val Arg
        210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Phe Asp Leu Tyr Leu Arg Gly Ala Thr Asn Leu Glu Glu Cys Leu Ala
                260                 265                 270

Arg Leu Glu Lys Ala Arg Pro Pro Arg Val Ile Asp Thr Phe Phe Asp
            275                 280                 285

Trp Asp Val Val Leu Pro Gly Val Glu Ala Ala Thr Gln Thr Ile Lys
        290                 295                 300

Leu Pro Gln Val Asn Gln Cys Arg Ala Leu Val Pro Val Val Thr Gln
305                 310                 315                 320
```

```
Lys Ser Leu Asp Asn Asn Ser Val Pro Leu Thr Ala Phe Ser Leu Ala
            325                 330                 335

Asn Tyr Tyr Arg Ala Gln Gly Asp Glu Val Arg His Arg Glu Arg
            340                 345                 350

Leu Thr Ala Val Leu Ser Lys Leu Glu Lys Val Val Arg Glu Glu Tyr
            355                 360                 365

Gly Leu Met Pro Thr Lys Pro Gly Pro Arg Pro Thr Leu Pro Arg Gly
        370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Ala Glu Gln Val
            405                 410                 415

Asp Leu Lys Thr Trp Val Lys Asn Tyr Pro Arg Trp Thr Pro Pro Pro
            420                 425                 430

Pro Ser Pro Lys Val Gln Leu Arg Lys Thr Lys Pro Val Lys Ser Leu
            435                 440                 445

Pro Lys Arg Lys Pro Val Pro Ala Pro Arg Arg Lys Val Gly Ser Asp
        450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Pro
            485                 490                 495

Ala Ile Pro Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
            515                 520                 525

Arg Gly Thr Val Ser Arg Pro Val Thr Pro Leu Ser Glu Pro Ile Pro
        530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asn Glu Pro Leu Asp Leu Ser Ala
            565                 570                 575

Ser Ser Gln Thr Glu Tyr Glu Ala Ser Pro Ala Pro Pro Gln Ser
            580                 585                 590

Gly Gly Val Leu Gly Val Glu Gly His Glu Ala Glu Glu Thr Leu Ser
        595                 600                 605

Glu Ile Ser Asp Met Ser Gly Asn Ile Lys Pro Ala Ser Val Ser Ser
        610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Pro Cys Ser Gly His Leu Gln Glu
            645                 650                 655

Val Lys Glu Thr Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
            675                 680                 685

Arg Val Asp Met Leu Thr Trp Arg Asn Thr Ser Val Tyr Gln Val Ile
        690                 695                 700

Cys Thr Leu Asp Gly Met Leu Lys Phe Leu Pro Lys Met Ile Leu Glu
705                 710                 715                 720

Thr Pro Pro Pro Tyr Pro Cys Glu Phe Val Met Met Pro His Thr Pro
            725                 730                 735

Ala Pro Ser Val Gly Ala Glu Ser Asp Leu Thr Ile Gly Ser Val Thr
```

-continued

```
                740                 745                 750
Thr Glu Asp Val Pro Arg Ile Leu Glu Lys Ile Gly Asn Val Gly Glu
            755                 760                 765
Met Ala Asn Gln Gly Pro Leu Ala Phe Ser Glu Asp Lys Pro Val Asp
        770                 775                 780
Asp Gln Leu Val Asn Asp Pro Arg Ile Ser Ser Arg Arg Pro Asp Glu
785                 790                 795                 800
Ser Thr Ser Ala Pro Ser Ala Gly Thr Gly Ala Gly Ser Phe Thr
                805                 810                 815
Asp Leu Pro Pro Ser Asp Gly Ala Asp Ala Asp Gly Gly Pro Phe
                820                 825                 830
Arg Thr Val Lys Arg Lys Ala Glu Arg Leu Phe Asp Gln Leu Ser Arg
            835                 840                 845
Gln Val Phe Asp Leu Val Ser His Leu Pro Val Phe Phe Ser Arg Leu
        850                 855                 860
Phe Tyr Pro Gly Gly Tyr Ser Pro Gly Asp Trp Gly Phe Ala Ala
865                 870                 875                 880
Phe Thr Leu Leu Cys Leu Phe Leu Cys Tyr Ser Tyr Pro Ala Phe Gly
                885                 890                 895
Ile Ala Pro Leu Leu Gly Val Phe Ser Gly Ser Ser Arg Arg Val Arg
            900                 905                 910
Met Gly Val Phe Gly Cys Trp Leu Ala Phe Ala Val Gly Leu Phe Lys
        915                 920                 925
Pro Val Ser Asp Pro Val Gly Ala Ala Cys Glu Phe Asp Ser Pro Glu
        930                 935                 940
Cys Arg Asn Ile Leu His Ser Phe Glu Leu Leu Lys Pro Trp Asp Pro
945                 950                 955                 960
Val Arg Ser Leu Val Val Gly Pro Val Gly Leu Gly Leu Ala Ile Leu
            965                 970                 975
Gly Arg Leu Leu Gly Gly Ala Arg Cys Ile Trp His Phe Leu Leu Arg
            980                 985                 990
Leu Gly Ile Val Ala Asp Cys Ile  Leu Ala Gly Ala Tyr  Val Leu Ser
        995                 1000                1005
Gln Gly  Arg Cys Lys Lys Cys  Trp Gly Ser Cys Ile  Arg Thr Ala
    1010                1015                1020
Pro Asn  Glu Val Ala Phe Asn  Val Phe Pro Phe Thr  Arg Ala Thr
    1025                1030                1035
Arg Ser  Ser Leu Ile Asp Leu  Cys Asp Arg Phe Cys  Ala Pro Lys
    1040                1045                1050
Gly Met  Asp Pro Ile Phe Leu  Ala Thr Gly Trp Arg  Gly Cys Trp
    1055                1060                1065
Ala Gly  Arg Ser Pro Ile Glu  Gln Pro Ser Glu Lys  Pro Ile Ala
    1070                1075                1080
Phe Ala  Gln Leu Asp Glu Lys  Lys Ile Thr Ala Arg  Thr Val Val
    1085                1090                1095
Ala Gln  Pro Tyr Asp Pro Asn  Gln Ala Val Lys Cys  Leu Arg Val
    1100                1105                1110
Leu Gln  Ala Gly Gly Ala Met  Val Ala Glu Ala Val  Pro Lys Val
    1115                1120                1125
Val Lys  Val Ser Ala Val Pro  Phe Arg Ala Pro Phe  Phe Pro Thr
    1130                1135                1140
Gly Val  Lys Val Asp Pro Asn  Cys Arg Val Val Val  Asp Pro Asp
    1145                1150                1155
```

```
Thr Phe Thr Ala Ala Leu Arg Ser Gly Tyr Ser Thr Thr Asn Leu
    1160                1165                1170

Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 80
<211> LENGTH: 1196
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 80

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Arg Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
        195                 200                 205

Gln Phe Phe Ala Arg His Ser Gly Gly Asn His Pro Asp Gln Val Arg
    210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Phe Phe Asp
        275                 280                 285

Trp Asp Val Val Leu Pro Gly Val Glu Ala Ala Thr Gln Thr Ile Lys
    290                 295                 300

Leu Pro Gln Val Asn Gln Cys Arg Ala Leu Val Pro Val Val Thr Gln
305                 310                 315                 320
```

-continued

```
Lys Ser Leu Asp Asn Ser Val Pro Leu Thr Ala Phe Ser Leu Ala
            325                 330                 335
Asn Tyr Tyr Arg Ala Gln Gly Asp Glu Val Arg His Arg Glu Arg
            340                 345                 350
Leu Thr Ala Val Leu Ser Asn Leu Glu Lys Val Val Arg Glu Glu Tyr
            355                 360                 365
Gly Leu Met Pro Thr Glu Pro Gly Pro Arg Pro Thr Leu Pro Arg Gly
    370                 375                 380
Leu Asp Glu Leu Lys Asp Gln Met Glu Glu Asp Leu Leu Lys Leu Ala
385                 390                 395                 400
Asn Ala Gln Thr Thr Ser Asp Met Met Ala Trp Ala Val Glu Gln Val
                405                 410                 415
Asp Leu Lys Thr Trp Val Lys Asn Tyr Pro Arg Trp Thr Pro Pro Pro
            420                 425                 430
Pro Pro Pro Lys Val Gln Pro Arg Lys Thr Lys Pro Val Lys Ser Leu
            435                 440                 445
Pro Glu Arg Lys Pro Val Pro Ala Pro Arg Arg Lys Val Gly Ser Asp
        450                 455                 460
Cys Gly Ser Pro Val Ser Leu Gly Gly Asp Val Pro Asn Ser Trp Glu
465                 470                 475                 480
Asp Leu Ala Val Ser Ser Pro Phe Asp Leu Pro Thr Pro Pro Glu Leu
                485                 490                 495
Ala Thr Pro Ser Ser Glu Leu Val Ile Val Ser Ser Pro Gln Cys Ile
            500                 505                 510
Phe Arg Pro Ala Thr Pro Leu Ser Glu Pro Ala Pro Ile Pro Ala Pro
            515                 520                 525
Arg Gly Thr Val Ser Arg Pro Val Thr Pro Leu Ser Glu Pro Ile Pro
        530                 535                 540
Val Pro Ala Pro Arg Arg Lys Phe Gln Gln Val Lys Arg Leu Ser Ser
545                 550                 555                 560
Ala Ala Ala Ile Pro Pro Tyr Gln Asn Glu Pro Leu Asp Leu Ser Ala
                565                 570                 575
Ser Ser Gln Thr Glu Tyr Glu Ala Ser Pro Pro Ala Pro Pro Gln Ser
            580                 585                 590
Gly Gly Val Leu Gly Val Glu Gly His Glu Ala Glu Glu Thr Leu Ser
            595                 600                 605
Glu Ile Ser Asp Met Ser Gly Asn Ile Lys Pro Ala Ser Val Ser Ser
        610                 615                 620
Ser Ser Ser Leu Ser Ser Val Arg Ile Thr Arg Pro Lys Tyr Ser Ala
625                 630                 635                 640
Gln Ala Ile Ile Asp Ser Gly Gly Pro Cys Ser Gly His Leu Gln Glu
                645                 650                 655
Val Lys Glu Thr Cys Leu Ser Val Met Arg Glu Ala Cys Asp Ala Thr
            660                 665                 670
Lys Leu Asp Asp Pro Ala Thr Gln Glu Trp Leu Ser Arg Met Trp Asp
            675                 680                 685
Arg Val Asp Met Leu Thr Cys Asn Thr Ser Val Tyr Gln Ala Ile Cys
        690                 695                 700
Thr Leu Asp Gly Arg Leu Lys Phe Leu Pro Lys Leu Ile Leu Glu Thr
705                 710                 715                 720
Pro Pro Pro Tyr Pro Cys Glu Phe Val Met Met Pro His Thr Pro Ala
                725                 730                 735
Pro Ser Val Gly Ala Glu Ser Asp Leu Thr Ile Gly Ser Val Ala Thr
            740                 745                 750
```

```
Glu Asp Val Pro Arg Ile Leu Glu Lys Thr Glu Asn Val Gly Glu Met
        755                 760                 765
Ala Asn Gln Gly Pro Leu Ala Phe Ser Glu Asp Lys Pro Val Asp Asp
770                 775                 780
Gln Leu Val Asn Asp Pro Arg Ile Ser Ser Arg Pro Asp Glu Ser
785                 790                 795                 800
Thr Ser Ala Pro Ser Ala Gly Thr Gly Gly Ala Gly Ser Phe Thr Asp
                    805                 810                 815
Leu Pro Pro Ser Asp Gly Ala Asp Ala Asp Gly Gly Pro Phe Arg
                820                 825                 830
Thr Val Lys Arg Lys Ala Glu Arg Leu Phe Asp Gln Leu Ser Arg Gln
                835                 840                 845
Val Phe Asp Leu Val Ser His Leu Pro Val Phe Ser Arg Leu Phe
    850                 855                 860
Tyr Pro Gly Gly Gly Tyr Ser Pro Gly Asp Trp Gly Phe Ala Ala Phe
865                 870                 875                 880
Thr Leu Leu Cys Leu Phe Leu Cys Tyr Ser Tyr Pro Ala Phe Gly Ile
                885                 890                 895
Ala Pro Leu Leu Gly Val Phe Ser Gly Ser Ser Arg Arg Val Arg Met
                900                 905                 910
Gly Val Phe Gly Cys Trp Leu Ala Phe Ala Val Gly Leu Phe Lys Pro
                915                 920                 925
Val Ser Asp Pro Val Gly Ala Ala Cys Glu Phe Asp Ser Pro Glu Cys
                930                 935                 940
Arg Asn Ile Leu His Ser Phe Glu Leu Leu Lys Pro Trp Asp Pro Val
945                 950                 955                 960
Arg Ser Leu Val Val Gly Pro Val Gly Leu Gly Leu Ala Ile Leu Gly
                965                 970                 975
Arg Leu Leu Gly Gly Ala Arg Cys Ile Trp His Phe Leu Leu Arg Leu
                980                 985                 990
Gly Ile Val Ala Asp Cys Ile Leu  Ala Gly Ala Tyr Val  Leu Ser Gln
                995                 1000                1005
Gly Arg  Cys Lys Lys Cys Trp  Gly Ser Cys Ile Arg  Thr Ala Pro
        1010                1015                1020
Asn Glu  Val Ala Phe Asn Val  Phe Pro Phe Thr Arg  Ala Thr Arg
        1025                1030                1035
Ser Ser  Leu Ile Asp Leu Cys  Asp Arg Phe Cys Ala  Pro Lys Gly
        1040                1045                1050
Met Asp  Pro Ile Phe Leu Ala  Thr Gly Trp Arg Gly  Cys Trp Ala
        1055                1060                1065
Gly Arg  Ser Pro Ile Glu Gln  Pro Ser Glu Lys Pro  Ile Ala Phe
        1070                1075                1080
Ala Gln  Leu Asp Glu Lys Lys  Ile Thr Ala Arg Thr  Val Val Ala
        1085                1090                1095
Gln Pro  Tyr Asp Pro Asn Gln  Ala Val Lys Cys Leu  Arg Val Leu
        1100                1105                1110
Gln Ala  Gly Gly Ala Met Val  Ala Lys Ala Val Pro  Lys Val Val
        1115                1120                1125
Lys Val  Ser Ala Val Pro Phe  Arg Ala Pro Phe Phe  Pro Thr Gly
        1130                1135                1140
Val Lys  Val Asp Pro Asp Cys  Arg Val Val Val Asp  Pro Asp Thr
        1145                1150                1155
Phe Thr  Ala Ala Leu Arg Ser  Gly Tyr Pro Thr Thr  Asn Leu Val
```

```
                   1160                1165                1170

Leu Gly  Val Gly Asp Phe Ala  Gln Leu Asn Gly Leu  Lys Ile Arg
        1175                1180                1185

Gln Ile  Ser Lys Pro Ser Gly  Gly
    1190                1195

<210> SEQ ID NO 81
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 81

Gly Ala Gly Lys Arg Ala Arg Lys Ala Arg Ser Cys Ala Thr Ala Thr
1               5                   10                  15

Val Ala Gly Arg Ala Leu Ser Val Cys Glu Thr Arg Gln Ala Lys Glu
            20                  25                  30

His Glu Val Ala Gly Thr Asn Lys Ala Glu His Leu Lys His Tyr Ser
        35                  40                  45

Pro Pro Ala Glu Gly Asn Cys Gly Trp His Cys Ile Ser Ala Ile Ala
50                  55                  60

Asn Arg Met Val Asn Ser Ile Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
        195                 200                 205

Gln Phe Phe Ala Arg His Ser Gly Gly Asn His Pro Asp Gln Val Arg
    210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Ser Phe Asp
        275                 280                 285

Trp Asp Val Val Leu Pro Gly Val Glu Ala Ala Thr Gln Met Ile Lys
    290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
```

```
                        325                 330                 335
Asn Tyr Tyr Tyr Arg Ala Gln Gly Asp Glu Val Arg His Arg Glu Arg
                340                 345                 350

Leu Thr Ala Val Leu Ser Lys Leu Glu Lys Val Val Arg Glu Glu Tyr
            355                 360                 365

Gly Leu Val Pro Thr Glu Pro Gly Pro Gln Pro Thr Leu Pro Arg Gly
            370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
                420                 425                 430

Pro Pro Pro Lys Val Gln Pro Arg Lys Thr Lys Pro Val Lys Ser Leu
            435                 440                 445

Pro Glu Arg Lys Pro Val Pro Ala Pro Arg Arg Lys Val Gly Ser Asp
            450                 455                 460

Cys Gly Gly Pro Val Ser Leu Gly Gly Asp Val Pro Asn Ser Trp Glu
465                 470                 475                 480

Asp Leu Ala Val Ser Ser Pro Phe Asp Leu Pro Thr Pro Glu Pro
                485                 490                 495

Ala Thr Pro Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
            515                 520                 525

Arg Gly Thr Val Ser Arg Pro Val Thr Pro Leu Ser Glu Pro Ile Pro
            530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asn Glu Pro Leu Asp Leu Ser Ala
                565                 570                 575

Ser Ser Gln Thr Glu Tyr Glu Ala Ser Pro Ala Pro Pro Gln Ser
            580                 585                 590

Gly Gly Val Leu Gly Val Glu Gly His Glu Ala Glu Glu Thr Leu Ser
            595                 600                 605

Glu Ile Ser Asp Met Ser Gly Asn Ile Lys Pro Ala Ser Val Ser Ser
            610                 615                 620

Ser Ser Ser Leu Ser Ser Val Arg Val Thr Arg Pro Lys Tyr Ser Ala
625                 630                 635                 640

Gln Ala Ile Ile Asp Ser Gly Gly Pro Cys Ser Gly His Leu Gln Glu
                645                 650                 655

Val Lys Glu Thr Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
            675                 680                 685

Arg Val Asp Met Leu Thr Trp Arg Asn Thr Ser Ala Tyr Gln Ala Ile
            690                 695                 700

Cys Thr Leu Asp Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
                725                 730                 735

Ala Pro Ser Val Gly Ala Glu Ser Asp Leu Thr Ile Gly Ser Val Ala
            740                 745                 750
```

```
Thr Glu Asp Val Pro Arg Ile Leu Glu Lys Met Glu Asn Val Gly Glu
        755                 760                 765

Met Ala Asn Gln Gly Pro Leu Ala Phe Ser Glu Asp Lys Pro Val Asp
    770                 775                 780

Asp Gln Leu Val Asn Asp Pro Arg Ile Ser Ser Arg Arg Pro Asp Glu
785                 790                 795                 800

Ser Thr Ser Ala Pro Ser Ala Gly Thr Gly Gly Ser Gly Ser Phe Thr
                805                 810                 815

Asp Leu Pro Pro Ser Asp Gly Ala Asp Ala Asp Gly Gly Gly Pro Phe
            820                 825                 830

Arg Thr Ala Lys Arg Lys Ala Glu Arg Leu Phe Asp Gln Leu Ser Arg
        835                 840                 845

Gln Val Phe Asp Leu Val Ser His Leu Pro Val Phe Phe Ser Arg Leu
    850                 855                 860

Phe His Pro Gly Gly Gly Tyr Ser Pro Gly Asp Trp Gly Phe Ala Ala
865                 870                 875                 880

Phe Thr Leu Leu Cys Leu Phe Leu Cys Tyr Ser Tyr Pro Ala Phe Gly
                885                 890                 895

Ile Ala Pro Leu Leu Gly Val Phe Ser Gly Ser Ser Arg Arg Val Arg
            900                 905                 910

Met Gly Val Phe Gly Cys Trp Leu Ala Phe Ala Val Gly Leu Phe Lys
        915                 920                 925

Pro Val Ser Asp Pro Val Gly Ala Ala Cys Glu Phe Asp Ser Pro Glu
    930                 935                 940

Cys Arg Asn Ile Leu His Ser Phe Glu Leu Leu Lys Pro Trp Asp Pro
945                 950                 955                 960

Val Arg Gly Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
            980                 985                 990

Leu Gly Ile Val Ala Asp Cys Ile  Leu Ala Gly Ala Tyr  Val Leu Ser
        995                 1000                1005

Gln Gly  Arg Cys Lys Lys Cys  Trp Gly Ser Cys Ile  Arg Thr Ala
    1010                1015                1020

Pro Asn  Glu Val Ala Phe Asn  Val Phe Pro Phe Thr  Arg Ala Thr
    1025                1030                1035

Arg Ser  Ser Leu Ile Asp Leu  Cys Asp Arg Leu Cys  Ala Pro Lys
    1040                1045                1050

Gly Met  Asp Pro Ile Ser Leu  Ala Thr Gly Trp Arg  Gly Cys Trp
    1055                1060                1065

Ala Gly  Arg Ser Pro Ile Glu  Gln Pro Ser Glu Lys  Pro Ile Ala
    1070                1075                1080

Phe Ala  Gln Leu Asp Glu Lys  Lys Ile Thr Ala Arg  Thr Val Ala
    1085                1090                1095

Ala Gln  Pro Tyr Asp Pro Asn  Gln Ala Val Lys Cys  Leu Arg Val
    1100                1105                1110

Leu Gln  Ala Gly Gly Ala Met  Val Ala Glu Ala Val  Pro Lys Val
    1115                1120                1125

Val Lys  Val Ser Ala Val Pro  Phe Arg Ala Pro Phe  Phe Pro Thr
    1130                1135                1140

Gly Val  Lys Val Asp Pro Asp  Cys Arg Val Val Val  Asp Pro Asp
    1145                1150                1155

Thr Phe  Thr Ala Ala Leu Arg  Ser Gly Tyr Ser Thr  Thr Asn Leu
    1160                1165                1170
```

```
Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 82
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 82

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asp Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Ile Phe Glu Thr Thr Leu Pro Glu Arg Val
65              70                  75                  80

Arg Pro Pro Asp Asp Trp Ala Thr Asp Asp Leu Ala Asn Ala Ile
            85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Glu His Lys Gly Gly Leu Gly Ser Pro Asp Ala Ile Glu
145                 150                 155                 160

Val Ser Gly Phe Asp Pro Ala Cys Leu Asp Trp Leu Ala Glu Val Met
            165                 170                 175

His Leu Pro Ser Ser Ala Ile Pro Ala Ala Leu Ala Glu Met Ser Gly
        180                 185                 190

Asp Ser Asp Arg Ser Ala Ser Pro Val Thr Thr Val Trp Thr Val Ser
    195                 200                 205

Gln Phe Phe Ala Arg His Ser Gly Gly Asn His Pro Asp Gln Val Arg
210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
            245                 250                 255

Ile Asp Leu Tyr Leu Arg Gly Ala Thr Asn Leu Glu Glu Cys Leu Ala
        260                 265                 270

Arg Leu Glu Lys Ala Arg Pro Pro Arg Val Ile Asp Thr Ser Phe Asp
    275                 280                 285

Trp Asp Val Val Leu Pro Gly Val Glu Ala Ala Thr Gln Thr Asn Lys
290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
            325                 330                 335
```

```
Asn Tyr Tyr Tyr Arg Ala Gln Gly Asp Glu Val Arg His Arg Glu Arg
            340                 345                 350

Leu Thr Ala Val Leu Ser Lys Leu Glu Glu Val Val Arg Glu Glu Tyr
        355                 360                 365

Gly Leu Met Pro Thr Glu Pro Gly Pro Arg Pro Thr Leu Pro Arg Gly
    370                 375                 380

Leu Asp Glu Leu Lys Asp Gln Met Glu Asp Leu Leu Arg Leu Ala
385                 390                 395                 400

Asn Ala Gln Ala Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
            420                 425                 430

Pro Pro Pro Lys Val Gln Pro Arg Lys Thr Lys Pro Val Lys Ser Leu
        435                 440                 445

Pro Glu Arg Lys Pro Val Pro Ala Pro Arg Arg Lys Val Gly Pro Asp
    450                 455                 460

Cys Gly Ser Pro Val Ser Leu Gly Gly Asp Val Pro Asn Ser Trp Glu
465                 470                 475                 480

Asp Leu Ala Val Ser Ser Pro Leu Asp Leu Pro Thr Pro Pro Glu Pro
                485                 490                 495

Ala Thr Leu Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
        515                 520                 525

Arg Gly Thr Val Ser Arg Pro Val Thr Pro Leu Ser Glu Pro Ile Pro
    530                 535                 540

Val Pro Ala Pro Arg Arg Lys Phe Gln Gln Val Lys Arg Leu Ser Ser
545                 550                 555                 560

Ala Ala Ala Val Pro Leu His Gln Asn Glu Pro Leu Asp Leu Ser Ala
                565                 570                 575

Ser Ser Gln Thr Glu Tyr Glu Ala Ser Pro Ser Ala Pro Pro Gln Ser
            580                 585                 590

Gly Gly Val Leu Gly Val Glu Gly His Glu Ala Glu Glu Thr Leu Ser
        595                 600                 605

Glu Ile Ser Asp Met Ser Gly Asn Ile Lys Pro Ala Ser Val Ser Ser
    610                 615                 620

Ser Ser Ser Leu Ser Ser Val Glu Ile Thr Arg Pro Lys Tyr Ser Ala
625                 630                 635                 640

Gln Ala Ile Ile Asp Ser Gly Gly Pro Cys Ser Gly His Leu Gln Gly
                645                 650                 655

Val Lys Glu Thr Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
        675                 680                 685

Arg Val Asp Met Leu Thr Trp Arg Asn Thr Ser Val Cys Gln Ala Ile
    690                 695                 700

Arg Thr Leu Asp Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
                725                 730                 735

Ala Pro Ser Val Gly Ala Glu Ser Asp Leu Thr Ile Gly Ser Val Ala
            740                 745                 750

Thr Glu Asp Val Pro Arg Ile Leu Glu Lys Ile Glu Asn Val Gly Glu
```

```
                    755                 760                 765
Met Ala Asn Gln Glu Pro Ser Ala Phe Ser Glu Asp Lys Pro Val Asp
770                 775                 780

Asp Gln Leu Val Asn Asp Pro Arg Ile Ser Ser Arg Arg Pro Asp Glu
785                 790                 795                 800

Ser Thr Ala Ala Pro Ser Ala Gly Thr Gly Ala Gly Ser Phe Thr
                805                 810                 815

Asp Leu Pro Ser Ser Asp Gly Ala Asp Ala Asp Gly Gly Pro Phe
                820                 825                 830

Arg Thr Ala Lys Arg Lys Ala Glu Arg Leu Phe Asp Gln Leu Ser Arg
                835                 840                 845

Gln Val Phe Asp Leu Val Ser His Leu Pro Val Phe Phe Ser Arg Leu
850                 855                 860

Phe His Pro Gly Gly Gly Tyr Ser Thr Gly Asp Trp Gly Phe Ala Ala
865                 870                 875                 880

Phe Thr Leu Leu Cys Leu Phe Leu Cys Tyr Ser Tyr Pro Ala Phe Gly
                885                 890                 895

Ile Ala Pro Leu Leu Gly Val Phe Ser Gly Thr Ser Arg Arg Val Arg
                900                 905                 910

Met Gly Val Phe Gly Cys Trp Leu Ala Phe Ala Val Gly Leu Phe Lys
                915                 920                 925

Pro Val Ser Asp Pro Val Gly Ala Ala Cys Glu Phe Asp Ser Pro Glu
                930                 935                 940

Cys Arg Asn Ile Leu Leu Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
                980                 985                 990

Leu Gly Ile Val Ala Asp Cys Ile  Leu Ala Gly Ala Tyr  Val Leu Ser
                995                 1000                1005

Gln Gly  Arg Cys Lys Lys Cys  Trp Gly Ser Cys Ile  Arg Thr Ala
    1010                1015                1020

Pro Asn  Glu Val Ala Phe Asn  Val Phe Pro Phe Thr  Arg Ala Thr
    1025                1030                1035

Arg Ser  Ser Leu Ile Asp Leu  Cys Asp Arg Phe Cys  Ala Pro Lys
    1040                1045                1050

Gly Met  Asp Pro Ile Phe Leu  Ala Thr Gly Trp Arg  Gly Cys Trp
    1055                1060                1065

Ala Gly  Arg Ser Pro Ile Glu  Gln Pro Ser Glu Lys  Pro Ile Ala
    1070                1075                1080

Phe Ala  Gln Leu Asp Glu Lys  Lys Ile Thr Ala Arg  Thr Val Val
    1085                1090                1095

Ala Gln  Pro Tyr Asp Pro Asn  Gln Ala Val Lys Cys  Leu Arg Val
    1100                1105                1110

Leu Gln  Ala Gly Gly Ala Met  Val Ala Glu Ala Val  Pro Lys Val
    1115                1120                1125

Val Lys  Val Ser Ala Val Pro  Phe Arg Ala Pro Phe  Phe Pro Thr
    1130                1135                1140

Gly Val  Lys Val Asp Pro Asp  Cys Arg Val Val Val  Asp Pro Asp
    1145                1150                1155

Thr Phe  Thr Ala Ala Leu Arg  Ser Gly Tyr Ser Thr  Thr Asn Leu
    1160                1165                1170
```

```
Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 83
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 83

Gly Ala Gly Lys Arg Ala Arg Lys Ala Arg Ser Gly Ala Thr Thr Met
1               5                   10                  15

Val Ala His Arg Ala Leu Ser Ala Arg Glu Thr Arg Gln Ala Lys Lys
                20                  25                  30

His Glu Gly Ala Asp Ala Asn Lys Ala Glu His Leu Glu His Tyr Ser
            35                  40                  45

Pro Pro Ala Glu Gly Asn Cys Gly Trp His Cys Ile Ser Ala Ile Ala
        50                  55                  60

Asn Arg Met Val Asn Ser Asn Phe Glu Thr Thr Leu Pro Glu Arg Ala
65                  70                  75                  80

Arg Pro Leu Asp Asp Trp Ala Thr Asp Glu Asp Leu Val Asn Thr Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Arg Leu Glu Gly Glu His Trp Thr Val Ser
        115                 120                 125

Val Thr Pro Gly Met Ser Pro Ser Leu Leu Pro Leu Glu Cys Val Gln
    130                 135                 140

Gly Cys Cys Glu His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Pro Val
            180                 185                 190

Asp Ser Asn Arg Pro Ala Ser Pro Val Thr Thr Ala Trp Thr Val Ser
        195                 200                 205

Gln Phe Tyr Ala Arg His Arg Gly Gly Asn His Arg Asp Gln Val Cys
    210                 215                 220

Leu Gly Lys Ile Ile Ser Leu Cys Gln Val Ile Glu Asp Cys Cys Cys
225                 230                 235                 240

His Gln Asn Lys Thr Asn Arg Ala Thr Pro Glu Glu Val Ala Ala Lys
                245                 250                 255

Ile Asp Gln Tyr Leu Arg Gly Ala Thr Ser Leu Glu Glu Cys Leu Ile
            260                 265                 270

Lys Leu Glu Arg Val Ser Pro Pro Ser Ala Ala Asp Thr Ser Phe Asp
        275                 280                 285

Trp Asn Val Val Leu Pro Gly Val Glu Ala Ala Asn Gln Thr Thr Lys
    290                 295                 300

Gln Leu His Val Asn Gln Cys Arg Ala Leu Val Pro Val Val Thr Gln
305                 310                 315                 320

Glu Pro Leu Asp Lys Asp Ser Val Pro Leu Thr Ala Phe Ser Leu Ser
                325                 330                 335
```

-continued

```
Asn Cys Tyr Tyr Pro Ala Gln Gly Asp Glu Val Arg His Arg Glu Arg
            340                 345                 350

Leu Asn Ser Val Leu Ser Lys Leu Glu Gly Val Val Leu Glu Glu Tyr
            355                 360                 365

Gly Leu Met Ser Thr Gly Leu Gly Pro Arg Pro Val Leu Pro Ser Gly
            370                 375                 380

Leu Asp Glu Leu Lys Asp Gln Met Glu Glu Asp Leu Leu Lys Leu Ala
385                 390                 395                 400

Asn Ala Gln Ala Thr Ser Glu Met Met Ala Trp Ala Ala Glu Gln Val
                    405                 410                 415

Asp Leu Lys Ala Trp Val Lys Ser Tyr Pro Arg Trp Thr Pro Pro Pro
            420                 425                 430

Pro Pro Pro Arg Val Gln Pro Arg Lys Thr Lys Pro Val Lys Ser Leu
            435                 440                 445

Pro Glu Asn Lys Pro Val Pro Ala Pro Arg Arg Lys Val Gly Ser Asp
            450                 455                 460

Cys Gly Ser Pro Ile Leu Met Gly Asp Asn Val Pro Asn Gly Trp Glu
465                 470                 475                 480

Asp Phe Ala Val Gly Gly Pro Leu Asp Phe Pro Thr Pro Ser Glu Pro
                    485                 490                 495

Met Thr Pro Leu Ser Glu Pro Val Leu Met Pro Ala Ser Gln His Ile
            500                 505                 510

Pro Arg Pro Val Thr Pro Leu Ser Gly Pro Ala Pro Val Pro Ala Pro
            515                 520                 525

Arg Arg Thr Val Ser Arg Pro Met Thr Pro Leu Ser Glu Pro Ile Phe
            530                 535                 540

Val Ser Ala Pro Arg His Lys Phe Gln Gln Val Glu Glu Ala Asn Pro
545                 550                 555                 560

Ala Ala Thr Thr Leu Thr Tyr Gln Asp Glu Pro Leu Asp Leu Ser Ala
                    565                 570                 575

Phe Ser Gln Thr Glu Cys Glu Ala Ser Pro Leu Ala Pro Leu Gln Asn
            580                 585                 590

Met Gly Ile Leu Glu Ala Gly Gly Gln Glu Ala Glu Glu Val Leu Ser
            595                 600                 605

Gly Ile Ser Asp Ile Leu Asn Asp Ile Asn Pro Ala Pro Val Ser Ser
            610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Gly Pro Cys Ser Gly His Leu Gln Arg
                    645                 650                 655

Glu Lys Glu Ala Cys Leu Ser Ile Met Arg Glu Ala Cys Asp Ala Ala
            660                 665                 670

Lys Leu Ser Asp Pro Ala Thr Gln Glu Trp Leu Ser Arg Met Trp Asp
            675                 680                 685

Arg Val Asp Met Leu Thr Trp Arg Asn Thr Ser Ala Tyr Gln Ala Leu
            690                 695                 700

His Thr Leu Asp Gly Arg Ser Gly Phe Leu Pro Lys Met Ile Leu Glu
705                 710                 715                 720

Thr Pro Pro His Pro Cys Gly Phe Val Met Leu Pro His Thr Pro
                    725                 730                 735

Ala Pro Ser Val Ser Ala Lys Ser Asp Leu Thr Ile Gly Ser Val Ala
            740                 745                 750

Thr Glu Asp Val Pro Arg Ile Leu Gly Lys Ile Glu Asn Thr Gly Glu
            755                 760                 765
```

Met Leu Asn Gln Gly Pro Leu Ala Pro Phe Glu Glu Pro Val Cys
770                 775                 780

Asp Gln Pro Ala Lys Asp Ser Arg Ile Ser Ser Arg Gly Ser Gly Glu
785                 790                 795                 800

Ser Thr Thr Ala Pro Ser Ala Asp Thr Gly Gly Ala Gly Leu Phe Thr
                805                 810                 815

Asp Leu Leu Pro Ser Asp Gly Met Asp Ala Asp Gly Gly Pro Leu
        820                 825                 830

Arg Thr Val Lys Lys Thr Glu Lys Leu Phe Asp Gln Leu Ser Arg
        835                 840                 845

Gln Val Phe Asn Leu Val Ser His Leu Pro Val Phe Phe Ser His Leu
850                 855                 860

Phe Lys Ser Asp Ser Gly Tyr Ser Ser Gly Asp Trp Ser Phe Ala Ala
865                 870                 875                 880

Phe Thr Leu Phe Cys Leu Phe Leu Cys Tyr Ser Tyr Pro Phe Phe Gly
                885                 890                 895

Phe Ala Pro Leu Leu Gly Val Phe Ser Gly Ser Ser Arg Arg Val Arg
                900                 905                 910

Met Gly Val Phe Gly Cys Trp Leu Ala Phe Ala Val Gly Leu Phe Lys
                915                 920                 925

Pro Val Ser Asp Pro Val Gly Thr Ala Cys Glu Phe Asp Ser Pro Glu
930                 935                 940

Cys Arg Asn Val Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Tyr Ile Trp His Phe Leu Leu Arg
                980                 985                 990

Leu Gly Ile Val Ala Asp Cys Ile Leu Ala Gly Ala Tyr Val Leu Ser
                995                 1000                1005

Gln Gly Arg Cys Lys Lys Cys Trp Gly Ser Cys Val Arg Thr Ala
        1010                1015                1020

Pro Asn Glu Ile Ala Phe Asn Val Phe Pro Phe Thr Arg Ala Thr
        1025                1030                1035

Arg Ser Ser Leu Ile Asp Leu Cys Asp Arg Phe Cys Ala Pro Lys
        1040                1045                1050

Cys Met Asp Pro Ile Phe Leu Ala Thr Gly Trp Arg Gly Cys Trp
        1055                1060                1065

Thr Gly Arg Ser Pro Ile Glu Gln Pro Ser Glu Lys Pro Ile Ala
        1070                1075                1080

Phe Ala Gln Leu Asp Glu Lys Lys Ile Thr Ala Arg Thr Val Val
        1085                1090                1095

Ala Gln Pro Tyr Asp Pro Asn Gln Ala Val Lys Cys Leu Arg Val
        1100                1105                1110

Leu Gln Ala Gly Gly Ala Met Val Ala Glu Ala Val Pro Lys Val
        1115                1120                1125

Val Lys Val Ser Ala Ile Pro Phe Arg Ala Pro Phe Phe Pro Thr
        1130                1135                1140

Gly Val Lys Val Asp Pro Glu Cys Arg Ile Val Val Asp Pro Asp
        1145                1150                1155

Thr Phe Thr Thr Ala Leu Arg Ser Gly Tyr Ser Thr Thr Asn Leu
        1160                1165                1170

Val Leu Gly Val Gly Asp Phe Ala Gln Leu Asn Gly Leu Lys Ile

-continued

```
          1175                1180                1185
Arg Gln  Ile Ser Lys Pro Ser   Gly Gly
    1190                1195
```

<210> SEQ ID NO 84
<211> LENGTH: 1186
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 84

```
Gly Ala Gly Lys Arg Ala Arg Lys Ala Arg Ser Gly Ala Thr Thr Thr
1               5                   10                  15

Val Ala His Arg Ala Ser Ser Ala Arg Glu Thr Arg Gln Ala Lys Lys
            20                  25                  30

His Glu Gly Val Asp Ala Asn Asn Ala Ala His Leu Glu His Tyr Ser
        35                  40                  45

Pro Pro Ala Glu Gly Asn Cys Gly Trp His Cys Ile Ser Ala Ile Val
    50                  55                  60

Asn Arg Met Val Asn Ser Asn Phe Glu Thr Thr Leu Pro Glu Arg Val
65                  70                  75                  80

Arg Pro Ser Asp Asp Trp Ala Thr Asp Glu Asp Phe Val Asn Thr Ile
                85                  90                  95

Gln Ile Leu Arg Leu Pro Ala Ala Leu Asp Arg Asn Gly Ala Cys Lys
            100                 105                 110

Ser Ala Lys Tyr Val Leu Lys Leu Glu Gly Glu His Trp Thr Val Ser
        115                 120                 125

Val Ala Pro Gly Met Ser Pro Ser Leu Leu Pro Leu Glu Cys Val Gln
    130                 135                 140

Gly Cys Cys Glu His Lys Gly Gly Leu Gly Ser Pro Asp Ala Val Glu
145                 150                 155                 160

Val Ser Gly Phe Asp Pro Thr Cys Leu Asp Arg Leu Ala Glu Val Met
                165                 170                 175

His Leu Pro Ser Ser Val Ile Pro Ala Ala Leu Ala Glu Met Ser Asn
            180                 185                 190

Asn Ser Asp Arg Pro Ala Ser Leu Val Asn Thr Ala Trp Thr Val Ser
        195                 200                 205

Gln Phe Tyr Ala Arg His Thr Gly Gly Asn His Arg Asp Gln Val Arg
    210                 215                 220

Leu Gly Lys Ile Ile Ser Leu Cys Gln Val Ile Glu Glu Cys Cys Cys
225                 230                 235                 240

His Gln Asn Lys Thr Asn Arg Ala Thr Pro Glu Glu Val Ala Ala Lys
                245                 250                 255

Ile Asp Gln Tyr Leu Arg Gly Ala Thr Ser Leu Glu Glu Cys Leu Ile
            260                 265                 270

Lys Leu Glu Arg Val Ser Pro Pro Ser Ala Ala Asp Thr Ser Phe Asp
        275                 280                 285

Trp Asn Val Val Leu Pro Gly Val Glu Ala Ala Gly Pro Thr Thr Glu
    290                 295                 300

Gln Pro His Ala Asn Gln Cys Cys Ala Pro Val Pro Val Val Thr Gln
305                 310                 315                 320

Glu Pro Leu Asp Lys Asp Ser Val Pro Leu Thr Ala Phe Ser Leu Ser
                325                 330                 335

Asn Cys Tyr Tyr Pro Ala Gln Gly Asp Glu Val Arg His Arg Glu Arg
```

-continued

```
                340                 345                 350
Leu Asn Ser Val Leu Ser Lys Leu Glu Glu Val Val Leu Glu Glu Tyr
                355                 360                 365
Gly Leu Met Pro Thr Gly Leu Gly Pro Arg Pro Val Leu Pro Ser Gly
                370                 375                 380
Leu Asp Glu Leu Lys Asp Gln Met Glu Glu Asp Leu Leu Lys Leu Ala
385                 390                 395                 400
Asn Ala Gln Ala Thr Ser Glu Met Met Ala Leu Ala Ala Glu Gln Val
                405                 410                 415
Asp Leu Lys Ala Trp Val Lys Ser Tyr Pro Arg Trp Ile Pro Pro Pro
                420                 425                 430
Pro Pro Pro Lys Val Gln Pro Arg Arg Met Lys Pro Val Lys Ser Leu
                435                 440                 445
Pro Glu Asn Lys Pro Val Pro Ala Pro Arg Arg Lys Val Arg Ser Asp
                450                 455                 460
Pro Gly Lys Ser Ile Leu Ala Val Gly Gly Pro Leu Asn Phe Ser Thr
465                 470                 475                 480
Pro Ser Glu Leu Val Thr Pro Leu Gly Glu Pro Val Leu Met Pro Ala
                485                 490                 495
Ser Gln His Val Ser Arg Pro Val Thr Pro Leu Ser Glu Pro Ala Pro
                500                 505                 510
Val Pro Ala Pro Arg Arg Ile Val Ser Arg Pro Met Thr Pro Leu Ser
                515                 520                 525
Glu Pro Thr Phe Val Phe Ala Pro Trp Arg Lys Ser Gln Gln Val Glu
                530                 535                 540
Glu Ala Asn Pro Ala Ala Ala Thr Leu Thr Cys Gln Asp Glu Pro Leu
545                 550                 555                 560
Asp Leu Ser Ala Ser Ser Gln Thr Glu Tyr Glu Ala Tyr Pro Leu Ala
                565                 570                 575
Pro Leu Glu Asn Ile Gly Val Leu Glu Ala Gly Gly Gln Glu Ala Glu
                580                 585                 590
Glu Val Leu Ser Gly Ile Ser Asp Ile Leu Asp Asn Thr Asn Pro Ala
                595                 600                 605
Pro Val Ser Ser Ser Ser Ser Leu Ser Ser Val Lys Ile Thr Arg Pro
                610                 615                 620
Lys Tyr Ser Ala Gln Ala Ile Ile Asp Ser Gly Gly Pro Cys Ser Gly
625                 630                 635                 640
His Leu Gln Lys Glu Lys Glu Ala Cys Leu Arg Ile Met Arg Glu Ala
                645                 650                 655
Cys Asp Ala Ala Arg Leu Gly Asp Pro Ala Thr Gln Glu Trp Leu Ser
                660                 665                 670
His Met Trp Asp Arg Val Asp Val Leu Thr Trp Arg Asn Thr Ser Val
                675                 680                 685
Tyr Gln Ala Phe Arg Thr Leu Asp Gly Arg Phe Gly Phe Leu Pro Lys
                690                 695                 700
Met Ile Leu Glu Thr Pro Pro Tyr Pro Cys Gly Phe Val Met Leu
705                 710                 715                 720
Pro His Thr Pro Thr Pro Ser Val Ser Ala Glu Ser Asp Leu Thr Ile
                725                 730                 735
Gly Ser Val Ala Thr Glu Asp Val Pro Arg Ile Leu Gly Lys Thr Glu
                740                 745                 750
Asn Thr Gly Asn Val Leu Asn Gln Lys Pro Leu Ala Leu Phe Glu Glu
                755                 760                 765
```

-continued

```
Glu Pro Val Cys Asp Gln Pro Ala Lys Asp Ser Arg Thr Leu Ser Arg
770                 775                 780
Glu Ser Gly Asp Ser Thr Thr Ala Pro Pro Val Gly Thr Gly Gly Ala
785                 790                 795                 800
Gly Leu Pro Thr Asp Leu Pro Pro Leu Asp Gly Val Asp Ala Asp Gly
                805                 810                 815
Gly Gly Leu Leu Arg Thr Ala Lys Gly Lys Ala Glu Arg Phe Phe Asp
                820                 825                 830
Gln Leu Ser Arg Gln Val Phe Asn Ile Val Ser His Leu Pro Val Phe
                835                 840                 845
Phe Ser His Leu Phe Lys Ser Asp Ser Gly Tyr Ser Pro Gly Asp Trp
850                 855                 860
Gly Phe Ala Ala Phe Thr Leu Phe Cys Leu Phe Leu Cys Tyr Ser Tyr
865                 870                 875                 880
Pro Phe Phe Gly Phe Ala Pro Leu Leu Gly Val Phe Ser Gly Ser Ser
                885                 890                 895
Arg Arg Val Arg Met Gly Val Phe Gly Cys Trp Leu Ala Phe Ala Val
                900                 905                 910
Gly Leu Phe Lys Pro Val Ser Asp Pro Val Gly Ala Ala Cys Glu Phe
                915                 920                 925
Asp Ser Pro Glu Cys Arg Asn Ile Leu His Ser Phe Glu Leu Leu Lys
930                 935                 940
Pro Trp Asp Pro Val Arg Ser Leu Val Val Gly Gly Pro Val Gly Leu
945                 950                 955                 960
Gly Leu Ala Ile Leu Gly Arg Leu Leu Gly Gly Ala Arg Tyr Ile Trp
                965                 970                 975
His Phe Leu Leu Arg Leu Gly Ile Val Ala Asp Cys Ile Leu Ala Gly
                980                 985                 990
Ala Tyr Val Leu Ser Gln Gly Arg Cys Lys Lys Cys Trp Gly Ser Cys
                995                1000                1005
Ile Arg Thr Ala Pro Asn Glu Ile Ala Phe Asn Val Phe Pro Phe
1010                1015                1020
Thr Arg Ala Thr Arg Ser Ser Leu Ile Asp Leu Cys Asp Arg Phe
1025                1030                1035
Cys Ala Pro Lys Gly Met Asp Pro Ile Phe Leu Ala Thr Gly Trp
1040                1045                1050
Arg Gly Cys Trp Thr Gly Gln Ser Pro Ile Glu Gln Pro Ser Glu
1055                1060                1065
Lys Pro Ile Ala Phe Ala Gln Leu Asp Glu Lys Arg Ile Thr Ala
1070                1075                1080
Arg Thr Val Val Ser Gln Pro Tyr Asp Pro Asn Gln Ala Val Lys
1085                1090                1095
Cys Leu Arg Val Leu Gln Ala Gly Gly Ala Met Val Ala Glu Ala
1100                1105                1110
Val Pro Lys Val Val Lys Val Ser Ala Ile Pro Phe Arg Ala Pro
1115                1120                1125
Phe Phe Pro Thr Gly Val Lys Val Asp Pro Glu Cys Arg Ile Val
1130                1135                1140
Val Asp Pro Asp Thr Phe Thr Thr Ala Leu Arg Ser Gly Tyr Ser
1145                1150                1155
Thr Thr Asn Leu Val Leu Gly Val Gly Asp Phe Ala Gln Leu Asn
1160                1165                1170
Gly Leu Lys Ile Arg Gln Ile Ser Lys Pro Ser Gly Gly
1175                1180                1185
```

<210> SEQ ID NO 85
<211> LENGTH: 1191
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 85

```
Gly Ala Gly Lys Arg Ala Arg Ala Arg Ser Gly Ala Thr Ala Thr
1               5                   10                  15

Val Ala His Cys Ala Leu Pro Ala Arg Glu Ala Gln Gln Ala Lys Lys
            20                  25                  30

Leu Glu Val Ala Ser Ala Asn Arg Ala Glu His Leu Lys Tyr Tyr Ser
        35                  40                  45

Pro Pro Ala Asp Gly Asn Cys Gly Trp His Cys Ile Ser Ala Ile Thr
    50                  55                  60

Asn Arg Met Val Asn Ser Lys Phe Glu Thr Thr Leu Pro Glu Arg Val
65                  70                  75                  80

Arg Pro Ser Asp Asp Trp Ala Thr Asp Glu Asp Leu Val Asn Thr Ile
                85                  90                  95

Gln Ile Leu Arg Leu Pro Ala Ala Leu Asp Arg Asn Gly Ala Cys Ala
            100                 105                 110

Gly Ala Lys Tyr Val Leu Lys Leu Glu Gly Glu His Trp Thr Val Ser
        115                 120                 125

Val Thr Pro Gly Met Thr Pro Ser Leu Leu Pro Leu Glu Cys Val Gln
    130                 135                 140

Gly Cys Cys Glu His Lys Ser Gly Leu Gly Phe Pro Asp Val Val Glu
145                 150                 155                 160

Val Ser Gly Phe Asp Pro Ala Cys Leu Asp Arg Leu Ala Glu Ile Met
                165                 170                 175

His Leu Pro Ser Ser Val Ile Pro Ala Ala Leu Ala Glu Met Ser Asp
            180                 185                 190

Asp Phe Asn Arg Leu Ala Ser Pro Ala Ala Thr Val Trp Thr Val Ser
        195                 200                 205

Gln Phe Phe Ala Arg His Arg Gly Gly Glu His Pro Asp Gln Val Cys
    210                 215                 220

Leu Gly Lys Ile Ile Asn Leu Cys Gln Val Ile Glu Glu Cys Cys Cys
225                 230                 235                 240

Ser Arg Asn Lys Ala Asn Arg Ala Thr Pro Glu Glu Val Ala Ala Lys
                245                 250                 255

Val Asp Gln Tyr Leu Arg Gly Ala Ala Ser Leu Gly Glu Cys Leu Ala
            260                 265                 270

Lys Leu Glu Arg Ala Arg Pro Pro Ser Ala Met Asp Thr Ser Phe Asp
        275                 280                 285

Trp Asn Val Val Leu Pro Gly Val Glu Thr Ala Asp Gln Thr Thr Lys
    290                 295                 300

Gln Leu His Val Asn Gln Cys Arg Ala Leu Val Pro Val Val Thr Gln
305                 310                 315                 320

Glu Pro Leu Asp Arg Asp Ser Val Pro Leu Thr Ala Phe Ser Leu Ser
                325                 330                 335

Asn Cys Tyr Tyr Pro Ala Gln Gly Asp Glu Val Arg His Arg Glu Arg
            340                 345                 350

Leu Asn Ser Val Leu Ser Lys Leu Glu Gly Val Val Arg Glu Glu Tyr
        355                 360                 365
```

```
Gly Leu Thr Pro Thr Gly Pro Gly Pro Arg Pro Ala Leu Pro Asn Gly
    370                 375                 380

Leu Asp Glu Leu Lys Asp Gln Met Glu Glu Asp Leu Leu Lys Leu Val
385                 390                 395                 400

Asn Ala Gln Ala Thr Ser Glu Met Met Ala Trp Ala Ala Glu Gln Val
                405                 410                 415

Asp Leu Lys Ala Trp Val Lys Asn Tyr Pro Arg Trp Thr Pro Pro Pro
            420                 425                 430

Pro Pro Pro Arg Val Gln Pro Arg Lys Thr Lys Ser Val Lys Ser Leu
        435                 440                 445

Leu Glu Asn Lys Pro Val Pro Ala Pro Arg Arg Lys Val Arg Ser Asp
    450                 455                 460

Tyr Gly Ser Pro Ile Leu Met Gly Asp Asn Val Pro Asn Gly Trp Glu
465                 470                 475                 480

Asp Ser Thr Val Gly Gly Pro Leu Asp Leu Ser Ala Pro Ser Glu Pro
                485                 490                 495

Met Thr Pro Leu Ser Glu Pro Val Leu Ile Ser Arg Pro Val Thr Ser
            500                 505                 510

Leu Ser Val Pro Ala Pro Val Pro Ala Pro Arg Arg Ala Val Ser Arg
        515                 520                 525

Pro Met Thr Pro Ser Ser Glu Pro Ile Phe Val Ser Ala Leu Arg His
    530                 535                 540

Lys Phe Gln Gln Val Glu Lys Ala Asn Leu Ala Ala Ala Ala Pro Met
545                 550                 555                 560

Tyr Gln Asp Glu Pro Leu Asp Leu Ser Ala Ser Ser Gln Thr Glu Tyr
                565                 570                 575

Gly Ala Ser Pro Leu Thr Pro Pro Gln Asn Val Gly Ile Leu Glu Val
            580                 585                 590

Arg Gly Gln Glu Ala Glu Glu Val Leu Ser Glu Ile Ser Asp Ile Leu
        595                 600                 605

Asn Asp Thr Asn Pro Ala Pro Val Ser Ser Ser Ser Leu Ser Ser
    610                 615                 620

Val Arg Ile Thr Arg Pro Lys Tyr Ser Ala Gln Ala Ile Ile Asp Leu
625                 630                 635                 640

Gly Gly Pro Cys Ser Gly His Leu Gln Arg Glu Lys Glu Ala Cys Leu
                645                 650                 655

Arg Ile Met Arg Glu Ala Cys Asp Ala Ala Lys Leu Ser Asp Pro Ala
            660                 665                 670

Thr Gln Glu Trp Leu Ser Arg Met Trp Asp Arg Val Asp Met Leu Thr
        675                 680                 685

Trp Arg Asn Thr Ser Ala Tyr Gln Ala Phe Arg Thr Leu Asp Gly Arg
    690                 695                 700

Phe Gly Phe Leu Pro Lys Met Ile Leu Glu Thr Pro Pro Pro Tyr Pro
705                 710                 715                 720

Cys Gly Phe Val Met Leu Pro His Thr Pro Ala Pro Ser Val Ser Ala
                725                 730                 735

Glu Ser Asp Leu Thr Ile Gly Ser Val Ala Thr Glu Asp Ile Pro Arg
            740                 745                 750

Ile Leu Gly Lys Ile Glu Asn Thr Gly Glu Met Ile Asn Gln Gly Pro
        755                 760                 765

Leu Ala Ser Ser Glu Glu Pro Val Tyr Asn Gln Pro Ala Lys Asp
    770                 775                 780

Ser Arg Ile Ser Ser Arg Gly Ser Asp Glu Ser Thr Ala Ala Pro Ser
```

```
            785                 790                 795                 800
Ala Gly Thr Gly Gly Ala Gly Leu Pro Thr Asp Leu Pro Pro Ser Asp
                    805                 810                 815

Gly Val Asp Ala Asp Gly Gly Pro Leu Gln Thr Val Arg Lys Lys
                820                 825                 830

Ala Glu Arg Leu Phe Asp Gln Leu Ser Arg Gln Val Phe Asn Leu Val
            835                 840                 845

Ser His Leu Pro Val Phe Phe Ser His Leu Phe Lys Ser Asp Ser Gly
850                 855                 860

Tyr Ser Pro Gly Asp Trp Gly Phe Ala Ala Phe Thr Leu Phe Cys Leu
865                 870                 875                 880

Phe Leu Cys Tyr Ser Tyr Pro Phe Phe Gly Phe Val Pro Leu Leu Gly
                885                 890                 895

Val Phe Ser Gly Ser Ser Arg Arg Val Arg Met Gly Val Phe Gly Cys
                900                 905                 910

Trp Leu Ala Phe Ala Val Gly Leu Phe Lys Pro Val Ser Asp Pro Val
            915                 920                 925

Gly Thr Ala Cys Glu Phe Asp Ser Pro Glu Cys Arg Asn Val Leu His
930                 935                 940

Ser Phe Glu Leu Leu Lys Pro Trp Asp Pro Val Arg Ser Leu Val Val
945                 950                 955                 960

Gly Pro Val Gly Leu Gly Leu Ala Ile Leu Gly Arg Leu Leu Gly Gly
                965                 970                 975

Ala Arg Tyr Ile Trp His Phe Leu Leu Arg Leu Gly Ile Val Ala Asp
            980                 985                 990

Cys Ile Leu Ala Gly Ala Tyr Val Leu Ser Gln Gly Arg Cys Lys Lys
            995                 1000                1005

Cys Trp Gly Ser Cys Ile Arg Thr Ala Pro Asn Glu Ile Ala Phe
    1010                1015                1020

Asn Val Phe Pro Phe Thr Arg Ala Thr Arg Ser Ser Leu Ile Asp
    1025                1030                1035

Leu Cys Asp Arg Phe Cys Ala Pro Lys Gly Met Asp Pro Ile Phe
    1040                1045                1050

Leu Ala Thr Gly Trp Arg Gly Cys Trp Thr Gly Arg Ser Pro Ile
    1055                1060                1065

Glu Gln Pro Ser Glu Lys Pro Ile Ala Phe Ala Gln Leu Asp Glu
    1070                1075                1080

Lys Arg Ile Thr Ala Arg Thr Val Val Ala Gln Pro Tyr Asp Pro
    1085                1090                1095

Asn Gln Ala Val Lys Cys Leu Arg Val Leu Gln Ala Gly Gly Ala
    1100                1105                1110

Met Val Ala Glu Ala Val Pro Lys Val Val Lys Val Ser Ala Ile
    1115                1120                1125

Pro Phe Arg Ala Pro Phe Phe Pro Thr Gly Val Lys Val Asp Pro
    1130                1135                1140

Glu Cys Arg Ile Val Val Asp Pro Asp Thr Phe Thr Thr Ala Leu
    1145                1150                1155

Arg Ser Gly Tyr Ser Thr Thr Asn Leu Val Leu Gly Val Gly Asp
    1160                1165                1170

Phe Ala Gln Leu Asn Gly Leu Lys Ile Arg Gln Ile Ser Lys Pro
    1175                1180                1185

Ser Gly Gly
    1190
```

<210> SEQ ID NO 86
<211> LENGTH: 1197
<212> TYPE: PRT
<213> ORGANISM: Artificial Sequence
<220> FEATURE:
<223> OTHER INFORMATION: Porcine reproductive and respiratory syndrome virus; Nsp2

<400> SEQUENCE: 86

```
Gly Ala Gly Lys Arg Ala Arg Lys Ala Arg Ser Gly Met Thr Thr Thr
1               5                   10                  15

Val Ala His Arg Ala Leu Pro Ala Arg Glu Ile Gln Gln Ala Lys Lys
            20                  25                  30

His Glu Asp Ala Gly Ala Asp Lys Ala Val His Leu Arg His Tyr Ser
        35                  40                  45

Pro Pro Ala Asp Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Ser Asp Asp Trp Ala Thr Asp Glu Asp Leu Val Asn Thr Ile
                85                  90                  95

Gln Ile Leu Lys Leu Pro Ala Ala Leu Asp Arg Asn Gly Ala Cys Val
            100                 105                 110

Gly Ala Lys Tyr Val Leu Lys Leu Glu Gly Glu His Trp Thr Val Ser
        115                 120                 125

Val Thr Leu Gly Met Ser Pro Ser Leu Leu Pro Leu Glu Cys Val Gln
    130                 135                 140

Gly Cys Cys Glu His Lys Ser Gly Leu Gly Pro Pro Asp Ala Val Glu
145                 150                 155                 160

Val Phe Gly Phe Asp Pro Ala Cys Leu Asp Arg Leu Ala Glu Val Met
                165                 170                 175

His Leu Pro Ser Ser Val Ile Pro Ala Ala Leu Ala Glu Met Ser Gly
            180                 185                 190

Asp Pro Asn Cys Pro Ala Ser Pro Val Thr Thr Val Trp Thr Val Ser
        195                 200                 205

Gln Phe Phe Ala Arg His Arg Gly Gly Glu His Pro Asp Gln Val Arg
    210                 215                 220

Leu Gly Lys Ile Ile Ser Leu Cys Gln Val Val Glu Glu Cys Cys Cys
225                 230                 235                 240

His Gln Asn Lys Thr Asn Arg Ala Thr Pro Glu Glu Val Ala Ala Arg
                245                 250                 255

Ile Asp Gln Tyr Leu His Gly Ala Thr Ser Leu Glu Glu Cys Leu Ile
            260                 265                 270

Arg Leu Glu Arg Val Cys Pro Pro Ser Ala Ala Asp Thr Phe Phe Asp
        275                 280                 285

Trp Asn Val Val Leu Pro Gly Val Gly Ala Ser Thr Gln Thr Thr Lys
    290                 295                 300

Gln Leu His Val Asn Gln Cys Arg Ala Leu Val Pro Val Val Thr Gln
305                 310                 315                 320

Glu Pro Leu Asp Lys Asp Ser Val Pro Leu Thr Ala Phe Ser Leu Ser
                325                 330                 335

Asn Cys Tyr Tyr Pro Ala Gln Gly Asp Glu Val Arg His Arg Glu Arg
            340                 345                 350

Leu Asn Ser Val Leu Ser Lys Leu Glu Gly Val Val Arg Glu Glu Tyr
        355                 360                 365
```

-continued

```
Gly Leu Thr Pro Thr Glu Pro Gly Arg Pro Ala Leu Pro Asn Gly
            370                 375                 380

Leu Val Glu Leu Lys Asp Gln Met Glu Asp Leu Leu Lys Leu Val
385                 390                 395                 400

Asn Ala Gln Ala Thr Ser Glu Met Met Ala Trp Ala Ala Glu Gln Val
                405                 410                 415

Asp Leu Lys Ala Trp Val Lys Asn Tyr Pro Arg Trp Thr Pro Pro
            420                 425                 430

Pro Pro Pro Arg Val Gln Pro Arg Lys Thr Lys Ser Val Lys Ser Leu
            435                 440                 445

Pro Gly Asn Lys Pro Val Pro Ala Pro Arg Arg Lys Val Arg Ser Asp
450                 455                 460

Cys Gly Ser Pro Ile Leu Met Gly Asp Asn Val Pro Asp Gly Arg Glu
465                 470                 475                 480

Asp Leu Thr Val Gly Gly Pro Leu Asp Leu Ser Thr Pro Ser Glu Pro
                485                 490                 495

Met Thr Pro Leu Ser Glu Pro Ala Leu Met Pro Ala Leu Gln Tyr Ile
                500                 505                 510

Ser Arg Pro Val Thr Ser Leu Ser Val Leu Ala Pro Val Pro Ala Pro
            515                 520                 525

Arg Arg Thr Val Ser Arg Pro Val Thr Pro Leu Ser Glu Pro Ile Phe
530                 535                 540

Val Ser Ala Pro Arg His Lys Phe Gln Gln Val Glu Glu Ala Asn Leu
545                 550                 555                 560

Ala Ala Thr Thr Leu Thr His Gln Asp Glu Pro Leu Asp Leu Ser Ala
                565                 570                 575

Ser Ser Gln Thr Glu Tyr Glu Ala Ser Pro Leu Thr Pro Leu Gln Asn
                580                 585                 590

Met Gly Ile Leu Glu Val Gly Gly Gln Glu Ala Glu Glu Val Leu Ser
            595                 600                 605

Glu Ile Ser Asp Thr Leu Asn Asp Ile Asn Pro Ala Pro Val Ser Ser
            610                 615                 620

Ser Ser Ser Leu Ser Ser Val Lys Ile Thr Arg Pro Lys His Ser Ala
625                 630                 635                 640

Gln Ala Ile Ile Asp Ser Gly Gly Pro Cys Ser Gly His Leu Arg Arg
                645                 650                 655

Glu Lys Glu Ala Cys Leu Ser Ile Met Arg Glu Ala Cys Asp Ala Ala
            660                 665                 670

Lys Leu Ser Asp Pro Ala Thr Gln Glu Trp Leu Ser Arg Met Trp Asp
            675                 680                 685

Arg Val Asp Met Leu Thr Trp Arg Asn Thr Ser Ala Tyr Gln Ala Phe
690                 695                 700

Arg Ile Leu Asp Gly Arg Phe Glu Phe Leu Pro Lys Met Ile Leu Glu
705                 710                 715                 720

Thr Pro Pro Pro Tyr Pro Cys Gly Phe Val Met Leu Pro His Thr Pro
                725                 730                 735

Ala Pro Ser Val Gly Ala Glu Ser Asp Leu Thr Ile Gly Ser Val Ala
            740                 745                 750

Thr Glu Asp Val Pro Arg Ile Leu Gly Lys Ile Glu Asn Ala Gly Glu
            755                 760                 765

Met Pro Asn Gln Gly Leu Leu Thr Ser Phe Gly Glu Pro Val Cys
770                 775                 780

Asp Gln Pro Val Lys Asp Ser Trp Met Ser Ser Arg Gly Phe Asp Glu
785                 790                 795                 800
```

```
Ser Thr Thr Ala Pro Ser Ala Gly Thr Gly Gly Ala Asp Leu Pro Thr
                805                 810                 815

Asp Leu Pro Pro Ser Asp Gly Leu Asp Ala Asp Glu Trp Gly Pro Leu
                820                 825                 830

Arg Thr Val Arg Lys Ala Glu Arg Leu Phe Asp Gln Leu Ser Arg
                835                 840                 845

Gln Val Phe Asn Leu Val Ser His Leu Pro Val Phe Ser His Leu
                850                 855                 860

Phe Lys Ser Asp Ser Gly Tyr Ser Pro Gly Asp Trp Gly Phe Ala Ala
865                 870                 875                 880

Phe Thr Leu Phe Cys Leu Phe Leu Cys Tyr Ser Tyr Pro Phe Phe Gly
                    885                 890                 895

Phe Val Pro Leu Leu Gly Val Phe Ser Gly Ser Ser Arg Val Arg
                900                 905                 910

Met Gly Val Phe Gly Cys Trp Leu Ala Phe Ala Val Gly Leu Phe Lys
                915                 920                 925

Pro Val Ser Asp Pro Val Gly Thr Ala Cys Glu Phe Asp Ser Pro Glu
                930                 935                 940

Cys Arg Asn Val Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Tyr Ile Trp His Phe Leu Leu Arg
                980                 985                 990

Leu Gly Ile Val Ala Asp Cys Ile  Leu Ala Gly Ala Tyr  Val Leu Ser
                995                 1000                 1005

Gln Gly  Arg Cys Lys Lys Cys  Trp Gly Ser Cys Val  Arg Thr Ala
     1010                 1015                 1020

Pro Asn  Glu Ile Ala Phe Asn  Val Phe Pro Phe Thr  Arg Ala Thr
     1025                 1030                 1035

Arg Ser  Ser Leu Ile Asp Leu  Cys Asp Arg Phe Cys  Ala Pro Lys
     1040                 1045                 1050

Gly Met  Asp Pro Ile Phe Leu  Ala Thr Gly Trp Arg  Gly Cys Trp
     1055                 1060                 1065

Thr Gly  Arg Ser Pro Ile Glu  Gln Pro Ser Glu Lys  Pro Ile Ala
     1070                 1075                 1080

Phe Ala  Gln Leu Asp Glu Lys  Arg Ile Thr Ala Arg  Thr Val Gly
     1085                 1090                 1095

Ala Gln  Pro Tyr Asp Pro Asn  Gln Ala Val Lys Cys  Leu Arg Val
     1100                 1105                 1110

Leu Gln  Ala Gly Gly Ala Ile  Val Ala Glu Ala Val  Pro Lys Val
     1115                 1120                 1125

Val Lys  Val Ser Ala Ile Pro  Phe Arg Ala Pro Phe  Phe Pro Thr
     1130                 1135                 1140

Gly Val  Lys Val Asp Pro Glu  Cys Arg Ile Val Val  Asp Pro Asp
     1145                 1150                 1155

Thr Phe  Thr Thr Ala Leu Arg  Ser Gly Tyr Ser Thr  Thr Asn Leu
     1160                 1165                 1170

Val Leu  Gly Val Gly Asp Phe  Ala Gln Leu Asn Gly  Leu Lys Ile
     1175                 1180                 1185

Arg Gln  Ile Ser Lys Pro Ser  Gly Gly
     1190                 1195
```

<210> SEQ ID NO 87
<211> LENGTH: 1194
<212> TYPE: PRT
<213> ORGANISM: Artificial Sequence
<220> FEATURE:
<223> OTHER INFORMATION: Porcine reproductive and respiratory syndrome virus; Nsp2

<400> SEQUENCE: 87
```
Gly Ala Gly Lys Arg Ala Arg Lys Ala Arg Ser Gly Ala Thr Thr Met
1               5                   10                  15

Val Ala His Arg Ala Ser Ser Ala His Glu Thr Arg Gln Ala Thr Lys
            20                  25                  30

His Glu Gly Ala Gly Ala Asn Lys Ala Glu His Leu Lys Leu Tyr Ser
        35                  40                  45

Pro Pro Ala Glu Gly Asn Cys Gly Trp His Cys Ile Ser Ala Ile Val
    50                  55                  60

Asn Arg Met Val Asn Ser Asn Phe Glu Thr Thr Leu Pro Glu Arg Val
65                  70                  75                  80

Arg Pro Pro Asp Asp Trp Ala Thr Asp Glu Asp Leu Val Asn Thr Ile
                85                  90                  95

Gln Ile Leu Arg Leu Pro Ala Ala Leu Asp Arg Asn Gly Ala Cys Gly
            100                 105                 110

Gly Ala Lys Tyr Val Leu Lys Leu Glu Gly Glu His Trp Thr Val Ser
        115                 120                 125

Val Asn Pro Gly Met Ser Pro Ser Leu Leu Pro Leu Glu Cys Val Gln
    130                 135                 140

Gly Cys Cys Glu His Lys Gly Gly Leu Gly Ser Pro Asp Ala Val Glu
145                 150                 155                 160

Val Ser Gly Phe Asp Pro Ala Cys Leu Asp Arg Leu Leu Gln Val Met
                165                 170                 175

His Leu Pro Ser Ser Thr Ile Pro Ala Ala Leu Ala Glu Leu Ser Asp
            180                 185                 190

Asp Ser Asn Arg Pro Val Ser Pro Ala Ala Ala Thr Trp Thr Val Ser
        195                 200                 205

Gln Ser Tyr Ala Arg His Arg Gly Gly Asn His His Asp Gln Val Cys
    210                 215                 220

Leu Gly Lys Ile Ile Ser Leu Cys Gln Val Ile Glu Asp Cys Cys Cys
225                 230                 235                 240

His Gln Asn Lys Thr Asn Arg Ala Thr Pro Glu Glu Val Ala Ala Lys
                245                 250                 255

Ile Asp Gln Tyr Leu Arg Gly Ala Thr Ser Leu Glu Glu Cys Leu Ala
            260                 265                 270

Lys Leu Glu Arg Val Ser Pro Pro Gly Ala Ala Asp Thr Ser Phe Asp
        275                 280                 285

Trp Asn Val Val Leu Pro Gly Val Glu Ala Ala His Gln Thr Thr Glu
    290                 295                 300

Gln Leu His Val Asn Pro Cys Arg Thr Leu Val Pro Pro Val Thr Glu
305                 310                 315                 320

Pro Leu Gly Lys Asp Ser Val Pro Leu Thr Ala Phe Ser Leu Ser Asn
                325                 330                 335

Cys Tyr Tyr Pro Ala Gln Gly Asn Glu Val Arg His Arg Glu Arg Leu
            340                 345                 350

Asn Ser Val Leu Ser Lys Leu Glu Glu Val Val Leu Glu Glu Tyr Gly
        355                 360                 365

Leu Met Ser Thr Gly Leu Gly Pro Arg Pro Val Leu Pro Ser Gly Leu
```

```
            370                 375                 380
Asp Glu Leu Lys Asp Gln Met Glu Asp Leu Leu Lys Leu Ala Asn
385                 390                 395                 400

Thr Gln Ala Thr Ser Glu Met Met Ala Trp Ala Ala Glu Gln Val Asp
                405                 410                 415

Leu Lys Ala Trp Val Lys Ser Tyr Pro Arg Trp Thr Pro Pro Pro
            420                 425                 430

Pro Pro Arg Val Gln Pro Arg Lys Thr Lys Ser Val Lys Ser Leu Pro
        435                 440                 445

Glu Asp Lys Pro Val Pro Ala Pro Arg Arg Lys Val Arg Ser Gly Cys
450                 455                 460

Gly Ser Pro Val Leu Met Gly Asp Asn Val Pro Asn Gly Ser Glu Asp
465                 470                 475                 480

Leu Thr Val Gly Gly Pro Leu Asn Phe Pro Thr Pro Ser Glu Pro Met
                485                 490                 495

Thr Pro Met Ser Glu Pro Val Leu Thr Pro Ala Leu Gln Arg Val Pro
                500                 505                 510

Lys Leu Met Thr Pro Leu Asp Gly Ser Ala Pro Val Pro Ala Pro Arg
            515                 520                 525

Arg Thr Val Ser Arg Pro Met Thr Pro Leu Ser Glu Pro Ile Phe Leu
530                 535                 540

Ser Ala Pro Arg His Lys Phe Gln Gln Val Glu Glu Ala Asn Pro Ala
545                 550                 555                 560

Thr Thr Thr Leu Thr His Gln Asn Glu Pro Leu Asp Leu Ser Ala Ser
                565                 570                 575

Ser Gln Thr Glu Tyr Glu Ala Ser Pro Leu Ala Ser Ser Gln Asn Met
            580                 585                 590

Ser Ile Leu Glu Ala Gly Gly Gln Glu Ala Glu Glu Val Leu Ser Glu
            595                 600                 605

Ile Ser Asp Ile Leu Asn Asp Thr Ser Pro Ala Pro Val Ser Ser Ser
610                 615                 620

Ser Ser Leu Ser Ser Val Lys Ile Thr Arg Pro Lys Tyr Ser Ala Gln
625                 630                 635                 640

Ala Ile Ile Asp Ser Gly Gly Pro Cys Ser Gly His Leu Gln Lys Glu
                645                 650                 655

Lys Glu Ala Cys Leu Ser Ile Met Arg Glu Ala Cys Asp Ala Ser Lys
            660                 665                 670

Leu Ser Asp Pro Ala Gln Glu Trp Leu Ser Arg Met Trp Asp Arg Val
            675                 680                 685

Asp Met Leu Thr Trp Arg Asn Thr Ser Ala Tyr Gln Ala Phe Arg Thr
690                 695                 700

Leu Asn Gly Arg Phe Glu Phe Leu Pro Lys Met Ile Leu Glu Thr Pro
705                 710                 715                 720

Pro Pro His Pro Cys Gly Phe Val Met Leu Pro His Thr Pro Ala Pro
                725                 730                 735

Ser Val Ser Ala Glu Ser Asp Leu Thr Ile Gly Ser Val Ala Thr Glu
                740                 745                 750

Asp Val Pro Arg Ile Leu Gly Lys Ile Gly Asp Thr Gly Glu Leu Leu
                755                 760                 765

Asn Gln Gly Pro Ser Ala Pro Phe Lys Gly Gly Pro Val Cys Asp Gln
            770                 775                 780

Pro Ala Lys Asn Ser Arg Met Ser Pro Arg Glu Ser Asp Glu Ser Ile
785                 790                 795                 800
```

```
Ile Ala Pro Pro Ala Asp Thr Gly Gly Ala Gly Ser Phe Thr Asp Leu
            805                 810                 815

Pro Ser Ser Asp Ser Val Asp Ala Asn Gly Gly Pro Leu Arg Thr Val
        820                 825                 830

Lys Thr Lys Ala Gly Arg Leu Leu Asp Gln Leu Ser Cys Gln Val Phe
    835                 840                 845

Ser Leu Val Ser His Leu Pro Val Phe Phe Ser His Leu Phe Lys Ser
850                 855                 860

Asp Ser Gly Tyr Ser Pro Gly Asp Trp Gly Phe Ala Ala Phe Thr Leu
865                 870                 875                 880

Phe Cys Leu Phe Leu Cys Tyr Ser Tyr Pro Phe Phe Gly Phe Ala Pro
                885                 890                 895

Leu Leu Gly Val Phe Ser Gly Ser Ser Arg Arg Val Arg Met Gly Val
            900                 905                 910

Phe Gly Cys Trp Leu Ala Phe Ala Val Gly Leu Phe Lys Pro Val Ser
        915                 920                 925

Asp Pro Val Gly Thr Ala Cys Glu Phe Asp Ser Pro Glu Cys Arg Asn
    930                 935                 940

Val Leu His Ser Phe Glu Leu Leu Lys Pro Trp Asp Pro Val Arg Ser
945                 950                 955                 960

Leu Val Val Gly Pro Val Gly Leu Gly Leu Ala Ile Leu Gly Arg Leu
                965                 970                 975

Leu Gly Gly Ala Arg Tyr Val Trp His Phe Leu Leu Arg Phe Gly Ile
            980                 985                 990

Val Ala Asp Cys Ile Leu Ala Gly Ala Tyr Val Leu Ser Gln Gly Arg
        995                 1000                1005

Cys Lys Lys Cys Trp Gly Ser Cys Val Arg Thr Ala Pro Asn Glu
    1010                1015                1020

Ile Ala Phe Asn Val Phe Pro Phe Thr Arg Ala Thr Arg Ser Ser
    1025                1030                1035

Leu Ile Asp Leu Cys Asp Arg Phe Cys Ala Pro Lys Gly Met Asp
    1040                1045                1050

Pro Ile Phe Leu Ala Thr Val Trp Arg Gly Cys Trp Thr Gly Arg
    1055                1060                1065

Ser Pro Ile Glu Gln Pro Ser Glu Lys Pro Ile Ala Phe Ala Gln
    1070                1075                1080

Leu Asp Glu Lys Arg Ile Thr Ala Arg Thr Val Val Ala Gln Pro
    1085                1090                1095

Tyr Asp Pro Asn Gln Ala Val Lys Cys Leu Arg Val Leu Gln Ala
    1100                1105                1110

Gly Gly Ala Met Val Ala Glu Ala Val Pro Lys Val Val Lys Val
    1115                1120                1125

Ser Ala Ile Pro Phe Arg Ala Pro Phe Phe Pro Ala Gly Val Lys
    1130                1135                1140

Val Asp Pro Glu Cys Arg Ile Val Val Asp Pro Asp Thr Phe Thr
    1145                1150                1155

Thr Ala Leu Arg Ser Gly Tyr Ser Thr Thr Asn Leu Val Leu Gly
    1160                1165                1170

Met Gly Asp Phe Ala Gln Leu Asn Gly Leu Lys Ile Arg Gln Ile
    1175                1180                1185

Ser Lys Pro Ser Gly Gly
    1190

<210> SEQ ID NO 88
```

```
<211> LENGTH: 1061
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 88
```

| | | | | | | | | | | | | | | |
|---|---|---|---|---|---|---|---|---|---|---|---|---|---|---|

-continued

```
Thr Pro Asp Asn Pro Gly Ser Asp Ala Ser Ala Leu Pro Ile Ala Val
385                 390                 395                 400

Arg Gly Phe Val Pro Thr Gly Pro Ile Leu Arg His Val Glu His Cys
            405                 410                 415

Gly Thr Glu Ser Gly Asp Ser Ser Pro Leu Asp Leu Ser Phe Ala
        420                 425                 430

Gln Thr Leu Asp Gln Pro Leu Asp Leu Ser Leu Ala Ala Trp Pro Val
        435                 440                 445

Lys Ala Thr Ala Ser Asp Pro Gly Trp Val Arg Gly Arg Cys Glu Pro
    450                 455                 460

Val Phe Leu Lys Pro Arg Lys Ala Phe Ser Asp Gly Asp Ser Ala Leu
465                 470                 475                 480

Gln Phe Gly Glu Leu Ser Glu Ser Ser Val Ile Glu Phe Asp Gln
        485                 490                 495

Thr Lys Asp Thr Leu Val Ala Asp Ala Pro Val Asp Leu Thr Thr Ser
            500                 505                 510

Asn Glu Ala Leu Ser Ala Val Asp Pro Ser Glu Phe Val Glu Leu Arg
        515                 520                 525

Arg Pro Arg His Ser Ala Gln Ala Leu Ile Asp Arg Gly Gly Pro Leu
    530                 535                 540

Ala Asp Val His Ala Lys Ile Lys Asn Arg Val Tyr Glu Gln Cys Leu
545                 550                 555                 560

Gln Ala Cys Glu Pro Gly Ser Arg Ala Thr Pro Ala Thr Arg Glu Trp
            565                 570                 575

Leu Asp Lys Met Trp Asp Arg Val Asp Met Lys Thr Trp Arg Cys Thr
        580                 585                 590

Ser Gln Phe Gln Ala Gly Arg Ile Leu Ala Ser Leu Lys Phe Leu Pro
        595                 600                 605

Asp Met Ile Gln Asp Thr Pro Pro Val Pro Arg Lys Asn Arg Ala
    610                 615                 620

Ser Asp Asn Ala Gly Leu Lys Gln Leu Val Ala Arg Trp Asp Lys Lys
625                 630                 635                 640

Leu Ser Val Thr Pro Pro Lys Ser Ala Gly Leu Val Leu Asp Gln
            645                 650                 655

Thr Val Pro Pro Pro Thr Asp Ile Gln Gln Glu Asp Ala Thr Pro Ser
            660                 665                 670

Asp Gly Leu Ser His Ala Ser Asp Phe Ser Ser Arg Val Ser Thr Ser
        675                 680                 685

Trp Ser Trp Lys Gly Leu Met Leu Ser Gly Thr Arg Leu Ala Gly Ser
    690                 695                 700

Ala Gly Gln Arg Leu Met Thr Trp Val Phe Glu Val Tyr Ser His Leu
705                 710                 715                 720

Pro Ala Phe Ile Leu Thr Leu Phe Ser Pro Arg Gly Ser Met Ala Pro
            725                 730                 735

Gly Asp Trp Leu Phe Ala Gly Val Val Leu Ala Leu Leu Leu Cys
        740                 745                 750

Arg Ser Tyr Pro Ile Leu Gly Cys Leu Pro Leu Gly Val Phe Ser
        755                 760                 765

Gly Ser Leu Arg Arg Val Arg Leu Gly Val Phe Gly Ser Trp Met Ala
        770                 775                 780

Phe Ala Val Phe Leu Phe Ser Thr Pro Ser Asn Pro Val Gly Ser Ser
785                 790                 795                 800

Cys Asp His Asp Ser Pro Glu Cys His Ala Glu Leu Leu Glu Leu Glu
```

805 810 815

Gln Arg Gln Leu Trp Glu Pro Val Arg Gly Leu Val Val Gly Pro Ser
820 825 830

Gly Leu Leu Cys Val Ile Leu Gly Lys Leu Leu Gly Gly Ser Arg His
835 840 845

Leu Trp His Val Ile Leu Arg Leu Cys Met Leu Thr Asp Leu Ala Leu
850 855 860

Ser Leu Val Thr Val Val Ser Gln Gly Arg Cys His Lys Cys Trp Gly
865 870 875 880

Lys Cys Ile Arg Thr Ala Pro Ala Glu Val Ala Leu Asn Val Phe Pro
885 890 895

Phe Ser Arg Ala Thr Arg Asn Ser Leu Thr Ser Leu Cys Asp Arg Phe
900 905 910

Gln Thr Pro Lys Gly Val Asp Pro Val His Leu Ala Thr Gly Trp Arg
915 920 925

Gly Cys Trp Arg Gly Glu Ser Pro Ile His Gln Pro His Gln Lys Pro
930 935 940

Ile Ala Tyr Ala Asn Leu Asp Glu Lys Lys Ile Ser Ala Gln Thr Val
945 950 955 960

Val Ala Val Pro Tyr Asp Pro Ser Gln Ala Ile Lys Cys Leu Lys Val
965 970 975

Leu Gln Ala Gly Gly Ala Ile Val Asp Gln Pro Thr Pro Glu Val Val
980 985 990

Arg Val Ser Glu Ile Pro Phe Ser Ala Pro Phe Phe Pro Lys Val Pro
995 1000 1005

Val Asn Pro Asp Cys Arg Ile Val Val Asp Ser Asp Thr Phe Val
1010 1015 1020

Ala Ala Val Arg Cys Gly Tyr Ser Thr Ala Gln Leu Val Leu Gly
1025 1030 1035

Arg Gly Asn Phe Ala Lys Leu Asn Gln Thr Pro Leu Arg Asp Ser
1040 1045 1050

Ala Ser Thr Lys Thr Thr Gly Gly
1055 1060

<210> SEQ ID NO 89
<211> LENGTH: 1060
<212> TYPE: PRT
<213> ORGANISM: Artificial Sequence
<220> FEATURE:
<223> OTHER INFORMATION: Porcine reproductive and respiratory syndrome virus; Nsp2

<400> SEQUENCE: 89

Ala Ala Gly Lys Arg Ala Arg Ala Lys Arg Thr Ala Lys Gly Gly Lys
1 5 10 15

Asp Ser Val Pro Ala Leu Lys Val Ala Leu Pro Val Pro Ala Cys Gly
20 25 30

Ile Thr Thr Tyr Ser Pro Pro Thr Asp Gly Ser Cys Gly Trp His Val
35 40 45

Leu Ala Ala Ile Met Asn Arg Met Met Asn Asp Asp Phe Thr Ser Pro
50 55 60

Leu Thr Gln Tyr Asn Arg Pro Glu Asp Asp Trp Ala Ser Asp Tyr Asp
65 70 75 80

Leu Ala Gln Ala Ile Gln Cys Leu Gln Leu Pro Ala Thr Val Val Arg
85 90 95

Asn Arg Ala Cys Pro Asn Ala Lys Tyr Leu Ile Lys Leu Asn Gly Val

-continued

```
                100                 105                 110
His Trp Glu Val Glu Val Arg Ser Gly Met Ala Pro Arg Ser Leu Ser
            115                 120                 125
Glu Cys Val Val Gly Val Cys Ser Glu Gly Cys Val Ala Pro Pro Tyr
            130                 135                 140
Pro Ala Asp Gly Leu Pro Lys Arg Ala Leu Glu Ala Leu Ala Ser Ala
145                 150                 155                 160
Tyr Arg Leu Pro Ser Asp Cys Val Cys Ser Gly Ile Ala Asp Phe Leu
                165                 170                 175
Ala Asn Pro Pro Gln Glu Phe Trp Thr Leu Asp Lys Met Leu Thr
            180                 185                 190
Ser Pro Ser Pro Glu Arg Ser Gly Phe Ser Ser Leu Tyr Asn Leu Leu
            195                 200                 205
Leu Glu Val Val Pro Gln Lys Cys Gly Val Thr Glu Gly Ala Phe Thr
            210                 215                 220
Tyr Ala Val Glu Arg Met Leu Met Asp Cys Pro Ser Ser Glu Gln Ala
225                 230                 235                 240
Met Ala Leu Leu Ala Lys Ile Lys Val Pro Ser Ser Lys Ala Pro Ser
                245                 250                 255
Val Ser Leu Asp Glu Cys Phe Pro Ala Asp Val Pro Ala Asp Phe Glu
                260                 265                 270
Pro Thr Ser Gln Lys Arg Pro Gln Ser Ser Gly Ala Ala Val Ala Leu
            275                 280                 285
Cys Ser Ser Asp Ala Glu Gly Phe Glu Glu Ala Ala Pro Glu Gly Val
            290                 295                 300
Gln Glu Arg Gly His Lys Ala Val His Ser Ala Leu Phe Ala Lys Gly
305                 310                 315                 320
Pro Asn Asn Glu Gln Val Gln Val Val Ala Gly Glu Gln Lys Leu
                325                 330                 335
Gly Gly Cys Gly Leu Ala Ile Gly Asn Ala Gln Ser Pro Leu Asn Ser
                340                 345                 350
Met Lys Glu Asn Met Arg Ser Ser Arg Glu Asp Glu Pro Leu Asp Leu
            355                 360                 365
Ser Gln Pro Ala Pro Val Ala Ala Thr Thr Leu Glu Arg Glu Gln Thr
370                 375                 380
Pro Asp Asn Pro Gly Ser Asp Ala Gly Ala Leu Pro Ala Thr Val Arg
385                 390                 395                 400
Glu Ser Val Pro Thr Gly Pro Met Leu Arg His Val Glu His Cys Gly
                405                 410                 415
Thr Glu Ser Gly Asp Ser Ser Ser Pro Leu Asp Leu Ser Tyr Ala Gln
                420                 425                 430
Thr Leu Asp Gln Pro Leu Asp Leu Ser Leu Ala Val Trp Pro Val Lys
            435                 440                 445
Ala Thr Ala Ser Asp Pro Gly Trp Val His Gly Arg Arg Glu Pro Val
            450                 455                 460
Phe Val Lys Pro Arg Lys Ala Phe Ser Asp Ser Asp Ser Ala Phe Gln
465                 470                 475                 480
Phe Gly Lys Leu Ser Glu Ser Gly Ser Val Ile Glu Phe Asp Arg Thr
                485                 490                 495
Lys Asp Ala Pro Val Val Asp Ala Pro Val Gly Ser Thr Thr Ser Asn
            500                 505                 510
Glu Ala Leu Ser Ile Ala Asp Pro Phe Glu Phe Ala Glu Leu Lys Arg
            515                 520                 525
```

-continued

```
Pro Arg Phe Ser Ala Gln Ala Leu Ile Asp Arg Gly Gly Pro Leu Ala
    530                 535                 540

Asp Val His Ala Lys Ile Lys Asn Arg Val Tyr Glu Arg Cys Leu Gln
545                 550                 555                 560

Ala Cys Glu Pro Gly Ser Arg Ala Thr Pro Ala Thr Lys Glu Trp Leu
                565                 570                 575

Asp Lys Met Trp Asp Arg Val Asp Met Lys Thr Trp Cys Cys Thr Ser
            580                 585                 590

Gln Phe Gln Ala Gly Arg Ile Leu Ala Ser Leu Lys Phe Leu Pro Asp
        595                 600                 605

Met Ile Gln Asp Thr Pro Pro Val Pro Arg Lys Asn Arg Ala Ser
    610                 615                 620

Asp Asn Ala Asp Leu Lys Gln Leu Val Ala Gln Trp Asp Arg Lys Leu
625                 630                 635                 640

Ser Met Thr Pro Pro Gln Lys Pro Val Glu Pro Val Leu Asp Gln Thr
                645                 650                 655

Val Ser Pro Pro Thr Asp Thr Gln Gln Glu Asp Val Thr Pro Ser Asp
            660                 665                 670

Gly Pro Pro His Ala Pro Asp Phe Pro Ser Arg Val Ser Thr Gly Gly
        675                 680                 685

Ser Trp Lys Asp Leu Met Cys Ser Gly Thr Arg Leu Ala Gly Ser Ile
    690                 695                 700

Ser Gln Arg Leu Met Thr Trp Val Phe Glu Val Phe Ser His Leu Pro
705                 710                 715                 720

Ala Phe Met Leu Thr Leu Phe Ser Pro Arg Gly Ser Met Ala Pro Gly
                725                 730                 735

Asp Trp Leu Phe Ala Gly Val Val Leu Leu Ala Leu Leu Leu Cys His
            740                 745                 750

Ser Tyr Pro Ile Leu Gly Cys Leu Pro Leu Leu Gly Val Phe Ser Gly
        755                 760                 765

Ser Leu Arg Arg Val Arg Leu Gly Val Phe Gly Ser Trp Met Ala Phe
    770                 775                 780

Ala Val Phe Leu Phe Ser Thr Pro Ser Asn Pro Val Gly Ser Ser Cys
785                 790                 795                 800

Asp His Asp Ser Pro Glu Cys His Ala Glu Leu Leu Ala Leu Glu Gln
                805                 810                 815

Arg Gln Leu Trp Glu Pro Val Arg Gly Leu Val Gly Pro Ser Gly
            820                 825                 830

Leu Leu Cys Val Ile Leu Gly Lys Leu Leu Gly Gly Ser Arg Tyr Leu
        835                 840                 845

Trp His Ile Leu Leu Arg Leu Cys Met Leu Thr Asp Leu Ala Leu Ser
    850                 855                 860

Leu Val Tyr Val Val Ser Gln Gly Arg Cys His Lys Cys Trp Gly Lys
865                 870                 875                 880

Cys Ile Arg Thr Ala Pro Thr Glu Val Ala Leu Asn Val Phe Pro Phe
                885                 890                 895

Thr Arg Ala Thr Arg Ser Ser Leu Val Ser Leu Cys Asp Arg Phe Gln
            900                 905                 910

Thr Pro Lys Gly Val Asp Pro Val His Leu Ala Thr Gly Trp Arg Gly
        915                 920                 925

Cys Trp Arg Gly Gly Ser Pro Val His Gln Pro His Gln Lys Pro Ile
    930                 935                 940

Ala Tyr Ala Asn Leu Asp Glu Lys Lys Ile Ser Ala Gln Thr Val Val
945                 950                 955                 960
```

```
Ala Val Pro Tyr Asp Pro Ser Gln Ala Ile Lys Cys Leu Lys Val Leu
            965                 970                 975

Gln Ala Gly Gly Ala Ile Val Asp Gln Pro Thr Pro Glu Val Val Arg
            980                 985                 990

Val Ser Glu Ile Pro Phe Ser Ala  Pro Phe Phe Pro Lys  Val Pro Val
            995                 1000                1005

Asn Pro Asp Cys Arg Val Val  Val Asp Ser Asp Thr  Phe Val Ala
           1010                1015                1020

Ala Val Arg Cys Gly Tyr Ser  Thr Ala Gln Leu Val  Leu Gly Gln
           1025                1030                1035

Gly Asn  Phe Ala Lys Leu Asn  Gln Thr Pro Pro Arg  Asn Ser Thr
           1040                1045                1050

Ser Thr  Lys Thr Thr Gly Gly
           1055                1060

<210> SEQ ID NO 90
<211> LENGTH: 1094
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 90

Ala Ala Gly Lys Arg Ala Arg Ala Lys Arg Ala Ala Lys Ser Glu Lys
1               5                   10                  15

Asp Ser Ala Pro Thr Pro Lys Val Ala Leu Pro Val Pro Thr Cys Gly
            20                  25                  30

Ile Thr Thr Tyr Ser Pro Pro Thr Asp Gly Ser Cys Gly Trp His Val
            35                  40                  45

Leu Ala Ala Ile Met Asn Arg Met Ile Asn Gly Asp Phe Thr Ser Pro
        50                  55                  60

Leu Thr Gln Tyr Asn Arg Pro Glu Asp Asp Trp Ala Ser Asp Tyr Asp
65                  70                  75                  80

Leu Val Gln Ala Ile Gln Cys Leu Arg Leu Pro Ala Thr Val Val Arg
                85                  90                  95

Asn Arg Ala Cys Pro Asn Ala Lys Tyr Leu Ile Lys Leu Asn Gly Val
            100                 105                 110

His Trp Glu Val Glu Val Arg Ser Gly Met Ala Pro Arg Ser Leu Ser
        115                 120                 125

Arg Glu Cys Val Val Gly Val Cys Ser Glu Gly Cys Val Ala Pro Pro
130                 135                 140

Tyr Pro Ala Asp Gly Leu Pro Lys Arg Ala Leu Glu Ala Leu Ala Ser
145                 150                 155                 160

Ala Tyr Arg Leu Pro Ser Asp Cys Val Ser Ser Gly Ile Ala Asp Phe
                165                 170                 175

Leu Ala Asn Pro Pro Gln Glu Phe Trp Thr Leu Asp Lys Met Leu
            180                 185                 190

Thr Ser Pro Ser Pro Glu Arg Ser Gly Phe Ser Ser Leu Tyr Lys Leu
        195                 200                 205

Leu Leu Glu Val Val Pro Gln Lys Cys Gly Ala Thr Glu Gly Ala Phe
    210                 215                 220

Ile Tyr Ala Val Glu Arg Met Leu Lys Asp Cys Pro Ser Ser Lys Gln
225                 230                 235                 240

Ala Met Ala Leu Leu Ala Lys Ile Lys Val Pro Ser Ser Lys Gln Ala
                245                 250                 255
```

```
Met Ala Leu Leu Ala Lys Ile Lys Val Pro Ser Ser Lys Ala Pro Ser
            260                 265                 270

Val Ser Leu Asp Glu Cys Phe Pro Thr Asp Val Leu Ala Asp Phe Glu
            275                 280                 285

Pro Ala Ser Gln Glu Arg Pro Gln Ser Ser Gly Ala Ala Val Val Leu
        290                 295                 300

Cys Ser Pro Asp Ala Lys Glu Phe Glu Glu Ala Ala Pro Glu Glu Val
305                 310                 315                 320

Gln Glu Ser Gly His Lys Ala Val His Ser Ala Leu Leu Ala Glu Gly
                325                 330                 335

Pro Asn Asn Glu Gln Val Gln Val Val Ala Gly Glu Gln Leu Lys Leu
            340                 345                 350

Gly Gly Cys Gly Leu Ala Val Gly Asn Ala His Glu Gly Ala Leu Val
            355                 360                 365

Ser Ala Gly Leu Ile Asn Leu Val Gly Gly Asn Leu Ser Pro Ser Asp
        370                 375                 380

Pro Met Lys Glu Asn Met Leu Asn Ser Arg Glu Asp Glu Pro Leu Asp
385                 390                 395                 400

Leu Ser Gln Pro Ala Pro Ala Ser Thr Thr Thr Leu Val Arg Glu Gln
                405                 410                 415

Thr Pro Asp Asn Pro Gly Ser Asp Ala Gly Ala Leu Pro Val Thr Val
            420                 425                 430

Arg Glu Phe Val Pro Thr Gly Pro Ile Leu Cys His Val Glu His Cys
            435                 440                 445

Gly Thr Glu Ser Gly Asp Ser Ser Pro Leu Asp Leu Ser Asp Ala
        450                 455                 460

Gln Thr Leu Asp Gln Pro Leu Asn Leu Ser Leu Ala Ala Trp Pro Val
465                 470                 475                 480

Arg Ala Thr Ala Ser Asp Pro Gly Trp Val His Gly Arg Arg Glu Pro
                485                 490                 495

Val Phe Val Lys Pro Arg Asn Ala Phe Ser Asp Gly Asp Ser Ala Leu
            500                 505                 510

Gln Phe Gly Glu Leu Ser Glu Ser Ser Val Ile Glu Phe Asp Arg
        515                 520                 525

Thr Lys Asp Ala Pro Val Val Asp Ala Pro Val Asp Leu Thr Thr Ser
            530                 535                 540

Asn Glu Ala Leu Ser Val Val Asp Pro Phe Glu Phe Ala Glu Leu Lys
545                 550                 555                 560

Arg Pro Arg Phe Ser Ala Gln Ala Leu Ile Asp Arg Gly Gly Pro Leu
                565                 570                 575

Ala Asp Val His Ala Lys Ile Lys Asn Arg Val Tyr Glu Gln Cys Leu
            580                 585                 590

Gln Ala Cys Glu Pro Gly Ser Arg Ala Thr Pro Ala Thr Arg Glu Trp
        595                 600                 605

Leu Asp Lys Met Trp Asp Arg Val Asp Met Lys Thr Trp Arg Cys Thr
        610                 615                 620

Ser Gln Phe Gln Ala Gly Arg Ile Leu Ala Ser Leu Lys Phe Leu Pro
625                 630                 635                 640

Asp Met Ile Gln Asp Thr Pro Pro Val Pro Arg Lys Asn Arg Ala
                645                 650                 655

Ser Asp Asn Ala Gly Leu Lys Gln Leu Val Ala Gln Trp Asp Arg Lys
            660                 665                 670

Leu Ser Val Thr Pro Pro Pro Lys Pro Val Gly Pro Val Leu Asp Gln
```

-continued

```
                675                 680                 685
Ile Val Pro Pro Pro Thr Asp Ile Gln Gln Glu Asp Val Thr Pro Ser
690                 695                 700
Asp Gly Pro Pro His Ala Pro Asp Phe Pro Ser Arg Val Ser Thr Gly
705                 710                 715                 720
Gly Ser Trp Lys Gly Leu Met Leu Ser Gly Thr Arg Leu Ala Gly Ser
                725                 730                 735
Ile Ser Gln Arg Leu Met Thr Trp Val Phe Glu Val Phe Ser His Leu
                740                 745                 750
Pro Ala Phe Met Leu Thr Leu Phe Ser Pro Arg Gly Ser Met Ala Pro
                755                 760                 765
Gly Asp Trp Leu Phe Ala Gly Val Val Leu Ala Leu Leu Leu Cys
770                 775                 780
Arg Ser Tyr Pro Ile Leu Gly Cys Leu Pro Leu Leu Gly Val Phe Ser
785                 790                 795                 800
Gly Ser Leu Arg Arg Val Arg Leu Gly Val Phe Gly Ser Trp Met Ala
                805                 810                 815
Phe Ala Ala Phe Leu Phe Ser Thr Pro Ser Asn Pro Val Gly Ser Ser
                820                 825                 830
Cys Asp His Asp Ser Pro Glu Cys His Ala Glu Leu Leu Ala Leu Glu
                835                 840                 845
Gln Arg Gln Leu Trp Glu Pro Val Arg Gly Leu Val Val Gly Pro Ser
850                 855                 860
Gly Leu Leu Cys Val Ile Leu Gly Lys Leu Leu Gly Gly Ser Arg Tyr
865                 870                 875                 880
Leu Trp His Val Leu Leu Arg Leu Cys Met Leu Ala Asp Leu Ala Leu
                885                 890                 895
Ser Leu Val Tyr Val Val Ser Gln Gly Arg Cys His Lys Cys Trp Gly
                900                 905                 910
Lys Cys Ile Arg Thr Ala Pro Ala Glu Val Ala Leu Asn Val Phe Pro
                915                 920                 925
Phe Ser Arg Ala Thr Arg Val Ser Leu Val Ser Leu Cys Asp Arg Phe
                930                 935                 940
Gln Thr Pro Lys Gly Val Asp Pro Val His Leu Ala Thr Gly Trp Arg
945                 950                 955                 960
Gly Cys Trp Arg Gly Glu Ser Pro Ile His Gln Pro His Gln Lys Pro
                965                 970                 975
Ile Ala Tyr Ala Asn Leu Asp Glu Lys Lys Met Ser Ala Gln Thr Val
                980                 985                 990
Val Ala Val Pro Tyr Asp Pro Ser Gln Ala Ile Lys Cys Leu Lys Val
                995                 1000                1005
Leu Gln Ala Gly Gly Ala Ile Val Asp Gln Pro Thr Pro Glu Val
    1010                1015                1020
Val Arg Val Ser Glu Ile Pro Phe Ser Ala Pro Phe Phe Pro Lys
    1025                1030                1035
Val Pro Val Asn Pro Asp Cys Arg Val Val Val Asp Ser Asp Thr
    1040                1045                1050
Phe Val Ala Ala Ala Val Arg Cys Gly Tyr Ser Thr Ala Gln Leu
    1055                1060                1065
Val Leu Gly Arg Gly Asn Phe Ala Lys Leu Asn Gln Thr Pro Pro
    1070                1075                1080
Arg Asn Ser Ile Ser Thr Lys Thr Thr Gly Gly
    1085                1090
```

PRRS VIRUSES, INFECTIOUS CLONES, MUTANTS THEREOF, AND METHODS OF USE

CONTINUING APPLICATION DATA

This application is a U.S. National Stage Application of International Application No. PCT/US2006/024355, filed Jun. 23, 2006, which claims the benefit of U.S. Provisional Application Ser. No. 60/694,021, filed Jun. 24, 2005, both of which are incorporated by reference herein.

BACKGROUND

Porcine reproductive and respiratory syndrome virus (PRRSV) is the causative agent of a disease characterized by respiratory disorders in young pigs and reproductive failure in sows (Benfield et al., *J. Vet. Diagn. Invest.*, 4:127-133 (1992); Collins et al., *J. Vet. Diagn. Invest.*, 4:117-126 (1992); Wensvoort et al., *Vet. Q.*, 13:121-130 (1991)) and is now endemic in most countries. The syndrome was first recognized as a "mystery swine disease" in the United States in 1987 and was discovered in Europe in 1990. The two prototype viral strains (Lelystad and VR-2332) differ in nucleotide sequence by approximately 40% and represent two distinct genotypes, referred to as European (EU or Type 1, Lelystad; Meulenberg et al., *Virology*, 192:62-72 (1993)) and North American (NA or Type 2, VR-2332; Nelsen et al., *J. Virol.*, 73:270-80 (1999)) strains (Fang et al., *Virus Res.*, 100:229-235 (2004); Mardassi et al., *J. Gen. Virol.*, 75:681-5 (1994); Meng et al., *Arch. Virol.*, 140:745-55 (1995); Ropp et al., *J. Virol.*, 78:3684-3703 (2004)). The disease has also been referred to as Wabash syndrome, mystery pig disease, porcine reproductive and respiratory syndrome, swine plague, porcine epidemic abortion and respiratory syndrome, blue abortion disease, blue ear disease, abortus blau, and seuchenhafter spatabort der schweine. The disease is characterized by reproductive failure in pregnant sows and respiratory problems in pigs of all ages. The disease has a significant negative impact on the swine industry.

PRRSV is an enveloped, positive-sense RNA virus belonging to the family Arteriviridae in the order Nidovirales (Cavanagh, *Arch. Virol.*, 142:629:633 (1997)). The PRRSV genome varies from 15.1-15.5 kb long (Meulenberg et al., *Virology*, 192:62-72 (1993); Nelsen et al., *J. Virol.*, 73:270-80 (1999)). The first 75% of the genome encodes the replicase polyprotein essential for virus replication and is comprised of two large open reading frames (ORFs) (1a and 1b) that are processed cotranslationally into smaller proteins by virally encoded proteases (Snijder et al., *J. Gen. Virol.*, 79:961-79 (1998)). The structural proteins are encoded by seven downstream ORFs and are translated from a 3'-coterminal nested set of subgenomic mRNAs (sgmRNA) (Meulenberg et al., *Virology*, 192:62-72 (1993); Pattnaik et al., *Cell*, 69:1011-1020 (1992)). In strain VR-2332, the coding region of the genome (15,411 bases) is flanked by 5' and 3' nontranslated regions of 189 and 151 nucleotides, respectively.

PRRSV strain VR-2332 has been well characterized in terms of its complete genome sequence (Pattnaik et al., *Cell*, 69:1011-1020 (1992)), the ability of PRRSV to constitutively produce defective subgenomic RNA species termed heteroclites (latin: uncommon forms) (Yuan et al., *Virology*, 275: 158-169 (2000)); Yuan et al., *Virus Research*, 105:75-87 (2004)), and its growth properties in vitro as well as in vivo (Murtaugh et al., *Vet. Immunol. Immunopathol.*, 102:105-349 (2004)). In addition, an infectious clone of this 15.4 kb NA PRRSV genome has been produced and examined for its ability to cause disease in swine (pVR-HN; Nielsen et al., *J. Virol.*, 77:3702-3711 (2003)).

PRRSV continues to cause significant economic losses throughout the world. Vaccines are available, but they are based on one PRRSV strain, and there is evidence that PRRSV strains vary at the antigenic and genetic levels. In addition, since the virus was identified in Europe and in the United States, new disease phenotypes have continued to emerge.

SUMMARY OF THE INVENTION

Prior reports had suggested that deletions and/or mutations of any strain of PRRS virus was often extremely detrimental to viral growth. Specifically, individual laboratories had made mutations in the 3' end of the virus, and the resultant virus was either unstable and quickly reverted back to wild-type sequence, or grew very poorly or not at all (Lee et al., *Virol.*, 331:47-62 (2005); Choi et al., *J. Virol.*, 80:723-736 (2006); Lee et al., *Virolog.*, 346:238-250 (2005)). Thus, in comparison of nucleotide sequences of European (Type 1 genotype) and VR-2332 (Type 2 genotype), where to make mutations in VR-2332 NSP2 that were not extremely detrimental was not known. However, alignment of the full genome sequences of new Type 2 PRRS viruses with VR-2332 began to provide insight as to where viable mutants could be made. Further deletion mutagenesis showed that the region between nsp2 amino acids 324-813 was not necessary for growth in vitro.

The present invention provides an isolated infectious polynucleotide having a nucleotide sequence with at least 88% identity to SEQ ID NO:1 and a deletion of at least 39 consecutive nucleotides selected from nucleotide 2062 to nucleotide 3864 of SEQ ID NO:1. Also provided is an isolated infectious polynucleotide having a nucleotide sequence with at least 88% identity to SEQ ID NO:14 and a deletion of at least 39 consecutive nucleotides selected from nucleotide 2061 to nucleotide 3545 of SEQ ID NO:14. The isolated polynucleotide may be present in a vector, in an isolated virus particle, present in a cell, or a combination thereof. When present in a vector an RNA polymerase promoter may be operably linked to the polynucleotide. The isolated polynucleotide may by an RNA. The isolated polynucleotide may include 2 or more deletions, and each deletion may be independently at least 37 consecutive nucleotides. The isolated polynucleotide may further include an exogenous polynucleotide present in the deletion, and the exogenous polynucleotide may encode a polypeptide, such as a detectable marker.

The present invention also provides an isolated polynucleotide having a nucleotide sequence with at least 88% identity to SEQ ID NO:1 and at least one deletion of at least 39 consecutive nucleotides selected from nucleotide 2062 to nucleotide 3864 of SEQ ID NO:1, and wherein the polynucleotide replicates and produces infectious virus particles when introduced into a cell. Also provided is an isolated polynucleotide having a nucleotide sequence with at least 88% identity to SEQ ID NO:14 and at least one deletion of at least 39 consecutive nucleotides selected from nucleotide 2061 to nucleotide 3545 of SEQ ID NO:14, wherein the polynucleotide replicates and produces infectious virus particles when introduced into a cell. The isolated polynucleotide may be present in a vector, in an isolated virus particle, present in a cell, or a combination thereof. When present in a vector an RNA polymerase promoter may be operably linked to the polynucleotide. The isolated polynucleotide may by an RNA. The isolated polynucleotide may include 2 or more deletions, and each deletion may be independently at least 37 consecutive nucleotides. The isolated polynucleotide may further include an exogenous polynucleotide present in the deletion, and the exogenous polynucleotide may encode a polypeptide, such as a detectable marker.

The present invention further provides an infectious clone having a polynucleotide with a nucleotide sequence having at least 88% identity to SEQ ID NO:1 and at least one deletion of at least 39 consecutive nucleotides selected from nucleotide 2062 to nucleotide 3864 of SEQ ID NO:1. Also provided is an infectious clone having a polynucleotide with a nucleotide sequence having at least 88% identity to SEQ ID NO:14 and at least one deletion of at least 39 consecutive nucleotides selected from nucleotide 2061 to nucleotide 3545 of SEQ ID NO:14. The infectious clone may be present in a cell. An RNA polymerase promoter may be operably linked to the polynucleotide. The infectious clone may include 2 or more deletions, and wherein each deletion is independently at least 37 consecutive nucleotides. The isolated polynucleotide may further include an exogenous polynucleotide present in the deletion, and the exogenous polynucleotide may encode a polypeptide, such as a detectable marker.

Also provided by the present invention is an isolated infectious polynucleotide comprising a nucleotide sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13, and an nsp2 polypeptide encoded by an infectious polynucleotide comprising a nucleotide sequence SEQ ID NO:7, SEQ ID NO:8, SEQ ID NO:9, SEQ ID NO:10, SEQ ID NO:11, SEQ ID NO:12, or SEQ ID NO:13.

The terms "comprises" and variations thereof do not have a limiting meaning where these terms appear in the description and claims. Unless otherwise specified, "a," "an," "the," and "at least one" are used interchangeably and mean one or more than one.

BRIEF DESCRIPTION OF THE FIGURES

FIG. 1. A. Nucleotide sequence (SEQ ID NO:1) of infectious polynucleotide VR-V7 (also referred to herein as V6G7475A). B. Nucleotide sequence (SEQ ID NO:2) of infectious polynucleotide VR-V5. C. Nucleotide sequence (SEQ ID NO:3) of infectious polynucleotide VR-V5G7475A. D. Nucleotide sequence (SEQ ID NO:4) of infectious polynucleotide VR-V6. E. Nucleotide sequence (SEQ ID NO:5) of infectious polynucleotide MN184A. F. Nucleotide sequence (SEQ ID NO:6) of infectious polynucleotide MN184B. G. Nucleotide sequence (SEQ ID NO:7) of infectious polynucleotide Nsp2 Δ324-434. H. Nucleotide sequence (SEQ ID NO:8) of infectious polynucleotide Nsp2 Δ324-523. I. Nucleotide sequence (SEQ ID NO:9) of infectious polynucleotide Nsp2 Δ543-632. J. Nucleotide sequence (SEQ ID NO: 10) of infectious polynucleotide Nsp2 Δ633-726. K. Nucleotide sequence (SEQ ID NO:11) of infectious polynucleotide Nsp2 Δ543-726. L. Nucleotide sequence (SEQ ID NO:12) of infectious polynucleotide Nsp2 Δ727-813. M. Nucleotide sequence (SEQ ID NO: 13) of infectious polynucleotide Nsp2 Δ324-726.

FIG. 6. A. Plaque assays on P3 progeny (second lineage) of all infectious clones as well as wt strain VR-2332 displayed plaque sizes that were different from first lineage virus preparations. B. Titers of P4 virus indicate infectious clone progeny were not replicating as wt strain VR-2332 or Sw612 virus in spite of having similar plaque size.

FIG. 7. A. P3 progeny of wt strain VR-2332 (♦), Sw612 (▲), pVR-HN (□), pVR-V5 (x), pVR-V5G7475A (*), pVR-V6 (●), pVR-V6G7475A (○) were simultaneously examined for one step growth kinetics as outlined in Example 1. wt strain VR-2332 and Sw612 viruses replicated to approximately 10-fold higher titers at all time points. pVR-V6G7475A, with no amino acid changes from native virus or vaccine, produced virus that replicated to a higher titer at all time points than all other infectious clone progeny. The final titer for each virus preparation is listed in the companion table.

FIG. 11. Nsp1β amino acid sequence alignment of divergent PRRSV. The figure derivation and color scheme was described in the FIG. 10 legend. The two completely conserved putative catalytic residues are identified by stars and the boxed amino acids identify MN184 sequence conservation with Type 1 isolates and EAV. The proposed cleavage site is identified by the downward arrow (↓). The following sequences were used for comparison: VR-2332 (SEQ ID NO: 61), Ingelvac MLV (SEQ ID NO: 60), PL97-1 (SEQ ID NO: 62), PA-8 (SEQ ID NO: 65), SP (SEQ ID NO: 66), HN1 (SEQ ID NO: 63), 16244B (SEQ ID NO: 64), HB-1 (SEQ ID NO: 71), HB-2 (SEQ ID NO: 70), CH-1a (SEQ ID NO: 68), P129 (SEQ ID NO: 69), JA142 (SEQ ID NO: 67), EuroPRRSV (SEQ ID NO: 56), Lelystad (SEQ ID NO: 57)., MN184A (SEQ ID NO:58), MN184B (SEQ ID NO:59).

DETAILED DESCRIPTION OF ILLUSTRATIVE EMBODIMENTS

Figure 2:
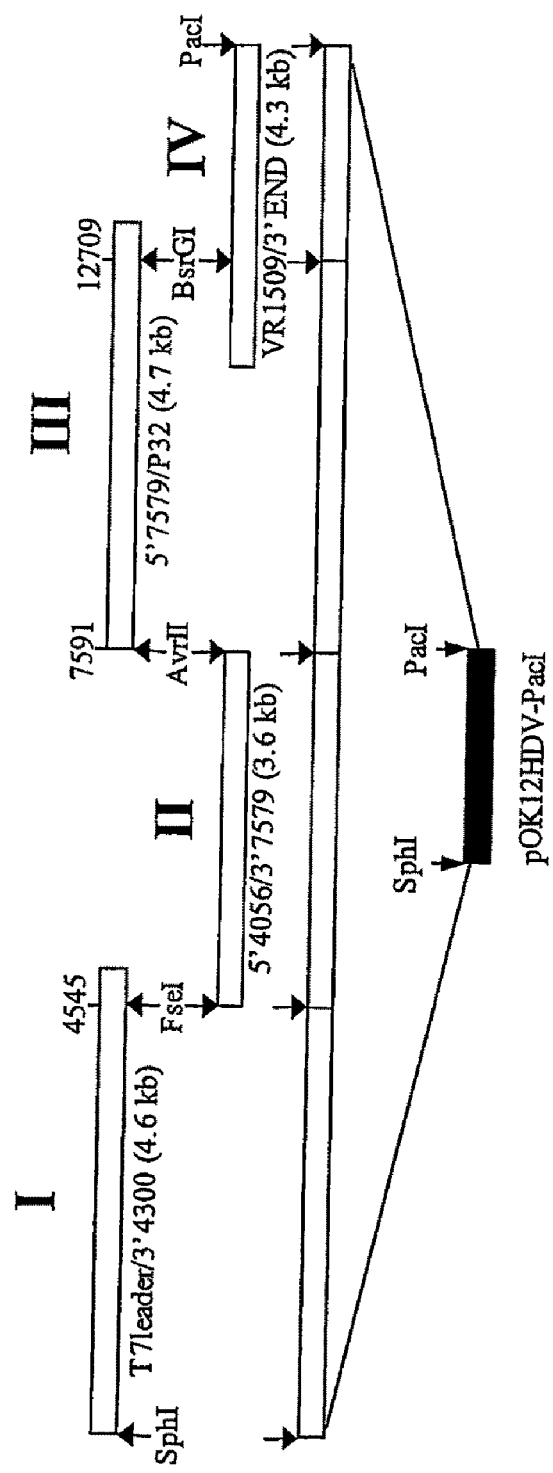
FIG. 2. Assembly of full-length clones of PRRSV strain VR-2332. The 15.4 genome was amplified in four sections (I-IV) that incorporated unique restriction enzyme cleavage sites present in viral cDNA (FseI, AvrII, BsrGI) or added to the PRRSV sequence at the 5' and 3' ends by insertion mutagenesis (SphI, Pac I respectively). A T7 polymerase promoter and 2 nontemplated G residues and a T residue preceded the viral sequence. The pOK12 vector (24) was modified to include a PacI site and a hepatitis delta ribozyme downstream of a poly adenosine tail of 50 nucleotides.

The present invention includes infectious clones of the Porcine reproductive and respiratory syndrome virus (PRRSV) VR-2332. As used herein, the term "infectious clone" is a polynucleotide having two components; a vector sequence that replicates in a prokaryotic host cell, and a second polynucleotide referred to herein as an infectious polynucleotide. When transcribed in vitro to yield an RNA polynucleotide and introduced into a permissive cell, the infectious polynucleotide replicates (as an RNA) and produces infectious virus particles. Thus, an infectious polynucleotide can be present in a vector as a DNA, as an RNA in a virus particle, or as an isolated DNA or RNA. The term "polynucleotide" refers to a polymeric form of nucleotides of any length, either ribonucleotides or deoxynucleotides, and includes both double- and single-stranded DNA and RNA. Unless otherwise noted, a polynucleotide includes the complement thereof. The nucleotide sequence of the complement of a polynucleotide can be easily determined by a person of skill in the art. A polynucleotide may include nucleotide sequences having different functions, including for instance coding sequences, and non-coding sequences such as regulatory sequences and/or untranslated regions. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

If naturally occurring, a polynucleotide is preferably isolated, more preferably, purified. An "isolated" compound, such as a polynucleotide, polypeptide, or virus particle, is one that is separate and discrete from its natural environment. A "purified" compound is one that is at least 60% free, preferably 75% free, and most preferably 90% free from other components with which they are naturally associated. Compounds such as polynucleotides and polypeptides that are produced outside the organism in which they naturally occur, e.g., through chemical or recombinant means, are considered to be isolated and purified by definition, since they were never present in a natural environment.

An example of an infectious polynucleotide of the present invention includes the infectious polynucleotide VR-V7 (SEQ ID NO:1). VR-V7 is also referred to herein as V6G7475A. Other examples of infectious polynucleotides of the present invention include VR-V5 (SEQ ID NO:2), VR-V5G7475A (SEQ ID NO:3), and VR-V6 (SEQ ID NO:4). It should be noted that while SEQ ID NOs:1, 2, 3, 4, 5, 6 and other virus nucleotide sequences are disclosed herein as a DNA sequence, the present invention contemplates the corresponding RNA sequence, and RNA and DNA complements thereof, as well.

Other infectious polynucleotides of the present invention have a polynucleotide sequence having structural similarity to a reference polynucleotide. Reference polynucleotides include SEQ ID NO:1, SEQ ID NO:2, SEQ ID NO:3, SEQ ID NO:4, SEQ ID NO:5, SEQ ID NO:6, the European prototype strain of PRRS virus, Lelystad (Genbank accession number M96262; SEQ ID NO:14), and the North American prototype strain of PRRS virus, VR-2332 (Genbank accession number U87392; SEQ ID NO:15). The similarity is referred to as "percent identity" and is determined by aligning the residues of the two polynucleotides (i.e., the nucleotide sequence of a candidate infectious polynucleotide and the nucleotide sequence of the reference polynucleotide) to optimize the number of identical nucleotides along the lengths of their sequences; gaps in either or both sequences are permitted in making the alignment in order to optimize the number of shared nucleotides, although the nucleotides in each sequence must nonetheless remain in their proper order. In some aspects of the present invention the gap (also referred to as a deletion) is present in the candidate infectious polynucleotide sequence. A candidate infectious polynucleotide is the polynucleotide that has the nucleotide sequence being compared to the reference polynucleotide. A candidate infectious polynucleotide can be isolated from an animal, such as a pig infected with PRRSV, isolated from a cultured cell line, or can be produced using recombinant techniques, or chemically or enzymatically synthesized. Two nucleotide sequences can be compared using any of the commercially available computer algorithms routinely used to produce alignments of nucleotide sequences. Preferably, two nucleotide sequences are compared using the GAP program of the GCG Wisconsin Package (Accelrys, Inc.) version 10.3 (2001). The GAP program uses the algorithm of Needleman et al. (*J. Mol. Biol.,* 48:443-453 (1970)) to find the alignment of two complete sequences that maximizes the number of matches and minimizes the number of gaps. Preferably, the default values for all GAP search parameters are used, including scoring matrix=NewsgapDNA.cmp, gap weight=50, length weight=3, average match=10, average mismatch=0. In the comparison of two nucleotide sequences using the GAP search algorithm, structural similarity is referred to as "percent identity." Preferably, a polynucleotide has structural similarity with a reference polynucleotide of at least 88%, at least 89%, at least 90%, at least 91%, at least 92%, at least 93%, at least 94%, at least 95%, at least 96%, at least 97%, at least 98%, or at least 99% identity when the structural similarity is determined using the GAP program.

Whether a polynucleotide is an infectious polynucleotide can be determined by inserting into a vector a candidate infectious polynucleotide, transcribing the candidate infectious polynucleotide in vitro, transfecting a permissive cell with the resulting RNA molecules, and detecting progeny viral RNA, progeny viral nucleocapsid protein, detecting infectious virus particles, or a combination thereof. The vector preferably has the characteristics of being low copy number and remains stable after insertion of large (e.g., 15 kb) inserts. An example of a suitable vector is pOK and pOK12 (GenBank Accession AF223639, Vieira et al., *Gene,* 100:189-194 (1991)), and other vectors having these characteristics are known and available. In the vector the candidate infectious polynucleotide is immediately downstream of a promoter. Useful promoters are those that can be induced to yield high levels of transcription, such as a T7 RNA polymerase promoter, for example TAATACGACTCACTATA (SEQ ID NO:16), or the RNA polymerase promoters SP6 and T3. Transcription of the candidate infectious polynucleotide typically includes restriction endonuclease digestion of the vector to make it linear, and producing RNA transcripts by use of routine and well known in vitro transcription methods. Kits for in vitro transcription are commercially available (for instance, mMessage mMachine, available from Ambion, Austin, Tex.).

After in vitro transcription the RNA is purified using routine methods and then used to transfect a permissive cell. Examples of permissive cells include, for instance, BHK-21 (which allows one round of virus particle production), CL-2621, MA-104 (ATCC CRL-2378), MARC-145 (Kim et al., *Arch. Virol.,* 133:477-483 (1993)), cell lines cloned from these cell lines, or primary porcine alveolar macrophages. Methods for efficiently transfecting cells include the use of 1,2-dimyristyloxypropyl-3-dimethyl-hydroxy ethyl ammonium bromide and cholesterol (DMRIE-C), and other commercially available products, preferably, DMRIE-C. Methods for efficiently transfecting primary porcine alveolar macrophages are known to the art (Groot Bramel-Verheige et al., *Virol.,* 278:380-389 (2000)). Generally, 2 to 3 micrograms of RNA can be used for transfection, but lower and higher amounts may be used. After a suitable period of time, the presence of progeny viral RNA can be detected by, for instance, reverse transcriptase-polymerase chain reaction (RT-PCR). Likewise, progeny viral nucleocapsid protein can be detected by, for instance, nucleocapsid specific antibody. Further, whether the virus particles produced by cells transfected with a candidate infectious polynucleotide will infect another cell can be detected by exposing uninfected permissive cells to supernatant from infected cells. Optionally, cytopathic effect (CPE) may be observed. A candidate infectious polynucleotide is considered to be an infectious polynucleotide when it produces progeny viral RNA, progeny viral proteins (nucleocapsid, membrane, GP5, and others), and infects other permissive cells.

In some aspects of the present invention an infectious polynucleotide includes a deletion of nucleotides encoding nonstructural protein 2 (nsp2), one of several (12 predicted) polypeptides present in the polyprotein encoded by ORF1. In a PRRS virus, and infectious polynucleotides thereof, the nucleotides encoding the first amino acid of nsp2 can be determined by identifying the cleavage site of papain-like protease 1 beta, predicted to be after the ORF1 amino acid glycine at position 383 in VR-2332.

With respect to identifying the nucleotides encoding the last amino acid of nsp2, the exact nsp2 C-terminal cleavage site of the ORF1a-encoded polyprotein has not been empirically determined, thus the nucleotides corresponding to the 3' end of the coding region are unknown. However, two predictions of the C-terminal cleavage site have been proposed, one Gly|Gly (where the vertical line between the two glycine residues indicates the cleavage location) at amino acid 980 in VR-2332, and the other at amino acid 1197 in VR-2332. In alignment of all available PRRSV sequences, there are several completely conserved Gly|Gly doublets within this protein that may also be the nsp2 C terminal cleavage site of the polyprotein (amino acids 646, 980, 1116, 1196, 1197, in VR-2332. The locations of the Gly|Gly doublets in the other viruses and infectious polynucleotides can be identified by comparison to the sequences of nsp2 and the Gly|Gly doublets disclosed in FIG. 12. Present studies suggest that there may be at least 3 cleavage sites in nsp2, corresponding to amino acid 980, 116, 1196 or 1197.

The nsp2 polypeptide includes a highly conserved chymotrypsin-like cysteine protease domain (identified as CP in FIG. 3 and PL2 in FIG. 9) present at the N-terminus, and 3-4 predicted transmembrane domains near the C terminus of nsp2 (where the number of transmembrane domains varies depending on the location of the C-terminal cleavage site). Typically, deletion of the nucleotides encoding the amino acids of the PL2 domain or all of the predicted transmembrane domains results in a polynucleotide that can replicate in permissive cells but will not produce infectious virus particles. Thus, an infectious clone of the present invention does not typically include deletion of the entire PL2 domain or all of the predicted transmembrane domains.

The nucleotides encoding the chymotrypsin-like cysteine protease domain are nucleotides 1474 to 1776 of VR-V7 (SEQ ID NO:1), nucleotides 1474 to 1776 of VR-2332 (Genbank accession number U87392), and nucleotides 1482 to 1784 of Lelystad (Genbank accession number M96262). The location of a chymotrypsin-like cysteine protease domain in the nucleotide sequence of other PRRS viruses can be identified by aligning the amino acid sequence of the nsp2 polypeptide encoded by a PRRS virus with the amino acid sequence alignment disclosed in FIG. 12, and determining which nucleotides encode those amino acids that line up with the chymotrypsin-like cysteine protease domain. Alternatively, the amino acid sequences of nsp2 polypeptides of other PRRS viruses can be identified by aligning the amino acid sequence of the nsp2 polypeptide encoded by a PRRS virus with the amino acid sequence of nsp2 polypeptides produced by other arteriviruses, such as equine arteritis virus (EAV) and lactate dehydrogenase-elevating virus (LDV).

The nucleotides encoding the predicted transmembrane domains of VR-V7 (SEQ ID NO:1), VR-2332 (Genbank accession number U87392), and Lelystad (Genbank accession number M96262) are shown in Table 1.

TABLE 1

Nsp2 nucleotides encoding predicted transmembrane domains.

|  | VR-V7 | VR-2332 | Lelystad |
|---|---|---|---|
| Transmembrane domain I | 881 to 901 | 881 to 901 | 761 to 781 |
| Transmembrane domain II | 913 to 934 | 913 to 934 | 793 to 814 |
| Transmembrane domain III | 963 to 980 | 963 to 980 | 843 to 860 |
| Transmembrane domain IV | 985 to 1003 | 985 to 1003 | 865 to 883 |

Figure 12:
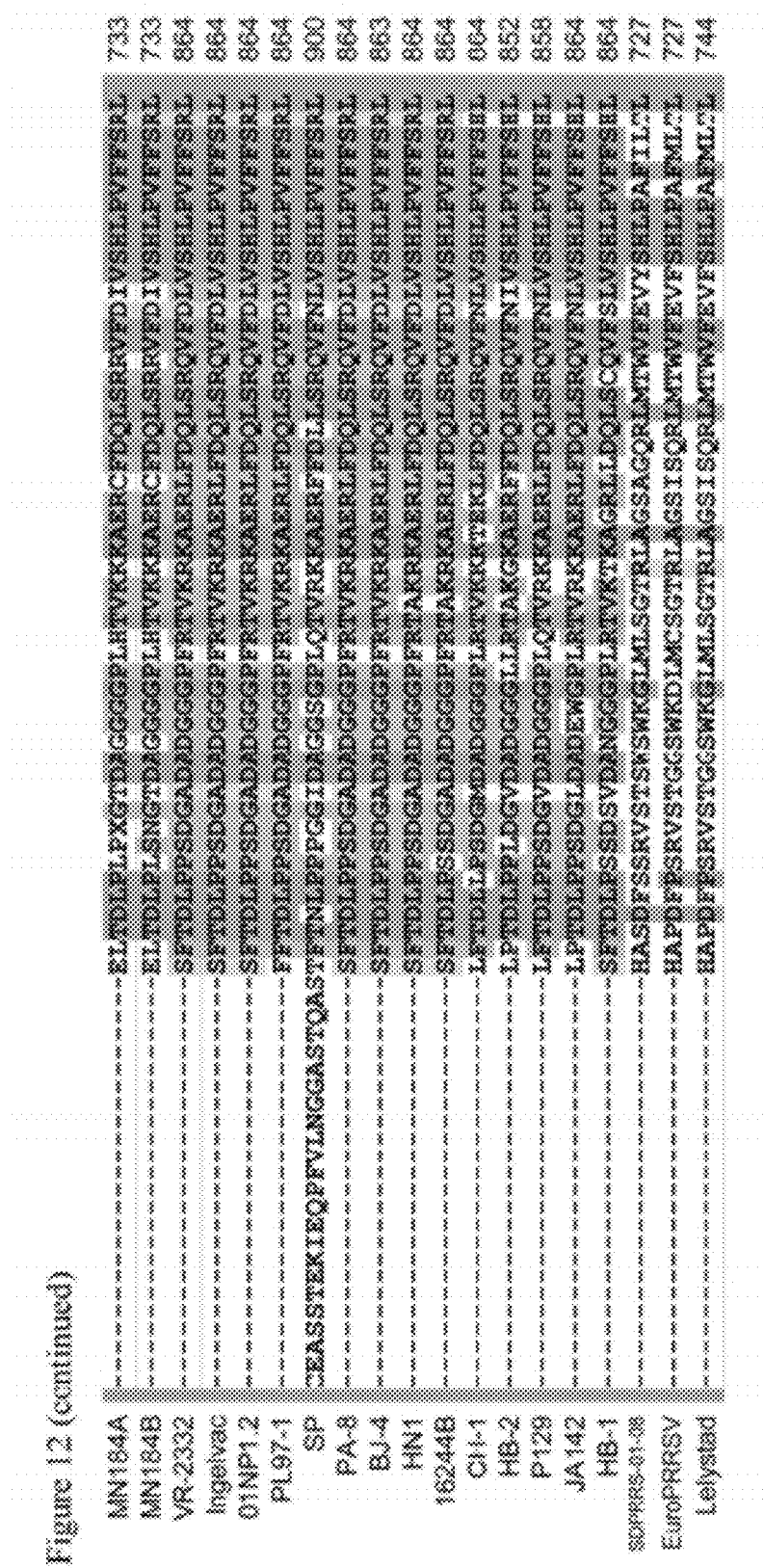
FIG. 12. Nsp2 amino acid sequence alignment of divergent PRRSV. The completely conserved putative cysteine protease catalytic residues (Cys and His) are identified by stars and the boxed amino acids signify protease sequence conservation within PRRSV and EAV. The proposed cleavage sites are identified by filled arrows (↓); additional possible cleavage sites are indicated by a hashed arrow; signal peptide, solid grey box; transmembrane regions, shown in hashed black boxes; potential N-glycosylation sites, indicated by an asterisk (*). The figure derivation and color scheme were described in the FIG. 10 legend. Nsp2 amino acid sequences from the following GenBank full-length sequences were used for comparison: VR-2332 (SEQ ID NO: 74), Ingelvac MLV (SEQ ID NO: 75), 01NP1.2 (DQ056373) (SEQ ID NO: 76), PL97-1 (SEQ ID NO: 77), PA-8 (SEQ ID NO: 79), SP (SEQ ID NO: 78), BJ-4 (SEQ ID NO: 80), HN1 (SEQ ID NO: 81), 16244B (SEQ ID NO: 82), HB-1 (SEQ ID NO: 87), HB-2 (SEQ ID NO: 84), CH-1a (SEQ ID NO: 83), P129 (SEQ ID NO: 85), JA142 (SEQ ID NO: 86), SDPRRS-01-08 (AY375474) (SEQ ID NO: 88), EuroPRRSV (SEQ ID NO: 89), Lelystad (SEQ ID NO:90)), MN184A (SEQ ID NO:72), MN184B (SEQ ID NO:73).
Figure 12:
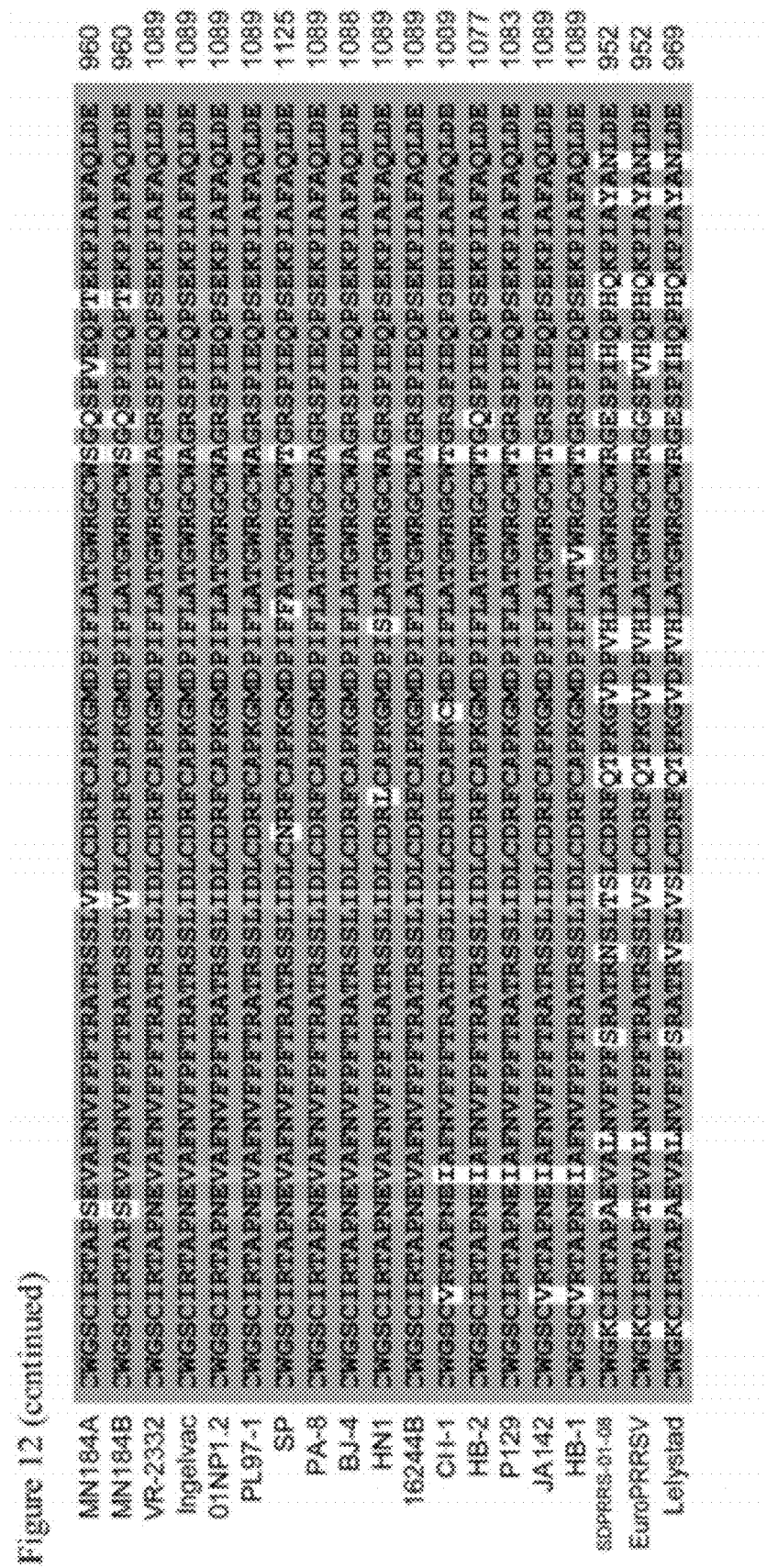
Figure 12:
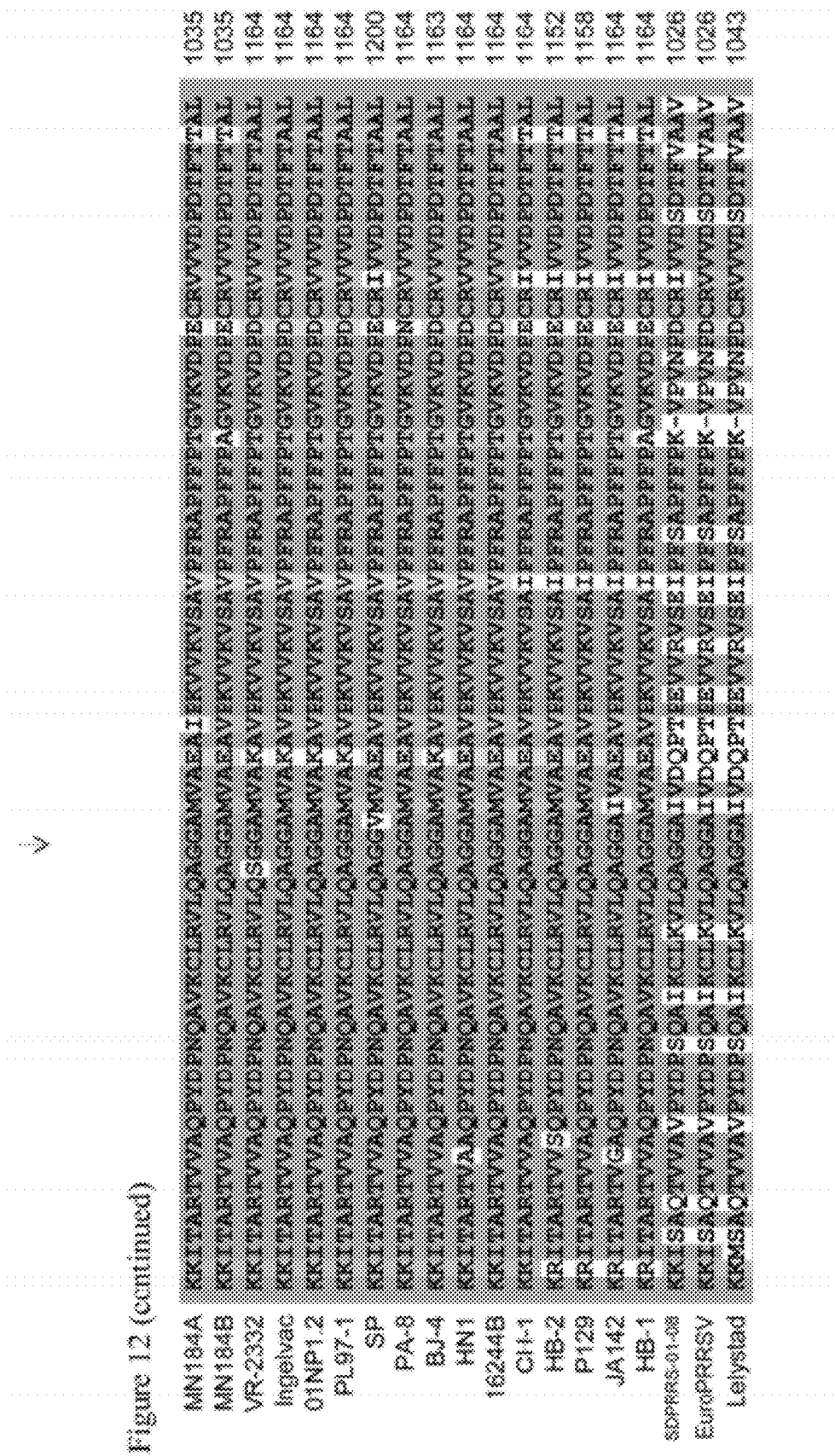

The location of the transmembrane domains in the nucleotide sequence of other PRRS viruses can be identified by aligning the amino acid sequence of the nsp2 polypeptide encoded by a PRRS virus with the amino acid sequence alignment disclosed in FIG. 12, and determining which nucleotides encode those amino acids that line up with the transmembrane domains. Alternatively, the location of the transmembrane domains can be identified with a computer algorithm, such as the PredictProtein algorithm as described by Rost et al. (*Nucleic Acids Res.*, 32 (Web Server issue):W321-326 (2004), or the TMHMM algorithm as described by Krogh et al. (*J. Mol. Biol.*, 305:567-580 (2001)) and available through the World Wide Web.

The deletion present in infectious polynucleotides of the present invention is typically between the nucleotides encoding the chymotrypsin-like cysteine protease domain and the nucleotides encoding the transmembrane domains, and does not result in a frameshift in the reading frame of ORF1. As discussed above, the deletion typically does not include all the nucleotides encoding the chymotrypsin-like cysteine protease domain, all the nucleotides encoding the transmembrane domains, or the combination thereof. In some aspects, for instance when the infectious polynucleotide has structural similarity with SEQ ID NO:1, the 5' boundary of a deletion is at nucleotide 2305, nucleotide 2205, nucleotide 2105, or nucleotide 2062, and the 3' boundary of a deletion is at nucleotide 3774, nucleotide 3804, nucleotide 3834, or nucleotide 3864. In other aspects, for instance when the infectious polynucleotide has structural similarity with SEQ ID NO:14, the 5' boundary of a deletion is at nucleotide 2304, nucleotide 2204, nucleotide 2104, or nucleotide 2061, and the 3' boundary of a deletion is at nucleotide 3455, nucleotide 3495, nucleotide 3525, or nucleotide 3545. The deletion can be at least 39 nucleotides, 48 nucleotides, or 57 nucleotides. In some aspects, the deletion can be at least 267 nucleotides, at least 276 nucleotides, or at least 285 nucleotides. In some aspects the deletion is no greater than 489 nucleotides, no greater than 459, no greater than 429, or no greater than 402 nucleotides. An infectious polynucleotide may have more than one deletion in the nsp2 region.

Examples of infectious polynucleotides derived from VR-V7 and containing a deletion are disclosed in Table 2.

TABLE 2

Infectious polynucleotides derived from VR-V7 (SEQ ID NO: 1).

| Polynucleotide* | deleted nucleotides of SEQ ID NO: 1 | amino acids of ORF1 deleted | viral titers (PFU/ml) | Summary of phenotype** |
|---|---|---|---|---|
| Nsp2 Δ180-323 | 1876-2304 | 563-705 | — | nonviable |
| Nsp2 Δ242-323 | 2056-2304 | 623-705 | — | nonviable |
| Nsp2 Δ324-434 | 2305-2637 | 706-816 | +(~10$^5$) | small plaque size |
| Nsp2 Δ324-523 | 2305-2904 | 706-905 | +(~10$^5$-10$^6$) | intermediate |
| Nsp2 Δ543-632 | 2962-3231 | 925-1014 | +(~10$^5$) | small plaque size |
| Nsp2 Δ633-726 | 3232-3513 | 1015-1108 | +(~10$^5$) | small plaque size |
| Nsp2 Δ543-726 | 2962-3513 | 925-1108 | +(~10$^5$) | small plaque size |
| Nsp2 Δ727-813 | 3514-3774 | 1109-1195 | +(~10$^5$) | small plaque size |
| Nsp2 Δ324-726 | 2305-3513 | 706-1108 | +(~10$^{1-2}$) | ND |
| Nsp2 Δ324-813 | 2305-3774 | 706-1195 | — | nonviable |
| Nsp2 Δ727-845 | 3514-3870 | 1109-1227 | — | nonviable |
| Nsp2 Δ324-845 | 2305-3870 | 706-1227 | — | nonviable |

*the deletion refers to the amino acids of nsp2 that are deleted, e.g., in the virus Nsp2 Δ180-323, amino acids 180-323 of nsp2 are deleted.
**plaque size is relative to plaques produced by wildtype VR-2332.

An infectious polynucleotide containing a deletion can include an exogenous polynucleotide inserted in place of the deletion. An "exogenous" polynucleotide refers to a foreign nucleotide sequence, i.e., a nucleotide sequence that is not normally present in a PRRS virus or an infectious clone thereof. The exogenous polynucleotide can, and preferably does encode a polypeptide. Suitable exogenous polynucleotides include those encoding a detectable marker, e.g., a molecule that is easily detected by various methods. Examples include fluorescent polypeptides (e.g., green, yellow, blue, or red fluorescent proteins), luciferase, chloramphenicol acetyl transferase, and other molecules (such as c-myc, flag, 6×his, HisGln (HQ) metal-binding peptide, and V5 epitope) detectable by their fluorescence, enzymatic activity or immunological properties, and are typically useful when detected in a cell, for instance, a cultured cell, or a tissue sample that has been removed from an animal. Other exogenous polynucleotides that can be used are those encoding polypeptides expressed by other entities, such as cells and pathogens. Expression of an exogenous polynucleotide results in an infectious polynucleotide that expresses foreign antigens. Examples of exogenous nucleotide sequences include those encoding proteins expressed by pathogens, preferably porcine pathogens, such as porcine circovirus type 2, *Mycoplasma hyopneumoniae* (e.g., the P46 and P65 proteins of *M. hyopneumoniae*), *Lawsonia intracellularis* (e.g., the outer membrane proteins of *L. intracellularis*), the ORF5 of different strains of PRRSV, and *Streptococcus suis* (e.g., the 38-kDa protein of *S. suis*). The nsp2 polypeptide has B-cell epitopes and is expected to be immunogenic. Inclusion of foreign epitopes in an nsp2 polypeptide is expected to result in an immune response to the foreign epitopes. Additional examples of exogenous polynucleotides include those encoding biological response modifiers, such as, for example, IFN-α, IFN-γ, IL-12, IL-2, TNF-α, and IL-6.

The exogenous polynucleotide is inserted into the deletion region such that it is in frame with the open reading frame encoding nsp1α and nsp1β, and more than one exogenous polynucleotide can be inserted in tandem, for instance, nucleotide sequences encoding three c-myc epitopes can be present. The total size of the infectious polynucleotide containing an exogenous polynucleotide inserted in the place of the deletion is typically no greater than 16,000 bases, no greater than 15,800 based, no greater than 15,600 bases, no greater than 15,400 bases, or no greater than 15,200 based (including the poly A tail). An insertion can be present in an infectious polynucleotide having the Nsp2 Δ324-434, Nsp2 Δ324-523, Nsp2 Δ543-632, Nsp2 Δ633-726, Nsp2 Δ543-726, Nsp2 Δ727-813, or Nsp2 Δ324-726 deletion, preferably, the Nsp2 Δ324-434, Nsp2 Δ543-632, Nsp2 Δ633-726, Nsp2 Δ543-726, Nsp2 Δ727-813, or Nsp2 Δ324-726 deletion. Preferred examples of infectious clones containing an exogenous polynucleotide in the location of a deletion include an infectious polynucleotide having the Nsp2 Δ324-434 deletion containing a coding region encoding a 238 amino acid green fluorescent protein, an infectious polynucleotide having the Nsp2 Δ543-632 deletion containing a coding region encoding a 238 amino acid green fluorescent protein, an infectious polynucleotide having the Nsp2 Δ324-434 deletion containing a coding region encoding a 10 amino acid c-myc epitope (EQKLISEEDL, SEQ ID NO:17), an infectious polynucleotide having the Nsp2 Δ324-434 deletion containing a coding region encoding a 10 amino acid c-myc epitope, and an infectious polynucleotide having the Nsp2 Δ324-726 or Nsp2 Δ543-726 deletions each containing a coding region encoding tandem repeat of the 10 amino acid c-myc epitope.

An infectious polynucleotide is typically present in a vector, and the combination of infectious polynucleotide and vector is referred to as an infectious clone, which is made through reverse genetics. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard recombinant DNA techniques known in the art (see, e.g., Sambrook et al, *Molecular Cloning: A Laboratory Manual*, Cold Spring Harbor Laboratory Press (1989)). A vector can provide for further cloning (amplification of the polynucleotide), i.e., a cloning vector, or for expression of the polypeptide encoded by the coding region, i.e., an expression vector, or the combination thereof. The term vector includes, but is not limited to, plasmid vectors, viral vectors, cosmid vectors, or artificial chromosome vectors. Typically, a vector is capable of replication in a bacterial host, for instance *E. coli*. Preferably the vector is a plasmid.

Selection of a vector depends upon a variety of desired characteristics in the resulting construct, such as a selection marker, vector replication rate, and the like. Preferably, a vector suitable for use as part of an infectious clone is both a cloning vector and an expression vector. Useful vectors have a low copy number in a host cell. Suitable host cells for cloning or expressing the vectors herein are prokaryote or eukaryotic cells. Preferably the host cell secretes minimal amounts of proteolytic enzymes. Suitable prokaryotes include eubacteria, such as gram-negative organisms, for example, *E. coli* or *S. typhimurium*. Exemplary host cells useful for making, manipulating, and maintaining an infectious clone are DH-5α, DH-1 (ATCC 33849), and AG-1, preferably, DH-1 or AG-1.

A vector includes regulatory sequences operably linked to the infectious polynucleotide. The term "operably linked" refers to a juxtaposition of components such that they are in a relationship permitting them to function in their intended manner. A regulatory sequence is "operably linked" to an infectious polynucleotide of the present invention when it is joined in such a way that expression of the coding region is achieved under conditions compatible with the regulatory sequence. Typically, a promoter is one that provides for high specificity binding of an RNA polymerase, and such promoters include T7, SP6, and T3. Typically the promoter is situated immediately upstream of the first nucleotide of the infectious polynucleotide. Preferably, a GGT is inserted between the promoter and the first nucleotide of the infectious polynucleotide. Optionally and preferably the vector also contains a hepatitis delta virus ribozyme downstream of the poly A region.

The vector optionally, and preferably, includes one or more selection marker sequences, which typically encode a molecule that inactivates or otherwise detects or is detected by a compound in the growth medium. For example, the inclusion of a selection marker sequence can render the transformed cell resistant to an antibiotic, or it can confer compound-specific metabolism on the transformed cell. Examples of a selection marker sequence are sequences that confer resistance to kanamycin, ampicillin, chloramphenicol, tetracycline, and neomycin.

When producing a deletion of nucleotides encoding an nsp2 polypeptide in an infectious clone, standard recombinant DNA techniques known in the art can be used (see, e.g., Sambrook et al, *Molecular Cloning: A Laboratory Manual*, Cold Spring Harbor Laboratory Press (1989)). As the skilled person will recognize, it is standard practice during construction of an infectious clone (and when construction deletions in an infectious clone) to verify by nucleotide sequence analysis the presence of expected nucleotide sequences, such as deletions or other alterations and the absence of other mutations. Likewise, when a candidate infectious polynucleotide is tested to determine if it is infectious, it is standard practice to verify by nucleotide sequence analysis the absence of contaminating wild-type virus.

The present invention also includes isolated infectious polynucleotides disclosed at SEQ ID NO:5 and SEQ ID NO:6, and infectious polynucleotides having structural similarity to SEQ ID NO:5 or SEQ ID NO:6. Methods for determining structural similarity are described herein. Preferably, an infectious polynucleotides of this aspect of the present invention has structural similarity to SEQ ID NO:5 or SEQ ID NO:6 of at least 88%, at least 89%, at least 90%, at least 91%, at least 92%, at least 93%, at least 94%, at least 95%, at least 96%, at least 97%, at least 98%, or at least 99%. A polynucleotide having structural similarity to SEQ ID NO:5 or SEQ ID NO:6 is considered to be an infectious polynucleotide if, when present in a virus particle and exposed to permissive cells, the polynucleotide replicates in the permissive cells and produces infectious virus particles.

The present invention also includes isolated virus particles. As used herein, the terms "virus particle" and "viral particle" are used interchangeably and refer to a polynucleotide of the present invention surrounded by an envelope. A virus particle of the present invention can, when added to a permissive cultured cell, can replicate to result in the production of more viral particles.

A virus particle can be grown by passage in vivo or in cell culture. Passage in vivo includes inoculating a pig (Faaberg et al., U.S. Pat. No. 7,041,443). Passage in cell culture includes exposing cultured cells to the virus particle and incubating the cells under conditions suitable for the virus to reproduce and produce more virus particles. Preferably, the cultured cells are not an immortalized or transformed cell line (i.e., the cells are not able to divide indefinitely). Preferably, primary porcine alveolar macrophages are used for passage in cell culture (Faaberg et al., U.S. Pat. No. 7,041,443).

A virus of the present invention can be inactivated, i.e., rendered incapable of reproducing in vivo and/or in cell culture. Methods of inactivation are known to the art and include, for instance, treatment of a virus particle of the invention with a standard chemical inactivating agent such as an aldehyde reagent including formalin, acetaldehyde and the like; reactive acidic alcohols including cresol, phenol and the like; acids such as benzoic acid, benzene sulfonic acid and the like; lactones such as beta propiolactone and caprolactone; and activated lactams, carbodiimides and carbonyl diheteroaromatic compounds such as carbonyl diimidazole. Irradiation such as with ultraviolet and gamma irradiation can also be used to inactivate the virus.

Also included in the present invention are attenuated virus particles (i.e., viruses having reduced ability to cause the symptoms of mystery swine disease in pigs), and methods of making an attenuated virus particle. Methods of producing an attenuated virus are known to the art. Typically, a virus of the present invention is passaged, i.e., used to infect a cell in culture, allowed to reproduce, and then harvested. This process is repeated until the virulence of the virus in pigs is decreased. For instance, the virus can be passaged 10 times in cell culture, and then the virulence of the virus measured. If virulence has not decreased, the virus that was not injected into the animal is passaged an additional 10 times in cell culture. This process is repeated until virulence is decreased. In general, virulence is measured by inoculation of pigs with virus, and evaluating the presence of clinical symptoms and/or $LD_{50}$ (see, for instance, Halbur et al., *J. Vet. Diagn. Invest.*, 8:11-20 (1996), Halbur et al., *Vet. Pathol.*, 32:200-204 (1995), and Park et al., *Am. J. Vet. Res.*, 57:320-323 (1996)). Preferably, virulence is decreased so the attenuated virus does not cause the death of animals, and preferably does not cause clinical symptoms of the disease.

Typically, a cell culture useful for producing an attenuated virus of the present invention includes cells of non-porcine mammal origin. Examples of non-porcine mammal cell cultures include, for instance, the cell line MA-104 (ATCC CRL-2378), the cell line MARC-145 (Kim et al., *Arch. Virol.*, 133:477-483 (1993)), and the cell line CL-2621 (Baustita et al., *J. Vet. Diagn. Invest.*, 5:163-165 (1993)). Preferably, a mixed cell culture is used for producing an attenuated virus particle of the present invention. In a mixed cell culture there are at least two types of cells present. Preferably, a mixed cell culture includes an immortalized or transformed cell line and a primary cell culture. A mixed cell culture is particularly useful when a virus reproduces slowly, or not at all, in an immortalized or transformed cell line. Preferred examples of an immortalized or transformed cell line for use in a mixed cell culture include, for example, the cell line MARC-145 (Kim et al., *Arch. Virol.*, 133:477-483 (1993)), and the cell line MA-104 (ATCC CRL-2378). Preferably, primary cell cultures for use in a mixed cell culture are porcine in origin. A preferred example of a primary cell culture for use in a mixed cell culture is primary porcine alveolar macrophages.

The present invention further includes the polypeptides encoded by the nsp2 coding regions present in the polynucleotides disclosed in Table 2, including those that are viable. Also included in the present invention are antibodies, including monoclonal and polyclonal antibodies, that specifically bind a polypeptide encoded by the nsp2 coding regions present in the polynucleotides disclosed in Table 2. The term "antibody," unless specified to the contrary, includes fragments of whole antibodies which retain their binding activity for a target antigen. Such fragments include Fv, F(ab') and F(ab')$_2$ fragments, as well as single chain antibodies (scFv). As used herein, an antibody that can "specifically bind" a polypeptide is an antibody that interacts only with the epitope of the antigen that induced the synthesis of the antibody, or interacts with a structurally related epitope. An antibody that "specifically binds" to an epitope will, under the appropriate conditions, interact with the epitope even in the presence of a diversity of potential binding targets. As used herein, the term "polypeptide:antibody complex" refers to the complex that results when an antibody specifically binds to a polypeptide, or a subunit or analog thereof. In some aspects, an antibody of the present invention include those that do not specifically bind to a full length nsp2 polypeptide encoded by VR-2332 (e.g., Genbank accession number U87392, ORF1 amino acids 384-1363 (also see Allende et al. *J. Gen. Virol.*, 80:307-315 (1999) or ORF1 amino acids 384-1580 (also see Ziebuhr et al., *J. Gen. Virol.*, 81:853-879 (2000)). Such antibodies can be identified using routine methods known in the art.

Antibodies of the present invention can be prepared using the intact polypeptide. Optionally, an nsp2 polypeptide described herein can be covalently bound or conjugated to a carrier polypeptide to improve the immunological properties of the polypeptide. Useful carrier polypeptides are known in the art.

The preparation of polyclonal antibodies is well known. Polyclonal antibodies may be obtained by immunizing a variety of warm-blooded animals such as horses, cows, goats, sheep, dogs, chickens, rabbits, mice, hamsters, guinea pigs and rats as well as transgenic animals such as transgenic sheep, cows, goats or pigs, with an immunogen. The resulting antibodies may be isolated from other proteins by using an affinity column having an Fc binding moiety, such as protein A, or the like.

Monoclonal antibodies can be obtained by various techniques familiar to those skilled in the art. Briefly, spleen cells from an animal immunized with a desired antigen are immortalized, commonly by fusion with a myeloma cell (see, for example, *Antibodies: A Laboratory Manual*, Harlow et al., eds., Cold Spring Harbor Laboratory Press: Cold Spring Harbor, N.Y., (1988)). Monoclonal antibodies can be isolated and purified from hybridoma cultures by techniques well known in the art.

In some embodiments, the antibody can be recombinantly produced, for example, by phage display or by combinatorial methods. Phage display and combinatorial methods can be used to isolate recombinant antibodies that bind to a polypeptide described herein, or a biologically active subunit or analog thereof (see, for example, Ladner et al., U.S. Pat. No. 5,223,409). Such methods can be used to generate human monoclonal antibodies.

The present invention also provides compositions including an infectious polynucleotide, PRRS polynucleotide, virus particle, or antibody of the present invention. Such compositions typically include a pharmaceutically acceptable carrier. As used herein "pharmaceutically acceptable carrier"

includes saline, solvents, dispersion media, coatings, antibacterial and antifungal agents, isotonic and absorption delaying agents, and the like, compatible with pharmaceutical administration. Additional active compounds can also be incorporated into the compositions.

A composition may be prepared by methods well known in the art of pharmacy. In general, a composition can be formulated to be compatible with its intended route of administration. Examples of routes of administration include perfusion and parenteral, e.g., intravenous, intradermal, subcutaneous, oral (e.g., inhalation), transdermal (topical), and transmucosal. Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile aqueous solutions (where water soluble) or dispersions and sterile powders for the extemporaneous preparation of sterile solutions or dispersions. For intravenous administration, suitable carriers include physiological saline, bacteriostatic water, Cremophor EL™ (BASF, Parsippany, N.J.) or phosphate buffered saline (PBS). A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (i.e., an infectious polynucleotide or PRRS virus of the present invention) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. These compositions may also be formed into a powder or suspended in an aqueous solution such that these powders and/or solutions can be added to animal feed or to the animals' drinking water. These compositions can be suitably sweetened or flavored by various known agents to promote the uptake of the vaccine orally by the pig.

The active compounds can also be administered by any method suitable for administration of polynucleotide agents, e.g., using gene guns, bio injectors, and skin patches as well as needle-free methods such as the micro-particle DNA vaccine technology disclosed by Johnston et al. (U.S. Pat. No. 6,194,389). Additionally, intranasal delivery is possible, as described in, for instance, Hamajima et al., *Clin. Immunol. Immunopathol.*, 88:205-210 (1998). Liposomes and microencapsulation can also be used.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from, for instance, Alza Corporation and Nova Pharmaceuticals, Inc. Liposomal suspensions can also be used as pharmaceutically acceptable carriers. These can be prepared according to methods known to those skilled in the art.

Toxicity and therapeutic efficacy of such active compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred.

The data obtained from cell culture assays and animal studies can be used in formulating a range of dosage for use in the field. The dosage of such compounds lies preferably within a range of circulating concentrations that include the $ED_{50}$ with little or no toxicity. The dosage may vary within this range depending upon the dosage form employed and the route of administration used.

The compositions can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a polypeptide can include a single treatment or, preferably, can include a series of treatments.

The present invention includes methods for using the compositions described herein. In one aspect the invention includes methods for treating one or more symptoms of mystery swine disease in an animal that may be caused by infection by a PRRS virus. The method includes administering an effective amount of a composition of the present invention to an animal having or at risk of having mystery swine disease, or symptoms of mystery swine disease.

Treatment of mystery swine disease, or symptoms of mystery swine disease, can be prophylactic or, alternatively, can be initiated after the development of disease or symptoms thereof. As used herein, the term "symptom" refers to objective evidence in a subject of mystery swine disease. Symptoms associated with mystery swine disease and the evaluations of such symptoms are routine and known in the art. Examples of symptoms include abortion, anorexia, fever, lethargy, pneumonia, red/blue discoloration of ears, labored breathing (dyspnea), and increased respiratory rate (tachypnea). Treatment that is prophylactic, for instance, initiated before a subject manifests symptoms of a condition caused by a PRRS virus, is referred to herein as treatment of a subject that is "at risk" of developing the disease or symptoms thereof. Typically, an animal "at risk" is an animal present in an area where animals having the disease or symptoms thereof have been diagnosed and/or is likely to be exposed to a PRRS virus. Accordingly, administration of a composition can be performed before, during, or after the occurrence of the conditions described herein. Treatment initiated after the development of a condition may result in decreasing the severity of the symptoms of one of the conditions, or completely removing the symptoms.

In some aspects, the methods typically include administering to an animal a composition including an effective amount of a virus particle of the present invention. An "effective amount" is an amount effective to prevent the manifestation of symptoms of mystery swine disease, decrease the severity of the symptoms of the disease, and/or completely remove the symptoms. Typically, the effective amount is an amount that results in a humoral and/or cellular immune response that protects the animal during future exposure to a PRRS virus. The virus particle used in the composition may contain an infectious polynucleotide that has a deletion as described herein. Optionally, the infectious polynucleotide also includes an exogenous polynucleotide present at the location of the deletion. An advantage of using a virus particle having a deletion (or an exogenous polynucleotide present in the location of the deletion) is it can be easily distinguished from other PRRS viruses, including wild type PRRS viruses present in the field. The virus particle can be identified by isolation of the virus from an animal followed, for instance, by sequencing, restriction enzyme digestion, or PCR-based amplification of specific nucleotides. Such a "marked" virus particle is often referred to in the art as a marker vaccine.

In other aspects of the present invention the infectious clones and/or infectious polynucleotides described herein can be used to investigate viable gene insertions, to investigate alternative expressed RNA or proteins other than full length virus, to investigate viral recombination, and to investigate immunogenic properties of full-length nsp2 as relative to truncated nsp2.

EXAMPLES

Example 1

Full-length cDNA clones of North American porcine reproductive and respiratory syndrome virus (PRRSV) prototype VR-2332 strain were developed, with each progressive version possessing less nucleotide changes than prior versions when compared to wt strain VR-2332. Progeny virus of each infectious clone was recovered and analyzed for nucleotide sequence verification, in vitro growth rate and plaque size. Progeny from one infectious clone confirmed robust in vivo replication, seen by the appearance of α-PRRSV antibodies at the same rate as wt virus. Northern blot analysis of the in vivo progeny also revealed that defective subgenomic RNA species, termed heteroclites (uncommon forms), were present along with full-length genomes. Concurrent northern blot analysis of a passage series of infected MA-104 cell cultures revealed that recombinant virus only gradually gained a profile of both full-length and heteroclite RNA similar to the RNA species seen in in vivo infection.

Materials and Methods

Cells and viral strains. MA-104 cells or its descendent MARC-145 cells (ATCC CRL-11171), an African green monkey kidney epithelial cell line which supports PRRSV replication (Meng et al., *J. Vet. Diagn. Invest.*, 8:374-81 (1996)), were maintained in Eagle's minimal essential medium (EMEM) (JRH Biosciences 56416), supplemented with 1 mg/ml NaHCO$_3$ and 10% fetal bovine serum (FBS), at 37° C. with 5% CO$_2$. The cultured cells were transfected with RNA or infected with virus when monolayer growth had reached 70-80% confluency. PRRSV North American prototype strains VR-2332 and Ingelvac® MLV have been described previously (Yuan et al., *Virus Res.*, 79:189-200 (2001)). Strain VR-2332 grows to equivalent titers on both cell lines.

Viral RNA purification. Viral RNA (vRNA) was purified as described. (Chen et al., *J. Gen. Virol.*, 75:925-930 (1994); Yuan et al., *Virus Res.*, 79:189-200 (2001)). Briefly, supernatant from MARC-145 cells infected with VR-2332 was harvested on day 4 post-infection (p.i.). After removal of cellular debris by centrifugation at 12,000 rpm, the supernatants were layered onto a 2 ml 0.5 M sucrose cushion and centrifuged at 76,000×g for 4 hours. The pelleted virions were resuspended in 0.5 ml LES (0.1 M LiCl/5 mM EDTA/1.0% SDS) and further digested by addition of 100 μg proteinase K at 56° C. to remove all protein. After 10 minutes of incubation, vRNA was extracted several times with acid phenol and phenol/chloroform and then precipitated in 70% v/v ethanol. Pelleted vRNA was immediately resuspended into 50 μl H$_2$O or RNase-free TE buffer (10 mM Tris-HCl, 1 mM EDTA, pH 8.0) and stored at −80° C.

Construction of full-length viral cDNA. cDNA synthesis was performed with Enhanced Avian HS RT-PCR Kit (Sigma, HSRT-100). Eight PCR primers (Table 3) were used to amplify four overlapping cDNA fragments covering the complete VR-2332 genome (FIG. 2). The cycling conditions were 94° C. for 2 minutes, then 35 cycles of 94° C. for 15 seconds, 68° C. for 4-5 seconds, followed by 68° C. for 5 minutes. Each PCR fragment was purified with the QIAEX II Gel Extraction Kit (Qiagen) and cloned into pCR®2.1-TOPO® vector with TOPO TA Cloning® Kit (Invitrogen K450001). Plasmids representing each fragment were submitted for nucleotide sequence analysis. The fragments with the minimum nucleotide mutations compared to parental VR-2332 sequence (GenBank submission number U87392) were used to assemble the full-length cDNA, as shown in FIG. 2. In each overlap region, a unique restriction enzyme site was utilized to join flanking fragments. Four digested fragments, representing full-length genomic sequence, were precisely assembled stepwise into a modified low copy plasmid vector (pOK12HDV-PacI). The vector was modified to include the HDV ribozyme by inserting a 244 bp SmaI to SacII fragment containing the HDV antigenome ribozyme and a T7 RNA polymerase terminator sequence from Transcription vector 2.0 (Johnson et al., *J. Virol.*, 71:3323-3327 (1997); Pattnaik et al., *Cell*, 69:1011-1020 (1992)) into the corresponding sites in pOK12 (Vieira et al., *Gene*, 100:189-194 (1991)). The NcoI restriction enzyme site in this 244 bp fragment was replaced with a unique PacI site by oligonucleotide mutation with primer sets 5' pOK12HDV-2157/3' pOK12HDV-257 and 5' pOK12HDV-257/polyA-modified (Table 3), followed by fusion PCR. In the full-length cDNA clones, viral genomic sequence was preceded by the T7 RNA polymerase promoter, 1 or 2 G residues and a T residue, and followed by a polyadenylic acid tail of 50 nucleotides. Assembled clones were propagated in the DH5a strain of *Eschericia coli* and then submitted for full-genome nucleotide sequence confirmation.

TABLE 3

Oligonucleotide primers used in this study. Forward primers are
indicated with a slash (/) after the designator, reverse primers
are preceded by a slash. Inserted restriction enzyme sites are
shown in underlined italics.

| Primer | Genome Position* | Sequence |
|---|---|---|
| Cloning: | | |
| T7Leader-VR long/ | 1-31 | 5'-ACAT*GCATGC*TTAATACGACTCACTATAGTATGACG<br>TATAGGTGTTGGCTCTATGCCTTGG<br>(SEQ ID NO: 18) |
| /3'-4300 | 4617-4635 | 5'-CTGGGCGACCACAGTCCTA<br>(SEQ ID NO: 19) |
| 5'-4056-AscI/ | 4055-4080 | 5'-CTTCTC*GGCGCGCC*CGAATGGGAGT<br>(SEQ ID NO: 20) |
| /3'-7579 | 7578-7603 | 5'-TCATCATA*CCTAGG*GCCTGCTCCACG<br>(SEQ ID NO: 21) |
| 5'-7579/ | 7578-7603 | 5'-CGTGGAGCAGGC*CCTAGG*TATGATGA<br>(SEQ ID NO: 22) |
| /P32 | 13293-13310 | 5'-TGCAGGCGAACGCCTGAG<br>(SEQ ED NO: 23) |
| VR1509/ | 11938-11958 | 5'-GTGAGGACTGGGAGGATTACA<br>(SEQ ID NO: 24) |
| /3'end-FL | 15405-15411 | 5'-GTCT*TTAATTAA*CTAG(T)$_{30}$AATTTCG<br>(SEQ ID NO: 25) |
| Mutagenesis: | | |
| 5'-pOK12HDV-257/<br>(SphI, PacI) | pOK12HDV-PacI<br>257-282 | 5'-GAT*GCATGC*CA*TTAATTAA*GGGTCGGC<br>(SEQ ID NO: 26) |
| /3'-pOK12HDV-257<br>(SphI, PacI) | pOK12HDV-PacI<br>257-282 | 5'-GCCGACCC*TTAATTAA*TG*GCATGC*ATC<br>(SEQ ID NO: 27) |
| T7leader-VR-2G/ | 1-5 | 5'-ACATGCATGCTTAATACGACTCACTATAGGTATGAC<br>(SEQ ID NO: 28) |
| 7475G2A/ | 7453-7477 | 5'-5Phos/CTGTGTGGACATGTCACCATTGAAA<br>(SEQ ID NO: 29) |
| 13860C2T/ | 13843-13867 | 5'-5Phos/GTGTATCGTGCCGTTCTGTTTTGCT<br>(SEQ ID NO: 30) |
| 14979A2G/ | 14958-14982 | 5'-5Phos/CAGATGCTGGGTAAGATCATCGCTC<br>(SEQ ID NO: 31) |
| Northern Blot Analyses: | | |
| /3'-UTR | 15298-15336 | 5'-GCACAATGTCAATCAGTGCCATTCACCACACATTCTTCC<br>(SEQ ID NO: 32) |
| /1a-p222 | 221-261 | 5'-TAGACTTGGCCCTCCGCCATAAACACCCTGGCATTGGGGGT<br>(SEQ ID NO: 33) |

*Genome position is based on GenBank Submission U87392

Modification and sequence analysis of full-length cDNA clones. QuikChange® Multi Site-Directed Mutagenesis Kit (Stratagene) was used to modify all cDNA clones from pVR-V4 to pVR-V6G7475A. The complete genomic cDNA plasmid inserts were then submitted to the University of Minnesota Advanced Genetic Analysis Center (AGAC) for nucleotide sequence analysis with appropriate sequencing primers (Table 3). Sequence differences between pVR-V4 through pVR-V6G7475A, as well as to those of parental VR-2332, its corresponding attenuated vaccine strain, Inglevac MLV, and pVR-HN, the first infectious clone of VR-2332, are listed in Table 4 (Nelsen et al., *J. Virol.*, 73:270-80 (1999); Yuan et al., *Virus Res.*, 79:189-200 (2001); Nielsen et al., *J. Virol.*, 77:3702-3711 (2003)).

TABLE 4

| Base* | Region | VR-2332 | V4 | V5 | V5-1-P3 | V5-2-P3 | V5-Swing 612 | V5G7475A | V5G7475A-P3 | V6 | V6G7475A | V6G7475A-P3 | VR-HN | MLV |
|---|---|---|---|---|---|---|---|---|---|---|---|---|---|---|
| -4 | 5'UTR | | | | | T | | | | | | | | |
| -3 | | | G | G | | T | | G | | G | G | | G | |
| -2 | | | G | G | | T | | G | | G | G | T/Ø | G | |
| -1 | | | T | T | | T | | T | T/Ø | T | T | T | T | T |
| 48 | | A | A | A | A | A | A | A | A | A | A | R (G/A) | A | A |
| 102 | | A | A | A | A | A | G | A | A | A | A | A | A | A |
| 258 | NSP1a | C | C | C | C | C | C | C | C | C | C | C | A | C |
| 309 | | A | G | G | G | G | G | G | G | G | G | G | A | A |
| 415 | | T | T | T | — | Y (C/T) | T | T | — | T | T | — | T | T |
| 642 | | T | C | C | — | C | C | C | — | C | C | — | T | T |

TABLE 4-continued

| Position | ORF | | | | | | | | | | | | | |
|---|---|---|---|---|---|---|---|---|---|---|---|---|---|---|
| 784 | NSP1b | G | G | G | — | G | G | G | — | G | G | — | G | A |
| 827 | | C | C | C | — | C | T | C | — | C | C | — | C | C |
| 1074 | | C | C | C | — | C | C | C | — | C | C | — | T | C |
| 1107 | | A | G | G | — | G | G | G | — | G | G | — | A | A |
| 1122 | | A | A | A | — | R (G/A) | A | A | — | A | A | — | A | T |
| 1181 | | C | C | C | — | C | C | C | — | C | C | — | C | T |
| 1294 | | A | A | A | — | R (G/A) | A | A | — | A | A | — | A | A |
| 1379 | NSP2 | C | C | C | — | C | T | C | — | C | C | — | C | C |
| 1595 | | C | A | C | — | C | C | C | — | C | C | — | C | C |
| 2192 | | C | C | C | — | C | C | C | — | C | C | — | C | T |
| 3040 | | G | G | G | — | G | G | G | — | G | G | — | G | A |
| 3457 | | G | G | G | — | G | G | G | — | G | G | — | G | C |
| 3657 | | C | C | C | — | Y (C/T) | C | C | — | C | C | — | C | C |
| 4407 | NSP3 | T | C | C | — | C | C | C | — | C | C | — | T | T |
| 4593 | | A | G | G | — | G | G | G | — | G | G | — | A | A |
| 4681 | | T | G | G | — | G | G | G | — | G | G | — | G | G |
| 4865 | | T | T | T | — | Y (C/T) | G | T | — | T | T | — | T | T |
| 4866 | | A | G | G | — | G | G | G | — | G | G | — | A | A |
| 5097 | | G | A | A | — | A | A | A | — | A | A | — | A | A |
| 5247 | | T | C | C | — | C | C | C | — | C | C | — | T | T |
| 5519 | | C | C | C | — | C | C | C | — | C | C | — | C | C |
| 5610 | | T | T | T | — | T | T | T | — | T | T | — | A | T |
| 6345 | NSP5 | A | A | A | — | A | A | A | — | A | A | — | A | T |
| 6674 | | C | T | T | — | T | T | T | — | T | T | — | C | T |
| 6853 | NSP7 | G | G | G | — | G | G | G | — | G | G | — | A | G |
| 6966 | | T | T | T | T | T | T | T | T | T | T | T | C | T |
| 7183 | | A | A | A | A | A | A | A | A | A | A | R (G/A) | A | A |
| 7188 | | C | C | C | C | C | C | C | Y (C/T) | C | C | Y (C/T) | C | C |
| 7189 | | C | C | C | C | C | C | C | C | C | C | Y (C/T) | C | C |
| 7213 | | C | C | C | C | C | C | C | M (A/C) | C | C | M (A/C) | C | C |
| 7329 | | G | A | A | A | A | A | A | A | A | A | A | G | G |
| 7475 | | A | G | G | G | G | A | A | A | G | A | A | A | A |
| 7554 | | T | C | C | C | C | C | C | C | C | C | C | C | T |
| 9220 | NSP9 | T | C | T | — | T | T | T | — | T | T | — | T | T |
| 9649 | NSP10 | G | A | G | — | G | G | G | — | G | G | — | G | G |
| 9918 | | T | T | T | — | T | T | T | — | T | T | — | T | G |
| 9958 | | G | A | G | — | G | G | G | — | G | G | — | A | A |
| 10040 | | A | G | A | — | A | A | A | — | A | A | — | A | A |
| 10533 | | T | T | T | — | T | T | T | — | T | T | — | T | G |
| 10643 | | T | T | T | — | T | T | T | — | T | T | — | C | T |
| 10697 | | T | C | T | — | T | T | T | — | T | T | — | C | C |
| 10739 | | C | T | C | — | C | C | C | — | C | C | — | C | C |
| 10781 | | G | A | G | — | G | G | G | — | G | G | — | A | A |
| 10803 | | T | A | T | — | T | T | T | — | T | T | — | A | C |
| 10895 | | C | C | C | — | C | C | C | — | C | C | — | C | T |
| 11055 | NSP11 | T | A | T | — | T | T | T | — | T | T | — | A | A |
| 11081 | | G | A | G | — | G | G | G | — | G | G | — | A | A |
| 11221 | | G | A | G | — | G | A | G | — | G | G | — | A | A |
| 11229 | | G | G | G | — | G | G | G | — | G | G | — | G | T |
| 11259 | | C | C | C | — | C | C | C | — | C | C | — | C | C |
| 11327 | | C | T | C | — | C | C | C | — | C | C | — | C | C |
| 11329 | | G | C | C | — | C | C | C | — | C | C | — | C | C |
| 11501 | | A | G | A | — | A | A | A | — | A | A | — | A | A |
| 11666 | NSP12 | C | T | C | — | C | C | C | — | C | C | — | C | C |
| 11744 | | G | C | G | — | G | G | G | — | G | G | — | G | G |
| 11760 | | G | G | G | — | R (A/G) | G | G | — | G | G | — | G | G |
| 11882 | | A | G | A | — | A | A | A | — | A | A | — | A | A |
| 12076 | ORF2a/b | A | G | A | — | A | A | A | — | A | A | — | A | A |
| 12102 | | G | G | G | — | G | G | G | — | G | G | — | G | T |
| 12153 | | A | G | A | — | A | A | A | — | A | A | — | A | A |
| 12432 | | A | A | A | — | A | A | A | — | A | A | — | A | A |
| 12501 | | T | A | T | — | T | T | T | — | T | T | — | T | T |
| 12600 | | G | G | G | — | G | G | G | — | G | G | — | G | C |
| 12943 | ORF3 | G | G | G | — | G | G | G | — | G | G | — | G | A |
| 12950 | | C | C | C | — | C | C | C | — | C | C | — | C | C |
| 12973 | | T | G | T | — | T | T | T | — | T | T | — | T | T |
| 13011 | | G | G | G | — | G | G | G | — | G | G | — | A | A |
| 13787 | No ORF | T | T | T | — | T | T | T | — | T | T | — | C | T |
| 13825 | ORF5 | G | G | G | — | G | G | G | — | G | G | — | G | A |
| 13860 | | T | C | C | — | C | C | C | — | T | T | — | T | T |
| 14238 | | A | A | A | — | A | A | A | — | A | A | — | A | G |
| 14336 | | T | T | C | — | C | Y (T/C) | C | — | C | C | — | T | T |
| 14404 | ORF6 | T | T | C | — | C | C | C | — | C | C | — | C | T |
| 14420 | | C | C | C | — | C | C | C | — | C | C | — | C | G |
| 14686 | | A | A | A | — | A | G | A | — | A | A | — | A | A |
| 14735 | | C | G | G | — | C | G | G | — | G | G | — | G | G |
| 14737 | | G | C | C | — | C | C | C | — | C | C | — | C | C |
| 14979 | ORF7 | G | A | A | — | A | A | A | — | G | G | — | G | G |

TABLE 4-continued

| | | | | | | | | | | | | | | |
|---|---|---|---|---|---|---|---|---|---|---|---|---|---|---|
| 15281 | 3'UTR | A | G | A | — | A | A | A | — | A | A | — | A | A |
| 15334 | | T | C | T | — | T | T | T | — | T | T | — | T | T |
| 15339 | | C | C | C | — | Y (T/C) | C | C | — | C | C | — | C | C |
| 15411 | | T | T | T | — | K (T/G) | Y (T/C) | T | — | T | T | — | T | T |

Nucleotide differences between PRRSV strains and VR-2332 infectious clones. Only positions where nucleotide differences were noted are shown. Nucleotides that are represented in strain VR-2332 are shown in unshaded boxes. Light shaded boxes represent nucleotide differences that are unique to the infectious clone, medium shaded boxes highlight those nucleotides that are also seen in Ingelvac ® MLV, and boxes that are shaded black indicate swine unique nucleotides. Regions that were not sequenced are indicated by a slash.
*The negative bases refer to those nucleotides present in the RNA after transcription and derived from the RNA polymerase promoter immediately upstream of the infectious polynucleotide. These promoter-derived nucleotides are typically no longer present in an infectious polynucleotide after it has been passaged 9 times.

In vitro transcription. The full-length cDNA clone was linearized by cleavage with PacI, which cuts downstream of the poly(A) tail. Capped [m$^7$G(5')ppp(5')G cap analog] RNA transcripts were produced using the mMESSAGE MACHINE™ Kit (Ambion) and an optimized 2:1 ratio of methylated cap analogue to GTP. Approximately 50 to 60 μg of RNA was generated from 2 μg of DNA template in a 20 μl of reaction mixture. Increasing the ratio of cap analogue to GTP substantially reduced the RNA yield. The RNA was subsequently purified by acid phenol-chloroform followed by isopropanol precipitation and resuspended in nuclease-free TE buffer (pH 8.0). RNA was evaluated for quality by size comparison with wild-type VR-2332 viral RNA on a 1% glyoxal denaturing agarose gel, and quantified by spectrophotometry at $OD_{260}$.

MARC-145 cell transfection. A modified transfection procedure was generated based on the approached described by Nielsen (Nielsen et al., (J. Virol., 77:3702-3711 (2003)). For transfection, MARC-145 cells were seeded onto six-well plates (2–3×10$^5$ cells/well) in 3 ml of complete medium [EMEM supplemented with 10% fetal bovine serum (FBS)] and then incubated at 37° C., 5% $CO_2$ for 20-24 hours until approximately 80% confluent (Collins et al., J. Vet. Diagn. Invest., 4:117-126 (1992)). 4 μg of in vitro transcribed RNA diluted in 500 μl Opti-MEM® I Reduced Serum Medium (Invitrogen) and 2 μl of 1,2-dimyristyloxypropyl-3-dimethylhydroxy ethyl ammonium bromide and cholesterol (DMRIE-C; Invitrogen) diluted in 1 ml Opti-MEM® medium were combined and vortexed briefly. The MARC-145 cells were washed once with 2 ml Opti-MEM® medium and then immediately overlayed with the lipid:RNA complex solution. DMRIE-C without RNA (2 μl) was used as a negative control and DMRIE-C with 10-100 ng strain (wild type) wt VR-2332 purified viral RNA was used as a positive control. After 4 hours of exposure to the lipid:RNA complexes, the monolayers were washed and fresh complete medium (EMEM with 10% FBS) was added. Supernatants from transfected cells were monitored daily for appearance of cytopathic effect (CPE) and passaged onto fresh MARC-145 at 72-96 hours posttransfection.

Detection of progeny viral RNA. To detect progeny viral RNA, cell culture supernatant from transfected and infected MARC-145 cells were harvested. RNA was isolated with QiaAmp viral RNA Kit (Qiagen). RT-PCR was performed with select primer pairs, specific to the VR-2332 strain nucleotides that were indicative of infectious clone mutated residues (Table 3). Confirmation of infectious clone progeny was obtained by nucleotide sequence verification of clone specific nucleotides present in the RT-PCR products.

Detection of progeny viral nucleocapsid protein. Indirect immunofluorescence assays (IFA) were used to detect viral protein expression in in vitro transcript RNA transfected, or progeny virus infected, MARC-145 cells prepared on coverslips. Infected cells were fixed in 3.7% paraformaldehyde with phosphate buffered saline (PBS), pH 7.5, at room temperature for 10 minutes. The fixed cells were washed with PBS, incubated at 37° C. for 45 minutes in PRRSV nucleocapsid protein specific monoclonal antibody SDOW17 (Magar et al., Can. J. Vet Res., 59:232-234 (1995)) and further incubated with goat anti-mouse immunoglobulin G (IgG) conjugated with fluorescein isothiocyanate at 37° C. for another 45 minutes (1:100 dilution) (Sigma). The coverslips were washed with PBS, mounted to a slide using gel mount oil, and observed under a fluorescence microscope.

Viral plaque assay. MARC-145 cell monolayers on six-well plates were infected with cell supernatant (in 10-fold dilutions) from transfected or infected MARC-145 cells by incubation at room temperature for 1 hour. Infected monolayers were subsequently washed once with fresh EMEM/ 10% FBS, overlaid immediately with sterile 1% SeaPlaque Agarose (BioWhittaker Molecular Applications, Rockland, Me.) in 1×MEM (Sigma M4144)/10% FBS/2% (w/v) $NaHCO_3$/1× glutamine/1× nonessential amino acids/10 mM HEPES/2% (v/v) gentamycin, and incubated at 37° C./5% $CO_2$, inverted, for 5 days. After careful removal of the agarose, cells were stained with 5% crystal violet in 20% ethanol for 10-30 minutes for visualization of plaque size.

Viral growth curve. MARC-145 monolayers in T-75 flasks were inoculated with either parental or recombinant PRRSV diluted in serum-free EMEM at a multiplicity of infection (MOI) of 0.001. After 1 hour attachment at room temperature with gentle mixing, the inocula were removed and the monolayers washed three times with serum-free EMEM. After washing, 4 ml complete medium was added and the flasks were subsequently incubated for up to 5 days at 37° C., 5% $CO_2$. Aliquots (0.5 ml) were harvested immediately after the addition of medium (0 hour time point) and at 24, 48, 72, 96 and 120 hours and stored at −80° C. Serial dilutions of the samples were used to infect fresh MARC-145 cells and the cells then processed as described above. After removal of the agarose, plaques were visualized and counted. Growth curve results were expressed as PFU/ml.

In vivo inoculation of progeny virus. Ten 4-week-old pigs of mixed breed and sex from a PRRSV-seronegative herd were divided into three groups, each consisting of two animals. The first group received 10$^{3.5}$ 50% tissue culture infectious dose ($TCID_{50}$) of cloned virus (pVR-V5, third passage on MARC-145 cells) per ml, the second group received 10$^{5.4}$ $TCID_{50}$ per ml of the parental virus strain VR-2332 (fourth passage on MARC-145 cells), and the third group was mock inoculated with EMEM. All of the animals received 2 ml of inoculum by intramuscular injection. The animals were kept in separate rooms throughout the experiment and observed daily for clinical signs. All pigs were euthanized on day 28 postinfection. To recover virus, individual serum samples were diluted 5-fold with incomplete EMEM and placed on fresh MARC-145 monolayers for 1 to 2 hours at room temperature with gentle agitation. The inocula were then removed and complete EMEM was added. Infected cells were incubated at 37° C., 5% $CO_2$ and observed daily. Once CPE was evident, infected cell supernatants were frozen at −80° C. until further characterized.

Northern Blot Analysis. pVR-V6G7475A transcripts were transfected into MA104 cells and then passaged onto fresh cells for several passages. For subsequent northern blot analysis, supernatants from passage 1 (P1), P3, P6, P8 and P10 were diluted 1:50 and then used to infect cells (1 ml/T75 flask) on the same day. At the same time, infected swine serum was diluted 10-fold and then used (1 ml) to infect a separate T75 flask. Cytopathic effect was seen on day 3 p.i. for all flasks. Intracellular RNA was extracted using a RNeasy Midi kit (Qiagen) and electrophoresced (15 μg/sample) on a glyoxal denaturing gel as described previously (Nelsen et al., *J. Virol.*, 73:270-80 (1999)). pVR-V6G7475A transcript RNA (100 ng) was run as a control. After RNA transfer to 0.45 micron MagnaGraph Nylon Transfer Membrane (Osmonics), the membrane was probed with labeled oligonucleotide/1a-p222, end labeled with $\gamma$-$^{32}$P-ATP (Amersham) using polynucleotide kinase (Promega) as described previously (Nelsen et al., *J. Virol.*, 73:270-80 (1999)).

Nucleic acid sequence analysis of progeny virus. 5'- and 3'-rapid amplification of cDNA ends (RACE) was performed with SMART™ RACE cDNA Amplification Kit (BD Bioscience) or 5' or 3'-Full Race Core Set (TaKaRa Bio Inc) on viral RNA isolated with the QIAmp®Viral RNA Mini Kit (Qiagen). The remaining nucleotide sequence was determined from RT-PCR products of primer pairs developed to cover the entire genome of strain VR-2332 (Table 3), as described previously (Yuan et al., *Virus Res.*, 79:189-200 (2001)). The products were submitted for nucleic acid sequence determination at the Advanced Genetic Analysis Center at the University of Minnesota. Complete viral sequence with at least three fold coverage was initially assembled with the SeqMan suite of the Lasergene® sequence analysis software (DNASTAR, Inc.), and further analyzed using GCG Wisconsin Package Version 10.3 software (Accelrys Inc.). Strain VR-2332 (GenBank Accession U87392) strain Ingelvac® MLV (GenBank Accession AF066183) and cDNA clone pVR-HN (GenBank Accession AY150564; Nielsen et al., *J. Virol.*, 77:3702-3711 (2003)) were used in all nucleotide comparisons to recombinant virus strains.

Results

Modification of pOK12 Vector. pOK12 (GenBank Accession AF223639; Vieira et al., *Gene*, 100:189-194 (1991)), a low copy cloning vector, was modified by digestion with SmaI (enzyme site at 273 bp in pOK12) and SalI (site at 307 bp) and inserting the 244 bp SmaI-SalI fragment of Vector 2.0 (7) containing the hepatitis delta virus (HDV) ribozyme. The vector (pOK12HDV) was then further modified by mutagenesis of an existing KpnI site (pOK12HDV site at 273 bp) to insert a PacI restriction enzyme site through the use of the primer pair 5'-pOK12HDV-257SphIPacI/3'-pOK12HDV-257SphIPacI. The HDV ribozyme was added to provide for effective cleavage precisely at the 3' end of the polyA tract. Studies revealed that the modification was not necessary to obtaining infectious progeny virus.

Construction of full-length cDNA clones. The cloning strategy is depicted in FIG. 2. Four overlapping genome fragments were amplified from purified VR-2332 viral RNA by RT-PCR using the primer pairs indicated (FIG. 2, Table 3). Each fragment was individually cloned into the pCR®2.1-TOPO® vector to generate intermediate clone pCR-SphI-FseI (segment I), pCR-FseI-AvrII (segment II), pCR-AvrII-BsrGI (segment III), and pCR-BsrGI-PacI (segment IV). The cDNA clones were then digested with two unique restriction enzymes, as indicated by the clone name. Four fragments were gel-purified and stepwise ligated to vector pOK12HDV-PacI to generate a full-length cDNA clone of PRRSV (pVR-V4). In the full-length cDNA clone, viral genomic sequence was driven by T7 RNA polymerase promoter and followed by polyadenylic acid tail of 50 nucleotides. RNA transcripts of clone pVR-V4 did not display typical PRRSV infectivity when transfected into permissive cells, although viral RNA could be detected over several passages. When compared to strain VR-2332, a total of 45 nucleotide mutations (Table 4) leading to 21 amino acid changes were detected (Table 5), although several mutations were the same as previously identified in Ingelvac® MLV (Yuan et al., *Virus Res.*, 61:87-98 (1999)).

TABLE 5

| NT Position | AA Position | Region | VR-2332 | V4 | V5 | V5-1-P3 | V5-2-P3 | V5-Sw612 | V5G7475A | V6 | V6G7475A | VR-HN | MLV |
|---|---|---|---|---|---|---|---|---|---|---|---|---|---|
| 258 | 23 | NSP1α | V | | | | | | | | | Silent | |
| 309 | 40 | | Q | Silent | Silent | Silent | Silent | Silent | Silent | Silent | Silent | | |
| 642 | 151 | | P | Silent | Silent | — | Silent | Silent | Silent | Silent | Silent | | |
| 784 | 199 | NSP1β | V | | | — | | | | | | | I |
| 827 | 213 | | A | | | — | | | V | | | | |
| 1074 | 295 | | Y | | | — | | | | | | Silent | |
| 1107 | 306 | | L | Silent | Silent | — | Silent | Silent | Silent | Silent | Silent | | |
| 1181 | 331 | | S | | | — | | | | | | | F |
| 1379 | 397 | NSP2 | A | | | — | | | V | | | | |
| 1595 | 469 | | A | D | | — | | | | | | | |
| 2192 | 668 | | S | | | — | | | | | | | T |
| 3040 | 951 | | D | | | — | | | | | | | N |
| 3457 | 1090 | | D | | | — | | | | | | | N |
| 4407 | 1406 | NSP3 | P | Silent | Silent | — | Silent | Silent | Silent | Silent | Silent | | |
| 4593 | 1468 | | Q | Silent | Silent | — | Silent | Silent | Silent | Silent | Silent | | |
| 4681 | 1498 | | S | A | A | — | A | A | A | A | A | A | A |
| 4866 | 1559 | | V | Silent | Silent | — | Silent | Silent | Silent | Silent | Silent | | |
| 5097 | 1636 | | R | Silent | Silent | — | Silent | Silent | Silent | Silent | Silent | Silent | Silent |
| 5247 | 1686 | | V | Silent | Silent | — | Silent | Silent | Silent | Silent | Silent | | |
| 5519 | 1777 | | T | | | — | | | | | | I | |
| 5610 | 1807 | | L | | | — | | | | | | Silent | |
| 6345 | 2052 | NSP5 | P | | | — | | | | | | | Silent |
| 6674 | 2162 | | P | L | L | — | L | L | L | L | L | | L |
| 6853 | 2222 | NSP7 | D | | | — | | | | | | N | |
| 6966 | 2259 | | D | | | — | | | | | | Silent | |
| 7329 | 2380 | | K | Silent | Silent | Silent | Silent | Silent | Silent | Silent | Silent | | |
| 7475 | 2429 | | E | G | G | G | G | | | G | | | |
| 7554 | 2455 | | V | Silent | | Silent | Silent | Silent | Silent | Silent | Silent | | Silent |
| 9220 | 3011 | NSP9 | L | P | | — | | | | | | | |

TABLE 5-continued

| nt | aa | NSP/ORF | aa | | | | | | | | | |
|---|---|---|---|---|---|---|---|---|---|---|---|---|
| 9649 | 3154 | NSP10 | G | E | — | | | | | | | |
| 9918 | 3244 | | L | | — | | | | | | | Silent |
| 9958 | 3257 | | G | E | — | | G/E | | | | | E | E |
| 10040 | 3284 | | V | Silent | — | | | | | | | |
| 10533 | 3449 | | Y | | — | | | | | | | H |
| 10643 | 3485 | | V | | — | | | | | | Silent | |
| 10697 | 3503 | | A | Silent | — | | | | | | Silent | Silent |
| 10739 | 3517 | | H | Silent | — | | | | | | | |
| 10781 | 3531 | | T | Silent | — | | | | | | Silent | Silent |
| 10803 | 3539 | | C | R | — | | | | | | Silent | R |
| 10895 | 3569 | | D | | — | | | | | | | Silent |
| 11055 | 3623 | NSP11 | S | T | — | | | | | | T | T |
| 11081 | 3631 | | P | Silent | — | | | | | | Silent | Silent |
| 11221 | 3678 | | G | E | — | | | E | | | | E | E |
| 11229 | 3681 | | V | | — | | | | | | E | L |
| 11259 | 3691 | | R | G | — | | | | | | | |
| 11327 | 3738 | | H | Silent | — | | | | | | | |
| 11329 | 3739 | | G | A | A | — | A | A | A | A | A | A | A |
| 11501 | 3771 | | E | Silent | — | | | | | | | |
| 11666 | 3826 | NSP12 | P | Silent | — | | | | | | Silent | Silent |
| 11744 | 3852 | | W | C | — | | | | | | | |
| 11882 | 3898 | | K | Silent | — | | | | | | | |
| 12076 | 2 | ORF2a/b | K | E | — | | | | | | | |
| 12102 | 10/9 | | L/D | | — | | | | | | | F/Y |
| 12153 | 27 | | P/I | P/V | — | | | | | | | |
| 12432 | 120 | | E | Silent | — | | | | | | | |
| 12501 | 143 | | D | E | — | | | | | | | |
| 12600 | 176 | | G | | — | | | | | | | Silent |
| 12943 | 83 | ORF3 | G | | — | | | | | | | F |
| 12950 | 85 | | D | | — | | | | | | | Silent |
| 12973 | 93 | | M | R | — | | | | | | | |
| 13011 | 106 | | G | | — | | | | | | S | S |
| 13825 | 13 | ORF5 | R | | — | | | | | | | Q |
| 13860 | 25 | | F | L | — | L | L | L | | | | G |
| 14238 | 151 | | R | | — | | | | | | | |
| 14336 | 183 | | G | Silent | — | Silent | Silent | Silent | Silent | Silent | | |
| 14404 | 10 | ORF6 | H | Silent | — | Silent | Silent | Silent | Silent | Silent | | |
| 14420 | 16 | | Q | | — | | | | | | | P |
| 14686 | 104 | | L | | — | | Silent | | | | | |
| 14735 | 121 | | R | G | G | — | G | G | G | G | G | G | G |
| 14737 | 121 | | R | G | G | — | G | G | G | G | G | G | G |
| 14979 | 31 | ORF7 | A | T | I | — | T | T | T | | | |

Amino acid differences between PRRSV strains and VR-2332 infectious clones. Only positions where nucleotide differences were noted are shown with corresponding amino acid position within the identified genomic retion. Amino acids that are represented in strain VR-2332 are shown in unshaded boxes and infectious clone amino acid identities with VR-2332 are represented by blank boxes. Text in each individual box represent silent or amino acid changes due to nucleotide differences shown in Table 2. Light shaded boxes represent nucleotide differences that are unique to the infectious clone, medium shaded boxes highlight those nucleotides that are also seen in Ingelvac ® MLV, and boxes that are shaded black indicate swine unique nucleotides. Amino acids separated by slashes indicate ORF2a/ORF2b amino acid numbers. Regions that were not sequenced are indicated by a slash.

Because many mutations in pVR-V4 occurred in the critical region encoding putative helicase, polymerase and other Nidovirus motifs (FIG. 3, Table 4), additional clones of genomic segment III (pCR-AvrII-BsrGI) were generated and sequenced in their entirety. After replacing segment III of pVR-V4 with the most sequence accurate fragment obtained, we again determined the nucleotide sequence of the entire genomic full-length clone (pVR-V5). Except for the replaced region and for four spontaneous mutations (nucleotides 1595, 13860, 14336, and 14404), these two genomic clones were identical (Table 4). Sequence analysis of pVR-V5 showed that this clone harbored a total of 23 mutations compared to strain VR-2332. Of these 23 changes, only 8 nucleotide mutations coded for a change in amino acid and five of the amino acid residue mutations were identical to Ingelvac® MLV and thus not predicted to adversely effect in vitro replication (Table 4).

Clone pVR-V6 was derived from site-directed mutagenesis of genome segment IV to repair nucleotides 13860 and 14979 using primers 13860C2T/ and 14979A2G/, respectively. Mutation of these two nucleotides would correct amino acid residue 25 of GP5 (L→F) and residue 31 of the nucleocapsid protein (T→A). Sequence analysis of clone pVR-V6 confirmed that the nucleotides had been corrected back to wild-type (wt) VR-2332 nucleotides and had not resulted in any other nucleotide changes elsewhere in the genome when compared to pVR-V5 (Tables 4 and 5). Finally, site-directed mutagenesis on genome segment III using oligomer 7475G2A was completed on both pVR-V5 and pVR-V6 in order to correct an alteration from wt VR-2332 at nt 7475. The change of G→A at nt 7475 resulted in a glycine (G) at ORF1 amino acid 2429 in the two recombinant clones to the glutamic acid (E) seen in the parental VR-2332 viral strain. The final two clones, pVR-V5G7475A and pVR-V6G7475A were again sequenced in their entirety and found to have only (nt 7475) altered from the original recombinant plasmids pVR-V5 and pVR-V6, respectively (Table 5). pVR-V6G7475A thus contains 11 nucleotide and no amino acid changes from strain VR-2332, besides those also seen in Ingelvac® MLV.

Figure 3:
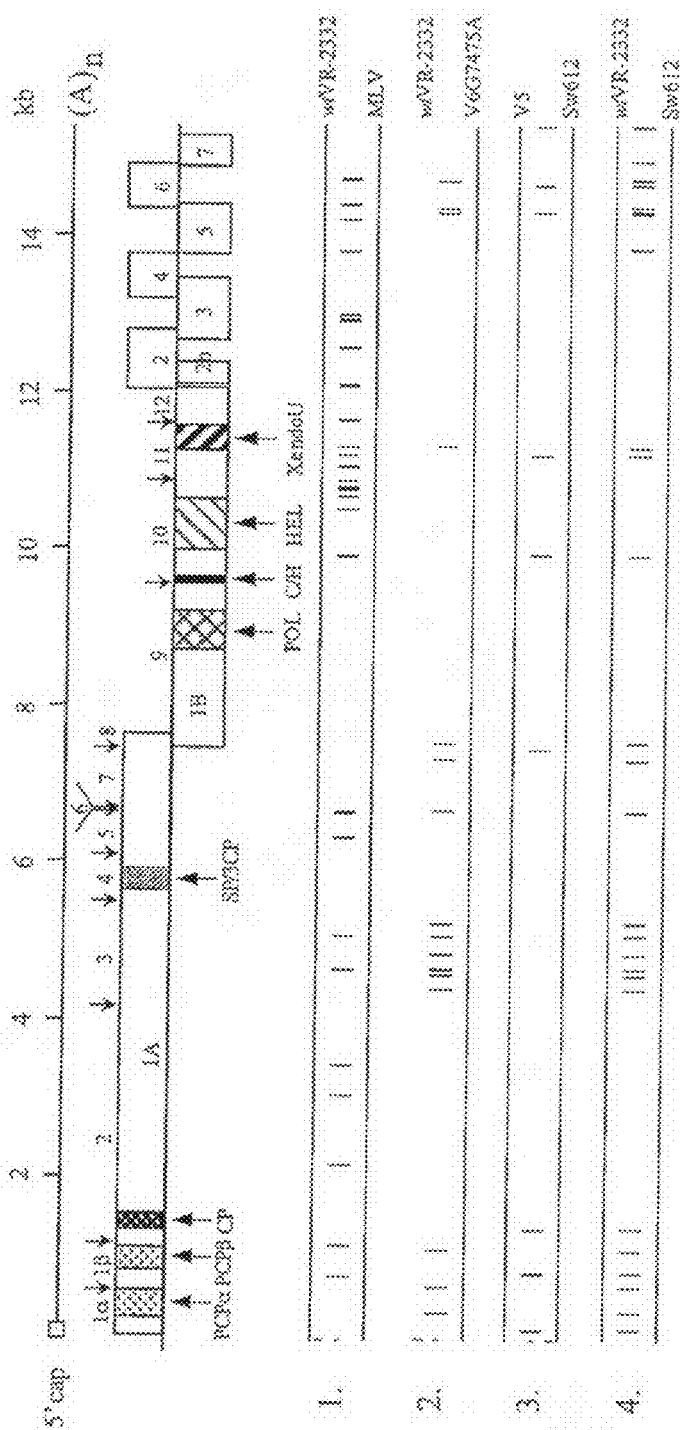
FIG. 3. Schematic of nucleotide changes of infectious clones or swine progeny. Diagram of the PRRSV genome organization is presented under which are full genome comparisons. Putative nonstructural protein cleavages are depicted above ORF1a and 1b, represented by downward arrows. Signature motifs are identified below ORF1a and 1b, with upward arrows indicating their placement in the PRRSV genome [papain-like cysteine protease α and β (PCPα, PCPβ); cysteine protease (CP); serine/3C protease (SP/3CP); polymerase (POL); cysteine/histidine rich (C/H); helicase (Hel); *Xenopus laevis* homolog poly(U)-specific endoribonuclease (XendoU); Ivanov et al., *Proc. Natl. Acad. Sci. USA*, 101:12694-12699 (2004); Ziebuhr et al., *J. Gen. Virol.*, 81:853-879 (2000)]. Nucleotide differences are represented by vertical bars. 1. wt strain VR-2332 (U87392) compared to VR-2332 derived vaccine (Ingelvac® MLV or RespPRRS, AF066183). 2. wt strain VR-2332 compared to pVR-V6G7475A. 3. pVR-V5 compared to in vivo passaged V5-1-P3 (Sw612). 4. wt strain VR-2332 compared to Sw612. Detailed nucleotide changes are listed in Tables 4 and 5.

As can be seen schematically in FIG. 3 for the final construct (pVR-V6G7475A), and detailed in Tables 4 and 5, all full-length clones still possess nucleotide changes scattered throughout the genome, primarily in the poorly defined regions of ORF1. However, the large cluster of ORF1b nucleotide changes that presumably prevented pVR-V4 from completing viral replication were repaired in later versions of the full-length genome clones. Only one nucleotide mutation (nt 11329 coding for G3739A mutation) remained in ORF1b of pVR-V5 and later clones, and this mutation does not prevent Ingelvac® MLV from infecting and replicating efficiently in cultured cells. Tables 4 and 5 also display the residue information for the previously published infectious clone, pVR-HN (Nielsen et al., *J. Virol.*, 77:3702-3711 (2003)), shown to replicate in animals. There is a substantial increase in the number of residues in pVR-HN (15 nucleotides) that directly display the sequence of Ingelvac® MLV over the final construct, pVR-V6G7475A (7 nucleotides).

Characterization of recombinant virus. Full-length RNA transcripts of each cDNA clone were produced. MARC-145 cell transfection with the cDNA transcripts or wt VR-2332 viral RNA (vRNA) resulted in CPE, characterized by cell clumping followed by lysis, at 48 to 72 hours post transfection. CPE caused by the recombinant transcripts were delayed and somewhat distinct compared to that induced by wt VR-2332 vRNA in which CPE presents as vigorous aggregation, detachment, and disruption. At 96 hours posttransfection, most of the cells transfected with VR-2332 vRNA had undergone lysis and detached from the plate, whereas less severe CPE was apparent in cells transfected with the cloned in vitro derived RNA transcripts.

Virus (P0) was harvested from the transfected cells and an aliquot (10 µl diluted to 1 ml in culture medium) was used to infect MARC-145 cells for progeny virus amplification. After CPE was detected, virus (P1) was again harvested and an aliquot used for reinfection of MARC-145 cells. Recombinant virus in the cell supernatant (P2) was utilized for purification of viral RNA, which was then used to obtain RT-PCR fragments with primer pairs 5'-6800/3'-ORF1b (nt 6796-7614) and P51/05P4 (nt 13757-14341). The PCR fragments obtained were submitted for nucleotide sequence analysis to confirm that the infectivity seen was due to transfected full-length RNA transcripts of the infectious construct and not a result of contamination due to wt virus. Nucleotide mutations at residues 7329, 7475, 7554, and 13860 nucleotide differences were seen in progeny virus from pVR-V5, and 7329, 7554, and 13860 were detected in virus from pVR-V5G7475A. Similarly, mutations at residues 7329, 7475, and 7554 were detected in pVR-V6 progeny and mutations at 7329 and 7554 were detected in virus resulting from pVR-V6G7475A (Tables 4 and 5). Corresponding mutations were not seen in P2 virus from wt vRNA transfections.

Immunofluorescence analysis of recombinant viruses. Direct immunofluorescence assays were used to detect the expression of PRRSV nucleocapsid protein in infected MARC-145 cells. All cells infected by recombinant virus transcripts (P2 and on) as well as vRNA were positive by this method. Massive nucleolar accumulation of the nucleocapsid protein was readily apparent, as previously reported by Rowland et al. (*Virus Res.*, 64:1-12 (1999)).

Figure 4:
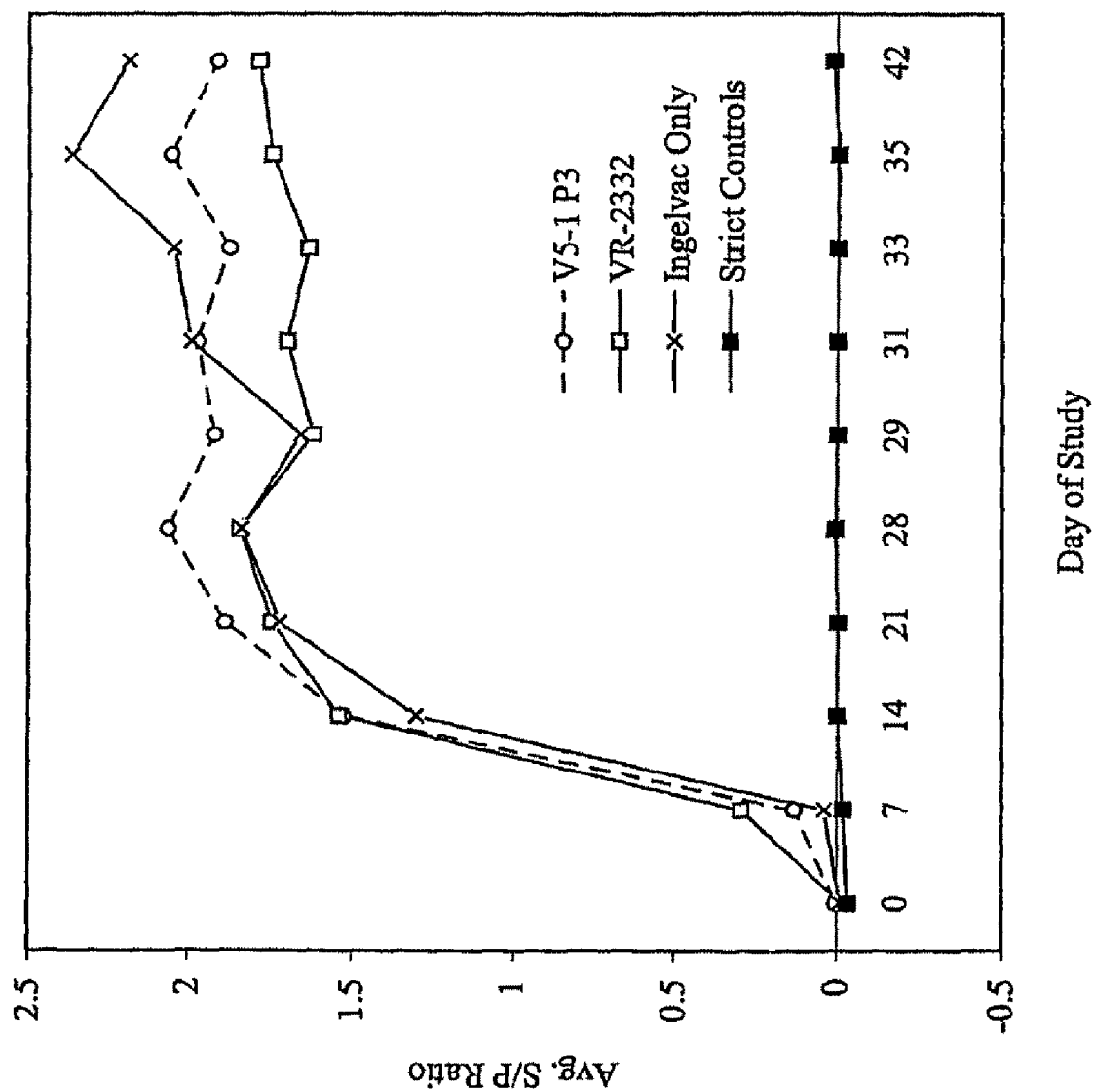
FIG. 4. Seroconversion of swine after PRRSV infection. Growing swine were infected with native wt strain VR-2332 (□), Ingelvac® MLV (x) V5-1 P3 (○) or remained uninfected (■). At days indicated, serum samples were taken and tested by IDEXX Elisa for indication of seroconversion by anti-PRRSV antibodies to the nucleocapsid protein.

In vivo infection with pVR-V5 derived recombinant virus. Recombinant viruses recovered from P3 of MARC-145 cells transfected with RNA transcripts of cDNA clone pVR-V5 were inoculated into young swine in parallel with wt VR-2332, vaccine virus Ingelvac® MLV and saline (negative control). Blood samples were collected on 0, 3, 5, 7, 14, 21 and 28 days p.i. and analyzed for seroconversion by Herd-Chek PRRS 2XR ELISA (IDEXX) and for virus recovery. At day 28, all infected animals had seroconverted with approximately the same kinetics, revealing that pVR-V5 recombinant viruses replicated well in vivo (FIG. 4). Clinical signs were absent from all animals during the course of the experiment, but this was not unexpected as wt strain VR-2332 often does not produce overt disease in young swine and results in enlarged lymph nodes only transiently, typically at day 14 p.i.

A serum sample from one animal infected with progeny of pVR-V5 (Sw612), taken at 14 days p.i., was used to infect fresh MARC-145 monolayers for recovery of in vivo passaged recombinant virus. As described previously, the virus derived from in vitro transfection of clone pVR-V5 RNA transcripts caused only minimal CPE (evidenced by aggregation of infected cells) while virus recovered from day 14 serum of the test animal caused typical CPE (cell aggregation, detachment, and disruption) at 96 hours postinfection. This suggested that a shift in viral genotype or phenotype had occurred while pVR-V5 replicated in vivo.

In order to elucidate the reason for the apparent change in phenotype, full-genome sequence analysis was completed on virus recovered from one pig (Sw612) and then passaged once in MARC-145 cells to amplify the Sw612 progeny (FIG. 3, Tables 4 and 5). When compared to the virus used to infect swine, pVR-V5, 17 infectious cDNA clone-specific nucleotide changes were retained in Sw612, some of which are also seen in Ingelvac® MLV (7/17 nucleotides). The two non-viral G residues followed by a T residue present at the 5' end of the original pVR-V5 clone transcript were not seen in the virus derived from in vivo infection. Degeneracy was seen at nucleotide positions 9958 (R), 14336 (Y) and 15411 (Y). The wt VR2332-like nucleotide (G) at position 9958 showed degeneracy with an Ingelvac® MLV-like nucleotide (A). This change results in a mutation of a glycine residue to a glutamic acid residue, respectively (Table 2). At position 14336, degeneracy was detected as an infectious clone-specific base (C) and a wt VR-2332-specific base (T), which reflected a silent mutation. Another mutation (nt 7475) occurred in which a G residue had reverted to the wt residue A. However, there were another 5 nucleotide differences (nt 102, 827, 1379, 14686 and 15411) not seen in any of the other viruses in this study. Nucleotide 102 is located in the leader sequence, thought not be translated. However, if the leader sequence were translated, the encoded ORF (VR-2332 nucleotides 1-100) would be extended by one amino acid residue (W). The mutations at residues 827 and 1379 led to mutations in ORF1a, in both cases resulting in an amino acid change of wt VR-2332 encoded alanine for a Sw612 valine. The guanine residue at nt 7475 of pVR-V5 had mutated to wt adenine. This resulted in a G3294A non-conservative amino acid mutation, which lies in ORF1a predicted protease cleavage product NSP7 and this genomic region has no defined function to date. Nucleotide 14686, located in ORF6, showed a change from a wt VR-2332 guanine to an alanine in Sw612, which still encodes the amino acid glycine. The other unique nucleotide change occurred at the very 3' end of the viral sequence (nt 15411), before the start of the polyA tail. In this case, a previously conserved thymine residue revealed degeneracy with a cytosine residue. These genetic changes, although informative, did not immediately reveal the cause(s) of the change in growth phenotype observed. However, it did reveal the errant nature of PRRSV replication in vivo and suggests that a moderately different viral genomic sequence from wt VR-2332 was able to replicate efficiently (FIG. 3).

Figure 5A:
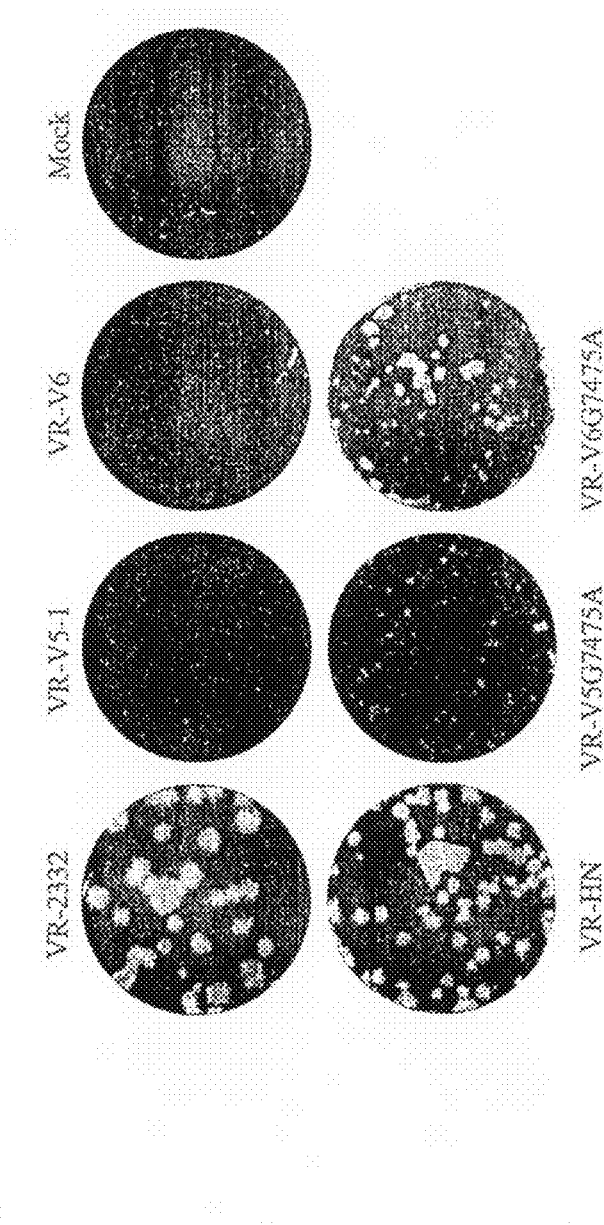
FIG. 5. A. Plaque assays on P3 progeny (first lineage) of all infectious clones as well as wt strain VR-2332 revealed different plaque sizes. B. Progeny of V5-1 P3 after growth in swine (Sw612) produced plaques similar to wt strain VR-2332.
Figure 5B:
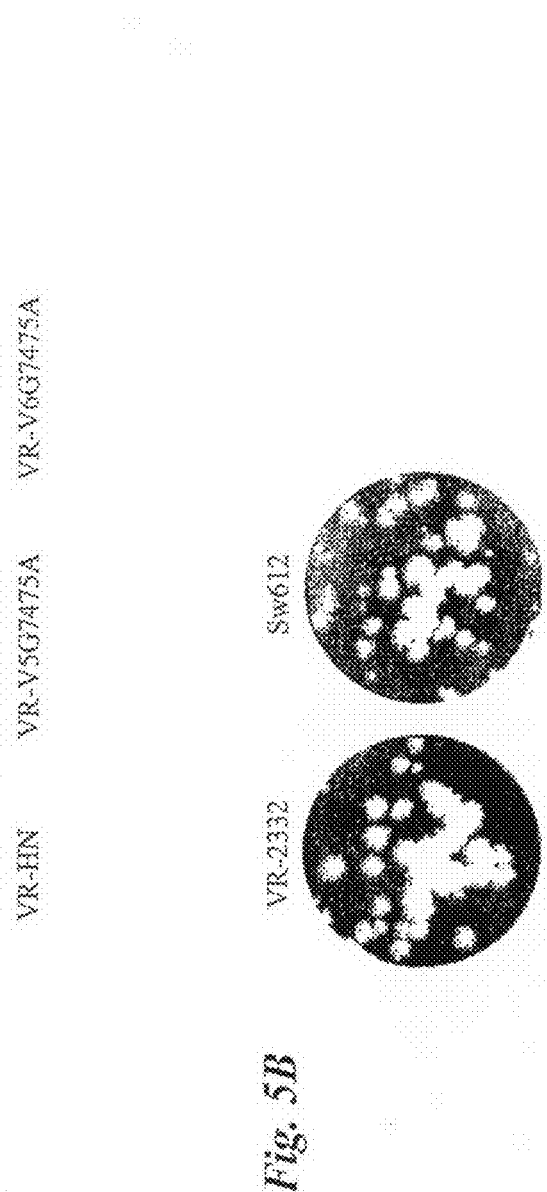

Comparison of viral plaque size. Plaque size determinations of the recombinant viruses as well as wt VR-2332 were completed in parallel on MARC-145 cells at 120 hours p.i. (FIG. 5A). Strain VR-2332 formed plaques that averaged 3 mm in size, while passage 3 progeny of pVR-HN cDNA clone formed slightly smaller plaques (2.5 mm average). In contrast, only pinpoint plaques were obtained from recombinant viruses derived from pVR-V5 and pVR-V6, and these were only readily apparent through microscopic examination (FIG. 5A). Recombinant virus recovered from clones pVR-V5G7475A and pVR-V6G7475A formed, on average, 1.5 mm and 2 mm plaques respectively. However, in another assay, the plaques produced by the viral progeny (Sw612) recovered from in vivo infection of VR-FLV5 derived recombinant virus were much larger, approximately equal in both size and number as those derived from wt VR2332 (FIG. 5B).

Only minimal volumes of the cell supernatants containing each recombinant virus remained. Therefore, in order to fully examine the role of nucleotide change in determining plaque size, we transfected fresh RNA transcripts produced from pVR-V5, pVR-V6, pVR-V5G7475A and pVR-V6G7475A into MARC-145 cells (termed second lineage). Passage 3 progeny viruses of each infectious clone at 5 days post-infection were again analyzed for plaque size in comparison to wt VR-2332, VR-HN and Sw612 viruses. In contrast to the previous plaque assay, all plaque sizes appeared similar, with the recombinant viruses obtained from pVR-V5, pVR-V6, pVR-V5G7475A only slightly smaller than the in vivo derived wt VR-2332, Sw612 and pVR-V6G7475A viruses (FIG. 6A). The recombinant viruses, however, were not yet directly mimicking authentic viral infection as shown by the approximately 10-fold lower titers when compared to wt VR-2332 or to pVR-V5 recombinant virus that had been passaged through swine (Sw612)(FIG. 6B).

Nucleotide Sequence Analysis of First and Second Lineage Virus Preparations. Limited nucleotide sequence analysis (due to virus stock limitation) of passage 3 pVR-V5-derived virus inoculated into swine (V5-1-P3) and complete nucleotide sequence analysis of passage 3 pVR-V5-derived virus obtained above (V5-2-P3) were completed in order to reveal the genetic reason for the plaque size discrepancies. Such analyses revealed that the two independently prepared V5 viruses differed in sequence at the 5' end (Table 4). The virus that had produced pinpoint plaques (V5-1-P3) had no extraneous 5'-end nucleotides, as shown in the nucleotide sequence of wt strain VR-2332, while that producing larger plaques (V5-2-P3) possessed 4 non-templated thymidine residues at the 5' terminus (Table 4). The remaining V5-1-P3 viral nucleotide sequence we could obtain exactly matched that of V5-2-P3 virus, as well as that of the parental clone. However, complete sequence analysis of V5-2-P3 virus revealed that the virus displayed nucleotide degeneracy at several genomic sites. Similar findings were obtained when analyzing limited regions of second lineage viruses VR-FLV5G7475A-P3 and VR-FLV6G7475A-P3. These last two infectious clone progeny displayed different 5'-termini as well as exhibiting degeneracy in sequence.

Viral Growth Curves. Simultaneous one-step viral growth curve determinations were completed using MARC-145 cells and passage 3 viruses (second lineage) (FIG. 7). The recombinant viruses recovered from pVR-V5, pVR-V5G7475A, pVR-V6, and pVR-V6G7475A and pVR-HN displayed similar one-step viral growth rates, but their peaks of replication were all significantly lower than wt strain VR-2332 and Sw612, the in vivo progeny of pVR-V5. Also, the replication rates of the recombinant virus preparations derived from pVR-V5, pVR-V6 and pVR-HN were somewhat decreased as compared to the virus derived from pVR-V5G7475A and pVR-V6G7475A. The last two infectious clones code for as little as 13 and 11 nucleotide differences, respectively, resulting in 2 and zero amino acid changes, from wt VR-2332 sequence besides the changes seen in Ingelvac® MLV. These data then reveal that viruses with as little as 11 nucleotide changes from wt VR-2332 and its attenuated offspring Ingelvac® MLV are somehow impaired in replication. Correspondingly, the resultant titers of wt VR-2332 and Sw612 viruses were approximately 6-15 fold higher than that of the recombinant viruses that had not been passaged in swine (FIG. 7).

Figure 8:
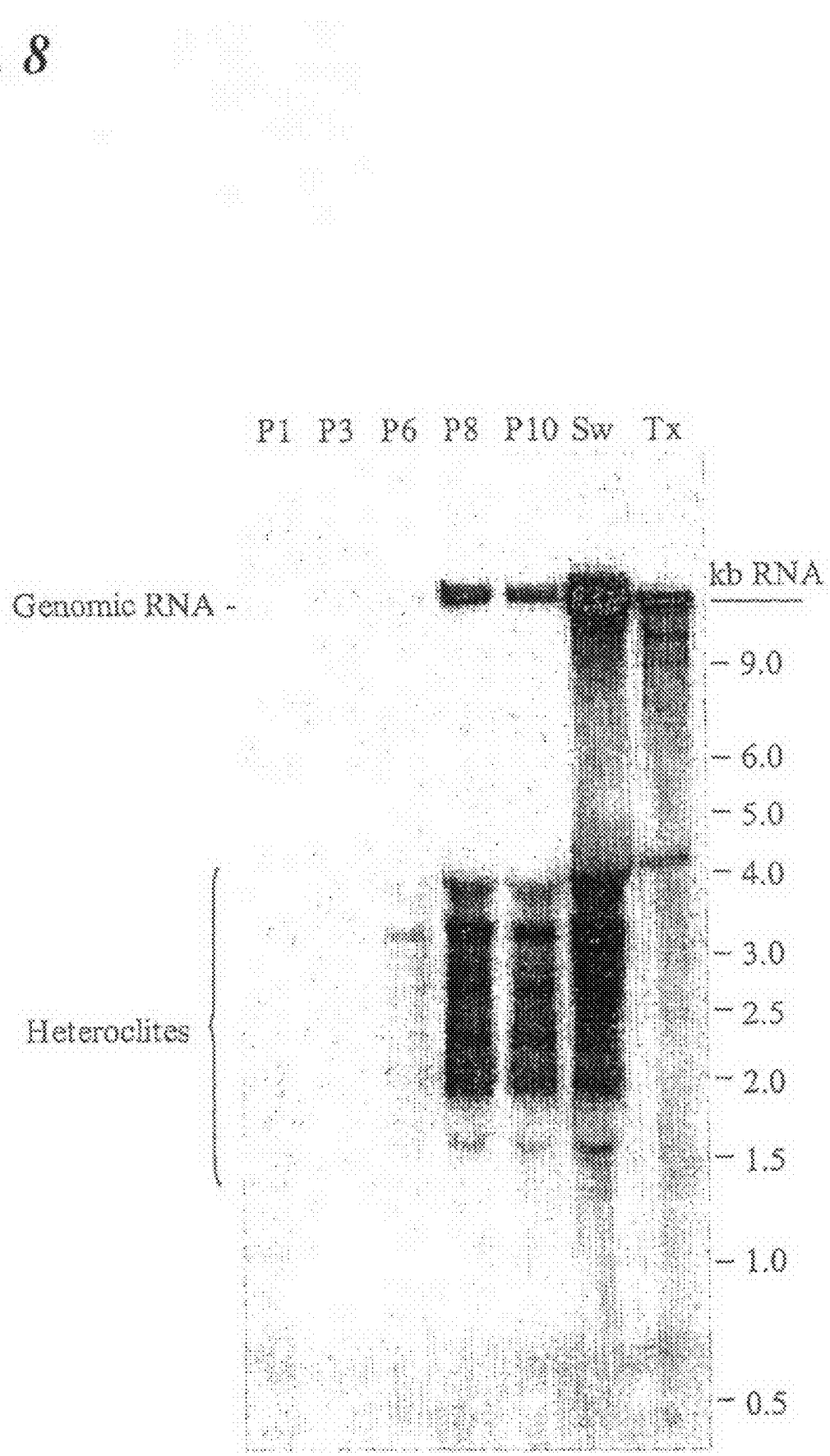
FIG. 8. Northern blot analysis of different progeny passages of pVR-V6G7475A as well as Sw612 and the initial in vitro transcript reveals heteroclites are produced as early as P1 and, along with genomic RNA, are more abundant with passage. However, transcript RNA (Tx) does not contain readily detectable heteroclite species.

Northern analyses of vRNA. PRRSV defective sgRNA species, identified previously as heteroclite subgenomic RNAs (latin: uncommon forms), have been shown to be a constituent of PRRSV infection and cannot be separated from full-length viral genomes by standard methods such as cultured cell passage at low multiplicities of infection or sucrose gradient centrifugation (Yuan et al., *Virology*, 275:158-169; 30 (2000); Yuan et al., *Virus Res.*, 105:75-87 (2004)). To explore whether or not PRRSV heteroclites are produced during in vitro transcription of full-length cDNA genome clones or appear after subsequent transfection/infection, northern blot analysis was completed. The full-length RNA transcript and passages 1, 3, 6, 8 and 10 of the virus produced from transfected MA-104 cells were used to inoculate fresh T-75 flasks of MA-104 cells with 10 μl supernatant diluted 1:100, as well as Sw612 serum diluted 1:10 (2 ml total/flask). After 4 days, intracellular PRRSV RNA was harvested and 15 μg of each preparation was separated by electrophoresis through a denaturing agarose gel and transferred to a nylon membrane. After RNA crosslinking, the membrane was hybridized with a $^{32}$P-radiolabeled probe complementary to the 5' end of ORF1a that selects for full-length VR-2332 genomes as well as heteroclites (/1a-222; 29). As shown in FIG. 8, the RNA transcript is mostly a single band, migrating as full-length vRNA, while PRRSV RNA species from passage 1 and later migrate as both full-length and subgenomic-sized species previously identified as heteroclites. In addition, the strength of hybridization increases over passage. Since the virus was harvested from an equal volume of infected cell supernatant at the same time point, this observation suggests that the vRNA becomes more efficient at replication over time. Lastly, when comparing virus generated from Sw612 with the cell culture generated virus, the RNA banding pattern is indistinguishable, strongly suggesting that the defective RNA species are readily formed and replicated in vitro as well as in vivo and thus are a natural part of PRRSV infection.

Discussion

In theory, an infectious cDNA clone of a virus should be identical to the parental sequence in order to generate a reverse genetic system that mimics wild-type infection. Considerable effort was exerted to reproduce a fully faithful PRRSV strain VR-2332 genome, yet due to unpredictable spontaneous mutations at several sites, we have not yet been successful at deriving an infectious clone that has no differences from the wt strain VR-2332 sequenced in our laboratory. High fidelity DNA polymerases, used in this study, are available to decrease artificial mutations, but such mutation cannot be avoided during reverse transcription (Malet et al., *J. Virol. Methods*, 109:161-70 (2003)). In addition, the fact that PRRSV exhibits astonishing viral evolution and strain variation (Chang et al., *J. Virol.*, 76:4750-6 (2002); Murtaugh et al., *Adv. Exp. Med. Biol.*, 440:787-94 (1998); Yoon et al., *Adv. Exp. Med. Biol.*, 494:25-30 (2001)) recombines readily at high frequency to result in intergenic recombinants between strains (Yuan et al., *Virus Res.*, 61:87-98 (1999)), undergoes intragenic recombination to form PRRSV subgenomic RNAs and heteroclites (Nelsen et al., *J. Virol.*, 73:270-80 (1999); Yuan et al., *Virology*, 275:158-169 (2000); Yuan et al., *Virus Research*, 105:75-87 (2004)) and often displays nucleotide degeneracy at unpredictable nucleotide sites in field isolates serve to make this initial goal time-consuming and of negligible gain. An infectious DNA construct possessing as little as 11 nucleotide mutations, as compared to strain VR-2332, outside of domains known to be involved in viral replication (5' and 3' ends, ORF1b) was thought sufficient for wt virus production and the downstream goals of infectious clone use for pathogenesis queries and structure:function studies. pVR-HN is more similar to Ingelvac® MLV in the region of the virus encoding the helicase motif (NSP 10). Further pathogenic comparison of these two infectious clones may shed light on the differences between the parental strain, VR-2332, and its vaccine strain offspring, Ingelvac® MLV.

Valuable information can be derived from the construction and evaluation of the infectious clones for PRRSV strain VR-2332. First of all, PRRSV strain VR-2332 cannot tolerate all mutations for survival. Particular nucleotide or amino acid mutations may help or hinder viral replication, and the challenge is to ascertain which are lethal to survival. In clone pVR-V4, which did not produce infectious virions, there were total of forty-two nucleotide differences from wt parental strain VR-2332. In these forty-two nucleotide changes, several nucleotides result in silent mutations (20 residues) or exist in other known PRRSV strains (9 amino acid residue mutations directly mimic Ingelvac® MLV) allowed prediction that these changes may be non-lethal for virus replication. Eleven nucleotide changes leading to 12 amino acid changes and two 3'UTR nucleotide mutations, each not seen in Ingelvac® MLV, were thus predicted to be lethal to PRRSV strain VR-2332. In pVR-V5 and later constructs, 19 changes were corrected, including several silent mutations and 9 aberrant amino acid changes not seen in the genome of Ingelvac® MLV and 8 other changes seen in the vaccine strain. This lead to the first evidence that the constructs were infectious, although in pVR-V5 two amino acid mutations were still present, one of which was altered through site directed mutagenesis to produce pVR-V6. The remaining amino acid change was repaired in pVR-V5G7475A and pVR-V6G7475A, although these clones still harbor silent mutations that are not found in strain VR-2332 and the derived vaccine strain.

Several unique observations were obtained from this study. First of all, each lineage of produced virus may result in a unique 5' terminal sequence that was not detected in wt strain VR-2332. We also cannot yet correlate plaque size with nucleotide sequence. Secondly, we saw unique nucleotide changes after replication in swine, which may reflect the inherent nature of the PRRSV polymerase. All nucleotide changes were transitional in nature and did not exhibit a bias (5 A/G and 4 C/T). Although the G A reversion at nucleotide 7475 was seen after in vivo passage, we could not correlate this site with the subsequent increased plaque size because other non-templated changes had occurred. In addition, full-genome sequence analyses of passage 3 of a V5-derived virus that produced larger plaques (V5-2-P3) revealed a different 5' terminal sequence from the pinpoint plaque-producing V5 virus used to infect swine (V5-1-P3). However, we can conclude that the mutations were not lethal to virus replication because this virus, after passage in swine, produced wt-sized plaques on MARC-145 cells ad grew at almost the same rate as the parental virus (FIGS. 5A, 6 and 7).

Of considerable interest is the fact that sequence analysis of the third in vitro passage of V5, V5G7475A and V6G7475A seemed to suggest that the PRRSV replicase complex allows frequent transitions, and infrequent transversions, to occur while undergoing viral replication. This may reflect a viral replicase that has evolved so that it may generate new genetic forms of a PRRSV genome and then assess their competence amid other variants, resulting in an optimally "fit" virus. These observations have also been noted during PRRSV sequential passage in vivo (Chang et al., *J. Virol.*, 76:4750-63 (2002)). Present sequencing efforts are to examine the full-length genomes of later passages, when a more robust replication is detected. Finally, it is now clear that PRRSV strain VR-2332 replicase readily synthesizes heteroclites at the same time it is producing full-length vRNA. This prototype strain, isolated and characterized in 1992, may be unique in the gradual acquisition of replication fitness, as other investigators producing infectious clones of more recent strain have not observed the same effect (Truong et al., *Virology*, 325:308-319 (2004)). The role of heteroclite formation and the concomitant appearance of vigorous viral replication suggest that there is an advantageous role for heteroclites in PRRSV evolution.

Example 2

Many virulent isolates of a seemingly novel PRRSV were recently identified in the State of Minnesota, USA. ORF5 nucleotide sequence analysis and comparison to the University of Minnesota Veterinary Diagnostic Laboratory PRRSV database (>5000 isolates) revealed that the isolates were of Type 2 lineage, but were significantly different than previous isolates. Furthermore, they were most closely related to those isolates previously seen in Canada in the early 1990s (Mardassi et al., *J. Gen. Viral.*, 75:681-685 (1994)) and in the State of Minnesota in 1998. Restriction fragment length polymorphism (RFLP) analysis of ORF5 also demonstrated that they belonged to the same group of viruses as these early cases, known as 1-8-4 isolates (Wesley et al., *J. Vet. Diagn. Invest.*, 10:140-144 (1998)) and were thus named MN184 isolates. Because of the striking dissimilarity with all but one previously isolated MN PRRSV isolate, two of these new isolates were amplified just one time on porcine alveolar macrophages (PAM), the host cell, and full-length genome analyses was completed on the viruses, designated as MN184A and MN184B. These two isolates were collected at different times from two separate farms.

Materials and Methods

To sequence the MN184 isolates, viral RNA (vRNA) was extracted from PRRSV infected cell supernatant with QIAmp® Viral RNA Mini Kit (Qiagen, Valencia, Calif.)) and RT-PCR was performed (Qiagen® OneStep RT-PCR Kit). Primers (available on request) were designed based on the published sequences of different strains of PRRSV deposited in GenBank as well as newly generated MN184 sequence. The 5' nucleotide sequence of the two PRRSV isolates was derived using the 5'-Full RACE Core Kit (TaKaRa Bio, Madison, Wis.). 3'-RACE was performed with SMART™ RACE cDNA Amplification Kit (Clontech, Mountain View, Calif.). RT-PCR products were gel purified (QIAquick®, Qiagen), cloned into the pGEM-T Vector (Promega, Madison, Wis.) and 3 to 5 clones for each RT-PCR product were chosen for sequencing. The nucleotide sequence determination was completed in both directions with the PCR specific primers or the vector encoded SP6 and T7 promoter primers. The products were submitted to the Advanced Genetic Analysis Center at the University of Minnesota for sequence determination with an ABI 377 automated DNA fragment analyzer. A quality sequence representing at least three-fold genome coverage was obtained. Sequence data was assembled and analyzed by using the GeneTool sequence analysis program (BioTools Inc., Edmonton, Alberta Calif.) and Lasergene (DNASTAR, Madison, Wis.).

Multiple sequence alignments were generated with CLUSTALX (Thompson et al., *Nucleic Acids Res.*, 24:4876-4882 (1997)) or Wisconsin Package Version 10.3 (Accelrys Inc., San Diego, Calif.). Full-length PRRSV sequences were aligned using ClustalX (version 1.83.1; IUB DNA weight matrix, gap penalty 15.00, gap length penalty 6.66). The resulting alignment was further analyzed using the Wisconsin Package Version 10.3 Distances Program (Jukes-Cantor distance method, partial matches due to degenerate symbols considered). For FIG. 10, sequences were aligned with the Pileup program of the Wisconsin Package (Blosum62 Scoring Matrix, Gap Weight=8, Length Weight=2, Weighted Ends). The alignment was scored for redundancy and colored for percent identity using Jalview (Clamp et al., *Bioinformatics,* 12:426-427 (2004)) and then transferred to Adobe® Photoshop® CS, version 8.0, for grayscale transformation. For FIG. 11, sequences were aligned with the Pileup program of the Wisconsin Package (Blosum62 Scoring Matrix, Gap Weight=8, Length Weight=2, Weighted Ends). For FIG. 12, a signal peptide was predicted using the SignalP server (Bendtsen et al., *J. Mol. Biol.,* 340:783-795 (2004)). Transmembrane regions were derived by PHDhtm (Rost et al., *Protein Sci.,* 5:1704-1718 (1996)) and potential N-glycosylation sites were identified by PROSITE (Bairoch et al., *Nucleic Acids Res.,* 25:217-221 (1997)) using the PredictProtein server (Rost et al., *Nucleic Acids Res.,* 32:W321-W326 (2003)). Sequences were aligned with the Pileup program of the Wisconsin Package (Blosum62 Scoring Matrix, Gap Weight=8, Length Weight=2, Weighted Ends).

Results

Genomic alignment demonstrated that these two PRRSV were quite distinct (>14.5% nucleotide dissimilarity) from other North American Type 2 full-length sequenced genomes, yet comparison with Type 1 (European) full-length sequences confirmed that the isolates were solely of Type 2 genotype origin as they were only approximately 59% similar at the nucleotide level to both EuroPRRSV and Lelystad strains. Strikingly, these Type 2 MN184 isolates represented the shortest PRRSV genomes detected to date (15019 nucleotides, not including the poly A tail). In addition, no specific area was discerned that suggested that these isolates were derived from viral recombination between Type 1 and Type 2 strains.

Figure 9A:
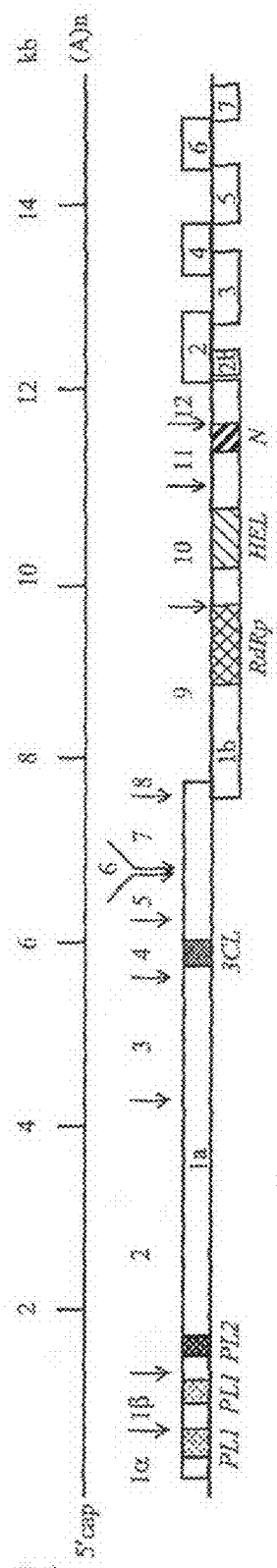
FIG. 9. A. Diagrammatic representation of the PRRSV genome. Putative nonstructural protein cleavages are depicted above ORF1a and 1b, represented by downward arrows. Signature motifs are identified below ORF1a and 1b, indicating their placement in the PRRSV genome [papain-like cysteine protease α and β (PL1); cysteine protease (PL2); serine/3C protease (3CL); polymerase (RdRp); helicase (Hel); *Xenopus laevis* homolog poly(U)-specific endoribonuclease (N); Ziebuhr et al., 2000; Ivanov et al., 2004; Gorbalenya et al., 2006]. B. Schematic diagram of the comparison of ORF1 protein (replicase) of MN184A and MN184B and putative processing. The degeneracy seen in nsp2 is included in the comparison. C. Schematic diagram of the comparison of ORF2-7 proteins of MN184A and MN184B.
Figure 9B:
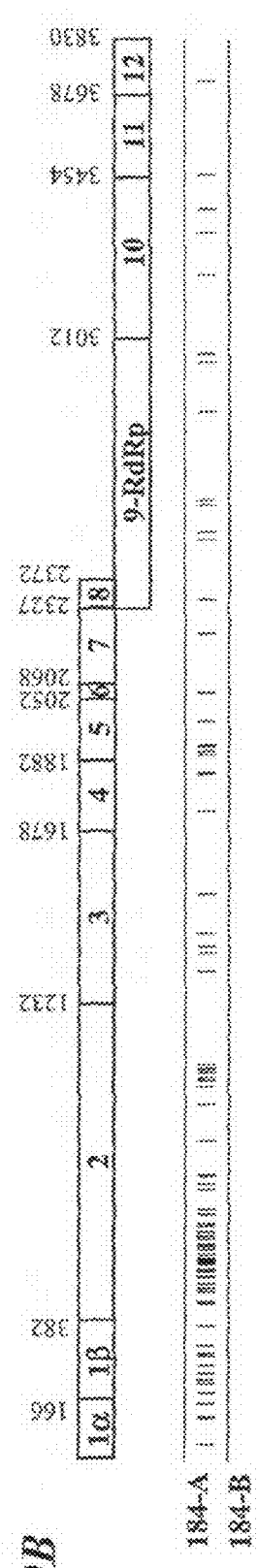
Figure 9C:
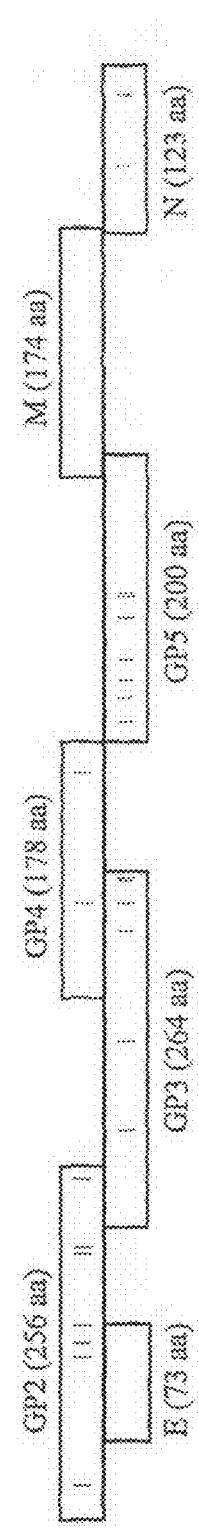

Full-length sequence analysis revealed that the two MN184 isolates were actually genetically distinct. They shared 98.0% nucleotide similarity or 2% difference. This percentage of dissimilarity was unexpected due to their sudden simultaneous appearance in Minnesota, with no clear recent related isolate seen in our PRRSV database at that time. Table 6 presents the detailed nucleotide and amino acid comparison between the two isolates and FIG. 9 depicts the amino acid differences seen between these two strains. Both of these isolates possessed nucleotide degeneracy in several regions of the genome, predominantly in the predicted nsp2 region of ORF1 (Table 6). The fact that nucleotide degeneracy was seen in these isolates suggested that PRRSV can be made up of several individual species, often referred to as a swarm of related but distinct viral sequences, within infected animals.

TABLE 6

Detailed analysis of individual PRRSV genomic regions and translated proteins, and number of degenerate bases detected in each region. Degeneracy is defined as more than one nucleotide detected for a particular base on separate trace files of three or more trace files.

| Region | Bases | Nucleotide length | % Nucleotide Similarity | % Nucleotide Identity | Number of Degenerate Bases (184A/184B) | Amino Acid Length | % Amino Acid Similarity | % Amino Acid Identity |
|---|---|---|---|---|---|---|---|---|
| 5' UTR | 1-190 | 190 | 99.5 | 98.9 | 1/0 | — | — | — |
| ORF1A | 191-7309 | 7119 | 98.5 | 96.7 | 16/109 | 2372 | 96.8 | 96.5 |
| NSP1a | 191-688 | 498 | 98.8 | 98.5 | 1/0 | 166 | 97.6 | 97.6 |
| NSP1b | 689-1339 | 651 | 98.3 | 97.5 | 2/3 | 217 | 97.2 | 95.9 |
| NSP2 | 1340-3886 | 2547 | 98.0 | 94.6 | 10/76 | 849 | 94.2 | 94.2 |
| NSP3 | 3887-5224 | 1338 | 98.7 | 98.7 | 0/0 | 446 | 99.3 | 98.9 |
| NSP4 | 5225-5836 | 612 | 98.5 | 96.4 | 0/13 | 204 | 97.1 | 97.1 |
| NSP5 | 5837-6346 | 510 | 99.2 | 95.3 | 3/17 | 170 | 97.1 | 97.1 |
| NSP6 | 6347-6394 | 48 | 100.0 | 100.0 | 0/0 | 16 | 100 | 100 |
| NSP7 | 6395-7171 | 777 | 99.3 | 99.3 | 0/0 | 259 | 99.6 | 99.2 |
| NSP8 | 7172-7309 | 138 | 99.3 | 99.3 | 0/0 | 46 | 97.6 | 97.6 |
| ORF1B | 7306-11679 | 4374 | 99.2 | 98.9 | 5/4 | 1457 | 99.5 | 99.2 |
| NSP9 | 7288-9225 | 1938 | 98.9 | 98.8 | 1/1 | 646 | 99.4 | 98.9 |
| NSP10 | 9226-10548 | 1323 | 99.3 | 98.9 | 3/3 | 441 | 99.8 | 99.3 |
| NSP11 | 10549-11217 | 669 | 99.3 | 99.3 | 0/0 | 223 | 99.5 | 99.5 |
| NSP12 | 11218-11679 | 462 | 99.6 | 99.4 | 1/0 | 153 | 99.3 | 99.3 |
| ORF2a/GP2 | 11681-12451 | 771 | 99.0 | 98.3 | 1/0 | 222 | 98.0 | 97.3 |
| ORF2b/E | 11686-11907 | 222 | 99.6 | 99.6 | 0/0 | 73 | 100 | 100 |
| ORF3/GP3 | 12304-13068 | 765 | 98.6 | 98.6 | 0/0 | 254 | 97.6 | 97.6 |
| ORF4/GP4 | 12849-13385 | 537 | 98.5 | 98.5 | 0/0 | 178 | 98.9 | 98.9 |
| ORF5/GP5 | 13396-13998 | 603 | 97.8 | 97.7 | 1/0 | 200 | 96.5 | 96.5 |
| ORF6/M | 13983-14507 | 525 | 99.6 | 97.4 | 0/0 | 174 | 100 | 100 |
| ORF7/N | 14497-14868 | 372 | 98.9 | 98.9 | 0/0 | 123 | 97.6 | 97.6 |
| 3' UTR | 14869-15019 | 151 | 100 | 98.0 | 1/1 | — | — | — |

In order to more closely pinpoint the individual regions of these MN184 isolates that showed the most dissimilarity from other PRRSV strains and to assign the region(s) accounting for the difference in Type 2 viral genome length, these two isolates were compared to the sequence of the prototype Type 2 strain VR-2332. The differences between the two isolates could again be discerned, with isolate MN184B possessing slightly increased similarity to strain VR-2332 than isolate MN184A. The nucleotide and amino acid comparisons to VR-2332 showed individual MN184 isolate regions varied from 81.5-94.7% and 78.4-100%, respectively, but the regions corresponding to ORF5 (86.4-86.7% and 87.0-87.5%, respectively) predicted nsp1β (83.8-84.0% and 84.8-85.4%, respectively, and nsp2 (81.5-85.5% and 78.4-79.5%, respectively) were the most variable. Most interesting was that only the predicted nsp2 genomic region showed a difference in nucleotide length and that both MN184 isolates possessed the same nsp2 deletion, detailed below. The comparison also revealed that the 5' and 3' UTR's were the most conserved regions of the genome (94.7% and 94.0%, respectively), indicating sequence conservation in important regions for viral replication and transcription.

Figure 10:
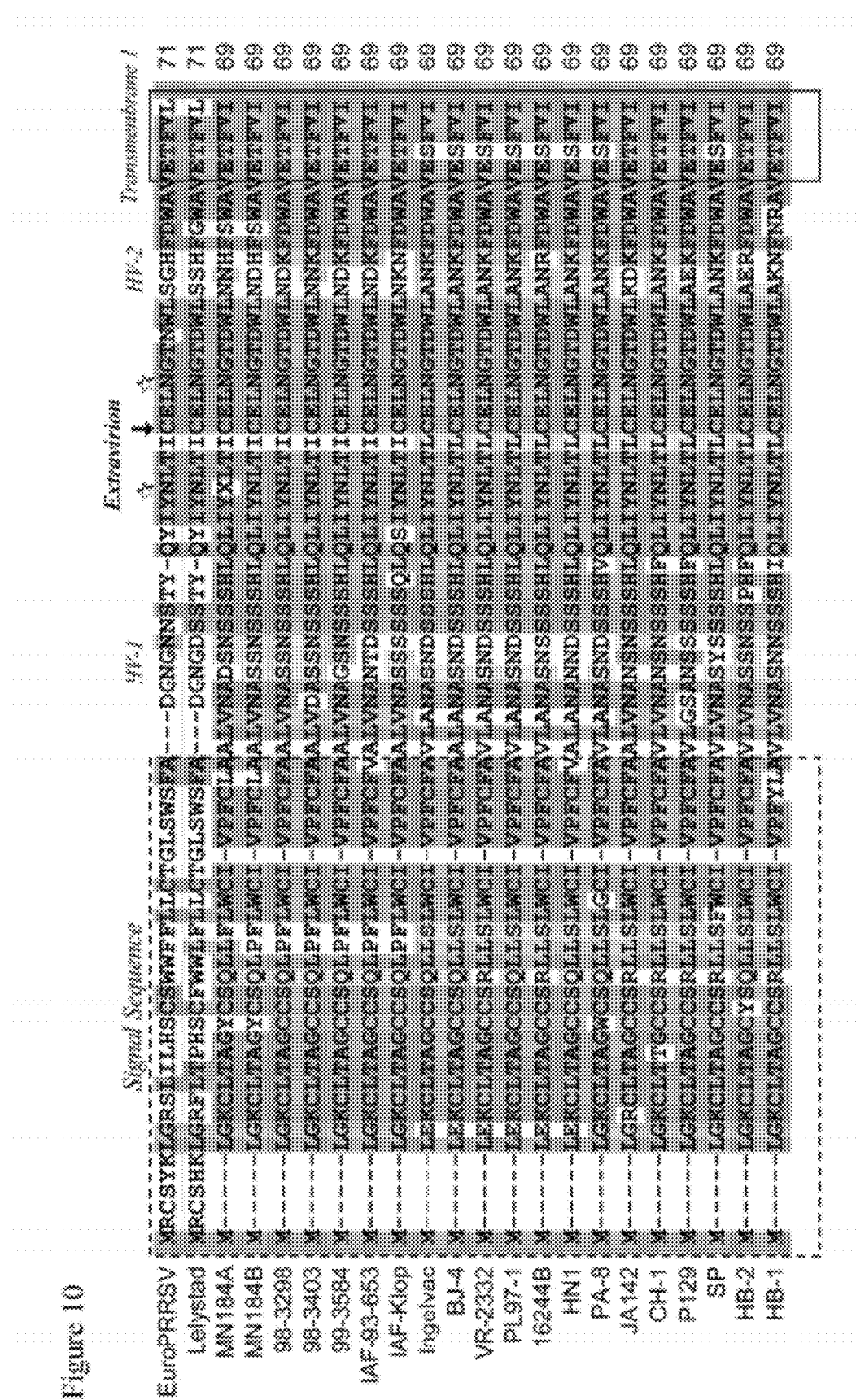
FIG. 10. ORF5 amino acid sequence alignment of divergent PRRSV. Dark grey boxes indicate high amino acid conservation (>80%; between 16 and 19 residues are identical), medium grey (>60%; between 12 and 15 residues are identical), lighter grey (>40%; between 8 and 11 residues are identical) and unshaded (<40%; less than 8 residues are identical) boxes identify less conserved residues. The dashed region indicates the putative signal sequence, the boxed regions identify the proposed transmembrane regions, the hypervariable regions are indicated (HV-1 and HV-2), and the proposed orientation of the protein in the virion is identified in bold italics. The conserved cysteine residue that is proposed to interact with the M protein is identified by the downward arrow (↓). The two conserved putative N-glycosylation sites are identified by stars and hypervariable region 1 contains strain/isolate specific N-glycosylation sites (N×S/T). ORF5 amino acid sequences from the following GenBank full-length sequences were used for comparison: VR-2332 (U87392) (SEQ ID NO: 45), Ingelvac MLV (AF066183) (SEQ ID NO: 43), PL97-1 (A Y58524) (SEQ ID NO: 46), PA-8 (AF176348) (SEQ ID NO: 49), SP (AF184212) (SEQ ID NO: 53), BJ-4 (AF331831) (SEQ ID NO: 44), HN1 (AY457635) (SEQ ID NO: 48), 16244B (AF046869) (SEQ ID NO: 47), HB-1 (AY150312) (SEQ ID NO: 55), HB-2 (AY262352) (SEQ ID NO: 54), CH-1a (AY032626) (SEQ ID NO: 51), P129 (AF494042) (SEQ ID NO: 52), JA142 (AY424271) (SEQ ID NO: 50), EuroPRRSV (AY366525) (SEQ ID NO: 34), Lelystad (M96262) (SEQ ID NO: 35), IAF-93-653 (U64931) (SEQ ID NO: 41), IAF-Klop (AY184209) (SEQ ID NO: 42), 98-3298 (DQ306877) (SEQ ID NO: 38), 98-3403 (DQ306878) (SEQ ID NO: 39), 99-3584 (DQ306879) (SEQ ID NO: 40), MN184A (SEQ ID NO:36), MN184B (SEQ ID NO:37).

ORF5 encodes a heterogeneous PRRSV structural protein (GP5) and is often used for PRRSV diagnostic identification (Kapur et al., *J. Gen. Virol.*, 77:1271-1276 (1996)). GP5 is a predicted three transmembrane protein with an endodomain and ectodomain. The 30 amino acid ectodomain is composed of a short highly conserved domain usually containing at least two N-glycosylation sites bounded by two hypervariable regions. The highly conserved domain of this 30 amino acid region has been shown to code for the viral attachment epitope in Type 2 strains (Plagemann, *Virology*, 290:11-20 (2001); Ostrowski et al., *J. Viral.*, 76:4241-4250 (2002); Plagemann et al., *Arch. Viral.*, 147:2327-2347 (2002)). GP5 of the same set of full-length genomes, as well as the original RFLP184 isolates identified in Canada (IAF-93-653, IAF-Kiop) and in 1998-1999 in Minnesota (98-3298, 98-3403, 99-3584) were aligned (FIG. 10). The alignment of PRRSV GP5 revealed amino acid identities ranging from 82.5% to 87.7% between the new MN184 isolates and other non-RFLP184 Type 2 strains. Interestingly, the amino acid differences between the new MN184 isolates and the older RFLP184 isolates were quite large (5.7%-12.2%) and thus we detected no clear origin of the new RFLP184 virus. The limited alignment shows that most of the amino acid differences observed were found in the hypervariable regions (FIG. 10). The two conserved N-glycosylation sites were maintained in the MN184 isolates, except for detected nucleotide degeneracy coding for amino acid 44 in isolate MN184B.

Figure 11:
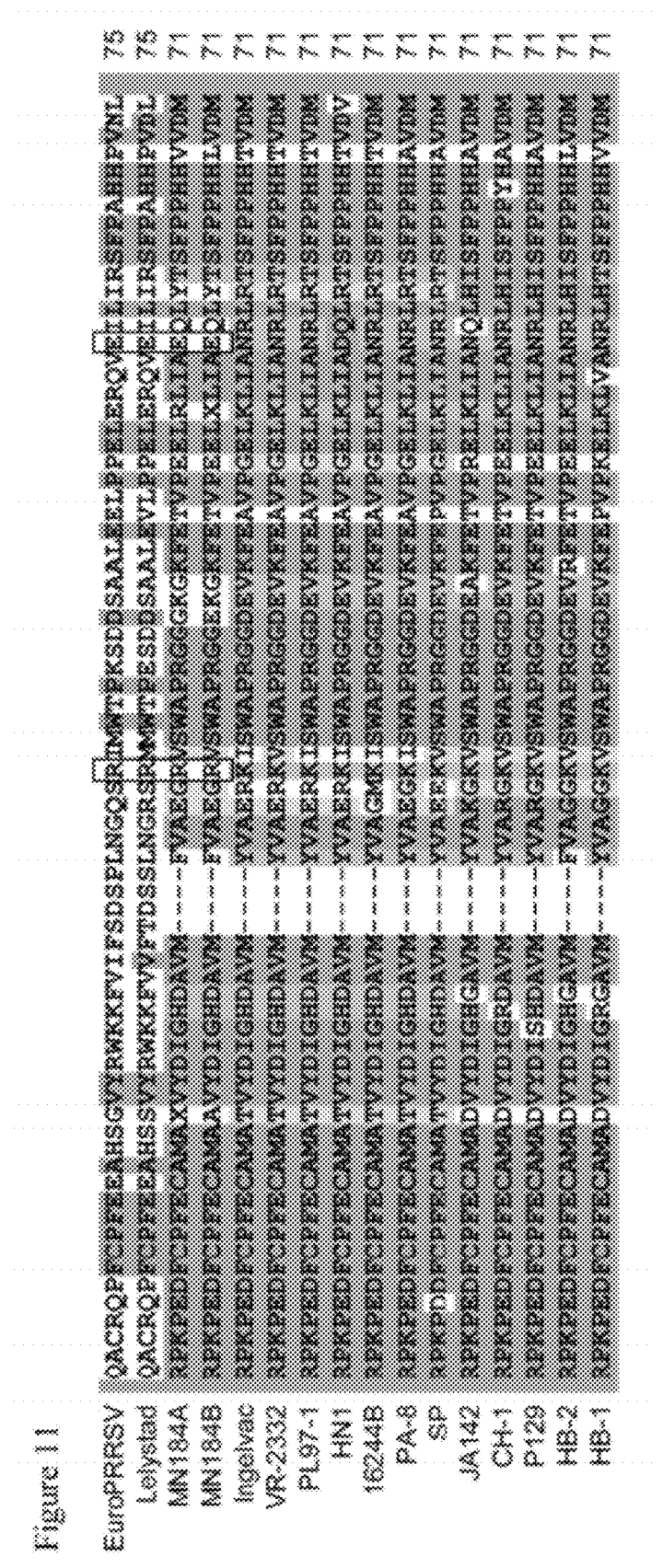
Figure 11:
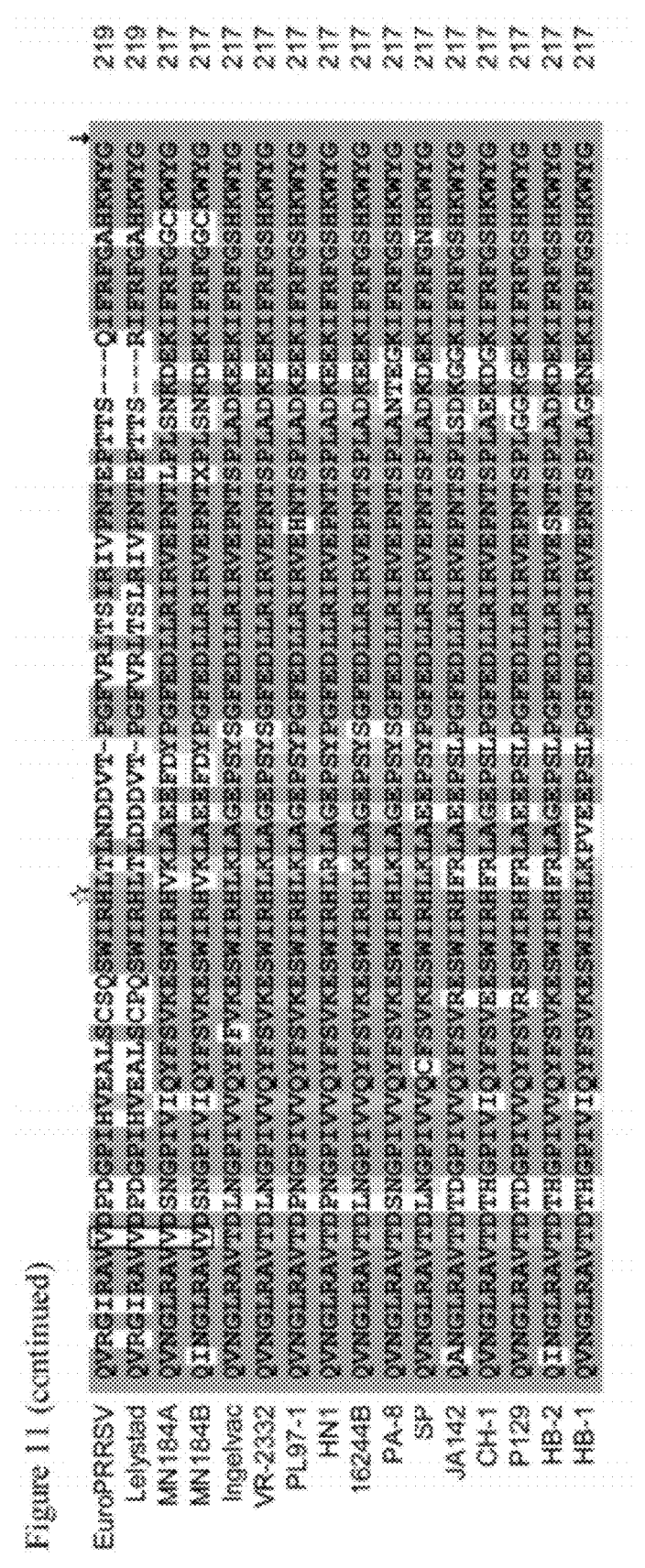

Nsp1β encodes a papain-like cysteine protease (den Boon et al., *J. Viral.*, 69:4500-4505 (1995)). An amino acid alignment of the MN184 isolates with a non-redundant set of available Type 2 nsp1β sequences as well as Type 1 strains EuroPRRSV and Lelystad was completed (FIG. 11). The nsp1β protein possesses a number of completely conserved amino acids, and the proposed catalytic residues were maintained in all sequenced genomes (den Boon et al., *J. Viral.*, 69:4500-4505 (1995)). The alignment, ordered by amino acid similarity, indicates that the MN184 isolates are more similar to Type 1 strains than the other sequenced full-length Type 2 sequences. In particular, five amino acids (boxed in FIG. 11) directly mimic the Type 1 strains. However, the amino acids that were conserved in the other non-redundant Type 2 sequences were also mostly conserved in the MN184 isolates, but scattered amino acids and the amino acid similarity (84.8-85.4%) revealed a more divergent Type 2 protein than had been evidenced to date. Thus, the alignment further defines maintained residues of nsp1β that may be critical to the replication cycle of PRRSV.

An amino acid alignment of non-redundant sequences of nsp2, ordered by pairwise identity, is shown in FIG. 12. A highly conserved chymotrypsin-like cysteine protease (PL2) domain is present at the N-terminus, previously predicted by alignment with equine arteritis virus (EAV) nsp2 (Snijder et al., *J. Gen. Virol.*, 79:961-979 (1998); Ziebuhr et al., *J. Gen. Viral.*, 81:853-879 (2000)). There are 3-4 predicted transmembrane domains near the C terminus of this protein (McGuffin et al., *Bioinformatics*, 16:404-405 (2000)), but the exact C terminal cleavage site has not been empirically determined. Two predictions of the C-terminal cleavage site have been proposed, one G|G at VR-2332 nsp2 amino acid 980 (Allende et al., *J. Gen. Viral.*, 80:307-315 (1999)) and the other at amino acid 1197 (Ziebuhr et al., *J. Gen. Viral.*, 81:853-879 (2000)), but there are several completely conserved G|G doublets within this protein (VR-23332 nsp2 amino acids 646, 980, 1116, 1196, 1197; downward arrows in FIG. 12). Prior work had also shown that the predicted nsp2 protein is proline rich and contains multiple potential B-cell epitopes (Oleksiewicz et al., *J. Viral.*, 75:3277-3290 (2001); Fang et al., *Virus Res.*, 100:229-235 (2004); Ropp et al., *J. Viral.*, 78:3684-3703 (2004)). The large middle region of PRRSV nsp2 (VR-2332 nsp2 amino acids 148-880) has no assigned function but is highly variable in length. Furthermore, the length difference between sequenced Type 1 and Type 2 strains of PRRSV has been mapped to this variable middle region of nsp2 (FIG. 12). Until now, sequenced Type 1 genomes have been shown to be 313-364 bases shorter than most Type 2 PRRSV (Meulenberg et al., *Virology*, 192:62-72 (1993); Fang et al., *Virus Res.*, 100:229-235 (2004), Ropp et al., *J. Virol.*, 78:3684-3703 (2004)). However, the multiple sequence alignment established that the MN184 genome contains the shortest predicted nsp2 to date (2547 bp), 393 bp shorter than prototype Type 2 strain VR-2332. Furthermore, it contained three discontinuous deletions in the translated protein with deletion sizes consisting of 111, 1 and 19 amino acids, respectively, corresponding to the amino acid positions in PRRSV strain VR-2332 nsp2 of 324-434, 486 and 505-523, respectively (FIG. 12). The three deletions resulted in the loss of several proline residues and predicted B-cell epitopes. Besides these deletions, significant alterations in nsp2 amino acid sequence from other Type 2 strains were also seen, sometimes corresponding to the Type 1 amino acid seen at the same relative position (FIG. 12). Comparison of the nsp2 predicted protein of the two PRRSV genotypes demonstrated that the amino acid identity within Type 2 viruses ranged from 66% to 99% and from 88-90% within Type 1 viruses, but differed greatly between genotypes (<45% similarity). In particular, the MN184 isolates displayed 66-80% amino acid identity to all Type 2 nsp2 predicted proteins and only 43-45% identity to Type 1 strains. When surveying the multiple sequence alignment in FIG. 12, we also noted that all instances of insertion or deletion in both genotypes occurred in this hypervariable middle region. To this point, Shen et al. (*Arch. Virol.*, 145:871-883 (2000)) first reported that PRRSV North American Type 2 strain SP has a unique insertion of 36 aa relative to the position between aa 813 and 814 of PRRSV VR-2332 nsp2. Another investigator found a unique 12 aa deletion at position 466-477 in PRRSV isolate HB-2(sh)/2002 nsp2 (Gao et al., *Arch. Virol.*, 149:1341-1351 (2004)). A 17 aa deletion occurred in newly identified European-like PRRSV isolates when compared to strain LV (Fang et al., *Virus Res.*, 100; 229-235 (2004); Ropp et al., *J. Virol.*, 78:3684-3703 (2004)). The instances of mutation did not consistently occur along the same stretch of amino acids, although the deletions seen between the MN184 isolates and other Type 2 viruses encompass most of the largest deletion detected between Type 1 and other Type 2 PRRSV. All of these data suggested that the nsp2 ORF contains a conserved protease motif and predicted transmembrane spanning regions that may be necessary for replication of PRRSV, but is highly susceptible to mutation in the large middle section.

The sudden appearance of field isolates of PRRSV in Minnesota reflecting the 184 RFLP pattern is still a mystery, but the consequences of this event are even now being realized. The Minnesota Veterinary Diagnostic Laboratory now performs routine sequencing on similar 184 RFLP isolates from approximately one fourth of the total number of ORF5 sequence requests. In addition, the 184 RFLP pattern has now been detected not only in Minnesota, but in Iowa, Wisconsin, South Dakota, Kansas, Missouri, Illinois, Nebraska, Kentucky, Oklahoma and Wyoming as well. We chose to derive the full-length sequences from two isolates because of the need to understand if this could be more than a single virus type and the fact that the swine herd diagnosed with isolate MN184A presented with a milder case of PRRS than the herd infected with isolate MN184B, as reported by the attending pathologist. The strains have not been inoculated into naïve animals to verify the case presentations, but it is interesting to note that isolate MN184B had many more nucleotide degeneracies detected when analyzing the genome and this might reflect the severity of the disease reported.

This genome analysis increased our understanding of the immense nucleotide and amino acid sequence variation that exists in the field. Factors driving this variation may be related to the way swine are now managed, the interstate and international transport of swine and boar semen, the intermixing of different PRRSV isolates within herds and the nature of the virus itself. Full genome sequence generation also allows us to monitor where on the genome variation is tolerated and which regions are more conserved. As a result of this study, as well as a previous publication (Ropp et al., *J. Virol.*, 78:3684-3703 (2004)), a picture is emerging that indicates nsp2, nsp1β and ORF5 are extraordinarily versatile proteins.

This study has also provided clear evidence that nsp2 size can no longer be used to differentiate between the two PRRSV genotypes. The novel finding that nsp2 evolved to display a Type 2 genome with three discontinuous deletions, leading to the shortest genome to date (15,019 kb), suggests that PRRSV may be evolving to eliminate dispensable genomic regions and make the genome more compact. Finally, although the significance of genetic variations in PRRSV can only be surmised at present, the evolutionary change seen in ORF5, nsp1β and nsp2 should reasonably be related to the biological fitness of PRRSV during selection pressure.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

---

What is claimed is:

1. An isolated infectious polynucleotide comprising a nucleotide sequence having at least 88% identity to SEQ ID NO: 14 and a deletion of at least 57 consecutive nucleotides corresponding to nucleotide 2061 to nucleotide 3545 of SEQ ID NO: 14.

2. The isolated infectious polynucleotide of claim 1 wherein the polynucleotide comprises 2 or more deletions, and wherein each deletion is independently at least 57 consecutive nucleotides.

3. The isolated infectious polynucleotide of claim 1 wherein an RNA polymerase promoter is operably linked to the polynucleotide.

4. The isolated infectious polynucleotide of claim 1 wherein the polynucleotide further comprises an exogenous polynucleotide present in the deletion.

5. The isolated infectious polynucleotide of claim 4 wherein the exogenous polynucleotide encodes a detectable marker.

6. An isolated polynucleotide comprising a nucleotide sequence having at least 88% identity to SEQ ID NO: 14 and at least one deletion of at least 57 consecutive nucleotides corresponding to nucleotide 2061 to nucleotide 3545 of SEQ ID NO: 14, and wherein the polynucleotide replicates and produces infectious virus particles when introduced into a cell.

7. The isolated infectious polynucleotide of claim 6 wherein the polynucleotide comprises 2 or more deletions, and wherein each deletion is independently at least 57 consecutive nucleotides.

8. The isolated infectious polynucleotide of claim 6 wherein an RNA polymerase promoter is operably linked to the polynucleotide.

9. The isolated infectious polynucleotide of claim 6 wherein the polynucleotide further comprises an exogenous polynucleotide present in the deletion.

10. The isolated infectious polynucleotide of claim 9 wherein the exogenous polynucleotide encodes a detectable marker.

11. The isolated polynucleotide of claim 1 wherein the polynucleotide is present in a vector.

12. The isolated infectious polynucleotide of claim 11 wherein the polynucleotide is present in a cell.

13. The isolated polynucleotide of claim 6 wherein the polynucleotide is present in a vector.

14. The isolated infectious polynucleotide of claim 13 wherein the polynucleotide is present in a cell.

15. An isolated infectious polynucleotide comprising a nucleotide sequence having at least 88% identity to SEQ ID NO:1 and a deletion of at least 39 consecutive nucleotides corresponding to nucleotide 2062 to nucleotide 3864 of SEQ ID NO:1, wherein the polynucleotide further comprises an exogenous polynucleotide present in the deletion.

16. The isolated polynucleotide of claim 15, wherein the exogenous polynucleotide encodes a detectable marker.

17. An isolated polynucleotide comprising a nucleotide sequence having at least 88% identity to SEQ ID NO: 1 and at least one deletion of at least 39 consecutive nucleotides corresponding to nucleotide 2062 to nucleotide 3864 of SEQ ID NO:1, wherein the polynucleotide replicates and produces infectious virus particles when introduced into a cell, and wherein the polynucleotide further comprises an exogenous polynucleotide present in the deletion.

18. The isolated polynucleotide of claim 17, wherein the exogenous polynucleotide encodes a detectable marker.

19. An isolated infectious polynucleotide comprising a nucleotide sequence having at least 88% identity to SEQ ID NO: 14 and 2 or more deletions of at least 37 consecutive nucleotides each corresponding to nucleotide 2061 to nucleotide 3545 of SEQ ID NO: 14.

20. An isolated infectious polynucleotide comprising a nucleotide sequence having at least 88% identity to SEQ ID NO: 14 and a deletion of at least 39 consecutive nucleotides corresponding to nucleotide 2061 to nucleotide 3545 of SEQ ID NO: 14, wherein the polynucleotide further comprises an exogenous polynucleotide present in the deletion.

21. An isolated polynucleotide comprising a nucleotide sequence having at least 88% identity to SEQ ID NO: 14 and 2 or more deletions of at least 39 consecutive nucleotides each corresponding to nucleotide 2061 to nucleotide 3545 of SEQ ID NO: 14, and wherein the polynucleotide replicates and produces infectious virus particles when introduced into a cell.

22. An isolated polynucleotide comprising a nucleotide sequence having at least 88% identity to SEQ ID NO: 14 and at least one deletion of at least 39 consecutive nucleotides corresponding to nucleotide 2061 to nucleotide 3545 of SEQ ID NO: 14, wherein the polynucleotide replicates and produces infectious virus particles when introduced into a cell, and wherein the polynucleotide further comprises an exogenous polynucleotide present in the deletion.

23. The isolated infectious polynucleotide of claim 22, wherein the exogenous polynucleotide encodes a detectable marker.

24. An isolated infectious polynucleotide comprising a nucleotide sequence SEQ ID NO: 7, SEQ ID NO: 8, SEQ ID NO: 9, SEQ ID NO: 10, SEQ ID NO: 11, SEQ ID NO: 12, or SEQ ID NO: 13.

25. An nsp2 polypeptide encoded by an infectious polynucleotide comprising a nucleotide sequence SEQ ID NO: 7, SEQ ID NO: 8, SEQ ID NO: 9, SEQ ID NO: 10, SEQ ID NO: 11, SEQ ID NO: 12, or SEQ ID NO: 13.

* * * * *